US011453867B2

(12) United States Patent
Scott et al.

(10) Patent No.: US 11,453,867 B2
(45) Date of Patent: *Sep. 27, 2022

(54) CRISPR DNA TARGETING ENZYMES AND SYSTEMS

(71) Applicant: ARBOR BIOTECHNOLOGIES, INC., Cambridge, MA (US)

(72) Inventors: David A. Scott, San Francisco, CA (US); David R. Cheng, Boston, MA (US); Winston X. Yan, Boston, MA (US); Tia M. DiTommaso, Waltham, MA (US)

(73) Assignee: ARBOR BIOTECHNOLOGIES, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/505,578

(22) Filed: Oct. 19, 2021

(65) Prior Publication Data
US 2022/0033793 A1 Feb. 3, 2022

Related U.S. Application Data

(63) Continuation of application No. PCT/US2020/049923, filed on Sep. 9, 2020.

(60) Provisional application No. 62/897,859, filed on Sep. 9, 2019.

(51) Int. Cl.
*C12N 9/22* (2006.01)
*C12N 15/11* (2006.01)
*C12N 15/90* (2006.01)

(52) U.S. Cl.
CPC ............. *C12N 9/22* (2013.01); *C12N 15/11* (2013.01); *C12N 15/907* (2013.01); *C12N 2310/20* (2017.05)

(58) Field of Classification Search
None
See application file for complete search history.

(56) References Cited

U.S. PATENT DOCUMENTS

| | | | | |
|---|---|---|---|---|
| 2004/0052799 | A1* | 3/2004 | Smith | C07K 14/205 424/184.1 |
| 2004/0216190 | A1* | 10/2004 | Kovalic | C12N 15/8242 800/289 |
| 2009/0202579 | A1* | 8/2009 | Cowman | A61P 33/06 424/191.1 |
| 2013/0330335 | A1* | 12/2013 | Bremel | A61P 37/04 424/134.1 |
| 2014/0341918 | A1* | 11/2014 | Kurtis | A61K 39/015 424/139.1 |
| 2019/0002875 | A1* | 1/2019 | Cheng | C12N 9/22 |

FOREIGN PATENT DOCUMENTS

WO 2018/071672 A1 4/2018
WO WO 2018/071672 A1 * 4/2018 ............. C12N 15/09

OTHER PUBLICATIONS

International Search Report and Written Opinion for International Application No. PCT/US2020/049923 dated Jan. 21, 2021.
Publication of Application No. PCT/US2020/049923 published Mar. 18, 2021.

* cited by examiner

*Primary Examiner* — Nancy J Leith
(74) *Attorney, Agent, or Firm* — K & L Gates LLP

(57) ABSTRACT

The disclosure describes novel systems, methods, and compositions for the manipulation of nucleic acids in a targeted fashion. The disclosure describes non-naturally occurring, engineered CRISPR systems, components, and methods for targeted modification of nucleic acids. Each system includes one or more protein components and one or more nucleic acid components that together target nucleic acids.

23 Claims, 28 Drawing Sheets
Specification includes a Sequence Listing.

| SEQ ID | 90 | 100 | 110 | 120 | 130 | 140 | 150 | 160 |
|---|---|---|---|---|---|---|---|---|
| SEQ ID NO:1 | QRYKEVLSKWVCDHLTTMKIGD-ILPYIDRYSKKIDNKTGEYPENT------------------------YYS--LCE------------ | | | | | | | |
| SEQ ID NO:29/36 | QAYKDTLSKWVAQNLTAMKIGD-LLPYLDKYSKKTNKETGERPVNV------------------------YYQ--LCE------------ | | | | | | | |
| SEQ ID NO:41 | QAYADLVNKWICSNLTN-KIGEVLLPYIDNKN------CV-----------------------------YYE--LCY------------ | | | | | | | |
| SEQ ID NO:22 | TAYYNRISDWICDRLINTTVGE-LIGIGYKTDKKGNA---LA-----------------------------YIKDGSSE----------- | | | | | | | |
| SEQ ID NO:48/55 | CNYNKLSKWIGDSLTTMKIGD-LAQYITNQN--------SA-----------------------------YYLAVTND----------- | | | | | | | |
| SEQ ID NO:31/39 | GDYYNKVSKWIADNLITMKIGD-LAQYITNQN--------SK-----------------------------YYTAVTNK----------- | | | | | | | |
| SEQ ID NO:2 | CDYYNKVSKWIADNLITMKIGD-LAQYITNQN--------SK-----------------------------YYTAVTNK----------- | | | | | | | |
| SEQ ID NO:49/54 | CTYYNKLSQWICNNLTSMKVKD-LFAYLDDKQ--KTKPCVDKKTGETKIGVGYYRYFIEN------------ | | | | | | | |
| SEQ ID NO:32/38 | CNYNKLSEWIGKNLISMKIGD-LAKYIDNPK--------SK-----------------------------YYLSVTDE----------- | | | | | | | |
| SEQ ID NO:44 | CTYNRVSKWICDNLTEMRIGD-LAQYIDNHG--------SA-----------------------------YYSAVTDI----------- | | | | | | | |
| SEQ ID NO:47 | TNYYNGVSNWICENLISMKIGD-LGQYIKNTE--------SV-----------------------------YYKFITDE----------- | | | | | | | |
| SEQ ID NO:42/46/51/53 | INYYNRTSDFICDNLTSMKIGD-LANYIKNKE--------NV-----------------------------YCKFVLND----------- | | | | | | | |
| SEQ ID NO:17/45 | SEYYKRLTTFLCERLTDMTWGE-VASFIPEKYRK------NE-----------------------------YYKYLIKE----------- | | | | | | | |
| SEQ ID NO:25 | INYYNKLSDWICKNLTSVTIGD-LLKYVGEKQINKG----VG-----------------------------YYTYFIDE----------- | | | | | | | |
| SEQ ID NO:15/24 | KGYYNTCSNWINNNLTSITIGE-MGKFLKDVMRKT-----TG-----------------------------YIDVALSD----------- | | | | | | | |
| SEQ ID NO:14 | KEYYNKCSDWIKNNLTSITIGE-MAKFLQETLGKD-----VA-----------------------------YISMGLSD----------- | | | | | | | |
| SEQ ID NO:4 | KKYYNICSEWIKDNLTSITIGD-IASFLKEATNKDTI---PT-----------------------------YINMGLSE----------- | | | | | | | |
| SEQ ID NO:23 | KNYYNKVSQWINNNLTKMTIGD-LIQYAPTVSKKGKKQPDGTMVYDTPL----------YVTYAMSD----------- | | | | | | | |
| SEQ ID NO:21 | NEYYNRLSDWICGNLTKMTIGE-LAELVPEKKRN------TS-----------------------------YYLAATDE----------- | | | | | | | |
| SEQ ID NO:27 | TNYYNKVSKWICDNLDT-PIGE-LSKNISEKRHN------SK-----------------------------YYRATNDP----------- | | | | | | | |
| SEQ ID NO:3 | NRYYNICSDWICNNLMT-PIGS-LYQYIDDKCKN------NA-----------------------------YAQNLIAE----------- | | | | | | | |
| SEQ ID NO:56 | QSYYNLCSDWICKNLTTMTIGD-LDRYIPEKSKD------NI-----------------------------YATVLLDE----------- | | | | | | | |
| SEQ ID NO:19 | QSYYNLCSDWICKNLTTMTIGD-LDQYIPEKAKG------NT-----------------------------YATVLLDE----------- | | | | | | | |
| SEQ ID NO:18 | TNYYNGLSKFIADRLLDDMVTT-LAPLIEEKKRN------SE-----------------------------YYKYLTNG----------- | | | | | | | |
| SEQ ID NO:28/35 | IEDSNNLSDWINNQLINKTICE-VGALIPIEKRE------TS-----------------------------YYKSTVDE----------- | | | | | | | |
| SEQ ID NO:43/52 | DQKFNNVSQWIADHLTSMTIGE-AASRISPHKMD------SQ-----------------------------YAMTSLSD----------- | | | | | | | |
| SEQ ID NO:30/33/37/40 | AEQGNHFSEFIHKNLTSKTIGE-FASQLPVEKRQ------FG-----------------------------YYQYAIGGTMPAKKNASDEDKPKG |

Fig. 1B

|  | 340 | 350 | 360 | 370 | 380 | 390 | 400 | 410 |
|---|---|---|---|---|---|---|---|---|
| Identity | | | | | | | | |
| SEQ ID NO:1 | HTDEIKEYVEYICVEQLKEFCGVKVNRSKSSMNINIQNF-----SITRVDGKCT-------YILHLPIGKK-VYDIKLWGNR |||||||
| SEQ ID NO:29/36 | HENEIKEYITLAAVEQLKSFGGVRVNNEKSSMNLEIQGF-----SITRVDGACT-------YILHLPINGK-IHGIKLWGNR |||||||
| SEQ ID NO:41 | HTDLIDTMAMNAGVEALKQFEGLKLNRDKFSMTITTNST-SPYTLTRVAGTCA-------YNLHIPCRKR-SYDIRLWGNR |||||||
| SEQ ID NO:22 | HEDAVKAKMENYAIESFKTFGGCHRN-SNRSMSIQFTNN-SPLEIKKV-GKTS-------FDLYMPINGE-VACLQLMGNK |||||||
| SEQ ID NO:48/55 | NEENIKNEIETMAISDLQKFGGCQRK-SLNTLTIHKQNS----LMEKV-GNTS-------FTLQLSFNKK-PYTINLLGNR |||||||
| SEQ ID NO:31/39 | NEKAINNEIETMAIADLQKFGGCQRK-SLNAFTIHKQDS----LMEKV-GNTS-------FRLQLSFRKK-TYVINLLGNR |||||||
| SEQ ID NO:2 | NEKAINNEIETMAIADLQKFGGCQRK-SLNAFTIHKQDS----LMEKV-GNTS-------FRLQLPFRKK-TYVINLLGNR |||||||
| SEQ ID NO:49/54 | HEEDIKNEIATMAIADLQKFGGCQRK-SMNTLTIHKQDS----PMEKV-GNTS-------FNLRLTFNKK-PYTLNLLGNR |||||||
| SEQ ID NO:32/38 | NTKTIKSEMENMAISDLQKFGGCVRK-SLNTITIHKQDS----KIEKE-GNTS-------FRLHMVFNKK-PYTITLLGNR |||||||
| SEQ ID NO:44 | HEEDIKKKIEELVVEELKTFGGCVRK-SMTSCTITVQDF----VMERI-GNTG-------YRINLTFNKK-PYVLGLLGNR |||||||
| SEQ ID NO:47 | HSEEIIEKSNLVAIEQLALFNGCKRK-SLSTMTIHSQHS----KLQKN-GLTS-------FV--FCINQK-IGSINLFGNR |||||||
| SEQ ID NO:42/46/51/53 | HKNEINEEIEKHAVESLKSFNGCRRNGNRKTMTVQMQKM----LLKKH-GLTS-------YILHLVLDKK-PYDINLMGNR |||||||
| SEQ ID NO:17/45 | NTDKINEYRESLVLDDIRKFGGCNRS-KSNSFSVTLEKA----DI-KEDGLTG-------YTMK--VSKK-LKEIHLLGHR |||||||
| SEQ ID NO:25 | HKQDVEQYINQKRVECLKDFGGCKRRADGLSMVILLNKK----LTKIEADGLTS-------YKLTTNLFGG-KYMINIFGHR |||||||
| SEQ ID NO:15/24 | NEDVIKNKIEILSIEQIKEFGGCIMKPHINSMTFGIQKF----KIEEIENSLG-------FTFNLPLNKN-NYKIELWGHR |||||||
| SEQ ID NO:14 | NENMIKNKLELLSIEQLKNFGGCIMKQHINSMTLIIQHF----KIEEKENSLG-------FILNLPLNKK-QYQIELWGNR |||||||
| SEQ ID NO:4 | NESTINCKMELLSVEQLKEFGGCVMKQHINSMTINIQDF----KIENKENSLG-------FILNLPLNKK-KYQIELWGNR |||||||
| SEQ ID NO:23 | NNDTIFQKMEELSIKQLTEFGGCKMKDNTTSMTINIQDF----KIKRKENSIG-------YIMTIPFNKK-NVDVELYGHK |||||||
| SEQ ID NO:21 | NRNDIMDKCRIMAVEQLVSFGGCKRNINGASMTLRNQCI----SVKRKDGCQG-------YVVAIPVGTKNSIVFDLYGRR |||||||
| SEQ ID NO:27 | NEEDVNNAFSRMSVEMLKNNNGCTRNGDKKTLNISSIDY----KVTRKEGCDG-------YILSFGSRNQ-KYNIDLWGRR |||||||
| SEQ ID NO:3 | NIERVKEEREIMAIAELKDFGGCRRKDDKLSMCIQSAGNSKDIKVSRVKTTHNYTELVDDYTENFNIKFS-ALDFNVMGRR |||||||
| SEQ ID NO:56 | HKSEIDAKMQEMAVENLVKFGGCRRNNSKKSMFIMGSNH-TNYTISYI-GENC------FNINF---AN-ILNFDVYGRR |||||||
| SEQ ID NO:19 | HKSEVDAKMQEMAVENLVKFGGCRRNNSKKSMFIMGSNT-TNYTISYI-GGNS------FNINF---AN-ILNFDVYGRR |||||||
| SEQ ID NO:18 | HKELVDERVANLVVDNIKEFGGCKRDIDCPSMGIQIQHN----FDISINEKRNG-------YTICFGPNKKNLTKLEVFGNR |||||||
| SEQ ID NO:28/35 | NTKLVEEKELELSVKSLVEFGGCRRGEKTMTLNLPDIGY----EIQRKDDKYG-------YIFTLKCSKKRKIIDVWGSK |||||||
| SEQ ID NO:43/52 | NRTTVLDKLDNLKVETLSKFRGSKRKSDRKILTLNGISY----DIKRKEGCQG-------FELKFSVDKN-HMEFDLLGHR |||||||
| SEQ ID NO:30/33/37/40 | NEEGITELYYDLSVKALEHSGQCTYKGGRTISILEIGDI----RISRKENAKG-------YLLTIPINRK-SVVFDLYGRK |||||||

Fig. 1E

```
SEQ ID NO:1              QVVVLN--VDGTPV--D------------IIDII--NRHGESIDIFKNGDIYFSFVVSEDFKKDDF--EI---GNVVGVDVNTKHMLIQTNI---
SEQ ID NO:29/36          QVVVN--KDGTPV--D------------ILDLT--NQHGSTINITIKNGEIYFAFTVTSDFVKPEH--QI---KNVVGVDVNTKHMLMQSNI---
SEQ ID NO:41             QTVRW--VNGELV--D------------IADII--NQHGQTIIFTIKNGNVYVHIPYGLNFEKTEH--EI---KNVVGVDVNTKHMLMQTSI---
SEQ ID NO:22             QAVCVGENGERC--D------------LVDIV--NSHSKTIFIKIINGEMYVDIPCVVNFEKKDE--DT---IKSVGVDVNIKHEILATSV---
SEQ ID NO:48/55          QVVKF--VDGKRV--D------------LIDIT--EKHGDWVTFNIKNDELFVHLTSPIDFEKEVC--EI---KNAVGVDVNIKHNMLATSI---
SEQ ID NO:31/39          QVVNF--VNGKRV--D------------LIDIA--ENHGDLITFNIKNGELFLHITSPIVFDKDVR--DI---RNVVGIDVNIKHSMLATSI---
SEQ ID NO:2              QVVNF--VNGKRV--D------------LIDIA--ENHGDLVTFNIKNGVLFVHLTSPIVFDKDVR--DI---RNVVGIDVNIKHSMLATSI---
SEQ ID NO:49/54          QVVKF--VGGKRI--D------------LINIT--ENHGDWITFNIKNNELFVHMTSPVDFEKEVC--EI---KNAVGVDVNIKHMLATSI---
SEQ ID NO:32/38          QVVKY--IDGKRV--D------------IVNIV--EKHGDWITFNIKNGELFVHLTKCVEFSKGQK--EI---KKAAGVDVNIKHAMLAASI---
SEQ ID NO:44             QVVRY--VDGDRV--E------------LVDIV--NNHGNQITFNLKNGELFVHLTSGVDFSKEES--SM---ENIVGVDVNIKHSMLASSI---
SEQ ID NO:47             QLVSVDENGNRN--D------------IIDIC--NNYGDFITFQIKNGKMFILLTAKVDFDKENI--EI---KNVVGADVNIKHNMIASSI---
SEQ ID NO:42/46/51/53    QTVKVDNNGNRV--D------------LVDIS--SKHGYDLTFEVKGKTLFFTFSSEKDFSKKEQ--EI---KNILGIDINTKHSMLATSI---
SEQ ID NO:17/45          RVVEV--VNGRRV--N------------LVDICGDKSGDSKVFVVDGDNLYVCISAPVKFSKNGM--EA---KKYIGVDMNKHSIISVSD---
SEQ ID NO:25             ALVSV--CNGERAENE------------NIDIC--NKHGERFTFKIENGNLFVALTADYNYEKQPN--LP---KNIVGVDINIKHSMLNSSI---
SEQ ID NO:15/24          QLKKG--NKESNVNVS------------LDDFI--NTYGQNVFTIKRKKLYIVFSYDYEFERGEC--NF---EKSVGLDVNFKHSLFVTSE---
SEQ ID NO:14             QVNKG--TKER----------------DAFLI--NTYGENIVFIINNDELYVVFSYEYELEKEEA--NF---VKTVGLDVNFKHAFFVTSE---
SEQ ID NO:4              QIKKG--NKDNYK--T------------LVDFI--NTYGQNIIFTIKNNKIYVVFSYFCELKEKEI--NF---DKIVGIDVNFKHALFVASERDK
SEQ ID NO:23             QTIKG--HKNSYT--E------------IVDIV--NKHGNTITFPKIKNNQLFAIITSDTEVTKPEP--QY---EKIVGVDVNIKHTLMVTSE---
SEQ ID NO:21             DVIK---DGV----E------------LVDVC--GKHTDTITTIKSVNGELFLDMPVAINFEKKSG--KC---TKTVGIDVNTKHMLIQTSV---
SEQ ID NO:27             DTIS---NGK----E------------LIDL---SEHGEPLTITSENGDYYVCMTVDVPFEKKSTGST--EKVASVDVNTKHTMLSTDV---
SEQ ID NO:3              DVVKTKLNKTEDDSNTWGGTELLVDII--NNHGCSLTFKLVDDKLYDIPIDTEHINKTT--DF---KKSVGIDVNLKHSLLNTDI---
SEQ ID NO:56             DVVK---NGE----V------------LVDIM--ANHGDSIVLKIVNGELYADVPCSVTLNKVES--NF---DKVVGIDVNMKHMLLSTSV---
SEQ ID NO:19             DVVK---NGE----V------------LVDIM--ANHGDSIVLKIVNGELYADVPCSVTLNKVES--NF---DKVVGIDVNMKHMLLSTSI---
SEQ ID NO:18             MVLL---NGE----E------------IVDLP--NTHGEKLTLIDRGNAIYAAITAQVPFEEKHMP--DG---NKTVGIDLNLKHSVFATSI---
SEQ ID NO:28/35          ATIDS--NGN----D------------KVDII--NTHGKSINFKIINNEMYIDITVDVPFAKRKL--GI---KKVVGIDVNTKHMLMATNI---
SEQ ID NO:43/52          ALIK---NGE----M------------LVDIE--NCHGSQLSLEIDGDDMYAIISMRTFCEKNES--KL---EKIIGADVNIKHMFLMTSE---
SEQ ID NO:30/33/37/40    DTIGG--DGR----D------------LIDIM--NTHGSSLQFTADGNDIYLTITATKNFIKEKP--TFNEDTVLGGDVNIKHSYTVFST---
```

| | 840 | 850 | 860 | 870 | 880 | 890 | 900 | 910 |
|---|---|---|---|---|---|---|---|---|

Identity

SEQ ID NO:1              KFIQLGNNGNVQTVLVPSYFTSQMNSKTHKIYVVNVK------NERTGKTEQKLANKNMVRLGQERH-INGLNADVNASM
SEQ ID NO:29/36          KFIQLGNYNKLQTVLVPSYFTSQMDSKTHSVYVVETA------NTKTSKKELKLVSKKRVRRQQEWH-INGLNADYNAAC
SEQ ID NO:41             KFIQLGNNGSIQTVLVPPSYTSQMDSKTHTIYVKETV------DPKNKNKKKLKLVDKKLVRHGQEYH-KNGLNADINAAL
SEQ ID NO:22             KEVQLSNNTNVSILFAPAAFTSQMDSNRHVIYTVK-------NNKGKLALVDKKYVLANKKMVRTQQETH-INGLHSGYNAAC
SEQ ID NO:48/55          KFVQLCNNNKMNIVFCPSAFTSQMDSITHTLYYVEKI-----TKKKNGKEEKKYVLANKKMVRTQQETH-INGLNADYNSAC
SEQ ID NO:31/39          KFVQLSNNNKMNIVFCPSAFSSQMDSITHTLYYVEKI-----TKNKKGKEKKKYVLANKKMVRTQQETH-INGLNADYNSAC
SEQ ID NO:2              KFVQLSNNNKMNIVFCPSAFSSQMDSITHTLYYVEKT-----TKNKKGKEKKKYVLANKKMVRTQQEKH-INGLNADYNSAC
SEQ ID NO:49/54          KFVQLCNNNSMNVVFCPSAFTSQMDSITHSLYYIEKT-----SKTKNGKEKKQYVLANKKMVRTQQEKH-INGLNADFNSAC
SEQ ID NO:32/38          KFAQLCNNNDVNVFGPSAFTSQMDSETHSLYYVEKE------TNGKNGKTGKKFVLADKKSVRRRQETH-INGLNADFNAAR
SEQ ID NO:44             KFVQLTNNSDMGVVFCPSAFTSQMDSKTHRLYFVEGL-----DGNGKNKYVLANKWSVRRQQERH-INGLNADFNSAC
SEQ ID NO:47             KFIQLSNNKPINIVIVPSAFSSQMDSKDHKLYVDE-------NGK---LINKRKVRKQQERH-INGLNADFNAAR
SEQ ID NO:42/46/51/53    KFVQLSNNTNMNVIFVPAAFTSQMDSNTHKIYVKEIM-----DKNNKKQLQLIDKRKVRTKQEFH-INGLNADFNAAN
SEQ ID NO:17/45          KFVQLSNYKDIQMVYVPSPYTSQTDSRTHSLYYIETV-----KVDEKTGKEKKEHIVAPKESVRTEQESF-VNGMNADTNSAN
SEQ ID NO:25             KFAQLTNNNTMNTVFIPSSFTSQIDSKTRKLYLLEYT-----EKCDNGKTKKVVKFINKRVLRKIQEQH-LNGMNADNNAAR
SEQ ID NO:15/24          EFILLSHNGKSQIALVPAEYTSQMDSIDHCIYMTK-------NDKGKLVKVDKRKVRTKQERH-INGLNADFNAAC
SEQ ID NO:14             EFVLLSNNGKTQIALVPSEFTSQMDSTDHCLYMKK-------NDKGKLVKADKKEVRTKQEKH-INGLNADFNAAN
SEQ ID NO:4              EFILLSNNGKTQIALVPSEYTSQMDSIEHCLYVDK-------NGK---KVDKKKVRQKQETH-INGLNADFNAAN
SEQ ID NO:23             EMIKLSNNNKVCVAIIPPEYTSQIDSNTHKLYFIN-------KDGKLLKADKKTVRKTQEKH-INGLNADFNAAS
SEQ ID NO:21             RFVLSSNNGNASVTFVPSYHTSQIDSTDHKMFVTN-------------KGKIVDKRKVRIQETH-VNGLNSDFNAAR
SEQ ID NO:27             VMCVMSNNGTASVAFEPSYFSSQMDSATHKVYTTR-------NKKGKDVIASKETVRPRQEKH-INGMNCDINSPK
SEQ ID NO:3              YFTTLSNKRKIAVAHVPAYYTSQIDSIDNKICMIKST-----DKNGKSTYKIADKTIVRPTQEKH-INGLNADYNAAR
SEQ ID NO:56             YFATLSNNGQTGIFFVPSQFTSQMDSNTHNLYFEN-------AKNGGLKIASKSKVRKSQEYH-LNGLPADYNAAR
SEQ ID NO:19             YFATLSNNGQTGIFFVPSQFTSQMDSNTHNLYFEN-------AKNGGLKIAPKYKVRQTQEYH-LNGLPADYNAAR
SEQ ID NO:18             YFVRLSNNGKVSVALVPPSFTSQMDSVEHKFFMKK-------NANGKLIVADKKDVRSCQEKHKINGLNADYNAAC
SEQ ID NO:28/35          KFIQLGNNGKTQVALVPSNYTSQMNSETHTVYLMK-------NPKTKKLVIMDKDKVRPIQEKYKLNGLNADFNSAR
SEQ ID NO:43/52          KFVELSNNGKVSVVIVPPYFSSQMDSVTHKVFTEEIVVQKKSSNGKVRKTKKTVLVDKRKVRKTQESH-INGLNADYNAAL
SEQ ID NO:30/33/37/40    RFIGLANSGRLQVGLVPSQYTSYIDSTTHTLYAVI-------EDGKTVLAPKEVVRASQERH-INGLNADYNSAL

Fig. 1K

```
SEQ ID NO:1           NIAYIVENKEMRNAMCTN------PKSETGYSVPFLTSRIKKQNIM-----VVELKKMGMVEVLNEKSTEI
SEQ ID NO:29/36       NIAHIAKNIELRQIMCKT------PQTKNGYSSPVLTSKVKSQVEM-----VRELKKMGKTILYSNDSLPF
SEQ ID NO:41          NIAYIVENQEMREVMCLH------PSKKDGVYDQPFLKATTKYPATV-----AGILLKMGKTTNWGEK
SEQ ID NO:22          NVKFICDNEFFRNTMTIS------NKGKNLYSQPTYDIKEAYKKNAGCKV--INDFIKNGNAVICCIENNKLIETNGRQ
SEQ ID NO:48/55       NLKYIALNDELRNEMTDTFKVTNRQKTMYGIPAYNIKRGFKKNLSAKT--INTFRKLGHYRDGKINEDGMFVETLA
SEQ ID NO:31/39       NLKYIALNYELRDKMTDRFKASKKIKTMYNIPAYNIKSNFKKNLSAKT--INTFRELGHYRDGKINEDGMFVEILE
SEQ ID NO:2           NLKYIALNDELRDKMTDRFKASKKIKTMYNIPAYNIKSNFKKNLSAKT--IQTFFRELGHYRDGKINEDGMFVENLE
SEQ ID NO:49/54       NLKYIALDEELRNAMTDEFN--PKKQKTMYGVPAYNIKNGFKKKNLSTKT-INTFRTLGHYRDGKINNEGLFVENLA
SEQ ID NO:32/38       NLEYIASNPELLERMTKR------TKSGKDMYNTPSWNIRQEFKKNLSVRT-INTFRELGNVKYGKINNEGLFVEDDV
SEQ ID NO:44          NCQHIAYDPILRDAMTIK------VEAGKGMYNKPSYDIRKKFKKNLSAAT-LKTFIKLGNTVKGMIVNGQFVEMES
SEQ ID NO:47          NLSYLAKNNELLEKVCLK------RKKFGKASYSVPYWNVKDAFKKNVSSNM-IATIKKMNMVKF
SEQ ID NO:42/46/51/53 NIKYIAENNDLLLTMCTK------TKENNRYGNPLYNIKDTFKKKIPSSI--LNIFKKKDMYQIICD
SEQ ID NO:17/45       NIKYIFENETLRDKFLKR------TKDGTEMYNRPAFDLKECYKKNSNVSV-FNTLKKTLGAIYGKLDENGNFIENECNK
SEQ ID NO:25          NIRDITKN--LRDVFTKK------QTDKNCYNSAEFMIQTKFKKRLPQATVFGELNRNGYVKVLTQEEYDELTKSAK
SEQ ID NO:15/24       NIKYIVTNEDWRKVFCIK------PKKEDYNTPLLDATKNGQFRI------LDKLKKLNATKLLEMEK
SEQ ID NO:14          NIKYIVENEVWREIFCTR------PKKAEYNVPSLDTTKKGPSAI------LHMLKKIEAIKILETEK
SEQ ID NO:4           NIKYIIENENLRKLFCGK------LKVSGYNTPILDATKKGQFNI------LAELKKQNKIKIFEIEK
SEQ ID NO:23          NIKYIVQNETWRNLFTNK------TNNTYGLPILTPSKKGQSNI------ITQLMKINATQELVV
SEQ ID NO:21          NIQYISENEEWRNALCKP------TENMYNEPIYVPLVKSQNGM------FKAIKKLGATKIWQE
SEQ ID NO:27          NLSYLITNEEFREMFLTP------TKNGYNEPFYKSRVKSAASM------MSGLKKLGATMPLTDENAIFSTPKPKKNIGKQ
SEQ ID NO:3           NINFIVADEKWRKKFVRP------TNTNKPLYNSPVFSPAVKSEGGT-----IKNLQILSATKTIIL
SEQ ID NO:56          NIAYIGLDEIMRNTFLKK------ANSNKSLYNQPIYDTGIKKTAGV-----FSRMKKLKKYKVI
SEQ ID NO:19          NIAYIGLDETMRNTFLKK------ANSNKSLYNQPIYDTGIKKTAGV-----FSRMKKLKRYEII
SEQ ID NO:18          NIGFIVEDDYMRESLLGS------PTGGTYDTAYFDTKIQGSKGV-----YDKIKENGETYIAVLSDDVITAEV
SEQ ID NO:28/35       NIAYIVENEILRNSFLKE------ETKKYTYNTPLFTPRLKSSEKI-----ITELKKLGMTTVIE
SEQ ID NO:43/52       NLKYIAETIDWRSTLCFK------TWNTYGSPQWDSKIKNQKTM-----IDRLDSLGAIELKNW
SEQ ID NO:30/33/37/40 NLKYMITDENFRKTFTSE------TSADKFGWGKPMFSPTTRSQDEV-----FSAIKKIGAITVLED
```

Fig. 1L

CRISPR DNA TARGETING ENZYMES AND SYSTEMS

RELATED APPLICATION

This application is a continuation of International Application No. PCT/US2020/049923, filed Sep. 9, 2020, which claims priority to U.S. Provisional Application 62/897,859 filed on Sep. 9, 2019, the entire contents of each of which is hereby incorporated by reference.

SEQUENCE LISTING

The instant application contains a Sequence Listing which has been submitted electronically in ASCII format and is hereby incorporated by reference in its entirety. Said ASCII copy, created on Oct. 19, 2021, is named A2186-702820FT.txt and is 475,746 bytes in size.

FIELD OF THE INVENTION

The present disclosure relates to systems and methods for genome editing and modulation of gene expression using novel Clustered Regularly Interspaced Short Palindromic Repeats (CRISPR) and CRISPR-associated (Cas) genes.

BACKGROUND

Recent advances in genome sequencing technologies and analyses have yielded significant insight into the genetic underpinnings of biological activities in many diverse areas of nature, ranging from prokaryotic biosynthetic pathways to human pathologies. To fully understand and evaluate the vast quantities of information yielded, equivalent increases in the scale, efficacy, and ease of sequence technologies for genome and epigenome manipulation are needed. These novel technologies will accelerate the development of novel applications in numerous areas, including biotechnology, agriculture, and human therapeutics.

Clustered Regularly Interspaced Short Palindromic Repeats (CRISPR) and CRISPR-associated (Cas) genes, collectively known as CRISPR-Cas or CRISPR/Cas systems, are adaptive immune systems in archaea and bacteria that defend particular species against foreign genetic elements. CRISPR-Cas systems comprise an extremely diverse group of proteins effectors, non-coding elements, and loci architectures, some examples of which have been engineered and adapted to produce important biotechnological advances.

The components of the system involved in host defense include one or more effector proteins capable of modifying a nucleic acid and an RNA guide element that is responsible for targeting the effector protein(s) to a specific sequence on a phage nucleic acid. The RNA guide is composed of a CRISPR RNA (crRNA) and may require an additional trans-activating RNA (tracrRNA) to enable targeted nucleic acid manipulation by the effector protein(s). The crRNA consists of a direct repeat responsible for protein binding to the crRNA and a spacer sequence that is complementary to the desired nucleic acid target sequence. CRISPR systems can be reprogrammed to target alternative DNA or RNA targets by modifying the spacer sequence of the crRNA.

CRISPR-Cas systems can be broadly classified into two classes: Class 1 systems are composed of multiple effector proteins that together form a complex around a crRNA, and Class 2 systems consists of one effector protein that complexes with the RNA guide to target nucleic acid substrates. The single-subunit effector composition of the Class 2 systems provides a simpler component set for engineering and application translation and have thus far been an important source of programmable effectors. Nevertheless, there remains a need for additional programmable effectors and systems for modifying nucleic acids and polynucleotides (i.e., DNA, RNA, or any hybrid, derivative, or modification) beyond the current CRISPR-Cas systems, such as smaller effectors and/or effectors having unique PAM sequence requirements, that enable novel applications through their unique properties.

SUMMARY

This disclosure provides non-naturally-occurring, engineered systems and compositions for novel single-effector Class 2 CRISPR-Cas systems, which were first identified computationally from genomic databases and subsequently engineered and experimentally validated. In particular, identification of the components of these CRISPR-Cas systems allows for their use in non-natural environments, e.g., in bacteria other than those in which the systems were initially discovered or in eukaryotic cells, such as mammalian cells. These new effectors are divergent in sequence and function compared to orthologs and homologs of existing Class 2 CRISPR effectors.

In one aspect, the disclosure provides engineered, non-naturally occurring Clustered Regularly Interspaced Short Palindromic Repeat (CRISPR)-Cas systems of CLUST.091979 including: a CRISPR-associated protein, wherein the CRISPR-associated protein includes an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to an amino acid sequence set forth in any one of SEQ ID NOs: 1-56; and an RNA guide including a direct repeat sequence and a spacer sequence capable of hybridizing to a target nucleic acid; wherein the CRISPR-associated protein is capable of binding to the RNA guide and of modifying the target nucleic acid sequence complementary to the spacer sequence. In one aspect, the disclosure provides engineered, non-naturally occurring Clustered Regularly Interspaced Short Palindromic Repeat (CRISPR)-Cas systems of CLUST.091979 including: a CRISPR-associated protein or a nucleic acid encoding the CRISPR-associated protein, wherein the CRISPR-associated protein includes an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to an amino acid sequence set forth in any one of SEQ ID NOs: 1-56; and an RNA guide including a direct repeat sequence and a spacer sequence capable of hybridizing to a target nucleic acid, or a nucleic acid encoding the RNA guide; wherein the CRISPR-associated protein is capable of binding to the RNA guide and of modifying the target nucleic acid sequence complementary to the spacer sequence.

In some aspects, the disclosure provides an engineered, non-naturally occurring Clustered Regularly Interspaced Short Palindromic Repeat (CRISPR)-Cas system of CLUST.091979 comprising a CRISPR-associated protein or a nucleic acid encoding the CRISPR-associated protein, wherein the CRISPR-associated protein comprises an amino acid sequence of SEQ ID NO: 241; and an RNA guide comprising a direct repeat sequence and a spacer sequence capable of hybridizing to a target nucleic acid; wherein the CRISPR-associated protein is capable of binding to the RNA guide and of modifying the target nucleic acid sequence complementary to the spacer sequence. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to an amino acid sequence set forth in SEQ ID NO: 4, SEQ ID NO: 10, SEQ ID NO: 12, or SEQ ID NO: 14.

In some embodiments of any of the systems described herein, the CRISPR-associated protein includes at least one (e.g., one, two, or three) RuvC domain or at least one split RuvC domain.

In some embodiments of any of the systems described herein, the CRISPR-associated protein comprises one or more of the following sequences: (a) $PX_1X_2X_3X_4F$ (SEQ ID NO: 216), wherein $X_1$ is L or M or I or C or F, $X_2$ is Y or W or F, $X_3$ is K or T or C or R or W or Y or H or V, and $X_4$ is I or L or M; (b) $RX_1X_2X_3L$ (SEQ ID NO: 217), wherein $X_1$ is I or L or M or Y or T or F, $X_2$ is R or Q or K or E or S or T, and $X_3$ is L or I or T or C or M or K; (c) $NX_1YX_2$ (SEQ ID NO: 218), wherein $X_1$ is I or L or F and $X_2$ is K or R or V or E; (d) $KX_1X_2X_3FAX_4X_5KD$ (SEQ ID NO: 219), wherein $X_1$ is T or I or N or A or S or F or V, $X_2$ is I or V or L or S, $X_3$ is H or S or G or R, $X_4$ is D or S or E, and $X_5$ is I or V or M or T or N; (e) $LX_1NX_2$ (SEQ ID NO: 220), wherein $X_1$ is G or S or C or T and $X_2$ is N or Y or K or S; $PX_1X_2X_3X_4SQX_5DS$ (SEQ ID NO: 221), wherein $X_1$ is S or P or A, $X_2$ is Y or S or A or P or E or Y or Q or N, $X_3$ is F or Y or H, $X_4$ is T or S, and $X_5$ is M or T or I; (g) $KX_1X_2VRX_3X_4QEX_5H$ (SEQ ID NO: 222), wherein $X_1$ is N or K or W or R or E or T or Y, $X_2$ is M or R or L or S or K or V or E or T or I or D, $X_3$ is L or R or H or P or T or K or Q of P or S or A, $X_4$ is G or Q or N or R or K or E or I or T or S or C, and $X_5$ is R or W or Y or K or T or F or S or Q; and (h) $X_1NGX_2X_3X_4DX_5NX_6X_7X_8N$ (SEQ ID NO: 223), wherein $X_1$ is I or K or V or L, $X_2$ is L or M, $X_3$ is N or H or P, $X_4$ is A or S or C, $X_5$ is V or Y or I or F or T or N, $X_6$ is A or S, $X_7$ is S or A or P, and $X_8$ is M or C or L or R or N or S or K or L. In some embodiments of any of the systems described herein, the sequence of SEQ ID NO: 216 is an N-terminal sequence. In some embodiments of any of the systems described herein, the sequence of SEQ ID NO: 219 is a C-terminal sequence. In some embodiments of any of the systems described herein, the sequence of SEQ ID NO: 220 is a C-terminal sequence. In some embodiments of any of the systems described herein, the sequence of SEQ ID NO: 221 is a C-terminal sequence. In some embodiments of any of the systems described herein, the sequence of SEQ ID NO: 222 is a C-terminal sequence. In some embodiments of any of the systems described herein, the sequence of SEQ ID NO: 223 is a C-terminal sequence.

In some embodiments of any of the systems described herein, the CRISPR-associated protein comprises one or more of the following sequences: (a) ECPITKDVINEYK (SEQ ID NO: 290); (b) NLTSITIG (SEQ ID NO: 231); (c) NYRTKIRTLN (SEQ ID NO: 232); (d) ISYIENVEN (SEQ ID NO: 233); (e) ELLSVEQLK (SEQ ID NO: 234); (f) HINSMTINIQDFKIE (SEQ ID NO: 235); (g) KENSLGFIL (SEQ ID NO: 236); (h) GNRQIKKG (SEQ ID NO: 237); (i) DVNFKHA (SEQ ID NO: 238); (j) GYINLYKYLLEH (SEQ ID NO: 239); (k) KEQVLSKLLY (SEQ ID NO: 240); (l) EYIYVSCVNKLRAKYVSYFILKEKYYEKQKEYDIEMGF (SEQ ID NO: 241); (m) DDSTESKESMDKRR (SEQ ID NO: 242); (n) NVQQDINGCLKNIINY (SEQ ID NO: 243); (o) ALENLENSNFEK (SEQ ID NO: 244); (p) QVLPTIKSLL (SEQ ID NO: 245); (q) YHKLENQN (SEQ ID NO: 246); (r) ASDKVKEYIE (SEQ ID NO: 247); (s) TNENNEIVDAKYT (SEQ ID NO: 248); (t) ANFFNLMMKSLHFAS (SEQ ID NO: 249); (u) LLSNNGKTQIALVPSE (SEQ ID NO: 250); (v) HINGLNADFNAANNIKYI (SEQ ID NO: 251), or a sequence having no more than 1, 2, or 3 sequence differences (e.g., substitutions) relative to any of the foregoing. In some embodiments, the CRISPR-associated protein has a sequence at least 70% identical to SEQ ID NO: 4. In some embodiments, the CRISPR-associated protein has a sequence at least 70% identical to SEQ ID NO: 10.

In some embodiments of any of the systems described herein, the direct repeat sequence includes a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to a nucleotide sequence set forth in any one of SEQ ID NOs: 57-90, SEQ ID NOs: 118-151, or SEQ ID NO: 213. In some embodiments of any of the systems described herein, the direct repeat sequence includes a nucleotide sequence that is at least 95% (e.g., 95%, 96%, 97%, 98%, 99% or 100%) identical to a nucleotide sequence set forth in any one of SEQ ID NOs: 57-90, SEQ ID NOs: 118-151, or SEQ ID NO: 213.

In some embodiments of any of the systems described herein, the direct repeat sequence comprises one or more of the following sequences: (a) $X_1X_2TX_3X_4X_5X_6X_7X_8$ (SEQ ID NO: 224), wherein $X_1$ is A or C or G, $X_2$ is T or C or A, $X_3$ is T or G or A, $X_4$ is T or G, $X_5$ is T or G or A, $X_6$ is G or T or A, $X_7$ is T or G or A, and $X_8$ is A or G or T (e.g., ATTGTTGDA (SEQ ID NO: 225)); (b) $X_1X_2X_3X_4X_5X_6X_7X_8X_9$ (SEQ ID NO: 226), wherein $X_1$ is T or C or A, $X_2$ is T or A or G, $X_3$ is T or C or A, $X_4$ is T or A, $X_5$ is T or A or G, $X_6$ is T or A, $X_7$ is A or T, $X_8$ is A or G or C or T, and $X_9$ is G or A or C (e.g., TTTTWTARG (SEQ ID NO: 227)); and (c) $X_1X_2X_3AC$ (SEQ ID NO: 228), wherein $X_1$ is A or C or G, $X_2$ is C or A, and $X_3$ is A or C (e.g., ACAAC (SEQ ID NO: 229)). In some embodiments of any of the systems described herein, SEQ ID NO: 224 is proximal to the 5' end of the direct repeat. In some embodiments of any of the systems described herein, SEQ ID NO: 228 is proximal to the 3' end of the direct repeat.

In some embodiments of any of the systems described herein, the CRISPR-associated protein is capable of recognizing a protospacer adjacent motif (PAM), wherein the PAM includes a nucleic acid sequence, including a nucleic acid sequence set forth as 5'-NTTN-3', 5'-NTTR-3', 5'-RTTR-3', 5'-TNNT-3', 5'-TNRT-3', 5'-TSRT-3', 5'-TGRT-3', 5'-TNRY-3', 5'-TTNR-3', 5'-TTYR-3', 5'-TTTR-3', 5'-TTCV-3', 5'-DTYR-3', 5'-WTTR-3', 5'-NNR-3', 5'-NYR-3', 5'-YYR-3', 5'-TYR-3', 5'-TTN-3', 5'-TTR-3', 5'-CNT-3', 5'-NGG-3', 5'-BGG-3', or 5'-R-3', wherein "N" is any nucleotide, "B" is C or G or T, "D" is A or G or T, "R" is A or G, "S" is G or C, "V" is A or C or G, "W" is A or T, and "Y" is C or T.

In some embodiments of any of the systems described herein, the CRISPR-associated protein is a protein having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identity to an amino acid sequence set forth in SEQ ID NO: 1, and wherein the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to a nucleotide sequence set forth in SEQ ID NO: 57. In some embodiments of any of the systems described herein, the CRISPR-associated protein is a protein having at least 95% (e.g., 95%, 96%, 97%, 98%, 99% or 100%) identity to an amino acid sequence set forth in SEQ ID NO: 1, and wherein the direct repeat sequence comprises a nucleotide sequence that is at least 95% (e.g., 95%, 96%, 97%, 98%, 99% or 100%) identical to a nucleotide sequence set forth in SEQ ID NO: 57. In some embodiments of any of the systems described herein, the CRISPR-associated protein is capable of recognizing a protospacer adjacent motif (PAM) sequence, wherein the PAM sequence comprises a nucleic acid sequence set forth as 5'-TNNT-3' or 5'-TNRT-3', wherein "N" is any nucleotide and "R" is A or G.

In some embodiments of any of the systems described herein, the CRISPR-associated protein is a protein having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identity to an amino acid sequence set forth in SEQ ID NO: 4, and wherein the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to a nucleotide sequence set forth in SEQ ID NO: 60. In some embodiments of any of the systems described herein, the CRISPR-associated protein is a protein having at least 95% (e.g., 95%, 96%, 97%, 98%, 99% or 100%) identity to an amino acid sequence set forth in SEQ ID NO: 4, and wherein the direct repeat sequence comprises a nucleotide sequence that is at least 95% (e.g., 95%, 96%, 97%, 98%, 99% or 100%) identical to a nucleotide sequence set forth in SEQ ID NO: 60. In some embodiments of any of the systems described herein, the CRISPR-associated protein is capable of recognizing a protospacer adjacent motif (PAM) sequence, wherein the PAM sequence comprises a nucleic acid sequence set forth as 5'-NTTN-3', 5'-NTTR-3' (e.g., 5'-TTTG-3'), or 5'-NNR-3', wherein "N" is any nucleotide and "R" is A or G.

In some embodiments of any of the systems described herein, the CRISPR-associated protein is a protein having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identity to an amino acid sequence set forth in SEQ ID NO: 10, and wherein the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to a nucleotide sequence set forth in SEQ ID NO: 62 or SEQ ID NO: 213. In some embodiments of any of the systems described herein, the CRISPR-associated protein is a protein having at least 95% (e.g., 95%, 96%, 97%, 98%, 99% or 100%) identity to an amino acid sequence set forth in SEQ ID NO: 10, and wherein the direct repeat sequence comprises a nucleotide sequence that is at least 95% (e.g., 95%, 96%, 97%, 98%, 99% or 100%) identical to a nucleotide sequence set forth in SEQ ID NO: 62 or SEQ ID NO: 213. In some embodiments of any of the systems described herein, the CRISPR-associated protein is capable of recognizing a protospacer adjacent motif (PAM) sequence, wherein the PAM sequence comprises a nucleic acid sequence set forth as 5'-NTTN-3' or 5'-RTTR-3' (e.g., 5'-ATTG-3' or 5'-GTTA-3'), wherein "N" is any nucleotide and "R" is A or G.

In some embodiments of any of the systems described herein, the spacer sequence of the RNA guide includes between about 15 nucleotides to about 55 nucleotides. In some embodiments of any of the systems described herein, the spacer sequence of the RNA guide includes between 20 and 45 nucleotides.

In some embodiments of any of the systems described herein, the CRISPR-associated protein comprises a catalytic residue (e.g., aspartic acid or glutamic acid). In some embodiments of any of the systems described herein, the CRISPR-associated protein cleaves the target nucleic acid. In some embodiments of any of the systems described herein, the CRISPR-associated protein further comprises a peptide tag, a fluorescent protein, a base-editing domain, a DNA methylation domain, a histone residue modification domain, a localization factor, a transcription modification factor, a light-gated control factor, a chemically inducible factor, or a chromatin visualization factor.

In some embodiments of any of the systems described herein, the nucleic acid encoding the CRISPR-associated protein is codon-optimized for expression in a cell, e.g., a eukaryotic cell, e.g., a mammalian cell, e.g., a human cell. In some embodiments of any of the systems described herein, the nucleic acid encoding the CRISPR-associated protein is operably linked to a promoter. In some embodiments of any of the systems described herein, the nucleic acid encoding the CRISPR-associated protein is in a vector. In some embodiments, the vector comprises a retroviral vector, a lentiviral vector, a phage vector, an adenoviral vector, an adeno-associated vector, or a herpes simplex vector.

In some embodiments of any of the systems described herein, the target nucleic acid is a DNA molecule. In some embodiments of any of the systems described herein, the target nucleic acid includes a PAM sequence.

In some embodiments of any of the systems described herein, the CRISPR-associated protein has non-specific nuclease activity.

In some embodiments of any of the systems described herein, recognition of the target nucleic acid by the CRISPR-associated protein and RNA guide results in a modification of the target nucleic acid. In some embodiments of any of the systems described herein, the modification of the target nucleic acid is a double-stranded cleavage event. In some embodiments of any of the systems described herein, the modification of the target nucleic acid is a single-stranded cleavage event. In some embodiments of any of the systems described herein, the modification of the target nucleic acid results in an insertion event. In some embodiments of any of the systems described herein, the modification of the target nucleic acid results in a deletion event. In some embodiments of any of the systems described herein, the modification of the target nucleic acid results in cell toxicity or cell death.

In some embodiments of any of the systems described herein, the system further includes a donor template nucleic acid. In some embodiments of any of the systems described herein, the donor template nucleic acid is a DNA molecule. In some embodiments of any of the systems described herein, wherein the donor template nucleic acid is an RNA molecule.

In some embodiments of any of the systems described herein, the RNA guide optionally includes a tracrRNA and/or a modulator RNA. In some embodiments of any of the systems described herein, the system further includes a tracrRNA. In some embodiments of any of the systems described herein, the system does not include a tracrRNA. In some embodiments of any of the systems described herein, the CRISPR-associated protein is self-processing. In some embodiments of any of the systems described herein, the system further includes a modulator RNA.

In some embodiments of any of the systems described herein, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 1, and the tracrRNA sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 152, SEQ ID NO: 153, or SEQ ID NO: 154.

In some embodiments of any of the systems described herein, the system is present in a delivery composition comprising a nanoparticle, a liposome, an exosome, a microvesicle, or a gene-gun.

In some embodiments of any of the systems described herein, the systems are within a cell. In some embodiments, the cell is a eukaryotic cell. In some embodiments, the cell is a mammalian cell. In some embodiments, the cell is a human cell. In some embodiments, the cell is a prokaryotic cell.

In another aspect, the disclosure provides a cell, wherein the cell includes: a CRISPR-associated protein, wherein the CRISPR-associated protein includes an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to an amino acid sequence set forth in any one of SEQ ID NOs: 1-56; and an RNA guide including a direct repeat sequence and a spacer sequence capable of hybridizing to a target nucleic acid. In another aspect, the disclosure provides a cell, wherein the cell includes: a CRISPR-associated protein or a nucleic acid encoding the CRISPR-associated protein, wherein the CRISPR-associated protein includes an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to an amino acid sequence set forth in any one of SEQ ID NOs: 1-56; and an RNA guide including a direct repeat sequence and a spacer sequence capable of hybridizing to a target nucleic acid, or a nucleic acid encoding the RNA guide.

In some embodiments of any of the cells described herein, the CRISPR-associated protein includes at least one (e.g., one, two, or three) RuvC domain or at least one split RuvC domain.

In some embodiments of any of the cells described herein, the CRISPR-associated protein comprises one or more of the following sequences: (a) $PX_1X_2X_3X_4F$ (SEQ ID NO: 216), wherein $X_1$ is L or M or I or C or F, $X_2$ is Y or W or F, $X_3$ is K or T or C or R or W or Y or H or V, and $X_4$ is I or L or M; (b) $RX_1X_2X_3L$ (SEQ ID NO: 217), wherein $X_1$ is I or L or M or Y or T or F, $X_2$ is R or Q or K or E or S or T, and $X_3$ is L or I or T or C or M or K; (c) $NX_1YX_2$ (SEQ ID NO: 218), wherein $X_1$ is I or L or F and $X_2$ is K or R or V or E; (d) $KX_1X_2X_3FAX_4X_5KD$ (SEQ ID NO: 219), wherein $X_1$ is T or I or N or A or S or F or V, $X_2$ is I or V or L or S, $X_3$ is H or S or G or R, $X_4$ is D or S or E, and $X_5$ is I or V or M or T or N; (e) $LX_1NX_2$ (SEQ ID NO: 220), wherein $X_1$ is G or S or C or T and $X_2$ is N or Y or K or S; $PX_1X_2X_3X_4SQX_5DS$ (SEQ ID NO: 221), wherein $X_1$ is S or P or A, $X_2$ is Y or S or A or P or E or Y or Q or N, $X_3$ is F or Y or H, $X_4$ is T or S, and $X_5$ is M or T or I; (g) $KX_1X_2VRX_3X_4QEX_5H$ (SEQ ID NO: 222), wherein $X_1$ is N or K or W or R or E or T or Y, $X_2$ is M or R or L or S or K or V or E or T or I or D, $X_3$ is L or R or H or P or T or K or Q of P or S or A, $X_4$ is G or Q or N or R or K or E or I or T or S or C, and $X_5$ is R or W or Y or K or T or F or S or Q; and (h) $X_1NGX_2X_3X_4DX_5NX_6X_7X_8N$ (SEQ ID NO: 223), wherein $X_1$ is I or K or V or L, $X_2$ is L or M, $X_3$ is N or H or P, $X_4$ is A or S or C, $X_5$ is V or Y or I or F or T or N, $X_6$ is A or S, $X_7$ is S or A or P, and $X_8$ is M or C or L or R or N or S or K or L. In some embodiments of any of the cells described herein, the sequence of SEQ ID NO: 216 is an N-terminal sequence. In some embodiments of any of the cells described herein, the sequence of SEQ ID NO: 219 is a C-terminal sequence. In some embodiments of any of the cells described herein, the sequence of SEQ ID NO: 220 is a C-terminal sequence. In some embodiments of any of the cells described herein, the sequence of SEQ ID NO: 221 is a C-terminal sequence. In some embodiments of any of the cells described herein, the sequence of SEQ ID NO: 222 is a C-terminal sequence. In some embodiments of any of the cells described herein, the sequence of SEQ ID NO: 223 is a C-terminal sequence.

In some embodiments of any of the cells described herein, the direct repeat sequence includes a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to a nucleotide sequence set forth in any one of SEQ ID NOs: 57-90, SEQ ID NOs: 118-151, or SEQ ID NO: 213. In some embodiments of any of the cells described herein, the direct repeat sequence includes a nucleotide sequence that is at least 95% (e.g., 95%, 96%, 97%, 98%, 99% or 100%) identical to a nucleotide sequence set forth in any one of SEQ ID NOs: 57-90, SEQ ID NOs: 118-151, or SEQ ID NO: 213.

In some embodiments of any of the cells described herein, the direct repeat sequence comprises one or more of the following sequences: (a) $X_1X_2TX_3X_4X_5X_6X_7X_8$ (SEQ ID NO: 224), wherein $X_1$ is A or C or G, $X_2$ is T or C or A, $X_3$ is T or G or A, $X_4$ is T or G, $X_5$ is T or G or A, $X_6$ is G or T or A, $X_7$ is T or G or A, and $X_8$ is A or G or T (e.g., ATTGTTGDA (SEQ ID NO: 225)); (b) $X_1X_2X_3X_4X_5X_6X_7X_8X_9$ (SEQ ID NO: 226), wherein $X_1$ is T or C or A, $X_2$ is T or A or G, $X_3$ is T or C or A, $X_4$ is T or A, $X_5$ is T or A or G, $X_6$ is T or A, $X_7$ is A or T, $X_8$ is A or G or C or T, and $X_9$ is G or A or C (e.g., TTTTWTARG (SEQ ID NO: 227)); and (c) $X_1X_2X_3AC$ (SEQ ID NO: 228), wherein $X_1$ is A or C or G, $X_2$ is C or A, and $X_3$ is A or C (e.g., ACAAC (SEQ ID NO: 229)). In some embodiments of any of the cells described herein, SEQ ID NO: 224 is proximal to the 5' end of the direct repeat. In some embodiments of any of the cells described herein, SEQ ID NO: 228 is proximal to the 3' end of the direct repeat.

In some embodiments of any of the cells described herein, the CRISPR-associated protein is a protein having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identity to an amino acid sequence set forth in SEQ ID NO: 1, and wherein the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to a nucleotide sequence set forth in SEQ ID NO: 57. In some embodiments of any of the cells described herein, the CRISPR-associated protein is a protein having at least 95% (e.g., 95%, 96%, 97%, 98%, 99% or 100%) identity to an amino acid sequence set forth in SEQ ID NO: 1, and wherein the direct repeat sequence comprises a nucleotide sequence that is at least 95% (e.g., 95%, 96%, 97%, 98%, 99% or 100%) identical to a nucleotide sequence set forth in SEQ ID NO: 57. In some embodiments of any of the cells described herein, the CRISPR-associated protein is capable of recognizing a protospacer adjacent motif (PAM) sequence, wherein the PAM sequence comprises a nucleic acid sequence set forth as 5'-TNNT-3' or 5'-TNRT-3', wherein "N" is any nucleotide and "R" is A or G.

In some embodiments of any of the cells described herein, the CRISPR-associated protein is a protein having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identity to an amino acid sequence set forth in SEQ ID NO: 4, and wherein the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to a nucleotide sequence set forth in SEQ ID NO: 60. In some embodiments of any of the cells described herein, the CRISPR-associated protein is a protein having at least 95% (e.g., 95%, 96%, 97%, 98%, 99% or 100%) identity to an amino acid sequence set forth in SEQ ID NO: 4, and wherein the direct repeat sequence comprises a nucleotide sequence that is at least 95% (e.g., 95%, 96%, 97%, 98%, 99% or 100%) identical to a nucleotide sequence set forth in SEQ ID NO: 60. In some embodiments of any of the cells described herein, the CRISPR-associated protein is capable of recognizing a protospacer adjacent motif (PAM) sequence, wherein the PAM sequence comprises a nucleic acid sequence set forth as 5'-NTTN-3', 5'-NTTR-3' (e.g., 5'-TTTG-3'), or 5'-NNR-3', wherein "N" is any nucleotide and "R" is A or G.

In some embodiments of any of the cells described herein, the CRISPR-associated protein is a protein having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identity to an amino acid sequence set forth in SEQ ID NO: 10, and wherein the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to a nucleotide sequence set forth in SEQ ID NO: 62 or SEQ ID NO: 213. In some embodiments of any of the cells described herein, the CRISPR-associated protein is a protein having at least 95% (e.g., 95%, 96%, 97%, 98%, 99% or 100%) identity to an amino acid sequence set forth in SEQ ID NO: 10, and wherein the direct repeat sequence comprises a nucleotide sequence that is at least 95% (e.g., 95%, 96%, 97%, 98%, 99% or 100%) identical to a nucleotide sequence set forth in SEQ ID NO: 62 or SEQ ID NO: 213. In some embodiments of any of the cells described herein, the CRISPR-associated protein is capable of recognizing a protospacer adjacent motif (PAM) sequence, wherein the PAM sequence comprises a nucleic acid sequence set forth as 5'-NTTN-3' or 5'-RTTR-3' (e.g., 5'-ATTG-3' or 5'-GTTA-3'), wherein "N" is any nucleotide and "R" is A or G.

In some embodiments of any of the cells described herein, the spacer sequence includes between about 15 nucleotides to about 55 nucleotides. In some embodiments of any of the cells described herein, the spacer sequence includes between 20 and 45 nucleotides.

In some embodiments of any of the cells described herein, the CRISPR-associated protein comprises a catalytic residue (e.g., aspartic acid or glutamic acid). In some embodiments of any of the cells described herein, the CRISPR-associated protein cleaves the target nucleic acid. In some embodiments of any of the cells described herein, the CRISPR-associated protein further comprises a peptide tag, a fluorescent protein, a base-editing domain, a DNA methylation domain, a histone residue modification domain, a localization factor, a transcription modification factor, a light-gated control factor, a chemically inducible factor, or a chromatin visualization factor.

In some embodiments of any of the cells described herein, the nucleic acid encoding the CRISPR-associated protein is codon-optimized for expression in a cell, e.g., a eukaryotic cell, e.g., a mammalian cell, e.g., a human cell. In some embodiments of any of the cells described herein, the nucleic acid encoding the CRISPR-associated protein is operably linked to a promoter. In some embodiments of any of the cells described herein, the nucleic acid encoding the CRISPR-associated protein is in a vector. In some embodiments, the vector comprises a retroviral vector, a lentiviral vector, a phage vector, an adenoviral vector, an adeno-associated vector, or a herpes simplex vector.

In some embodiments of any of the cells described herein, the RNA guide optionally includes a tracrRNA and/or a modulator RNA. In some embodiments of any of the cells described herein, the cell further includes a tracrRNA. In some embodiments of any of the cells described herein, the cell does not include a tracrRNA. In some embodiments of any of the cells described herein, the CRISPR-associated protein is self-processing. In some embodiments of any of the cells described herein, the cell further includes a modulator RNA.

In some embodiments of any of the cells described herein, the cell is a eukaryotic cell. In some embodiments of any of the cells described herein, the cell is a mammalian cell. In some embodiments of any of the cells described herein, the cell is a human cell. In some embodiments of any of the cells described herein, the cell is a prokaryotic cell.

In some embodiments of any of the cells described herein, the target nucleic acid is a DNA molecule. In some embodiments of any of the cells described herein, the target nucleic acid includes a PAM sequence.

In some embodiments of any of the cells described herein, the CRISPR-associated protein has non-specific nuclease activity.

In some embodiments of any of the cells described herein, recognition of the target nucleic acid by the CRISPR-associated protein and RNA guide results in a modification of the target nucleic acid. In some embodiments of any of the cells described herein, the modification of the target nucleic acid is a double-stranded cleavage event. In some embodiments of any of the cells described herein, the modification of the target nucleic acid is a single-stranded cleavage event. In some embodiments of any of the cells described herein, the modification of the target nucleic acid results in an insertion event. In some embodiments of any of the cells described herein, the modification of the target nucleic acid results in a deletion event. In some embodiments of any of the cells described herein, the modification of the target nucleic acid results in cell toxicity or cell death.

In another aspect, the disclosure provides a method of binding a system described herein to a target nucleic acid in a cell comprising: (a) providing the system; and (b) delivering the system to the cell, wherein the cell comprises the target nucleic acid, wherein the CRISPR-associated protein binds to the RNA guide, and wherein the spacer sequence binds to the target nucleic acid. In some embodiments, the cell is a eukaryotic cell, e.g., a mammalian cell, e.g., a human cell.

In another aspect, the disclosure provides methods of modifying a target nucleic acid, the method including delivering to the target nucleic acid an engineered, non-naturally occurring CRISPR-Cas system including: a CRISPR-associated protein, wherein the CRISPR-associated protein includes an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%)

identical to an amino acid sequence set forth in any one of SEQ ID NOs: 1-56; and an RNA guide including a direct repeat sequence and a spacer sequence capable of hybridizing to the target nucleic acid; wherein the CRISPR-associated protein is capable of binding to the RNA guide; and wherein recognition of the target nucleic acid by the CRISPR-associated protein and RNA guide results in a modification of the target nucleic acid. In another aspect, the disclosure provides methods of modifying a target nucleic acid, the method including delivering to the target nucleic acid an engineered, non-naturally occurring CRISPR-Cas system including: a CRISPR-associated protein or a nucleic acid encoding the CRISPR-associated protein, wherein the CRISPR-associated protein includes an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to an amino acid sequence set forth in any one of SEQ ID NOs: 1-56; and an RNA guide including a direct repeat sequence and a spacer sequence capable of hybridizing to the target nucleic acid; wherein the CRISPR-associated protein is capable of binding to the RNA guide; and wherein recognition of the target nucleic acid by the CRISPR-associated protein and RNA guide results in a modification of the target nucleic acid.

In some embodiments of any of the methods described herein, the CRISPR-associated protein comprises one or more of the following sequences: (a) $PX_1X_2X_3X_4F$ (SEQ ID NO: 216), wherein $X_1$ is L or M or I or C or F, $X_2$ is Y or W or F, $X_3$ is K or T or C or R or W or Y or H or V, and $X_4$ is I or L or M; (b) $RX_1X_2X_3L$ (SEQ ID NO: 217), wherein $X_1$ is I or L or M or Y or T or F, $X_2$ is R or Q or K or E or S or T, and $X_3$ is L or I or T or C or M or K; (c) $NX_1YX_2$ (SEQ ID NO: 218), wherein $X_1$ is I or L or F and $X_2$ is K or R or V or E; (d) $KX_1X_2X_3FAX_4X_5KD$ (SEQ ID NO: 219), wherein $X_1$ is T or I or N or A or S or F or V, $X_2$ is I or V or L or S, $X_3$ is H or S or G or R, $X_4$ is D or S or E, and $X_5$ is I or V or M or T or N; (e) $LX_1NX_2$ (SEQ ID NO: 220), wherein $X_1$ is G or S or C or T and $X_2$ is N or Y or K or S; (f) $PX_1X_2X_3X_4SQX_5DS$ (SEQ ID NO: 221), wherein $X_1$ is S or P or A, $X_2$ is Y or S or A or P or E or Y or Q or N, $X_3$ is F or Y or H, $X_4$ is T or S, and $X_5$ is M or T or I; (g) $KX_1X_2VRX_3X_4QEX_5H$ (SEQ ID NO: 222), wherein $X_1$ is N or K or W or R or E or T or Y, $X_2$ is M or R or L or S or K or V or E or T or I or D, $X_3$ is L or R or H or P or T or K or Q of P or S or A, $X_4$ is G or Q or N or R or K or E or I or T or S or C, and $X_5$ is R or W or Y or K or T or F or S or Q; and (h) $X_1NGX_2X_3X_4DX_5NX_6X_7X_8N$ (SEQ ID NO: 223), wherein $X_1$ is I or K or V or L, $X_2$ is L or M, $X_3$ is N or H or P, $X_4$ is A or S or C, $X_5$ is V or Y or I or F or T or N, $X_6$ is A or S, $X_7$ is S or A or P, and $X_8$ is M or C or L or R or N or S or K or L. In some embodiments of any of the methods described herein, the sequence of SEQ ID NO: 216 is an N-terminal sequence. In some embodiments of any of the methods described herein, the sequence of SEQ ID NO: 219 is a C-terminal sequence. In some embodiments of any of the methods described herein, the sequence of SEQ ID NO: 220 is a C-terminal sequence. In some embodiments of any of the methods described herein, the sequence of SEQ ID NO: 221 is a C-terminal sequence. In some embodiments of any of the methods described herein, the sequence of SEQ ID NO: 222 is a C-terminal sequence. In some embodiments of any of the methods described herein, the sequence of SEQ ID NO: 223 is a C-terminal sequence.

In some embodiments of any of the methods described herein, the direct repeat sequence includes a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to a nucleotide sequence set forth in any one of SEQ ID NOs: 57-90, SEQ ID NOs: 118-151, or SEQ ID NO: 213. In some embodiments of any of the methods described herein, the direct repeat sequence includes a nucleotide sequence that is at least 95% (e.g., 95%, 96%, 97%, 98%, 99% or 100%) identical to a nucleotide sequence set forth in any one of SEQ ID NOs: 57-90, SEQ ID NOs: 118-151, or SEQ ID NO: 213.

In some embodiments of any of the methods described herein, the direct repeat sequence comprises one or more of the following sequences: (a) $X_1X_2TX_3X_4X_5X_6X_7X_8$ (SEQ ID NO: 224), wherein $X_1$ is A or C or G, $X_2$ is T or C or A, $X_3$ is T or G or A, $X_4$ is T or G, $X_5$ is T or G or A, $X_6$ is G or T or A, $X_7$ is T or G or A, and $X_8$ is A or G or T (e.g., ATTGTTGDA (SEQ ID NO: 225)); (b) $X_1X_2X_3X_4X_5X_6X_7X_8X_9$ (SEQ ID NO: 226), wherein $X_1$ is T or C or A, $X_2$ is T or A or G, $X_3$ is T or C or A, $X_4$ is T or A, $X_5$ is T or A or G, $X_6$ is T or A, $X_7$ is A or T, $X_8$ is A or G or C or T, and $X_9$ is G or A or C (e.g., TTTTWTARG (SEQ ID NO: 227)); and (c) $X_1X_2X_3AC$ (SEQ ID NO: 228), wherein $X_1$ is A or C or G, $X_2$ is C or A, and $X_3$ is A or C (e.g., ACAAC (SEQ ID NO: 229)). In some embodiments of any of the methods described herein, SEQ ID NO: 224 is proximal to the 5' end of the direct repeat. In some embodiments of any of the methods described herein, SEQ ID NO: 228 is proximal to the 3' end of the direct repeat.

In some embodiments of any of the methods described herein, the CRISPR-associated protein is a protein having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identity to an amino acid sequence set forth in SEQ ID NO: 1, and wherein the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to a nucleotide sequence set forth in SEQ ID NO: 57. In some embodiments of any of the methods described herein, the CRISPR-associated protein is a protein having at least 95% (e.g., 95%, 96%, 97%, 98%, 99% or 100%) identity to an amino acid sequence set forth in SEQ ID NO: 1, and wherein the direct repeat sequence comprises a nucleotide sequence that is at least 95% (e.g., 95%, 96%, 97%, 98%, 99% or 100%) identical to a nucleotide sequence set forth in SEQ ID NO: 57. In some embodiments of any of the methods described herein, the CRISPR-associated protein is capable of recognizing a protospacer adjacent motif (PAM) sequence, wherein the PAM sequence comprises a nucleic acid sequence set forth as 5'-TNNT-3' or 5'-TNRT-3', wherein "N" is any nucleotide and "R" is A or G.

In some embodiments of any of the methods described herein, the CRISPR-associated protein is a protein having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identity to an amino acid sequence set forth in SEQ ID NO: 4, and wherein the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to a nucleotide sequence set forth in SEQ ID NO: 60. In some embodiments of any of the methods described herein, the CRISPR-associated protein is a protein having at least 95% (e.g., 95%, 96%, 97%, 98%, 99% or 100%) identity to an amino acid sequence set forth in SEQ ID NO: 4, and wherein the direct repeat sequence comprises a nucleotide sequence that is at least 95% (e.g., 95%, 96%, 97%, 98%, 99% or 100%) identical to a nucleotide sequence set forth in SEQ ID NO: 60. In some embodiments of any of the methods described herein, the CRISPR-associated protein is capable of recognizing a protospacer adjacent motif (PAM) sequence, wherein the PAM sequence comprises a nucleic acid sequence set forth as 5'-NTTN-3', 5'-NTTR-3' (e.g., 5'-TTTG-3'), or 5'-NNR-3', wherein "N" is any nucleotide and "R" is A or G.

In some embodiments of any of the methods described herein, the CRISPR-associated protein is a protein having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identity to an amino acid sequence set forth in SEQ ID NO: 10, and wherein the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to a nucleotide sequence set forth in SEQ ID NO: 62 or SEQ ID NO: 213. In some embodiments of any of the methods described herein, the CRISPR-associated protein is a protein having at least 95% (e.g., 95%, 96%, 97%, 98%, 99% or 100%) identity to an amino acid sequence set forth in SEQ ID NO: 10, and wherein the direct repeat sequence comprises a nucleotide sequence that is at least 95% (e.g., 95%, 96%, 97%, 98%, 99% or 100%) identical to a nucleotide sequence set forth in SEQ ID NO: 62 or SEQ ID NO: 213. In some embodiments of any of the methods described herein, the CRISPR-associated protein is capable of recognizing a protospacer adjacent motif (PAM) sequence, wherein the PAM sequence comprises a nucleic acid sequence set forth as 5'-NTTN-3' or 5'-RTTR-3' (e.g., 5'-ATTG-3' or 5'-GTTA-3'), wherein "N" is any nucleotide and "R" is A or G.

In some embodiments of any of the methods described herein, the spacer sequence includes between about 15 nucleotides to about 55 nucleotides. In some embodiments of any of the methods described herein, the spacer sequence includes between 20 and 45 nucleotides.

In some embodiments of any of the methods described herein, the RNA guide optionally includes a tracrRNA and/or a modulator RNA. In some embodiments of any of the methods described herein, the system further includes a tracrRNA. In some embodiments of any of the methods described herein, the system does not include a tracrRNA. In some embodiments of any of the methods described herein, the CRISPR-associated protein is self-processing. In some embodiments of any of the methods described herein, the system further includes a modulator RNA.

In some embodiments of any of the methods described herein, the target nucleic acid is a DNA molecule. In some embodiments of any of the methods described herein, the target nucleic acid includes a PAM sequence.

In some embodiments of any of the methods described herein, the CRISPR-associated protein has non-specific nuclease activity.

In some embodiments of any of the methods described herein, the modification of the target nucleic acid is a double-stranded cleavage event. In some embodiments of any of the methods described herein, the modification of the target nucleic acid is a single-stranded cleavage event. In some embodiments of any of the methods described herein, the modification of the target nucleic acid results in an insertion event. In some embodiments of any of the methods described herein, the modification of the target nucleic acid results in a deletion event. In some embodiments of any of the methods described herein, the modification of the target nucleic acid results in cell toxicity or cell death.

In another aspect, the disclosure provides a method of editing a target nucleic acid, the method comprising contacting the target nucleic acid with a system described herein. In another aspect, the disclosure provides a method of modifying expression of a target nucleic acid, the method comprising contacting the target nucleic acid with a system described herein. In another aspect, the disclosure provides a method of targeting the insertion of a payload nucleic acid at a site of a target nucleic acid, the method comprising contacting the target nucleic acid with a system described herein. In another aspect, the disclosure provides a method of targeting the excision of a payload nucleic acid from a site at a target nucleic acid, the method comprising contacting the target nucleic acid with a system described herein. In another aspect, the disclosure provides a method of non-specifically degrading single-stranded DNA upon recognition of a DNA target nucleic acid, the method comprising contacting the target nucleic acid with a system described herein.

In some embodiments of any of the systems or methods provided herein, the contacting comprises directly contacting or indirectly contacting. In some embodiments of any of the systems or methods provided herein, contacting indirectly comprises administering one or more nucleic acids encoding an RNA guide or CRISPR-associated protein described herein under conditions that allow for production of the RNA guide and/or CRISPR-related protein. In some embodiments of any of the systems or methods provided herein, contacting includes contacting in vivo or contacting in vitro. In some embodiments of any of the systems or methods provided herein, contacting a target nucleic acid with the system comprises contacting a cell comprising the nucleic acid with the system under conditions that allow the CRISPR-related protein and guide RNA to reach the target nucleic acid. In some embodiments of any of the systems or methods provided herein, contacting a cell in vivo with the system comprises administering the system to the subject that comprises the cell, under conditions that allow the CRISPR-related protein and guide RNA to reach the cell or be produced in the cell.

In another aspect, the disclosure provides a system provided herein for use in an in vitro or ex vivo method of: (a) targeting and editing a target nucleic acid; (b) non-specifically degrading a single-stranded nucleic acid upon recognition of the nucleic acid; (c) targeting and nicking a non-spacer complementary strand of a double-stranded target upon recognition of a spacer complementary strand of the double-stranded target; (d) targeting and cleaving a double-stranded target nucleic acid; (e) detecting a target nucleic acid in a sample; (f) specifically editing a double-stranded nucleic acid; (g) base editing a double-stranded nucleic acid; (h) inducing genotype-specific or transcriptional-state-specific cell death or dormancy in a cell; (i) creating an indel in a double-stranded nucleic acid target; (j) inserting a sequence into a double-stranded nucleic acid target; or (k) deleting or inverting a sequence in a double-stranded nucleic acid target.

In another aspect, the disclosure provides method of introducing an insertion or deletion into a target nucleic acid in a mammalian cell, comprising a transfection of: (a) a nucleic acid sequence encoding a CRISPR-associated protein, wherein the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to an amino acid sequence set forth in any one of SEQ ID NOs: 1-56; and (b) an RNA guide (or a nucleic acid encoding the RNA guide) comprising a direct repeat sequence and a spacer sequence capable of hybridizing to the target nucleic acid; wherein the CRISPR-associated protein is capable of binding to the RNA guide; and wherein recognition of the target nucleic acid by the CRISPR-associated protein and RNA guide results in a modification of the target nucleic acid.

In some embodiments of any of the methods provided herein, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to an amino acid sequence set forth in SEQ ID NO: 4. In some embodiments of any of the methods provided herein, the CRISPR-associated protein comprises an amino acid sequence that is at least 95% (e.g., 95%, 96%, 97%, 98%, 99% or 100%) identical to an amino acid sequence set forth in SEQ ID NO: 4. In some embodiments of any of the methods provided herein, the direct repeat comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to a nucleotide sequence set forth in SEQ ID NO: 60. In some embodiments of any of the methods provided herein, wherein the direct repeat comprises a nucleotide sequence that is at least 95% (e.g., 95%, 96%, 97%, 98%, 99% or 100%) identical to a nucleotide sequence set forth in SEQ ID NO: 60. In some embodiments of any of the methods provided herein, the target nucleic acid is adjacent to a PAM sequence, and the PAM sequence comprises a nucleic acid sequence set forth as 5'-NTTN-3', 5'-NTTR-3' (e.g., 5'-TTTG-3'), or 5'-NNR-3', wherein "N" is any nucleotide and "R" is A or G.

In some embodiments of any of the methods provided herein, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to an amino acid sequence set forth in SEQ ID NO: 10. In some embodiments of any of the methods provided herein, the CRISPR-associated protein comprises an amino acid sequence that is at least 95% (e.g., 95%, 96%, 97%, 98%, 99% or 100%) identical to an amino acid sequence set forth in SEQ ID NO: 10. In some embodiments of any of the methods provided herein, the direct repeat comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to a nucleotide sequence set forth in SEQ ID NO: 62 or SEQ ID NO: 213. In some embodiments of any of the methods provided herein, wherein the direct repeat comprises a nucleotide sequence that is at least 95% (e.g., 95%, 96%, 97%, 98%, 99% or 100%) identical to a nucleotide sequence set forth in SEQ ID NO: 62 or SEQ ID NO: 213. In some embodiments of any of the methods provided herein, the target nucleic acid is adjacent to a PAM sequence, and the PAM sequence comprises a nucleic acid sequence set forth as 5'-NTTN-3' or 5'-RTTR-3' (e.g., 5'-ATTG-3' or 5'-GTTA-3'), wherein "N" is any nucleotide and "R" is A or G.

In some embodiments of any of the methods provided herein, the transfection is a transient transfection. In some embodiments of any of the methods provided herein, the cell is a human cell.

In another aspect, the disclosure provides a composition comprising: (a) a CRISPR-associated protein or a nucleic acid encoding the CRISPR-associated protein, and (b) an RNA guide comprising a direct repeat sequence and a spacer sequence; wherein the CRISPR-associated protein comprises one or more of the following amino acid sequences: (i) $PX_1X_2X_3X_4F$ (SEQ ID NO: 216), wherein $X_1$ is L or M or I or C or F, $X_2$ is Y or W or F, $X_3$ is K or T or C or R or W or Y or H or V, and $X_4$ is I or L or M; (ii) $RX_1X_2X_3L$ (SEQ ID NO: 217), wherein $X_1$ is I or L or M or Y or T or F, $X_2$ is R or Q or K or E or S or T, and $X_3$ is L or I or T or C or M or K; (iii) $NX_1YX_2$ (SEQ ID NO: 218), wherein $X_1$ is I or L or F and $X_2$ is K or R or V or E; (iv) $KX_1X_2X_3FAX_4X_5KD$ (SEQ ID NO: 219), wherein $X_1$ is T or I or N or A or S or F or V, $X_2$ is I or V or L or S, $X_3$ is H or S or G or R, $X_4$ is D or S or E, and $X_5$ is I or V or M or T or N; (v) $LX_1NX_2$ (SEQ ID NO: 220), wherein $X_1$ is G or S or C or T and $X_2$ is N or Y or K or S; (vi) $PX_1X_2X_3X_4SQX_5DS$ (SEQ ID NO: 221), wherein $X_1$ is S or P or A, $X_2$ is Y or S or A or P or E or Y or Q or N, $X_3$ is F or Y or H, $X_4$ is T or S, and $X_5$ is M or T or I; (vii) $KX_1X_2VRX_3X_4QEX_5H$ (SEQ ID NO: 222), wherein $X_1$ is N or K or W or R or E or T or Y, $X_2$ is M or R or L or S or K or V or E or T or I or D, $X_3$ is L or R or H or P or T or K or Q of P or S or A, $X_4$ is G or Q or N or R or K or E or I or T or S or C, and $X_5$ is R or W or Y or K or T or F or S or Q; and (viii) $X_1NGX_2X_3X_4DX_5NX_6X_7X_8N$ (SEQ ID NO: 223), wherein $X_1$ is I or K or V or L, $X_2$ is L or M, $X_3$ is N or H or P, $X_4$ is A or S or C, $X_5$ is V or Y or I or F or T or N, $X_6$ is A or S, $X_7$ is S or A or P, and $X_8$ is M or C or L or R or N or S or K or L; and wherein the CRISPR-associated protein is capable of binding to the RNA guide and of modifying the target nucleic acid sequence complementary to the spacer sequence.

In some embodiments of any of the compositions described herein, the direct repeat sequence comprises one or more of the following sequences: (a) $X_1X_2TX_3X_4X_5X_6X_7X_8$ (SEQ ID NO: 224), wherein $X_1$ is A or C or G, $X_2$ is T or C or A, $X_3$ is T or G or A, $X_4$ is T or G, $X_5$ is T or G or A, $X_6$ is G or T or A, $X_7$ is T or G or A, and $X_8$ is A or G or T (e.g., ATTGTTGDA (SEQ ID NO: 225)); (b) $X_1X_2X_3X_4X_5X_6X_7X_8X_9$ (SEQ ID NO: 226), wherein $X_1$ is T or C or A, $X_2$ is T or A or G, $X_3$ is T or C or A, $X_4$ is T or A, $X_5$ is T or A or G, $X_6$ is T or A, $X_7$ is A or T, $X_8$ is A or G or C or T, and $X_9$ is G or A or C (e.g., TTTTWTARG (SEQ ID NO: 227)); and (c) $X_1X_2X_3AC$ (SEQ ID NO: 228), wherein $X_1$ is A or C or G, $X_2$ is C or A, and $X_3$ is A or C (e.g., ACAAC (SEQ ID NO: 229)). In some embodiments of any of the compositions described herein, SEQ ID NO: 224 is proximal to the 5' end of the direct repeat. In some embodiments of any of the compositions described herein, SEQ ID NO: 228 is proximal to the 3' end of the direct repeat.

In some embodiments of any of the compositions described herein, the CRISPR-associated protein includes at least one (e.g., one, two, or three) RuvC domain or at least one split RuvC domain.

In some embodiments of any of the compositions described herein, the spacer sequence of the RNA guide includes between about 15 nucleotides to about 55 nucleotides. In some embodiments of any of the compositions described herein, the spacer sequence of the RNA guide includes between 20 and 45 nucleotides.

In some embodiments of any of the compositions described herein, the CRISPR-associated protein comprises a catalytic residue (e.g., aspartic acid or glutamic acid). In some embodiments of any of the compositions described herein, the CRISPR-associated protein cleaves the target nucleic acid. In some embodiments of any of the compositions described herein, the CRISPR-associated protein further comprises a peptide tag, a fluorescent protein, a base-editing domain, a DNA methylation domain, a histone residue modification domain, a localization factor, a transcription modification factor, a light-gated control factor, a chemically inducible factor, or a chromatin visualization factor.

In some embodiments of any of the compositions described herein, the nucleic acid encoding the CRISPR-associated protein is codon-optimized for expression in a cell, e.g., a eukaryotic cell, e.g., a mammalian cell, e.g., a human cell. In some embodiments of any of the compositions described herein, the nucleic acid encoding the CRISPR-associated protein is operably linked to a promoter. In some embodiments of any of the compositions described herein, the nucleic acid encoding the CRISPR-associated protein is in a vector. In some embodiments, the vector comprises a retroviral vector, a lentiviral vector, a phage vector, an adenoviral vector, an adeno-associated vector, or a herpes simplex vector.

In some embodiments of any of the compositions described herein, the target nucleic acid is a DNA molecule. In some embodiments of any of the compositions described herein, the target nucleic acid includes a PAM sequence.

In some embodiments of any of the compositions described herein, the CRISPR-associated protein has non-specific nuclease activity.

In some embodiments of any of the compositions described herein, recognition of the target nucleic acid by the CRISPR-associated protein and RNA guide results in a modification of the target nucleic acid. In some embodiments of any of the compositions described herein, the modification of the target nucleic acid is a double-stranded cleavage event. In some embodiments of any of the compositions described herein, the modification of the target nucleic acid is a single-stranded cleavage event. In some embodiments of any of the compositions described herein, the modification of the target nucleic acid results in an insertion event. In some embodiments of any of the compositions described herein, the modification of the target nucleic acid results in a deletion event. In some embodiments of any of the compositions described herein, the modification of the target nucleic acid results in cell toxicity or cell death.

In some embodiments of any of the compositions described herein, the system further includes a donor template nucleic acid. In some embodiments of any of the compositions described herein, the donor template nucleic acid is a DNA molecule. In some embodiments of any of the compositions described herein, wherein the donor template nucleic acid is an RNA molecule.

In some embodiments of any of the compositions described herein, the RNA guide optionally includes a tracrRNA. In some embodiments of any of the compositions described herein, the system further includes a tracrRNA. In some embodiments of any of the compositions described herein, the system does not include a tracrRNA. In some embodiments of any of the compositions described herein, the CRISPR-associated protein is self-processing.

In some embodiments of any of the compositions described herein, the system is present in a delivery composition comprising a nanoparticle, a liposome, an exosome, a microvesicle, or a gene-gun.

In some embodiments of any of the compositions described herein, the compositions are within a cell. In some embodiments, the cell is a eukaryotic cell. In some embodiments, the cell is a mammalian cell. In some embodiments, the cell is a human cell. In some embodiments, the cell is a prokaryotic cell.

The effectors described herein provide additional features that include, but are not limited to, 1) novel nucleic acid editing properties and control mechanisms, 2) smaller size for greater versatility in delivery strategies, 3) genotype triggered cellular processes such as cell death, and 4) programmable RNA-guided DNA insertion, excision, and mobilization, and 5) differentiated profile of pre-existing immunity through a non-human commensal source. See, e.g., Examples 1, 4, and 5 and FIGS. 1-3 and 5-11D. Addition of the novel DNA-targeting systems described herein to the toolbox of techniques for genome and epigenome manipulation enables broad applications for specific, programmed perturbations.

Other features and advantages of the invention will be apparent from the following detailed description and from the claims.

BRIEF FIGURE DESCRIPTION

The figures are a series of schematics that represent the results of analysis of a protein cluster referred to as CLUST.091979.

Figure 1H:
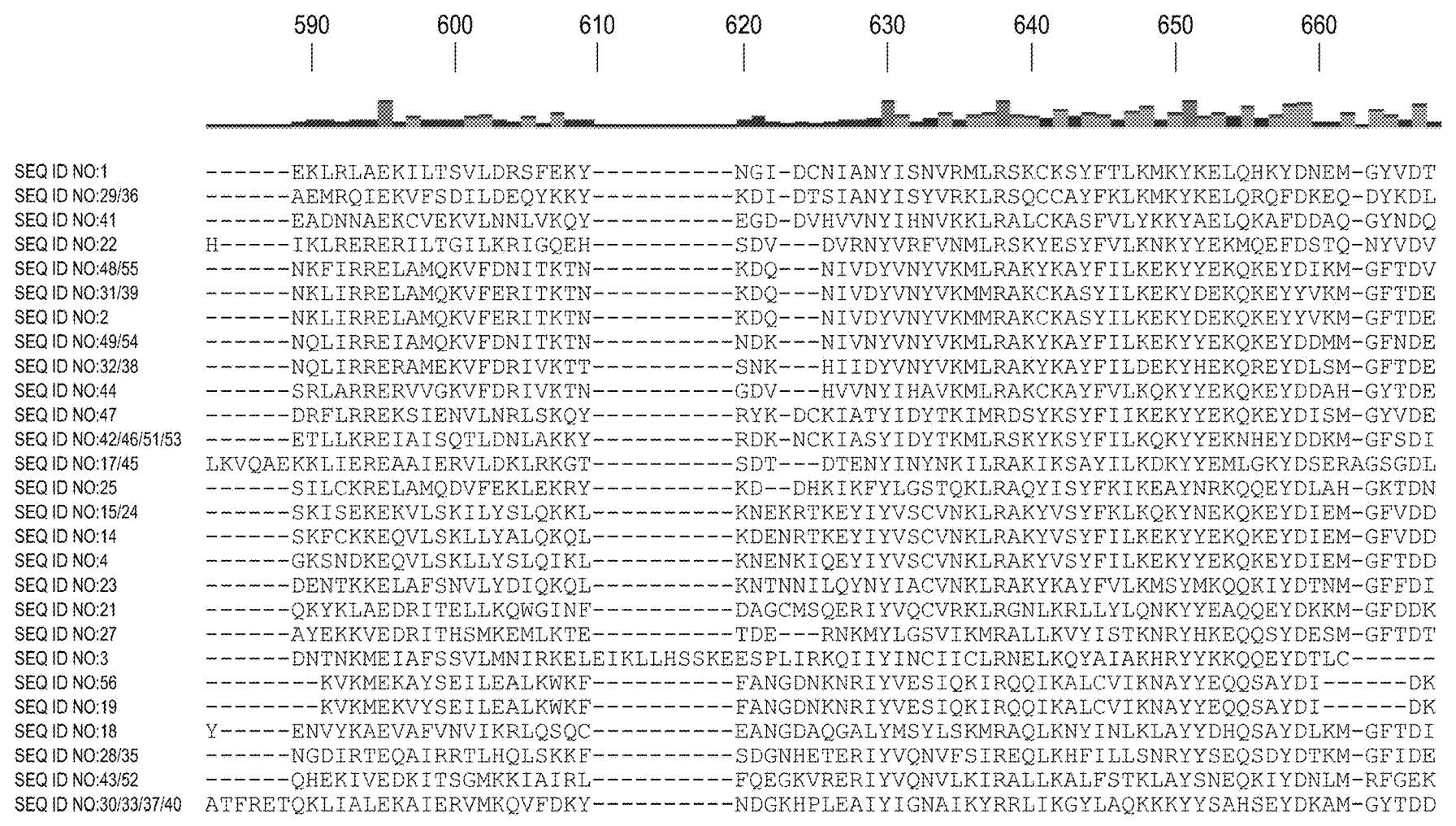

FIG. 1A, FIG. 1B, FIG. 1C, FIG. 1D, FIG. 1E, FIG. 1F, FIG. 1G, FIG. 1H, FIG. 1I, FIG. 1J, FIG. 1K, and FIG. 1L collectively show an alignment of the effectors of SEQ ID NOs: 1-4, 14, 15, 17-19, 21-25, 27-33, 35-49, 51-56.

Figure 4A:
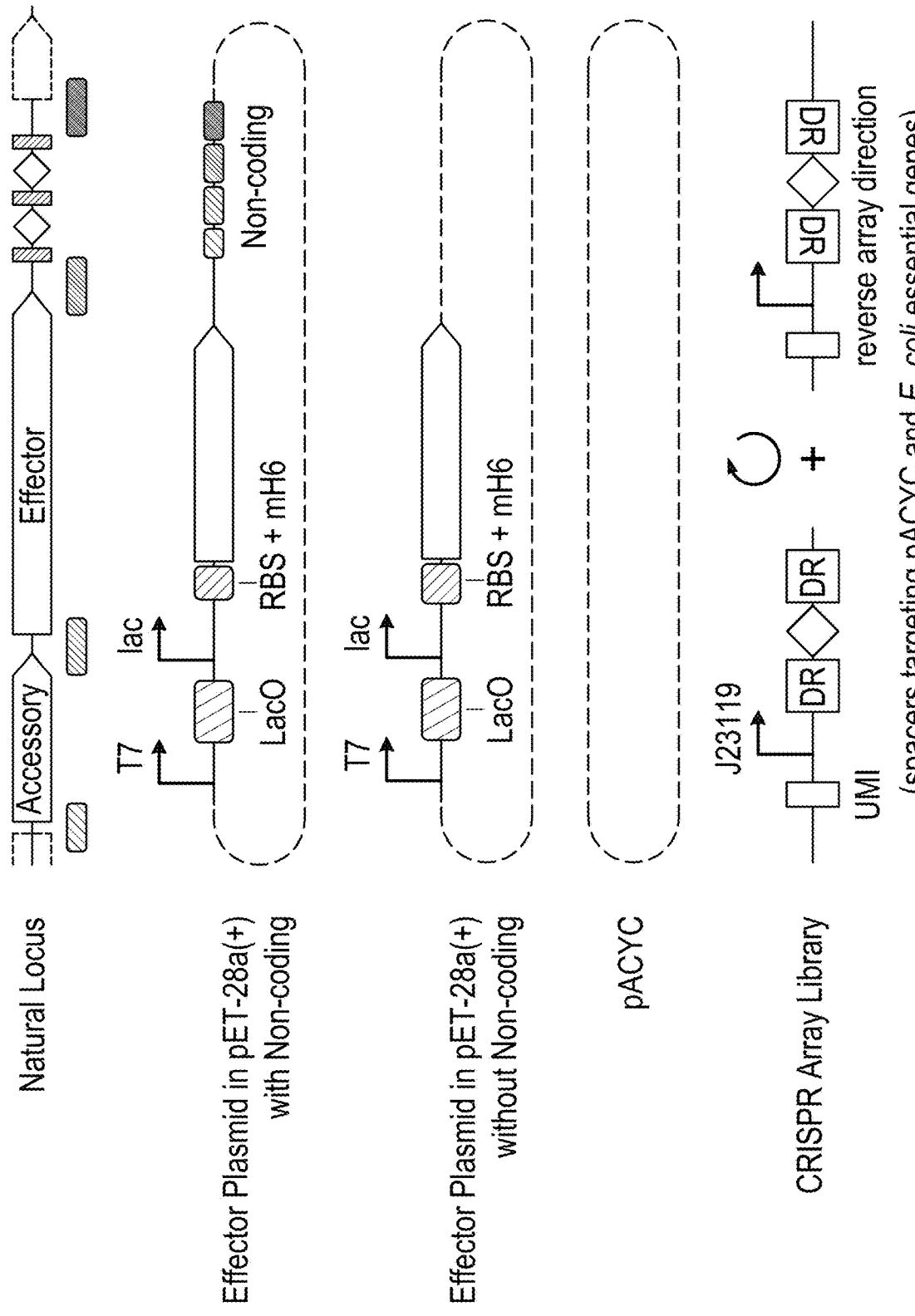
FIG. 4A is a schematic representation of the components of the in vivo negative selection screening assay described in Example 4. CRISPR array libraries were designed including non-representative spacers uniformly sampled from both strands of the pACYC184 or E. coli essential genes flanked by two DRs and expressed by J23119.
Figure 4B:
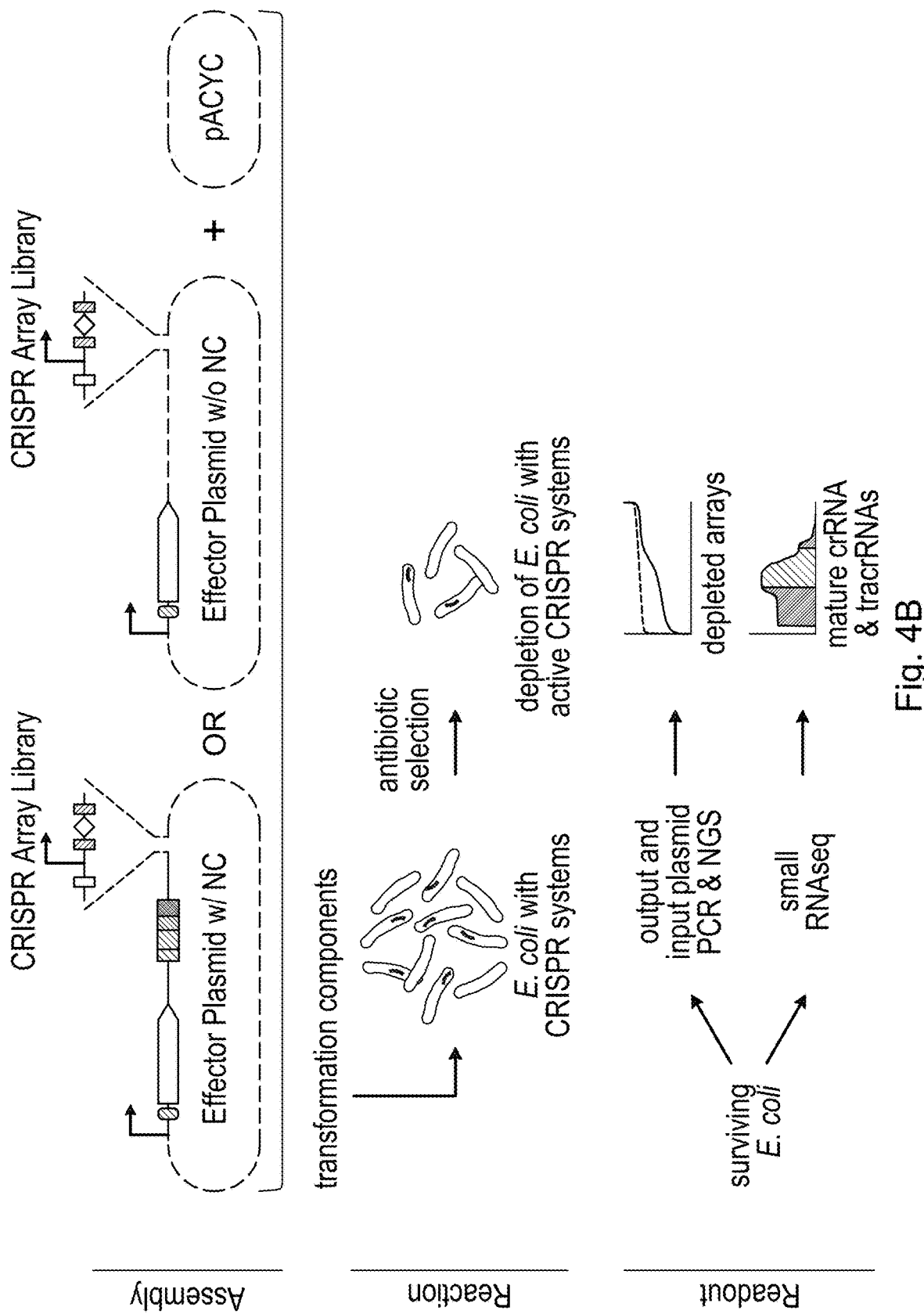

FIG. 4B is a schematic representation of the in vivo negative selection screening workflow described in Example 4. CRISPR array libraries were cloned into the effector plasmid. The effector plasmid and the non-coding plasmid were transformed into E. coli followed by outgrowth for negative selection of CRISPR arrays conferring interference against transcripts from pACYC184 or E. coli essential genes. Targeted sequencing of the effector plasmid was used to identify depleted CRISPR arrays Small RNAseq was further performed to identify mature crRNAs and potential tracrRNA requirements.

Figure 5:
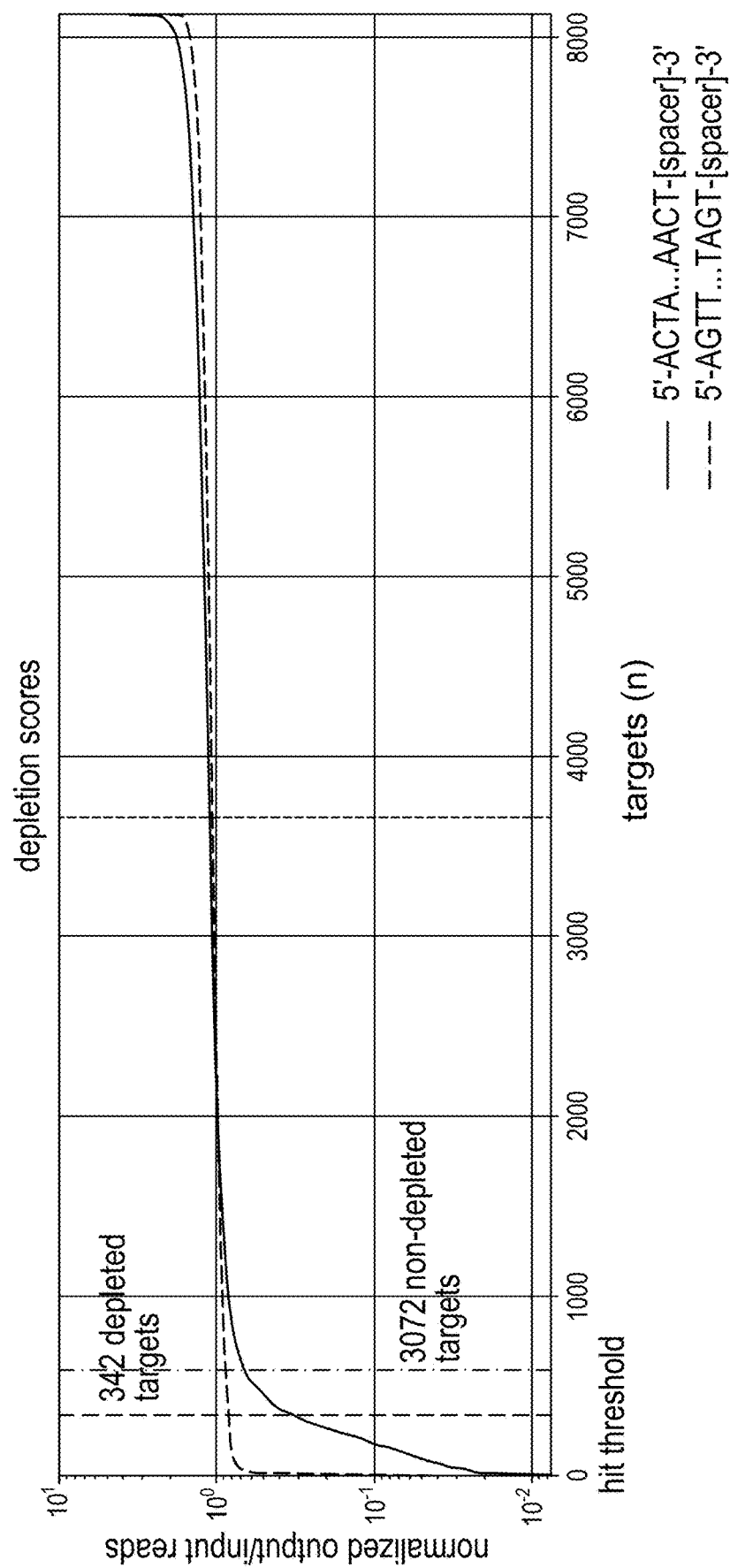

FIG. 5 is a graph for CLUST.091979 AUXO013988882 (effector set forth in SEQ ID NO: 1) showing the degree of depletion activity of the engineered compositions for spacers targeting pACYC184 and direct repeat transcriptional orientations, with a non-coding sequence. The degree of depletion with the direct repeat in the "forward" orientation (5'-ACTA . . . AACT-[spacer]-3') and with the direct repeat in the "reverse" orientation (5 AGTT . . . TAGT-[spacer]-3') are depicted.

Figure 6A:
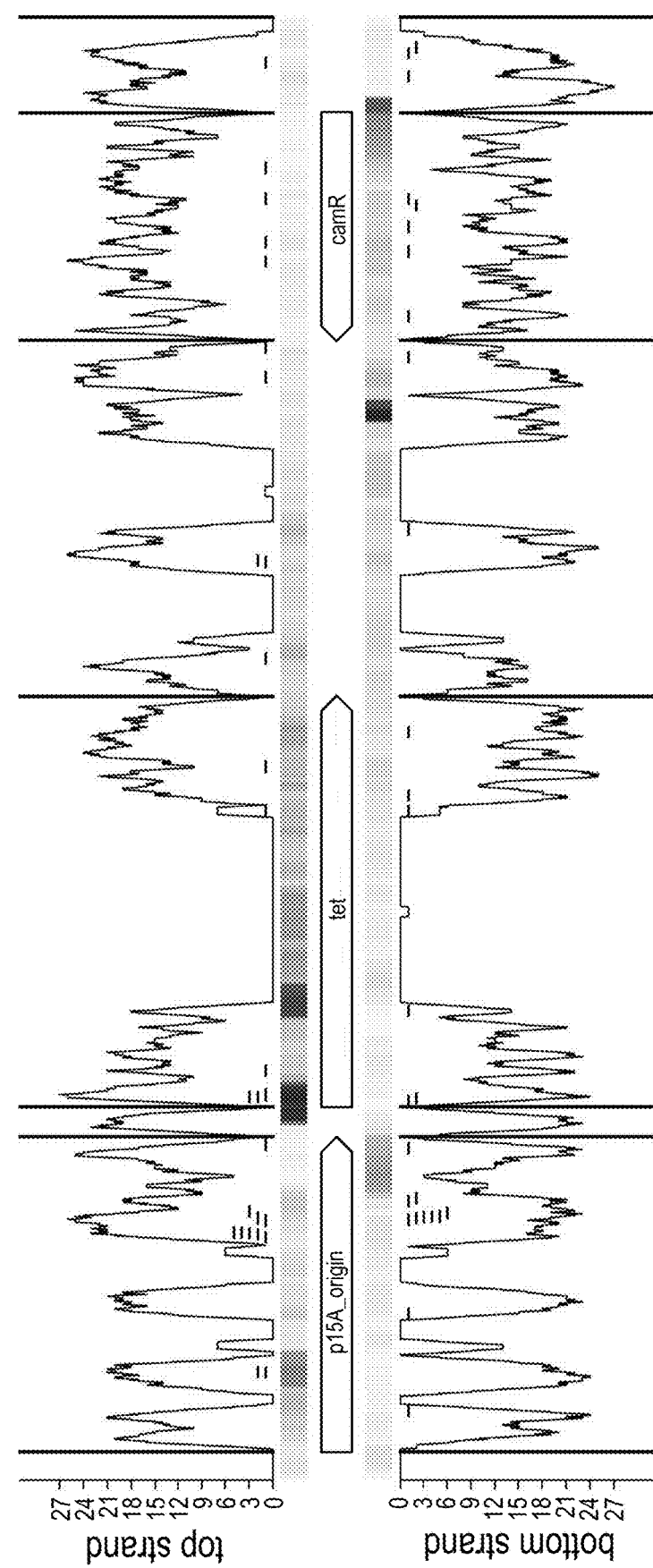
Figure 6B:
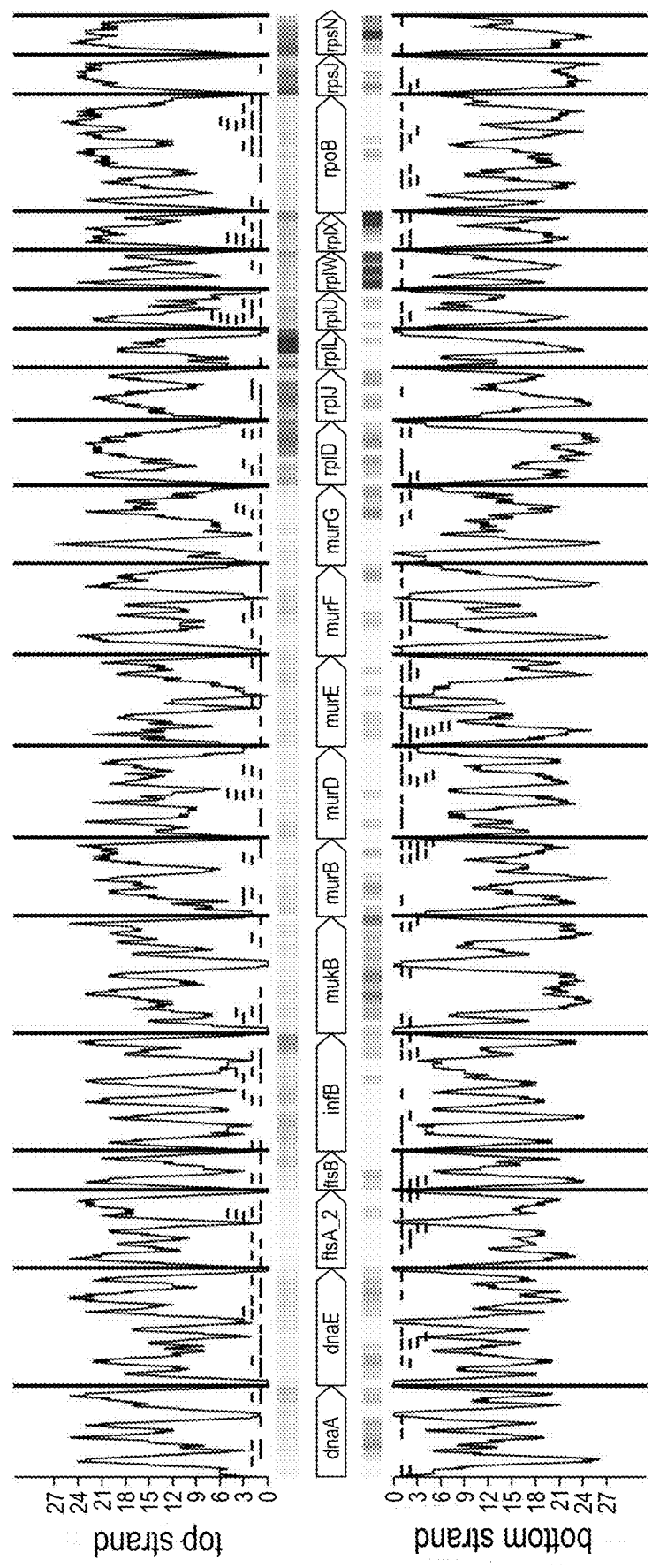

FIG. 6A is a graphical representation showing the density of depleted and non-depleted targets for CLUST.091979 AUXO013988882, with a non-coding sequence, by location on the pACYC184 plasmid. FIG. 6B is a graphic representation showing the density of depleted and non-depleted targets for CLUST.091979 AUXO013988882, with a non-coding sequence, by location on the *E. coli* strain, E. Cloni. Targets on the top strand and bottom strand are shown separately and in relation to the orientation of the annotated genes. The magnitude of the bands indicates the degree of depletion, wherein the lighter bands are close to the hit threshold of 3. The gradients are heatmaps of RNA sequencing showing relative transcript abundance.

Figure 7:
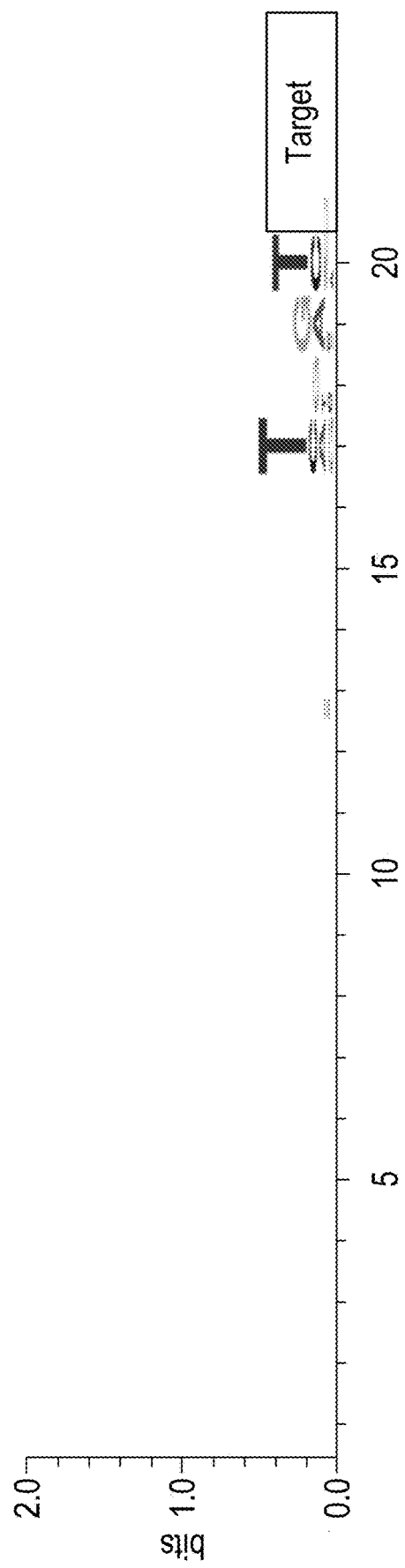

FIG. 7 is a WebLogo of the sequences flanking depleted targets in E. Cloni as a prediction of the PAM sequence for CLUST.091979 AUXO013988882 (with a non-coding sequence).

Figure 8:
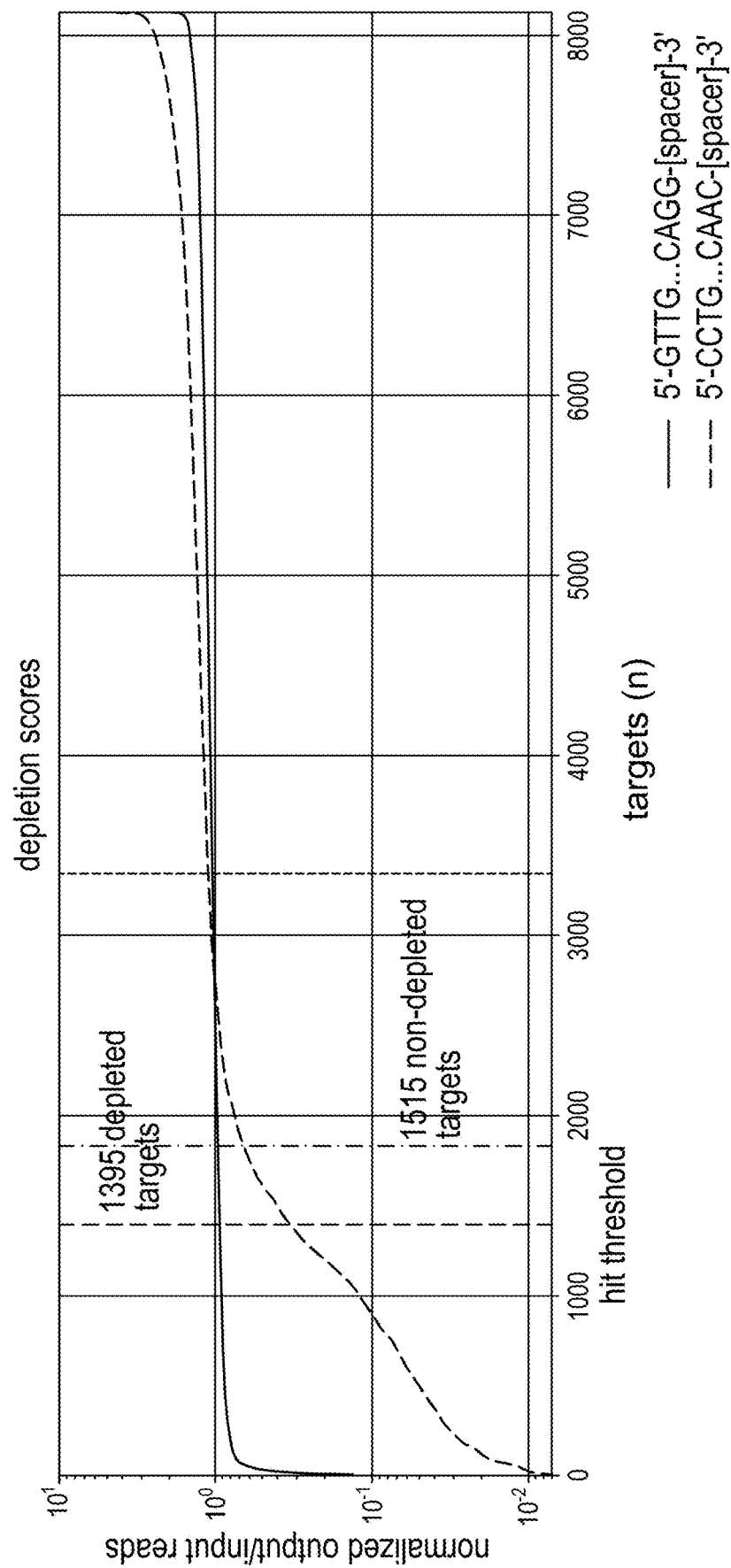

FIG. 8 is a graph for CLUST.091979 SRR3181151 (effector set forth in SEQ ID NO: 4) showing the degree of depletion activity of the engineered compositions for spacers targeting pACYC184 and direct repeat transcriptional orientations, with a non-coding sequence. The degree of depletion with the direct repeat in the "forward" orientation (5'-GTTG . . . CAGG-[spacer]-3') and with the direct repeat in the "reverse" orientation (5'-CCTG . . . CAAC-[spacer]-3') are depicted.

Figure 9A:
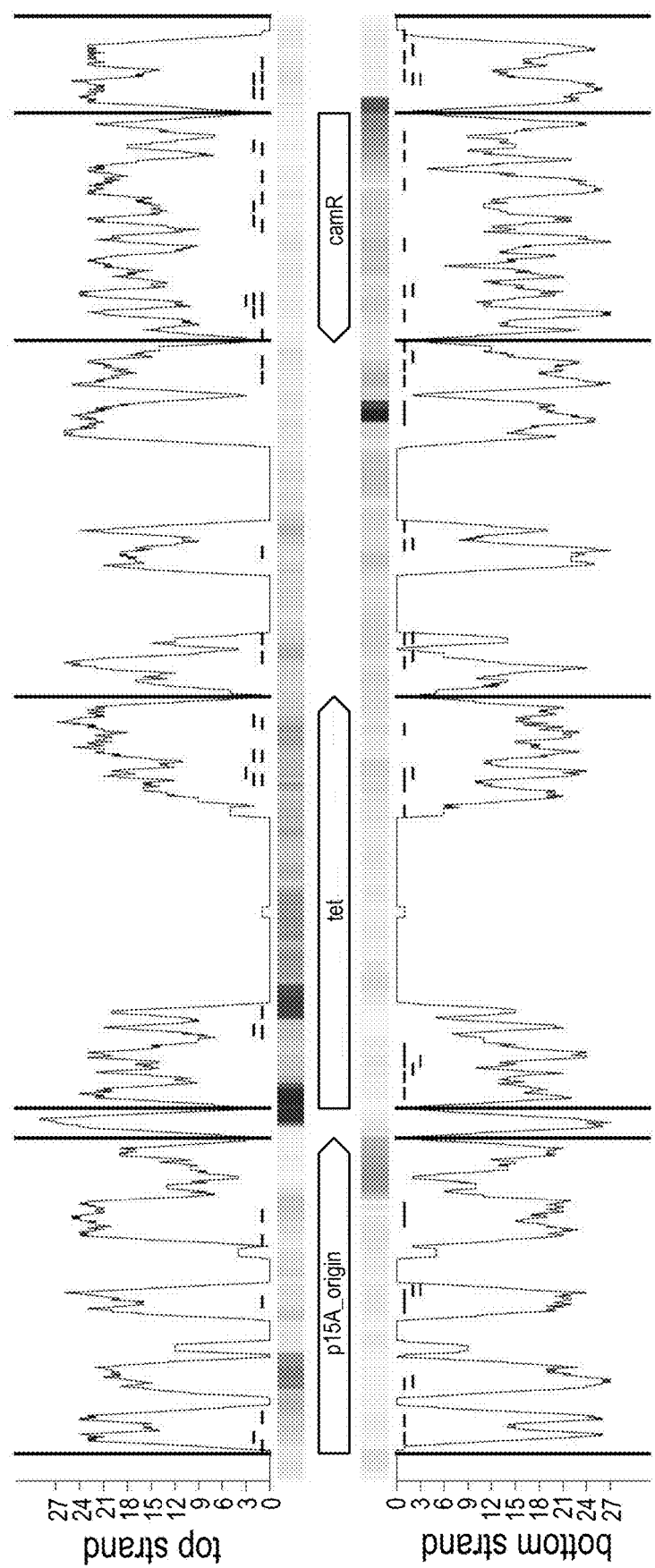
Figure 9B:
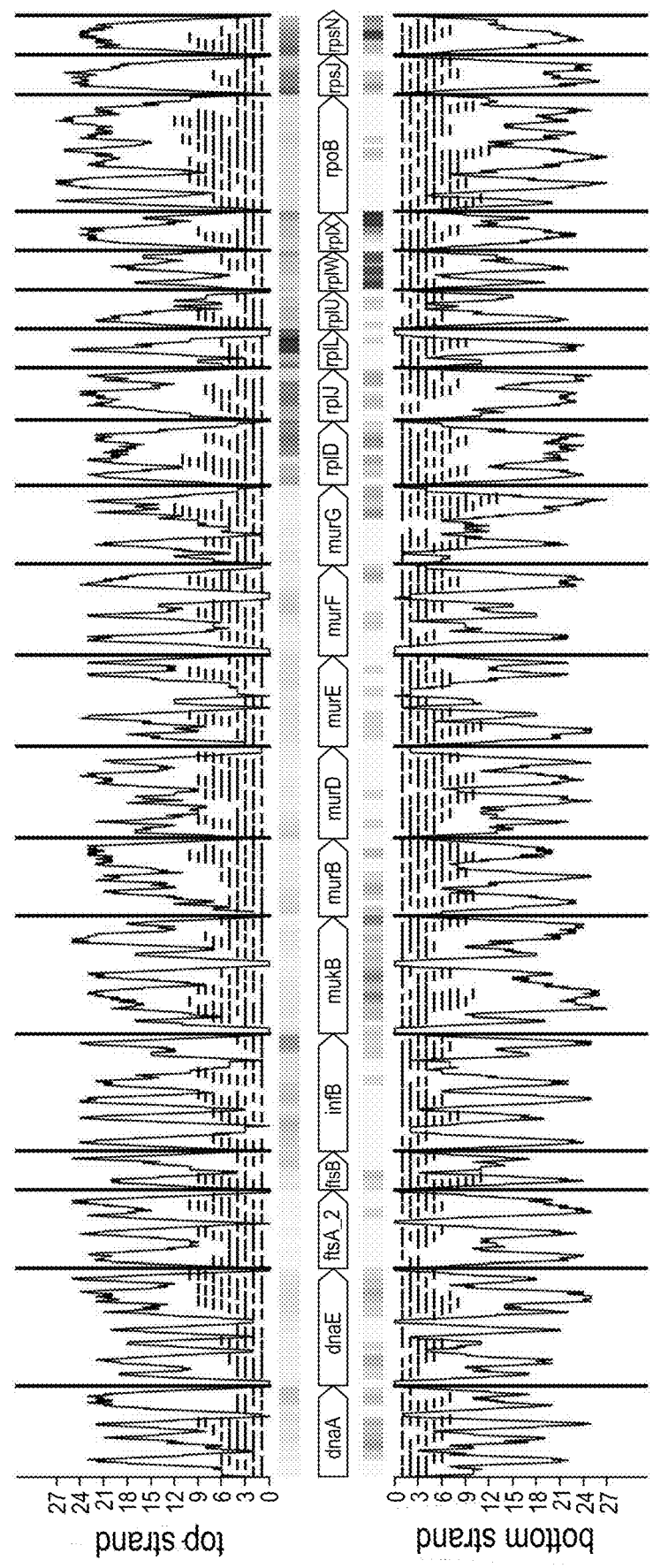

FIG. 9A is a graphical representation showing the density of depleted and non-depleted targets for CLUST.091979 SRR3181151, with a non-coding sequence, by location on the pACYC184 plasmid. FIG. 9B is a graphic representation showing the density of depleted and non-depleted targets for CLUST.091979 SRR3181151, with a non-coding sequence, by location on the *E. coli* strain, E. Cloni. Targets on the top strand and bottom strand are shown separately and in relation to the orientation of the annotated genes. The magnitude of the bands indicates the degree of depletion, wherein the lighter bands are close to the hit threshold of 3. The gradients are heatmaps of RNA sequencing showing relative transcript abundance.

Figure 10:
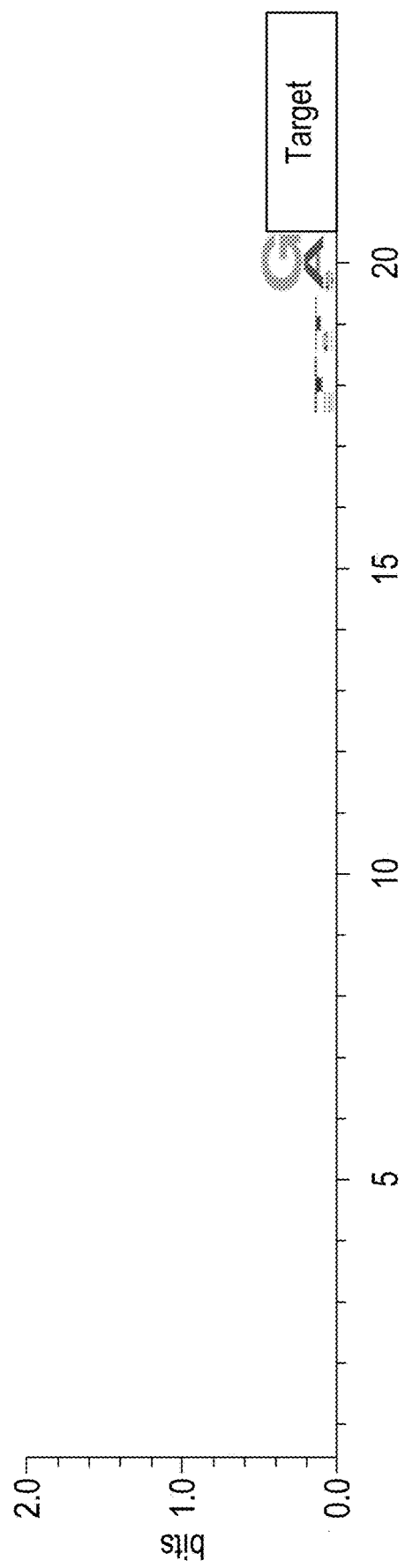

FIG. 10 is a WebLogo of the sequences flanking depleted targets in E. Cloni as a prediction of the PAM sequence for CLUST.091979 SRR3181151 (with a non-coding sequence).

Figure 11A:
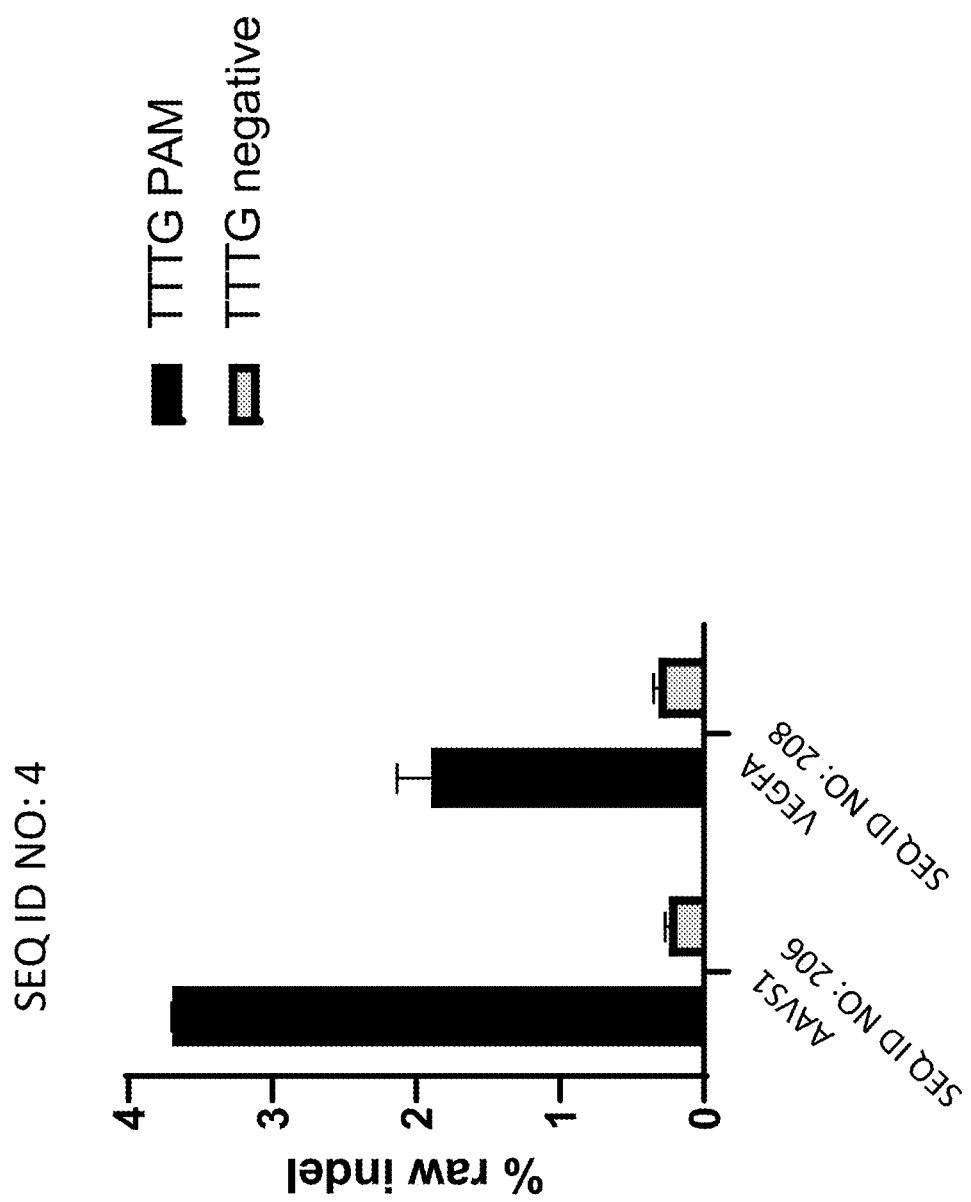
Figure 11B:
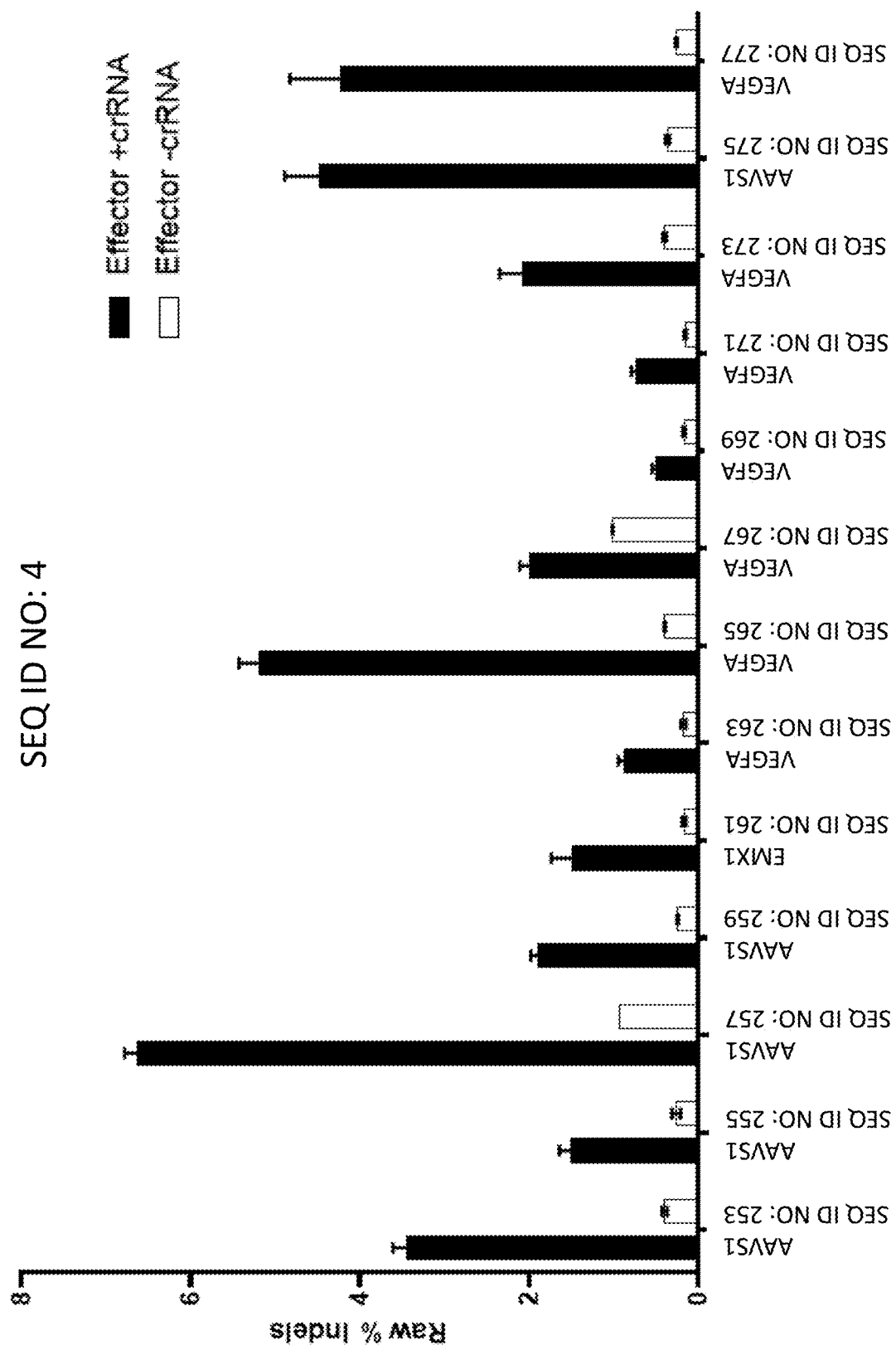
Figure 11C:
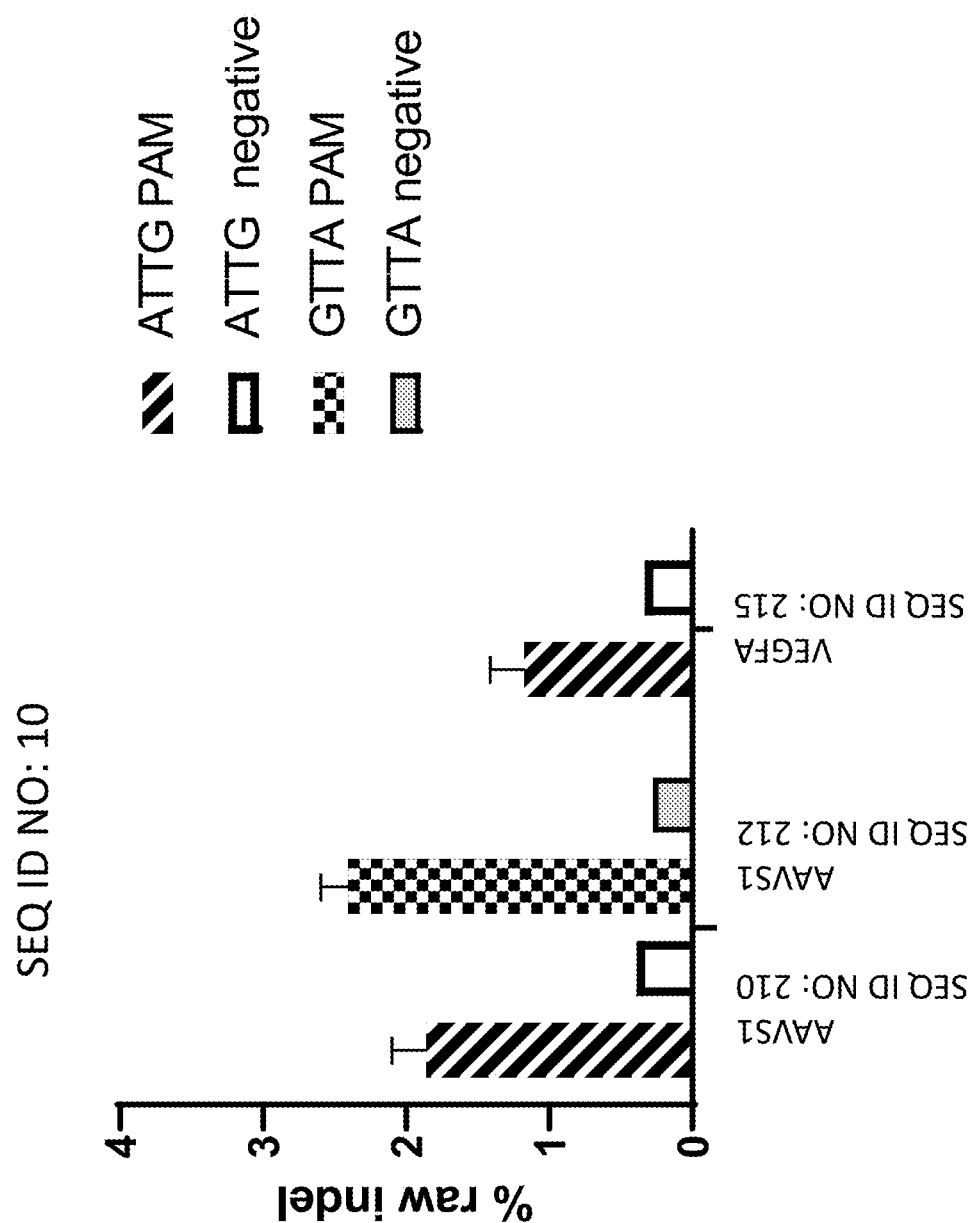
Figure 11D:
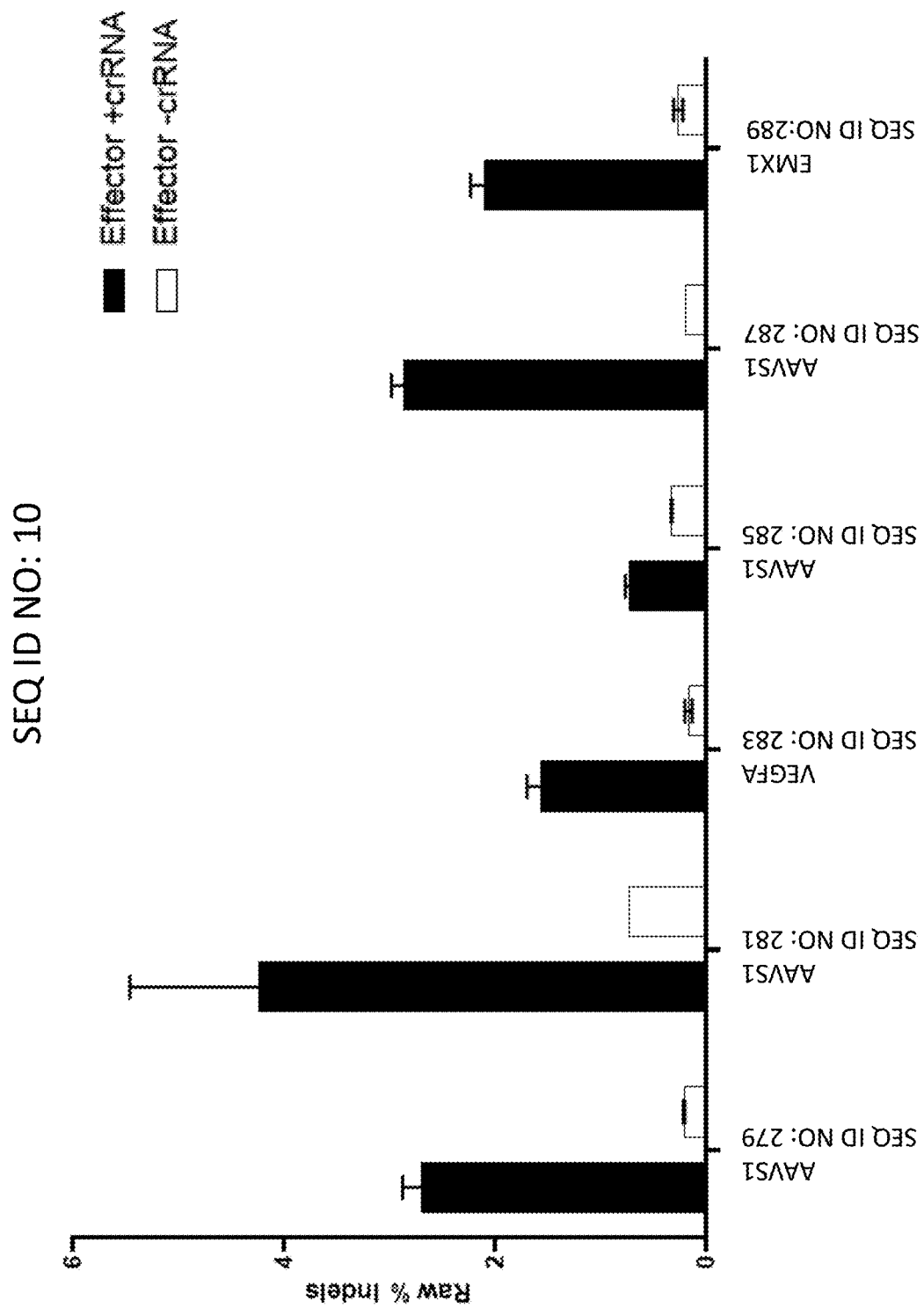

FIG. 11A shows indels induced by the effector of SEQ ID NO: 4 at an AAVS1 target locus of SEQ ID NO: 206 and a VEGFA target locus of SEQ ID NO: 208 in HEK293 cells. FIG. 11B shows indels induced by the effector of SEQ ID NO: 4 at AAVS1 target loci of SEQ ID NOs: 253, 255, 257, 259, and 275, VEGFA target loci of SEQ ID NOs: 263, 265, 267, 269, 271, 273, and 277, and an EMX1 target locus of SEQ ID NO: 261 in HEK293 cells, FIG. 11C shows indels induced by the effector of SEQ ID NO: 10 at an AAVS1 target loci of SEQ ID NO: 210, an AAVS1 target locus of SEQ ID NO: 212, and a VEGFA target locus of SEQ ID NO: 215 in HEK293 cells. FIG. 11D shows indels induced by the effector of SEQ ID NO: 10 at AAVS1 target loci of SEQ ID NOs: 279, 281, 285, and 287, a VEGFA target locus of SEQ ID NO: 283 and an EMX1 target locus of SEQ ID NO: 289 in HEK293 cells.

DETAILED DESCRIPTION

CRISPR-Cas systems, which are naturally diverse, comprise a wide range of activity mechanisms and functional elements that can be harnessed for programmable biotechnologies. In nature, these systems enable efficient defense against foreign DNA and viruses while providing self versus non-self discrimination to avoid self-targeting. In an engineered setting, these systems provide a diverse toolbox of molecular technologies and define the boundaries of the targeting space. The methods described herein have been used to discover additional mechanisms and parameters within single subunit Class 2 effector systems, which expand the capabilities of RNA-programmable nucleic acid manipulation.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting. Applicant reserves the right to alternatively claim any disclosed invention using the transitional phrase "comprising," "consisting essentially of," or "consisting of," according to standard practice in patent law.

As used herein, the singular forms "a," "an," and "the" include plural referents unless the context clearly dictates otherwise. For example, reference to "a nucleic acid" means one or more nucleic acids.

It is noted that terms like "preferably," "suitably," "commonly," and "typically" are not utilized herein to limit the scope of the claimed invention or to imply that certain features are critical, essential, or even important to the structure or function of the claimed invention. Rather, these terms are merely intended to highlight alternative or additional features that can or cannot be utilized in a particular embodiment of the present invention.

For the purposes of describing and defining the present invention, it is noted that the term "substantially" is utilized herein to represent the inherent degree of uncertainty that can be attributed to any quantitative comparison, value, measurement, or other representation. The term "substantially" is also utilized herein to represent the degree by which a quantitative representation can vary from a stated reference without resulting in a change in the basic function of the subject matter at issue.

The term "CRISPR-Cas system," as used herein, refers to nucleic acids and/or proteins involved in the expression of, or directing the activity of, CRISPR effectors, including sequences encoding CRISPR effectors, RNA guides, and other sequences and transcripts from a CRISPR locus.

The terms "CRISPR-associated protein," "CRISPR-Cas effector," "CRISPR effector," "effector," "effector protein," "CRISPR enzyme," or the like, as used interchangeably herein, refer to a protein that carries out an enzymatic activity or that binds to a target site on a nucleic acid specified by an RNA guide. In some embodiments, a CRISPR effector has endonuclease activity, nickase activity, and/or exonuclease activity.

The terms "RNA guide," "guide RNA," "gRNA," and "guide sequence," as used herein, refer to any RNA molecule that facilitates the targeting of an effector described herein to a target nucleic acid, such as DNA and/or RNA. Exemplary "RNA guides" include, but are not limited to, crRNAs, as well as crRNAs hybridized to or fused to either tracrRNAs and/or modulator RNAs. In some embodiments, an RNA guide includes both a crRNA and a tracrRNA, either fused into a single RNA molecule or as separate RNA molecules. In some embodiments, an RNA guide includes a crRNA and a modulator RNA, either fused into a single RNA molecule or as separate RNA molecules. In some embodiments, an RNA guide includes a crRNA, a tracrRNA, and a modulator RNA, either fused into a single RNA molecule or as separate RNA molecules.

The terms "CRISPR effector complex," "effector complex," or "surveillance complex," as used herein, refer to a complex containing a CRISPR effector and an RNA guide. A CRISPR effector complex may further comprise one or more accessory proteins. The one or more accessory proteins may be non-catalytic and/or non-target binding.

The terms "CRISPR RNA" and "crRNA," as used herein, refer to an RNA molecule comprising a guide sequence used by a CRISPR effector specifically to recognize a nucleic acid sequence. A crRNA "spacer" sequence is complementary to and capable of partially or completely binding to a nucleic acid target sequence. A crRNA may comprise a sequence that hybridizes to a tracrRNA. In turn, the crRNA: tracrRNA duplex may bind to a CRISPR effector. As used herein, the term "pre-crRNA" refers to an unprocessed RNA molecule comprising a DR-spacer-DR sequence. As used herein, the term "mature crRNA" refers to a processed form of a pre-crRNA; a mature crRNA may comprise a DR-spacer sequence, wherein the DR is a truncated form of the DR of a pre-crRNA and/or the spacer is a truncated form of the spacer of a pre-crRNA.

The terms "trans-activating crRNA" or "tracrRNA," as used herein, refer to an RNA molecule comprising a sequence that forms a structure and/or sequence motif required for a CRISPR effector to bind to a specified target nucleic acid.

The term "CRISPR array," as used herein, refers to a nucleic acid (e.g., DNA) segment that comprises CRISPR repeats and spacers, starting with the first nucleotide of the first CRISPR repeat and ending with the last nucleotide of the final (terminal) CRISPR repeat. Typically, each spacer in a CRISPR array is located between two repeats. The terms "CRISPR repeat," "CRISPR direct repeat," and "direct repeat," as used herein, refer to multiple short direct repeating sequences, which show very little or no sequence variation within a CRISPR array.

The term "modulator RNA" as described herein refers to any RNA molecule that modulates (e.g., increases or decreases) an activity of a CRISPR effector or a nucleoprotein complex that includes a CRISPR effector. In some embodiments, a modulator RNA modulates a nuclease activity of a CRISPR effector or a nucleoprotein complex that includes a CRISPR effector.

As used herein, the term "target nucleic acid" refers to a nucleic acid that comprises a nucleotide sequence complementary to the entirety or a part of the spacer in an RNA guide. In some embodiments, the target nucleic acid comprises a gene. In some embodiments, the target nucleic acid comprises a non-coding region (e.g., a promoter). In some embodiments, the target nucleic acid is single-stranded. In some embodiments, the target nucleic acid is double-stranded. A "transcriptionally-active site," as used herein, refers to a site in a nucleic acid sequence being actively transcribed.

As used herein, the term "protospacer adjacent motif" or "PAM" refers to a DNA sequence adjacent to a target sequence to which a complex comprising an effector and an RNA guide binds. In some embodiments, a PAM is required for enzyme activity. As used herein, the term "adjacent" includes instances in which an RNA guide of the complex specifically binds, interacts, or associates with a target sequence that is immediately adjacent to a PAM. In such instances, there are no nucleotides between the target sequence and the PAM. The term "adjacent" also includes instances in which there are a small number (e.g., 1, 2, 3, 4, or 5) of nucleotides between the target sequence, to which the targeting moiety binds, and the PAM. As used herein, the term "recognizing a PAM sequence" refers to the binding of a complex comprising a CRISPR-associated protein and a crRNA to a target nucleic acid, wherein the target nucleic acid is adjacent to a PAM sequence.

The terms "activated CRISPR effector complex," "activated CRISPR complex," and "activated complex," as used herein, refer to a CRISPR effector complex capable of modifying a target nucleic acid. In some embodiments, an activated CRISPR complex is capable of modifying a target nucleic acid following binding of the activated CRISPR complex to the target nucleic acid. In some embodiments, binding of an activated CRISPR complex to a target nucleic acid results in an additional cleavage event, such as collateral cleavage.

The term "cleavage event," as used herein, refers to a break in a nucleic acid, such as DNA and/or RNA. In some embodiments, a cleavage event refers to a break in a target nucleic acid created by a nuclease of a CRISPR system described herein. In some embodiments, the cleavage event is a double-stranded DNA break. In some embodiments, the cleavage event is a single-stranded DNA break. In some embodiments, a cleavage event refers to a break in a collateral nucleic acid.

The term "collateral nucleic acid," as used herein, refers to a nucleic acid substrate that is cleaved non-specifically by an activated CRISPR complex. The term "collateral DNase activity," as used herein in reference to a CRISPR effector, refers to non-specific DNase activity of an activated CRISPR complex. The term "collateral RNase activity," as used herein in reference to a CRISPR effector, refers to non-specific RNase activity of an activated CRISPR complex.

The term "donor template nucleic acid," as used herein, refers to a nucleic acid molecule that can be used to make a templated change to a target sequence or target-proximal sequence after a CRISPR effector described herein has modified the target nucleic acid. In some embodiments, the donor template nucleic acid is a double-stranded nucleic acid. In some embodiments, the donor template nucleic acid is a single-stranded nucleic acid. In some embodiments, the donor template nucleic acid is linear. In some embodiments, the donor template nucleic acid is circular (e.g., a plasmid). In some embodiments, the donor template nucleic acid is an exogenous nucleic acid molecule. In some embodiments, the donor template nucleic acid is an endogenous nucleic acid molecule (e.g., a chromosome).

As used herein, the terms "polynucleotide," "nucleotide," "oligonucleotide," and "nucleic acid" can be used interchangeably to refer to nucleic acid comprising DNA, RNA, derivatives thereof, or combinations thereof. Methods well known to those skilled in the art can be used to construct genetic expression constructs and recombinant cells according to this invention. These methods include in vitro recombinant DNA techniques, synthetic techniques, in vivo recombination techniques, and polymerase chain reaction (PCR) techniques. See, for example, techniques as described in Maniatis et al., 1989, MOLECULAR CLONING: A LABORATORY MANUAL, Cold Spring Harbor Laboratory, New York; Ausubel et al., 1989, CURRENT PROTOCOLS IN MOLECULAR BIOLOGY, Greene Publishing Associates and Wiley Interscience, New York, and PCR Protocols: A Guide to Methods and Applications (Innis et al., 1990, Academic Press, San Diego, Calif.)

The term "genetic modification" or "genetic engineering" broadly refers to manipulation of the genome or nucleic acids of a cell. Likewise, the terms "genetically engineered" and "engineered" refer to a cell comprising a manipulated genome or nucleic acids. Methods of genetic modification of include, for example, heterologous gene expression, gene or promoter insertion or deletion, nucleic acid mutation, altered gene expression or inactivation, enzyme engineering, directed evolution, knowledge-based design, random mutagenesis methods, gene shuffling, and codon optimization.

The term "recombinant" indicates that a nucleic acid, protein, or cell is the product of genetic modification, engineering, or recombination. Generally, the term "recombinant" refers to a nucleic acid, protein, or cell that contains or is encoded by genetic material derived from multiple sources. As used herein, the term "recombinant" may also be used to describe a cell that comprises a mutated nucleic acid or protein, including a mutated form of an endogenous nucleic acid or protein. The terms "recombinant cell" and "recombinant host" can be used interchangeably. In some embodiments, a recombinant cell comprises a CRISPR effector disclosed herein. The CRISPR effector can be codon-optimized for expression in the recombinant cell. In some embodiments, a recombinant cell disclosed herein further comprises an RNA guide. In some embodiments, an RNA guide of a recombinant cell disclosed herein comprises a tracrRNA. In some embodiments, a recombinant cell disclosed herein comprises a modulator RNA. In some embodiments, the recombinant cell is a prokaryotic cell, such as an *E. coli* cell. In some embodiments, the recombinant cell is a eukaryotic cell, such as a mammalian cell, including a human cell.

Identification of CLUST.091979

Figure 1A:
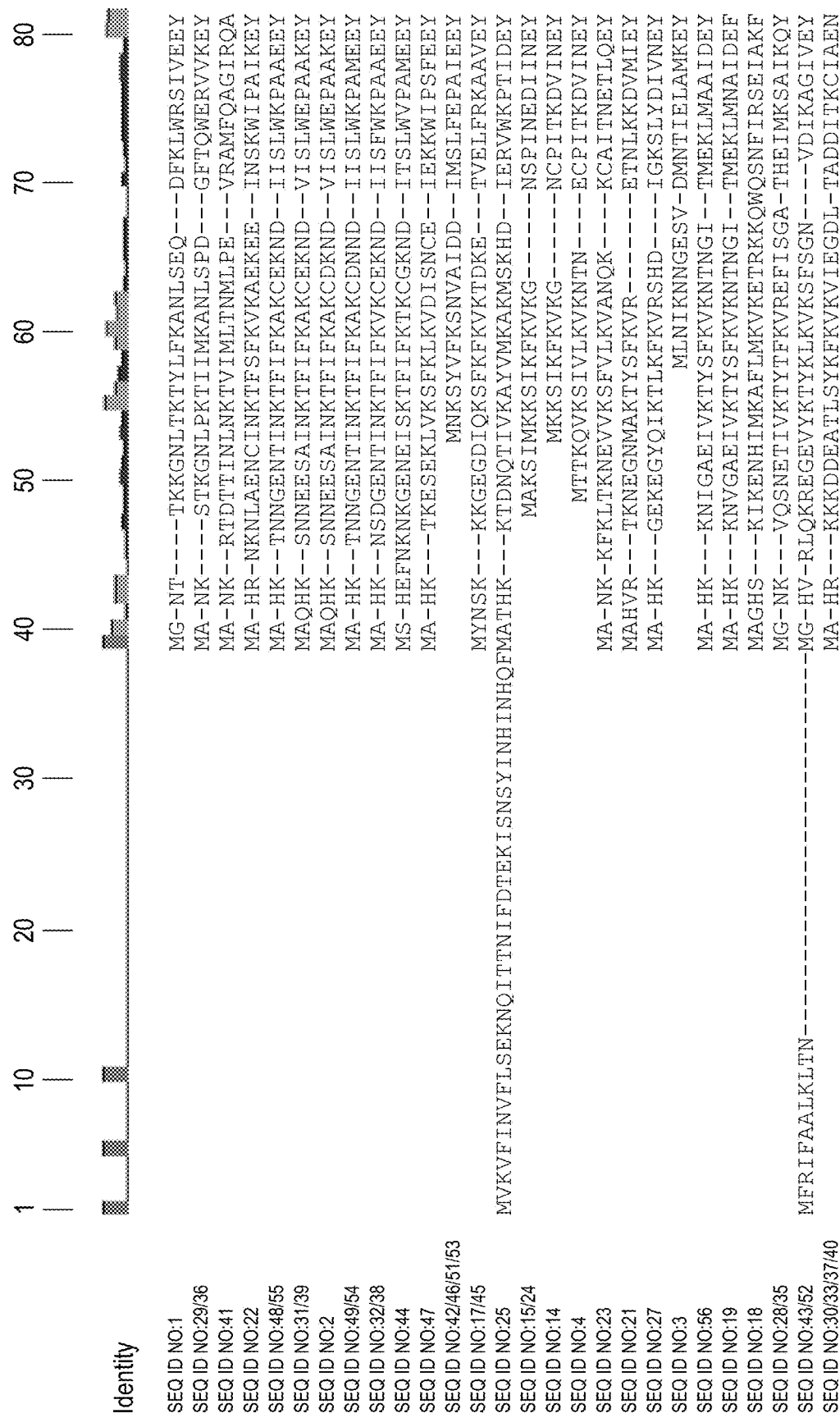
Figure 1C:
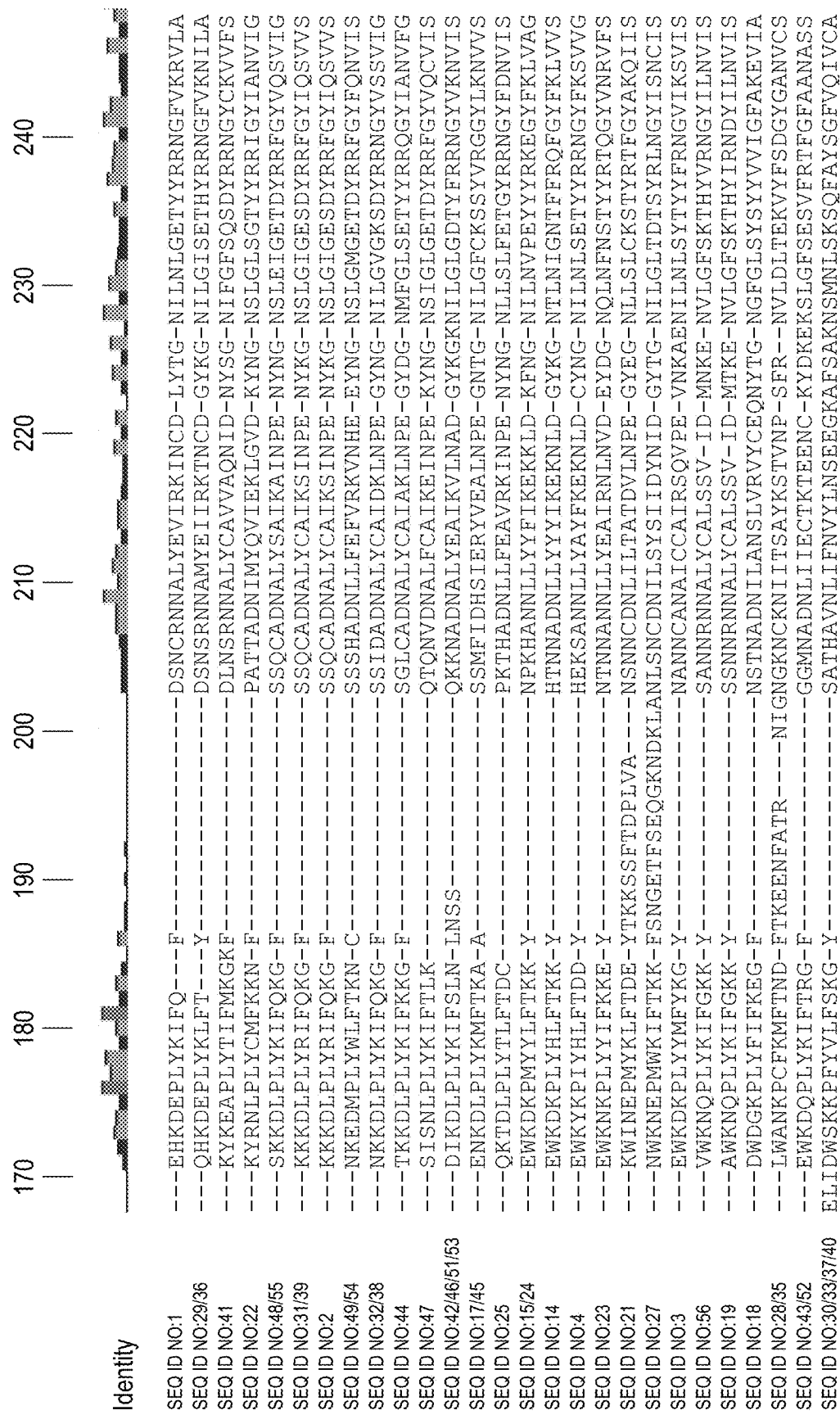
Figure 1D:
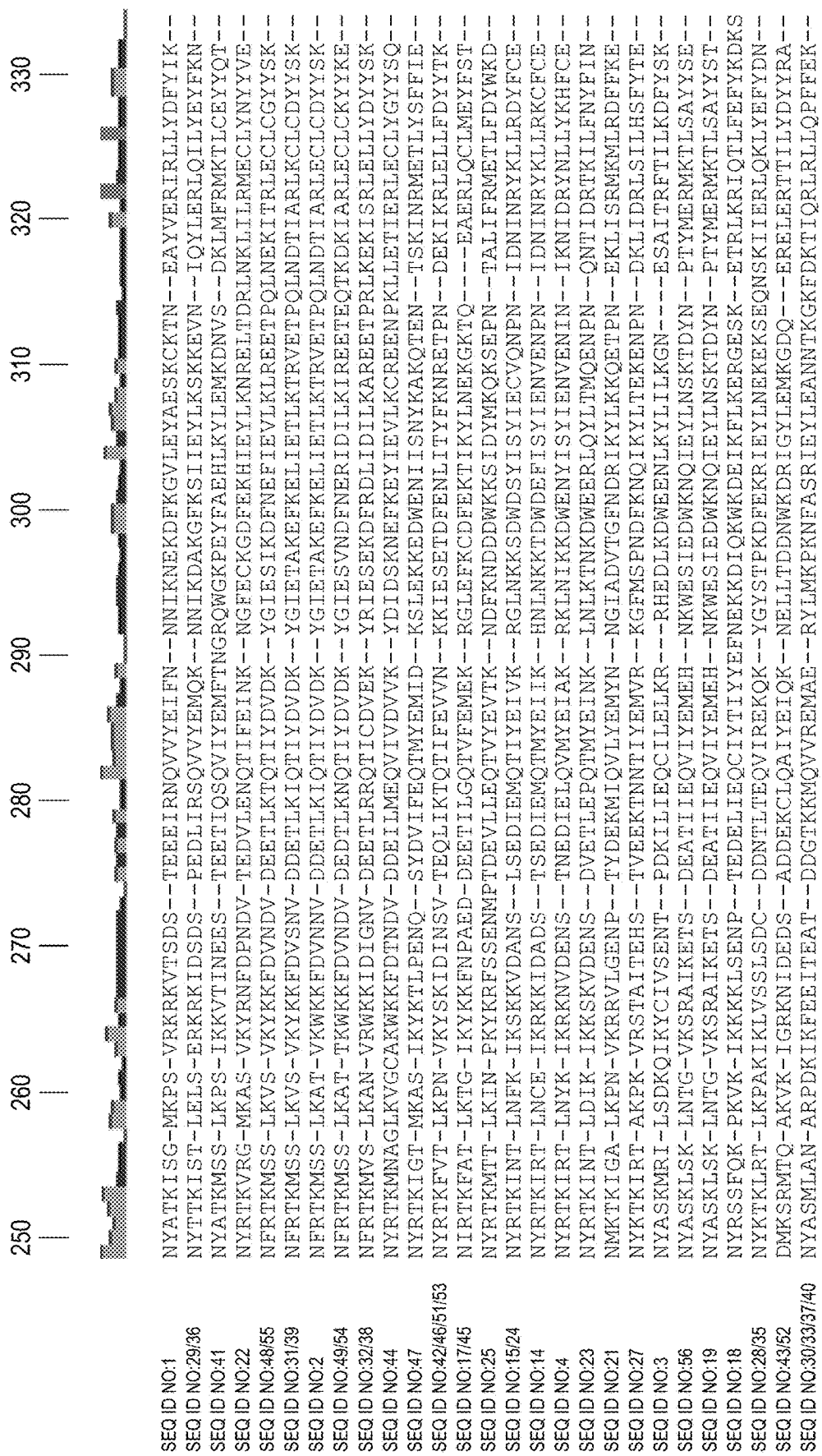
Figure 1G:
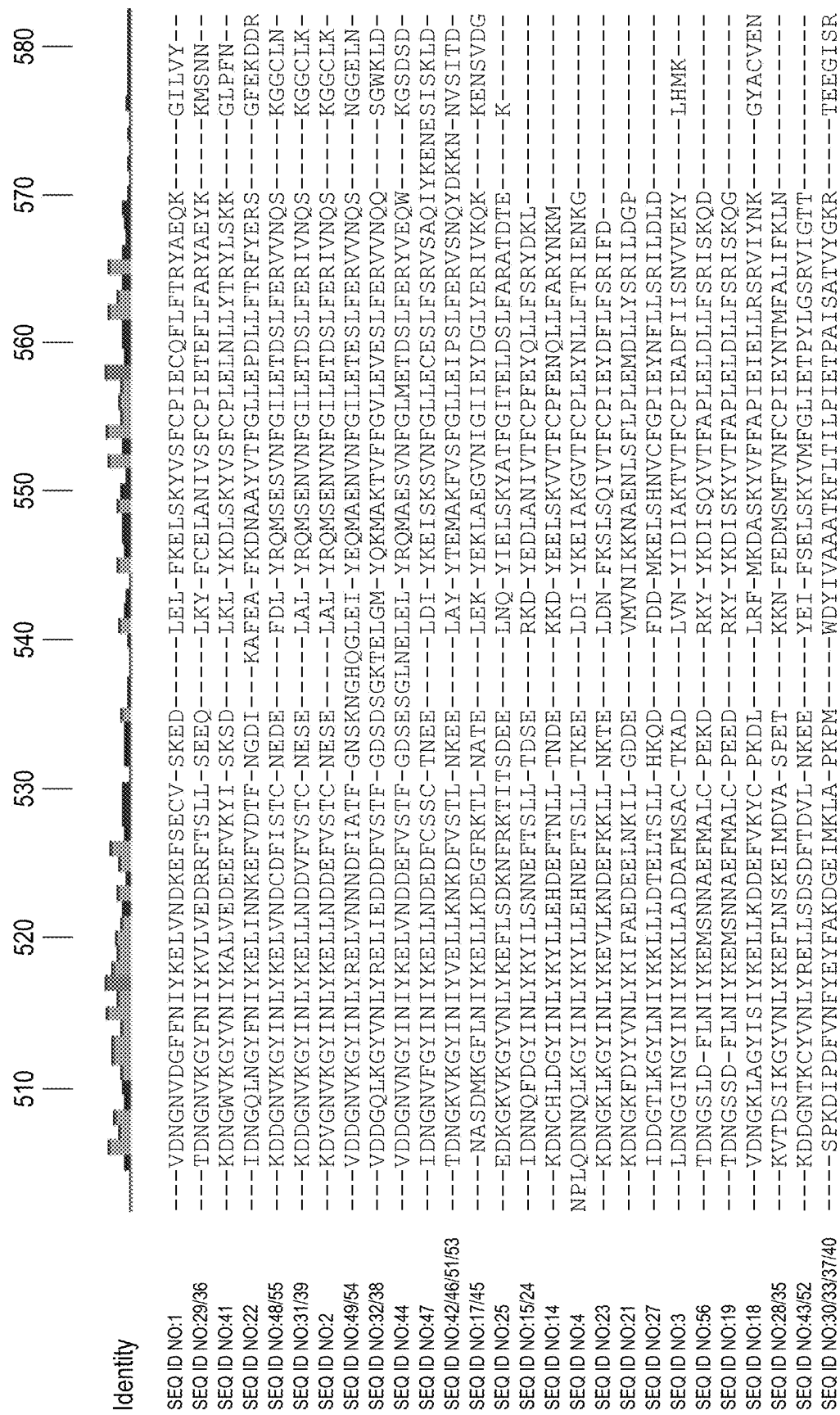
Figure 1I:
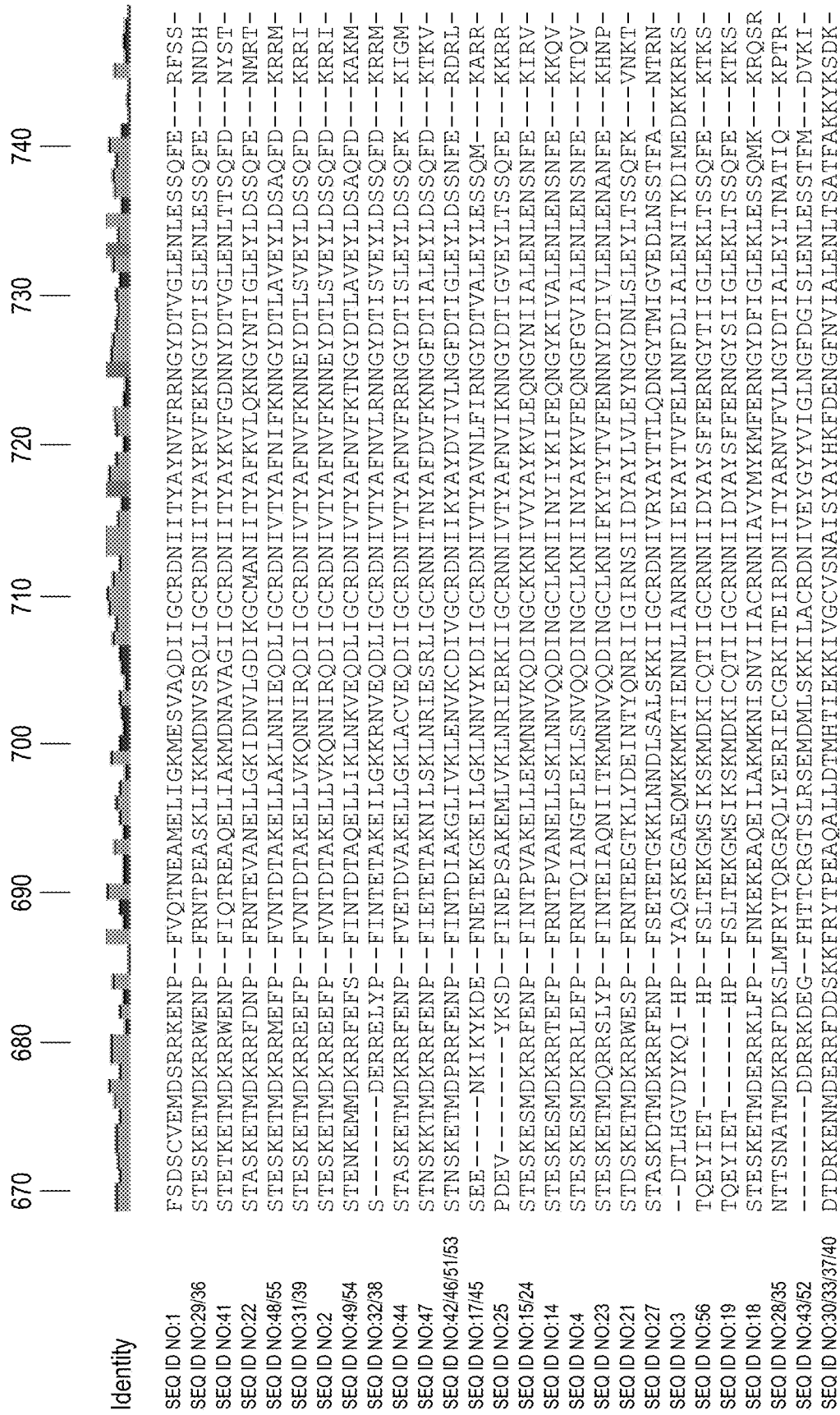
Figure 1J:
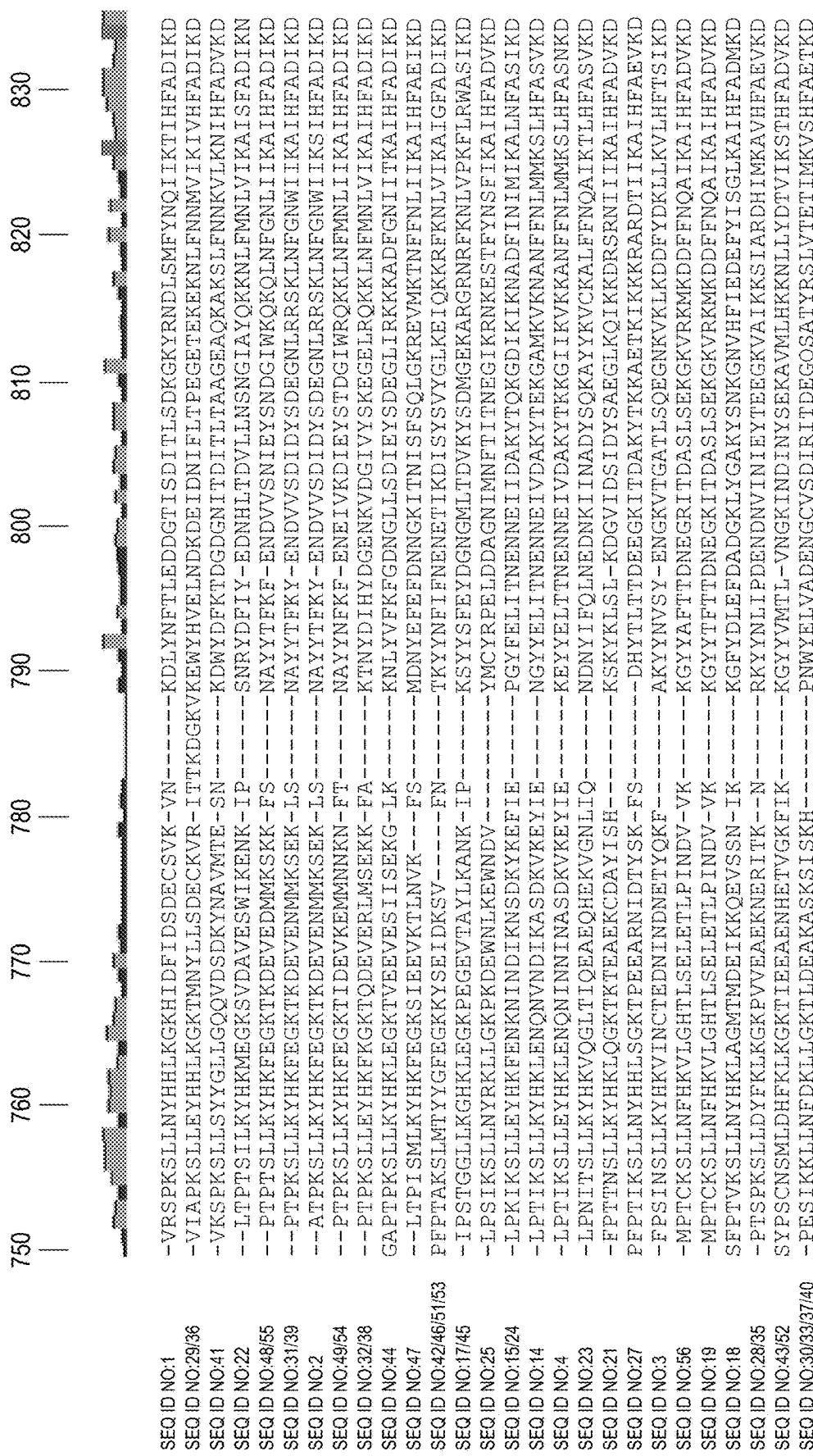
Figure 2:
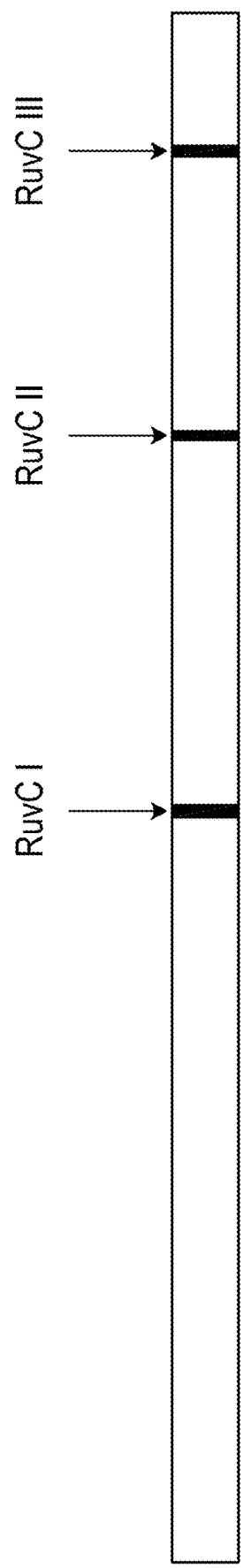
FIG. 2 is a schematic showing the RuvC domains of CLUST.091979 effectors, which is based upon the consensus sequence of the sequences shown in Table 6.

This application relates to the identification, engineering, and use of a novel protein family referred to herein as "CLUST.091979." As shown in FIG. 2, the proteins of CLUST.091979 comprise a RuvC domain (denoted RuvC I, RuvC II, and RuvC III). As shown in TABLE 5, effectors of CLUST.091979 range in size from about 700 amino acids to about 800 amino acids. Therefore, the effectors of CLUST.091979 are smaller than effectors known in the art, as shown below. See, e.g., TABLE 1.

TABLE 1

Sizes of known CRISPR-Cas system effectors.

| Effector | Size (aa) |
|---|---|
| StCas9 | 1128 |
| SpCas9 | 1368 |
| SaCas9 | 1053 |
| FnCpf1 | 1300 |
| AsCpf1 | 1307 |
| LbCpf1 | 1246 |
| C2c1 | 1127 (average) |
| CasX | 982 (average) |
| CasY | 1189 (average) |
| C2c2 | 1232 (average) |

The effectors of CLUST.091979 were identified using computational methods and algorithms to search for and identify proteins exhibiting a strong co-occurrence pattern with certain other features. In certain embodiments, these computational methods were directed to identifying proteins that co-occurred in close proximity to CRISPR arrays. The methods disclosed herein are also useful in identifying proteins that naturally occur within close proximity to other features, both non-coding and protein-coding (e.g., fragments of phage sequences in non-coding areas of bacterial loci or CRISPR Cas1 proteins). It is understood that the methods and calculations described herein may be performed on one or more computing devices.

Sets of genomic sequences were obtained from genomic or metagenomic databases. The databases comprised short reads, or contig level data, or assembled scaffolds, or complete genomic sequences of organisms. Likewise, the databases may comprise genomic sequence data from prokaryotic organisms, or eukaryotic organisms, or may include data from metagenomic environmental samples. Examples of database repositories include the National Center for Biotechnology Information (NCBI) RefSeq, NCBI GenBank, NCBI Whole Genome Shotgun (WGS), and the Joint Genome Institute (JGI) Integrated Microbial Genomes (IMG).

In some embodiments, a minimum size requirement is imposed to select genome sequence data of a specified minimum length. In certain exemplary embodiments, the minimum contig length may be 100 nucleotides, 500 nt, 1 kb, 1.5 kb, 2 kb, 3 kb, 4 kb, 5 kb, 10 kb, 20 kb, 40 kb, or 50 kb.

In some embodiments, known or predicted proteins are extracted from the complete or a selected set of genome sequence data. In some embodiments, known or predicted proteins are taken from extracting coding sequence (CDS) annotations provided by the source database. In some embodiments, predicted proteins are determined by applying a computational method to identify proteins from nucleotide sequences. In some embodiments, the GeneMark Suite is used to predict proteins from genome sequences. In some embodiments, Prodigal is used to predict proteins from genome sequences. In some embodiments, multiple protein prediction algorithms may be used over the same set of sequence data with the resulting set of proteins de-duplicated.

In some embodiments, CRISPR arrays are identified from the genome sequence data. In some embodiments, PILER-CR is used to identify CRISPR arrays. In some embodiments, CRISPR Recognition Tool (CRT) is used to identify CRISPR arrays. In some embodiments, CRISPR arrays are identified by a heuristic that identifies nucleotide motifs repeated a minimum number of times (e.g., 2, 3, or 4 times), where the spacing between consecutive occurrences of a repeated motif does not exceed a specified length (e.g., 50, 100, or 150 nucleotides). In some embodiments, multiple CRISPR array identification tools may be used over the same set of sequence data with the resulting set of CRISPR arrays de-duplicated.

In some embodiments, proteins in close proximity to CRISPR arrays (referred to herein as "CRISPR-proximal protein clusters") are identified. In some embodiments, proximity is defined as a nucleotide distance, and may be within 20 kb, 15 kb, or 5 kb. In some embodiments, proximity is defined as the number of open reading frames (ORFs) between a protein and a CRISPR array, and certain exemplary distances may be 10, 5, 4, 3, 2, 1, or 0 ORFs. The proteins identified as being within close proximity to a CRISPR array are then grouped into clusters of homologous proteins. In some embodiments, blastclust is used to form CRISPR-proximal protein clusters. In certain other embodiments, mmseqs2 is used to form CRISPR-proximal protein clusters.

To establish a pattern of strong co-occurrence between the members of a CRISPR-proximal protein cluster, a BLAST search of each member of the protein cluster may be performed over the complete set of known and predicted proteins previously compiled. In some embodiments, UBLAST or mmseqs2 may be used to search for similar proteins. In some embodiments, a search may be performed only for a representative subset of proteins in the family.

In some embodiments, the CRISPR-proximal protein clusters are ranked or filtered by a metric to determine co-occurrence. One exemplary metric is the ratio of the number of elements in a protein cluster against the number of BLAST matches up to a certain E value threshold. In some embodiments, a constant E value threshold may be used. In other embodiments, the E value threshold may be determined by the most distant members of the protein cluster. In some embodiments, the global set of proteins is clustered and the co-occurrence metric is the ratio of the number of elements of the CRISPR-proximal protein cluster against the number of elements of the containing global cluster(s).

In some embodiments, a manual review process is used to evaluate the potential functionality and the minimal set of components of an engineered system based on the naturally occurring locus structure of the proteins in the cluster. In some embodiments, a graphical representation of the protein cluster may assist in the manual review and may contain information including pairwise sequence similarity, phylogenetic tree, source organisms/environments, predicted functional domains, and a graphical depiction of locus structures. In some embodiments, the graphical depiction of locus structures may filter for nearby protein families that have a high representation. In some embodiments, representation may be calculated by the ratio of the number of related nearby proteins against the size(s) of the containing global cluster(s). In certain exemplary embodiments, the graphical representation of the protein cluster may contain a depiction of the CRISPR array structures of the naturally occurring loci. In some embodiments, the graphical representation of the protein cluster may contain a depiction of the number of conserved direct repeats versus the length of the putative CRISPR array or the number of unique spacer sequences versus the length of the putative CRISPR array. In some embodiments, the graphical representation of the protein cluster may contain a depiction of various metrics of co-occurrence of the putative effector with CRISPR arrays predict new CRISPR-Cas systems and identify their components.

Pooled-Screening of CLUST.091979

To efficiently validate the activity, mechanisms, and functional parameters of the engineered CLUST.091979 CRISPR-Cas systems identified herein, a pooled-screening approach in E. coli was used, as described in Example 4. First, from the computational identification of the conserved protein and noncoding elements of the CLUST.091979 CRISPR-Cas system, DNA synthesis and molecular cloning were used to assemble the separate components into a single artificial expression vector, which in one embodiment is based on a pET-28a+ backbone. In a second embodiment, the effectors and noncoding elements are transcribed on an mRNA transcript, and different ribosomal binding sites are used to translate individual effectors.

Second, the natural crRNA and targeting spacers were replaced with a library of unprocessed crRNAs containing non-natural spacers targeting a second plasmid, pACYC184. This crRNA library was cloned into the vector backbone comprising the effectors and noncoding elements (e.g., pET-28a+), and the library was subsequently transformed into E. coli along with the pACYC184 plasmid target. Consequently, each resulting E. coli cell contains no more than one targeting array. In an alternate embodiment, the library of unprocessed crRNAs containing non-natural spacers additionally target E. coli essential genes, drawn from resources such as those described in Baba et al. (2006) Mol. Syst. Biol. 2: 2006.0008; and Gerdes et al. (2003) J. Bacteriol. 185(19): 5673-84, the entire contents of each of which are incorporated herein by reference. In this embodiment, positive, targeted activity of the novel CRISPR-Cas systems that disrupts essential gene function results in cell death or growth arrest. In some embodiments, the essential gene targeting spacers can be combined with the pACYC184 targets.

Third, the E. coli were grown under antibiotic selection. In one embodiment, triple antibiotic selection is used: kanamycin for ensuring successful transformation of the pET-28a+ vector containing the engineered CRISPR effector system and chloramphenicol and tetracycline for ensuring successful co-transformation of the pACYC184 target vector. Since pACYC184 normally confers resistance to chloramphenicol and tetracycline, under antibiotic selection, positive activity of the novel CRISPR-Cas system targeting the plasmid will eliminate cells that actively express the effectors, noncoding elements, and specific active elements of the crRNA library. Typically, populations of surviving cells are analyzed 12-14 h post-transformation. In some embodiments, analysis of surviving cells is conducted 6-8 h post-transformation, 8-12 h post-transformation, up to 24 h post-transformation, or more than 24 h post-transformation. Examining the population of surviving cells at a later time point compared to an earlier time point results in a depleted signal compared to the inactive crRNAs.

In some embodiments, double antibiotic selection is used. Withdrawal of either chloramphenicol or tetracycline to remove selective pressure can provide novel information about the targeting substrate, sequence specificity, and potency. For example, cleavage of dsDNA in a selected or unselected gene can result in negative selection in E. coli, wherein depletion of both selected and unselected genes is observed. If the CRISPR-Cas system interferes with transcription or translation (e.g., by binding or by transcript cleavage), then selection will only be observed for targets in the selected resistance gene, rather than in the unselected resistance gene.

In some embodiments, only kanamycin is used to ensure successful transformation of the pET-28a+ vector comprising the engineered CRISPR-Cas system. This embodiment is suitable for libraries containing spacers targeting E. coli essential genes, as no additional selection beyond kanamycin is needed to observe growth alterations. In this embodiment, chloramphenicol and tetracycline dependence is removed, and their targets (if any) in the library provide an additional source of negative or positive information about the targeting substrate, sequence specificity, and potency.

Since the pACYC184 plasmid contains a diverse set of features and sequences that may affect the activity of a CRISPR-Cas system, mapping the active crRNAs from the pooled screen onto pACYC184 provides patterns of activity that can be suggestive of different activity mechanisms and functional parameters. In this way, the features required for reconstituting the novel CRISPR-Cas system in a heterologous prokaryotic species can be more comprehensively tested and studied.

The key advantages of the in vivo pooled-screen described herein include:

(1) Versatility—Plasmid design allows multiple effectors and/or noncoding elements to be expressed; library cloning strategy enables both transcriptional directions of the computationally predicted crRNA to be expressed;

(2) Comprehensive tests of activity mechanisms & functional parameters—Evaluates diverse interference mechanisms, including nucleic acid cleavage; examines co-occurrence of features such as transcription, plasmid DNA replication; and flanking sequences for crRNA library can be used to reliably determine PAMs with complexity equivalence of 4N's;

(3) Sensitivity—pACYC184 is a low copy plasmid, enabling high sensitivity for CRISPR-Cas activity since even modest interference rates can eliminate the antibiotic resistance encoded by the plasmid; and (4) Efficiency—Optimized molecular biology steps to enable greater speed and throughput RNA-sequencing and protein expression samples can be directly harvested from the surviving cells in the screen.

The novel CLUST.091979 CRISPR-Cas family described herein was evaluated using this in vivo pooled-screen to evaluate is operational elements, mechanisms, and parameters, as well as its ability to be active and reprogrammed in an engineered system outside of its endogenous cellular environment.

CRISPR Effector Activity and Modifications

In some embodiments, a CRISPR effector of CLUST.091979 and an RNA guide form a "binary" complex that may include other components. The binary complex is activated upon binding to a nucleic acid substrate that is complementary to a spacer sequence in the RNA guide (i.e., a sequence-specific substrate or target nucleic acid). In some embodiments, the sequence-specific substrate is a double-stranded DNA. In some embodiments, the sequence-specific substrate is a single-stranded DNA. In some embodiments, the sequence-specific substrate is a single-stranded RNA. In some embodiments, the sequence-specific substrate is a double-stranded RNA. In some embodiments, the sequence-specificity requires a complete match of the spacer sequence in the RNA guide (e.g., crRNA) to the target substrate. In other embodiments, the sequence specificity requires a partial (contiguous or non-contiguous) match of the spacer sequence in the RNA guide (e.g., crRNA) to the target substrate.

In some embodiments, a CRISPR effector of the present invention has enzymatic activity, e.g., nuclease activity, over a broad range of pH conditions. In some embodiments, the nuclease has enzymatic activity, e.g., nuclease activity, at a pH of from about 3.0 to about 12.0. In some embodiments, the CRISPR effector has enzymatic activity at a pH of from about 4.0 to about 10.5. In some embodiments, the CRISPR effector has enzymatic activity at a pH of from about 5.5 to about 8.5. In some embodiments, the CRISPR effector has enzymatic activity at a pH of from about 6.0 to about 8.0. In some embodiments, the CRISPR effector has enzymatic activity at a pH of about 7.0.

In some embodiments, a CRISPR effector of the present invention has enzymatic activity, e.g., nuclease activity, at a temperature range of from about 10° C. to about 100° C. In some embodiments, a CRISPR effector of the present invention has enzymatic activity at a temperature range from about 20° C. to about 90° C. In some embodiments, a CRISPR effector of the present invention has enzymatic activity at a temperature of about 20° C. to about 25° C. or at a temperature of about 37° C.

In some embodiments, the binary complex becomes activated upon binding to the target substrate. In some embodiments, the activated complex exhibits "multiple turnover" activity, whereby upon acting on (e.g., cleaving) the target substrate the activated complex remains in an activated state. In some embodiments, the activated binary complex exhibits "single turnover" activity, whereby upon acting on the target substrate the binary complex reverts to an inactive state. In some embodiments, the activated binary complex exhibits non-specific (i.e., "collateral") cleavage activity whereby the complex cleaves non-target nucleic acids. In some embodiments, the non-target nucleic acid is a DNA molecule (e.g., a single-stranded or a double-stranded DNA). In some embodiments, the non-target nucleic acid is an RNA molecule (e.g., a single-stranded or a double-stranded RNA).

In some embodiments wherein a CRISPR effector of the present invention induces double-stranded breaks or single-stranded breaks in a target nucleic acid, (e.g. genomic DNA), the double-stranded break can stimulate cellular endogenous DNA-repair pathways, including Homology Directed Recombination (HDR), Non-Homologous End Joining (NHEJ), or Alternative Non-Homologues End-Joining (A-NHEJ). NHEJ can repair cleaved target nucleic acid without the need for a homologous template. This can result in deletion or insertion of one or more nucleotides at the target locus. HDR can occur with a homologous template, such as the donor DNA. The homologous template can comprise sequences that are homologous to sequences flanking the target nucleic acid cleavage site. In some cases, HDR can insert an exogenous polynucleotide sequence into the cleave target locus. The modifications of the target DNA due to NHEJ and/or HDR can lead to, for example, mutations, deletions, alterations, integrations, gene correction, gene replacement, gene tagging, transgene knock-in, gene disruption, and/or gene knock-outs.

In some embodiments, a CRISPR effector described herein can be fused to one or more peptide tags, including a His-tag, GST-tag, FLAG-tag, or myc-tag. In some embodiments, a CRISPR effector described herein can be fused to a detectable moiety such as a fluorescent protein (e.g., green fluorescent protein or yellow fluorescent protein). In some embodiments, a CRISPR effector and/or accessory protein of this disclosure is fused to a peptide or non-peptide moiety that allows the protein to enter or localize to a tissue, a cell, or a region of a cell. For instance, a CRISPR effector of this disclosure may comprise a nuclear localization sequence (NLS) such as an SV40 (simian virus 40) NLS, c-Myc NLS, or other suitable monopartite NLS. The NLS may be fused to the N-terminus and/or C-terminus of the CRISPR effector, and may be fused singly (i.e., a single NLS) or concatenated (e.g., a chain of 2, 3, 4, etc. NLS).

In some embodiments, at least one Nuclear Export Signal (NES) is attached to a nucleic acid sequences encoding the CRISPR effector. In some embodiments, a C-terminal and/or N-terminal NLS or NES is attached for optimal expression and nuclear targeting in eukaryotic cells, e.g., human cells.

In those embodiments where a tag is fused to a CRISPR effector, such tag may facilitate affinity-based or charge-based purification of the CRISPR effector, e.g., by liquid chromatography or bead separation utilizing an immobilized affinity or ion-exchange reagent. As a non-limiting example, a recombinant CRISPR effector of this disclosure comprises a polyhistidine (His) tag, and for purification is loaded onto a chromatography column comprising an immobilized metal ion (e.g. a $Zn^{2+}$, $Ni^{2+}$, $Cu^{2+}$ ion chelated by a chelating ligand immobilized on the resin, which resin may be an individually prepared resin or a commercially available resin or ready to use column such as the HisTrap FF column commercialized by GE Healthcare Life Sciences, Marlborough, Mass. Following the loading step, the column is optionally rinsed, e.g., using one or more suitable buffer solutions, and the His-tagged protein is then eluted using a suitable elution buffer. Alternatively, or additionally, if the recombinant CRISPR effector of this disclosure utilizes a FLAG-tag, such protein may be purified using immunoprecipitation methods known in the industry. Other suitable purification methods for tagged CRISPR effectors or accessory proteins of this disclosure will be evident to those of skill in the art.

The proteins described herein (e.g., CRISPR effectors or accessory proteins) can be delivered or used as either nucleic acid molecules or polypeptides. When nucleic acid molecules are used, the nucleic acid molecule encoding the CRISPR effector can be codon-optimized. The nucleic acid can be codon optimized for use in any organism of interest, in particular human cells or bacteria. For example, the nucleic acid can be codon-optimized for any non-human eukaryote including mice, rats, rabbits, dogs, livestock, or non-human primates. Codon usage tables are readily available, for example, at the "Codon Usage Database" available at www.kazusa.orjp/codon/and these tables can be adapted in a number of ways. See Nakamura et al. *Nucl. Acids Res.* 28:292 (2000), which is incorporated herein by reference in its entirety. Computer algorithms for codon optimizing a particular sequence for expression in a particular host cell are also available, such as Gene Forge (Aptagen; Jacobus, Pa.).

In some instances, nucleic acids of this disclosure which encode CRISPR effectors for expression in eukaryotic (e.g., human, or other mammalian cells) cells include one or more introns, i.e., one or more non-coding sequences comprising, at a first end (e.g., a 5' end), a splice-donor sequence and, at second end (e.g., the 3' end) a splice acceptor sequence. Any suitable splice donor/splice acceptor can be used in the various embodiments of this disclosure, including without limitation simian virus 40 (SV40) intron, beta-globin intron, and synthetic introns. Alternatively, or additionally, nucleic acids of this disclosure encoding CRISPR effectors or accessory proteins may include, at a 3' end of a DNA coding sequence, a transcription stop signal such as a polyadenylation (polyA) signal. In some instances, the polyA signal is located in close proximity to, or adjacent to, an intron such as the SV40 intron.

Deactivated/Inactivated CRISPR Effectors

The CRISPR effectors described herein can be modified to have diminished nuclease activity, e.g., nuclease inactivation of at least 50%, at least 60%, at least 70%, at least 80%, at least 90%, at least 95%, at least 97%, or 100% as compared with the wild type CRISPR effectors. The nuclease activity can be diminished by several methods known in the art, e.g., introducing mutations into the nuclease domains of the proteins. In some embodiments, catalytic residues for the nuclease activities are identified, and these amino acid residues can be substituted by different amino acid residues (e.g., glycine or alanine) to diminish the nuclease activity.

The inactivated CRISPR effectors can comprise or be associated with one or more functional domains (e.g., via fusion protein, linker peptides, "GS" linkers, etc.). These functional domains can have various activities, e.g., methylase activity, demethylase activity, transcription activation activity, transcription repression activity, transcription release factor activity, histone modification activity, RNA cleavage activity, DNA cleavage activity, nucleic acid binding activity, and switch activity (e.g., light inducible). In some embodiments, the functional domains are Krüppel associated box (KRAB), VP64, VP16, Fok1, P65, HSF1, MyoD1, and biotin-APEX.

The positioning of the one or more functional domains on the inactivated CRISPR effectors is one that allows for correct spatial orientation for the functional domain to affect the target with the attributed functional effect. For example, if the functional domain is a transcription activator (e.g., VP16, VP64, or p65), the transcription activator is placed in a spatial orientation that allows it to affect the transcription of the target. Likewise, a transcription repressor is positioned to affect the transcription of the target, and a nuclease (e.g., Fok1) is positioned to cleave or partially cleave the target. In some embodiments, the functional domain is positioned at the N-terminus of the CRISPR effector. In some embodiments, the functional domain is positioned at the C-terminus of the CRISPR effector. In some embodiments, the inactivated CRISPR effector is modified to comprise a first functional domain at the N-terminus and a second functional domain at the C-terminus.

Split Enzymes

The present disclosure also provides a split version of the CRISPR effectors described herein. The split version of the CRISPR effectors may be advantageous for delivery. In some embodiments, the CRISPR effectors are split to two parts of the enzymes, which together substantially comprises a functioning CRISPR effector.

The split can be done in a way that the catalytic domain(s) are unaffected. The CRISPR effectors may function as a nuclease or may be inactivated enzymes, which are essentially RNA-binding proteins with very little or no catalytic activity (e.g., due to mutation(s) in its catalytic domains).

In some embodiments, the nuclease lobe and α-helical lobe are expressed as separate polypeptides. Although the lobes do not interact on their own, the RNA guide recruits them into a ternary complex that recapitulates the activity of full-length CRISPR effectors and catalyzes site-specific DNA cleavage. The use of a modified RNA guide abrogates split-enzyme activity by preventing dimerization, allowing for the development of an inducible dimerization system. The split enzyme is described, e.g., in Wright et al. "Rational design of a split-Cas9 enzyme complex," Proc. Natl. Acad. Sci., 112.10 (2015): 2984-2989, which is incorporated herein by reference in its entirety.

In some embodiments, the split enzyme can be fused to a dimerization partner, e.g., by employing rapamycin sensitive dimerization domains. This allows the generation of a chemically inducible CRISPR effector for temporal control of CRISPR effector activity. The CRISPR effector can thus be rendered chemically inducible by being split into two fragments, and rapamycin-sensitive dimerization domains can be used for controlled reassembly of the CRISPR effector.

The split point is typically designed in silico and cloned into the constructs. During this process, mutations can be introduced to the split enzyme and non-functional domains can be removed. In some embodiments, the two parts or fragments of the split CRISPR effector (i.e., the N-terminal and C-terminal fragments) can form a full CRISPR effector, comprising, e.g., at least 70%, at least 80%, at least 90%, at least 95%, or at least 99% of the sequence of the wild-type CRISPR effector.

Self-Activating or Inactivating Enzymes

The CRISPR effectors described herein can be designed to be self-activating or self-inactivating. In some embodiments, the CRISPR effectors are self-inactivating. For example, the target sequence can be introduced into the CRISPR effector coding constructs. Thus, the CRISPR effectors can cleave the target sequence, as well as the construct encoding the enzyme thereby self-inactivating their expression. Methods of constructing a self-inactivating CRISPR system is described, e.g., in Epstein et al., "Engineering a Self-Inactivating CRISPR System for AAV Vectors," Mol. Ther., 24 (2016): S50, which is incorporated herein by reference in its entirety.

In some other embodiments, an additional RNA guide, expressed under the control of a weak promoter (e.g., 7SK promoter), can target the nucleic acid sequence encoding the CRISPR effector to prevent and/or block its expression (e.g., by preventing the transcription and/or translation of the nucleic acid). The transfection of cells with vectors expressing the CRISPR effector, RNA guides, and RNA guides that target the nucleic acid encoding the CRISPR effector can lead to efficient disruption of the nucleic acid encoding the CRISPR effector and decrease the levels of CRISPR effector, thereby limiting the genome editing activity.

In some embodiments, the genome editing activity of a CRISPR effector can be modulated through endogenous RNA signatures (e.g., miRNA) in mammalian cells. The CRISPR effector switch can be made by using a miRNA-complementary sequence in the 5'-UTR of mRNA encoding the CRISPR effector. The switches selectively and efficiently respond to miRNA in the target cells. Thus, the switches can differentially control the genome editing by sensing endogenous miRNA activities within a heterogeneous cell population. Therefore, the switch systems can provide a framework for cell-type selective genome editing and cell engineering based on intracellular miRNA information (Hirosawa et al. "Cell-type-specific genome editing with a microRNA-responsive CRISPR-Cas9 switch," Nucl. Acids Res., 2017 Jul. 27; 45(13): e118).

Inducible CRISPR Effectors

The CRISPR effectors can be inducible, e.g., light inducible or chemically inducible. This mechanism allows for activation of the functional domain in a CRISPR effector. Light inducibility can be achieved by various methods known in the art, e.g., by designing a fusion complex wherein CRY2 PHR/CIBN pairing is used in split CRISPR effectors (see, e.g., Konermann et al., "Optical control of mammalian endogenous transcription and epigenetic states," Nature, 500.7463 (2013): 472). Chemical inducibility can be achieved, e.g., by designing a fusion complex wherein FKBP/FRB (FK506 binding protein/FKBP rapamycin binding domain) pairing is used in split CRISPR effectors. Rapamycin is required for forming the fusion complex, thereby activating the CRISPR effectors (see, e.g., Zetsche et al., "A split-Cas9 architecture for inducible genome editing and transcription modulation," Nature Biotech., 33.2 (2015): 139-142).

Furthermore, expression of a CRISPR effector can be modulated by inducible promoters, e.g., tetracycline or doxycycline controlled transcriptional activation (Tet-On and Tet-Off expression system), hormone inducible gene expression system (e.g., an ecdysone inducible gene expression system), and an arabinose-inducible gene expression system. When delivered as RNA, expression of the RNA targeting effector protein can be modulated via a riboswitch, which can sense a small molecule like tetracycline (see, e.g., Goldfless et al., "Direct and specific chemical control of eukaryotic translation with a synthetic RNA-protein interaction," Nucl. Acids Res., 40.9 (2012): e64-e64).

Various embodiments of inducible CRISPR effectors and inducible CRISPR systems are described, e.g., in U.S. Pat. No. 8,871,445, US 20160208243, and WO 2016205764, each of which is incorporated herein by reference in its entirety.

Functional Mutations

Various mutations or modifications can be introduced into a CRISPR effector as described herein to improve specificity and/or robustness. In some embodiments, the amino acid residues that recognize the Protospacer Adjacent Motif (PAM) are identified. The CRISPR effectors described herein can be modified further to recognize different PAMs, e.g., by substituting the amino acid residues that recognize PAM with other amino acid residues. In some embodiments, the CRISPR effectors can recognize, e.g., 5'-NTTN-3', 5'-NTTR-3', 5'-RTTR-3', 5'-TNNT-3', 5'-TNRT-3', 5'-TSRT-3', 5'-TGRT-3', 5'-TNRY-3', 5'-TTNR-3', 5'-TTYR-3', 5'-TTTR-3', 5'-TTCV-3', 5'-DTYR-3', 5'-WTTR-3', 5'-NNR-3', 5'-NYR-3', 5'-YYR-3', 5'-TYR-3', 5'-TTN-3', 5'-TTR-3', 5'-CNT-3', 5'-NGG-3', 5'-BGG-3', or 5'-R-3', wherein "N" is any nucleotide, "B" is C or G or T, "D" is A or G or T, "R" is A or G, "S" is G or C, "V" is A or C or G, "W" is A or T, and "Y" is C or T.

In some embodiments, the CRISPR effectors described herein can be mutated at one or more amino acid residue to modify one or more functional activities. For example, in some embodiments, the CRISPR effector is mutated at one or more amino acid residues to modify its helicase activity. In some embodiments, the CRISPR effector is mutated at one or more amino acid residues to modify its nuclease activity (e.g., endonuclease activity or exonuclease activity). In some embodiments, the CRISPR effector is mutated at one or more amino acid residues to modify its ability to functionally associate with an RNA guide. In some embodiments, the CRISPR effector is mutated at one or more amino acid residues to modify its ability to functionally associate with a target nucleic acid.

In some embodiments, the CRISPR effectors described herein are capable of cleaving a target nucleic acid molecule. In some embodiments, the CRISPR effector cleaves both strands of the target nucleic acid molecule. However, in some embodiments, the CRISPR effector is mutated at one or more amino acid residues to modify its cleaving activity. For example, in some embodiments, the CRISPR effector may comprise one or more mutations that increase the ability of the CRISPR effector to cleave a target nucleic acid. In another example, in some embodiments, the CRISPR effector may comprise one or more mutations that render the enzyme incapable of cleaving a target nucleic acid. In other embodiments, the CRISPR effector may comprise one or more mutations such that the enzyme is capable of cleaving a strand of the target nucleic acid (i.e., nickase activity). In some embodiments, the CRISPR effector is capable of cleaving the strand of the target nucleic acid that is complementary to the strand that the RNA guide hybridizes to. In some embodiments, the CRISPR effector is capable of cleaving the strand of the target nucleic acid that the RNA guide hybridizes to.

In some embodiments, one or more residues of a CRISPR effector disclosed herein are mutated to an arginine moiety. In some embodiments, one or more residues of a CRISPR effector disclosed herein are mutated to a glycine moiety. In some embodiments, one or more residues of a CRISPR effector disclosed herein are mutated based upon consensus residues of a phylogenetic alignment of CRISPR effectors disclosed herein.

In some embodiments, a CRISPR effector described herein may be engineered to comprise a deletion in one or more amino acid residues to reduce the size of the enzyme while retaining one or more desired functional activities (e.g., nuclease activity and the ability to interact functionally with an RNA guide). The truncated CRISPR effector may be used advantageously in combination with delivery systems having load limitations.

In one aspect, the present disclosure provides nucleic acid sequences that are at least 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99% identical to the nucleic sequences described herein, while maintaining the domain architecture shown in FIG. 2. In another aspect, the present disclosure also provides amino acid sequences that are at least 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99% identical to the amino acid sequences described herein, while maintaining the domain architecture shown in FIG. 2.

In some embodiments, the nucleic acid sequences have at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that are the same as the sequences described herein. In some embodiments, the nucleic acid sequences have at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that is different from the sequences described herein.

In some embodiments, the amino acid sequences have at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is the same as the sequences described herein. In some embodiments, the amino acid sequences have at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is different from the sequences described herein.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In general, the length of a reference sequence aligned for comparison purposes should be at least 80% of the length of the reference sequence, and in some embodiments at least 90%, 95%, or 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences. For purposes of the present disclosure, the comparison of sequences and determination of percent identity between two sequences can be accomplished using a Blossum 62 scoring matrix with a gap penalty of 12, a gap extend penalty of 4, and a frameshift gap penalty of 5.

In some embodiments, a nuclease comprises a sequence set forth as $PX_1X_2X_3X_4F$ (SEQ ID NO: 216), wherein $X_1$ is L or M or I or C or F, $X_2$ is Y or W or F, $X_3$ is K or T or C or R or W or Y or H or V, and $X_4$ is I or L or M. In some embodiments, the sequence set forth in SEQ ID NO: 216 is an N-terminal sequence. In some embodiments, a nuclease comprises a sequence set forth as $RX_1X_2X_3L$ (SEQ ID NO: 217), wherein $X_1$ is I or L or M or Y or T or F, $X_2$ is R or Q or K or E or S or T, and $X_3$ is L or I or T or C or M or K. In some embodiments, a nuclease comprises a sequence set forth as $NX_1YX_2$ (SEQ ID NO: 218), wherein $X_1$ is I or L or F and $X_2$ is K or R or V or E. In some embodiments, a nuclease comprises a sequence set forth as $KX_1X_2X_3FAX_4X_5KD$ (SEQ ID NO: 219), wherein $X_1$ is T or I or N or A or S or F or V, $X_2$ is I or V or L or S, $X_3$ is H or S or G or R, $X_4$ is D or S or E, and $X_5$ is I or V or M or T or N. In some embodiments of any of the systems described herein, the sequence of SEQ ID NO: 219 is a C-terminal sequence. In some embodiments, a nuclease comprises a sequence set forth as $LX_1NX_2$ (SEQ ID NO: 220), wherein $X_1$ is G or S or C or T and $X_2$ is N or Y or K or S. In some embodiments of any of the systems described herein, the sequence of SEQ ID NO: 220 is a C-terminal sequence. In some embodiments, a nuclease comprises a sequence set forth as $PX_1X_2X_3X_4SQX_5DS$ (SEQ ID NO: 221), wherein $X_1$ is S or P or A, $X_2$ is Y or S or A or P or E or Y or Q or N, $X_3$ is F or Y or H, $X_4$ is T or S, and $X_5$ is M or T or I. In some embodiments of any of the systems described herein, the sequence of SEQ ID NO: 221 is a C-terminal sequence. In some embodiments, a nuclease comprises a sequence set forth as $KX_1X_2VRX_3X_4QEX_5H$ (SEQ ID NO: 222), wherein $X_1$ is N or K or W or R or E or T or Y, $X_2$ is M or R or L or S or K or V or E or T or I or D, $X_3$ is L or R or H or P or T or K or Q of P or S or A, $X_4$ is G or Q or N or R or K or E or I or T or S or C, and $X_5$ is R or W or Y or K or T or F or S or Q. In some embodiments of any of the systems described herein, the sequence of SEQ ID NO: 222 is a C-terminal sequence. In some embodiments, a nuclease comprises a sequence set forth as $X_1NGX_2X_3X_4DX_5NX_6X_7X_8N$ (SEQ ID NO: 223), wherein $X_1$ is I or K or V or L, $X_2$ is L or M, $X_3$ is N or H or P, $X_4$ is A or S or C, $X_5$ is V or Y or I or F or T or N, $X_6$ is A or S, $X_7$ is S or A or P, and $X_8$ is M or C or L or R or N or S or K or L. In some embodiments of any of the systems described herein, the sequence of SEQ ID NO: 223 is a C-terminal sequence.

RNA and RNA Guide Modifications

In some embodiments, an RNA guide described herein comprises a uracil (U). In some embodiments, an RNA guide described herein comprises a thymine (T). In some embodiments, a direct repeat sequence of an RNA guide described herein comprises a uracil (U). In some embodiments, a direct repeat sequence of an RNA guide described herein comprises a thymine (T). In some embodiments, a direct repeat sequence according to TABLE 2 or TABLE 8 comprises a sequence comprising a uracil, in one or more places indicated as thymine in the corresponding sequences in TABLE 2 or TABLE 8.

In some embodiments, the direct repeat comprises only one copy of a sequence that is repeated in an endogenous CRISPR array. In some embodiments, the direct repeat is a full-length sequence adjacent to (e.g., flanking) one or more spacer sequences found in an endogenous CRISPR array. In some embodiments, the direct repeat is a portion (e.g., processed portion) of a full-length sequence adjacent to (e.g., flanking) one or more spacer sequences found in an endogenous CRISPR array.

Spacer and Direct Repeat

The spacer length of RNA guides can range from about 15 to 55 nucleotides. The spacer length of RNA guides can range from about 20 to 45 nucleotides. In some embodiments, the spacer length of an RNA guide is at least 15 nucleotides, at least 16 nucleotides, at least 17 nucleotides, at least 18 nucleotides, at least 19 nucleotides, at least 20 nucleotides, at least 21 nucleotides, or at least 22 nucleotides. In some embodiments, the spacer length is from 15 to 17 nucleotides, from 15 to 23 nucleotides, from 16 to 22 nucleotides, from 17 to 20 nucleotides, from 20 to 24 nucleotides (e.g., 20, 21, 22, 23, or 24 nucleotides), from 23 to 25 nucleotides (e.g., 23, 24, or 25 nucleotides), from 24 to 27 nucleotides, from 27 to 30 nucleotides, from 30 to 45 nucleotides (e.g., 30, 31, 32, 33, 34, 35, 40, or 45 nucleotides), from 30 or 35 to 40 nucleotides, from 41 to 45 nucleotides, from 45 to 50 nucleotides, or longer.

In some embodiments, the direct repeat length of the RNA guide is at least 16 nucleotides, or is from 16 to 20 nucleotides (e.g., 16, 17, 18, 19, or 20 nucleotides). In some embodiments, the direct repeat length of the RNA guide is about 19 to about 40 nucleotides.

Exemplary direct repeat sequences (e.g., direct repeat sequences of pre-crRNAs (e.g., unprocessed crRNAs) or mature crRNAs (e.g., direct repeat sequences of processed crRNAs)) are shown in TABLE 2. See also TABLE 8.

TABLE 2

Exemplary direct repeat sequences of crRNA sequences.

| Effector | Direct Repeat Sequence |
| --- | --- |
| SEQ ID NO: 1 | ACTATGTTGGAATACATTTTTATAGGT ATTTACAACT (SEQ ID NO: 57) |
| SEQ ID NO: 2 | ATTGTTGGAATATCACTTTTGTAGGGT ATTCACAAC (SEQ ID NO: 58) |
| SEQ ID NO: 3 | AATGTTGTTCACCCTTTTT (SEQ ID NO: 59) |
| SEQ ID NO: 4 | CCTGTTGTGAATACTCTTTTATAGGTA TCAAACAAC (SEQ ID NO: 60) |
| SEQ ID NO: 10 | ATTGTTGTAGACACCTTTTTATAAGGA TTGAACAAC (SEQ ID NO: 62) CTTGTTGTATATGTCCTTTTATAGGTA TTAAACAAC (SEQ ID NO: 213) |
| SEQ ID NO: 14 | GTTGTTTAATACCTATAAAAGAATATA TACAACAAG (SEQ ID NO: 128) |
| SEQ ID NO: 15 | CTTGTTGTATATACTCTTTTATAGGTA TTAAACAAC (SEQ ID NO: 63) |
| SEQ ID NO: 17 | GTTGTATCCACCGTATAAAACATAGTG TCCAACATC (SEQ ID NO: 130) |
| SEQ ID NO: 18 | GATGTTGTTATGCTGTTTTTGTAAGTA ATAAACAAC (SEQ ID NO: 70) |
| SEQ ID NO: 21 | ATTGTTGTACGAACCATTTTATATGGT AATAACAAC (SEQ ID NO: 72) |
| SEQ ID NO: 22 | ACTGTAAAACCCCTGCAGATGAAAGGA AAGTACAACAGT (SEQ ID NO: 73) |
| SEQ ID NO: 23 | ATCATGTTGTACATACTATTTTTTAAG TATTAAACAACTA (SEQ ID NO: 74) |
| SEQ ID NO: 24 | CTTGTTGTATATACTCTTTTATAGGTA TTAAACAAC (SEQ ID NO: 63) |
| SEQ ID NO: 27 | ATTGTTGGGGTACTTCTTTTATAGGGT ACTCACAAC (SEQ ID NO: 76) |
| SEQ ID NO: 28 | ATTGTTGTAGACCTTGTGTTTTAGGGG TCTAACAACG (SEQ ID NO: 77) |
| SEQ ID NO: 29 | GTTGTAAATACATCTCATATTGTATTC CAACACAGT (SEQ ID NO: 139) |
| SEQ ID NO: 31 | ATTGTTGGAATATCACTTTTGTAGGGT ATTCACAAC (SEQ ID NO: 58) |
| SEQ ID NO: 32 | AATTGTTGAGATACCGTTTTTTATGGT ATTGGCAAC (SEQ ID NO: 80) |

TABLE 2-continued

Exemplary direct repeat sequences of crRNA sequences.

| Effector | Direct Repeat Sequence |
| --- | --- |
| SEQ ID NO: 35 | ATTGTTGTAGACCTTGTGTTTTAGGGG TCTAACAACG (SEQ ID NO: 77) |
| SEQ ID NO: 36 | GTTGTAAATACATCTCATATTGTATTC CAACACAGT (SEQ ID NO: 139) |
| SEQ ID NO: 38 | AATTGTTGAGATACCGTTTTTTATGGT ATTGGCAAC (SEQ ID NO: 80) |
| SEQ ID NO: 39 | ATTGTTGGAATATCACTTTTGTAGGGT ATTCACAAC (SEQ ID NO: 58) |
| SEQ ID NO: 41 | ATTGTGTTGGGATACACTTTTATAGGT ATTTACAAC (SEQ ID NO: 83) |
| SEQ ID NO: 42 | TATTGTTGAATACCTTTCTTATAAAGG TAATTACAAC (SEQ ID NO: 84) |
| SEQ ID NO: 44 | ATTGTTGAATGTATTCTTTTTTAGGAC AGATACAAC (SEQ ID NO: 86) |
| SEQ ID NO: 45 | GTTGTATCCACCGTATAAAACATAGTG TCCAACATC (SEQ ID NO: 130) |
| SEQ ID NO: 46 | TATTGTTGAATACCTTTCTTATAAAGG TAATTACAAC (SEQ ID NO: 84) |
| SEQ ID NO: 47 | ATTGTTGAATGGTATCTTTTATAGACT GATTACAACT (SEQ ID NO: 87) |
| SEQ ID NO: 48 | ATTGTTGGATAATAGGTTTTTTATCTT AATTACAAC (SEQ ID NO: 88) |
| SEQ ID NO: 51 | TATTGTTGAATACCTTTCTTATAAAGG TAATTACAAC (SEQ ID NO: 84) |
| SEQ ID NO: 53 | TATTGTTGAATACCTTTCTTATAAAGG TAATTACAAC (SEQ ID NO: 84) |
| SEQ ID NO: 55 | ATTGTTGGATAATAGGTTTTTTATCTT AATTACAAC (SEQ ID NO: 88) |
| SEQ ID NO: 56 | ATTGTTGTAGATACCTTTTGTAAGGA TTGAACAAC (SEQ ID NO: 90) |

In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 1, and the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 57. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 2, and the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 58. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 3, and the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 59. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 4, and the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 60. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 10, and the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 62 or SEQ ID NO: 213. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 14, and the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 128. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 15, and the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 63. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 17, and the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 130. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 18, and the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 70. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 21, and the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 72. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 22, and the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 73. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 23, and the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 74. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 24, and the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 63. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 27, and the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 76. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 28, and the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 77. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 29, and the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 139. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 31, and the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 58. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 32, and the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 80. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 35, and the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 77. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 36, and the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 139. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 38, and the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 80. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 39, and the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 58. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 41, and the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 83. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 42, and the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 84. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 44, and the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 86. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 45, and the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 130. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 46, and the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 84. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 47, and the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 87. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 48, and the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 88. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 51, and the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 84. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 53, and the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 84. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 55, and the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 88. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 56, and the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 90.

Figure 3:
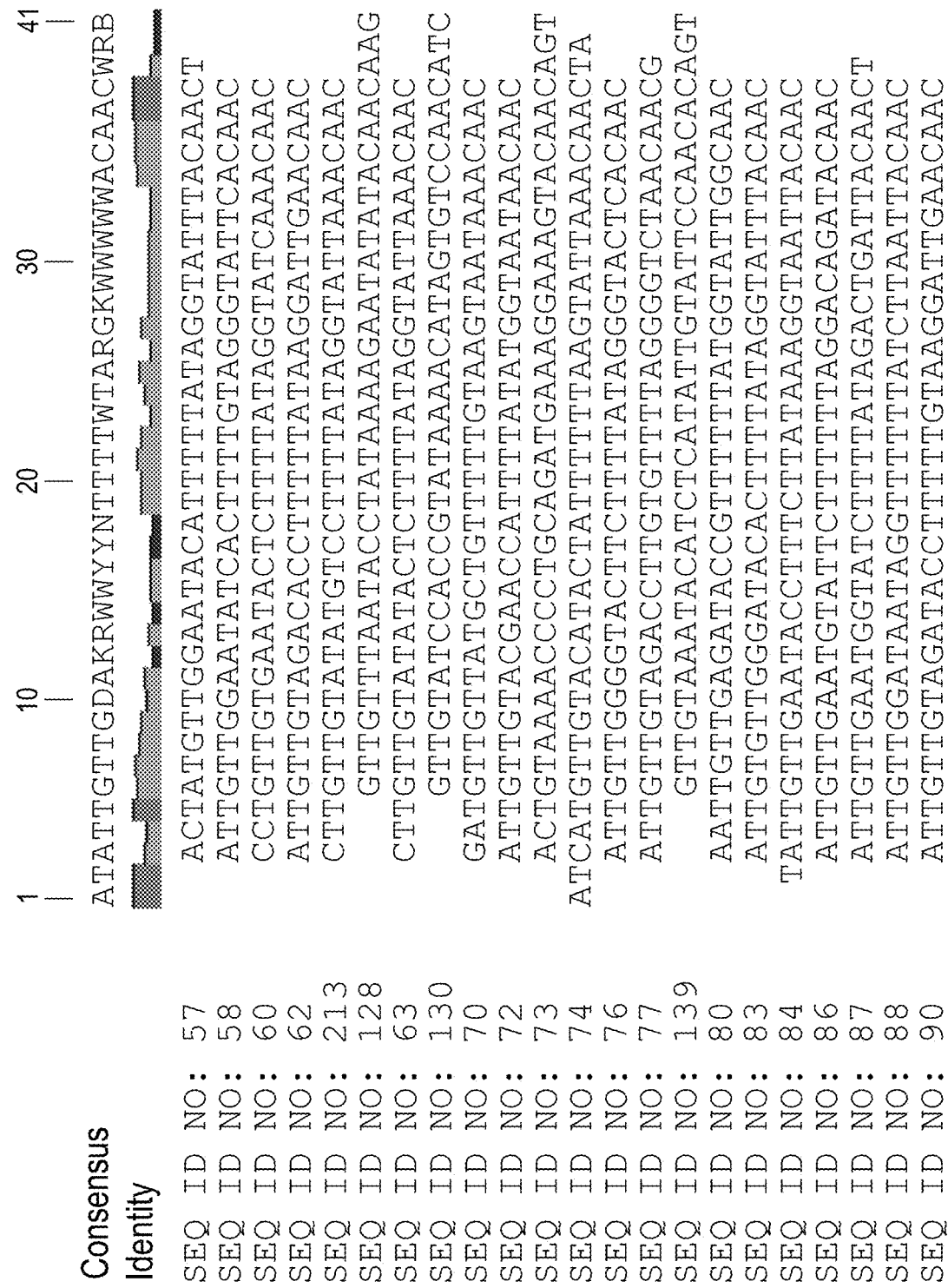
FIG. 3 shows an alignment of the direct repeat sequences of SEQ ID NOs: 57, 58, 60, 62, 63, 70, 72-74, 76, 77, 80, 83, 84, 86-88, 90, 128, 130, 139, and 213. The consensus sequence (SEQ ID NO: 230) is shown at the top of the alignment.

In some embodiments, an RNA guide comprises a direct repeat sequence set forth in FIG. 3. For example, in some embodiments, the RNA guide comprises a direct repeat of the consensus sequence shown in FIG. 3 or a portion of the consensus sequence shown in FIG. 3. In some embodiments, an RNA guide comprises a direct repeat having a sequence set forth as $X_1X_2TX_3X_4X_5X_6X_7X_8$ (SEQ ID NO: 224), wherein $X_1$ is A or C or G, $X_2$ is T or C or A, $X_3$ is T or G or A, $X_4$ is T or G, $X_5$ is T or G or A, $X_6$ is G or T or A, $X_7$ is T or G or A, and $X_8$ is A or G or T. For example, in some embodiments, an RNA guide comprises a direct repeat having a sequence set forth as ATTGTTGDA (SEQ ID NO: 225). In some embodiments, SEQ ID NO: 224 is proximal to the 5' end of the direct repeat. In some embodiments, SEQ ID NO: 225 is proximal to the 5' end of the direct repeat. In some embodiments, an RNA guide comprises a direct repeat having a sequence set forth as $X_1X_2X_3X_4X_5X_6X_7X_8X_9$ (SEQ ID NO: 226), wherein $X_1$ is T or C or A, $X_2$ is T or A or G, $X_3$ is T or C or A, $X_4$ is T or A, $X_5$ is T or A or G, $X_6$ is T or A, $X_7$ is A or T, $X_8$ is A or G or C or T, and $X_9$ is G or A or C. For example, in some embodiments, an RNA guide comprises a direct repeat having a sequence set forth as TTTTWTARG (SEQ ID NO: 227). In some embodiments, an RNA guide comprises a direct repeat having a sequence set forth as $X_1X_2X_3AC$ (SEQ ID NO: 228), wherein $X_1$ is A or C or G, $X_2$ is C or A, and $X_3$ is A or C. For example, in some embodiments, an RNA guide comprises a direct repeat having a sequence set forth as ACAAC (SEQ ID NO: 229). In some embodiments, SEQ ID NO: 228 is proximal to the 3' end of the direct repeat. In some embodiments, SEQ ID NO: 229 is proximal to the 3' end of the direct repeat.

In some embodiments, the spacer of an RNA guide binds to a target nucleic acid adjacent to a PAM sequence of TABLE 3. For example, in some embodiments, a complex of an effector and an RNA guide disclosed herein binds to a target nucleic acid adjacent to a PAM sequence as indicated in TABLE 3.

TABLE 3

PAM sequences corresponding to CLUST.091979 effectors.

| Effector | PAM Sequence |
|---|---|
| SEQ ID NO: 1 | 5'-TTNT-3'<br>5'-TNRT-3' |
| SEQ ID NO: 2 | 5'-TTR-3'<br>5'-WTTR-3' |
| SEQ ID NO: 4 | 5'-NNR-3'<br>5'-NTTN-3'<br>5'-NTTR-3'<br>5'-TTTN-3'<br>5'-TTTG-3' |
| SEQ ID NO: 10 | 5'-NTTN-3'<br>5'-RTTR-3'<br>5'-ATTR-3'<br>5'-RTTG-3'<br>5'-ATTG-3'<br>5'-GTTA-3' |
| SEQ ID NO: 14 | 5'-TTN-3'<br>5'-TTY-3'<br>5'-YYR-3' |
| SEQ ID NO: 15 | 5'-CNT-3' |
| SEQ ID NO: 21 | 5'-TTCV-3'<br>5'-TTYR-3' |
| SEQ ID NO: 23 | 5'-GTA-3' |
| SEQ ID NO: 24 | 5'-CNT-3' |
| SEQ ID NO: 27 | 5'-TTR-3'<br>5'-YYR-3'<br>5'-TYR-3' |
| SEQ ID NO: 28 | 5'-NGG-3'<br>5'-BGG-3'<br>5'-CGG-3'<br>5'-GG-3' |
| SEQ ID NO: 31 | 5'-TTR-3' |
| SEQ ID NO: 32 | 5'-TYR-3' |
| SEQ ID NO: 35 | 5'-NGG-3'<br>5'-BGG-3'<br>5'-CGG-3'<br>5'-GG-3' |
| SEQ ID NO: 38 | 5'-TYR-3' |
| SEQ ID NO: 39 | 5'-TTR-3' |
| SEQ ID NO: 41 | 5'-TYR-3' |
| SEQ ID NO: 42 | 5'-TYR-3'<br>5'-TTYR-3'<br>5'-DTYR-3' |
| SEQ ID NO: 44 | 5'-TTNR-3'<br>5'-TTTR-3' |
| SEQ ID NO: 46 | 5'-TYR-3'<br>5'-TTYR-3'<br>5'-DTYR-3' |
| SEQ ID NO: 48 | 5'-YYR-3'<br>5'-TTR-3'<br>5'-TTG-3' |
| SEQ ID NO: 51 | 5'-TYR-3'<br>5'-TTYR-3'<br>5'-DTYR-3' |

TABLE 3-continued

PAM sequences corresponding to CLUST.091979 effectors.

| Effector | PAM Sequence |
|---|---|
| SEQ ID NO: 53 | 5'-TYR-3' |
|  | 5'-TTYR-3' |
|  | 5'-DTYR-3' |
| SEQ ID NO: 55 | 5'-YYR-3' |
|  | 5'-TTR-3' |
|  | 5'-TTG-3' |
| SEQ ID NO: 56 | 5'-TTG-3' |
|  | 5'-NYR-3' |
|  | 5'-TYR-3' |

In some embodiments, an RNA guide further comprises a tracrRNA. In some embodiments, the tracrRNA is not required (e.g., the tracrRNA is optional). In some embodiments, the tracrRNA is a portion of the non-coding sequences shown in TABLE 9. For example, in some embodiments, the tracrRNA is a sequence of TABLE 4.

TABLE 4

Exemplary tracrRNA sequences.

| Effector | tracrRNA Sequence |
|---|---|
| SEQ ID NO: 1 | ATTGGGACTTCCGGAAGTAAAATATCCACCTGAGGATTTTAGGACAT ATAATTTCTAATAAAAATGAACGGAAAAATTTCCGTTCATTTTTTTT TGTTTATT (SEQ ID NO: 152) TATTGGGACTTCCGGAAGTAAAATATCCACCTGAGGATTTTAGGACA TATAATTTCTAATAAAAATGAACGGAAAAATTTCCGTTCATTTTTTT TTGTTTATTG (SEQ ID NO: 153) GACGAGAACGGAGTGTGGCTCCTGAGGAAAAACGACAAACATCCAA CATATTTTATCTACCAGAACGGAACACTCTATCAATATGAGGAAGAT TGATTAGTTGATGTTTTCATAATAATTTTATCTGGAATTTGAAAAGAT TCCAGATTTTTTTTTATTTCG (SEQ ID NO: 154) |
| SEQ ID NO: 2 | GCAATCAACAAGACTTTCATTTTCAAGGCAAAATGCGATAAGAACG ATGTCATATCGTTATGGGAA (SEQ ID NO: 155) GATGCTCCGAAAACGTGGTTGTTCGGACAACAAAAAAATGAATGTT TCTAATGTATTAA (SEQ ID NO: 156) GACGGAAAAATAAATGAGGATGGTATGTTTGTTGAAAACTTGGAAT AATTCTGTATATACCAATTAGAAT (SEQ ID NO: 157) TGTTGATTGCTGATTCTTCGTTGTTTGATTTGTGTTGTGCCATAATCT TAAAATT (SEQ ID NO: 158) |
| SEQ ID NO: 3 | CGCAAGATATAAGGCAATCGGAAACGGATGGACAGTTGATGTAATT TCACATATTTTTAAGAATTTGAAAAATTAATTTGGTA (SEQ ID NO: 159) GGACATTTCGTAAATCATATGGAGATACGGAGTTCAAGTCAATTGA AGAGCTTCCTGAATTTAGAGATAACATACTTATACAACTAGATTGAT TG (SEQ ID NO: 160) ATCAATACATAGATGATGAGAAATGGAGAAAAAAATTTGTTCGCCC AACAAACACTAAT (SEQ ID NO: 161) |
| SEQ ID NO: 14 | CTGGTAATACTGTAAAATCTCCGTGTATAGGGCAAGTAATTGTAACT GGGGTAATTCTATCTACTATTATAGTTTTAGAA (SEQ ID NO: 162) |
| SEQ ID NO: 17 | CAGAAGTCGTTCAAGTTCAAGGTCAAAACGGACAAGGAGACGGTCG AATTATTCAG (SEQ ID NO: 163) GGGAGGGTGACATTCAGAAGTCGTTCAAGTTCAAGGTCAAAACGGA CAAGGAGACGGTCGAATTAT (SEQ ID NO: 164) AAGTGTCTTCAACACATTGAAGAAAACTCTCGGTGCAATATATGGA AAGCTCGATGAAAACGGAAATTTTATTGAGAATGAATGTAATAAGT AACTGGAATA (SEQ ID NO: 165) CCGTGGGAGGATTTGGATTTGGTTGAAGACATCAGAAAAATTTTCGA AATGGAATAGAGGGAACCGGAATTTTTTCCGGTTTTCTTTGTCCTTT CGA (SEQ ID NO: 166) |
| SEQ ID NO: 18 | CAGAGTAACCTTTCCTGATATGTTGTTACACATTTTTGTAAGTGTTAA ACAACTGACGCATTGATATTGCCTTGTCTATTAA (SEQ ID NO: 167) CAATCGCGAGTTTATACTGAAATGTTGTTACACTGTTTTTGTAAGTGT TAAACAACCTTGCACAAATGTCATCTACCAGTAC (SEQ ID NO: 168) |
| SEQ ID NO: 21 | CCGAGCGACCCACAAACCTATTGTCGTACGCATCATTTCACATGATA ATAACAACGAATATTCCTGCAAGCATGATTT (SEQ ID NO: 169) TATGACATTATGATATTGTTGTATGCATCATTTCACATGGTAATAAC AACGAAGAGAAACACCGAGCGACCCACAAA (SEQ ID NO: 170) ACATCTTTTATGACATTATGATATTGTTGTATGCATCATTTCACATGG TAATAACAACGAAGAGAAACACCGAGCGACCCACAAA (SEQ ID NO: 171) |

TABLE 4-continued

Exemplary tracrRNA sequences.

| Effector | tracrRNA Sequence |
|---|---|
| SEQ ID NO: 22 | GCTAAAATATAGTCCTGTGGATGTTGAATACATTTCTTTTAAGTGTA<br>CTTACAACCAACGCTGTACACATTGCTAATGGATG (SEQ ID NO: 172)<br>TGCTAAAATATAGTCCTGTGGATGTTGAATACATTTCTTTTAAGTGT<br>ACTTACAACCAACGCTGTACACATTGCTAATGGATG (SEQ ID NO: 173)<br>CAACACCAAGGCTGAGGCAAAGAAGAGGGCTGATGATATGAACAA<br>ACAGAATAGGGTCATACACCAGCTGTCTGTTTATTTGTGTCC (SEQ ID NO: 174)<br>AATTAGACTGATAAACAAAGAATAATGAGAACTATAATAGGGAGGT<br>GTACCCCCGAATTTAAGCCAGTGGAGAACCATACAAACCTATCATAT<br>AG (SEQ ID NO: 175) |
| SEQ ID NO: 23 | TGGGTATGCGTTGTTTAATACTTAAAAAAATGTATGTACAACATGTC<br>TGTGGAAAGTCTTTCTATTGTATAT (SEQ ID NO: 176)<br>CGTTGTTTAATACTTAAAAAAATGTATGTACAACATGTCTGTGGAAA<br>GTCTTTCTATTGTATATAGGA (SEQ ID NO: 177)<br>TGGGTATGCGTTGTTTAATACTTAAAAAAATGTATGTACAACATGTC<br>TGTGGAAAGTCTTTCTATTGTATATAGGAATTTTATATAATTATTTAA<br>TTATCAATGAATTATATTAGTAT (SEQ ID NO: 178)<br>GGTGGGTATGCGTTGTTTAATACTTAAAAAAATGTATGTACAACATG<br>TCTGTGGAAAG (SEQ ID NO: 179) |
| SEQ ID NO: 27 | AATGAACGAGATTGTTGGGATATACCTTTTATAGGATTTTCACAACA<br>TCTGAGTTGTTTGATGTTAAAAACTT (SEQ ID NO: 180)<br>GATAAAAATGAACGAGATTGTTGGGATATACCTTTTATAGGATTTTC<br>ACAACATCTGAGTTGTTTGATGTTAAAAACTTT (SEQ ID NO: 181) |
| SEQ ID NO: 29 | GCTAATATAAAGATTGTACTGTGTTGAGATACACTTTTAGAGGTATT<br>TACAACAAAATGCGTGATATGGAAATGA (SEQ ID NO: 182)<br>ATACCAACATAAATACAGGTCTTGCTGTTTCTGGTCGGTCGTAAACA<br>CCTCTAAAAGGATTGTTTCGACATAGGTTACTGACGCTTCAAG (SEQ ID NO: 183)<br>AATGAAGAAATAACTGTGTTGAGATACACTTTTAGAGGTATTTACAA<br>CACCATATAAACCTGACCATCTCCT (SEQ ID NO: 184) |
| SEQ ID NO: 31 | AGGAAGATGTCAGACGTTTTTATTGTTGGAATACTCGTTTTTTACGG<br>TATTTACAACTGCCCCGTAGCGGAATCAAAATACCAC (SEQ ID NO: 185)<br>ATGTCAGACGTTTTTATTGTTGGAATACTCGTTTTTTACGGTATTTAC<br>AACTGCCCCGTAGCGGAATCAAAATACC (SEQ ID NO: 186)<br>AAATAACAAAAATTCTGGACGGGAAAGGAAGATGTCAGACGTTTTT<br>ATTGTTGGAATACTCGTTTTTTACGGTATTTACAACTGCCCCGTAGCG<br>GAATC (SEQ ID NO: 187)<br>ATAACAAAAATTCTGGACGGGAAAGGAAGATGTCAGACGTTTTTAT<br>TGTTGGAATACTCGTTTTTTACGGTATTTACAACTGCCCCGTAGCGG<br>AAT (SEQ ID NO: 188) |
| SEQ ID NO: 32 | TATTGCAACTATTACAACAAACTTAGCGAATGGATTGGCAAAGATAT<br>GTATAACACGCCG (SEQ ID NO: 189)<br>ATTGCAACTATTACAACAAACTTAGCGAATGGATTGGCAAAGATAT<br>GTATAACACGCCG (SEQ ID NO: 190) |
| SEQ ID NO: 36 | GCTAATATAAAGATTGTACTGTGTTGAGATACACTTTTAGAGGTATT<br>TACAACAAAATGCGTGATATGGAAATGA (SEQ ID NO: 182)<br>ATACCAACATAAATACAGGTCTTGCTGTTTCTGGTCGGTCGTAAACA<br>CCTCTAAAAGGATTGTTTCGACATAGGTTACTGACGCTTCAAG (SEQ ID NO: 183)<br>AATGAAGAAATAACTGTGTTGAGATACACTTTTAGAGGTATTTACAA<br>CACCATATAAACCTGACCATCTCCT (SEQ ID NO: 184) |
| SEQ ID NO: 38 | TATTGCAACTATTACAACAAACTTAGCGAATGGATTGGCAAAGATAT<br>GTATAACACGCCG (SEQ ID NO: 189)<br>ATTGCAACTATTACAACAAACTTAGCGAATGGATTGGCAAAGATAT<br>GTATAACACGCCG (SEQ ID NO: 190) |
| SEQ ID NO: 39 | AGGAAGATGTCAGACGTTTTTATTGTTGGAATACTCGTTTTTTACGG<br>TATTTACAACTGCCCCGTAGCGGAATCAAAATACCAC (SEQ ID NO: 185)<br>ATGTCAGACGTTTTTATTGTTGGAATACTCGTTTTTTACGGTATTTAC<br>AACTGCCCCGTAGCGGAATCAAAATACC (SEQ ID NO: 186)<br>AAATAACAAAAATTCTGGACGGGAAAGGAAGATGTCAGACGTTTTT<br>ATTGTTGGAATACTCGTTTTTTACGGTATTTACAACTGCCCCGTAGCG<br>GAATC (SEQ ID NO: 187)<br>ATAACAAAAATTCTGGACGGGAAAGGAAGATGTCAGACGTTTTTAT<br>TGTTGGAATACTCGTTTTTTACGGTATTTACAACTGCCCCGTAGCGG<br>AAT (SEQ ID NO: 188) |

TABLE 4-continued

Exemplary tracrRNA sequences.

| Effector | tracrRNA Sequence |
|---|---|

SEQ ID NO: 41 GTATGATGACAGAAGAAACACGGAAGACAATAGAGAGCGTCATAGT
GGTTCTCGGCATAGCAATCATGCTG (SEQ ID NO: 191)
ATGATGACAGAAGAAACACGGAAGACAATAGAGAGCGTCATAGTG
GTTCTCGGCATAGCAATCATGCTGGCAGCCGCCGTCCGAATAATGAC
GCAGAACAAAGCAATTGTGAAATATG (SEQ ID NO: 192)
AGAAGGTACTGCCGCCTTATGACCGACGAGAACGGAGTGTGGCTCC
TGAGGAAAAAC (SEQ ID NO: 193)
GACGAGAACGGAGTGTGGCTCCTGAGGAAAAACGACAAACATCCAA
CATATTTTATCTACCAGAACGGAACACTCTATCAATATGAGGAAGAT
TGATTAGTTGATGTTTTCATAATAATTTTATCTGGAATTTGAAAAGAT
TCCAGATTTTTTTTTATTTCG (SEQ ID NO: 194)

SEQ ID NO: 43 TCGTTGAATACGATATCGCCGAAACAATTGATTGGAGAAGTACGCTT
TGTTTCAAGACATGGAATACGTATGGTTCTCCTCAATGGGACTCGAA
GATCAAGAA (SEQ ID NO: 197)
ATCGTTGAATACGATATCGCCGAAACAATTGATTGGAGAAGTACGC
TTTGTTTCAAGACATGGAATACGTATGGTTCTCCTCAATGGGACTCG
AAGATCAAGAACCAG (SEQ ID NO: 198)
GAGCTTTTCTGGCAATGTAGACATTAAAGCTGGTATCGTTGAATACG
ATATCGCCGAAACAATTGATTGGAGA (SEQ ID NO: 199)

SEQ ID NO: 44 TTTTTGTTATATATTTGTCCTGTTAGGTTAAATCACCGCGCCTGATGA
CGAAGTCGGTGGTAGAATTAGACTAATATTAAATATGTCTCATG
(SEQ ID NO: 195)
CCTATTAGATATTCCGTATTTCTTTAAGACTGTTATAATACAAATATA
CTACAAATCATGCAATTTTTGATTTTTAACAAAA (SEQ ID NO: 196)

SEQ ID NO: 45 CAGAAGTCGTTCAAGTTCAAGGTCAAAACGGACAAGGAGACGGTCG
AATTATTCAG (SEQ ID NO: 163)
GGGAGGGTGACATTCAGAAGTCGTTCAAGTTCAAGGTCAAAACGGA
CAAGGAGACGGTCGAATTAT (SEQ ID NO: 164)
AAGTGTCTTCAACACATTGAAGAAAACTCTCGGTGCAATATATGGA
AAGCTCGATGAAAACGGAAATTTTATTGAGAATGAATGTAATAAGT
AACTGGAATA (SEQ ID NO: 165)
CCGTGGGAGGATTTGGATTTGGTTGAAGACATCAGAAAAATTTTCGA
AATGGAATAGAGGGAACCGGAATTTTTTCCGGTTTTTCTTTGTCCTTT
CGA (SEQ ID NO: 166)

SEQ ID NO: 48 TTTTTCATTGTTCTCAAATTGTTGGATAATGTTTTGTGTGTTTCATTTT
TGTCATTGTGTCACCTTAACTGACAAGGTGGCACATTTTTTATGTCA
AT (SEQ ID NO: 200)
TTTTCATTGTTCTCAAATTGTTGGATAATGTTTTGTGTGTTTCATTTTT
GTCATTGTGTCACCTTAACTGACAAGGTGGCACATTTTTTATGTCAA
TA (SEQ ID NO: 201)
AATATATCTGCTAAGGTCATATTTTTCATTGTTCTCAAATTGTTGGAT
AATGTTTTGTGTGTTTCATTTTTGTCATTGTGTCACCTTAACTGACAA
GGTGGCACATTTTTTATGTCAATATG (SEQ ID NO: 202)

SEQ ID NO: 52 TCGTTGAATACGATATCGCCGAAACAATTGATTGGAGAAGTACGCTT
TGTTTCAAGACATGGAATACGTATGGTTCTCCTCAATGGGACTCGAA
GATCAAGAA (SEQ ID NO: 197)
ATCGTTGAATACGATATCGCCGAAACAATTGATTGGAGAAGTACGC
TTTGTTTCAAGACATGGAATACGTATGGTTCTCCTCAATGGGACTCG
AAGATCAAGAACCAG (SEQ ID NO: 198)
GAGCTTTTCTGGCAATGTAGACATTAAAGCTGGTATCGTTGAATACG
ATATCGCCGAAACAATTGATTGGAGA (SEQ ID NO: 199)

SEQ ID NO: 55 TTTTTCATTGTTCTCAAATTGTTGGATAATGTTTTGTGTGTTTCATTTT
TGTCATTGTGTCACCTTAACTGACAAGGTGGCACATTTTTTATGTCA
AT (SEQ ID NO: 200)
TTTTCATTGTTCTCAAATTGTTGGATAATGTTTTGTGTGTTTCATTTTT
GTCATTGTGTCACCTTAACTGACAAGGTGGCACATTTTTTATGTCAA
TA (SEQ ID NO: 201)
AATATATCTGCTAAGGTCATATTTTTCATTGTTCTCAAATTGTTGGAT
AATGTTTTGTGTGTTTCATTTTTGTCATTGTGTCACCTTAACTGACAA
GGTGGCACATTTTTTATGTCAATATG (SEQ ID NO: 202)

SEQ ID NO: 56 ACAAATTTTTGATTATGGCACACAAAAAGAACATAGGAGCAGAGAT
AGTAAAAACTTACTCTTTTAAGGTGAAGA (SEQ ID NO: 203)
TTATTTTATAGGTAATAATAGAGCTAACAAGCATTAACAATTATTAAAA
CGATTTATATTGAAAATAAATTTTGTGGGAATATTTATTTTTACTACC
TTTGCATCGTAATACAATTAAACAAATTTTTGATTATGGCA (SEQ ID
NO: 204)

In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 1, and the tracrRNA sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 152, SEQ ID NO: 153, or SEQ ID NO: 154. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 2, and the tracrRNA sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 155, SEQ ID NO: 156, SEQ ID NO: 157, or SEQ ID NO: 158. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 3, and the tracrRNA sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO:159, SEQ ID NO: 160, or SEQ ID NO: 161. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 14, and the tracrRNA sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 162. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 17, and the tracrRNA sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 163, SEQ ID NO: 164, SEQ ID NO: 165, or SEQ ID NO: 166. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 18, and the tracrRNA sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 167 or SEQ ID NO: 168. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 21, and the tracrRNA sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO:169, SEQ ID NO: 170, or SEQ ID NO: 171. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 22, and the tracrRNA sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 172, SEQ ID NO: 173, SEQ ID NO: 174, or SEQ ID NO: 175. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 23, and the tracrRNA sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 176, SEQ ID NO: 177, SEQ ID NO: 178, or SEQ ID NO: 179. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 27, and the tracrRNA sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 180 or SEQ ID NO: 181. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 29, and the tracrRNA sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 182, SEQ ID NO: 183, or SEQ ID NO: 184. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 31, and the tracrRNA sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 185, SEQ ID NO: 186, SEQ ID NO: 187, or SEQ ID NO: 188. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 32, and the tracrRNA sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 189 or SEQ ID NO: 190. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 36, and the tracrRNA sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 182, SEQ ID NO: 183, or SEQ ID NO: 184. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 38, and the tracrRNA sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 189 or SEQ ID NO: 190. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 39, and the tracrRNA sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 185, SEQ ID NO: 186, SEQ ID NO:187, or SEQ ID NO: 188. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 41, and the tracrRNA sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 191, SEQ ID NO: 192, SEQ ID NO: 193, or SEQ ID NO: 194. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 43, and the tracrRNA sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 197, SEQ ID NO: 198, or SEQ ID NO: 199. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 44, and the tracrRNA sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 195 or SEQ ID NO: 196. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 45, and the tracrRNA sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 163, SEQ ID NO: 164, SEQ ID NO: 165, or SEQ ID NO: 166. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 48, and the tracrRNA sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 200, SEQ ID NO: 201, or SEQ ID NO: 202. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 52, and the tracrRNA sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 197, SEQ ID NO: 198, or SEQ ID NO: 199. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 55, and the tracrRNA sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 200, SEQ ID NO: 201, or SEQ ID NO: 202. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 56, and the tracrRNA sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 203 or SEQ ID NO: 204.

The RNA guide sequences can be modified in a manner that allows for formation of the CRISPR complex and successful binding to the target, while at the same time not allowing for successful nuclease activity (i.e., without nuclease activity/without causing indels). These modified guide sequences are referred to as "dead guides" or "dead guide sequences." These dead guides or dead guide sequences may be catalytically inactive or conformationally inactive with regard to nuclease activity. Dead guide sequences are typically shorter than respective guide sequences that result in active RNA cleavage. In some embodiments, dead guides are 5%, 10%, 20%, 30%, 40%, or 50% shorter than respective RNA guides that have nuclease activity. Dead guide sequences of RNA guides can be from 13 to 15 nucleotides in length (e.g., 13, 14, or 15 nucleotides in length), from 15 to 19 nucleotides in length, or from 17 to 18 nucleotides in length (e.g., 17 nucleotides in length).

Thus, in one aspect, the disclosure provides non-naturally occurring or engineered CRISPR systems including a functional CLUST.091979 CRISPR effector as described herein, and an RNA guide wherein the RNA guide comprises a dead guide sequence, whereby the RNA guide is capable of hybridizing to a target sequence such that the CRISPR system is directed to a genomic locus of interest in a cell without detectable cleavage activity. A detailed description of dead guides is described, e.g., in WO 2016094872, which is incorporated herein by reference in its entirety.

Inducible RNA Guides

RNA guides can be generated as components of inducible systems. The inducible nature of the systems allows for spatiotemporal control of gene editing or gene expression. In some embodiments, the stimuli for the inducible systems include, e.g., electromagnetic radiation, sound energy, chemical energy, and/or thermal energy.

In some embodiments, the transcription of RNA guide can be modulated by inducible promoters, e.g., tetracycline or doxycycline controlled transcriptional activation (Tet-On and Tet-Off expression systems), hormone inducible gene expression systems (e.g., ecdysone inducible gene expression systems), and arabinose-inducible gene expression systems. Other examples of inducible systems include, e.g., small molecule two-hybrid transcription activations systems (FKBP, ABA, etc.), light inducible systems (Phytochrome, LOV domains, or cryptochrome), or Light Inducible Transcriptional Effector (LITE). These inducible systems are described, e.g., in WO 2016205764 and U.S. Pat. No. 8,795,965, each of which is incorporated herein by reference in its entirety.

Chemical Modifications

Chemical modifications can be applied to the phosphate backbone, sugar, and/or base of the RNA guide. Backbone modifications such as phosphorothioates modify the charge on the phosphate backbone and aid in the delivery and nuclease resistance of the oligonucleotide (see, e.g., Eckstein, "Phosphorothioates, essential components of therapeutic oligonucleotides," *Nucl. Acid Ther.*, 24 (2014), pp. 374-387); modifications of sugars, such as 2'-O-methyl (2'-OMe), 2'-F, and locked nucleic acid (LNA), enhance both base pairing and nuclease resistance (see, e.g., Allerson et al. "Fully 2'-modified oligonucleotide duplexes with improved in vitro potency and stability compared to unmodified small interfering RNA," *J. Med. Chem.*, 48.4 (2005): 901-904). Chemically modified bases such as 2-thiouridine or N6-methyladenosine, among others, can allow for either stronger or weaker base pairing (see, e.g., Bramsen et al., "Development of therapeutic-grade small interfering RNAs by chemical engineering," *Front. Genet.*, 2012 Aug. 20; 3:154). Additionally, RNA is amenable to both 5' and 3' end conjugations with a variety of functional moieties including fluorescent dyes, polyethylene glycol, or proteins.

A wide variety of modifications can be applied to chemically synthesized RNA guide molecules. For example, modifying an oligonucleotide with a 2'-OMe to improve nuclease resistance can change the binding energy of Watson-Crick base pairing. Furthermore, a 2'-OMe modification can affect how the oligonucleotide interacts with transfection reagents, proteins or any other molecules in the cell. The effects of these modifications can be determined by empirical testing.

In some embodiments, the RNA guide includes one or more phosphorothioate modifications. In some embodiments, the RNA guide includes one or more locked nucleic acids for the purpose of enhancing base pairing and/or increasing nuclease resistance.

A summary of these chemical modifications can be found, e.g., in Kelley et al., "Versatility of chemically synthesized guide RNAs for CRISPR-Cas9 genome editing," *J. Biotechnol.* 2016 Sep. 10; 233:74-83; WO 2016205764; and U.S. Pat. No. 8,795,965, each which is incorporated by reference in its entirety.

Sequence Modifications

The sequences and the lengths of the RNA guides, tracrRNAs, and crRNAs described herein can be optimized. In some embodiments, the optimized length of RNA guide can be determined by identifying the processed form of tracrRNA and/or crRNA, or by empirical length studies for RNA guides, tracrRNAs, crRNAs, and the tracrRNA tetraloops.

The RNA guides can also include one or more aptamer sequences. Aptamers are oligonucleotide or peptide molecules that can bind to a specific target molecule. The aptamers can be specific to gene effectors, gene activators, or gene repressors. In some embodiments, the aptamers can be specific to a protein, which in turn is specific to and recruits/binds to specific gene effectors, gene activators, or gene repressors. The effectors, activators, or repressors can be present in the form of fusion proteins. In some embodiments, the RNA guide has two or more aptamer sequences that are specific to the same adaptor proteins. In some embodiments, the two or more aptamer sequences are specific to different adaptor proteins. The adaptor proteins can include, e.g., MS2, PP7, Qβ, F2, GA, fr, JP501, M12, R17, BZ13, JP34, JP500, KU1, M11, MX1, TW18, VK, SP, FI, ID2, NL95, TW19, AP205, φCb5, φCb8r, φCb12r, φCb23r, 7s, and PRR1. Accordingly, in some embodiments, the aptamer is selected from binding proteins specifically binding any one of the adaptor proteins as described herein. In some embodiments, the aptamer sequence is a MS2 loop. A detailed description of aptamers can be found, e.g., in Nowak et al., "Guide RNA engineering for versatile Cas9 functionality," *Nucl. Acid. Res.*, 2016 Nov. 16; 44(20):9555-9564; and WO 2016205764, each of which is incorporated herein by reference in its entirety.

Guide: Target Sequence Matching Requirements

In CRISPR systems, the degree of complementarity between a guide sequence and its corresponding target sequence can be about 50%, 60%, 75%, 80%, 85%, 90%, 95%, 97.5%, 99%, or 100%. To reduce off-target interactions, e.g., to reduce the guide interacting with a target sequence having low complementarity, mutations can be introduced to the CRISPR systems so that the CRISPR systems can distinguish between target and off-target sequences that have greater than 80%, 85%, 90%, or 95% complementarity. In some embodiments, the degree of complementarity is from 80% to 95%, e.g., about 83%, 84%, 85%, 86%, 87%, 88%, 89%, 90%, 91%, 92%, 93%, 94%, or 95% (for example, distinguishing between a target having 18 nucleotides from an off-target of 18 nucleotides having 1, 2, or 3 mismatches). Accordingly, in some embodiments, the degree of complementarity between a guide sequence and its corresponding target sequence is greater than 94.5%, 95%, 95.5%, 96%, 96.5%, 97%, 97.5%, 98%, 98.5%, 99%, 99.5%, or 99.9%. In some embodiments, the degree of complementarity is 100%.

It is known in the field that complete complementarity is not required provided that there is sufficient complementarity to be functional. Modulations of cleavage efficiency can be exploited by introduction of mismatches, e.g., one or more mismatches, such as 1 or 2 mismatches between spacer sequence and target sequence, including the position of the mismatch along the spacer/target. The more central (i.e., not at the 3' or 5' ends) a mismatch, e.g., a double mismatch, is located; the more cleavage efficiency is affected. Accordingly, by choosing mismatch positions along the spacer sequence, cleavage efficiency can be modulated. For example, if less than 100% cleavage of targets is desired (e.g., in a cell population), 1 or 2 mismatches between spacer and target sequence can be introduced in the spacer sequences.

Methods of Using CRISPR Systems

The CRISPR systems described herein have a wide variety of utilities including modifying (e.g., deleting, inserting, translocating, inactivating, or activating) a target polynucleotide in a multiplicity of cell types. The CRISPR systems have a broad spectrum of applications in, e.g., DNA/RNA detection (e.g., specific high sensitivity enzymatic reporter unlocking (SHERLOCK)), tracking and labeling of nucleic acids, enrichment assays (extracting desired sequence from background), detecting circulating tumor DNA, preparing next generation library, drug screening, disease diagnosis and prognosis, and treating various genetic disorders.

DNA/RNA Detection

In one aspect, the CRISPR systems described herein can be used in DNA/RNA detection. Single effector RNA-guided DNases can be reprogrammed with CRISPR RNAs (crRNAs) to provide a platform for specific single-stranded DNA (ssDNA) sensing. Upon recognition of its DNA target, activated Type V single effector DNA-guided DNases engage in "collateral" cleavage of nearby non-targeted ssDNAs. This crRNA-programmed collateral cleavage activity allows the CRISPR systems to detect the presence of a specific DNA by nonspecific degradation of labeled ssDNA.

The collateral ssDNA activity can be combined with a reporter in DNA detection applications such as a method called the DNA Endonuclease-Targeted CRISPR trans reporter (DETECTR) method, which achieves attomolar sensitivity for DNA detection (see, e.g., Chen et al., Science, 360(6387):436-439, 2018), which is incorporated herein by reference in its entirety. One application of using the enzymes described herein is to degrade non-specific ssDNA in an in vitro environment. A "reporter" ssDNA molecule linking a fluorophore and a quencher can also be added to the in vitro system, along with an unknown sample of DNA (either single-stranded or double-stranded). Upon recognizing the target sequence in the unknown piece of DNA, the effector complex cleaves the reporter ssDNA resulting in a fluorescent readout.

In other embodiments, the SHERLOCK method (Specific High Sensitivity Enzymatic Reporter UnLOCKing) also provides an in vitro nucleic acid detection platform with attomolar (or single-molecule) sensitivity based on nucleic acid amplification and collateral cleavage of a reporter ssDNA, allowing for real-time detection of the target. Methods of using CRISPR in SHERLOCK are described in detail, e.g., in Gootenberg, et al. "Nucleic acid detection with CRISPR-Cas13a/C2c2," Science, 356(6336):438-442 (2017), which is incorporated herein by reference in its entirety.

In some embodiments, the CRISPR systems described herein can be used in multiplexed error-robust fluorescence in situ hybridization (MERFISH). These methods are described in, e.g., Chen et al., "Spatially resolved, highly multiplexed RNA profiling in single cells," Science, 2015 Apr. 24; 348(6233):aaa6090, which is incorporated herein by reference in its entirety.

Tracking and Labeling of Nucleic Acids

Cellular processes depend on a network of molecular interactions among proteins, RNAs, and DNAs. Accurate detection of protein-DNA and protein-RNA interactions is key to understanding such processes. In vitro proximity labeling techniques employ an affinity tag combined with, a reporter group, e.g., a photoactivatable group, to label polypeptides and RNAs in the vicinity of a protein or RNA of interest in vitro. After UV irradiation, the photoactivatable groups react with proteins and other molecules that are in close proximity to the tagged molecules, thereby labelling them. Labelled interacting molecules can subsequently be recovered and identified. The RNA targeting effector proteins can for instance be used to target probes to selected RNA sequences. These applications can also be applied in animal models for in vivo imaging of diseases or difficult-to culture cell types. The methods of tracking and labeling of nucleic acids are described, e.g., in U.S. Pat. No. 8,795,965; WO 2016205764; and WO 2017070605, each of which is incorporated herein by reference in its entirety.

High-Throughput Screening

The CRISPR systems described herein can be used for preparing next generation sequencing (NGS) libraries. For example, to create a cost-effective NGS library, the CRISPR systems can be used to disrupt the coding sequence of a target gene, and the CRISPR effector transfected clones can be screened simultaneously by next-generation sequencing (e.g., on the Ion Torrent PGM system). A detailed description regarding how to prepare NGS libraries can be found, e.g., in Bell et al., "A high-throughput screening strategy for detecting CRISPR-Cas9 induced mutations using next-generation sequencing," BMC Genomics, 15.1 (2014): 1002, which is incorporated herein by reference in its entirety.

Engineered Cells

Microorganisms (e.g., *E. coli*, yeast, and microalgae) are widely used for synthetic biology. The development of synthetic biology has a wide utility, including various clinical applications. For example, the programmable CRISPR systems can be used to split proteins of toxic domains for targeted cell death, e.g., using cancer-linked RNA as target transcript. Further, pathways involving protein-protein interactions can be influenced in synthetic biological systems with e.g., fusion complexes with the appropriate effectors such as kinases or enzymes.

In some embodiments, RNA guide sequences that target phage sequences can be introduced into the microorganism. Thus, the disclosure also provides methods of "vaccinating" a microorganism (e.g., a production strain) against phage infection.

In some embodiments, the CRISPR systems provided herein can be used to engineer microorganisms, e.g., to improve yield or improve fermentation efficiency. For example, the CRISPR systems described herein can be used to engineer microorganisms, such as yeast, to generate biofuel or biopolymers from fermentable sugars, or to degrade plant-derived lignocellulose derived from agricultural waste as a source of fermentable sugars. More particularly, the methods described herein can be used to modify the expression of endogenous genes required for biofuel production and/or to modify endogenous genes, which may interfere with the biofuel synthesis. These methods of engineering microorganisms are described e.g., in Verwaal et al., "CRISPR/Cpf1 enables fast and simple genome editing of *Saccharomyces cerevisiae*," Yeast, 2017 Sep. 8. doi: 10.1002/yea.3278; and Hlavova et al., "Improving microalgae for biotechnology—from genetics to synthetic biology," Biotechnol. Adv., 2015 Nov. 1; 33:1194-203, each of which is incorporated herein by reference in its entirety.

In some embodiments, the CRISPR systems provided herein can be used to engineer eukaryotic cells or eukaryotic organisms. For example, the CRISPR systems described herein can be used to engineer eukaryotic cells not limited to a plant cell, a fungal cell, a mammalian cell, a reptile cell, an insect cell, an avian cell, a fish cell, a parasite cell, an arthropod cell, an invertebrate cell, a vertebrate cell, a rodent cell, a mouse cell, a rat cell, a primate cell, a non-human primate cell, or a human cell. In some embodiments, eukaryotic cell is in an in vitro culture. In some embodiments, the eukaryotic cell is in vivo. In some embodiments, the eukaryotic cell is ex vivo.

In some embodiments, the cell is derived from a cell line. A wide variety of cell lines for tissue culture are known in the art. Examples of cell lines include, but are not limited to, 293T, MF7, K562, HeLa, and transgenic varieties thereof. Cell lines are available from a variety of sources known to those with skill in the art (see, e.g., the American Type Culture Collection (ATCC) (Manassas, Va.)). In some embodiments, a cell transfected with one or more nucleic acids (such as nuclease polypeptide encoding vector and RNA guide) is used to establish a new cell line comprising one or more vector-derived sequences to establish a new cell line comprising modification to the target nucleic acid or target locus. In some embodiments, the cell is an immortal or immortalized cell.

In some embodiments, the cell is a primary cell. In some embodiments, the cell is a stem cell such as a totipotent stem cell (e.g., omnipotent), a pluripotent stem cell, a multipotent stem cell, an oligopotent stem cell, or an unipotent stem cell. In some embodiments, the cell is an induced pluripotent stem cell (iPSC) or derived from an iPSC. In some embodiments, the cell is a differentiated cell. For example, in some embodiments, the differentiated cell is a muscle cell (e.g., a myocyte), a fat cell (e.g., an adipocyte), a bone cell (e.g., an osteoblast, osteocyte, osteoclast), a blood cell (e.g., a monocyte, a lymphocyte, a neutrophil, an eosinophil, a basophil, a macrophage, a erythrocyte, or a platelet), a nerve cell (e.g., a neuron), an epithelial cell, an immune cell (e.g., a lymphocyte, a neutrophil, a monocyte, or a macrophage), a liver cell (e.g., a hepatocyte), a fibroblast, or a sex cell. In some embodiments, the cell is a terminally differentiated cell. For example, in some embodiments, the terminally differentiated cell is a neuronal cell, an adipocyte, a cardiomyocyte, a skeletal muscle cell, an epidermal cell, or a gut cell. In some embodiments, the cell is a mammalian cell, e.g., a human cell or a murine cell. In some embodiments, the murine cell is derived from a wild-type mouse, an immunosuppressed mouse, or a disease-specific mouse model.

Gene Drives

Gene drive is the phenomenon in which the inheritance of a particular gene or set of genes is favorably biased. The CRISPR systems described herein can be used to build gene drives. For example, the CRISPR systems can be designed to target and disrupt a particular allele of a gene, causing the cell to copy the second allele to fix the sequence. Because of the copying, the first allele will be converted to the second allele, increasing the chance of the second allele being transmitted to the offspring. A detailed method regarding how to use the CRISPR systems described herein to build gene drives is described, e.g., in Hammond et al., "A CRISPR-Cas9 gene drive system targeting female reproduction in the malaria mosquito vector *Anopheles gambiae*," *Nat. Biotechnol.*, 2016 January; 34(1):78-83, which is incorporated herein by reference in its entirety.

Pooled-Screening

As described herein, pooled CRISPR screening is a powerful tool for identifying genes involved in biological mechanisms such as cell proliferation, drug resistance, and viral infection. Cells are transduced in bulk with a library of RNA guide-encoding vectors described herein, and the distribution of gRNAs is measured before and after applying a selective challenge. Pooled CRISPR screens work well for mechanisms that affect cell survival and proliferation, and they can be extended to measure the activity of individual genes (e.g., by using engineered reporter cell lines). Arrayed CRISPR screens, in which only one gene is targeted at a time, make it possible to use RNA-seq as the readout. In some embodiments, the CRISPR systems as described herein can be used in single-cell CRISPR screens. A detailed description regarding pooled CRISPR screenings can be found, e.g., in Datlinger et al., "Pooled CRISPR screening with single-cell transcriptome read-out," *Nat. Methods.*, 2017 March; 14(3):297-301, which is incorporated herein by reference in its entirety.

Saturation Mutagenesis ("Bashing")

The CRISPR systems described herein can be used for in situ saturating mutagenesis. In some embodiments, a pooled RNA guide library can be used to perform in situ saturating mutagenesis for particular genes or regulatory elements. Such methods can reveal critical minimal features and discrete vulnerabilities of these genes or regulatory elements (e.g., enhancers). These methods are described, e.g., in Canver et al., "BCL11A enhancer dissection by Cas9-mediated in situ saturating mutagenesis," *Nature*, 2015 Nov. 12; 527(7577):192-7, which is incorporated herein by reference in its entirety.

Therapeutic Applications

In some embodiments, the CRISPR systems described herein can be used to edit a target nucleic acid to modify the target nucleic acid (e.g., by inserting, deleting, or mutating one or more amino acid residues). For example, in some embodiments the CRISPR systems described herein comprise an exogenous donor template nucleic acid (e.g., a DNA molecule or an RNA molecule), which comprises a desirable nucleic acid sequence. Upon resolution of a cleavage event induced with the CRISPR system described herein, the molecular machinery of the cell can utilize the exogenous donor template nucleic acid in repairing and/or resolving the cleavage event. Alternatively, the molecular machinery of the cell can utilize an endogenous template in repairing and/or resolving the cleavage event. In some embodiments, the CRISPR systems described herein may be used to modify a target nucleic acid resulting in an insertion, a deletion, and/or a point mutation). In some embodiments, the insertion is a scarless insertion (i.e., the insertion of an intended nucleic acid sequence into a target nucleic acid resulting in no additional unintended nucleic acid sequence upon resolution of the cleavage event). Donor template nucleic acids may be double-stranded or single-stranded nucleic acid molecules (e.g., DNA or RNA). Methods of designing exogenous donor template nucleic acids are described, for example, in WO 2016094874, the entire contents of which is expressly incorporated herein by reference.

In another aspect, the disclosure provides the use of a system described herein in a method selected from the group consisting of RNA sequence specific interference; RNA sequence-specific gene regulation;

screening of RNA, RNA products, lncRNA, non-coding RNA, nuclear RNA, or mRNA; mutagenesis; inhibition of RNA splicing; fluorescence in situ hybridization; breeding; induction of cell dormancy; induction of cell cycle arrest; reduction of cell growth and/or cell proliferation; induction of cell anergy; induction of cell apoptosis; induction of cell necrosis; induction of cell death; or induction of programmed cell death.

The CRISPR systems described herein can have various therapeutic applications. In some embodiments, the new CRISPR systems can be used to treat various diseases and disorders, e.g., genetic disorders (e.g., monogenetic diseases) or diseases that can be treated by nuclease activity (e.g., Pcsk9 targeting or BCL11a targeting). In some embodiments, the methods described here are used to treat a subject, e.g., a mammal, such as a human patient. The mammalian subject can also be a domesticated mammal, such as a dog, cat, horse, monkey, rabbit, rat, mouse, cow, goat, or sheep.

The methods can include the condition or disease being infectious, and wherein the infectious agent is selected from the group consisting of human immunodeficiency virus (HIV), herpes simplex virus-1 (HSV1), and herpes simplex virus-2 (HSV2).

In one aspect, the CRISPR systems described herein can be used for treating a disease caused by overexpression of RNAs, toxic RNAs and/or mutated RNAs (e.g., splicing defects or truncations). For example, expression of the toxic RNAs may be associated with the formation of nuclear inclusions and late-onset degenerative changes in brain, heart, or skeletal muscle. In some embodiments, the disorder is myotonic dystrophy. In myotonic dystrophy, the main pathogenic effect of the toxic RNAs is to sequester binding proteins and compromise the regulation of alternative splicing (see, e.g., Osborne et al., "RNA-dominant diseases," *Hum. Mol. Genet.*, 2009 Apr. 15; 18(8):1471-81). Myotonic dystrophy (dystrophia myotonica (DM)) is of particular interest to geneticists because it produces an extremely wide range of clinical features. The classical form of DM, which is now called DM type 1 (DM1), is caused by an expansion of CTG repeats in the 3'-untranslated region (UTR) of DMPK, a gene encoding a cytosolic protein kinase. The CRISPR systems as described herein can target overexpressed RNA or toxic RNA, e.g., the DMPK gene or any of the mis-regulated alternative splicing in DM1 skeletal muscle, heart, or brain.

The CRISPR systems described herein can also target trans-acting mutations affecting RNA-dependent functions that cause various diseases such as, e.g., Prader Willi syndrome, Spinal muscular atrophy (SMA), and Dyskeratosis congenita. A list of diseases that can be treated using the CRISPR systems described herein is summarized in Cooper et al., "RNA and disease," *Cell*, 136.4 (2009): 777-793, and WO 2016205764, each of which is incorporated herein by reference in its entirety.

The CRISPR systems described herein can also be used in the treatment of various tauopathies, including, e.g., primary and secondary tauopathies, such as primary age-related tauopathy (PART)/Neurofibrillary tangle (NFT)-predominant senile dementia (with NFTs similar to those seen in Alzheimer Disease (AD), but without plaques), dementia pugilistica (chronic traumatic encephalopathy), and progressive supranuclear palsy. A useful list of tauopathies and methods of treating these diseases are described, e.g., in WO 2016205764, which is incorporated herein by reference in its entirety.

The CRISPR systems described herein can also be used to target mutations disrupting the cis-acting splicing codes that can cause splicing defects and diseases. These diseases include, e.g., motor neuron degenerative disease that results from deletion of the SMN1 gene (e.g., spinal muscular atrophy), Duchenne Muscular Dystrophy (DMD), frontotemporal dementia, and Parkinsonism linked to chromosome 17 (FTDP-17), and cystic fibrosis.

The CRISPR systems described herein can further be used for antiviral activity, in particular, against RNA viruses. The effector proteins can target the viral RNAs using suitable RNA guides selected to target viral RNA sequences.

Furthermore, in vitro RNA sensing assays can be used to detect specific RNA substrates. The RNA targeting effector proteins can be used for RNA-based sensing in living cells. Examples of applications are diagnostics by sensing of, for examples, disease-specific RNAs.

A detailed description of therapeutic applications of the CRISPR systems described herein can be found, e.g., in U.S. Pat. No. 8,795,965, EP 3009511, WO 2016205764, and WO 2017070605, each of which is incorporated herein by reference in its entirety.

Applications in Plants

The CRISPR systems described herein have a wide variety of utility in plants. In some embodiments, the CRISPR systems can be used to engineer genomes of plants (e.g., improving production, making products with desired post-translational modifications, or introducing genes for producing industrial products). In some embodiments, the CRISPR systems can be used to introduce a desired trait to a plant (e.g., with or without heritable modifications to the genome) or regulate expression of endogenous genes in plant cells or whole plants.

In some embodiments, the CRISPR systems can be used to identify, edit, and/or silence genes encoding specific proteins, e.g., allergenic proteins (e.g., allergenic proteins in peanuts, soybeans, lentils, peas, green beans, and mung beans). A detailed description regarding how to identify, edit, and/or silence genes encoding proteins is described, e.g., in Nicolaou et al., "Molecular diagnosis of peanut and legume allergy," *Curr. Opin. Allergy Clin. Immunol.*, 11(3): 222-8 (2011) and WO 2016205764, each of which is incorporated herein by reference in its entirety.

Delivery of CRISPR Systems

Through this disclosure and knowledge in the art, the CRISPR systems described herein, components thereof, nucleic acid molecules thereof, or nucleic acid molecules encoding or providing components thereof can be delivered by various delivery systems such as vectors, e.g., plasmids or viral delivery vectors. The CRISPR effectors and/or any of the RNAs (e.g., RNA guides) disclosed herein can be delivered using suitable vectors, e.g., plasmids or viral vectors, such as adeno-associated viruses (AAV), lentiviruses, adenoviruses, and other viral vectors, or combinations thereof. An effector and one or more RNA guides can be packaged into one or more vectors, e.g., plasmids or viral vectors.

In some embodiments, vectors, e.g., plasmids or viral vectors, are delivered to the tissue of interest by, e.g., intramuscular injection, intravenous administration, transdermal administration, intranasal administration, oral administration, or mucosal administration. Such delivery may be either via one dose or multiple doses. One skilled in the art understands that the actual dosage to be delivered herein may vary greatly depending upon a variety of factors, including, but not limited to, the vector choices, the target cells, organisms, tissues, the general conditions of the subject to be treated, the degrees of transformation/modification sought, the administration routes, the administration modes, and the types of transformation/modification sought.

In certain embodiments, delivery is via adenoviruses, which can be one dose containing at least $1 \times 10^5$ particles (also referred to as particle units, pu) of adenoviruses. In some embodiments, the dose preferably is at least about $1 \times 10^6$ particles, at least about $1 \times 10^7$ particles, at least about $1 \times 10^8$ particles, and at least about $1 \times 10^9$ particles of the adenoviruses. The delivery methods and the doses are described, e.g., in WO 2016205764 and U.S. Pat. No. 8,454,972, each of which is incorporated herein by reference in its entirety.

In some embodiments, delivery is via plasmids. The dosage can be a sufficient number of plasmids to elicit a response. In some cases, suitable quantities of plasmid DNA in plasmid compositions can be from about 0.1 to about 2 mg. Plasmids will generally include (i) a promoter; (ii) a sequence encoding a nucleic acid-targeting CRISPR effector, operably linked to the promoter; (iii) a selectable marker; (iv) an origin of replication; and (v) a transcription terminator downstream of and operably linked to (ii). The plasmids can also encode the RNA components of a CRISPR complex, but one or more of these may instead be encoded on different vectors. The frequency of administration is within the ambit of the medical or veterinary practitioner (e.g., physician, veterinarian), or a person skilled in the art.

In another embodiment, delivery is via liposomes or lipofectin formulations or the like and can be prepared by methods known to those skilled in the art. Such methods are described, for example, in WO 2016205764, U.S. Pat. Nos. 5,593,972, 5,589,466, and 5,580,859, each of which is incorporated herein by reference in its entirety.

In some embodiments, delivery is via nanoparticles or exosomes. For example, exosomes have been shown to be particularly useful in delivery RNA.

Further means of introducing one or more components of the CRISPR systems described herein to a cell is by using cell-penetrating peptides (CPP). In some embodiments, a cell penetrating peptide is linked to a CRISPR effector. In some embodiments, a CRISPR effector and/or RNA guide is coupled to one or more CPPs for transportation into a cell (e.g., plant protoplasts). In some embodiments, the CRISPR effector and/or RNA guide(s) are encoded by one or more circular or non-circular DNA molecules that are coupled to one or more CPPs for cell delivery.

CPPs are short peptides of fewer than 35 amino acids derived either from proteins or from chimeric sequences capable of transporting biomolecules across cell membrane in a receptor independent manner CPPs can be cationic peptides, peptides having hydrophobic sequences, amphipathic peptides, peptides having proline-rich and anti-microbial sequences, and chimeric or bipartite peptides. Examples of CPPs include, e.g., Tat (which is a nuclear transcriptional activator protein required for viral replication by HIV type 1), penetratin, Kaposi fibroblast growth factor (FGF) signal peptide sequence, integrin β3 signal peptide sequence, polyarginine peptide Args sequence, Guanine rich-molecular transporters, and sweet arrow peptide. CPPs and methods of using them are described, e.g., in Hallbrink et al., "Prediction of cell-penetrating peptides," *Methods Mol. Biol.*, 2015; 1324:39-58; Ramakrishna et al., "Gene disruption by cell-penetrating peptide-mediated delivery of Cas9 protein and guide RNA," *Genome Res.*, 2014 June; 24(6):1020-7; and WO 2016205764, each of which is incorporated herein by reference in its entirety.

Various delivery methods for the CRISPR systems described herein are also described, e.g., in U.S. Pat. No. 8,795,965, EP 3009511, WO 2016205764, and WO 2017070605, each of which is incorporated herein by reference in its entirety.

EXAMPLES

The invention is further described in the following examples, which do not limit the scope of the invention described in the claims.

Example 1—Identification of Components of CLUST.091979 CRISPR-Cas System

This protein family was identified using the computational methods described above. The CLUST.091979 system comprises single effectors associated with CRISPR systems found in uncultured metagenomic sequences collected from environments not limited to gut, bovine gut, human gut, sheep gut, terrestrial, feces, and mammalian digestive system environments (TABLE 5). Exemplary CLUST.091979 effectors include those shown in TABLE 5 and TABLE 6, below. The effector sequences set forth in SEQ ID NOs: 1-4, 14, 15, 17-19, 21-25, 27-33, 35-49, 51-56 were aligned to identify regions of sequence similarity, as shown in FIGS. 1A-1L. A bar graph depicts sequence similarity, with the tallest bars indicating the residues with the highest sequence similarity. Non-limiting regions of sequence similarity are shown in TABLE 7. The regions of sequence similarity indicate that the effectors disclosed herein are a family with a conserved C-terminal RuvC domain representative of nucleases.

TABLE 51

Representative CLUST.091979 Effector Proteins

| source | effector accession | # spacers | effector size | SEQ ID NO |
|---|---|---|---|---|
| gut metagenome | AUXO013988882_8\|P | 4 | 775 | 1 |
| bovine gut metagenome | SRR094437_845781_4\|M | 11 | 786 | 2 |
| gut metagenome | SRR1221442_316828_61\|P | 2 | 774 | 3 |
| bovine gut metagenome | SRR3181151_741875_3\|M | 8 | 756 | 4 |
| bovine gut metagenome | SRR5371369_1764679_7\|P | 7 | 746 | 5 |
| bovine gut metagenome | SRR5371371_1138852_2\|M | 3 | 733 | 6 |
| bovine gut metagenome | SRR5371379_2478682_1\|M | 9 | 744 | 7 |
| bovine gut metagenome | SRR5371385_201181_1\|P | 4 | 754 | 8 |
| bovine gut metagenome | SRR5371385_201181_1\|M | 4 | 746 | 9 |
| bovine gut metagenome | SRR5371401_1055766_58\|M | 15 | 745 | 10 |
| bovine gut metagenome | SRR5371439_988701_11\|M | 5 | 744 | 11 |
| bovine gut metagenome | SRR5371497_203858_6\|M | 5 | 745 | 12 |
| bovine gut metagenome | SRR5371501_2762794_1\|M | 2 | 712 | 13 |
| terrestrial metagenome | SRR5678926_1309611_3\|P | 6 | 741 | 14 |
| feces metagenome | SRR6059713_382107_4\|P | 4 | 752 | 15 |
| feces metagenome | SRR6060192_2608084_13\|P | 16 | 766 | 16 |
| sheep gut metagenome | SRR7634052_1662339_24\|M | 8 | 784 | 17 |
| gut metagenome | AUXO017332817_2\|M | 5 | 782 | 18 |

TABLE 51-continued

Representative CLUST.091979 Effector Proteins

| source | effector accession | # spacers | effector size | SEQ ID NO |
|---|---|---|---|---|
| human gut metagenome | OQVL01000914_15\|P | 6 | 735 | 19 |
| mammals-digestive system-asian elephant fecal-elephas maximus | 3300001598\|EMG_10017415_6\|P | 2 | 774 | 20 |
| mammals-digestive system-cattle and sheep rumen | 3300021254\|Ga0223824_10022219_2\|P | 3 | 755 | 21 |
| mammals-digestive system-cattle and sheep rumen | 3300021431\|Ga0224423_10015012_2\|P | 11 | 789 | 22 |
| mammals-digestive system-fecal | 3300012973\|Ga0123351_1009859_3\|P | 6 | 766 | 23 |
| mammals-digestive system-fecal | 3300012979\|Ga0123348_10005323_4\|M | 4 | 752 | 24 |
| mammals-digestive system-rumen-bos taurus | 3300028797\|Ga0265301_10000251_12\|M | 26 | 814 | 25 |
| mammals-digestive system-rumen-bos taurus | 3300028797\|Ga0265301_10000251_10\|P | 26 | 776 | 26 |
| mammals-digestive system-rumen-bos taurus | 3300028797\|Ga0265301_10009039_3\|M | 2 | 778 | 27 |
| mammals-digestive system-rumen-bos taurus | 3300028887\|Ga0265299_10000013_320\|P | 8 | 772 | 28 |
| mammals-digestive system-rumen-bos taurus | 3300028887\|Ga0265299_10000026_77\|P | 2 | 781 | 29 |
| mammals-digestive system-rumen-bos taurus | 3300028887\|Ga0265299_10000133_30\|M | 11 | 798 | 30 |
| mammals-digestive system-rumen-bos taurus | 3300028887\|Ga0265299_10011526_3\|M | 15 | 786 | 31 |
| mammals-digestive system-rumen-bos taurus | 3300028887\|Ga0265299_10012919_3\|P | 10 | 781 | 32 |
| mammals-digestive system-rumen-bos taurus | 3300028914\|Ga0265300_10009460_3\|M | 2 | 798 | 33 |
| mammals-digestive system-rumen-bos taurus | 3300031853\|Ga0326514_10013355_6\|M | 4 | 724 | 34 |
| mammals-digestive system-rumen-bos taurus | 3300031993\|Ga0310696_10000014_323\|P | 8 | 772 | 35 |
| mammals-digestive system-rumen-bos taurus | 3300031993\|Ga0310696_10000226_76\|P | 2 | 781 | 36 |
| mammals-digestive system-rumen-bos taurus | 3300031993\|Ga0310696_10000447_27\|M | 11 | 798 | 37 |
| mammals-digestive system-rumen-bos taurus | 3300031993\|Ga0310696_10026614_2\|M | 2 | 781 | 38 |
| mammals-digestive system-rumen-bos taurus | 3300031993\|Ga0310696_10030100_3\|M | 14 | 786 | 39 |
| mammals-digestive system-rumen-bos taurus | 3300031998\|Ga0310786_10000003_467\|M | 9 | 798 | 40 |
| mammals-digestive system-rumen-ovis aries | AUXO013988882\|Ga0247611_10000101_23\|P | 6 | 771 | 41 |
| mammals-digestive system-rumen-ovis aries | 3300028805\|Ga0247608_10000186_37\|P | 7 | 764 | 42 |
| mammals-digestive system-rumen-ovis aries | 3300028805\|Ga0247608_10000895_42\|M | 8 | 768 | 43 |
| mammals-digestive system-rumen-ovis aries | 3300028805\|Ga0247608_10006074_1\|M | 10 | 789 | 44 |
| mammals-digestive system-rumen-ovis aries | 3300028833\|Ga0247610_10000007_379\|M | 8 | 784 | 45 |
| mammals-digestive system-rumen-ovis aries | 3300028833\|Ga0247610_10004486_2\|M | 7 | 764 | 46 |
| mammals-digestive system-rumen-ovis aries | 3300028888\|Ga0247609_10000668_74\|M | 11 | 758 | 47 |
| mammals-digestive system-rumen-ovis aries | 3300028888\|Ga0247609_10003329_9\|M | 8 | 785 | 48 |
| mammals-digestive system-rumen-ovis aries | 3300028888\|Ga0247609_10016480_8\|M | 2 | 805 | 49 |
| mammals-digestive system-rumen-ovis aries | 3300031992\|Ga0310694_10000010_351\|M | 8 | 784 | 50 |
| mammals-digestive system-rumen-ovis aries | 3300031992\|Ga0310694_10022272_2\|M | 7 | 764 | 51 |
| mammals-digestive system-rumen-ovis aries | 3300031994\|Ga0310691_10000084_157\|M | 8 | 768 | 52 |
| mammals-digestive system-rumen-ovis aries | 3300031994\|Ga0310691_10000270_20\|M | 7 | 764 | 53 |
| mammals-digestive system-rumen-ovis aries | 3300032030\|Ga0310697_10001273_44\|P | 2 | 805 | 54 |
| mammals-digestive system-rumen-ovis aries | 3300032030\|Ga0310697_10005481_13\|P | 8 | 785 | 55 |
| pig gut metagenome | OBLI01003123_14\|M | 4 | 735 | 56 |

TABLE 62

Amino Acid Sequences of Representative CLUST.091979 Effector Proteins

```
>AUX0013988882_8|P
[gut metagenome]
MGNTTKKGNLTKTYLFKANLSEQDFKLWRSIVEEYQRYKEVLSKWVCDHLTTMKIGDILPYIDRYSKKIDNKTGEYPENTYYSL
CEEEHKDEPLYKIFQFDSNCRNNALYEVIRKINCDLYTGNILNLGETYYRRNGFVKRVLANYATKISGMKPSVRKRKVTSDSTEE
EIRNQVVYEIFNNNIKNEKDFKGVLEYAESKCCKTNEAYVERIRLLYDFYIKHTDEIKEYVEYICVEQLKEFCGVKVNRSKSSMN
INIQNFSITRVDGKCTYILHLPIGKKVYDIKLWGNRQVVLNVDGTPLNDGGFFNIYKELVNDKEFSECVSKEDLELFKELSKYVSFCPIECQFLFTRYAEQKGILV
YEKLRLAEKILTSVLDRSFEKYNGIDCNIANYISNVRMLRSKCKSYFTLKMKYKELQHKYDNEMGYVDTFSDSCVEMDSRRKEN
PFVQTNEAMELIGKMESVAQDIIGCRDNIITYAYNVFRRNGYDTVGLENLESSQFERFSSVRSPKSLLNYHHLKGKHIDFIDSD
ECSVKVNKDLYNFTLEDDGTISDITLSDKGKYRNDLSMFYNQIIKTIHFADIKDKFIQLGNNGNVQTVLVPSYFTSQMNSKTHK
IYVVNVKNERTGKTEQKLANKNMVRLGQERHINGLNADVNASMNIAYIVENKEMRNAMCTNPKSETGYSVPFLTSRIKKQNIMV
VELKKMGMVEVLNEKSTEI (SEQ ID NO: 1)

>SRR094437_845781_4|M
[bovine gut metagenome]
MAQHKSNNEESAINKTFIFKAKCDKNDVISLWEPAAKEYCDYYNKVSKWIADNLITMKIGDLAQYITNQNSKYYTAVTNKKKD
LPLYRIFQKGFSSQCADNALYCAIKSINPENYKGNSLGIGESDYRRFGYIQSVVSNFRTKMSSLKATVKWKKFDVNNVDDETLK
IQTIYDVDKYGIETAKEFKELIETLKTRVETPQLNDTIARLECLCDYYSKNEKAINNEIETMAIADLQKFGGCQRKSLNAFTIH
KQDSLMEKVGNTSFRLQLPFRKKTYVINLLGNRQVVNFVNGKRVDLIDIAENHGDLVTFNIKNGVLFVHLTSPIVFDKVRDIR
NVVGIDVNIKHSMLATSIKDVGNVKGYINLYKELLNDDEFVSTCNESELALYRQMSENVNFGILETDSLFERIVNQSKGGCLKN
KLIRRELAMQKVFERITKTNKDQNIVDYVNYVKMMRAKCKASYILKEKYDEKQKEYYVKMGFTDESTESKETMDKRREEFPPVN
TDTAKELLVKQNNIRQDIIGCRDNIVTYAFNVFKNNEYDTLSVEYLDSSQFDKRRIATPKSLLKYRKFEGKTKDEVENMMKSEK
LSNAYYTFKYENDVVSDIDYSDEGNLRRSKLNFGNWIIKSIHFADIKDKFVQLSNNNKMNIVFCPSAFSSQMDSITHTLYYVEK
ITKNKKGKEKKKYVLANKKMVRTQQEKHINGLNADYNSACNLKYIALNDELRDKMTDRFKASKKIKTMYNIPAYNIKSNFKKNL
SAKTIQTFRELGHYRDGKINEDGMFVENLE (SEQ ID NO: 2)

>SRR1221442_316828_61|P
[gut metagenome]
MLNIKNNGESVDMNTIELAMKEYNRYYNICSDWICNNLMTPIGSLYQYIDDKCKNNAYAQNLIAEEWKDKPLYYMFYKGYNANN
CANAICCAIRSQVPEVNKAENILNLSYTYYFRNGVIKSVISNYASKMRILSDKQIKYCIVSENTPDKILIEQCILELKRRHEDL
KDWEENLKYLILKGNESAITRFTILKDFYSKNIERVKEEREIMAIAELKDFGGCRRKDDKLSMCIQSAGNSKDIKVSRVKTTHN
YTELVDDYTENFNIKFSALDFNVMGRRDVVKTKLNKTEDDSNTWGGTELLVDIINNHGCSLTFKLVDDKLYVDIPIDTEHINKT
TDFKKSVGIDVNLKHSLLNTDILDNGGINGYINIYKKLLADDAFMSACTKADLVNYIDIAKTVTFCPIEADFIISNVVEKYLHM
KONTNKMEIAFSSVLMNIRKELEIKLLHSSKEESPLIRKQIIYINCIICLRNELKQYAIAKHRYYKKQQEYDTLCDTLHGVDYK
QIHPYAQSKEGAEQMKKMKTIENNLIANRNNIIEYAYTVFELNNFDLIALENITKDIMEDKKKRKSPPSINSLLKYHKVINCTE
DNINDNETYQKFAKYYNVSYENGKVTGATLSQEGNKVKLKDDFYDKLLKVLHFTSIKDYFTTLSNKRKIAVAHVPAYYTSQIDS
IDNKICMIKSTDKNGKSTYKIADKTIVRPTQEKHINGLNADYNAARNINFIVADEKWRKKFVRPTNTNKPLYNSPVFSPAVKSE
GGTIKNLQILSATKTIIL (SEQ ID NO: 3)

>SRR3181151_741875_3|M
[bovine gut metagenome]
MTTKQVKSIVLKVKNTNECPITKDVINEYKKYYNICSEWIKDNLTSITIGDIASFLKEATNKDTIPTYINMGLSEEWKYKPIYH
LFTDDYHEKSANNLLYAYFKEKNLDCYNGNILNLSETYYRRNGYFKSVVGNYRTKIRTLNYKIKRKNVDENSTNEDIELQVMYE
IAKRKLNIKKDWENYISYIENVENINIKNIDRYNLLYKHFCENESTINCKMELLSVEQLKEFGGCVMKQHINSMTINIQDFKIE
NKENSLGFILNLPLNKKKYQIELWGNRQIKKGNKDNYKTLVDFINTYGQNIIFTIKNNKIYVVFSYECELKEKEINFDKIVGID
VNFKHALFVASERDKNPLQDNNQLKGYINLYKYLLEHNEFTSLLTKEELDIYKEIAKGVTFCPLEYNLLFTRIENKGGKSNDKE
QVLSKLLYSLQIKLKNENKIQEYIYVSCVNKLRAKYVSYFILKEKYYEKQKEYDIEMGFTDDSTESKESMDKRRLEFPPFRNTQI
ANGFLEKLSNVQQDINGCLKNIINYAYKVFEQNGFGVIALENLENSNFEKTQVLPTIKSLLEYHKLENQNINNINASDKVKEYI
EKEYYELTTNENNEIVDAKYTKKGIIKVKKANFFNLMMKSLHFASNKDEFILLSNNGKTQIALVPSEYTSQMDSIEHCLYVDKN
GKKVDKKKVRQKQETHINGLNADFNAANNIKYIIENENLRKLFCGKLKVSGYNTPILDATKKGQFNILAELKKQNKIKIFEIEK
(SEQ ID NO: 4)

>SRR5371369_1764679_7|P
[bovine gut metagenome]
MASHKKTESNQIIKTFPFKLKNANGLSLDVLNDAITEYQNYYNICSDWIKDHLTMKISELYKYIPDEKKNSGYALTLISDEWKD
KPMYMMFKKGYPANNRDNAIYETLNTCNTEHYTGNILNFPDTYYRRFGYVASTISNYVTKISKMSTGSRSKNISNDSDVDTIME
QVIYEMEHNGWTSVKDWENQMEYLESKTDSNPNFVYRMTTLYEFYKSHIDEVNSKMETMSIDLLIKFGGCRRKDSKKSMYIMGG
SNTPFDITQIGDNSLNIKFSKNLNVDVFGRYDVIKONTLLVDIINGHGASFVLKIINDEIYIDINVSVPFDKKIATTNKVVGID
VNIKHMLLATNILDDGNVKGYVNIYKEVINDSDFKKVCNSTVMKYFTDFSKFVTFCPLEFDFLFSRVCNQKGIYNDNSVMEKSF
SDVLNKLKWNFIETGDNTKRIYIENVMKLRTQMKAYAIVKNAYYKQQSEYDFGKSEEFIQEHPFSNTDKGIEILHKLDNISKKI
LGCRNNIIQYSYNLFEINGYDMISLEKLTSSQFKKKSFPTVNSLLKYHKILGCTQEEMEKKDIYSVIKKGYYDIIFDNDVVTDA
KLSTKGELSKFKDDFFNLMIKSIHFADIKDYFITLSNNGTAGVSLVPSFFTSQMDSIDHKIYFVQDNKSGKLKLANKHKVRSSQ
EKHINGLNADYNAARNIAYIMENTECRNMFMKQSRTDKSLYNKPSYETFIKTQGSAVAKLKKEGFMKILDEASV
(SEQ ID NO: 5)

>SRR5371371_1138852_2|M
[bovine gut metagenome]
MAHKKNIGAEIVKTYSFKVKNTNGITMEKLMNAIDEYQSYYNLCSDWICKNLTTMTIGDLDRYIPEKAKDNIYATVLLDEVWKN
QPLYKIFGKKYSSNNRNNALYCALSSVIDMTKENVLGFSKTHYIRNGYILNVISNYASKLSKLNTGVKSRAIKETSDEATIIEQ
VIYEMEHNKWESIEDWKNQIEYLNSKTDYNPTYMERMKTLSAYYSTHKDEVNCDAKMQEMAVENLVKFGGCRRNNSKKSMFIMGSN
TTNYTISYIGDNCFNINFANILNFDVYGRRDVVKNGEVLVDIMANHGDSIVLKIVNGELYADVPCSVTLNKVESNFDKVVGIDV
NMKHMLLSTSVTDNGSSDFVNIYKEMSNNAEFMALCPEKDRKYYKDISQYVTFAPLELDLLFSRISKQGEVKMEKAYSEILESL
KWKFFANGDNKNRIYVESIQKIRQQIKALCVIKNAYYEQQSAYDIDKTQEYIETHPPSLTEKGMSIKSKMDICQTIIGCRNNI
IDLAYSFFERNGYSIIGLEKLTSSQFKNTKSMPTCKSLLNLHKVLGHTLSELETLPINDIVKYYTFTTDNEGRITDASLSEKGK
IRKMKDRFLNQAIKAIHFADVKDYFATLSNNGQTGIFFVPSQFTSQMDSNTHNLYFEVDKNGGLKMASKDKTRPKQEYHRNGLP
ADYNAARNIAYIGLDETMRNTFLKKVSNKSLYNQPIYDTGIKKTAGVFSRMKKLKRYEII (SEQ ID NO: 6)
```

TABLE 62-continued

Amino Acid Sequences of Representative CLUST.091979 Effector Proteins

\>SRR5371379_2478682_1|M
[bovine gut metagenome]
MIKSIKLKVKGDCPITKDVINEYKEYYNRCSDWIKNNLTSITIGEIGKFLQDVTGKTTGYIEVALSDKWKDKPMYYLFTDQYDT
NHANNLLYSFIQENNLDGYDGNSLNISGTYYRKQGYFKLVSSNYRTKIRTLNCKIKRKKVDVDSTSEDIESQVMYEIINRSLNK
KSDWDSFISYIENVENPNIDSINRYTLLRDYFCDNEDVIKNKIELLSIEQLKDFGGCIMKQHINTMSLNIQHFKIEEKENSLGF
ILYLPLNKKQYQIELWGHRQIKKGSKESCETLVDFINTYGENIVFTINNDELYVVFSYESEFGKEETNFEKSVGLDINFKHALF
VTSELDNDQFDGYINLYKYILSHSEFTNLLTEDERKDYEELSKVVTFCPFENQLLFARYDKMSKFCKKEQVLSKLLYSLQKKLK
NENRTKEYIYVSCVNKLRAKYISYFILREKYDEKNKEYDIEMGFVDDSTESKESMDKRRFENPFRNTLVANELLAKMSKVQQDI
NGCMSNIINYVYKVFEQNGYNIIALENLENSNFEKRQVLPTIKSLLKYRKLENQNINDIKASDKIKEYIENGYYSFTTNENNEI
VDAKYTAKGDIKVKNAKFFNLMMKILHFASIKDEFVLLSNNGKSQIALVPPEYTSQMDSIDHCIYMTENDKGKIVKVDKRKVRT
KQERHINGLNADFNAANNIKYIVSNEKWRNVFCTPKKAKYNTPALDATKKGQFRILDDMKKLNATKLLEIEK
(SEQ ID NO: 7)

\>SRR5371385_201181_1|P
[bovine gut metagenome]
MYQLNQYIMASHKKTESNQIIKTFSFKIKNANGLSLDVLNDAITEYQNYYNICSDWIKDHLTMKISELYKYIPDEKKNSGYALT
LISDEWKDKPMYMMFKKGYPANNRDNAIYETLNTCNTEHYTGNILNFSDTYYRRFGYVASAISNYVTKISKMSTGSRYKNISND
SDVDTIMEQVIYEMEHNGWTSVSKDWENQMEYLESKTDSNPNFVYRMTTLYEFYKSHIDEVNSKMETMSIDSLIKFGGCRRKDS
KSMYIMGGSNTPFDITQIGGNSLNIKFSKNLNVDVFGRYDVIKONTLLVDIINGHGASFVLKIINDEIYIDINVSVPFDKKIAT
TNKVVGIDVNIKHMLLATNILDDGNVKGYVNIYKEVINDSDFKKVCNSTVMKYFTDFSKFVTFCPLEFDFLFSRVCNQKGIYND
NSAMEKSFSDVLNKLKWNFIETGDNTKRIYIENVMKLRSQMKAYAIVKNAYYKQQSEYDFGKSEEFIQEHPFSNTDKGIEILHK
LDNISKKILGCRNNIIQYSYNLFEINGYDMISLEKLTSSQFKKKPFPTVNSLLKYHKILGCTQEEMEKKDIYSVIKKGYYDIIF
DNGVVIDAKLSAKGELSKFKDDFFNLMIKSIHFADIKDYFITLSNNGTAGVSLVPSYFTSQMDSIDHKIYFVQDNKSGKLKLAN
KHKVRSSQEKHINGLNADYNAARNIAYIMENTECRNMFMKQSRTDKSLYNKPSYETFIKTQGSAVSKLKKDGFVKILDEASV
(SEQ ID NO: 8)

\>SRR5371385_201181_1|M
[bovine gut metagenome]
MASHKKTESNQIIKTFSFKIKNANGLSLDVLNDAITEYQNYYNICSDWIKDHLTMKISELYKYIPDEKKNSGYALTLISDEWKD
KPMYMMFKKGYPANNRDNAIYETLNTCNTEHYTGNILNFSDTYYRRFGYVASAISNYVTKISKMSTGSRYKNISNDSDVDTIME
QVIYEMEHNGWTSVKDWENQMEYLESKTDSNPNFVYRMTTLYEFYKSHIDEVNSKMETMSIDSLIKFGGCRRKDSKKSMYIMGG
SNTPFDITQIGGNSLNIKFSKNLNVDVFGRYDVIKONTLLVDIINGHGASFVLKIINDEIYIDINVSVPFDKKIATTNKVVGID
VNIKHMLLATNILDDGNVKGYVNIYKEVINDSDFKKVCNSTVMKYFTDFSKFVTFCPLEFDFLFSRVCNQKGIYNDNSAMEKSF
SDVLNKLKWNFIETGDNTKRIYIENVMKLRSQMKAYAIVKNAYYKQQSEYDFGKSEEFIQEHPFSNTDKGIEILHKLDNISKKI
LGCRNNIIQYSYNLFEINGYDMISLEKLTSSQFKKKPFPTVNSLLKYHKILGCTQEEMEKKDIYSVIKKGYYDIIFDNGVVIDA
KLSAKGELSKFKDDFFNLMIKSIHFADIKDYFITLSNNGTAGVSLVPSYFTSQMDSIDHKIYFVQDNKSGKLKLANKHKVRSSQ
EKHINGLNADYNAARNIAYIMENTECRNMFMKQSRTDKSLYNKPSYETFIKTQGSAVSKLKKDGFVKILDEASV
(SEQ ID NO: 9)

\>SRR5371401_1055766_58|M
[bovine gut metagenome]
MIKSIQLKVKGECPITKDVINEYKEYYNNCSDWIKNNLTSITIGEMAKFLQSLSDKEVAYISMGLSDEWKDKPLYHLFTKKYHT
KNADNLLYYYIKEKNLDGYKGNTLNISNTSFRQFGYFKLVVSNYRTKIRTLNCKIKRKKIDADSTSEDIEMQVMYEIIKYSLNK
KSDWDNFISYIENVENPNIDNINRYKLLRECFCENENMIKNKLELLSVEQLKKFGGCIMKPHINSMTINIQDFKIEEKENSLGF
ILHLPLNKKQYQIELLGNRQIKKGTKEIHETLVDITNTHGENIVFTIKNDNLYIVFSYESEFEKEEVNFAKTVGLDVNFKHAFF
VTSEKDNCHLDGYINLYKYLLEHDEFTNLLTEDERKDYEELSKVVTFCPFENQLLFARYNKMSKFCKKEQVLSKLLYALQKKLK
DENRTKEYIYVSCVNKLRAKYVSYFILKEKYYEKQKEYDIEMGFVDDSTESKESMDKRRTEYPFRNTPVANELLSKLNNVQQDI
NGCLKNIINYIYKIFEQNGYKVVALENLENSNFEKKQVLPTIKSLLKYRKLENQNVNDIKASDKVKEYIENGYYELMTNENNEI
VDAKYTEKGAMKVKNANFFNLMMKSLHFASVKDEFVLLSNNGKTQIALVPSEFTSQMDSTDHCLYMKKNDKGKLVKADKKEVRT
KQERHINGLNADFNAANNIKYIVENEVWRGIFCTRPKKTEYNVPSLDTTKKGPSAILNMLKKIEAIKVLETEK
(SEQ ID NO: 10)

\>SRR5371439_988701_11|M
[bovine gut metagenome]
MIKSIVFKVKGDCPITKDVIKEYKEYYNNCSEWIKNNLTSITIGEIGKFLQDTMGKTHGYIKVALSDEWKDKPMYYLFTEKYDT
KHANNLLYYFIQENNLDRYEGNSLNIPSYYYKREGYFKLVTSNYRTKIRTLNCKIKRKKIDVDSTCVDIENQVIYEIIKKGLNK
KSDWDNYISYIENIEMPNIDSINRYKLLRDYFCENENVIKNKIELLSIEQLKNFGGCIMKQHINTMILNIKRLKIEEKENSLGF
ILHLPLNKKQYQIELWGNRQIKKGTKESNETLVDFINTYGEDVVFTIKKNELYAKFSYECEFEKEETNFEKSVGLDINFKHALF
VTSELDDDQFYGYINLYKYILSHSEFTNLLTEDEKKDYEDLSNAITFCPFENQLLFTRYDKKSKLYKKEQVLSKILYSLQKKLK
DENRKQEYIYVSCVNKLRAKYVSYFILKEKYNEKQKEYDIEMGFVDDSTESKESMDKRRTEYPFRNTVANELLEKMNNVQQDI
SGCLKNIINYAYKVFEQNGYNIVALENLENSNFEKRNVLPTIKSLLKYRKLENQNITDIKASDKIKEYIENGYYELITNENNEI
IDAKYTENGDIKVKNARFFNLMMKSLHFASIKDEFVLLSNNGKSQIALVPSEYTSQMDSTDHCIYMTENDKGKLVKVDKRKVRT
KQERHINGLNADFNAANNIKYIVENEKWRKVFCAPQKAKYNTPTLDATKKGQFRILEDLKKLKATKLLEIGK
(SEQ ID NO: 11)

\>SRR5371497_203858_6|M
[bovine gut metagenome]
MIKSIQLKVKGECPITKDVINEYKEYYNNCSDWIKNNLTSITIGEMAKFLQSLSDKEVAYISMGLSDEWKDKPLYHLFTKKYHT
KNADNLLYYYIKEKNLDGYKGNTLNISNTSFRQFGYFKLVVSNYRTKIRTLNCKIKRKKIDADSTSEDIEMQVMYEIIKYSLNK
KSDWDNFISYIENVENPNIDNINRYKLLRECFCENENMIKNKLELLSVEQLKKFGGCIMKPHINSMTINIQDFKIEEKENSLGF
ILHLPLNKKQYQIELLGNRQIKKGTKESHETLVDITNTHGENIVFTIKNDNLYIVFSYESEFEKEEVNFAKTVGLDVNFKHAFF
VTSEKDNCHLDGYINLYKYLLEHDEFTNLLTEDERKDYEELSKVVTFCPFENQLLFARYNKMSKFCKKEQVLSKLLYALQKKLK
DENRTKEYIYVSCVNKLRAKYVSYFILKEKYYEKQKEYDIEMGFVDDSTESKESMDKRRTEYPFRNTPVANELLSKLNNVQQDI
NGCLKNIINYIYKIFEQNGYKVVALENLENSNFEKKQVLPTIKSLLKYRKLENQNVNDIKASDKVKEYIENGYYELMTNENNEI
VDAKYTEKGAMKVKNANFFNLMMKSLHFASVKDEFVLLSNNGKTQIALVPSEFTSQMDSTDHCLYMKKNDKGKLVKADKKEVRT
KQERHINGLNADFNAANNIKYIVENEVWRGIFCTRPKKTEYNVPSLDTTKKGPSAILNMLKKIEAVKILETEK
(SEQ ID NO: 12)

TABLE 62-continued

Amino Acid Sequences of Representative CLUST.091979 Effector Proteins

>SRR5371501_2762794_1|M
[bovine gut metagenome]
MKNNLTTVTIGEMAKFLQETTGKNVTYITMGLSEEWKDKPLYHLFYGKYHTKNADNLLYYFIKAKKLDEYDGNMLNLGDTYYRQ
FGYFKLVVSNYRTKIRTLNLNVKRKRVDVDSTSEDIESQVMYEIVKRNLNTISDWENYISYIEDVETPNIDNINRYKFLQNYFC
ENEEDIKNKIEFLSIEQLKDFGGCIMKPHINSMTINIQDFKIEEIENSLGFVLQLPLNKKYHQIELYGNRQVKKGTKENYKTLV
DIINTHGENIVFTIENNELYVVFSYEYELKKKDINFEKMAGIDVNFKHALFVTSETDNNQLNHYINLYKHILEHNEFTTLLTDS
ERKDYEEIAKTVTFCPPFEYQLLFTRFDKNSNANVKEQALSKILYDLQKKLKSQNKIKEYIYVSCVNKLRAKYVSYFILKEKYYE
KQKEYDIQMGFVDDSTESKSSMVKRRVEYPFRNTPVANALLAIVNNVQQDINGCLKNIINYAYKVFELNDYNVVALENLENANF
EKKQVIPTIKSLLKYRKLEMQNINDIKANDTIKKYIENEYYQLITNENNEIVNAIYTPKGITKLKYANFFNLLMKSLHFASIKD
EPILLSNNGNTNIALVPHEYTSQMDSIDHCIYMVQNDKGNLVKARKTKVRTKQEKHINGLNADFNAANNIKYIVENEKWRNIFC
KIPKKIEYNTPVLDVTKKGQSNIIKTLKNLNATKILEIKK
(SEQ ID NO: 13)

>SRR5678926_1309611_3|P
[terrestrial metagenome]
MKKSIKFKVKGNCPITKDVINEYKEYYNKCSDWIKNNLTSITIGEMAKFLQETLGKDVAYISMGLSDEWKDKPLYHLFTKKYHT
NNADNLLYYYIKEKNLDGYKGNTLNIGNTFFRQFGYFKLVVSNYRTKIRTLNCEIKRKKIDADSTSEDIEMQTMYEIIKHNLNK
KTDWDEFISYIENVENPNIDNINRYKLLRKCFCENENMIKNKLELLSIEQLKNFGGCIMKQHINSMTLIIQHFKIEEKENSLGF
ILNLPLNKKQYQIELWGNRQVNKGTKERDAFLNTYGENIVFIINNDELYVVFSYEYELEKEEANFVKTVGLDVNFKHAFFVTSE
KONCHLDGYINLYKYLLEHDEFTNLLTNDEKKDYEELSKVVTFCPFENQLLFARYNKMSKFCKKEQVLSKLLYALQKQLKDENR
TKEYIYVSCVNKLRAKYVSYFILKEKYYEKQKEYDIEMGFVDDSTESKESMDKRRTEFPFPRNTPVANELLSKLNNVQQDINGCL
KNIINYIYKIFEQNGYKIVALENLENSNFEKKQVLPTIKSLLKYRKLENQNVNDIKASDKVKEYIENGYYELITNENNEIVDAK
YTEKGAMKVKNANFFNLMMKSLHFASVKDEFVLLSNNGKTQIALVPSEFTSQMDSTDHCLYMKKNDKGKLVKADKKEVRTKQEK
HINGLNADFNAANNIKYIVENEVWREIFCTRPKKAEYNVPSLDTTKKGPSAILHMLKKIEAIKILETEK
(SEQ ID NO: 14)

>SRR6059713_382107_4|P
[feces metagenome]
MAKSIMKKSIKFKVKGNSPINEDIINEYKGYYNTCSNWINNNLTSITIGEMGKFLKDVMRKTTGYIDVALSDEWKDKPMYYLFT
KKYNPKHANNLLYYFIKEKKLDKFNGNILNVPEYYYRKEGYFKLVAGNYRTKINTLNFKIKSKKVDANSLSEDIEMQTIYEIVK
RGLNKKSDWDSYISYIECVQNPNIDNINRYKLLRDYFCENEDVIKNKIEILSIEQIKEFGGCIMKPHINSMTFGIQKFKIEEIE
NSLGFTFNLPLNKNNYKIELWGHRQLKKGNKESNVNVSLDDFINTYGQNVVFTIKRKKLYIVFSYDYEFERGECNFEKSVGLDV
NFKHSLFVTSEIDNNQFDGYINLYKYILSNNEFTSLLTDSERKDYEDLANIVTFCPFEYQLLFSRYDKLSKISEKEKVLSKILY
SLQKKLKNEKRTKEYIYVSCVNKLRAKYVSYFKLKQKYNEKQKEYDIEMGFVDDSTESKESMDKRRFENPFINTPVAKELLEKM
NNVKQDINGCKKNIVVYAYKVLEQNGYNIIALENLENSNFEKIRVLPKIKSLLYHFKFENKNINDIKNSDKYKEFIEPGYFELI
TNENNEIIDAKYTQKGDIKIKNADFINIMIKALNFASIKDEFILLSHNGKSQIALVPAEYTSQMDSIDHCIYMTKNDKGKLVKV
DKRKVRTKQERHINGLNADFNAACNIKYIVTNEDWRKVFCIKPKKEDYNTPLLDATKNGQFRILDKLKKLNATKLLEMEK
(SEQ ID NO: 15)

>SRR6060192_2608084_13|P
[feces metagenome]
MANKKFKLTKNEVVKSFVLKVANQKKCAITNETLQEYKNYYNKVSQWINNNLTKMTIGDLIQYAPTVSKKGKKQPDGTMVYDTP
LYVTYAMSDEWKNKPLYYIFKKEYNTNNANNLLYEAIRNLNVDYDGNQLNFNSTYYRTQGYVNRVFSNYRTKINTLDIKIKKS
KVDENSDVETLELQTMYEINKLNLKTNKDWEERLQYLTMQENPNQNTIDRTKILFNYFINNNDTIFQKMEELSIKQLTEFGGCK
MKDNTTSMTINIQDFKIKRKENSIGYIMTIPPFNKKNVDVELYGHKQTIKGHKNSYTEIVDIVNKHGNTITPFKIKNNQLFAIITS
DTEVTKPEPQYEKIVGVDVNIKHTLMVTSEKDNGKLKGYINLYKEVLKNDEFKKLLNKTELDNFKSLSQIVTFCPIEYDFLFSR
IFDDENTKKELAFSNVLYDIQKQLKNTNNILQYNYIACVNKLRAKYKAYFVLKMSYMKQQKIYDTNMGFFDISTESKETMDQRR
SLYPFINTEIAQNIITKMNNVQQDINGCLKNIFKYTYTVFENNNYDTIVLENLENANFEKHNPLPNITSLLKYHKVQGLTIQEA
EQHEKVGNLIQNDNYIFQLNEDNKIINADYSQKAYYKVCKALFFNQAIKTLHFASVKDEMIKLSNNNKVCVAIIPPEYTSQIDS
NTHKLYFINKDGKLLKADKKTVRKTQEKHINGLNADFNAASNIKYIVQNETWRNLFTNKTNNTYGLPILTPSKKGQSNIITQLM
KINATQELVV (SEQ ID NO: 16)

>SRR7634052_1662339_24|M
[sheep gut metagenome]
MYNSKKKGEGDIQKSFKFKVKTDKETVELFRKAAVEYSEYYKRLTTFLCERLTDMTWGEVASFIPEKYRKNEYYKYLIKEENKD
LPLYKMFTKAASSMFIDHSIERYVEALNPEGNTGNILGFCKSSYVRGGYLKNVVSNIRTKFATLKTGIKYKKFNPAEDDEETIL
GQTVFEMEKRGLEFKCDFEKTIKYLNEKGKTQEAERLQCLMEYFSTNTDKINEYRESLVLDDIRKFGGCNRSKSNSFSVTLEKA
DIKEDGLTGYTMKVSKKLKEIHLLGHRRVVEVVNGRRVNLVDICGDKSGDSKVFVVDGDNLYVCISAPVKFSKNGMEAKKYIGV
DMNMKHSIISVSDNASDMKGFLNIYKELLKDEGFRKTLNATELEKYEKLAEGVNIGIIEYDGLYERIVKQKKENSVDGLKVQAE
KKLIEREAAIERVLDKLRKGTSDTDTENYINYNKILRAKIKSAYILKDKYYEMLGKYDSERAGSGDLSEENKIKYKDEFNETEK
GKEILGKLNNVYKDIIGCRDNIVTYAVNLFIRNGYDTVALEYLESSQMKARRIPSTGGLLKGRKLEGKPEGEVTAYLKANKIPK
SYYSFEYDGNGMLTDVKYSDMGEKARGRNRFKNLVPKFLRWASIKDKFVQLSNYKDIQMVYVPSPYTSQTDSRTHSLYYIETVK
VDEKTGKEKKEHIVAPKESVRTEQESFVNGMNADTNSANNIKYIFENETLRDKFLKRTKDGTEMYNRPAFDLKECYKKNSNVSV
FNTLKKTLGAIYGKLDENGNFIENECNK (SEQ ID NO: 17)

>AUX0017332817_2|M
[gut metagenome]
MAGHSKIKENHIMKAFLMKVKETRKKQWQSNFIRSEIAKFTNYYNGLSKFIADRLLDDMVTTLAPLIEEKKRNSEYYKYLTNGD
WDGKPLYFIFKEGFNSTNADNILANSLVRVYCEQNYTGNGFGLSYSYYVVIGFAKEVIANYRSSFQKPKVKIKKKKLSENPTED
ELIEQCIYTIYYEFNEKKDIQKWKDEIKFLKERGESKETRLKRIQTLFEFYDKSHKELVDERVANLVVDNIKEFGGCKRDIDC
PSMGIQIQHNFDISINEKRNGYTICFGPNKKNLTKLEVFGNRMVLLNGEEIVDLPNTHGEKLTLIDRGNAIYAAITAQVPFEKH
MPDGNKTVGIDLNLKHSVFATSIVDNGKLAGYISIYKELLKDDEFVKYCPKDLLRFMKDASKYVFFAPIEIELLRSRVIYNKGY
ACVENYENVYKAEVAFVNVIKRLQSQCEANGDAQGALYMSYLSKMRAQLKNYINLKLAYYDHQSAYDLKMGFTDISTESKETMD
ERRKLFPFNKEKEAQEILAKMKNISNVIIACRNNIAVYMYKMFERNGYDFIGLEKLESSQMKKRQSRSFPTVKSLLNYHKLAGM
TMDEIKKQEVSSNIKKGFYDLEFDADGKLYGAKYSNKGNVHFIEDEFYISGLKAIHFADMKDYFVRLSNNGKVSVALVPPSFTS
QMDSVERKFFMKKNANGKLIVADKKDVRSCQEKHKINGLNADYNAACNIGFIVEDDYMRESLLGSPTGGTYDTAYFDTKIQGSK
GVYDKIKENGETYIAVLSDDVITAEV (SEQ ID NO: 18)

TABLE 62-continued

Amino Acid Sequences of Representative CLUST.091979 Effector Proteins

```
>OQVL01000914_15|P
[human gut metagenome]
MAHKKNVGAEIVKTYSFKVKNTNGITMEKLMNAIDEFQSYYNLCSDWICKNLTTMTIGDLDQYIPEKAKGNTYATVLLDEAWKN
QPLYKIFGKKYSSNNRNNALYCALSSVIDMTKENVLGFSKTHYIRNDYILNVISNYASKLSKLNTGVKSRAIKETSDEATIIEQ
VIYEMEHNKWESIEDWKNQIEYLNSKTDYNPTYMERMKTLSAYYSTHKSEVDAKMQEMAVENLVKFGGCRRNNSKKSMFIMGSN
TTNYTISYIGGNSFNINFANILNFDVYGRRDVVKNGEVLVDIMANHGDSIVLKIVNGELYADVPCSVTLNKVESNFDKVVGIDV
NMKHMLLSTSITDNGSSDFLNIYKEMSNNAEFMALCPEEDRKYYKDISKYVTFAPLELDLLFSRISKQGKVKMEKVYSEILEAL
KWKFFANGDNKNRIYVESIQKIRQQIKALCVIKNAYYEQQSAYDIDKTQEYIETHPFSLTEKGMSIKSKMDKICQTIIGCRNNI
IDYAYSFFERNGYSIIGLEKLTSSQFEKTKSMPTCKSLLNFHKVLGHTLSELETLPINDVVKKGYYTFTTDNEGKITDASLSEK
GKVRKMKDDFFNQAIKAIHFADVKDYFATLSNNGQTGIFFVPSQFTSQMDSNTHNLYFENAKNGGLKLAPKYKVRQTQEYHLNG
LPADYNAARNIAYIGLDETMRNTFLKKANSNKSLYNQPIYDTGIKKTAGVFSRMKKLKRYEII (SEQ ID NO: 19)

>3300001598|EMG_10017415_6|P
[mammals-digestive system-asian elephant fecal-elephas maximus]
MLNIKNNGESVDMNTIELAMKEYNRYYNICSDWICNNLMTPIGSLYQYIDDKCKNNAYAQNLIAEEWKDKPLYYMFYKGYNANN
CANAICCAIRSQVPEVNKAENILNLSYTYYFRNGVIKSVISNYASKMRILSDKQIKYCIVSENTPDKILIEQCILELKRRHEDL
KDWEENLKYLILKGNESAITRFTILKDFYSKNIERVKEEREIMAIAELKDFGGCRRKDDKLSMCIQSAGNSKDIKVSRVKTTHN
YTELVDDYTENFNIKFSALDFNVMGRRDVVKTKLNKTEDDSNTWGGTELLVDIINNHGCSLTFKLVDDKLYVDIPIDTEHINKT
TDFKKSVGIDVNLKHSLLNTDILDNGGINGYINIYKKLLADDAFMSACTKADLVNYIDIAKTVTFCPIEADFIISNVVEKYLHM
KONTNKMEIAFSSVLMNIRKELEIKLLHSSKEESPLIRKQIIYINCIICLRNELKQYAIAKHRYYKKQQEYDTLCDTLHGVDYK
QIHPYAQSKEGAEQMKKMKTIENNLIANRNNIIEYAYTVFELNNFDLIALENITKDIMEDKKKRKSFPSINSLLKYHKVINCTE
DNINDNETYQKFAKYYNVSYENGKVTGATLSQEGNKVKLKDDFYDKLLKVLHFTSIKDYFTTLSNKRKIAVAHVPAYYTSQIDS
IDNKICMIKSTDKNGKSTYKIADKTIVRPTQEKHINGLNADYNAARNINFIVADEKWRKKFVRPTNTNKPLYNSPVFSPAVKSE
GGTIKNLQILSATKTIIL (SEQ ID NO: 20)

>3300021254|Ga0223824_10022219_2|P
[mammals-digestive system-cattle and sheep rumen]
MAHVRTKNEGNMAKTYSFKVRETNLKKDVMIEYNEYYNRLSDWICGNLTKMTIGELAELVPEKKRNTSYYLAATDEKWINEPMY
KLFTDEYTKKSSFTDPLVANSNNCDNLILTATDVLNPEGYEGNLLSLCKSTYRTFGYAKQIISNMKTKIGALKPNVKRRVLGEN
PTYDEKMIQVLYEMYNNGIADVTGFNDRIKYLKKQETPNEKLISRMKQRLLIDFFKENRNDIMDKCRIMAVEQLVSFGGCKRNING
ASMTLRNQCISVKRKDGCQGYVVAIPVGTKNSIVFDLYGRRDVIKDGVELVDVCGKHTDTITIKSVNGELFLDMPVAINFEKKS
GKCTKTVGIDVNTKHMLIQTSVKDNGKFDYYVNLYKIFAEDEELNKILGDDEVMVNIKKNAENLSFLPLEMDLLYSRILDGPQK
YKLAEDRITELLKQWGINFDAGCMSQERIYVQCVRKLRGNLKRLLYLQNKYYEAQQEYDKKMGFDDKSTDSKETMDKRRWESPF
RNTEEGTKLYDEINTYQNRIIGIRNSIIDYAYLVLEYNGYDNLSLEYLTSSQFKVNKTFPTTNSLLKYRKLQGKTKTEAEKCDA
YISHKSKYKLSLKDGVIDSIDYSAEGLKQIKKDRSRNIIIKAIHFADVKDRFVLSSNNGNASVTFVPSYHTSQIDSTDHKMFVT
NKGKIVDKRKVRQIQETHVNGLNSDFNAARNIQYISENEEWRNALCKPTENMYNEPIYVPLVKSQNGMFKAIKKLGATKIWQE
(SEQ ID NO: 21)

>3300021431|Ga0224423_10015012_2|P
[mammals-digestive system-cattle and sheep rumen]
MAHRNKNLAENCINKTFSFKVKAEKEEINSKWIPAIKEYTAYYNRISDWICDRLTNTTVGELIGIIGYKTDKKGNALAYIKDGS
SEKYRNLPLYCMFKKNFPATTADNIMYQVIEKLGVDKYNGNSLGLSGTYYRRIGYIANVIGNYRTKVRGMKASVKYRNFDPNDV
TEDVLENQTIFEINKNGFECKGDFEKHIEYLKNRELTDRLNKLILRMECLYNYVEHEDAVKAKMENYAIESFKTFGGCHRNSN
RSMSIQFTNNSPLEIKKVGKTSFDLYMPINGEVACLQLMGNKQAVCVGENGERCDLVDIVNSHSKTITIKIINGEMYVDIPCVV
NFEKKDEDTIKSVGVDVNIKHEILATSVIDNGQLNGYFNIYKELINNKEFVDTFNGDIKAFEAFKDNAAYVTFGLLEPDLLFTR
FYERSGFEKDDRHIKLRERERILTGILKRIGQEHSDVDVRNYVRFVNMLRSKYESYFVLKNKYYEKMQEFDSTQNYVDVSTASK
ETMDKRRFDNPFRNTEVANELLGKIDNVLGDIKGCMANIITYAFKVLQKQNTIGLEYLDSSQFENMRTLTPTSILKYRKMEG
KSVDAVESWIKENKIPSNRYDFIYEDNHLTDVLLNSNGIAYQKKNLFMNLVIKAISFADIKNKFVQLSNNTNVSILFAPAAFTS
QMDSNRHVIYTVKNNKGKLALVDKKRVRPNQEKHINGLHSGYNAACNVKFICDNEFFRNTMTISNKGKNLYSQPTYDIKEAYKK
NAGCKVINDFIKNGNAVICCIENNKLIETNGRQ (SEQ ID NO: 22)

>3300012973|Ga0123351_1009859_3|P
[mammals-digestive system-fecal]
MANKKFKLTKNEVVKSFVLKVANQKKCAITNETLQEYKNYYNKVSQWINNNLTKMTIGDLIQYAPTVSKKGKKQPDGTMVYDTP
LYVTYAMSDEWKNKPLYYIFKKEYNTNNANNLLYEAIRNLNVDGNQLNFNSTYYRTQGYVNRVFSNYRTKINTLDIKIKKS
KVDENSDVETLEPQTMYEINKLNLKTNKDWEERLQYLTMQENPNQNTIDRTKILFNYFINNNDTIFQKMEELSIKQLTEFGGCK
MKONTTSMTINIQDFKIKRKENSIGYIMTIPFNKKNVDVELYGHKQTIKGHKNSYTEIVDIVNKHGNTITFKIKNNQLFAIITS
DTEVTKPEPQYEKIVGVDVNIKHTLMVTSEKDNGKLKGYINLYKEVLKNDEFKKLLNKTELDNFKSLSQIVTFCPIEYDFLFSR
IFDDENTKKELAFSNVLYDIQKQLKNTNNILQYNYIACVNKLRAKYKAYFVLKMSYMKQQKIYDTNMGFFDISTESKETMDQRR
SLYPFINTEIAQNIITKMNNVQQDINGCLKNIFKYTYTVFENNNYDTIVLENLEANFEKHNPLPNITSLLKYHKVQLTIQEA
EQHEKVGNLIQNDNYIFQLNEDNKIINADYSQKAYYKVCKALFFNQAIKTLHFASVKDEMIKLSNNNKVCVAIIPPEYTSQIDS
NTHKLYFINKDGKLLKADKKTVRKTQEKHINGLNADFNAASNIKYIVQNETWRNLFTNKTNNTYGLPILTPSKKGQSNIITQLM
KINATQELVV (SEQ ID NO: 23)

>3300012979|Ga0123348_10005323_4|M
[mammals-digestive system-fecal]
MAKSIMKKSIKFKVKGNSPINEDIINEYKGYYNTCSNWINNNLTSITIGEMGKFLKDVMRKTTGYIDVALSDEWKDKPMYYLFT
KKYNPKHANNLLYYFIKEKKLDKFNGNILNVPEYYYRKEGYPKLVAGNYRTKINTLNFKIKSKKVDANSLSEDIEMQTIYEIVK
RGLNKKSDWDSYISYIECVQNPNIDNINRYKLLRDYFCENEDVIKNKIEILSIEQIKEFGGCIMKPHINSMTFGIQKFKIEEIE
NSLGFTFNLPLNKNNYKIELWGHRQLKKGNKESNVNVSLDDFINTYGQNVVFTIKRKKLYIVFSYDYEFERGECNFEKSVGLDV
NFKHSLFVTSEIDNNQFDGYINLYKYILSNNEFTSLLTDSERKDYEDLANIVTFCPFEYQLLFSRYDKLSKISEKEKVLSKILY
SLQKKLKNEKRTKEYIYVSCVNKLRAKYVSYPLKLQKVNEKQKEYDIEMGFVDDSTESKESMDKRRFENPFINTPVAKELLEKM
NNVKQDINGCKKNIVVYAYKVLEQNGYNIIALENLENSNFEKIRVLPKIKSLLEYHKFENKNINDIKNSDKYKEFIEPGYFELI
TNENNEIIDAKYTQKGDIKIKNADFINIMIKALNFASIKDEFILLSHNGKSQIALVPAEYTSQMDSIDHCIYMTKNDKGKLVKV
DKRKVRTKQERHINGLNADFNAACNIKYIVTNEDWRKVFCIKPKKEDYNTPLLDATKNGQFRILDKLKKLNATKLLEMEK
(SEQ ID NO: 24)
```

TABLE 62-continued

Amino Acid Sequences of Representative CLUST.091979 Effector Proteins

>3300028797|Ga0265301_10000251_12|M
[mammals-digestive system-rumen-bos taurus]
MVKVFINVFLSEKNQITTNIFDTEKISNSYINHINHQFMATHKKTDNQTIVKAYVMKAKMSKHDIERVWKPTIDEYINYYNKLS
DWICKNLTSVTIGDLLKYVGEKQINKGVGYYTYFIDEQKTDLPLYTLFTDCPKTHADNLLFEAVRKINPENYNGNLLSLFETGY
RRNGYFDNVISNYRTKMTTLKINPKYKRFSSENMPTDEVLLEQTVYEVTKNDFKNDDDWKKSIDYMKQKSEPNTALIFRMETLF
DYWKDHKQDVEQYINQKRVECLKDFGGCKRRADGLSMVILLNKKLTKIEADGLTSYKLTTNLFGGKYMINIFGHRALVSVCNGE
RAENENIDICNKHGERFTFKIENGNLFVALTADYNYEKQPNLPKNIVGVDINIKHSMLNSSIEDKGKVKGYVNLYKEFLSDKNF
RKTITSDEELNQYIELSKYATFGITELDSLFARATDTEKSILCKRELAMQDVFEKLEKRYKDDHKIKFYLGSTQKLRAQYISYF
KIKEAYNRKQQEYDLAHGKTDNPDEVYKSDFINEPSAKEMLVKLNRIERKIIGCRNNIVTYAFNVIKNNGYDTIGVEYLTSSQF
EKKRRLPSIKSLLNYRKLLGKPKDEWNLKEWNDVYMCYRPELDDAGNIMNFTITNEGIKRNKESTFYNSFIKAIHFADVKDKFA
QLTNNNTMNTVFIPSSFTSQIDSKTRKLYLLEYTEKCDNGKTKKVVKFINKRVLRKIQEQHLNGMNADNNAARNIRDITKNLRD
VFTKKQTDKNCYNSAEFMIQTKFKKRLPQATVFGELNRNGYVKVLTQEEYDELTKSAK (SEQ ID NO: 25)

>3300028797|Ga0265301_10000251_10|P
[mammals-digestive system-rumen-bos taurus]
MATHKKTDNQTIVKAYVMKAKMSKHDIERVWKPTIDEYINYYNKLSDWICKNLTSVTIGDLLKYVGEKQINKGVGYYTYFIDEQ
KTDLPLYTLFTDCPKTHADNLLFEAVRKINPENYNGNLLSLFETGYRRNGYFDNVISNYRTKMTTLKINPKYKRFSSENMPTDE
VLLEQTVYEVTKNDFKNDDDWKKSIDYMKQKSEPNTALIFRMETLFDYWKDHKQDVEQYINQKRVECLKDFGGCKRRADGLSMV
ILLNKKLTKIEADGLTSYKLTTNLFGGKYMINIFGHRALVSVCNGERAENENIDICNKHGERFTFKIENGNLFVALTADYNYEK
QPNLPKNIVGVDINIKHSMLNSSIEDKGKVKGYVNLYKEFLSDKNFRKTITSDEELNQYIELSKYATFGITELDSLFARATDTE
KSILCKRELAMQDVFEKLEKRYKDDHKIKFYLGSTQKLRAQYISYFKIKEAYNRKQQEYDLAHGKTDNPDEVYKSDFINEPSAK
EMLVKLNRIERKIIGCRNNIVTYAFNVIKNNGYDTIGVEYLTSSQFEKKRRLPSIKSLLNYRKLLGKPKDEWNLKEWNDVYMCY
RPELDDAGNIMNFTITNEGIKRNKESTFYNSFIKAIHFADVKDKFAQLTNNNTMNTVFIPSSFTSQIDSKTRKLYLLEYTEKCD
NGKTKKVVKFINKRVLRKIQEQHLNGMNADNNAARNIRDITKNLRDVFTKKQTDKNCYNSAEFMIQTKFKKRLPQATVFGELNR
NGYVKVLTQEEYDELTKSAK (SEQ ID NO: 26)

>3300028797|Ga0265301_10009039_3|M
[mammals-digestive system-rumen-bos taurus]
MAHKGEKEGYQIKTLKFPKVRSHDIGKSLYDIVNEYTNYYNKVSKWICDNLDTPIGELSKNISEKRHNSKYYRATNDPNWKNEPM
WKIFTKKFSNGETFSEQGKNDKLANLSNCDNILSYSIIDYNIDGYTGNILGLTDTSYRLNGYISNCISNYKTKIRTAKPKVRST
AITEHSTVEEKTNNTIYEMVRKGFMSPNDFKNQIKYLTEKENPNDKLIDRLSILHSPYTENEEDVNNAFSRMSVEMLKNNNGCT
RNGDKKTLNISSIDYKVTRKEGCDGYILSFGSRNQKYNIDLWGRRDTISNGKELIDLSEHGEPLTITSENGDYYVCMTVDVPFE
KKSTGSTEKVASVDVNTKHTMLSTDVIDDGTLKGYLNIYKKLLLDTELTSLLHKQDFDDMKELSHNVCFGPIEYNFLLSRILDL
DAYEKKVEDRITHSMKEMLKTETEDERNKMYLGSVIKMRALLKVYISTKNRYHKEQQSYDESMGFTDTSTASKDTMDKRRFENPF
SETETGKKLNNDLSALSKKIIGCRDNIVRYAYTTLQDNGYTMIGVEDLNSSTFANTRNPFPTIKSLLNYHHLSGKTPEEARNID
TYSKFSDHYTLTTDEEGKITDAKYTKKAETKIKKKRARDTIIKAIHFAEVKDVMCVMSNNGTASVAFEPSYFSSQMDSATHKVY
TTRNKKGKDVIASKETVRPRQEKHINGMNCDINSPKNLSYLITNEEFREMFLTPTKNGYNEPFYKSRVKSAASMMSGLKKLGAT
MPLTDENAIFSTPKPKKNIGKQ (SEQ ID NO: 27)

>3300028887|Ga0265299_10000013_320|P
[mammals-digestive system-rumen-bos taurus]
MGNKVQSNETIVKTYTFKVREFISGATHEIMKSAIKQYIEDSNNLSDWINNQLTNKTICEVGALIPIEKRETSYYKSTVDELWA
NKPCFKMFTNDFTKEENFATRNIGNGKNCKNIITSAYKSTVNPSFRNVLDLTEKVYFSDGYGANVCSNYKTKLRTLKPAKIKLV
SSLSDCDDNTLTEQVIREKQKYGYSTPKDFEKRIEYLNEKEKSEQNSKIIERLQKLYEFYDNNTKLVEEKELELSVKSLVEFGG
CRRGEKTMTLNLPDIGYEIQRKDDKYGYIFTLKCSKKRKIIIDVWGSKATIDSNGNDKVDIINTHGKSINFKIINNEMYIDITV
DVPFAKRKLGIKKVVGIDVNTKHMLMATNIKVTDSIKGYVNLYKEFLNSKEIMDVASPETKKNFEDMSMFVNFCPIEYNTMFAL
IFKLNNGDIRTEQAIRRTLHQLSKKFSDGNHETERIYVQNVFSIREQLKHFILLSNRYYSEQSDYDTKMGFIDENTTSNATMDK
RRFDKSLMFRYTQRGRQLYEERIECGRKITEIRDNIITYARNVFVKNGYDTISLENLESSQFENNDHVIAPKSLLEYHHLKGKTH
VVEAEKNERITKNRKYYNLIPDENDNVINIEYTEEGKVAIKKSIARDHIMKAVHFAEVKDKFIQLSNNGKTQVALVPSNYTSQM
NSETHTVYLMKNPKTKKLVIMDKDKVRPIQEKYKLNGLNADFNSARNIAYIVENEILRNSFLKEETKKYTNTPLFTPRLKSSE
KIITELKKLGMTTVIE (SEQ ID NO: 28)

>3300028887|Ga0265299_10000026_77|P
[mammals-digestive system-rumen-bos taurus]
MANKSTKGNLPKTIIMKANLSPDGFTQWERVVKEYQAYKDTLSKWVAQNLTAMKIGDLLPYLDKYSKKTNKETGERPVNVYYQL
CEQHKDEPLYKLFTYDSNSRNNAMYEIIRKTNCDGYKGNILGISETHYRRNGFYPVKNILANYTTKISTLELSERKRKIDSDSPED
LIRSQVVYEMQKNNIKDAKGFKSIIEYLKSKKEVNIQYLERLQILYEYFKNHENEIKEYITLAAVEQLKSFGGVRVNNEKSSMN
LEIQGFSITRVDGACTYILHLPINGKIRGIKLWGNRQVVVNKDGTPVDILDLTNQHGSTINITIKNGEIYFAFTVTSDFVKPER
QIKNVVGVDVNTKHMLMQSNITDNGNVKGYFNIYKVLVEDRRFTSLLSEEQLKYFCELANIVSFCPIETEFLFARYAEYKKMSN
NAEMRQIEKVFSDILDEQYKKYKDIDTSIANYISYVRKLRSQCCAYFKLKMKYKELQRQFDKEQDYKDLSTESKETMDKRRWEN
PFRNTPEASKLIKKMDNVSRQLIGCRDNIITYAYRVFEKNGYDTISLENLESSQFENNDHVIAPKSLLEYHHLKGKTMYSLLD
ECKVRITTKDGKVKEWYHVELNDKDEIDNIFLTPEGETEKEKNLFNNMVIKIVHFADIKDKFIQLGNYNKLQTVLVPSYFTSQM
DSKTHSVYVVETANTKTSKKELKLVSKKRVRRQQEWHINGLNADYNAACNIAHIAKNIELRQIMCKTPQTKNGYSSPVLTSKVK
SQVEMVRELKKMGKTILYSNDSLPF (SEQ ID NO: 29)

>3300028887|Ga0265299_10000133_30|M
[mammals-digestive system-rumen-bos taurus]
MAHRKKKDDEATLSYKFPKVKVIEGDLTADDITKCIAENAEQGNHFSEFIHKNLTSKTIGEFASQLPVEKRQFGYYQYAIGGTMP
AKKNASDEDKPKGELIDWSKKPFYVLFSKGYSATHAVNLIFNVYLNSEEGKAFSAKNSMNLSKSQFAYSGFVQIVCANYASMLA
NARPDKIKFEEITEATDDGTKKMQVVREMAERYLMKPKNFASRIEYLEANNTKGKFDKTIQRLRLLQPFFEKNEEGITELYYDL
SVKALEHSGQCTYKGGRTISILEIGDIRISRKENAKGYLLTIPINRKSVVFDLYGRKDTIGGDGRDLIDIMNTHGSSLQFTADG
NDIYLTITATKNFIKEKPTFNEDTVLGGDVNIKHSYTVFSTSPKDIPDFVNFYEYFAKDGEIMKLAPKPMWDYIVAAATKFLTI
LPIETPAISATVYGKRTEEGISRATFRETQKLIALEKAIERVMKQVPDKVNDGLKPHPLEAIYIGNAIKYRRLIKGYLAQKKKYS
AHSEYDKAMGYTDDDTDRKENMDERRFDDSKKFRYTPEAQALLDTMHTIEKKIVGCVSNAISYAYHKFDENGFNVIALENLTSA
TFAKKYKSDKPESIKKLLNFDKLLGKTLDEAKASKSISKHPNWYELVADENGCVSDIRITDEGQSATYRSLVTETIMKVSHFAE
TKDRFIGLANSGRLQVGLVPSQYTSYIDSTTHTLYAVIEDGKTVLAPKEVVRASQERHINGLNADYNSALNLKYMITDENFRKT
FTSETSADKFGWGKPMFSPTTRSQDEVFSAIKKIGAITVLED (SEQ ID NO: 30)

TABLE 62-continued

Amino Acid Sequences of Representative CLUST.091979 Effector Proteins

>3300028887|Ga0265299_10011526_3|M
[mammals-digestive system-rumen-bos taurus]
MAQHKSNNEESAINKTFIFKAKCEKNDVISLWEPAAKEYGDYYNKVSKWIADNLITMKIGDLAQYITNQNSKYYTAVTNKKKKD
LPLYRIFQKGFSSQCADNALYCAIKSINPENYKGNSLGIGESDYRRFGYIQSVVSNFRTKMSSLKVSVKYKKFDVSNVDDETLK
IQTIYDVDKYGIETAKEFKELIETLKTRVETPQLNDTIARLKCLCDYYSKNEKAINNEIETMAIADLQKFGGCQRKSLNAFTIH
KQDSLMEKVGNTSFRLQLSFRKKTYVINLLGNRQVVNFVNGKRVDLIDIAENHGDLITFNIKNGELFLHITSPIVFDKVDRDIR
NVVGIDVNIKHSMLATSIKDDGNVKGYINLYKELLNDDVFVSTCNESELALYRQMSENVNFGILETDSLFERIVNQSKGGCLKN
KLIRRELAMQKVFERITKTNKDQNIVDYVNYVKMMRAKCKASYILKEKYDEKQKEYYVKMGFTDESTESKETMDKRREEFPPVN
TDTAKELLVKQNNIRQDIIGCRDNIVTYAFNVFKNNEYDTLSVEYLDSSQFDKRRIPTPKSLLKYRKFEGKTKDEVENMMKSEK
LSNAYYTFKYENDVVSDIDYSDEGNLRRSKLNFGNWIIKAIHFADIKDKFVQLSNNNKMNIVFCPSAFSSQMDSITHTLYYVEK
ITKNKKGKEKKKYVLANKKMVRTQQETHINGLNADYNSACNLKYIALNYELRDKMTDRFKASKKIKTMYNIPAYNIKSNFKKNL
SAKTIQTFRELGHYRDGKINEDGMFVEILE (SEQ ID NO: 31)

>3300028887|Ga0265299_10012919_3|P
[mammals-digestive system-rumen-bos taurus]
MAHKNSDGENTINKTFIFKVKCEKNDIISFWKPAAEEYCNYYNKLSEWIGKNLISMKIGDLAKYIDNPKSKYYLSVTDENKKDL
PLYKIFQKGFSSIDADNALYCAIDKLNPEGYNGNILGVGKSDYRRNGYVSSVIGNFRTKMVSLKANVRWKKIDIGNVDEETLRR
QTICDVEKYRIESEKDFRDLIDILKAREETPRLKEKISRLELLYDYYSKNTKTIKSEMENMAISDLQKFGGCVRKSLNTITIHK
QDSKIEKEGNTSFRLHMVFNKKPYTITLLGNRQVVKYIDGKRVDLIDLTNQHGDWITFNIKNGELFVHLTKCVEFSKGQKEIKK
AAGVDVNIKHAMLAASIVDDGQLKGYVNLYRELIEDDDFVSTFGDSDSGKTELGMYQKMAKTVFFGVLEVESLFERVVNQQSGW
KLDNQLIRRERAMEKVFDRIVKTTSNKHIIDYVNYVKMLRAKYKAYPILDEKYHEKQREYDLSMGFTDESDERRELYPFINTET
AKEILGKKRNVEQDLIGCRDNIVTYAFNVLRNNGYDTISVEYLDSSQFDKRRMPTPKSLLEYHKFKGKTQDEVERLMSEKKFAK
TNYDIHYDGENKVDGIVYSKEGELRQKKLNFMNLVIKAIHFADIKDKFAQLCNNNDVNVVFGPSAFTSQMDSETHSLYYVEKET
NGKNGKTGKKFVLADKKSVRRRQETHINGLNADFNAARNLEYIASNPELLERMTKRTKSGKDMYNTPSWNIRQEFKKNLSVRTI
NTFRELGNVKYGKINNEGLFVEDDV (SEQ ID NO: 32)

>3300028914|Ga0265300_10009460_3|M
[mammals-digestive system-rumen-bos taurus]
MAHRKKKDDEATLSYKFKVKVIEGDLTADDITKCIAENAEQGNHFSEFIHKNLTSKTIGEFASQLPAEKRQFGYYQYAIGGTMP
AKKNASDEDKPKGELIDWSKKPFYVLFSKGYSATHAVNLIFNVYLNSEEGKAFSAKNSMNLSKSQFAYSGFVQIVCANYASMLA
NARPDKIKFEEITEATDDGTKKMQVVREMAERYLMKPKNFASRIEYLEANNTKGKFDKTIQRLRLLQPFFEKNEESITELYYDL
SVKALEHSGQCTYKGGRTISILEIGDIRISRKENAKGYLLTIPINRKSVVFDLYGRKDTIGGDGRDLIDIMNTHGSSLQFTADE
NDIYLTITATKNFIKEKPTFNEDTVLGGDVNIKHSYTVFSASPKDIPDFVNFYEYFAKDGEIMKLAPKPMWDYIVAAATKFLTI
LPIETPAISATVYGKRTEEGISRATFRETQKLIALEKAIERVMKQVFDKYNDGKHPLEAIYIGNAIKYRRLIKGYLAQKKKYYS
AHSEYDKAMGYTDDDTDRKENMDERRFDDSKKFRYTPEAQALLDTMHTIEKKIVGCVSNAISYAYHKFDENGFNVIALENLTSA
TFAKKYKSDKPESIKKLLNFDKLLGKTLDEAKASKSISKHPNWYELVADENGCVSDIRITDEGQSATYRSLVTETIMKVSHFAE
TKDRFIGLANSGRLQVGLVPSQYTSYIDSTTHTLYAVIEDGKTVLAPKEVVRASQERHINGLNADYNSALNLKYMITDENFRKT
FTSETSADKFGWGKPMFSPTTRSQDEVFSAIKKIGAITVLED (SEQ ID NO: 33)

>3300031853|Ga0326514_10013355_6|M
[mammals-digestive system-rumen-bos taurus]
MVTTLAPLIEEKKRDSEYYKYLTNGDWDGKPLYFIFKEGFNSTNADNILANSLVRVYCEQNYTGNGFGLSYSYYVVIGFAKEVI
ANYRSSFQKPKVKIKKKKLSENPTEDELIEQCIYTIYYEFNEKKDIKKWKDEIKFLKERGESKETRLKRIQTLFEFYKDKNHKE
LVDERVANLVVDNIKEFGGCKRDIGCPSMGIQIQHNFDISINEKRNGYTICFGPNKNLTKLEVFGNRMVLLNGEEIVDLPNTH
GEKLTLIDRGNAIYAALTAQVPFEKHMPDGNKTVGIDLNLKHSVFATSIVDNGKLAGYISIYKELLKDDEFVKYCPKDLLRFMK
DASKYVFFAPIEIELLRSRVIYNKGYACVENYENVYKAEVAFVNVIKRLQSQCEANGDAQGALYMSYLSKMRAQLKNYINLKLA
YYDHQSAYDLKMGFNDISAESKETIDERRKLFPPFSKEKEAQEILAKMKNISNVIIACRNNIAVYMYKMFERNGYDFIGLEKLES
SQMKKRQSRSFPTVKSLLNYHKLAGMTMDEIKKQEVSSNIKKGFYDLEFDADGKLYGAKYSNKGNVHFIEDEFYISGLKAIHFA
DMKDYFVRLSNNGKVSVALVPPSFTSQMDSVERKFFMKKNANGKLIVADKKDVRSCQEKHKINGLNADYNAACNIGFIVEDDYM
RESLLGSPTGGTYDTAYFDTKIQGSKGVYDKIKENGTEYIAVLSDDVITAEE (SEQ ID NO: 34)

>3300031993|Ga0310696_10000014_323|P
[mammals-digestive system-rumen-bos taurus]
MGNKVQSNETIVKTYTFKVREFISGATHEIMKSAIKQYIEDSNNLSDWINNQLTNKTICEVGALIPIEKRETSYYKSTVDELWA
NKPCFKMFTNDFTKEENFATRNIGNGKNCKNIITSAYKSTVNPSFRNVLDLTEKVYFSDGYGANVCSNYKTKLRTLFQKAIKLV
SSLSDCDDNTLTEQVIREKQKYGYSTPKDFEKRIEYLNEKEKSEQNSKIIERLQKLYEFYDNNTKLVEEKELELSVKSLVEFGG
CRRGEKTMTLNLPDIGYEIQRKDDKYGYIFTLKCSKKRKIIIDVWGSKATIDSNGNDKVDIINTHGKSINFKIINNEMYIDITV
DVPFAKRKLGIKKVVGIDVNTKHMLMATNIKVTDSIKGYVNLYKEFLNSKEIMDVASPETKKNFEDMSMFVNFCPIEYNTMFAL
IFKLNNGDIRTEQAIRRTLHQLSKKFSDGNHETERIYVQNVFSIREQLKHFILLSNRYYSEQSDYDTKMGFIDENTTSNATMDK
RRFDKSLMFRYTQRGRQLYEERIECGRKITEIRDNIITYARNVFVLNGYDTIALEYLTNATIQKPTRPTSPKSLLDYFKLKGKP
VVEAEKNERITKNRKYYNLIPDENDNVINIEYTEEGKVAIKKSIARDHIMKAVHFAEVKDKFIQLSNNGKTQVALVPSNYTSQM
NSETHTVYLMKNPKTKKLVIMDKDKVRPIQEKYKLNGLNADFNSARNIAYIVENEILRNSFLKEETKKYTYNTPLFTPRLKSSE
KIITELKKLGMTTVIE (SEQ ID NO: 35)

>3300031993|Ga0310696_10000226_76|P
[mammals-digestive system-rumen-bos taurus]
MANKSTKGNLPKTIIMKANLSPDGFTQWERVVKEYQAYKDTLSKWVAQNLTAMKIGDLLPYLDKYSKKTNKETGERPVNVYYQL
CEQHKDEPLYKLFTYDSNSRNNAMYEIIRKTNCDGYKGNILGISETHYRRNGFVKNILANYTTKISTLELSERKRKIDSDSPED
LIRSQVVYEMQKNNIKDAKGFKSIIEYLKSKKEVNIQYLERLQILYEYFKNHENEIKEYITLAAVEQLKSFGGVRVNNEKSSMN
LEIQGFSITRVDGACTYILHLPINGKIRGIKLWGNRQVVVNKDFTPVDILDLTNQHGSTINITIKNGEIYFAFTVTSDFVKPER
QIKNVVGVDVNTKHMLMQSNITDNGNVKGYFNIYKVLVEDRRFTSLLSEEQLKYFCELANIVSFCPIETEFLFARYAEYKKMSN
NAEMRQIEKVFSDILDEQYKYKDIDTSIANYISYVRKLRSQCCAYFKLMKYKELQRQFDKEQDYKDLSTESKETMDKRRWEN
PFRNTPEASKLIKKMDNVSRQLIGCRDNIITYAYRVFEKNGYDTISLENLESSQFENNDHVIAPKSLLEYHHLKGKTMNYLLSD
ECKVRITTKDGKVKEWYHVELNDKDEIDNIFLTPEGETEKEKNLFNNMVIKIVHFADIKDKFIQLGNYNKLQTVLVPSYFTSQM
DSKTHSVYVVETANTKTSKKELKLVSKKRVRRQQEWHINGLNADYNAACNIAHIAKNIELRQIMCKTPQTKNGYSSPVLTSKVK
SQVEMVRELKKMGKTILYSNDSLPF (SEQ ID NO: 36)

TABLE 62-continued

Amino Acid Sequences of Representative CLUST.091979 Effector Proteins

```
>3300031993|Ga0310696_10000447_27|M
[mammals-digestive system-rumen-bos taurus]
MAHRKKKDDEATLSYKFKVKVIEGDLTADDITKCIAENAEQGNHFSEFIHKNLTSKTIGEFASQLPVEKRQFGYYQYAIGGTMP
AKKNASDEDKPKGELIDWSKKPFYVLFSKGYSATHAVNLIFNVYLNSEEGKAFSAKNSMNLSKSQFAYSGFVQIVCANYASMLA
NARPDKIKFEEITEATDDGTKKMQVVREMAERYLMKPKNFASRIEYLEANNTKGKFDKTIQRLRLLQPFFEKNEEGITELYYDL
SVKALEHSGQCTYKGGRTISILEIGDIRISRKENAKGYLLTIPINRKSVVFDLYGRKDTIGGDGRDLIDIMNTHGSSLQFTADG
NDIYLTITATKNFIKEKPTFNEDTVLGGDVNIKHSYTVFSTSPKDIPDFVNFYEYFAKDGEIMKLAPKPMWDYIVAAATKFLTI
LPIETPAISATVYGKRTEEGISRATFRETQKLIALEKAIERVMKQVFDKYNDGKHPLEAIYIGNAIKYRRLIKGYLAQKKKYYS
AHSEYDKAMGYTDDDTDRKENMDERRFDDSKKFRYTPEAQALLDTMHTIEKKIVGCVSNAISYAYHKFDENGFNVIALENLTSA
TFAKKYKSDKPESIKKLLNFDKLLGKTLDEAKASKSISKHPNWYELVADEGCVSDIRITDEGQSATYRSLVTETIMKVSHFAE
TKDRFIGLANSGRLQVGLVPSQYTSYIDSTTHTLYAVIEDGKTVLAPKEVVRASQERHINGLNADYNSALNLKYMITDENFRKT
FTSETSADKFGWGKPMFSPTTRSQDEVFSAIKKIGAITVLED (SEQ ID NO: 37)

>3300031993|Ga0310696_10026614_2|M
[mammals-digestive system-rumen-bos taurus]
MAHKNSDGENTINKTFIFKVKCEKNDIISFWKPAAEEYCNYYNKLSEWIGKNLISMKIGDLAKYIDNPKSKYYLSVTDENKKDL
PLYKIFQKGFSSIDADNALYCAIDKLNPEGYNGNILGVGKSDYRRNGYVSSVIGNFRTKMVSLKANVRWKKIDIGNVDEETLRR
QTICDVEKYRIESEKDFRDLIDILKAREETPRLKEKISRLELLYDYYVSKNTKTIKSEMENMAISDLQKFGGCVRKSLNTITIHK
QDSKIEKEGNTSFRLHMVFNKKPYTITLLGNRQVVKYIDGKRVDIVNIVEKHGDWITFNIKNGELFVHLTKCVEFSKGQKEIKK
AAGVDVNIKHAMLAASIVDDGQLKGYVNLYRELIEDDDFVSTFGDSDSGKTELGMYQKMAKTVFFGVLEVESLFERVVNQQSGW
KLDNQLIRRERAMEKVFDRIVKTTSNKHIIDYVNYVKMLRAKYKAYFILDEKYHEKQREYDLSMGFTDESDERRELYPFINTET
AKEILGKKRNVEQDLIGCRDNIVTYAFNVLRNNGYDTISVEYLDSSQFDKRRMPTPKSLLEYHKFKGKTQDEVERLMSEKKFAK
TNYDIHYDGENKVDGIVYSKEGELRQKKLNFMNLVIKAIHFADIKDKFAQLCNNNDVNVVFGPSAFTSQMDSETHSLYYVEKET
NGKNGKTGKKFVLADKKSVRRRQETHINGLNADFNAARNLEYIASNPELLERMTKRTKSGKDMYNTPSWNIRQEFKKNLSVRTI
NTFRELGNVKYGKINNEGLFVEDDV (SEQ ID NO: 38)

>3300031993|Ga0310696_10030100_3|M
[mammals-digestive system-rumen-bos taurus]
MAQHKSNNEESAINKTFIFKAKCEKNDVISLWEPAAKEYGDYYNKVSKWIADNLITMKIGDLAQYITNQNSKYYTAVTNKKKKD
LPLYRIFQKGFSSQCADNALYCAIKSINPENYKGNSLGIGESDYRRFGYIQSVVSNFRTKMSSLKVSVKYKKFDVSNVDDETLK
IQTIYDVDKYGIETAKEFKELIETLKTRVETPQLNDTIARLKCLCDYYSKNEKAINNEIETMAIADLQKFGGCQRKSLNAFTIH
KQDSLMEKVGNTSFRLQLSFRKKTYVINLLGNRQVVNFVNGKRVDLIDIAENHGDLITFNIKNGELFLHITSPIVFDKDVRDIR
NVVGIDVNIKHSMLATSIKDDGNVKGYINLYKELLNDDVFVSTCNESELALYRQMSENVNFGILETDSLFERIVNQSKGGCLKN
KLIRRELAMQKVFERITKTNKDQNIVDYVNYVKMMRAKCKASYILKEKYDEKQKEYYVKMGFTDESTESKETMDKRREEFPPVN
TDTAKELLVKQNNIRQDIIGCRDNIVTYAFNVFKNNEYDTLSVEYFDDRSSQFDKRRIPTPKSLLKYRKFEGKTKDEVENMMKSEK
LSNAYYTFKYENDVVSDIDYSDEGNLRRSKLNFGNWIIKAIHFADIKDKFVQLSNNNKMNIVFCPSAFSSQMDSITHTLYYVEK
ITKNKKGKEKKKYVLANKKMVRTQQETHINGLNADYNSACNLKYIALNYELRDKMTDRFKASKKIKTMYNIPAYNIKSNFKKNL
SAKTIQTFRELGHYRDGKINEDGMFVEILE (SEQ ID NO: 39)

>3300031998|Ga0310786_10000003_467|M
[mammals-digestive system-rumen-bos taurus]
MAHRKKKDDEATLSYKFKVKVIEGDLTADDITKCIAENAEQGNHFSEFIHKNLTSKTIGEFASQLPAEKRQFGYYQYAIGGTMP
AKKNASDEDKPKGELIDWSKKPFYVLFSKGYSATHAVNLIFNVYLNSEEGKAFSAKNSMNLSKSQFAYSGFVQIVCANYASMLA
NARPDKIKFEEITEATDDGTKKMQVVREMAERYLMKPKNFASRIEYLEANNTKGKFDKTIQRLRLLQPFFEKNEESITELYYDL
SVKALEHSGQCTYKGGRTISILEIGDIRISRKENAKGYLLTIPINRKSVVFDLYGRKDTIGGDGRDLIDIMNTHGSSLQFTADE
NDIYLTITATKNFIKEKPTFNEDTVLGGDVNIKHSYTVFSASPKDIPDFVNFYEYFAKDGEIMKLAPKPMWDYIVAAATKFLTI
LPIETPAISATVYGKRTEEGISRATFRETQKLIALEKAIERVMKQVFDKYNDGKHPLEAIYIGNAIKYRRLIKGYLAQKKKYYS
AHSEYDKAMGYTDDDTDRKENMDERRFDDSKKFRYTPEAQALLDTMHTIEKKIVGCVSNAISYAYHKFDENGFNVIALENLTSA
TFAKKYKSDKPESIKKLLNFDKLLGKTLDEAKASKSISKHPNWYELVADENGCVSDIRITDEGQSATYRSLVTETIMKVSHFAE
TKDRFIGLANSGRLQVGLVPSQYTSYIDSTTHTLYAVIEDGKTVLAPKEVVRASQERHINGLNADYNSALNLKYMITDENFRKT
FTSETSADKFGWGKPMFSPTTRSQDEVFSAIKKIGAITVLED (SEQ ID NO: 40)

>AUXO013988882|Ga0247611_10000101_23|P
[mammals-digestive system-rumen-ovis aries]
MANKRTDTTINLNKTVIMLTNMLPEVRAMFQAGIRQAQAYADLVNKWICSNLTNKIGEVLLPYIDNKNCVYYELCYKYKEAPLY
TIFMKGKFDLNSRNNALYCAVVAQNIDNYSGNIFGFSQSDYRRNGYCKVVFSNYATKMSSLKPSIKKVTINEESTEETIQSQVI
YEMFTNGRQWGKPEYFAEHLKYLEMKDNVSDKLMFRMKTLCEYYQTHTDLIDTMAMNAGVEALKQFEGLKLNRDKFSMTITTNS
TSPYTLTRVAGTCAYNLHIPCRKRSYDIRLWGNRQTVRWVNGELVDIADIINQHGQTIIFTIKNGNVYVHIPYGLNFEKTEHEI
KNVVGVDVNTKHMLMQTSIKDNGWVKGYVNIYKALVEDEEFVKYISKSDLKLYKDLSKYVSFCPLELNLLYTRYLSKKGLPFNE
ADNNAEKCVEKVLNNLVKQYEGDDVHVVNYIHNVKKLRALCKASFVLYKKYAELQKAFDDAQGYNDQSTETKETMDKRRWENPF
IQTREAQELIAKMDNAVAGIIGCRDNIITYAYKVFGDNNYDTVGLENLTTSQFDNYSTVKSPKSLLSYYGLLGQQVDSDKYNAV
MTESNKDWYDFKTDGDGNITDITLTAAGEAQKAKSLFNNKVLKNIHFADVKDKFIQLGNNGSIQTVLVPPSYTSQMDSKTHTIY
VKETVDPKNKNKKKLKLVDKKLVRHGQEYHKNGLNADINAALNIAYIVENQEMREVMCLHPSKKDGVYDQPFLKATTKYPATVA
GILLKMGKTTNWGEK (SEQ ID NO: 41)

>3300028805|Ga0247608_10000186_37|P
[mammals-digestive system-rumen-ovis aries]
MNKSYVFKSNVAIDDIMSLFEPAIEEYINYYNRTSDPFICDNLTSMKIGDLANYIKNKENVYCKFVLNDDIKDLPLYKIFSLNLN
SSQKKNADNALYEAIKVLNADGYKGKNILGLGDTYFRRNGYVKNVISNYRTKFVTLKPNVKYSKIDINSVTEQLIKTQTIFEVV
NKKIESETDFENLITYFKNRETPNDEKIKRLELLFDYYTKHKNEINEEIEKHAVESLKSFNGCRRNGNRKTMTVQMQKMLLKKH
GLTSYILHLVLDKKPYDINLMGNRQTVKVDNNGNRVDLVDISSKHGYDLTFEVKGKTLFFTFSSEKDFSKKEQEIKNILGIDIN
TKHSMLATSITDNGKVKGYINIYVELLKNKDFVSTLNKEELAYYTEMAKFVSFGLLEIPSLFERVSNQYDKKNNVSITDETLLK
REIAISQTLDNLAKKYRDKNCKIASYIDYTKMLRSKYKSYFILKQKYYEKNHEYDDKMGFSDISTNSKETMDPRRFENPFINTD
IAKGLIVKLENVKCDIVGCRDNIIKYAYDVIVLNGPDTIGLEYLDSSNFERDRLPFPTAKSLMTYYGFEGKKYSEIDKSVFNTK
YYNFIFNENETIKDISYSVYGLKEIQKKRFKNLVIKAIGFADIKDKFVQLSNNTNMNVIFVPAAFTSQMDSNTHKIYVKEIMDK
NNKKQLQLIDKRKVRTKQEFHINGLNADFNAANNIKYIAENNDLLLTMCTKTKENNRYGNPLYNIKDTFKKKIPSSILNIFKKK
DMYQIICD (SEQ ID NO: 42)
```

TABLE 62-continued

Amino Acid Sequences of Representative CLUST.091979 Effector Proteins

\>3300028805|Ga0247608_10000895_42|M
[mammals-digestive system-rumen-ovis aries]
MFRIFAALKLTNMGHVRLQKREGEVYKTYKLKVKSFSGNVDIKAGIVEYDQKFNNVSQWIADHLTSMTIGEAASRISPHKMDSQ
YAMTSLSDEWKDQPLYKIFTRGFGGMNADNLIIECTKTEENCKYDKEKSLGFSESVFRTFGFAANASSDMKSRMTQAKVKIGRK
NIDEDSADDEKCLQAIYEIQKNELLTDDNWKDRIGYLEMKGDQERELERTTILYDYYRANRTTVLDKLDNLKVETLSKFRGSKR
KSDRKILTLNGISYDIKRKEGCQGFELKFSVDKNHMEFDLLGHRALIKNGEMLVDIENCHGSQLSLEIDGDDMYAIISMRTFCE
KNESKLEKIIGADVNIKHMFLMTSEKDDGNTKCYVNLYRELLSDSDFTDVLNKEEYEIFSELSKYVMFGLIETPYLGSRVIGTT
QHEKIVEDKITSGMKKIAIRLFQEGKVRERIYVQNVLKIRALLKALFSTKLAYSNEQKIYDNLMRFGEKDDRRKDEGFHTTCRG
TSLRSEMDMLSKKILACRDNIVEYGYYVIGLNGFDGISLENLESSTFMDVKISYPSCNSMLDHFKLKGKTIEEAENHETVGKFI
KKGYYVMTLVNGKINDINYSEKAVMLHKKNLLYDTVIKSTHFADVKDKFVELSNNGKVSVVIVPPYFSSQMDSVTHKVFTEEIV
VQKKSSNGKVRKTKKTVLVDKRKVRKTQESHINGLNADYNAALNLKYIAETIDWRSTLCFKTWNTYGSPQWDSKIKNQKTMIDR
LDSLGAIELKNW (SEQ ID NO: 43)

\>3300028805|Ga0247608_10006074_1|M
[mammals-digestive system-rumen-ovis aries]
MSHEFNKNKGENEISKTFIFKTKCGKNDITSLWVPAMEEYCTYYNRVSKWICDNLTEMRIGDLAQYIDNHGSAYYSAVTDITKK
DLPLYKIFKKGFSGLCADNALYCAIAKLNPEGYDGNMFGLSETYYRRQGYIANVFGNYRTKMNAGLKVGCAKWKKFDTNDVDDE
ILMEQVIVDVVKYDIDSKNEFKEYIEVLKCREENPKLLETIERLECLYGYYSQHEEDIKKKIEELVVEELKTFGGCVRKSMTSC
TITVQDFVMERIGNTGYRINLTFNKKPYVLGLLGNRQVVRYVDGDRVELVDIVNNHGNQITFNLKNGELFVHLTSGVDFSKEES
SMENIVGVDVNIKHSMLASSIVDDGNVNGYINIYKELVNDDEFVSTFGDSESGLNELELYRQMAESVNFGLMETDSLFERYVEQ
WKGSDSDSRLARRERVVGKVFDRIVKTNGDVHVVNYIHAVKMLRAKCKAYFVLKQKYYEKQKEYDDAHGYTDESTASKETMDKR
RPFENPFVETDVAKELLGKLACVEQDIIGCRDNIVTYAFNVFRRNGYDTISLEYLDSSQFKKILGRKLEGKPEGEVTAYLKANKIPK
EVESIISEKGLKKNLYVFKFGDNGLLSDIEYSDEGLIRKKKADFGNIITKAIHFADIKDKFVQLTNNSDMGVVFCPSAFTSQMD
SKTHRLYFVEGLDGNGKNKYVLANKWSVRRQQERHINGLNADFNSACNCQHIAYDPILRDAMTIKVEAGKGMYNKPSYDIRKKF
KKNLSAATLKTFIKLGNTVKGMIVNGQFVEMES (SEQ ID NO: 44)

\>3300028833|Ga0247610_10000007_379|M
[mammals-digestive system-rumen-ovis aries]
MYNSKKKGEGDIQKSFKFKVKTDKETVELFRKAAVEYSEYYKRLTTFLCERLTDMTWGEVASFIPEKYRKNEYYKYLIKEENKD
LPLYKMFTKAASSMFIDHSIERYVEALNPEGNTGNILGFCKSSYVRGGYLKNVSNIRTKFATLKTGIKYKKFNPAEDDEETIL
GQTVFEMEKRGLEFKCDFEKTIKYLNEKGKTQEAERLQCLMEYFSTNTDKINEYRESLVLDDIRKFGGCNRSKSNSFSVTLEKA
DIKEDGLTGYTMKVSKKLKEIHLLGHRRVVEVVNGRRVNLVDICGDKSGDSKVFVVDGDNLYVCISAPVKFSKNGMEAKKYIGV
DMNMKHSIISVSDNASDMKGFLNIYKELLKDEGFRKTLNATELEKYEKLAEGVNIGIIEYDGLYERIVKQKKENSVDGLKVQAE
KKLIEREAAIERVLDKLRKGTSDTDTENYINYNKILRAKIKSAYILKDKYYEMLGKYDSERAGSGDLSEENKIKYKDEFNETEK
GKEILGKLNNVYKDIIGCRDNIVTYAVNLFIRNGYDTVALEYLESSQMKARRIPSTGGLLKGRKLEGKPEGEVTAYLKANKIPK
SYYSFEYDGNGMLTDVKYSDMGEKARGRNRFKNLVPKFLRWASIKDKFVQLSNYKDIQMVYVPSPYTSQTDSRTHSLYYIETVK
VDEKTGKEKKEHIVAPKESVRTEQESFVNGMNADTNSANNIKYIFENETLRDKFLKRTKDGTEMYNRPAFDLKECYKKNSNVSV
FNTLKKTLGAIYGKLDENGNFIENECNK (SEQ ID NO: 45)

\>3300028833|Ga0247610_10004486_2|M
[mammals-digestive system-rumen-ovis aries]
MNKSYVFKSNVAIDDIMSLFEPAIEEYINYYNRTSDFICDNLTSMKIGDLANYIKNKENVYCKFVLNDDIKDLPLYKIFSLNLN
SSQKKNADNALYEAIKVLNADGYKGKNILGLGDTYFRRNGYVKNVISNYRTKVFTLKPNVKYSKIDINSVTEQLIKTQTIFEVV
NKKIESETDFENLITYFKNRETPNDEKIKRLELLFDYYTKHKNEINEEIEKHAVESLKSFNGCRRNGNRKTMTVQMQKMLLKKH
GLTSYILHLVLDKKPYDINLMGNRQTVKVDNNGNRVDLVDISSKHGYDLTFEVKGKTLFFTFSSSEKDFSKKEQEIKNILGIDIN
TKHSMLATSITDNGKVKGYINIYVELLKNKDFVSTLNKEELAYYTEMAKFVSFGLLEIPSLFERVSNQYDKKNNVSITDETLLK
REIAISQTLDNLAKKYRDKNCKIASYIDYTKMLRSKYKSYFILKQYYEKNHEYDDKMGFSDISTNSKETMDPRRFENPFINTD
IAKGLIVKLENVKCDIVGCRDNIIKYAYDVIVLNGFDTIGLEYLDSSNFERDRLPFPTAKSLMTYYGFEGKKYSEIDKSVFNTK
YYNFIFNENETIKDISYSVYGLKEIQKKRFKNLVIKAIGFADIKDKFVQLSNNTMMNVIFVPAAFTSQMDSNTHKIYVKEIMDK
NNKKQLQLIDKRKVRTKQEFHINGLNADFNAANNIKYIAENNDLLLTMCTKTKENNRYGNPLYNIKDTFKKKIPSSILNIFKKK
DMYQIICD (SEQ ID NO: 46)

\>3300028888|Ga0247609_10000668_74|M
[mammals-digestive system-rumen-ovis aries]
MAHKTKESEKLVKSFKLKVDISNCEIEKKWIPSFEEYTNYYNGVSNWICENLISMKIGDLGQYIKNTESVYYKFITDESISNLP
LYKIFTLKQTQNVDNALFCAIKEINPEKYNGNSIGLGETDYRRFGYVQCVISNYRTKIGTMKASIKYKTLPENQSYDVIFEQTM
YEMIDKSLEKKEDWENIISNYKAKQTENTSKINRMETLYSFFIEHSEEIIEKSNLVAIEQLALFNGCKRKSLSTMTIHSQHSKL
QKNGLTSFVFCINQKIGSINLFGNRQLVSVDENGNRNDIIDICNNYGDFITFQIKNGKMFIILTAKVDFDKENIEIKNVVGADV
NIKHNMIASSIIDNGNVFGYINIYKELLNDEDFCSSCTNEELDIYKEISKSVNFGLLECESLFSRVSAQIYKENESISKLDDRF
LRREKSIENVLNRLSKQYRYKDCKIATYIDYTKIMRDSYKSYFIIKEKVYQYEKNHEYDDKRRFENPFIE
TETAKNILSKLNRIESRLIGCRNNITNYAFDVFKNNGFDTIALEYLDSSQFDKTKVLTPISMLKYRKFEGKSIEEVKTLNVKFS
MDNYEFEFDNNGKITNISFSQLGKREVMKTNFFNLIIKAIHFAEIKDKFIQLSNNKPINIVLVPSAFSSQMDSKDHKLYVDENG
KLINKRKVRKQQERHINGLNADFNAACNLSYLAKNNELLEKVCLKRKKFGKASYSVPYWNVKDAFKKNVSSNMIATIKKMNMVK
VF (SEQ ID NO: 47)

\>3300028888|Ga0247609_10003329_9|M
[mammals-digestive system-rumen-ovis aries]
MAHKTNNGENTINKTFIFKAKCEKNDIISLWKPAAEEYCNYYNKLSKWIGDSLTTMKIGDLAQYITNQNSAYYLAVTNDSKKDL
PLYKIFQKGFSSQCADNALYSAIKAINPENYNGNSLEIGETDYRRFGYVQSVIGNFRTKMSSLKVSVKYKKFDVNDVDEETLKT
QTIYDVDKYGIESIKDFNEFIEVLKLREETPQLNEKITRLECLCGYYSKNEENIKNEIETMAISDLQKFGGCQRKSLNTLTIHK
QNSLMEKVGNTSFTLQLSFNKKPYTINLLGNRQVVKFVDGKRVDLIDITEKHGDWVTFNIKNDELFVHLTSPIDFEKEVCEIKN
AVGVDVNIKHNMLATSIKDDGNVKGYINLYKELVNDGDFISTCNEDEFDLYRQMSESVNFGILETDSLFERVVNQSKGGCLNNK
FIRRELAMQKVFDNITKTNKDQNIVDYVNYVKMLRAKYKAYFILKEKYYEKQKEYDIKMGFTDVSTESKETMDKRRMEFPFVNT
DTAKELLAKLNNIEQDLIGCRDNIVTYAFNIPKNNGYDTLAVEYLDSAQFDKRRMPTPTSLLKYRKFEGKTKDEVEDMMKSKKF
SNAYYTFKFENDVVSNIEYSNDGIWKQKQLNFGNLIIKAIHFADIKDKFVQLCNNNKMNIVFCPSAFTSQMDSITHTLYYVEKI
TKKKNGKEEKKYVLANKKMVRTQQETHINGLNADYNSACNLKYIALNDELRNEMTDTFKVTNRQKTMYGIPAYNIKRGFKKNLS
AKTINTFRKLGHYRDGKINEDGMFVETLA (SEQ ID NO: 48)

TABLE 62-continued

Amino Acid Sequences of Representative CLUST.091979 Effector Proteins

>3300028888|Ga0247609_10016480_8|M
[mammals-digestive system-rumen-ovis aries]
MAHKTNNGENTINKTFIFKAKCDNNDIISLWKPAMEEYCTYYNKLSQWICNNLTSMKVKDLFAYLDDKQKTKPCVDKKTGETKI
GVGYRYFIENNKEDMPLYWLFTKNCSSSHADNLLFEFVRKVNHEEYNGNSLGMGETDYRRFGYFQNVISNFRTKMSSLKATTK
WKKFDVNDVDEDTLKNQTIYDVDKYGIESVNDFNERIDILKIREETEQTKDKIARLECLCKYYKEHEEDIKNEIATMAIADLQK
FGGCQRKSMNTLTIHKQDSPMEKVGNTSFNLRLTFNKKPYTLNLLGNRQVVKFVGGKRIDLINITENHGDWITFNIKNNELFVH
MTSPVDFEKEVCEIKNAVGVDVNIKHMMLATSIVDDGNVKGYINLYRELVNNNDFIATFGNSKNGHQGLEIYEQMAENVNFGIL
ETESLFERVVNQSNGGELNNQLIRREIAMQKVFDNITKTNNDKNIVNYVNYVKMLRAKYKAYFILKEKYYEKQKEYDDMMGFND
ESTENKEMMDKRRFEFSFINTDTAQELLIKLNKVEQDLIGCRDNIVTYAFNVFKTNGYDTLAVEYLDSAQFDKAKMPTPKSLLK
YHKFEGKTIDEVKEMMNNKNFTNAYYNFKFENEIVKDIEYSTDGIWRQKKLNFMNLIIKAIHFADIKDKFVQLCNNNSMNVVFC
PSAFTSQMDSITHSLYYIEKTSKTKNGKEKKQYVLANKKMVRTQQEKHINGLNADFNSACNLKYIALDEELRNAMTDEFNPKKQ
KTMYGVPAYNIKNGFKKNLSTKTINTFRTLGHYRDGKINEDGVFVENLA (SEQ ID NO: 49)

>3300031992|Ga0310694_10000010_351|M
[mammals-digestive system-rumen-ovis aries]
MYNSKKKGEGDIQKSFKFKVKTDKETVELFRKAAVEYSEYYKRLTTFLCERLTDMTWGEVASFIPEKYRKNEYYKYLIKEENKD
LPLYKMPTKAASSMFIDHSIERYVEALNPEGNTGNILGFCKSSYVRGGYLKNVVSNIRTKFATLKTGIKYKKFNPAEDDEETIL
GQTVFEMEKRGLEFKCDFEKTIKYLNEKGKTQEAERLQCLMEYFSTNTDKINEYRESLVLDDIRKFGGCNRSKSNSFSVTLEKA
DIKEDGLTGYTMKVSKKLKEIHLLGHRRVVEVVNGRRVNLVDICGDKSGDSKVFVVDGDNLYVCISAPVKFSKNGMEAKKYIGV
DMNMKHSIISVSDNASDMKGFLNIYKELLKDEGFRKTLNATELEKYEKLAEGVNIGIIEYDGLYERIVKQKKENSVDGLKVQAE
KKLIEREAAIERVLDKLRKGTSDTDTENYINYNKILRAKIKSAYILKDKYYEMLGKYDSERAGSGDLSEENKIKYKDEFNETEK
GKEILGKLNNVYKDIIGCRDNIVTYAVNLFIRNGYDTVALEYLESQNMKARRIPSTGGLLKGRKLEGKPEGEVTAYLKANKIPK
SYYSFEYDGNGMLTDVKYSDMGEKARGRNRFKNLVPKFLRWASIKDKFVQLSNYKDIQMVYVPSPYTSQTDSRTHSLYYIETVK
VDEKTGEKKEHIVAPKESVRTEQESFVNGMNADTNSANNIKYIFENETLRDKFLKRTKDGTEMYNRPAFDLKECYKKNSNVSV
FNTLKKTLGAIYGKLDENGNFIENECNK (SEQ ID NO: 50)

>3300031992|Ga0310694_10022272_2|M
[mammals-digestive system-rumen-ovis aries]
MNKSYVFKSNVAIDDIMSLFEPAIEEYINYYNRTSDFICDNLTSMKIGDLANYIKNKENVYCKFVLNDDIKDLPLYKIFSLNLN
SSQKKNADNALYEAIKVLNADGYKGKNILGLGDTYFRRNGYVKNVISNYRTKFVTLKPNVKYSKIDINSVTEQLIKTQTIFEVV
NKKIESETDFENLITYFKNRETPNDEKIKRLELLFDYYTKHKNEINEEIEKHAVESLKSFNGCRRNGNRKTMTVQMQKMLLKKH
GLTSYILHLVLDKKPYDINLMGNRQTVKVDNNGNRVDLVDISSKHGYDLTFEVKGKTLFFTSSEKDFSKKEQEIKNILGIDIN
TKHSMLATSITDNGKVKGYINIYVELLKNKDFVSTLNKEELAYYTEMAKFVSFGLLEIPSLFERVSNQYDKKNNVSITDETLLK
REIAISQTLDNLAKKYRDKNCKIASYIDYTKMLRSKYKSYFILKQKYYEKNHEYDDKMGFSDISTNSKETMDPRRFENPFINTD
IAKGLIVKLENVKCDIVGCRDNIIKYAYDVIVLNGFDTIGLEYLDSSNFERDRLPFPTAKSLMTYYGFEGKKYSEIDKSVFNTK
YYNFIFNENETIKDISYSVYGLKEIQKKRFKNLVIKAIGFADIKDKFVQLSNNTNMNVIFVPAAFTSQMDSNTHKIYVKEIMDK
NNKKQLQLIDKRKVRTKQEFHINGLNADFNAANNIKYIAENNDLLLTMCTKTKENNRYGNPLYNIKDTFKKKIPSSILNIFKKK
DMYQIICD (SEQ ID NO: 51)

>3300031994|Ga0310691_10000084_157|M
[mammals-digestive system-rumen-ovis aries]
MFRIFAALKLTNMGHVRLQKREGEVYKTYKLKVKSFSGNVDIKAGIVEYDQKFNNVSQWIADHLTSMTIGEAASRISPHKMDSQ
YAMTSLSDEWKDQPLYKIFTRGFGGMNADNLIIECTKTEENCKYDKEKSLGFSESVFRTFGFAANASSDMKSRMTQAKVKIGRK
NIDEDSADDEKCLQAIYEIQKNELLTDDNWKDRIGYLEMKGDQERELERTTILYDYYRANRTTVLDKLDNLKVETLSKFRGSKR
KSDRKILTLNGISYDIKRKEGCQGFELKFSVDKNHMEFDLLGHRALIKNGEMLVDIENCHGSQLSLEIDGDDMYAIISMRTFCE
KNESKLEKIIGADVNIKHMFLMTSEKDDGNTKCYVNLYRELLSDSDFTDVLNKEEYEIFSELSKYVMFGLIETPYLGSRVIGTT
QHEKIVEDKITSGMKKIAIRLFQEGKVRERIYVQNVLKIRALKALFSTKLAYSNEQKIYDNLMRFGEKDDRRKDEGFHTTCRG
TSLRSEMDMLSKKILACRDNIVEYGYYVIGLNGFDGISLENLESSTFMDVKISYPSCNSMLDHFKLKGKTIEEAENHETVGKFI
KKGYYVMTLVNGKINDINYSEKAVMLHKKNLLYDTVIKSTHFADVKDKFVELSNNGKVSVVIVPPYFSSQMDSVTHKVFTEEIV
VQKKSSNGKVRKTKKTVLVDKRKVRTQESHINGLNADYNAALNLKYIAETIDWRSTLCFKTWNTYGSPQWDSKIKNQKTMIDR
LDSLGAIELKNW (SEQ ID NO: 52)

>3300031994|Ga0310691_10000270_20|M
[mammals-digestive system-rumen-ovis aries]
MNKSYVFKSNVAIDDIMSLFEPAIEEYINYYNRTSDFICDNLTSMKIGDLANYIKNKENVYCKFVLNDDIKDLPLYKIFSLNLN
SSQKKNADNALYEAIKVLNADGYKGKNILGLGDTYFRRNGYVKNVISNYRTKFVTLKPNVKYSKIDINSVTEQLIKTQTIFEVV
NKKIESETDFENLITYFKNRETPNDEKIKRLELLFDYYTKHKNEINEEIEKHAVESLKSFNGCRRNGNRKTMTVQMQKMLLKKH
GLTSYILHLVLDKKPYDINLMGNRQTVKVDNNGNRVDLVDISSKHGYDLTFEVKGKTLFFTSSEKDFSKKEQEIKNILGIDIN
TKHSMLATSITDNGKVKGYINIYVELLKNKDFVSTLNKEELAYYTEMAKFVSFGLLEIPSLFERVSNQYDKKNNVSITDETLLK
REIAISQTLDNLAKKYRDKNCKIASYIDYTKMLRSKYKSYFILKQKYYEKNHEYDDKMGFSDISTNSKETMDPRRFENPFINTD
IAKGLIVKLENVKCDIVGCRDNIIKYAYDVIVLNGFDTIGLEYLDSSNFERDRLPFPTAKSLMTYYGFEGKKYSEIDKSVFNTK
YYNFIFNENETIKDISYSVYGLKEIQKKRFKNLVIKAIGFADIKDKFVQLSNNTNMNVIFVPAAFTSQMDSNTHKIYVKEIMDK
NNKKQLQLIDKRKVRTKQEFHINGLNADFNAANNIKYIAENNDLLLTMCTKTKENNRYGNPLYNIKDTFKKKIPSSILNIFKKK
DMYQIICD (SEQ ID NO: 53)

>3300032030|Ga0310697_10001273_44|P
[mammals-digestive system-rumen-ovis aries]
MAHKTNNGENTINKTFIFKAKCDNNDIISLWKPAMEEYCTYYNKLSQWICNNLTSMKVKDLFAYLDDKQKTKPCVDKKTGETKI
GVGYRYFIENNKEDMPLYWLFTKNCSSSHADNLLFEFVRKVNHEEYNGNSLGMGETDYRRFGYFQNVISNFRTKMSSLKATTK
WKKFDVNDVDEDTLKNQTIYDVDKYGIESVNDFNERIDILKIREETEQTKDKIARLECLCKYYKEHEEDIKNEIATMAIADLQK
FGGCQRKSMNTLTIHKQDSPMEKVGNTSFNLRLTFNKKPYTLNLLGNRQVVKFVGGKRIDLINITENHGDWITFNIKNNELFVH
MTSPVDFEKEVCEIKNAVGVDVNIKHMMLATSIVDDGNVKGYINLYRELVNNNDFIATFGNSKNGHQGLEIYEQMAENVNFGIL
ETESLFERVVNQSNGGELNNQLIRREIAMQKVFDNITKTNNDKNIVNYVNYVKMLRAKYKAYFILKEKYYEKQKEYDDMMGFND
ESTENKEMMDKRRFEFSFINTDTAQELLIKLNKVEQDLIGCRDNIVTYAFNVFKTNGYDTLAVEYLDSAQFDKAKMPTPKSLLK
YHKFEGKTIDEVKEMMNNKNFTNAYYNFKFENEIVKDIEYSTDGIWRQKKLNFMNLIIKAIHFADIKDKFVQLCNNNSMNVVFC
PSAFTSQMDSITHSLYYIEKTSKTKNGKEKKQYVLANKKMVRTQQEKHINGLNADFNSACNLKYIALDEELRNAMTDEFNPKKQ
KTMYGVPAYNIKNGFKKNLSTKTINTFRTLGHYRDGKINEDGVFVENLA (SEQ ID NO: 54)

TABLE 62-continued

Amino Acid Sequences of Representative CLUST.091979 Effector Proteins

>3300032030|Ga0310697_10005481_13|P
[mammals-digestive system-rumen-ovis aries]
MAHKTNNGENTINKTFIFKAKCEKNDIISLWKPAAEEYCNYYNKLSKWIGDSLTTMKIGDLAQYITNQNSAYYLAVTNDSKKDL
PLYKIFQKGFSSQCADNALYSAIKAINPENYNGNSLEIGETDYRRFGYVQSVIGNFRTKMSSLKVSVKYKKFDVNDVDEETLKT
QTIYDVDKYGIESIKDFNEFIEVLKLREETPQLNEKITRLECLCGYYSKNEENIKNEIETMAISDLQKFGGCQRKSLNTLTIHK
QNSLMEKVGNTSFTLQLSFNKKPYTINLLGNRQVVKFVDGKRVDLIDITEKHGDWVTFNIKNDELFVHLTSPIDFEKEVCEIKN
AVGVDVNIKHNMLATSIKDDGNVKGYINLYKELVNDCDFISTCNEDEFDLYRQMSESVNFGILETDSLFERVVNQSKGGCLNNK
FIRRELAMQKVFDNITKTNKDQNIVDYVNYVKMLRAKYKAYFILKEKYYEKQKEYDIKMGFTDVSTESKETMDKRRMEFPFVNT
DTAKELLAKLNNIEQDLIGCRDNIVTYAFNIFKNNGYDTLAVEYLDSAQFDKRRMPTPTSLLKYRKFEGKTKDEVEDMMKSKKF
SNAYYTFKFENDVVSNIEYSNDGIWKQKQLNFGNLIIKAIHFADIKDKFVQLCNNNKMNIVFCPSAFTSQMDSITHTLYYVEKI
TKKKNGKEEKKYVLANKKMVRTQQETHINGLNADYNSACNLKYIALNDELRNEMTDTFKVTNRQKTMYGIPAYNIKRGFKKNLS
AKTINTFRKLGHYRDGKINEDGMFVETLA (SEQ ID NO: 55)

>OBLI01003123_14|M
[pig gut metagenome]
MAHKKNIGAEIVKTYSFKVKNTNGITMEKLMAAIDEYQSYYNLCSDWICKNLTTMTIGDLDRYIPEKSKDNIYATVLLDEVWKN
QPLYKIFGKKYSANNRNNALYCALSSVIDMNKENVLGFSKTHYVRNGYILNVISNYASKLSKLNTGVKSRAIKETSDEATIIEQ
VIYEMEHNKWESIEDWKNQIEYLNSKTDYNPTYMERMKTLSAYYSEHKSEIDAKMQEMAVENLVKFGGCRRNNSKKSMFIMGSN
HTNYTISYIGENCFNINFANILNFDVYGRRDVVKNGEVLVDIMANHGDSIVLKIVNGELYADVPCSVTLNKVESNFDKVVGIDV
NMKHMLLSTSVTDNGSLDFLNIYKEMSNNAEFMALCPEKDRKYYKDISQYVTFAPLELDLLFSRISKQDKVKMEKAYSEILEAL
KWKFFANGDNKNRIYVESIQKIRQQIKALCVIKNAYYEQQSAYDIDKTQEYIETHPFSLTEKGMSIKSKMDKICQTIIGCRNNI
IDYAYSFFERNGYTIIGLEKLTSSQFEKTKSMPTCKSLLNFHKVLGHTLSELETLPINDVVKKGYYAFTTDNEGRITDASLSEK
GKVRKMKDDFFNQAIKAIHFADVKDYFATLSNNGQTGIFFVPSQFTSQMDSNTHNLYFENAKNGGLKLASKSKVRKSQEYHLNG
LPADYNAARNIAYIGLDEIMRNTFLKKANSNKSLYNQPIYDTGIKKTAGVFSRMKKLKKYKVI (SEQ ID NO: 56)

TABLE 73

Conserved Sequences of CLUST.091979 Effectors.

| Sequence | Residues | Position |
|---|---|---|
| PX$_1$X$_2$X$_3$X$_4$F (SEQ ID NO: 216) | X$_1$ is L or M or I or C or F<br>X$_2$ is Y or W or F<br>X$_3$ is K or T or C or R or W or Y or H or V<br>X$_4$ is I or L or M | N-terminal |
| RX$_1$X$_2$X$_3$L (SEQ ID NO: 217) | X$_1$ is I or L or M or Y or T or F<br>X$_2$ is R or Q or K or E or S or T<br>X$_3$ is L or I or T or C or M or K | Mid sequence |
| NX$_1$YX$_2$ (SEQ ID NO: 218) | X$_1$ is I or L or F<br>X$_2$ is K or R or V or E | Mid sequence |
| KX$_1$X$_2$X$_3$FAX$_4$X$_5$KD (SEQ ID NO: 219) | X$_1$ is T or I or N or A or S or F or V<br>X$_2$ is I or V or L or S<br>X$_3$ is H or S or G or R<br>X$_4$ is D or S or E<br>X$_5$ is I or V or M or T or N | C-terminal |
| LX$_1$NX$_2$ (SEQ ID NO: 220) | X$_1$ is G or S or C or T<br>X$_2$ is N or Y or K or S | C-terminal |
| PX$_1$X$_2$X$_3$X$_4$SQX$_5$DS (SEQ ID NO: 221) | X$_1$ is S or P or A<br>X$_2$ is Y or S or A or P or E or Y or Q or N<br>X$_3$ is F or Y or H<br>X$_4$ is T or S<br>X$_5$ is M or T or I | C-terminal |
| KX$_1$X$_2$VRX$_3$X$_4$QEX$_5$H (SEQ ID NO: 222) | X$_1$ is N or K or W or R or E or T or Y<br>X$_2$ is M or R or L or S or K or V or E or T or I or D<br>X$_3$ is L or R or H or P or T or K or Q of P or S or A<br>X$_4$ is G or Q or N or R or K or E or I or T or S or C<br>X$_5$ is R or W or Y or K or T or F or S or Q | C-terminal |
| X$_1$NGX$_2$X$_3$X$_4$DX$_5$NX$_6$X$_7$X$_8$N (SEQ ID NO: 223) | X$_1$ is I or K or V or L<br>X$_2$ is L or M<br>X$_3$ is N or H or P<br>X$_4$ is A or S or C<br>X$_5$ is V or Y or I or F or T or N<br>X$_6$ is A or S<br>X$_7$ is S or A or P<br>X$_8$ is M or C or L or R or N or S or K or L | C-terminal |

Examples of direct repeat sequences and spacer lengths for these systems are shown in TABLE 8.

TABLE 84

Nucleotide Sequences of Representative CLUST.091979 Direct Repeats and Spacer Lengths

| CLUST.091979 Effector Protein Accession | Direct Repeat Nucleotide Sequence | Spacer Length(s) |
|---|---|---|
| AUXO013988882_8|P (SEQ ID NO: 1) | ACTATGTTGGAATACATTTTTATAGGTATTTACAACT (SEQ ID NO: 57)<br>AGTTGTAAATACCTATAAAAATGTATTCCAACATAGT (SEQ ID NO: 118) | 28-29 |
| SRR094437_845781_4|M (SEQ ID NO: 2) | ATTGTTGGAATATCACTTTTGTAGGGTATTCACAAC (SEQ ID NO: 58)<br>GTTGTGAATACCCTACAAAAGTGATATTCCAACAAT (SEQ ID NO: 119) | 30-31 |

TABLE 84-continued

Nucleotide Sequences of Representative CLUST.091979 Direct Repeats and Spacer Lengths

| CLUST.091979 Effector Protein Accession | Direct Repeat Nucleotide Sequence | Spacer Length(s) |
|---|---|---|
| SRR1221442_316828_61\|P (SEQ ID NO: 3) | AATGTTGTTCACCCTTTTT (SEQ ID NO: 59)<br>AAAAAGGGTGAACAACATT (SEQ ID NO: 120) | 47 |
| SRR3181151_741875_3\|M (SEQ ID NO: 4) | CCTGTTGTGAATACTCTTTTATAGGTATCAAACAAC (SEQ ID NO: 60)<br>GTTGTTTGATACCTATAAAAGAGTATTCACAACAGG (SEQ ID NO: 121) | 26-30 |
| SRR5371369_1764679_7\|P (SEQ ID NO: 5) | ATTGTTGTAACTCTTATTTTGTATGGAGTAAACAAC (SEQ ID NO: 61)<br>GTTGTTTACTCCATACAAAATAAGAGTTACAACAAT (SEQ ID NO: 122) | 30 |
| SRR5371371_1138852_2\|M (SEQ ID NO: 6) | ATTGTTGTAGACACCTTTTTATAAGGATTGAACAAC (SEQ ID NO: 62)<br>GTTGTTCAATCCTTATAAAAAGGTGTCTACAACAAT (SEQ ID NO: 123) | 29-43 |
| SRR5371379_2478682_1\|M (SEQ ID NO: 7) | CTTGTTGTATATACTCTTTTATAGGTATTAAACAAC (SEQ ID NO: 63)<br>GTTGTTTAATACCTATAAAAGAGTATATACAACAAG (SEQ ID NO: 124) | 29-38 |
| SRR5371385_201181_1\|P (SEQ ID NO: 8) | ATTGTTGTAACTCTTATTTTGTATGGAGTAAACAAC (SEQ ID NO: 61)<br>GTTGTTTACTCCATACAAAATAAGAGTTACAACAAT (SEQ ID NO: 122) | 25-30 |
| SRR5371385_201181_1\|M (SEQ ID NO: 9) | ATTGTTGTAACTCTTATTTTGTATGGAGTAAACAAC (SEQ ID NO: 61)<br>GTTGTTTACTCCATACAAAATAAGAGTTACAACAAT (SEQ ID NO: 122) | 25-30 |
| SRR5371401_1055766_58\|M (SEQ ID NO: 10) | CTTGTTGTATATGTCCTTTTATAGGTATT (SEQ ID NO: 64)<br>AATACCTATAAAAGGACATATACAACAAG (SEQ ID NO: 125) | 30-51 |
| SRR5371439_988701_11\|M (SEQ ID NO: 11) | CTTGTTGTATATACTCTTTTATAGGTATTAAACAAC (SEQ ID NO: 63)<br>GTTGTTTAATACCTATAAAAGAGTATATACAACAAG (SEQ ID NO: 124) | 29-30 |
| SRR5371497_203858_6\|M (SEQ ID NO: 12) | CTTGTTGTATATGTCTTTTTATAGGTATTGAACAAC (SEQ ID NO: 65)<br>GTTGTTCAATACCTATAAAAAGACATATACAACAAG (SEQ ID NO: 126) | 30 |
| SRR5371501_2762794_1\|M (SEQ ID NO: 13) | TACTCTTTTTTAGGTAATGAACAAC (SEQ ID NO: 66)<br>GTTGTTCATTACCTAAAAAAGAGTA (SEQ ID NO: 127) | 41 |
| SRR5678926_1309611_3\|P (SEQ ID NO: 14) | CTTGTTGTATATATTCTTTTATAGGTATTAAACAAC (SEQ ID NO: 67)<br>GTTGTTTAATACCTATAAAAGAATATATACAACAAG (SEQ ID NO: 128) | 24-37 |
| SRR6059713_382107_4\|P (SEQ ID NO: 15) | CTTGTTGTATATACTCTTTTATAGGTATTAAACAAC (SEQ ID NO: 63)<br>GTTGTTTAATACCTATAAAAGAGTATATACAACAAG (SEQ ID NO: 124) | 28-31 |
| SRR6060192_2608084_13\|P (SEQ ID NO: 16) | CATGTTGTACATACTATTTTTAAGTATTAAACAAC (SEQ ID NO: 68)<br>GTTGTTTAATACTTAAAAAATAGTATGTACAACATG (SEQ ID NO: 129) | 27-42 |
| SRR7634052_1662339_24\|M (SEQ ID NO: 17) | GATGTTGGACACTATGTTTTATCGGTGGATACAAC (SEQ ID NO: 69)<br>GTTGTATCCACCGTATAAAACATAGTGTCCAACATC (SEQ ID NO: 130) | 30 |

TABLE 84-continued

Nucleotide Sequences of Representative CLUST.091979 Direct Repeats and Spacer Lengths

| CLUST.091979 Effector Protein Accession | Direct Repeat Nucleotide Sequence | Spacer Length(s) |
|---|---|---|
| AUXO017332817_2\|M (SEQ ID NO: 18) | GATGTTGTTATGCTGTTTTTGTAAGTAATAAACAAC (SEQ ID NO: 70)<br>GTTGTTTATTACTTACAAAAACAGCATAACAACATC (SEQ ID NO: 131) | 29-30 |
| OQVL01000914_15\|P (SEQ ID NO: 19) | ATTGTTGTAGACCTCTTTTTATAAGGATTGAACAAC (SEQ ID NO: 71)<br>GTTGTTCAATCCTTATAAAAAGAGGTCTACAACAAT (SEQ ID NO: 132) | 30 |
| 3300001598\|EMG_10017415_6\|P (SEQ ID NO: 20) | AATGTTGTTCACCCTTTTT (SEQ ID NO: 59)<br>AAAAAGGGTGAACAACATT (SEQ ID NO: 120) | 47 |
| 3300021254\|Ga0223824_10022219_2\|P (SEQ ID NO: 21) | ATTGTTGTACGAACCATTTTATATGGTAATAACAAC (SEQ ID NO: 72)<br>GTTGTTATTACCATATAAAATGGTTCGTACAACAAT (SEQ ID NO: 133) | 29-30 |
| 3300021431\|Ga0224423_10015012_2\|P (SEQ ID NO: 22) | ACTGTAAAACCCCTGCAGATGAAAGGAAAGTACAACAGT (SEQ ID NO: 73)<br>ACTGTTGTACTTTCCTTTCATCTGCAGGGGTTTTACAGT (SEQ ID NO: 134) | 27-42 |
| 3300012973\|Ga0123351_1009859_3\|P (SEQ ID NO: 23) | ATCATGTTGTACATACTATTTTTTAAGTATTAAACAACTA (SEQ ID NO: 74)<br>TAGTTGTTTAATACTTAAAAAATAGTATGTACAACATGAT (SEQ ID NO: 135) | 26-29 |
| 3300012979\|Ga0123348_10005323_4\|M (SEQ ID NO: 24) | CTTGTTGTATATACTCTTTTATAGGTATTAAACAAC (SEQ ID NO: 63)<br>GTTGTTTAATACCTATAAAAGAGTATATACAACAAG (SEQ ID NO: 124) | 28-31 |
| 3300028797\|Ga0265301_10000251_12\|M (SEQ ID NO: 25) | ATTGTTGAATGGCTATGTTTGTATGCTATTTACAAC (SEQ ID NO: 75)<br>GTTGTAAATAGCATACAAACATAGCCATTCAACAAT (SEQ ID NO: 136) | 28-30 |
| 3300028797\|Ga0265301_10000251_10\|P (SEQ ID NO: 26) | ATTGTTGAATGGCTATGTTTGTATGCTATTTACAAC (SEQ ID NO: 75)<br>GTTGTAAATAGCATACAAACATAGCCATTCAACAAT (SEQ ID NO: 136) | 28-30 |
| 3300028797\|Ga0265301_10009039_3\|M (SEQ ID NO: 27) | ATTGTTGGGGTACTTCTTTTATAGGGTACTCACAAC (SEQ ID NO: 76)<br>GTTGTGAGTACCCTATAAAAGAAGTACCCCAACAAT (SEQ ID NO: 137) | 29-30 |
| 3300028887\|Ga0265299_10000013_320\|P (SEQ ID NO: 28) | ATTGTTGTAGACCTTGTGTTTTAGGGGTCTAACAACG (SEQ ID NO: 77)<br>CGTTGTTAGACCCCTAAAACACAAGGTCTACAACAAT (SEQ ID NO: 138) | 29-30 |
| 3300028887\|Ga0265299_10000026_77\|P (SEQ ID NO: 29) | ACTGTGTTGGAATACAATATGAGATGTATTTACAAC (SEQ ID NO: 78)<br>GTTGTAAATACATCTCATATTGTATTCCAACACAGT (SEQ ID NO: 139) | 30 |
| 3300028887\|Ga0265299_10000133_30\|M (SEQ ID NO: 30) | ATTGTTGTGGCATACCGCAAGGCGGATGCTGACAAC (SEQ ID NO: 79)<br>GTTGTCAGCATCCGCCTTGCGGTATGCCACAACAAT (SEQ ID NO: 140) | 26-34 |
| 3300028887\|Ga0265299_10011526_3\|M (SEQ ID NO: 31) | ATTGTTGGAATATCACTTTTGTAGGGTATTCACAAC (SEQ ID NO: 58)<br>GTTGTGAATACCCTACAAAAGTGATATTCCAACAAT (SEQ ID NO: 119) | 30-31 |
| 3300028887\|Ga0265299_10012919_3\|P (SEQ ID NO: 32) | AATTGTTGAGATACCGTTTTTATGGTATTGGCAAC (SEQ ID NO: 80)<br>GTTGCCAATACCATAAAAAACGGTATCTCAACAATT (SEQ ID NO: 141) | 28-43 |

TABLE 84-continued

Nucleotide Sequences of Representative CLUST.091979 Direct Repeats and Spacer Lengths

| CLUST.091979 Effector Protein Accession | Direct Repeat Nucleotide Sequence | Spacer Length(s) |
|---|---|---|
| 3300028914\|Ga0265300_10009460_3\|M (SEQ ID NO: 33) | ATTGTTGTGGCATACCGTATTACGGGTGCTGACAA (SEQ ID NO: 81)<br>TTGTCAGCACCCGTAATACGGTATGCCACAACAAT (SEQ ID NO: 142) | 31 |
| 3300031853\|Ga0326514_10013355_6\|M (SEQ ID NO: 34) | GATGTTGTTATGCTGTTTTTGTAAGTAATAAACAAC (SEQ ID NO: 70)<br>GTTGTTTATTACTTACAAAAACAGCATAACAACATC (SEQ ID NO: 131) | 28-30 |
| 3300031993\|Ga0310696_10000014_323\|P (SEQ ID NO: 35) | ATTGTTGTAGACCTTGTGTTTTAGGGGTCTAACAACG (SEQ ID NO: 77)<br>CGTTGTTAGACCCCTAAAACACAAGGTCTACAACAAT (SEQ ID NO: 138) | 29-30 |
| 3300031993\|Ga0310696_10000226_76\|P (SEQ ID NO: 36) | ACTGTGTTGGAATACAATATGAGATGTATTTACAAC (SEQ ID NO: 78)<br>GTTGTAAATACATCTCATATTGTATTCCAACACAGT (SEQ ID NO: 139) | 30 |
| 3300031993\|Ga0310696_10000447_27\|M (SEQ ID NO: 37) | ATTGTTGTGGCATACCGCAAGGCGGATGCTGACAAC (SEQ ID NO: 79)<br>GTTGTCAGCATCCGCCTTGCGGTATGCCACAACAAT (SEQ ID NO: 140) | 26-34 |
| 3300031993\|Ga0310696_10026614_2\|M (SEQ ID NO: 38) | AATTGTTGAGATACCGTTTTTTATGGTATTGGCAAC (SEQ ID NO: 80)<br>GTTGCCAATACCATAAAAAACGGTATCTCAACAATT (SEQ ID NO: 141) | 30 |
| 3300031993\|Ga0310696_10030100_3\|M (SEQ ID NO: 39) | ATTGTTGGAATATCACTTTTGTAGGGTATTCACAAC (SEQ ID NO: 58)<br>GTTGTGAATACCCTACAAAAGTGATATTCCAACAAT (SEQ ID NO: 119) | 30-31 |
| 3300031998\|Ga0310786_10000003_467\|M (SEQ ID NO: 40) | ATTGTTGTGGCATACCGTATTACGGGTGCTGACAAC (SEQ ID NO: 82)<br>GTTGTCAGCACCCGTAATACGGTATGCCACAACAAT (SEQ ID NO: 143) | 25-31 |
| AUXO013988882\|Ga0247611_10000101_23\|P (SEQ ID NO: 41) | ATTGTGTTGGGATACACTTTTATAGGTATTTACAAC (SEQ ID NO: 83)<br>GTTGTAAATACCTATAAAAGTGTATCCCAACACAAT (SEQ ID NO: 144) | 29-31 |
| 3300028805\|Ga0247608_10000186_37\|P (SEQ ID NO: 42) | TATTGTTGAATACCTTTCTTATAAAGGTAATTACAAC (SEQ ID NO: 84)<br>GTTGTAATTACCTTTATAAGAAAGGTATTCAACAATA (SEQ ID NO: 145) | 29-46 |
| 3300028805\|Ga0247608_10000895_42\|M (SEQ ID NO: 43) | TGTTGTAAATGGCTTTTTATGGGCAACGAACAACTC (SEQ ID NO: 85)<br>GAGTTGTTCGTTGCCCATAAAAAGCCATTTACAACA (SEQ ID NO: 146) | 28-45 |
| 3300028805\|Ga0247608_10006074_1\|M (SEQ ID NO: 44) | ATTGTTGAATGTATTCTTTTTAGGACAGATACAAC (SEQ ID NO: 86)<br>GTTGTATCTGTCCTAAAAAAGAATACATTCAACAAT (SEQ ID NO: 147) | 28-30 |
| 3300028833\|Ga0247610_10000007_379\|M (SEQ ID NO: 45) | GATGTTGGACACTATGTTTTATACGGTGGATACAAC (SEQ ID NO: 69)<br>GTTGTATCCACCGTATAAAACATAGTGTCCAACATC (SEQ ID NO: 130) | 30 |
| 3300028833\|Ga0247610_10004486_2\|M (SEQ ID NO: 46) | TATTGTTGAATACCTTTCTTATAAAGGTAATTACAAC (SEQ ID NO: 84)<br>GTTGTAATTACCTTTATAAGAAAGGTATTCAACAATA (SEQ ID NO: 145) | 29-46 |
| 3300028888\|Ga0247609_10000668_74\|M (SEQ ID NO: 47) | ATTGTTGAATGGTATCTTTTATAGACTGATTACAACT (SEQ ID NO: 87)<br>AGTTGTAATCAGTCTATAAAAGATACCATTCAACAAT (SEQ ID NO: 148) | 29-41 |

TABLE 84-continued

Nucleotide Sequences of Representative CLUST.091979 Direct Repeats and Spacer Lengths

| CLUST.091979 Effector Protein Accession | Direct Repeat Nucleotide Sequence | Spacer Length(s) |
|---|---|---|
| 3300028888\|Ga0247609_10003329_9\|M (SEQ ID NO: 48) | ATTGTTGGATAATAGGTTTTTTATCTTAATTACAAC (SEQ ID NO: 88)<br>GTTGTAATTAAGATAAAAAACCTATTATCCAACAAT (SEQ ID NO: 149) | 29-30 |
| 3300028888\|Ga0247609_10016480_8\|M (SEQ ID NO: 49) | ACTGTTGAATAGTTGATTTTATATCCTATTTACAAC (SEQ ID NO: 89)<br>GTTGTAAATAGGATATAAAATCAACTATTCAACAGT (SEQ ID NO: 150) | 29-30 |
| 3300031992\|Ga0310694_10000010_351\|M (SEQ ID NO: 50) | GATGTTGGACACTATGTTTTATACGGTGGATACAAC (SEQ ID NO: 69)<br>GTTGTATCCACCGTATAAAACATAGTGTCCAACATC (SEQ ID NO: 130) | 30 |
| 3300031992\|Ga0310694_10022272_2\|M (SEQ ID NO: 51) | TATTGTTGAATACCTTTCTTATAAAGGTAATTACAAC (SEQ ID NO: 84)<br>GTTGTAATTACCTTTATAAGAAAGGTATTCAACAATA (SEQ ID NO: 145) | 29-46 |
| 3300031994\|Ga0310691_10000084_157\|M (SEQ ID NO: 52) | TGTTGTAAATGGCTTTTTATGGGCAACGAACAACTC (SEQ ID NO: 85)<br>GAGTTGTTCGTTGCCCATAAAAAGCCATTTACAACA (SEQ ID NO: 146) | 28-45 |
| 3300031994\|Ga0310691_10000270_20\|M (SEQ ID NO: 53) | TATTGTTGAATACCTTTCTTATAAAGGTAATTACAAC (SEQ ID NO: 84)<br>GTTGTAATTACCTTTATAAGAAAGGTATTCAACAATA (SEQ ID NO: 145) | 29-46 |
| 3300032030\|Ga0310697_10001273_44\|P (SEQ ID NO: 54) | ACTGTTGAATAGTTGATTTTATATCCTATTTACAAC (SEQ ID NO: 89)<br>GTTGTAAATAGGATATAAAATCAACTATTCAACAGT (SEQ ID NO: 150) | 29-30 |
| 3300032030\|Ga0310697_10005481_13\|P (SEQ ID NO: 55) | ATTGTTGGATAATAGGTTTTTTATCTTAATTACAAC (SEQ ID NO: 88)<br>GTTGTAATTAAGATAAAAAACCTATTATCCAACAAT (SEQ ID NO: 149) | 29-30 |
| OBLI01003123_14\|M (SEQ ID NO: 56) | ATTGTTGTAGATACCTTTTTGTAAGGATTGAACAAC (SEQ ID NO: 90)<br>GTTGTTCAATCCTTACAAAAAGGTATCTACAACAAT (SEQ ID NO: 151) | 30 |

Example 2—Identification of Transactivating RNA Elements

In addition to an effector protein and a crRNA, some CRISPR systems described herein may also include an additional small RNA that activates robust enzymatic activity referred to as a transactivating RNA (tracrRNA). Such tracrRNAs typically include a complementary region that hybridizes to the crRNA. The crRNA-tracrRNA hybrid forms a complex with an effector resulting in the activation of programmable enzymatic activity.

tracrRNA sequences can be identified by searching genomic sequences flanking CRISPR arrays for short sequence motifs that are homologous to the direct repeat portion of the crRNA. Search methods include exact or degenerate sequence matching for the complete direct repeat (DR) or DR subsequences. For example, a DR of length n nucleotides can be decomposed into a set of overlapping 6-10 nt kmers. These kmers can be aligned to sequences flanking a CRISPR locus, and regions of homology with 1 or more kmer alignments can be identified as DR homology regions for experimental validation as tracrRNAs. Alternatively, RNA cofold free energy can be calculated for the complete DR or DR subsequences and short kmer sequences from the genomic sequence flanking the elements of a CRISPR system. Flanking sequence elements with low minimum free energy structures can be identified as DR homology regions for experimental validation as tracrRNAs.

tracrRNA elements frequently occur within close proximity to CRISPR associated genes or a CRISPR array. As an alternative to searching for DR homology regions to identify tracrRNA elements, non-coding sequences flanking CRISPR effectors or the CRISPR array can be isolated by cloning or gene synthesis for direct experimental validation of tracrRNAs.

Experimental validation of tracrRNA elements can be performed using small RNA sequencing of the host organism for a CRISPR system or synthetic sequences expressed heterologously in non-native species. Alignment of small RNA sequences from the originating genomic locus can be used to identify expressed RNA products containing DR homology regions and sterotyped processing typical of complete tracrRNA elements.

Complete tracrRNA candidates identified by RNA sequencing can be validated in vitro or in vivo by expressing the crRNA and effector in combination with or without the tracrRNA candidate and monitoring the activation of effector enzymatic activity.

In engineered constructs, the expression of tracrRNAs can be driven by promoters including, but not limited to U6, U1, and H1 promoters for expression in mammalian cells or J23119 promoter for expression in bacteria.

In some instances, a tracrRNA can be fused with a crRNA and expressed as a single RNA guide.

The system can include a tracrRNA that is contained within a non-coding sequence listed in TABLE 9. For example, in some embodiments, the system includes a tracrRNA set forth in any one of SEQ ID NOs: 152-204.

TABLE 95

Non-coding Sequences of Representative CLUST.091979 Systems

>3300028887|Ga0265299_10012919_3|P
TATATCGTGGCCGAATATGTTAACGCGGACGACGTCCGTCTTGTGAAGTTTCAGGACGAGGATTTCGACAGGCTTCTTGACAAG
GTTAGAGAATGGAACAAGAAACATCTTGTTGTTGGAAATCGGAACTTCGAAGAAAAATTTGCGTAATCCAAAAATTTTCCGTAT
ATTTGCGGCGTGAAATTAAAAATATGTTTAACTAAAAACAAAGATTATGGCACACAAGAATCCTGATGGGGAGAACACCATCAA
CAAAACTTTTATTTTCAAAGTGAAATGCGAGAAGAATGATATTATATCGTTCTGGAAACCCGCAGCTGAAGAGTATTGCAACTA
TTACAACAAACTTAGCGAATGGATTGGCAAAGATATGTATAACACGCCGTCATGGAACATCCGGCAAGAGTTCAAGAAGAATTT
AAGTGTTAGAACCATAAACACGTTTCGTGAGCTTGGCAATGTGAAATACGGCAAAATCAACAATGAAGGGCTTTTTGTCGAAGA
CGATGTGTAAACATTAAGATTTCCATACGACAGGATTCAAAAAAACGTTCTTTGAAATATTGGATTGGTGGCAAGAGGCTGTTT
TTTTTAGGCTAAAAAGTTGTGTAAATAGCAGAAACACAGAACATAACATAAAATCT (SEQ ID NO: 91)

>3300028797|Ga0265301_10000251_12|M
AACTGCTACAATTCTGCCGAGTTTATGATTCAGACAAAATTCAAAAAAAGACTTCCGCAAGCAACCGTTTTGGTGAATTGAAC
AGAAACGGGTATGTTAAAGTATTGACCCAAGAAGAATATGACGAACTCACAAAATCAGCAAAATAATTTATTACTGATTGAAAA
ATAAAGCGTTCTTTGACATATTGTATAACAAACAAGCATTTTTGTAAGAGATAACCCATTTCATTTTATTGATATACAATGAAA
TGAAAAGAATAT (SEQ ID NO: 92)

>SRR094437_845781_4|M
GATAAATTTGCCCGTAATGTTATCGGGTTCAAGTCATATCACGAACTGCTTGATAATGCTATCATAAAAGAAAAATTACAACGG
GAATTTGGTTATGAAGATGCTCCGAAAACGTGGTTGTTCGGACAACAAAAAAATGAATGTTTCTAATGTATTAAAACAATAATT
CAATTACAATTTTAAGATTATGGCACAACACAAATCAAACAACGAAGAATCAGCAATCAACAAGACTTTCATTTTCAAGGCAAA
ATGCGATAAGAACGATGTCATATCGTTATGGGAACCAGCGGCAAAGGAATACTGCGACTATTATAACAAAGTGAGCAAGTGGAT
TAAAACTATGTATAACATACCCGCATATAACATTAAGTCCAATTTCAAGAAAAATTTGAGCGCCAAAACAATTCAAACTTTTAG
AGAACTTGGACACTACCGTGACGGAAAAATAAATGAGGATGGTATGTTTGTTGAAAACTTGGAATAATTCTGTATATACCAATT
AGAATTGAAAAAAAAACGCTCTTTGACATATTGTTTTCTACATAAAAACAAGATTTTACACAACGCAATACATCATAAAGTGTT
GCGTTATAACAAATAACAAAAATTCT (SEQ ID NO: 93)

>3300021254|Ga0223824_10022219_2|P
TTTATTCAATGCGAACCAGAGGTCTTGACGCATGAATCTGGCTATACATATCGTTATGCGACCGACGAAGAGAAAATATTGATT
AAAAGATGCAAATATTGAATAGGCAATTTTAAATTGTGAAAAAAAAATGATTGAATATAAGTTTACGTTTGAACTGGATGGAC
ATCTATCGGCGTACGATTTTGTTACGTTGCAAGAACGGTTTGAAAGGGAATTGAATCCTTATTTTGATGATGGGAGCATATCTG
GTACTCTTTCTTATGCAAATGATGATTAATATGCAAATAATATGGCACATGTAAGAACAAAAAATGAAGGAAACATGGCAAAAA
CATATTCTTTTAAGGTCAGAGAAACAAACCTTAAAAAGGATGTGATGATTGAATATAACGAATATTATAACAGGTTATCCGATT
GGATATGTGGCAATTTAACCAAAATCTCGGAAAATGAAGAATGGAGGAATGCCTTATGCAAACCAACAGAAAACATGTACAACG
AACCGATTTACGTTCCCTTGGTTAAATCACAGAACGGAATGTTCAAGGCAATTAAAAATTGGGCGCAACGAAGATATGGCAAG
AATAGAAAGACCGATTTTTAAATCTGAAATCACTTCTAACGAATTGTATACTAAAGAAATATAAAGAATATACATCTTTTATGA
CATTATGATATTGTTGTATGCATCATTTCACATGGTAATAACAACGAAGAGAAACACCGAGCGACCCACAAACCTATTGTCGTA
CGCATCATTTCACATGATAATAACAACGAATATTCCTGCAAGCATGATTTAACAATTTTTAAGAACCTGGTGGTTTCTCCGTTG
GGTTCTTTTTAGTATCTTTGCCTTGTTGAAACAAATAAAACAAATTGAATTATGATTTATAAAGGCAAAGAAATAGACGAAAGT
TACCACATCAATAAATGGGAAGATGAAGAGATTTACTCTGGTCCAACCCATTATGAATCATTCGAAGCCGATGAAATAAAAGAG
TTCTACCTCAAGGCACTTGCAAAGGAAAAGGAA (SEQ ID NO: 94)

>AUXO017332817_2|M
GTGCGCATATACACTCAATTCGCCGATGACCGTGTGTACGCGAAGGATTGTATCGACGGATTCTTTAGTATAAGACAAGATACC
GAAATGCGCCTCGTGTATAAAAATGAGATAGCACGCGGGCTTGAGTGTATCAATATTGTAAGATAGTAGTTTTCTGTTATTTTA
CATATTGATGTGTTTGGCATGGTTTTTGTTAAAATATAATCTAGCAGTATTGAGACTGCGGAGTAACGTGTCTAACTGTTTCA
TTATAAGCAGTAAAGACTAATATTTTTATATCTTAAACTTATTTTTATTATGGCTGGTCACAGCAAAATCAAAGAAAATCACAT
TATGAAGGCGTTTCTTATGAAAGTAAAAGAAACGCGAAAAAAACAGTGGCAATCAAATTTTATTAGAAGTGAGATTGCTAAGTT
TACAAATTATTACAATGGGCTGTCAAAGTTCCTTCTTGGAAGCCCGACTGGAGGGACATATGACACTGCATATTTTGATACAAA
GATTCAAGGCTCCAAGGGGGTATATGATAAGATTAAAGAAAACGGAGAAACTTATATTGCAGTATTAAGTGATGACGTTATTAC
GGCAGAGGTGTAAAATCCTCTGCCAACATCGCAAGTAACTCATTGAAAATTAGTTAAATGCGAATGCCAACAAAAGTGAACGAA
CTGACTTGTAAAGCAGGATGTTGTTATATCTTTTTGTAGATAATAAGCAACAAGATACAATCAATCGCGAGTTTATACTGAAAT
GTTGTTACACTGTTTTTGTAAGTGTTAAACAACCTTGCACAAATGTCATCTACCAGTACAATAGATGTTGTTATACTGTTTTGT
AGGTATTAAACAACCATTGCGCAGACTGACAGAGTAACCTTTCCTGATATGTTGTTACACATTTTTGTAAGTGTTAAACAACTG
ACGCATTGATATTGCCTTGTCTATTAAGAATGTTGTTATGCTCTTTTTATTGGTATAAACAACCGAGCAACTGGTACTCAAATT
TTAAATACTGTCGCGCTATGTTATGTACATCGAACAGCTACCACTCAATGGCTTTGTTTGCAACCGTGATTAATTCAATCGCGG
TTGCATTTGTTTTATGATGTGTTTTTGTATATATTATGTATATATGGAAAAGGAAAACAGGGTATCGGAGTTATGGAGCAAGTT
CTCTGATATTGACTTGCGCCGAAGCCAAATGACATATATGCCAATAAGAGGTAGTAAAAGATACGGCAGAAGAATAAAACGTAG
TGACATCGAGTACGAGTACAGATATCTGTATAGAGCAAACAAACATTGGTAATATGACCGTAGCTAAATTATCAAGTAATCATA
AGCCAGCGTGCCTTGGACGAATCTCAGCTTTAAACACCCCGATTAGATTTGAGTGTCGGGCTGGTAATAGTATAAGGCCTGGCA
ACATAGAGTATAGCTATAAAAGATGGAAAACGTCGTAATTTCAACTATGCACAACCCGCATACGCTGGCTTATTACCAAGGTAA
GCTGGCTCCTATGCATTTCAGACAAGATACAGG (SEQ ID NO: 95)

>3300021431|Ga0224423_10015012_2|P
AGCCTGTATACAGGGACAAGGTTAAGTACAACACCAAGGCTGAGGCAAAGAAGAGGGCTGATGATATGAACAAACAGAATAGGG
TCATACACCAGCTGTCTGTTTATTTGTGTCCTAAATGTCATAAGTGGCATATAGGTAGGAGCAGTGTGGAGAGTGTGCGCAGGG

TABLE 95-continued

Non-coding Sequences of Representative CLUST.091979 Systems

AAGGGTACTTTAGTCAGATTTGAAATTAATTGTTATATGGCGCATAGAAATAAAAACCTAGCAGAAAACTGCATTAACAAAACA
TTCAGTTTTAAAGTCAAAGCCGAAAAAGAGGAGATAAATTCAAAATGGATTCCAGCCATTAAAGAATATACTGCTTATTATAAC
AGGATAAGTGACTGGATAAACCTGTATTCACAGCCTACTTATGATATTAAGGAAGTTTATAAGAAAAACGCTGGTTGCAAAGTG
ATAAACGACTTCATTAAAAACGGTAACGCCGTTATATGTTGTATCGAAAATAACAAACTAATTGAGACAAATGGAAGACAATAG
TTCAAATTTTAAATGTAAAACAGTCATTAATGTATTAATATATAATACATAGCAAAAATCCAGATGTTGAATACATTTCTTTTA
AGTGTACTTACAACGCGGTGGCATTGCTAAAATATAGTCCTGTGGATGTTGACATCATTTCTTTTAAGTGTACTTACAACCAAC
GCTGTACACATTGCTAATGGATGATGACGATATAGAGGTGTTGAACTACCTTAATGAAAACTACACCAATGAAAACATTGAGTA
TATACGCGGTTGGTGGATGGATGACGACGATAAACTCCAGACACTTGACAGGTTTTTGAAAAATTTTTCAATATAGACCTGTCA
CTGTTGCGGCTATAAGAAGACCGATTTGACACTGAAAGACCGATACTGGGTTTGCCCCGAATGCGGTGCAAAACTAGACCGCGA
TACCAATGCAGGAATAAACATTAAGAATGAGACAATTAGACTGATAAACAAAGAATAATGAGAACTATAATAGGGAGGTGTACC
CCCGAATTTAAGCCAGTGGAGAACCATACAAACCTATCATATAGGGGTTCAATGAATCTGGAATTTCTGACAAAAACAGGGTTT
AACAGCCAGTGTACCAATGACTAACACAGGACATATAAAGACAAATCTAACAATAAAAAAAAATATTGACCAATTCTGCAGAAA
AAACAGGTTGGTTTCGGTTATGTTGGTGAATAAAGACAGTTAGATTAATTTTATATGGAAATGAAAATAGAGACAAAGACGAG
AACATCTACGTATTCATCTATGCCAAGTCCGCCTACTTCGGCAATACATTTGAATATGGCGGCACATTTTCCGTCGGCAAGGAC
GACAACTGGAACGATGTGAGAGGCCACGTTACCGAA (SEQ ID NO: 96)

>AUX0013988882|Ga0247611_10000101_23|P
GACAACATCCTGGTCAAGACCGAGGTTAACAGAAGGTACTGCCGCCTTATGACCGACGAGAACGGAGTGTGGCTCCTGAGGAAA
AACGACAAACATCCAACATATTTTATCTACCAGAACGGAACACTCTATCAATATGAGGAAGATTGATTAGTTGATGTTTTCATA
ATAATTTTATCTGGAATTTGAAAAGATTCCAGATTTTTTTTTATTTCGACTGTACAAAAAACAGGTTCCGTTGCGTTATATAG
GTGTAAATTAAAAATTCAGTCAAACAAAAATTGGAATAAAATATGGCTAACAAGAGAACAGACACAACAATCAACCTTAACAAA
ACCGTTATAATGTTAACGAACATGCTGCCAGAAGTACGGGCAATGTTTCAGGCGGGAATACGCCAGGCTCAAGTTTATGCAGAC
TTGGTGAACAAGTGGATATGTTCACAGGAAATGAGAGAGGTTATGTGTCTCCATCCGTCAAAAAAGGACGGGGTGTACGACCAA
CCGTTCCTGAAAGCTACAACCAAATACCCAGCCACGGTAGCTGGTATCCTGCTTAAGATGGGAAAAACAACCAATTGGGGTGAA
AAATAATACCCACCCGCCCCATTTTTTTACACTGATTAGTTCTTTGACTTATTGATTTATATTGGTTTACACAAATTATCGACA
CAATAAATAAAAAAAATTGTATATTAGTAGTATGATGACAGAAGAAACACGGAAGACAATAGAGAGCGTCATAGTGGTTCTCGG
CATAGCAATCATGCTGGCAGCCGCCGTCCGAATAATGACGCAGAACAAAGCAATTGTGAAATATGATGAACAGGTTGAAACCAT
GCAAACTTGCATA (SEQ ID NO: 97)

>AUX0013988882_8|P
ATGGAAGTTGTACGTGGTGGAAATCAATGGGAGGTTTATGACAATTACGATGAGACTATGAAAGCATCAAAAAATGTAAGGTCT
GTATTGGGACTTCCGGAAGTAAAATATCCACCTGAGGATTTTAGGACATATAATTTCTAATAAAAATGAACGGAAAAATTTCCG
TTCATTTTTTTTTTGTTTATTGGTGAAAAAATAGTATCTTTGTAAAAAATAAATGTTAAAATATTTTTTATGGGAAATACTACA
AAAAAAGGAAATTTGACGAAGACTTATTTATTCAAAGCCAATCTTTCAGAACAAGACTTTAAATTATGGAGGTCTATTGTTGAA
GAGTATCAAAGATATAAGGAAGTGTTGAGTAAATGGGTATGTGACCATCTTAGAAATGCAATGTGTACGAACCCGAAAAGTGAG
ACTGGATATTCTGTACCGTTCTTGACTTCAAGAATCAAGAAACAGAACATTATGGTTGTGAATTGAAAAAAATGGGCATGGTT
GAAGTCTTGAATGAAAAATCAACAGAAATTTAAGAAAAAATATTTATATAATGTACTGAAAATAAGTAAATAATAAATATTGT
GTAAAAAACTTGATATTTTTTTTTGTTATCTTTATAATATAAAATAAAATGTAAATATGAAAAATCTGTTAAAACTCAAAGAA
CAAATCAAGGATTACAAACATCTTCAGTTTGTGTTGGAGAAAGAAGATGAATCTGAACTCCATTATAGATGTATGACTGAAGAT
TTTTCGTTCAAGGTATCTGAAGAAAAAGACGGAACACTT (SEQ ID NO: 98)

>SRR3181151_741875_3|M
TTATAAACATCTAAAAGAAAGACTTATGACAACAAAACAAGTTAAATCAATCGTTTTAAAAGTAAAAAACACTAATGAATGCC
CTATTACAAAAGATGTAATAAATGAATATAAAAAATATTATAATATGTAGTGAATGGATTAAAGATAATCTAACAAGTATTA
CTATTGGAAACGAAAATTTACGAAAATTATTTTGTGGTAAACTTAAAGTAAGTGGATATAATACACCAATATTAGACGCAACAA
AAAAAGGTCAATTTAATATATTGGCAGAATTAAAAAACAGAATAAAATTAAAATATTTGAAATAGAAAAATAAGTCTTATGAT
TACAAAAATAATAGATTTCAAACATTTTTTTTAATTCTATTTTATTGACTAATTCATTGAAATATAAATAATTACAAATAACCC
(SEQ ID NO: 99)

>3300028805|Ga0247608_10000186_37|P
GATAGATATAGTATTGCAGCATTTCTGGCTTGCGAATCATCAGCAATGCAAAAATGTGACTATTGGAACAATGATGATGCCCAA
GATTACATAAGAAACTACAAAGAGGCTTATAGTAATGCAGTAAGACTTGCGTTTTTAAATGACTTAAGCAACACGCTTAACATTG
TCAAATGTAACGACATTAAGTGCGTGTTTCATAAGGGCAGCGAACCTTTCGCCGCCCTTCTTTTTTGTTGCTGTAACGGAATT
ATGTTTACTTTTGTGCCATCAAGTATATAGTTCCCTTAATAAATTGTATATTAATTAAAAGTTTGGCACAATATTTGATGCGTA
CAAATTAAAATAAAAACATTTTGAATTTTAAAATTTAATTTGTAATTTTAAATAAGAAAGTTTTATTTAACTAAAATAAAAAAA
ATGAATAAATCTTATGTTTTTAAGTCGAATGTGGCTATTGATGACATTATGTCTTTATTTGAACCGGCAATTGAAGAGTACATA
AACTATTACAATAGAACCAGCGATTTCATTTGTGATAATCTTACATCAATGAAAATCGGAGATTTGTTGCTTCTAACAATGTGT
ACTAAGACAAAAGAAATAATAGATACGGTAACCCCCTCTATAATATCAAAGATACTTTTAAAAAGAAAATACCATCTTCAATA
CTTAATATATTCAAAAAAAAGGATATGTATCAAATAATATGTGATTAATTATGCCTTTTTTTAATAAAAAATTGTTAAATAATA
CTTTGTTTATTAATAAATTATAAATATCACAGTAAACTATTAGGGATTTGTAAAATTTATGGAAATTATATACATGATGGCACT
AAGATTTGGTTATTAAGAAATTTTTCTGTATAAGTATAATAACCTATTTATAATTATAATTGAATAAAATGTATAATATGGAAA
ACACAGGCTTTTATACAGTTTCAAATATTGAAACTTCTCATAAGCCAACCGAAAATTCTAATGACGAAATTCTTAGGATTTTCA
ATAAAAGAAGGCCTTATTGCCCTTCAGACTTTAAGAAGCAACATTTTATT (SEQ ID NO: 100)

>3300028833|Ga0247610_10000007_379|M
AGGCTCAACCTCCTCAACCCGATTTATCTTGAGATCGCCAAGTACGGACACTTCGGGAGGAAGAGCTATGTGAAGGACGGCATC
AAGTACTTCCCGTGGGAGGATTTGGATTTGGTTGAAGACATCAGAAAAATTTTCGAAATGGAATAGAGGGAACCGGAATTTTTT
CCGGTTTTTCTTTGTCCTTTCGAAAATAAATAGTATCTTTGTAAAAAACAACAGATTATGTACAATAGTAAGAAGAAGGGGA
GGGTGACATTCAGAAGTCGTTCAAGTTCAAGGTCAAAACGGACAAGGAGACGGTCGAATTATTCAGAAAGGCCGCAGTGAATA
CTCGGAATACTACAAGAGGCTGACAACATTCCTCTGTGAGATGTATAACAGACCAGCGTTTGACTTGAAGGAGTGCTACAAGAA
AAATTCCAATGTAAGTGTCTTCAACACATTGAAGAAAACTCTCGGTGCAATATATGGAAAGCTCGATGAAAACGGAAATTTTAT
TGAGAATGAATGTAATAAGTAACTGGAATAAAAGAAATTAGACAGAGTAA (SEQ ID NO: 101)

>3300028887|Ga0265299_10011526_3|M
TTGTATTGGTTGCTGTATGGCGACGGAAGTGACATATATGATGACGGGTGGTTTGACTGTGTTCATAATTTTGCCCGTAATGTT
ATCGGGTTTCAGTCATATCACGAACTGCTTGATAATGCTATTATAAAAGAAAAATTACAACGGTAATTTGGTTATGAAGATGCT
CCGAAAACGTGGTTGTTCGGACAACAAAAAAATGAATGTTTCTAATGTATTAAAACAATAATTCAATTACATTTTTAAGGATTAT
GGCACAACACAAATCAAACAACGAAGAATCAGCAATCAACAAGACTTTCATTTTCAAGGCAAAATGCGAGAAGAACGATGTCAT

TABLE 95-continued

Non-coding Sequences of Representative CLUST.091979 Systems

ATCGTTATGGGAACCAGCAGCAAAGGAATACGGCGACTATTATAACAAAGTGAGCAAGTGGATTAAAACTATGTATAACATACC
CGCATATAACATTAAGTCCAATTTCAAGAAAAATTTGAGCGCCAAAACAATTCAAACTTTTAGAGAACTTGGACACTACCGTGA
CGGAAAAATAAATGAGGATGGTATGTTTGTTGAAATTTTGGAATAATTCTGTATATACCAATTAGAATTGAAAAAAAAACGCTC
TTTGACATATTGTTTTCTACATAAAAACAAGATTTTACACAACGCAATACATCATAAAGTGTTGCGTTATAACAAATAACAAAA
ATTCTGGACGGGAAAGGAAGATGTCAGACGTTTTTATTGTTGGAATACTCGTTTTTTACGGTATTTACAACTGCCCCGTAGCGG
AATCAAAATACCACCGCATTGTTGGAGTACAAGTTTTACACGGTATTCACAGTACGAACACCGAATGAACTGAAAAAAATAAAC
CCGACCTTGCAACCGTAGATATAAATAAAGCAATACAAAATTTGAAACTATGGCACACATTAAAAAAATTGACGAAATGGCAAG
TCAAACTGTTTCACTCCGTTCTGACGCATTGTTCAAAAAAGCGTTTGAGGAATTTGAAAAGGAGTTGAAAGAAGTTCTCAAATC
GCACAACAATATCATTTATTGTGGAGGTGAT (SEQ ID NO: 102)

>3300028797|Ga0265301_10009039_3|M
CTCATCAAATTGTACAAGTCGTTGACGGACACTGAATTTGACAAGAAGAAAATCATCAATGATGTCTACGACGGCACTTTTGAG
ATAATCCTCAAATACCCAAAGAAGAAGAACGGGACATTCGTGTTCTGGAAACATTACAAGAAGTAACACAATGATACACAGTAT
GTTGTAAGAAATAAGATTTAGGCTTTAATTTTAATATATGAAAATATGGCACACAAAGGAGAAAAGGAAGGCTACCAAATCAAG
ACACTGAAGTTCAAGGTACGCTCGCATGACATCGGGAAATCACTTTATGATATTGTCAACGAATACACCAACTACTATAACAAA
GTAAGCAAATGGATATGTGACAACCTTGGTTACAACGAGCCATTCTACAAGTCAAGGGTGAAAAGCGCCGCCTCCATGATGTCA
GGATTGAAAAAACTGGGCGCCACCATGCCATTGACGGATGAAAATGCCATTTTTTCAACACCAAAACCGAAGAAAAACATTGGA
AAACAATAATTTACACAAAGTCTACGGCGGGAATCGTGATAAAAATGAACGAGATTGTTGGGATATACCTTTTATAGGATTTTC
ACAACATCTGAGTTGTTTGATGTTAAAAACTTTAACTAATAAGGCAAGAAGTCCATTCCTTCAGGTGGGGGTAGTTCATTTGT
TGGGATACTCGTTTCACACGGTATTCACAACTTCCAACCAACCATTAAAAAACCTTCAAATATTGTTGGAGTACCCGTTTTATA
CGGTGCAAAGCCTCCCCGACGATTTCAAGTTCCTGTACGAAGATGTCAATTTTGGATAGCAACTGTTACCAATAAACATATTCA
AAAGTAATCAAATATATTCAAAAACAACTCGTATAAATATATAAAGTTCGTGATATTTATTATAAAGAAGCCGAAGGAGAGAGC
GGTTTCCGAACAATAAAGATATACAGAGGTTTTATTCTTGACGGCACTCTCTCTCCTTTAGCCGCAAGTTTAATTCCTCTTTTTA
TTGCACTATGGTCATCGACAGCAAATATACCAAGACATTCAAGTCAAACGGACTGACCCATCAGAAATATGACGAGTTGCTCTC
GTTTGCTTCTATGCTGCGTGACCATAAGAACACCATCTCCGAATATGTCAATGCCAACCTTGAACACTACCTCGAATACTCAAA
ACTCGACTTCCTTAAGGAAATGCGTGCGAGGTACAAGGATGTCGTTCCGAGTTCGTTTGACGCTCAACTCTACACG
(SEQ ID NO: 103)

>OBLI01003123_14|M
AGAATCTGTCCTATATGTGGGAAACATTGCGAATATGAGGAAATGGAGGGCGACCACATTGTTCCATGGTCAAAGGGCGGTAAA
ACCGATATAGGCAACCTCCAAATGCTATGCAAGAAGTGCAATCACGAAAAGTCCAATAGATATTAGTGGCGTAATCAAAAATTT
GTTTGTGTTGAGGAAAAGCAGTGAAAAAAAACATTGTTTTTCCTCAATTTTTATTTGCATAATTCAAATAATTTTTTATTTTAT
AGGATAATAGAGCTAACAAGCATTAACAATTATTAAAACGATTTATATTGAAAATAAATTTTGTGGGAATATTTATTTTTACTA
CCTTTGCATCGTAATACAATTAAACAAATTTTTGATTATGGCACACAAAAAGAACATAGGAGCAGAGATAGTAAAACTTACTC
TTTTAAGGTGAAGAATACCAATGGTATCACAATGGAAAAATTAATGGCCGCCATTGATGAGTATCAGTCGTACTATAACCTTTG
CAGTGATTGGATATGCAAGGGTCTTGACGAAATAATGAGGAATACTTTTCTGAAAAAAGCAAATAGCAATAAATCATTGTATAA
TCAGCCAATCTACGATACGGGTATCAAGAAAACCGCAGGTGTGTTTCCTAGAATGAAAAAATTAAAGAAATATAAAGTTATCTG
AAATAAAATATGTATTTTTCTTTGTGGAAATACCTATTAATAGACTGATTTCTAATAAGTTATAAGAAATACTGTATGTAGTAA
ATAAGATATCATATTTTTGCGGAGAGGCACATGGAGTATGCTATAGGGTTTTTGCTACCGAGCAGAAAGCAAAAGAAAAAATGC
AGGGATGATATCATTTCATTCTTGCATTTTGCTTATACATATTCAATCAAGTATCATTTCATGTTTTTACTATTATCCTATAAA
ATAAAATTTTCCTCAACATTTCCAAATTTAATTTGCAATAATTTTTTTTGATAAAAAGTGCAAATAAATTTTATAGATTCAAAA
CTTTTGATTAACTTTGTAACAAGAAAAACATTAAGGATTATGGGTTACACATATTTTAGGGTTACTGATGAAAGGGCAAGGGAT
GTTATGCCAAAGGCGGCTGAAATCATAAAGGATATTTTC (SEQ ID NO: 104)

>3300028887|Ga0265299_10000133_30|M
CTTCACCTCGTACAGCCGACAATAAGTTTCGCTTGGACTGAACTTATGTGCGCCTGCGCATTCATAGCGGGTGGCGTATCAGGC
TATCTCATCAAGGGCAAGATGCCAAACGACGGGAACAAGTACCAGTCGGTAGAGGGAAAGGAATAGGACAAAAAAAAACACATC
ACCCCCAGCGCATCGGGCGCGGAGGTCGGGTGTGCATATAACGGTGTCTGTGGCGCAACTGGTAGCGCAGTGGATTGTGGTTCC
AAAGGTTGCGAGTTCGAGCCTCGCCAGACACCCATTATCACACGGAAGCATTGGATGGAAGTGCAAGTACCTACTGGGAACTTC
CTGAAAGCGCAAGCAAAGTCGAGGTCTAACGGTACTTATGACGAGGTAATGGCGGGGCGTTGGTTCGAGTCCAACACAATGTT
TCCATTTACACGGAGAGTTGCAGGAGTGGTAACTGGTCAGATTGCTAATCTGAAGCCCACCTCGTTGTGGCAGGGGTCCGAATC
CCTTACTCTCCGCCAAGCAACATACCCGCAGAGTAGTCGCGTATATTCTGTCGGTGTGGTCAGAAAGAAGTGAATGTGATGCGA
ACGCGCGAAACCATCGCATTTAGAGTCCGAATCTCCTCTGCGGTAGCCAGTCCGCATAGTTTAATCAGGTTAAAACATTCTGAC
GCTTTTTAAATCGCGGGAGTAGTTCAGTGGTAGAACATCGGCTTCCCAAGCCGAGGGTCGCGGGTTCGAGTCCCGTTTCCCGC
TCAACACATAGGCTGTGGACAAGGTGGGCGAAAGTATTTTTTCCATAGTTTTACACCAACGCCCGCCTTTTCCTAAACGCATTG
GAGAGATAGAGGACTTGCCTTCTAAACAAGCAGTACGGGGGAACTTGCATCCGACCTCCGTTTCAATGCGGTAGAACTCCGCTC
CCGTGACAGCGACGAATGATGCAATAGCGGTTCACGAGATACCTCAAGAAACTTCATTTTTCAAAAGCCACAATAGTTCAACTG
GTAGAACGGCGGTATCGTAAACCGCAGGTTGCTGGTTCAATTCCTGCTTGTGGCTCAACAATTTCGGGGGCTTGCAACGCTGCC
ACTGCGGGTGGAAGCCAGCGACAAGAACTTGTGTGAAGCCGAAACGCAGTCCTTCGGGAGAGGGGCGAAGGGGCAAGCGAGATG
TGTCCCACTTTTTTAAAGTAACAGGCTTTAATAAATATTTATCATTCCCGAAAGGCTGTGCGGAACAGCCTCTCGGCTTTTACG
GGGATTTAGTTCAGTTGGTAGAACATCTGGTTCGCAATCAGAAGGTCGCGGGTTCGACTCCCCGCAATCTCCACAAATATAAATA
TAGTATTGCCCTGTGGTGCAATCGGTAACACACCAGATTCTGAATCTGGAATTTCGAGTTCGAGCCTCGGTGGGGCAACACAAT
AGGCAGCCGTACTGCCGAATACAAGCCTGTGGAGAACCCAACCGTGGATGACCGTTGCCTATGCAACCTAAAAAGCGGTGGTTC
TGTGAAGCAGGAAGCGGAAATACAATATTCCGCATACGGTGGTGGTGTAATCGGTAACATAACAATATCCGAAAAGTTTAAACC
ATACACCCGACGATTATTTTTATTCATTGTTAGCGACCGCCGTAGAGCCGTCAGGCTGGCGGTCGGATAATGACGCATAATG
GCGGTTGTGAAAGCCGACGGAAAGCACTACATCGTTAAGTGCCAGCCACCATAATAGGCAGCCGTACTGCCGAATTTAAGCCTG
TGGAGAACCCAACCGTGGATGACCGTTGCGTAAGCAACCTAAAAAGCGATGGTTCTGCGAAGCAGGAAGGAAATGCCCAATTTA
TTAGGTTTTTCCATACGGTATGACAGCCTCTAACTGTAGCGCATTACAAAACAAACGCTACCATTACATAAATGGTCAGAGGCA
TAACGCCGAGCGCAGGTATGGTATGCGTTCAAGTCGCAGTCACGGAGCCCGATAAAAATGGGAGGTGCTTGCGGTCAAGCG
AGTGGTCAGCGGGCTTGCACTCGGTGTGGCAACAATGGTCGTTTCCGAACTTACGACCATTCAAAAAGATAAGGTAGTGGCTTG
TGAGTGAAAGAAACTCTCGATACGCTCCTTTCGTCAACGGTCAGGACGCGAGATTCTCAATCTCGTAATGCGGGTTCGATTC
CCGCAGGGAGTACAATGGCGAACACACGACAATCCAAACTGAAGGGGAACTGGAAAACCCTCGCTCCGAGATAACATCAGCGCA
GAGAGGTTGGTGAGGCAACCGTAAAAGTAATCCTGTGTGCAAGGAAGTTCGGGTTCAAGTCCCGATGAGGATTATTG
TTGAAGAGGGATATGATTCAACCATAGCACTTATGGTGCTGTGCAAGGGTTATAGGCAGCCGTACTGCCGAATACAAGCCTGTG
GAGAACCCAACAGTGGATGACCGTTGCCTATGCAACCTAAAAAGCGGTGGTTCTGCGAAGCAGGAAGGAAATGCCCAATTTATT
AGGTTTTTCCATACGGTATCACTACTCGCGGTGGATGTGAAATAACCGCGATTTGGTCAGTTGGTGAAGTTGGTTATCATACC
TGCCTGTCACGCAGGTGTTCACGAGTTCGAGCCTCGTACTGACCGCAGACAAAGACAAAGAACGAGAGGACTTGTATGACTTGC
AAATGTCACGGACTCAAACAAGAAAAGTTTATAGGCTATTAGAGGATGACTGTTTCTTTAATTTGTTTTCTTGTACTGAAGGTC

TABLE 95-continued

Non-coding Sequences of Representative CLUST.091979 Systems

ATCACTGCCGTGCCACCAAGCCGTGCAAGTCCAAATGGTGCGTTAGTTCAGTTGGTTAGAATGCCAGCCTGTCACGCTGGAGGT
CGCGGGTTCGATTCCCGCACGCACCGCAATAATCTGGATATAGGCAAATTACACATATCATATGTCGCCCCGCGTAATCATAGA
CGACACTGCGGACGACAGCGGCGAGAATGTCGAAAGGCTCGACAGCATAATGACATTCGACATCACCGACACCCCGATATACGA
AGGCGGGGAGGAACTTGAGATAAACGCAAAATTCAACAGATAGAAATAATTAAAACAAACGGCAATGGCACACAGAAAAAAGAA
AGATGACGAAGCAACGCTATCGTACAAGTTCAAGGTAAAGGTCATAGAGGGCGACCTGACGGCAGACGACATAACGAAGTGTAT
CGCGGAAAACGCGGAGCAGGGCAACCATTTCTCCGAGTTCATACACGATGAGAATTTCAGGAAGACCTTCACATCCGAGATCAG
CGCGGACAAGTTCGGATGGGGCAAGCCGATGTTCAGCCCGACCACCAGAAGTCAGGACGAAGTGTTCTCCGCGATAAAGAAAAT
CGGGGCGATAACCGTGCTGGAAGATTAGCGCATATTATTCTCATATCTAAAATTGGAAGGACACCTGCGGACGCGGGTGTCCTT
TTTTCTTAAAATGCCAATTTATAAATAATATATAACTTATATTTATTGTACTTTTTTTGTTTAACTAAAACACATAGACAAATA
TGGAAATTCAACAGATTAGGTTTATAAACCCAGTTGATTTTGAAGAAACAATCGTTAATGTACCCACGGAGAAGGGCGAAAGAT
TCCTGAGAACAAAAATCTATACGGACGAGTATTCACCCGAAACATTCATAAAACTCTGCGAGAAG (SEQ ID NO: 105)

>3300028888|Ga0247609_10000668_74|M
TGGCGATTATTCTTACGGCAAAGGCCTTATCCATGCATACATAAATCGAGACATCAAAAGTTTTTGCTTGCCAAACACTTTAAT
ATGTGAATGCCATATACCAAAACATACCAGATATATTACTGATTACTCAGGTACAAATATAGCCGCAAAGAAAATCATCATCGA
CAAAGTTGTCTGGGAGAAGGTATGTATAAAAACATAATGGTATTAGGGGAGAAATTTTCTTGGACGGAATGAATATAATTTCAT
ACCAACACCGTGCATTGATTAAACTAAATTAAATTATCAAGCATAAAAGTTTGGCACGGTTTTTGATATAGTAAATTTGTATT
TAAAATTTTTAATATGGCACACAAAACTAAAGAATCAGAAAAATTAGTAAAGTCTTTCAAATTAAAAGTAGACATTAGCAATTG
CGAAATTGAAAAGAAATGGATTCCTTCTTTTGAAGAATACACAAATTATTATAATGGATAAGTAATTGGATTTGTGAACTATT
AGAAAAAGTTTGCCTGAAAAGAAAAAAATTTGGAAAGGCTTCTTATTCAGTACCATATTGGAACGTTAAAGACGCATTTAAGAA
AAACGTTAGCTCAAACATGATTGCTACAATTAAAAAAATGAATATGGTAAAGGTTTTTTAATGCGTGATTATGGCGTTTTTTAA
ACATAAAATCATTTATAATATATTGAAAAACATTTTATTATATAAAATATGCATCTTAGTGAAACCGTGTTTTCGTATAGATTG
CTGGATTATACTTTTTTATAGGATAATTACAGCTCGAACTTCTTTGATGGCATTAATAAGATATTGTTGGATTAT
(SEQ ID NO: 106)

>3300028805|Ga0247608_10000895_42|M
ATCATGGCTGAAAGCGTCCGCCTGATTGCAGAGCAAACCGCAAGCCCGAAGGTTGTCATCAAGAGCCGTTACGCTCGGTCGAC
GCAGGTTTCTATCCTGAGTTGAACTATGTGACCTTCTTCGTGAACACTCCAGATCAACTGGTTTAATCACTGCGGGTAGCAAGC
GATTGACTACGGAAGGCCGATTCGATAGAGTCGGTCTTCTTTTTTTTTTGTATATTTTCTTTTTTTGGTTTGGAAATGTTCCGT
ATATTTGCAGCACTAAAACTAACCAATATGGGACATGTACGTTTGCAAAAAAGAGAGGGAGAGGTTTATAAGACCTACAAACTT
AAAGTAAAGAGCTTTTCTGGCAATGTAGACATTAAAGCTGGTATCGTTGAATACGATATCGCCGAAACAATTGATTGGAGAAGT
ACGCTTTGTTTCAAGACATGGAATACGTATGGTTCTCCTCAATGGGACTCGAAGATCAAGAACCAGAAAACGATGATCGATCGA
CTGGATTCGTTGGGTGCAATAGAATTGAAAAACTGGTGATTTTGATCATGGTTTTGAAACAAAATATTGATTTTTCGTTCTTTG
ACATGCTTGTTAAAAATTGAGTATCAGTTTAATATAAAGAATATAT (SEQ ID NO: 107)

>OQVL01000914_15|P
GGAAACAATTATAACGATGCCTACAAAACGTTAATTCAAATGAGAGACAAAGGAATTTTAACGCAGGAAGTTGTAAATGTATTT
ACCCTATTGAAAGGGCGGTATATTAAAGAAAAAGAATACGGAACACAATATAATACTATCAATTAAATTTTTTGGTAGTTTCAT
TTGGAATTGCCAATTATTTTTTATTTTATAGAATAATAGAGCCAACAAGCATTAGCAATTATTAAATCGATTTATATTGAAAA
TAAATTTTGTGGGAATATTTATTTTTACTATCTTTGCATCGTAAGATAATTACAAAACATTAACAACATTTATTAAACAATTAA
ACAAATTTTAATTATGGCGCACAAAAAGAACGTAGGAGCAGAGATAGTAAAAACTTACTCTTTTAAGGTAAAGAATACCAATGG
TATCACAATGGAAAAATTGATGAACGCCATTGACGAGTTTCAGTCATACTATAACCTTTGTAGCGATTGGATATGCAAGGGTCT
TGACGAAACAATGAGGAACACTTTTCTGAAAAAAGCAAATAGCAAATAATCATTGTATAATCAGCCAATCTACGATACGGGTAT
CAAGAAGACCGCAGGTGTGTTTTCCAGAATGAAAAAATTAAAGAGATATGAAATTATCTAAAATAAAATATGAATTTTTCTTTG
CGGAAATACCTTTTAATAGATTGATTTCTAATAAGTTATAAGAAATACAATAGATACTGAAGGAAAATCAAAGTGTAATCAAAA
ATTTGTTTGTGTTGAGGAAGCAGTGAAGAAATTTCATTGTTTCCTCAATTTTTATTTGCATAATCCAAAAAGTTTTTTATTTTA
TAGGATAATAAGACTAACAAATCTCAACGACTATTAAAACGATTTATATAAAAAAAGTTTTGCAGTTCCAATCTTTTTTGCTAT
CTTTGCAGTGTTGAAAGACAACAAAGATTTAAGTTTAACAAACAAATACTTTTTATTACATATTTTAATTTTTTTGTATTATGA
CAATAGAAGAAAAAGCAAGGGAAGAATAACCCTTATATAACCCCATCTGATGGGTATGAATGCCATGATTATAATGAAGCCGCTA
AAGACGGTTTTATTGAGGGGGCAAAATGGATGCTTGAAAAAGCCGCTGAATGGTTTAAGAAT (SEQ ID NO: 108)

>3300028888|Ga0247609_10003329_9|M
ATATGGGCAAAGCGTGATAAAATTGAAAACAAATATGTCAAAGAACCATTAAAACGAGTCAATGAAGATATGTGGTGGATGTAC
TATGTTTATGAATGGAATGTGTTTTATGTGCTTGAAGAAAATGTCCATCCATATATGAAAAATAAATTTTACCACACATATTA
TTATTCGTGTCATGCCGATGAGGTTTGGCACGATTTTTGTTTATATGGAGAGACATAATGTCAGTCAATACATGACAACTTGTC
ACAATAACTGACATTAAAAGTTTGGCACAATATTTGCTTATAAGAAAAACGAACAAGTAAAATTAAAATTTTATAGATTATGGC
ACACAAAACAAACAACGGAGAAAACACCATCAACAAAACTTTCATCTTCAAAGCAAAATGCGAGAAGAACGATATTATATCGTT
ATGGAAACCCGCAGCAGAAGAGTATTGCAACTATTATAACAAATTGAGCAAATGGATTGGTAAAACAATGTACGGCATTCCTGC
ATATAACATCAAAAGAGGTTTTAAGAAGAATTTAAGTGCCAAAACTATAAACACATTTAGAAAACTTGGACACTATCGTGATGG
AAAAATAAATGAGGATGGCATGTTTGTTGAAACTTTGGCATAGAATTTGCATATACCAATTAGAATTGAAAAAATCGCTCTTTG
ACACACTGAAACATACAAAAACACCACAATTTTTTAATCCTTTTCTATTTGTATTTTATTGAATAAAATGTATTATAGTAATA
TATCTGCTAAGGTCATATTTTTCATTGTTCTCAAATTGTTGGATAATGTTTTGTGTGTTTCATTTTTGTCATTGTGTCACCTTA
ACTGACAAGGTGGCACATTTTTTATGTCAATATGTCAGTTGAGGTTTTGGCATAATTTTTGTATAATGGTAAATGGATAAGAAT
TGAAATTACAATGACAACAAAACAAAGGTTAATAAAGAGAATAAACAAGGCATTCGGATTTGAATTAACGGATGCAACACCTTG
TTTCCACCATCAAGGTAGAAGATGGGGAAGCGGTGGTTTC (SEQ ID NO: 109)

>3300028805|Ga0247608_10006074_1|M
GAAGGCGGCGCGTTTGAAATCGCTAACGTAATTGAAAATGCCAAGAAGCAGAATCTCGGGGAGGGTGGATACAAGGAATTGTGC
AATGATTTCCTGAAACATGCGAGGGAAACGTTTTTCAGTGGGAAATACGAACCATTCTTGGTAGTGGATTTGTTATTTTGGT
AAATATAATTAACGCGGCATTGTCGTCAGTGAATATAATATTGCATTTCGACAGTATTTTATAAGTATTTTGACTTATAAACAG
TATTTATAAGTTATTCGGCTTATAGGTTAATTAGCCTATAGATGTTGTTTATAGGTTGGATGACCTATAGTGCCAAGTTTTGAA
GAAATCGTTATAGTCATCGTTCTGCCCTATTAGATATTCCGTATTTCTTAAGACTGTTATAATACAAATATACTACAAATCAT
GCAATTTTTGATTTTTAACAAAAATTAAGAAATAGGGTATTATTGTGTATTGTTTTTTGTTATATATTTGTCCTGTTAGGTTAA
ATCACCGCGCCTGATGACGAAGTCGGTGGTAGAATTAGACTAATATTAAATATGCTCATGAATTTAACAAGAATAAAGGTGAG
AATGAGATTAGCAAGACCTTTATTTTCAAAACAAAATGCGGGAAGAATGATATTACATCATTATGGGTTCCCGCGATGGAGGAG

TABLE 95-continued

Non-coding Sequences of Representative CLUST.091979 Systems

TATTGCACGTATTACAACAGGGTAAGCAAATGGGGGAAAGGTATGTACAACAAGCCGTCATATGACATACGGAAGAAATTCAAG
AAGAACTTGAGTGCGGCTACTTTGAAAACTTTCATTAAGTTGGGAAACACGGTGAAAGGGATGATTGTCAACGGACAGTTTGTT
GAAATGGAATCATAGGTTGACAGAAACGGAAAATCGGTTTGTTTGTTAGAAGAATATTTGTTGAAATTCATTTTTCTTTTGCTA
ACGTATATACAAATAACTGTAATAGAATATCTTATATAAGATAT (SEQ ID NO: 110)

>3300012973|Ga0123351_1009859_3|P
ACAAATGAAATTATGGGACAAGTAAAACTTAATAAACCTCTTCTGTATATCAAAATATTGACTATCTTTAGACATAACCTTGTC
AAATAATAAATCTAAATTACTCTTTTCCTTTTCTTTTTTAAATAATTTCATATTAAATATTCCCATAATTTATTAATATATTTT
TTTTTCATTACTTATTTCTCTGTTATATAAATAGTTACATAAAAAAATTAAAACTATTTTTTAAAAAGTCTTGTGTATATAAAA
AAAATATAGTACCTTTGCACCCGAAATCAAGATTTAATCCTGTTTTCATATTATATTTATCAATTTTATACTAATTAATAAACT
TATGGCAAATAAAAAATTTAAACTTACAAAAAATGAAGTCGTGAAATCATTCGTACTCAAAGTTGCTAACCAAAAAAAATGTGC
TATCACTAACGAAACACTTCAAGAATATAAAAACTATTATAATAAGGTAAGTCAGTGGATTAATAACATCGTACAAAATGAAAC
GTGGAGAAATCTATTTACTAACAAAACCAATAATACATATGGATTACCTATACTAACACCTTCAAAAAAAGGACAATCTAATAT
CATTACACAATTAATGAAAATTAATGCAACACAAGAACTTGTTGTATAATATAATCTATTTTTAAATTTATAATACTAATATAA
TTCATTGATAATTAAATAATTATATAAAATTCCTATATACAATAGAAAGACTTTCCACAGACATGTTGTACATACATTTTTTTA
AGTATTAAACAACGCATACCCACCAATGGTACACGAAAATTTTCATGTTGTACATACTATTTTTAGGTATTAAACAACTCACTG
TTTTGACGATTAATATAGGCATGTTGTACATACTCTTTTTAGATATTAACAACCTGTAAACAATAACAATATTTACAACAATAA
TCCATTTTTGAAATAATGAAAAATTTTCTGGAAAAATTTTTTAACAAGTCTGTTTTTGAAATAATGAAAAAATTTCTGGAAAAA
TTTTTTAACAAACCCATTTTTGATTGGTTCATTTTTTATTGGAAAATTAGTGTGTGGAACTACCCACCCGTATATGAGCAAGT
GTTATGGGGTGTAACGTGGGGAGGGTTACATAGGGGGGTCTTTGGTAGGGGGTACATAGGTAGGGTAATAATGGGGTCTTTGGT
AGGGGGTACATAGGTAGTCCCCATATATTATTATAAAAAGTAAAATAAATGATATATGCAAGAGTTTTTGAAAATTTATTTTTA
TTTTGCTACTTAGACTTTACAAAAAGTAGATATATAGTATTTTCTTTTCAAAATATTTTGTAGTTTGGAAAAAAAGCAGTACCT
TTGCACACGGAAACGAAAAACAAGTTTAACCTATTAAATTTTTAGTTTATGGCAATAAACATTTTGACTTATTCTGCTATGGCA
GAAAAATCTTGGGAAAATTTTATGCGTGAAAATTGCCGGTTACGAGCGCATTAGTACATTTTATAGTGATTTCACTATTGCAGAC
CATTGTGGTGGTGTAAACGCAATAAAAGAC (SEQ ID NO: 111)

>3300012979|Ga0123348_10005323_4|M
GATGTGAATGAAGAATTTCTTGGTGGCTTGCGAAGCACTATGACATATCTTGGAGCAAAGAGATTGAAAGATATTCCGAAATGT
TGCGTTTTCTATCGTGTAAATCATCAGTTGAATACAATTTATGAGAATACAACGATAGGAAAATAATATAAATTTTATATTATT
TTGAGAAAAAGAGTCTAAATTTGGGCTCTTTTTTCGTTTTTTATGAAAAAATATGAAAAAAGTTTGTAAAAAATTTGTAATATT
GAAAAAATAGTATTATATTTGTATCAAATTTAAAAATAAAATATAAATATGCAAAATCAATAATGAAAAAATCAATTAAATTC
AAAGTAAAAGGAAATAGTCCAATAAACGAAGATATTATAAATGAGTATAAAGGTTATTATAATACCTGTAGTAATTGGATTAAT
AATAATTTAACAAGCATAACTATTGGTGAAAATGAAGACTGGAGAAAAGTGTTTTGTATCAAACCAAAAAAAGAAGATTACAAT
ACACCTTTATTGGATGCTACGAAAAATGGTCAATTTAGAATACTTGACAAGTTGAAAAAATTAAATGCTACTAAATTATTAGAA
ATGGAAAATAATAAATATATACAATAAATTTATATAATTTTGTCTATTTTTAATTTTAGTTCATTAGATAATATGTTCATAAA
TTCATTGACATATAATTTATAAATAAATATATATGCAATAAAATTCGAGAGATCATTTCATCAGAGATGTCTCTTTTTTATTTTT
GTTATATTTATATTATGAATATTAGATTGGAACTCATAAAGACAAAGGATAAACAGAACATTGCAAAGCGTATAGTGGAAAGCA
ATCACTCATATGTTCCAACCTGGCGTAGTGTAGGACGAAGGATAGATTATCTTATTTATTTGGATAATGATGTTGTCGGA
(SEQ ID NO: 112)

>3300028888|Ga0247609_10016480_8|M
GTGAACTATATCTACGAATCAATCGAAGGAATATTGACAAAAACAATGAATCCAACCACTTTACAGGATATCATCCTTAACGGA
ATCACATATACACCAGTGGAAGACAACACAACAACATGCGACGGATGTGAATTTAAAGACACATAAGGCCAATGTATGCTAACA
CACCTATTCGATAACGACATGGTCCAAAACTGCCTCAAGGAAAAAAACGGCGTTGCAGATATCATATATGTCAAAAAAGAAAAT
TAATCGGAATCTTGATTTGGATTTTAATATTATTTGTTGTATAATTACAATAGAAAGAAAATTTTGTATATTTTAAAATTTGTA
AATTAAAAATTTAGAAAAATGGCACACAAAACAAACAACGGAGAAAATACAATCAATAAAACTTTTATTTTCAAAGCAAAGTGCG
ATAATAACGATATTATATCGTTATGGAAACCCGCAATGGAAGAGTATTGTACTTATTACAATAAATTAAGCCAATGGATTTGCA
AGACAATGTATGGAGTACCAGCTTACAACATTAAAAACGGTTTCAAAAAAAATCTGAGCACAAAGACAATCAATACGTTTAGAA
CGCTTGGCCACTATCGTGACGGAAAAATAAACGAAGACGGCGTATTCGTTGAAAACCTGGCATAATAAGGAGTAAAAAAATGTT
CTTTGATATTCTGACACAAATGAAAAAACAATCAAAAATTTATTTCTGTTTTGCTTGTAATTTATTGAAATAAAATGTATTATA
TAGAAATATGTCGGTGGATAATAGTCAAATAGTCTGTTGACTGTTGAATAGTAAGTTTTTTACTCTATTGACAACAGGTGATGT
GGATGGAACATACAAAGTTTATTGTTGAGTAATAGGTTTTACACTTTTACCACAACTTTTCATCATCAAAAAATAATTC
AAATCATATATAAAAATTTTTCCAGAAAGTAGTACTTATTGAATTAAAATTATATTGTGAAAAATGGTTTTTGATTTTAATTTT
ATTTGTTGTATAATTGAAATGTAATTTAATTTAGAATTGTATAAATAAAAAACGTAAAAATGAGACTGCCAACAGAAATTTATG
AGTCAGGCACAATGGTTAGTAAGATATCGGAAAAACCATTTAAATCAGGTTTAAGGGTTAATACTGTAAAGTCTGTAGTTGAAC
ATCCACATAAGATTGACCCGAATACTAATAAGGGTGTTCCA (SEQ ID NO: 113)

>3300028887|Ga0265299_10000013_320|P
GACTACGACTGGTTCTCAAATGTGTACGGCGCCATCAGGGAGGAACGTGAGAAAATGAGAAGGGAAGAGGAGGAACGCAGGAAG
AACGAACCCAAGACGGTGAAAACCAAAGAGGTTGACTTGTTCGGGGATGATGACCTGCCGTTCTAATAAAAAAAAAACAAACC
TCTCCGAAATTGAACGTATCAACTTCGGAGAGGTTATATAGGGTGATGGAAATGTTAAATAAAAAGTTTAAAAATAACTATGGG
AAACAAAGTACAAAGTAATGAAACAATAGTTAAGACTTATACATTTAAAGTGCGTGGATTCATAAGTGGTGCTACCCACGAAAT
AATGAAATCAGCCATAAACAATATATAGAAGATTCTAACAATCTATCAGATTGGATTAATGTAGAGAATGAAATACTTAGGAA
CTCTTTCCTTAAAGAAGAGACTAAAAAATACACTTATAATACACCATTATTCACTCCCAGACTTAAGTCATCGGAAAAAATAAT
AACAGAATTGAAAAAATTGGGTATGACTACGGTTATAGAATAACCATTACACATTTTTTCTAACAAACGTTCTTTAACATAT
TGGAAAATAAGAAAATACGATATTCATATAAAAATCCGTCCCACACAAAATTAATGTAATATCTTAGTTTTGTTACATCAACAC
TATATAATTAAAAAAATAAAAAAATATTTTGTGGATTCAAAAAATCATTATATATTTGCGTCCGAAAATTAACACTTATGTCAA
ACAAATTTAAAATGTAAAAGAACTATGCAAACAGAAACACAGAATTTCACAGGCGAGTTGAGAGCAATCAACACAACAATGGGT
TCAAGCAAGAGCTACAAGACAATCTGCCGTTGCGCACTTGACATCCTCAAGGGATATATCGTTACGCACGACATTAGGGACAAC
TTCTCA (SEQ ID NO: 114)

>3300028887|Ga0265299_10000026_77|P
ACAGAGGGTGTATGGATAGGCATGAACCACCAAGGCAAAATACTGATGGCTTGCAGGGAGGCTTTGTGTAACAACTGTGAACCC
CCGATTGATTCAAGGCACTGAACGATGCCGAGATATATTTTTATGGAAAAGAAGTTAAATTTTAAAAATTAAAAGATATGGCG
AACAAAAGCACAAAAGGAAACCTGCCCAAGACAATCATAATGAAGGCAAACCTTAGCCCCGATGGTTTCACTCAATGGGAAGG
GTTGTAAAAGAATACCAAGCCTACAAAGACACGTTGAGTAAATGGGTAGCCCAAAATCTCAGACAAATAATGTGCAAGACACCG
CAGACAAAGAACGGCTACTCATCACCTGTGCTCACCTCAAAGGTTAAAAGCCAAGTGGAAATGGTAAGAGAATTGAAAAAAATG
GGAAAAACCATTCTTTATTCCAATGATTCACTTCCTTTTTGAAACTAAAATGTCTTATGTGTATTTGAATTATAGGCTAATATA

TABLE 95-continued

Non-coding Sequences of Representative CLUST.091979 Systems

```
AAGATTGTACTGTGTTGAGATACACTTTTAGAGGTATTTACAACAAAATGCGTGATATGGAAATGAAGAAATAACTGTGTTGAG
ATACACTTTTAGAGGTATTTACAACACCATATAAACCTGACCATCTCCTGAATCTCGCCCGACACGGATAATGTTAGATATGTT
CACAATACAACTGCATGTGCTATTCAAGAAAAAATAGTATATTTACAATATGTTGGTGCATAATATTAGATGTGCTTACACAAC
GCAGACCTGAAAAGCCAGGATAAAAGTATGCGGGATTGTGTTTTTAGAACACTGTTCAATCCGCTGTATGTCGCTTGAAGCGTC
AGTAACCTATGTCGAAACAATCCTTTTAGAGGTGTTTACGACCGACCAGAAACAGCAAGACCTGTATTTATGTTGGTATACGGT
TCTTTTTAGGGGATTAGTAGTTGAATCCCTTTTCACCCTTGGTGTTCACGGGTTGTGAGACATTCTTCATACCCATGCGTGTCT
TCTCAGCCATCTTACCGAAAGTTATAGGCACAATATGTTCAATGCCTGCCTGCTGAGCATTGTAGCATATATCAGACAG
(SEQ ID NO: 115)

>SRR1221442_316828_61|P
AGAATGCTTTCCCCAATTGAATGTGAAAGACTACAGACACTGCCAGATAACTATACCGAAGGTGTTAGCAAATGCGCAAGATAT
AAGGCAATCGGAAACGGATGGACAGTTGATGTAATTTCACATATTTTTAAGAATTTGAAAAATTAATTTGGTATTTTGAAATAT
TTGACTTATTTTTGCAACATAAAATTTAAAACAAATTTATATGGCACACGCGAAAAAAAAATTTTGACAAAGGAAAGCAAATAA
CAAAAACGTTCTCTTTCAAGGTGTTAAATATTAAGAACAATGGCGAATCAGTTGATATGAATACTATAGAATTAGCCATGAAAG
AGTACAATAGGTATTATAACATTTGTAGTGATTGGATTTGCAACAATCTAATGACGCAATCGTTTCCCTATATCAATACATAG
ATGATGAGAAATGGAGAAAAAAATTTGTTCGCCCAACAAACACTAATAAACCGTTGTATAACTCTCCAGTTTTCTCCCCTGCTG
TAAAATCTGAAGGTGGTACTATTAAAAATCTCCAAATTTTAAGCGCAACAAAGACCATAATTCTTTGATTTAATTATTAATACA
TATATCGTTCGTAAATTTAATACAACCACAACCAAATATGATAATTTGCATAATTAAAAAAATTCACATATCTTTGTAGCATAA
AAACAAATAGAGAAAAAATGACACTTTACAGATTTACACTTTTAGGCAATACACAAATTTATGTATATGCTGGCACGTTTGAAG
ATGCTCTCAGGACATTTCGTAAATCATATGGAGATACGGGATTCAAGTCAATTGAAGAGCTTCCTGAATTTAGAGATAACATAC
TTATACAACTAGATTGATTGAAACAAACGTCAATTACCCACCACTGAAGTAGTGGGTTTCTTTGCAGTGATTTTATGAAAACGA
TAGAAGACAGAGCAGACATAGCAAGCGATATTGCTAAAAGAGAATTTGAAGAAGATAGTTATTGGAGTCATTACGCAGACGATA
TGGTAACATCTGCTTTTGTTGAAGGATGCTATAAAGGCTATATTTCAGGTGCGACA (SEQ ID NO: 116)

>SRR5678926_1309611_3|P
AAGGAGATAGATTATGACAGGGAAGGTAATATCACAAATATATATCTTTACTATGAGTCAGATAGTTTATGGAATGAAAAATTT
GAATTTATATTAACATTAGATGGTTATGAATTAAAGATACCTATTTTTATAGTAAGTGTAAGATAGTTTTGGCACGGAAATTGC
AGTAATGTTTTCCTGTCAAGAACAAATAAAATAAAAAATATGAAAAAATCAATTAAATTCAAAGTAAAAGGAAATTGTCCAATA
ACCAAAGATGTTATAAATGAATATAAAGAATATTATAATAAATGCAGTGATTGGATTAAGAATAATTTAACAAGCATAACTATT
GGGGAAATGGCAAAATTTCTCAATGAAGTGTGGAGAGAAATATTTTGTACAAGGCCTAAAAAGGCAGAATATAACGTTCCATCG
TTGGATACAACAAAAAAAGGACCATCTGCAATATTGCATATGTTGAAAAAAACGCAATTAAAATATTAGAAACAGAAAAG
TAGTGACTATAGATATAAACTTCTATGATAGATATCTGTTTTTTAATTCTATTATGCAATATAATATATTGAAATATAAACAAT
TATAAATAAAACGGGTGTATACAACAAGTTTTTTGTTTTCTTATTCATTATCTGTATATTTGTATTATAAACAAATACAAATA
TGTATAATGAATCAGGAATATATTGCTATAAAAACAAAATAAACGGAAAATTATATATTGGACAGGCGCTAAATCTTAAAAGAA
GATATTTAAACTTTTTAAATATCAACCACAGATATGCGGGTCAAGTAATAGAAAACGCACGTAAAAAATATGGTGTAGATAACT
TTGAATATTCAATCCTTACTCACTGTCCAGTAGACGAATTAAATTATTGGGAAGCATTTTATGTAGAAAGATTAAATTGTGTCA
CACCCCACGGTTATAATATGACTAATGGGGGCGATTCAGTATATACTTCTACACAAGCATTTAAAGATGCACAAACTGAAAAGT
TGAAGCAAACTATTCTATCTAAGAATCCTAATCTTAATGTCAGCAAAGTAAAATATGAAGGTAATAGAATTTCAGTTATAATTA
CTTGCCCAATACATGGCACATTTAAAAAAACGCCTGATTACTTTAGAAATCCAGAAATAAATGATTTGTGTTGTCCTAAATGTG
TGAGGGAAGATATAAGACAAAAGACTGAAGATAGTTTCTTTAAACAAGCAACAAAGAAATGGGGAGATAAGTATGATTATTCTA
AAACTATAATAGTAGATAGAATTACCCCAGTTACAATTACTTGCCCTATACACGGAGATTTTACAGTATTACCAGGGAACCATG
TGTGTAAAGATAAAAATACTGGAGGATGCCAACAATGTAGTGAAGAAAGACAACATATTGAATCATTAGAAAAAGGTAGCGTGA
AGGTCATTAAGATGATAAAGAAAAAGTTTGGAAACAAATATTCATTAGATAAATTCGAATATAGGGGAGATAAAGAAAAAGTAA
TTCTTATTTGCCCTATTCATGGAGAATTTTCAATGACGCCAGGTAATTTAAGATATAGCAACGGTTGTCCACAATGCACTTTAG
AAAATGCTTATCGTATAAAAT (SEQ ID NO: 117)
```

Example 3—Identification of Novel RNA Modulators of Enzymatic Activity

In addition to the effector protein and the crRNA, some CRISPR systems described herein may also include an additional small RNA to activate or modulate the effector activity, referred to herein as an RNA modulator.

RNA modulators are expected to occur within close proximity to CRISPR-associated genes or a CRISPR array. To identify and validate RNA modulators, non-coding sequences flanking CRISPR effectors or the CRISPR array can be isolated by cloning or gene synthesis for direct experimental validation.

Experimental validation of RNA modulators can be performed using small RNA sequencing of the host organism for a CRISPR system or synthetic sequences expressed heterologously in non-native species. Alignment of small RNA sequences to the originating genomic locus can be used to identify expressed RNA products containing DR homology regions and stereotyped processing.

Candidate RNA modulators identified by RNA sequencing can be validated in vitro or in vivo by expressing a crRNA and an effector in combination with or without the candidate RNA modulator and monitoring alterations in effector enzymatic activity.

In engineered constructs, RNA modulators can be driven by promoters including U6, U1, and H1 promoters for expression in mammalian cells, or J23119 promoter for expression in bacteria.

In some instances, the RNA modulators can be artificially fused with either a crRNA, a tracrRNA, or both and expressed as a single RNA element.

Example 4—Functional Validation of Engineered CLUST.091979 CRISPR-Cas Systems

Having identified components of CLUST.091979 CRISPR-Cas systems, loci from the metagenomic source designated AUXO013988882 (SEQ ID NO: 1) and from the metagenomic source designated SRR3181151 (SEQ ID NO: 4) were selected for functional validation.

DNA Synthesis and Effector Library Cloning

To test the activity of the exemplary CLUST.091979 CRISPR-Cas systems, systems were designed and synthesized using a pET28a(+) vector. Briefly, an E. coli codon-optimized nucleic acid sequence encoding the CLUST.091979 AUXO013988882 effector (SEQ ID NO: 1 shown in TABLE 6) and an E. coli codon-optimized nucleic acid sequence encoding the CLUST.091979 SRR3181151 effector (SEQ ID NO: 4 shown in TABLE 6) were synthesized (Genscript) and individually cloned into a custom expression system derived from pET-28a(+) (EMD-Millipore). The vectors included the nucleic acid encoding the CLUST.091979 effector under the control of a lac promoter and an E. coli ribosome binding sequence. The vector also included an acceptor site for a CRISPR array library driven by a J23119 promoter following the open reading frame for the CLUST.091979 effector. The non-coding sequence used for the CLUST.091979 AUXO013988882 effector (SEQ ID NO: 1) is set forth in SEQ ID NO: 98, and the non-coding sequence used for the CLUST.091979 SRR3181151 effector (SEQ ID NO: 4) is set forth in SEQ ID NO: 99, as shown in TABLE 9. Additional conditions were tested, wherein the CLUST.091979 effectors were individually cloned into pET28a(+) without a non-coding sequence. See FIG. 4A.

An oligonucleotide library synthesis (OLS) pool containing "repeat-spacer-repeat" sequences was computationally designed, where "repeat" represents the consensus direct repeat sequence found in the CRISPR array associated with the effector, and "spacer" represents sequences tiling the pACYC184 plasmid or E. coli essential genes. In particular, the repeat sequence used for the CLUST.091979 AUXO013988882 effector (SEQ ID NO: 1) is set forth in SEQ ID NO: 57, and the repeat sequence used for the CLUST.091979 SRR3181151 effector (SEQ ID NO: 4) is set forth in SEQ ID NO: 60, as shown in TABLE 8. The spacer length was determined by the mode of the spacer lengths found in the endogenous CRISPR array. The repeat-spacer-repeat sequence was appended with restriction sites enabling the bi-directional cloning of the fragment into the aforementioned CRISPR array library acceptor site, as well as unique PCR priming sites to enable specific amplification of a specific repeat-spacer-repeat library from a larger pool.

Next, the repeat-spacer-repeat library was cloned into the plasmid using the Golden Gate assembly method. Briefly, each repeat-spacer-repeat was first amplified from the OLS pool (Agilent Genomics) using unique PCR primers and pre-linearized the plasmid backbone using BsaI to reduce potential background. Both DNA fragments were purified with Ampure XP (Beckman Coulter) prior to addition to Golden Gate Assembly Master Mix (New England Biolabs) and incubated per the manufacturer's instructions. The Golden Gate reaction was further purified and concentrated to enable maximum transformation efficiency in the subsequent steps of the bacterial screen.

The plasmid library containing the distinct repeat-spacer-repeat elements and CRISPR effectors was electroporated into E. Cloni electrocompetent E. coli (Lucigen) using a Gene Pulser Xcell® (Bio-rad) following the protocol recommended by Lucigen. The library was either co-transformed with purified pACYC184 plasmid or directly transformed into pACYC184-containing E. Cloni electrocompetent E. coli (Lucigen), plated onto agar containing chloramphenicol (Fisher), tetracycline (Alfa Aesar), and kanamycin (Alfa Aesar) in BioAssay® dishes (Thermo Fisher), and incubated for 10-12 hours at 37° C. After estimation of approximate colony count to ensure sufficient library representation on the bacterial plate, the bacteria were harvested, and plasmid DNA WAS extracted using a QIAprep Spin Miniprep® Kit (Qiagen) to create an "output library." By performing a PCR using custom primers containing barcodes and sites compatible with Illumina sequencing chemistry, a barcoded next generation sequencing library was generated from both the pre-transformation "input library" and the post-harvest "output library," which were then pooled and loaded onto a Nextseq 550 (Illumina) to evaluate the effectors. At least two independent biological replicates were performed for each screen to ensure consistency. See FIG. 4B.

Bacterial Screen Sequencing Analysis

Next generation sequencing data for screen input and output libraries were demultiplexed using Illumina bcl2fastq. Reads in resulting fastq files for each sample contained the CRISPR array elements for the screening plasmid library. The direct repeat sequence of the CRISPR array was used to determine the array orientation, and the spacer sequence was mapped to the source (pACYC184 or E. Cloni) or negative control sequence (GFP) to determine the corresponding target. For each sample, the total number of reads for each unique array element ($r_a$) in a given plasmid library was counted and normalized as follows: ($r_a$+1)/total reads for all library array elements. The depletion score was calculated by dividing normalized output reads for a given array element by normalized input reads.

To identify specific parameters resulting in enzymatic activity and bacterial cell death, next generation sequencing (NGS) was used to quantify and compare the representation of individual CRISPR arrays (i.e., repeat-spacer-repeat) in the PCR product of the input and output plasmid libraries. The array depletion ratio was defined as the normalized output read count divided by the normalized input read count. An array was considered to be "strongly depleted" if the depletion ratio was less than 0.3 (more than 3-fold depletion), depicted by the dashed line in FIG. 5 and FIG. 8. When calculating the array depletion ratio across biological replicates, the maximum depletion ratio value for a given CRISPR array was taken across all experiments (i.e. a strongly depleted array must be strongly depleted in all biological replicates). A matrix including array depletion ratios and the following features were generated for each spacer target: target strand, transcript targeting, ORI targeting, target sequence motifs, flanking sequence motifs, and target secondary structure. The degree to which different features in this matrix explained target depletion for CLUST.091979 systems was investigated.

FIG. 5 and FIG. 8 show the degree of interference activity of the engineered CLUST.091979 compositions, with a non-coding sequence, by plotting for a given target the normalized ratio of sequencing reads in the screen output versus the screen input. The results are plotted for each DR transcriptional orientation. In the functional screen for the composition, an active effector complexed with an active RNA guide will interfere with the ability of the pACYC184 to confer E. coli resistance to chloramphenicol and tetracycline, resulting in cell death and depletion of the spacer element within the pool. Comparison of the results of deep sequencing the initial DNA library (screen input) versus the surviving transformed E. coli (screen output) suggests specific target sequences and DR transcriptional orientations that enable an active, programmable CRISPR system. The screen also indicates that the effector complex is only active with one orientation of the DR. As such, the screen indicated that the CLUST.091979 AUXO013988882 effector was active in the "forward" orientation (5'-ACTA . . . AACT-[spacer]-3') of the DR (FIG. 5) and that the CLUST.091979 SRR3181151 effector was active in the "reverse" orientation (5'-CCTG . . . CAAC-[spacer]-3') of the DR (FIG. 8).

FIG. 6A and FIG. 6B depict the location of strongly depleted targets for the CLUST.091979 AUXO013988882 effector (plus non-coding sequence) targeting pACYC184 and E. coli E. Cloni essential genes, respectively. Likewise, FIG. 9A and FIG. 9B show the location of strongly depleted targets for the CLUST.091979 SRR3181151 effector targeting pACYC184 and *E. coli* E. Cloni essential genes, respectively. Flanking sequences of depleted targets were analyzed to determine the PAM sequences for CLUST.091979 AUXO013988882 and CLUST.091979 SRR3181151. WebLogo representations (Crooks et al., Genome Research 14: 1188-90, 2004) of the PAM sequences for CLUST.091979 AUXO013988882 and CLUST.091979 SRR3181151 are shown in FIG. 7 and FIG. 10, respectively, wherein the "20" position corresponds to the nucleotide adjacent to the 5' end of the target.

Thus, multiple effectors of CLUST.091979 CRISPR-Cas show activity in vivo.

Example 5—Targeting of Mammalian Genes by CLUST.091979

This Example describes indel assessment on multiple targets using nucleases from CLUST.091979 introduced into mammalian cells by transient transfection.

The effectors of SEQ ID NO: 4 and SEQ ID NO: 10 were cloned into a pcda3.1 backbone (Invitrogen). The plasmids were then maxi-prepped and diluted to 1 µg/µL. For RNA guide preparation, a dsDNA fragment encoding a crRNA was derived by ultramers containing the target sequence scaffold, and the U6 promoter. Ultramers were resuspended in 10 mM Tris•HCl at a pH of 7.5 to a final stock concentration of 100 µM. Working stocks were subsequently diluted to 10 µM, again using 10 mM Tris•HCl to serve as the template for the PCR reaction. The amplification of the crRNA was done in 50 µL reactions with the following components: 0.02 µl of aforementioned template, 2.5 µl forward primer, 2.5 µl reverse primer, 25 µL NEB HiFi Polymerase, and 20 µl water. Cycling conditions were: 1×(30s at 98° C.), 30×(10s at 98° C., 15s at 67° C.), 1×(2 min at 72° C.). PCR products were cleaned up with a 1.8×SPRI treatment and normalized to 25 ng/µL. The prepared crRNA sequences and their corresponding target sequences are shown in TABLE 10. The direct repeat sequence of the mature crRNAs of SEQ ID NO: 205, SEQ ID NO: 207, SEQ ID NO: 252, SEQ ID NO: 254, SEQ ID NO: 256, SEQ ID NO: 258, SEQ ID NO: 260, SEQ ID NO: 262, SEQ ID NO: 264, SEQ ID NO: 266, SEQ ID NO: 268, SEQ ID NO: 270, SEQ ID NO: 272, SEQ ID NO: 274, and SEQ ID NO: 276 is set forth in SEQ ID NO: 60. The direct repeat of the mature crRNAs of SEQ ID NO: 209 and SEQ ID NO: 214 is set forth in SEQ ID NO: 62. The direct repeat of the mature crRNAs of SEQ ID NO: 211, SEQ ID NO: 278, SEQ ID NO: 280, SEQ ID NO: 282, SEQ ID NO: 284, SEQ ID NO: 286, and SEQ ID NO: 288 is set forth in SEQ ID NO: 213.

TABLE 10

RNA guide and Target Sequences for Transient Transfection Assay.

| Effector Sequence | mature crRNA Sequence | Target Sequence | PAM Sequence |
|---|---|---|---|
| SEQ ID NO: 4 | CCTGTTGTGAATACTCTTTTATA GGTATCAAACAACGGAAGTGGT TGGTCAGCATGGATTA (SEQ ID NO: SEQ ID NO: 205) | AAVS1: GGAAGTGGTTGGTCAGCAT GGATTA (SEQ ID NO: 206) | 5'-TTTG-3' |
| SEQ ID NO: 4 | CCTGTTGTGAATACTCTTTTATA GGTATCAAACAACTGTGAAGTG ACCTGGGAGCTAACTG (SEQ ID NO: 207) | VEGFA: TGTGAAGTGACCTGGGAGCT AACTG (SEQ ID NO: 208) | 5-TTTG-3' |
| SEQ ID NO: 4 | CCTGTTGTGAATACTCTTTTATA GGTATCAAACAACGAGAGGTG AGGGACTTGGGGGGTAA (SEQ ID NO: 252) | AAVS1: GAGAGGTGAGGGACTTGGG GGGTAA (SEQ ID NO: 253) | 5-TTTG-3' |
| SEQ ID NO: 4 | CCTGTTGTGAATACTCTTTTATA GGTATCAAACAACTGAGAATGG TGCGTCCTAGGTGTTC (SEQ ID NO: 254) | AAVS1: TGAGAATGGTGCGTCCTAGG TGTTC (SEQ ID NO: 255) | 5-TTTG-3' |
| SEQ ID NO: 4 | CCTGTTGTGAATACTCTTTTATA GGTATCAAACAACGCAGCCTGT GCTGACCCATGCAGTC (SEQ ID NO: 256) | AAVS1: GCAGCCTGTGCTGACCCATG CAGTC (SEQ ID NO: 257) | 5-TTTG-3' |
| SEQ ID NO: 4 | CCTGTTGTGAATACTCTTTTATA GGTATCAAACAACGGAAGTGGT TGGTCAGCATGGATTA (SEQ ID NO: 258) | AAVS1: GGAAGTGGTTGGTCAGCAT GGATTA (SEQ ID NO: 259) | 5-TTTG-3' |
| SEQ ID NO: 4 | CCTGTTGTGAATACTCTTTTATA GGTATCAAACAACAGCCAGTGT TGCTAGTCAAGGGCAG (SEQ ID NO: 260) | EMX1: AGCCAGTGTTGCTAGTCAAG GGCAG (SEQ ID NO: 261) | 5-TTTG-3' |
| SEQ ID NO: 4 | CCTGTTGTGAATACTCTTTTATA GGTATCAAACAACTTGACATTG TCCACACCTGGAATCG (SEQ ID NO: 262) | VEGFA: TTGACATTGTCCACACCTGG AATCG (SEQ ID NO: 263) | 5-TTTG-3' |
| SEQ ID NO: 4 | CCTGTTGTGAATACTCTTTTATA GGTATCAAACAACGAAATCTAT | VEGFA: GAAATCTATTGAGGCTCTGG | 5-TTTG-3' |

TABLE 10-continued

RNA guide and Target Sequences for Transient Transfection Assay.

| Effector Sequence | mature crRNA Sequence | Target Sequence | PAM Sequence |
|---|---|---|---|
| | TGAGGCTCTGGAGAGA (SEQ ID NO: 264) | AGAGA (SEQ ID NO: 265) | |
| SEQ ID NO: 4 | CCTGTTGTGAATACTCTTTTATA GGTATCAAACAACGGAAGCTGG ATGAGCCTGGTCCATG (SEQ ID NO: 266) | VEGFA: GGAAGCTGGATGAGCCTGG TCCATG (SEQ ID NO: 267) | 5-TTTG-3' |
| SEQ ID NO: 4 | CCTGTTGTGAATACTCTTTTATA GGTATCAAACAACCCCATACTG GGGACCAAGGAAGTGT (SEQ ID NO: 268) | VEGFA: CCCATACTGGGGACCAAGG AAGTGT (SEQ ID NO: 269) | 5-TTTG-3' |
| SEQ ID NO: 4 | CCTGTTGTGAATACTCTTTTATA GGTATCAAACAACATGATGCTT TGCCGTAACCCTTCGT (SEQ ID NO: 270) | VEGFA: ATGATGCTTTGCCGTAACCC TTCGT (SEQ ID NO: 271) | 5-TTTG-3' |
| SEQ ID NO: 4 | CCTGTTGTGAATACTCTTTTATA GGTATCAAACAACAAGAGTCAT TGCCCCACTTTACCCT (SEQ ID NO: 272) | VEGFA: AAGAGTCATTGCCCCACTTT ACCCT (SEQ ID NO: 273) | 5-TTTG-3' |
| SEQ ID NO: 4 | CCTGTTGTGAATACTCTTTTATA GGTATCAAACAACGAGAGGTG AGGGACTTGGGGGGTAA (SEQ ID NO: 274) | AAVS1: GAGAGGTGAGGGACTTGGG GGGTAA (SEQ ID NO: 275) | 5-TTTG-3' |
| SEQ ID NO: 4 | CCTGTTGTGAATACTCTTTTATA GGTATCAAACAACGTGAAGTTC TAAACTTCATATTACC (SEQ ID NO: 276) | VEGFA: GTGAAGTTCTAAACTTCATA TTACC (SEQ ID NO: 277) | 5-TTTG-3' |
| SEQ ID NO: 10 | ATTGTTGTAGACACCTTTTATA AGGATTGAACAACAACCCCCGT CTACCTGCCCACAGGG (SEQ ID NO: 209) | AAVS1: AACCCCCGTCTACCTGCCCA CAGGG (SEQ ID NO: 210) | 5-ATTG-3' |
| SEQ ID NO: 10 | CTTGTTGTATATGTCCTTTTATA GGTATTAAACAACGTAGAGGGA GAAATGGAATCCATAT (SEQ ID NO: 211) | AAVS1: GTAGAGGGAGAAATGGAAT CCATAT (SEQ ID NO: 212) | 5'-GTTA-3' |
| SEQ ID NO: 10 | ATTGTTGTAGACACCTTTTATA AGGATTGAACAACGCACCAACG GGTAGATTTGGTGGTG (SEQ ID NO: 214) | VEGFA: GCACCAACGGGTAGATTTG GTGGTG (SEQ ID NO: 215) | 5-ATTG-3' |
| SEQ ID NO: 10 | CTTGTTGTATATGTCCTTTTATA GGTATTAAACAACGTAGAGGGA GAAATGGAATCCATAT (SEQ ID NO: 278) | AAVS1: GTAGAGGGAGAAATGGAAT CCATAT (SEQ ID NO: 279) | 5'-GTTA-3' |
| SEQ ID NO: 10 | CTTGTTGTATATGTCCTTTTATA GGTATTAAACAACGAGTCGCTT TAACTGGCCCTGGCTT (SEQ ID NO: 280) | AAVS1: GAGTCGCTTTAACTGGCCCT GGCTT (SEQ ID NO: 281) | 5-ATTG-3' |
| SEQ ID NO: 10 | CTTGTTGTATATGTCCTTTTATA GGTATTAAACAACTCCACACCT GGAATCGGCTTTCAGC (SEQ ID NO: 282) | VEGFA: TCCACACCTGGAATCGGCTT TCAGC (SEQ ID NO: 283) | 5-ATTG-3' |
| SEQ ID NO: 10 | CTTGTTGTATATGTCCTTTTATA GGTATTAAACAACAACCCCCGT CTACCTGCCCACAGGG (SEQ ID NO: 284) | AAVS1: AACCCCCGTCTACCTGCCCA CAGGG (SEQ ID NO: 285) | 5-ATTG-3' |
| SEQ ID NO: 10 | CTTGTTGTATATGTCCTTTTATA GGTATTAAACAACGTAGAGGGA GAAATGGAATCCATAT (SEQ ID NO: 286) | AAVS1: GTAGAGGGAGAAATGGAAT CCATAT (SEQ ID NO: 287) | 5'-GTTA-3' |
| SEQ ID NO: 10 | CTTGTTGTATATGTCCTTTTATA GGTATTAAACAACGACCCATGG | EMX1: GACCCATGGGAGCAGCTGG | 5'-GTTA-3' |

TABLE 10-continued

RNA guide and Target Sequences for Transient Transfection Assay.

| Effector Sequence | mature crRNA Sequence | Target Sequence | PAM Sequence |
|---|---|---|---|
| | GAGCAGCTGGTCAGAG (SEQ ID NO: 288) | TCAGAG (SEQ ID NO: 289) | |

Approximately 16 hours prior to transfection, 100 µl of 25,000 HEK293T cells in DMEM/10% FBS+Pen/Strep were plated into each well of a 96-well plate. On the day of transfection, the cells were 70-90% confluent. For each well to be transfected, a mixture of 0.5 µl of Lipofectamine 2000 and 9.5 µl of Opti-MEM was prepared and then incubated at room temperature for 5-20 minutes (Solution 1). After incubation, the lipofectamine:OptiMEM mixture was added to a separate mixture containing 182 ng of effector plasmid and 14 ng of crRNA and water up to 10 µL (Solution 2). In the case of negative controls, the crRNA was not included in Solution 2. The solution 1 and solution 2 mixtures were mixed by pipetting up and down and then incubated at room temperature for 25 minutes. Following incubation, 20 µL of the Solution 1 and Solution 2 mixture were added dropwise to each well of a 96 well plate containing the cells. 72 hours post transfection, cells are trypsinized by adding 10 µL of TrypLE to the center of each well and incubated for approximately 5 minutes. 100 µL of D10 media was then added to each well and mixed to resuspend cells. The cells were then spun down at 500 g for 10 minutes, and the supernatant was discarded. QuickExtract buffer was added to ⅕ the amount of the original cell suspension volume. Cells were incubated at 65° C. for 15 minutes, 68° C. for 15 minutes, and 98° C. for 10 minutes.

Samples for Next Generation Sequencing were prepared by two rounds of PCR. The first round (PCR1) was used to amplify specific genomic regions depending on the target. PCR1 products were purified by column purification. Round 2 PCR (PCR2) was done to add Illumina adapters and indexes. Reactions were then pooled and purified by column purification. Sequencing runs were done with a 150 cycle NextSeq v2.5 mid or high output kit.

FIG. 11A, FIG. 11B, FIG. 11C, and FIG. 11D show percent indels in AAVS1, VEGFA, and EMX1 target loci in HEK293T cells following transfection with the effectors of SEQ ID NO: 4 or SEQ ID NO: 10, respectively. The bars reflect the mean percent indels measured in two bioreplicates. For the effectors of SEQ ID NO: 4 and SEQ ID NO: 10, the percent indels were higher than the percent indels of the negative control at each of the targets.

As shown in FIG. 11A, a complex formed by the effector of SEQ ID NO: 4 and the crRNA of SEQ ID NO: 205 was active at the AAVS1 target of SEQ ID NO: 206, and a complex formed by the effector of SEQ ID NO: 4 and the crRNA of SEQ ID NO: 207 was active at the VEGFA target of SEQ ID NO: 208. As shown in FIG. 11B, a complex formed by the effector of SEQ ID NO: 4 and the crRNA of SEQ ID NO: 252 was active at the AAVS1 target of SEQ ID NO: 253, a complex formed by the effector of SEQ ID NO: 4 and the crRNA of SEQ ID NO: 254 was active at the AAVS1 target of SEQ ID NO: 255, a complex formed by the effector of SEQ ID NO: 4 and the crRNA of SEQ ID NO: 256 was active at the AAVS1 target of SEQ ID NO: 257, a complex formed by the effector of SEQ ID NO: 4 and the crRNA of SEQ ID NO: 258 was active at the AAVS1 target of SEQ ID NO: 259, and a complex formed by the effector of SEQ ID NO: 4 and the crRNA of SEQ ID NO: 274 was active at the AAVS1 target of SEQ ID NO: 275. Also as shown in FIG. 11B, a complex formed by the effector of SEQ ID NO: 4 and the crRNA of SEQ ID NO: 260 was active at the EMX1 target of SEQ ID NO: 261. Also as shown in FIG. 11B, a complex formed by the effector of SEQ ID NO: 4 and the crRNA of SEQ ID NO: 262 was active at the VEGFA1 target of SEQ ID NO: 263, a complex formed by the effector of SEQ ID NO: 4 and the crRNA of SEQ ID NO: 264 was active at the VEGFA1 target of SEQ ID NO: 265, a complex formed by the effector of SEQ ID NO: 4 and the crRNA of SEQ ID NO: 266 was active at the VEGFA1 target of SEQ ID NO: 267, a complex formed by the effector of SEQ ID NO: 4 and the crRNA of SEQ ID NO: 268 was active at the VEGFA1 target of SEQ ID NO: 269, a complex formed by the effector of SEQ ID NO: 4 and the crRNA of SEQ ID NO: 270 was active at the VEGFA1 target of SEQ ID NO: 271, a complex formed by the effector of SEQ ID NO: 4 and the crRNA of SEQ ID NO: 272 was active at the VEGFA1 target of SEQ ID NO: 273, and a complex formed by the effector of SEQ ID NO: 4 and the crRNA of SEQ ID NO: 274 was active at the VEGFA1 target of SEQ ID NO: 275. The effector of SEQ ID NO: 4 utilized a 5'-TTTG-3' PAM for each of the targets in FIG. 11A and FIG. 11B.

As shown in FIG. 11C, a complex formed by the effector of SEQ ID NO: 10 and the crRNA of SEQ ID NO: 209 was active at the AAVS1 target of SEQ ID NO: 210, a complex formed by the effector of SEQ ID NO: 10 and the crRNA of SEQ ID NO: 211 was active at the AAVS1 target of SEQ ID NO: 212, and a complex formed by the effector of SEQ ID NO: 10 and the crRNA of SEQ ID NO: 214 was active at the VEGFA target of SEQ ID NO: 215. As shown in FIG. 11D, a complex formed by the effector of SEQ ID NO: 10 and the crRNA of SEQ ID NO: 278 was active at the AAVS1 target of SEQ ID NO: 279, a complex formed by the effector of SEQ ID NO: 10 and the crRNA of SEQ ID NO: 280 was active at the AAVS1 target of SEQ ID NO: 281, a complex formed by the effector of SEQ ID NO: 10 and the crRNA of SEQ ID NO: 284 was active at the AAVS1 target of SEQ ID NO: 285, and a complex formed by the effector of SEQ ID NO: 10 and the crRNA of SEQ ID NO: 286 was active at the AAVS1 target of SEQ ID NO: 287. Also as shown in FIG. 11D, a complex formed by the effector of SEQ ID NO: 10 and the crRNA of SEQ ID NO: 288 was active at the EMX1 target of SEQ ID NO: 289, and a complex formed by the effector of SEQ ID NO: 10 and the crRNA of SEQ ID NO: 282 was active at the VEGFA target of SEQ ID NO: 283. The effector of SEQ ID NO: 10 utilized a 5'-ATTG-3' PAM and a 5'-GTTA-3' PAM for the targets in FIG. 11C and FIG. 11D.

This Example suggests that nucleases in the CLUST.091979 family have activity in mammalian cells.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An engineered, non-naturally occurring Clustered Regularly Interspaced Short Palindromic Repeat (CRISPR)-associated (Cas) system comprising:
   (a) an RNA guide or a nucleic acid encoding the RNA guide, wherein the RNA guide comprises a direct repeat sequence and a spacer sequence; and
   (b) a CRISPR-Cas effector protein or a nucleic acid encoding the CRISPR-Cas effector protein, wherein the CRISPR-Cas effector protein comprises the amino acid sequence set forth in SEQ ID NO: 4,
   wherein the CRISPR-Cas effector protein binds to the RNA guide, and wherein the spacer sequence binds to a target nucleic acid.

2. The system of claim 1, wherein the direct repeat sequence comprises a nucleotide sequence with at least 95% sequence identity to the nucleotide sequence set forth in SEQ ID NO: 291.

3. The system of claim 2, wherein the direct repeat sequence comprises the nucleotide sequence set forth in SEQ ID NO: 291.

4. The system of claim 1, wherein the spacer sequence comprises between 15 and 55 nucleotides in length.

5. The system of claim 4, wherein the spacer sequence comprises between 20 and 45 nucleotides in length.

6. The system of claim 1, wherein the target nucleic acid comprises a sequence complementary to a nucleotide sequence in the spacer sequence.

7. The system of claim 1, wherein the system does not include a tracrRNA.

8. The system of claim 1, wherein the CRISPR-Cas effector protein recognizes a protospacer adjacent motif (PAM) sequence, wherein the PAM sequence comprises a nucleotide sequence set forth as 5'-NTTN-3', 5'-NTTR-3', or 5'-NNR-3', wherein "N" is any nucleotide and "R" is A or G.

9. The system of claim 1, wherein the CRISPR-Cas effector protein further comprises at least one nuclear localization signal (NLS), at least one nuclear export signal (NES), or at least one NLS and at least one NES.

10. The system of claim 1, wherein the CRISPR-Cas effector protein further comprises a peptide tag, a fluorescent protein, a base-editing domain, a DNA methylation domain, a histone residue modification domain, a localization factor, a transcription modification factor, a light-gated control factor, a chemically inducible factor, or a chromatin visualization factor.

11. The system of claim 1, wherein the nucleic acid encoding the CRISPR-Cas effector protein is codon-optimized for expression in a cell.

12. The system of claim 1, wherein the nucleic acid encoding the CRISPR-Cas effector protein is operably linked to a promoter.

13. The system of claim 1, wherein the nucleic acid encoding the CRISPR-Cas effector protein is in a vector.

14. The system of claim 13, wherein the vector is a retroviral vector, a lentiviral vector, a phage vector, an adenoviral vector, an adeno-associated vector, or a herpes simplex vector.

15. The system of claim 1, wherein the system is present in a delivery system comprising a nanoparticle, a liposome, an exosome, a microvesicle, or a gene-gun.

16. An isolated cell comprising the system of claim 1.

17. The cell of claim 16, wherein the cell is a prokaryotic cell or a eukaryotic cell.

18. The cell of claim 16, wherein the cell is a mammalian cell or a plant cell.

19. The cell of claim 18, wherein the cell is an isolated human cell.

20. A method of binding the system of claim 1 to the target nucleic acid of claim 1 comprising:
(a) providing the system of claim 1; and
(b) delivering the system to a cell,
wherein the cell comprises the target nucleic acid, wherein the CRISPR-Cas effector protein binds to the RNA guide, and wherein the spacer sequence binds to the target nucleic acid.

21. The method of claim 20, wherein the target nucleic acid is a single-stranded DNA or a double-stranded DNA.

22. The method of claim 20, wherein binding the system to the target nucleic acid results in cleavage of the target nucleic acid.

23. The method of claim 22, wherein cleavage of the target nucleic acid results in formation of an insertion or a deletion in the target nucleic acid.

* * * * *

SEQUENCE LISTING

<160> NUMBER OF SEQ ID NOS: 291

<210> SEQ ID NO 1
<211> LENGTH: 775
<212> TYPE: PRT
<213> ORGANISM: Unknown
<220> FEATURE:
<223> OTHER INFORMATION: Description of Unknown:
      gut metagenome sequence

<400> SEQUENCE: 1

Met Gly Asn Thr Thr Lys Lys Gly Asn Leu Thr Lys Thr Tyr Leu Phe
1               5                   10                  15

Lys Ala Asn Leu Ser Glu Gln Asp Phe Lys Leu Trp Arg Ser Ile Val
            20                  25                  30

Glu Glu Tyr Gln Arg Tyr Lys Glu Val Leu Ser Lys Trp Val Cys Asp
        35                  40                  45

His Leu Thr Thr Met Lys Ile Gly Asp Ile Leu Pro Tyr Ile Asp Arg
    50                  55                  60

Tyr Ser Lys Lys Ile Asp Asn Lys Thr Gly Glu Tyr Pro Glu Asn Thr
65                  70                  75                  80

Tyr Tyr Ser Leu Cys Glu Glu His Lys Asp Glu Pro Leu Tyr Lys Ile
                85                  90                  95

Phe Gln Phe Asp Ser Asn Cys Arg Asn Asn Ala Leu Tyr Glu Val Ile
            100                 105                 110

Arg Lys Ile Asn Cys Asp Leu Tyr Thr Gly Asn Ile Leu Asn Leu Gly
        115                 120                 125

Glu Thr Tyr Tyr Arg Arg Asn Gly Phe Val Lys Arg Val Leu Ala Asn
    130                 135                 140

Tyr Ala Thr Lys Ile Ser Gly Met Lys Pro Ser Val Arg Lys Arg Lys
145                 150                 155                 160

Val Thr Ser Asp Ser Thr Glu Glu Ile Arg Asn Gln Val Val Tyr
                165                 170                 175

Glu Ile Phe Asn Asn Asn Ile Lys Asn Glu Lys Asp Phe Lys Gly Val
            180                 185                 190

Leu Glu Tyr Ala Glu Ser Lys Cys Lys Thr Asn Glu Ala Tyr Val Glu
        195                 200                 205

Arg Ile Arg Leu Leu Tyr Asp Phe Tyr Ile Lys His Thr Asp Glu Ile
    210                 215                 220

Lys Glu Tyr Val Glu Tyr Ile Cys Val Glu Gln Leu Lys Glu Phe Cys
225                 230                 235                 240

Gly Val Lys Val Asn Arg Ser Lys Ser Ser Met Asn Ile Asn Ile Gln
                245                 250                 255

Asn Phe Ser Ile Thr Arg Val Asp Gly Lys Cys Thr Tyr Ile Leu His
            260                 265                 270

Leu Pro Ile Gly Lys Lys Val Tyr Asp Ile Lys Leu Trp Gly Asn Arg
        275                 280                 285

Gln Val Val Leu Asn Val Asp Gly Thr Pro Val Asp Ile Ile Asp Ile
    290                 295                 300

Ile Asn Arg His Gly Glu Ser Ile Asp Ile Phe Lys Asn Gly Asp
305                 310                 315                 320

Ile Tyr Phe Ser Phe Val Val Ser Glu Asp Phe Lys Lys Asp Asp Phe
                325                 330                 335

Glu Ile Gly Asn Val Val Gly Val Asp Val Asn Thr Lys His Met Leu
            340                 345                 350

```
Ile Gln Thr Asn Ile Val Asp Asn Gly Asn Val Asp Gly Phe Phe Asn
            355                 360                 365

Ile Tyr Lys Glu Leu Val Asn Asp Lys Glu Phe Ser Glu Cys Val Ser
    370                 375                 380

Lys Glu Asp Leu Glu Leu Phe Lys Glu Leu Ser Lys Tyr Val Ser Phe
385                 390                 395                 400

Cys Pro Ile Glu Cys Gln Phe Leu Phe Thr Arg Tyr Ala Glu Gln Lys
                405                 410                 415

Gly Ile Leu Val Tyr Glu Lys Leu Arg Leu Ala Glu Lys Ile Leu Thr
            420                 425                 430

Ser Val Leu Asp Arg Ser Phe Glu Lys Tyr Asn Gly Ile Asp Cys Asn
            435                 440                 445

Ile Ala Asn Tyr Ile Ser Asn Val Arg Met Leu Arg Ser Lys Cys Lys
    450                 455                 460

Ser Tyr Phe Thr Leu Lys Met Lys Tyr Lys Glu Leu Gln His Lys Tyr
465                 470                 475                 480

Asp Asn Glu Met Gly Tyr Val Asp Thr Phe Ser Asp Ser Cys Val Glu
                485                 490                 495

Met Asp Ser Arg Arg Lys Glu Asn Pro Phe Val Gln Thr Asn Glu Ala
            500                 505                 510

Met Glu Leu Ile Gly Lys Met Glu Ser Val Ala Gln Asp Ile Ile Gly
            515                 520                 525

Cys Arg Asp Asn Ile Ile Thr Tyr Ala Tyr Asn Val Phe Arg Arg Asn
    530                 535                 540

Gly Tyr Asp Thr Val Gly Leu Glu Asn Leu Glu Ser Ser Gln Phe Glu
545                 550                 555                 560

Arg Phe Ser Ser Val Arg Ser Pro Lys Ser Leu Leu Asn Tyr His His
                565                 570                 575

Leu Lys Gly Lys His Ile Asp Phe Ile Asp Ser Asp Glu Cys Ser Val
            580                 585                 590

Lys Val Asn Lys Asp Leu Tyr Asn Phe Thr Leu Glu Asp Asp Gly Thr
    595                 600                 605

Ile Ser Asp Ile Thr Leu Ser Asp Lys Gly Lys Tyr Arg Asn Asp Leu
610                 615                 620

Ser Met Phe Tyr Asn Gln Ile Ile Lys Thr Ile His Phe Ala Asp Ile
625                 630                 635                 640

Lys Asp Lys Phe Ile Gln Leu Gly Asn Asn Gly Asn Val Gln Thr Val
                645                 650                 655

Leu Val Pro Ser Tyr Phe Thr Ser Gln Met Asn Ser Lys Thr His Lys
            660                 665                 670

Ile Tyr Val Val Asn Val Lys Asn Glu Arg Thr Gly Lys Thr Glu Gln
            675                 680                 685

Lys Leu Ala Asn Lys Asn Met Val Arg Leu Gly Gln Glu Arg His Ile
690                 695                 700

Asn Gly Leu Asn Ala Asp Val Asn Ala Ser Met Asn Ile Ala Tyr Ile
705                 710                 715                 720

Val Glu Asn Lys Glu Met Arg Asn Ala Met Cys Thr Asn Pro Lys Ser
                725                 730                 735

Glu Thr Gly Tyr Ser Val Pro Phe Leu Thr Ser Arg Ile Lys Lys Gln
            740                 745                 750

Asn Ile Met Val Val Glu Leu Lys Lys Met Gly Met Val Glu Val Leu
            755                 760                 765

Asn Glu Lys Ser Thr Glu Ile
```

770            775

<210> SEQ ID NO 2
<211> LENGTH: 786
<212> TYPE: PRT
<213> ORGANISM: Unknown
<220> FEATURE:
<223> OTHER INFORMATION: Description of Unknown:
      bovine gut metagenome sequence

<400> SEQUENCE: 2

Met Ala Gln His Lys Ser Asn Asn Glu Glu Ser Ala Ile Asn Lys Thr
1               5                   10                  15

Phe Ile Phe Lys Ala Lys Cys Asp Lys Asn Asp Val Ile Ser Leu Trp
            20                  25                  30

Glu Pro Ala Ala Lys Glu Tyr Cys Asp Tyr Tyr Asn Lys Val Ser Lys
        35                  40                  45

Trp Ile Ala Asp Asn Leu Ile Thr Met Lys Ile Gly Asp Leu Ala Gln
    50                  55                  60

Tyr Ile Thr Asn Gln Asn Ser Lys Tyr Tyr Thr Ala Val Thr Asn Lys
65                  70                  75                  80

Lys Lys Lys Asp Leu Pro Leu Tyr Arg Ile Phe Gln Lys Gly Phe Ser
                85                  90                  95

Ser Gln Cys Ala Asp Asn Ala Leu Tyr Cys Ala Ile Lys Ser Ile Asn
            100                 105                 110

Pro Glu Asn Tyr Lys Gly Asn Ser Leu Gly Ile Gly Glu Ser Asp Tyr
        115                 120                 125

Arg Arg Phe Gly Tyr Ile Gln Ser Val Val Ser Asn Phe Arg Thr Lys
    130                 135                 140

Met Ser Ser Leu Lys Ala Thr Val Lys Trp Lys Lys Phe Asp Val Asn
145                 150                 155                 160

Asn Val Asp Asp Glu Thr Leu Lys Ile Gln Thr Ile Tyr Asp Val Asp
                165                 170                 175

Lys Tyr Gly Ile Glu Thr Ala Lys Glu Phe Lys Glu Leu Ile Glu Thr
            180                 185                 190

Leu Lys Thr Arg Val Glu Thr Pro Gln Leu Asn Asp Thr Ile Ala Arg
        195                 200                 205

Leu Glu Cys Leu Cys Asp Tyr Tyr Ser Lys Asn Glu Lys Ala Ile Asn
    210                 215                 220

Asn Glu Ile Glu Thr Met Ala Ile Ala Asp Leu Gln Lys Phe Gly Gly
225                 230                 235                 240

Cys Gln Arg Lys Ser Leu Asn Ala Phe Thr Ile His Lys Gln Asp Ser
                245                 250                 255

Leu Met Glu Lys Val Gly Asn Thr Ser Phe Arg Leu Gln Leu Pro Phe
            260                 265                 270

Arg Lys Lys Thr Tyr Val Ile Asn Leu Leu Gly Asn Arg Gln Val Val
        275                 280                 285

Asn Phe Val Asn Gly Lys Arg Val Asp Leu Ile Asp Ile Ala Glu Asn
    290                 295                 300

His Gly Asp Leu Val Thr Phe Asn Ile Lys Asn Gly Val Leu Phe Val
305                 310                 315                 320

His Leu Thr Ser Pro Ile Val Phe Asp Lys Asp Val Arg Asp Ile Arg
                325                 330                 335

Asn Val Val Gly Ile Asp Val Asn Ile Lys His Ser Met Leu Ala Thr
            340                 345                 350

```
Ser Ile Lys Asp Val Gly Asn Val Lys Gly Tyr Ile Asn Leu Tyr Lys
    355                 360                 365
Glu Leu Leu Asn Asp Asp Glu Phe Val Ser Thr Cys Asn Glu Ser Glu
    370                 375                 380
Leu Ala Leu Tyr Arg Gln Met Ser Glu Asn Val Asn Phe Gly Ile Leu
385                 390                 395                 400
Glu Thr Asp Ser Leu Phe Glu Arg Ile Val Asn Gln Ser Lys Gly Gly
                405                 410                 415
Cys Leu Lys Asn Lys Leu Ile Arg Arg Glu Leu Ala Met Gln Lys Val
            420                 425                 430
Phe Glu Arg Ile Thr Lys Thr Asn Lys Asp Gln Asn Ile Val Asp Tyr
                435                 440                 445
Val Asn Tyr Val Lys Met Met Arg Ala Lys Cys Lys Ala Ser Tyr Ile
        450                 455                 460
Leu Lys Glu Lys Tyr Asp Glu Lys Gln Lys Glu Tyr Tyr Val Lys Met
465                 470                 475                 480
Gly Phe Thr Asp Glu Ser Thr Glu Ser Lys Glu Thr Met Asp Lys Arg
                485                 490                 495
Arg Glu Glu Phe Pro Phe Val Asn Thr Asp Thr Ala Lys Glu Leu Leu
            500                 505                 510
Val Lys Gln Asn Asn Ile Arg Gln Asp Ile Ile Gly Cys Arg Asp Asn
            515                 520                 525
Ile Val Thr Tyr Ala Phe Asn Val Phe Lys Asn Asn Glu Tyr Asp Thr
        530                 535                 540
Leu Ser Val Glu Tyr Leu Asp Ser Ser Gln Phe Asp Lys Arg Arg Ile
545                 550                 555                 560
Ala Thr Pro Lys Ser Leu Leu Lys Tyr His Lys Phe Glu Gly Lys Thr
                565                 570                 575
Lys Asp Glu Val Glu Asn Met Met Lys Ser Glu Lys Leu Ser Asn Ala
            580                 585                 590
Tyr Tyr Thr Phe Lys Tyr Glu Asn Asp Val Val Ser Asp Ile Asp Tyr
            595                 600                 605
Ser Asp Glu Gly Asn Leu Arg Arg Ser Lys Leu Asn Phe Gly Asn Trp
    610                 615                 620
Ile Ile Lys Ser Ile His Phe Ala Asp Ile Lys Asp Lys Phe Val Gln
625                 630                 635                 640
Leu Ser Asn Asn Asn Lys Met Asn Ile Val Phe Cys Pro Ser Ala Phe
                645                 650                 655
Ser Ser Gln Met Asp Ser Ile Thr His Thr Leu Tyr Tyr Val Glu Lys
            660                 665                 670
Ile Thr Lys Asn Lys Lys Gly Lys Glu Lys Lys Lys Tyr Val Leu Ala
        675                 680                 685
Asn Lys Lys Met Val Arg Thr Gln Gln Glu Lys His Ile Asn Gly Leu
    690                 695                 700
Asn Ala Asp Tyr Asn Ser Ala Cys Asn Leu Lys Tyr Ile Ala Leu Asn
705                 710                 715                 720
Asp Glu Leu Arg Asp Lys Met Thr Asp Arg Phe Lys Ala Ser Lys Lys
                725                 730                 735
Ile Lys Thr Met Tyr Asn Ile Pro Ala Tyr Asn Ile Lys Ser Asn Phe
            740                 745                 750
Lys Lys Asn Leu Ser Ala Lys Thr Ile Gln Thr Phe Arg Glu Leu Gly
        755                 760                 765
His Tyr Arg Asp Gly Lys Ile Asn Glu Asp Gly Met Phe Val Glu Asn
```

Leu Glu
785

<210> SEQ ID NO 3
<211> LENGTH: 774
<212> TYPE: PRT
<213> ORGANISM: Unknown
<220> FEATURE:
<223> OTHER INFORMATION: Description of Unknown:
    gut metagenome sequence

<400> SEQUENCE: 3

Met Leu Asn Ile Lys Asn Asn Gly Glu Ser Val Asp Met Asn Thr Ile
1               5                   10                  15

Glu Leu Ala Met Lys Glu Tyr Asn Arg Tyr Tyr Asn Ile Cys Ser Asp
            20                  25                  30

Trp Ile Cys Asn Asn Leu Met Thr Pro Ile Gly Ser Leu Tyr Gln Tyr
        35                  40                  45

Ile Asp Asp Lys Cys Lys Asn Asn Ala Tyr Ala Gln Asn Leu Ile Ala
    50                  55                  60

Glu Glu Trp Lys Asp Lys Pro Leu Tyr Tyr Met Phe Tyr Lys Gly Tyr
65                  70                  75                  80

Asn Ala Asn Asn Cys Ala Asn Ala Ile Cys Cys Ala Ile Arg Ser Gln
                85                  90                  95

Val Pro Glu Val Asn Lys Ala Glu Asn Ile Leu Asn Leu Ser Tyr Thr
            100                 105                 110

Tyr Tyr Phe Arg Asn Gly Val Ile Lys Ser Val Ile Ser Asn Tyr Ala
        115                 120                 125

Ser Lys Met Arg Ile Leu Ser Asp Lys Gln Ile Lys Tyr Cys Ile Val
    130                 135                 140

Ser Glu Asn Thr Pro Asp Lys Ile Leu Ile Glu Gln Cys Ile Leu Glu
145                 150                 155                 160

Leu Lys Arg Arg His Glu Asp Leu Lys Asp Trp Glu Asn Leu Lys
                165                 170                 175

Tyr Leu Ile Leu Lys Gly Asn Glu Ser Ala Ile Thr Arg Phe Thr Ile
            180                 185                 190

Leu Lys Asp Phe Tyr Ser Lys Asn Ile Glu Arg Val Lys Glu Glu Arg
        195                 200                 205

Glu Ile Met Ala Ile Ala Glu Leu Lys Asp Phe Gly Gly Cys Arg Arg
    210                 215                 220

Lys Asp Asp Lys Leu Ser Met Cys Ile Gln Ser Ala Gly Asn Ser Lys
225                 230                 235                 240

Asp Ile Lys Val Ser Arg Val Lys Thr Thr His Asn Tyr Thr Glu Leu
                245                 250                 255

Val Asp Asp Tyr Thr Glu Asn Phe Asn Ile Lys Phe Ser Ala Leu Asp
            260                 265                 270

Phe Asn Val Met Gly Arg Arg Asp Val Val Lys Thr Lys Leu Asn Lys
        275                 280                 285

Thr Glu Asp Asp Ser Asn Thr Trp Gly Gly Thr Glu Leu Leu Val Asp
    290                 295                 300

Ile Ile Asn Asn His Gly Cys Ser Leu Thr Phe Lys Leu Val Asp Asp
305                 310                 315                 320

Lys Leu Tyr Val Asp Ile Pro Ile Asp Thr Glu His Ile Asn Lys Thr
                325                 330                 335

```
Thr Asp Phe Lys Lys Ser Val Gly Ile Asp Val Asn Leu Lys His Ser
                340                 345                 350

Leu Leu Asn Thr Asp Ile Leu Asp Asn Gly Gly Ile Asn Gly Tyr Ile
                355                 360                 365

Asn Ile Tyr Lys Lys Leu Leu Ala Asp Asp Ala Phe Met Ser Ala Cys
                370                 375                 380

Thr Lys Ala Asp Leu Val Asn Tyr Ile Asp Ile Ala Lys Thr Val Thr
385                 390                 395                 400

Phe Cys Pro Ile Glu Ala Asp Phe Ile Ile Ser Asn Val Val Glu Lys
                    405                 410                 415

Tyr Leu His Met Lys Asp Asn Thr Asn Lys Met Glu Ile Ala Phe Ser
                420                 425                 430

Ser Val Leu Met Asn Ile Arg Lys Glu Leu Glu Ile Lys Leu Leu His
                435                 440                 445

Ser Ser Lys Glu Glu Ser Pro Leu Ile Arg Lys Gln Ile Ile Tyr Ile
                450                 455                 460

Asn Cys Ile Ile Cys Leu Arg Asn Glu Leu Lys Gln Tyr Ala Ile Ala
465                 470                 475                 480

Lys His Arg Tyr Tyr Lys Lys Gln Gln Glu Tyr Asp Thr Leu Cys Asp
                    485                 490                 495

Thr Leu His Gly Val Asp Tyr Lys Gln Ile His Pro Tyr Ala Gln Ser
                500                 505                 510

Lys Glu Gly Ala Glu Gln Met Lys Lys Met Lys Thr Ile Glu Asn Asn
                515                 520                 525

Leu Ile Ala Asn Arg Asn Asn Ile Ile Glu Tyr Ala Tyr Thr Val Phe
530                 535                 540

Glu Leu Asn Asn Phe Asp Leu Ile Ala Leu Glu Asn Ile Thr Lys Asp
545                 550                 555                 560

Ile Met Glu Asp Lys Lys Lys Arg Lys Ser Phe Pro Ser Ile Asn Ser
                    565                 570                 575

Leu Leu Lys Tyr His Lys Val Ile Asn Cys Thr Glu Asp Asn Ile Asn
                580                 585                 590

Asp Asn Glu Thr Tyr Gln Lys Phe Ala Lys Tyr Asn Val Ser Tyr
                595                 600                 605

Glu Asn Gly Lys Val Thr Gly Ala Thr Leu Ser Gln Glu Gly Asn Lys
                610                 615                 620

Val Lys Leu Lys Asp Asp Phe Tyr Asp Lys Leu Lys Val Leu His
625                 630                 635                 640

Phe Thr Ser Ile Lys Asp Tyr Phe Thr Thr Leu Ser Asn Lys Arg Lys
                    645                 650                 655

Ile Ala Val Ala His Val Pro Ala Tyr Tyr Thr Ser Gln Ile Asp Ser
                660                 665                 670

Ile Asp Asn Lys Ile Cys Met Ile Lys Ser Thr Asp Lys Asn Gly Lys
                675                 680                 685

Ser Thr Tyr Lys Ile Ala Asp Lys Thr Ile Val Arg Pro Thr Gln Glu
                690                 695                 700

Lys His Ile Asn Gly Leu Asn Ala Asp Tyr Asn Ala Ala Arg Asn Ile
705                 710                 715                 720

Asn Phe Ile Val Ala Asp Glu Lys Trp Arg Lys Phe Val Arg Pro
                    725                 730                 735

Thr Asn Thr Asn Lys Pro Leu Tyr Asn Ser Pro Val Phe Ser Pro Ala
                740                 745                 750

Val Lys Ser Glu Gly Gly Thr Ile Lys Asn Leu Gln Ile Leu Ser Ala
```

```
                    755                 760                 765

Thr Lys Thr Ile Ile Leu
            770

<210> SEQ ID NO 4
<211> LENGTH: 756
<212> TYPE: PRT
<213> ORGANISM: Unknown
<220> FEATURE:
<223> OTHER INFORMATION: Description of Unknown:
      bovine gut metagenome sequence

<400> SEQUENCE: 4

Met Thr Thr Lys Gln Val Lys Ser Ile Val Leu Lys Val Lys Asn Thr
1               5                   10                  15

Asn Glu Cys Pro Ile Thr Lys Asp Val Ile Asn Glu Tyr Lys Lys Tyr
            20                  25                  30

Tyr Asn Ile Cys Ser Glu Trp Ile Lys Asp Asn Leu Thr Ser Ile Thr
        35                  40                  45

Ile Gly Asp Ile Ala Ser Phe Leu Lys Glu Ala Thr Asn Lys Asp Thr
    50                  55                  60

Ile Pro Thr Tyr Ile Asn Met Gly Leu Ser Glu Glu Trp Lys Tyr Lys
65                  70                  75                  80

Pro Ile Tyr His Leu Phe Thr Asp Asp Tyr His Glu Lys Ser Ala Asn
                85                  90                  95

Asn Leu Leu Tyr Ala Tyr Phe Lys Glu Lys Asn Leu Asp Cys Tyr Asn
            100                 105                 110

Gly Asn Ile Leu Asn Leu Ser Glu Thr Tyr Tyr Arg Arg Asn Gly Tyr
        115                 120                 125

Phe Lys Ser Val Val Gly Asn Tyr Arg Thr Lys Ile Arg Thr Leu Asn
    130                 135                 140

Tyr Lys Ile Lys Arg Lys Asn Val Asp Glu Asn Ser Thr Asn Glu Asp
145                 150                 155                 160

Ile Glu Leu Gln Val Met Tyr Glu Ile Ala Lys Arg Lys Leu Asn Ile
                165                 170                 175

Lys Lys Asp Trp Glu Asn Tyr Ile Ser Tyr Ile Glu Asn Val Glu Asn
            180                 185                 190

Ile Asn Ile Lys Asn Ile Asp Arg Tyr Asn Leu Leu Tyr Lys His Phe
        195                 200                 205

Cys Glu Asn Glu Ser Thr Ile Asn Cys Lys Met Glu Leu Leu Ser Val
    210                 215                 220

Glu Gln Leu Lys Glu Phe Gly Gly Cys Val Met Lys Gln His Ile Asn
225                 230                 235                 240

Ser Met Thr Ile Asn Ile Gln Asp Phe Lys Ile Glu Asn Lys Glu Asn
                245                 250                 255

Ser Leu Gly Phe Ile Leu Asn Leu Pro Leu Asn Lys Lys Tyr Gln
            260                 265                 270

Ile Glu Leu Trp Gly Asn Arg Gln Ile Lys Gly Asn Lys Asp Asn
        275                 280                 285

Tyr Lys Thr Leu Val Asp Phe Ile Asn Thr Tyr Gly Gln Asn Ile Ile
    290                 295                 300

Phe Thr Ile Lys Asn Asn Lys Ile Tyr Val Phe Ser Tyr Glu Cys
305                 310                 315                 320

Glu Leu Lys Glu Lys Glu Ile Asn Phe Asp Lys Ile Val Gly Ile Asp
                325                 330                 335
```

```
Val Asn Phe Lys His Ala Leu Phe Val Ala Ser Glu Arg Asp Lys Asn
            340                 345                 350

Pro Leu Gln Asp Asn Asn Gln Leu Lys Gly Tyr Ile Asn Leu Tyr Lys
        355                 360                 365

Tyr Leu Leu Glu His Asn Glu Phe Thr Ser Leu Leu Thr Lys Glu Glu
    370                 375                 380

Leu Asp Ile Tyr Lys Glu Ile Ala Lys Gly Val Thr Phe Cys Pro Leu
385                 390                 395                 400

Glu Tyr Asn Leu Leu Phe Thr Arg Ile Glu Asn Lys Gly Gly Lys Ser
                405                 410                 415

Asn Asp Lys Glu Gln Val Leu Ser Lys Leu Leu Tyr Ser Leu Gln Ile
            420                 425                 430

Lys Leu Lys Asn Glu Asn Lys Ile Gln Glu Tyr Ile Tyr Val Ser Cys
        435                 440                 445

Val Asn Lys Leu Arg Ala Lys Tyr Val Ser Tyr Phe Ile Leu Lys Glu
    450                 455                 460

Lys Tyr Tyr Glu Lys Gln Lys Glu Tyr Asp Ile Glu Met Gly Phe Thr
465                 470                 475                 480

Asp Asp Ser Thr Glu Ser Lys Glu Ser Met Asp Lys Arg Arg Leu Glu
                485                 490                 495

Phe Pro Phe Arg Asn Thr Gln Ile Ala Asn Gly Phe Leu Glu Lys Leu
            500                 505                 510

Ser Asn Val Gln Gln Asp Ile Asn Gly Cys Leu Lys Asn Ile Ile Asn
        515                 520                 525

Tyr Ala Tyr Lys Val Phe Glu Gln Asn Gly Phe Gly Val Ile Ala Leu
    530                 535                 540

Glu Asn Leu Glu Asn Ser Asn Phe Glu Lys Thr Gln Val Leu Pro Thr
545                 550                 555                 560

Ile Lys Ser Leu Leu Glu Tyr His Lys Leu Glu Asn Gln Asn Ile Asn
                565                 570                 575

Asn Ile Asn Ala Ser Asp Lys Val Lys Glu Tyr Ile Glu Lys Glu Tyr
            580                 585                 590

Tyr Glu Leu Thr Thr Asn Glu Asn Asn Glu Ile Val Asp Ala Lys Tyr
        595                 600                 605

Thr Lys Lys Gly Ile Ile Lys Val Lys Ala Asn Phe Phe Asn Leu
    610                 615                 620

Met Met Lys Ser Leu His Phe Ala Ser Asn Lys Asp Glu Phe Ile Leu
625                 630                 635                 640

Leu Ser Asn Asn Gly Lys Thr Gln Ile Ala Leu Val Pro Ser Glu Tyr
                645                 650                 655

Thr Ser Gln Met Asp Ser Ile Glu His Cys Leu Tyr Val Asp Lys Asn
            660                 665                 670

Gly Lys Lys Val Asp Lys Lys Val Arg Gln Lys Gln Glu Thr His
        675                 680                 685

Ile Asn Gly Leu Asn Ala Asp Phe Asn Ala Ala Asn Ile Lys Tyr
    690                 695                 700

Ile Ile Glu Asn Glu Asn Leu Arg Lys Leu Phe Cys Gly Lys Leu Lys
705                 710                 715                 720

Val Ser Gly Tyr Asn Thr Pro Ile Leu Asp Ala Thr Lys Lys Gly Gln
                725                 730                 735

Phe Asn Ile Leu Ala Glu Leu Lys Lys Gln Asn Lys Ile Lys Ile Phe
            740                 745                 750

Glu Ile Glu Lys
```

-continued

755

<210> SEQ ID NO 5
<211> LENGTH: 746
<212> TYPE: PRT
<213> ORGANISM: Unknown
<220> FEATURE:
<223> OTHER INFORMATION: Description of Unknown:
      bovine gut metagenome sequence

<400> SEQUENCE: 5

Met Ala Ser His Lys Lys Thr Glu Ser Asn Gln Ile Ile Lys Thr Phe
1               5                   10                  15

Pro Phe Lys Leu Lys Asn Ala Asn Gly Leu Ser Leu Asp Val Leu Asn
                20                  25                  30

Asp Ala Ile Thr Glu Tyr Gln Asn Tyr Tyr Asn Ile Cys Ser Asp Trp
            35                  40                  45

Ile Lys Asp His Leu Thr Met Lys Ile Ser Glu Leu Tyr Lys Tyr Ile
50                  55                  60

Pro Asp Glu Lys Lys Asn Ser Gly Tyr Ala Leu Thr Leu Ile Ser Asp
65                  70                  75                  80

Glu Trp Lys Asp Lys Pro Met Tyr Met Met Phe Lys Lys Gly Tyr Pro
                85                  90                  95

Ala Asn Asn Arg Asp Asn Ala Ile Tyr Glu Thr Leu Asn Thr Cys Asn
            100                 105                 110

Thr Glu His Tyr Thr Gly Asn Ile Leu Asn Phe Pro Asp Thr Tyr Tyr
        115                 120                 125

Arg Arg Phe Gly Tyr Val Ala Ser Thr Ile Ser Asn Tyr Val Thr Lys
130                 135                 140

Ile Ser Lys Met Ser Thr Gly Ser Arg Ser Lys Asn Ile Ser Asn Asp
145                 150                 155                 160

Ser Asp Val Asp Thr Ile Met Glu Gln Val Ile Tyr Glu Met Glu His
                165                 170                 175

Asn Gly Trp Thr Ser Val Lys Asp Trp Glu Asn Gln Met Glu Tyr Leu
            180                 185                 190

Glu Ser Lys Thr Asp Ser Asn Pro Asn Phe Val Tyr Arg Met Thr Thr
        195                 200                 205

Leu Tyr Glu Phe Tyr Lys Ser His Ile Asp Glu Val Asn Ser Lys Met
210                 215                 220

Glu Thr Met Ser Ile Asp Leu Leu Ile Lys Phe Gly Cys Arg Arg
225                 230                 235                 240

Lys Asp Ser Lys Lys Ser Met Tyr Ile Met Gly Gly Ser Asn Thr Pro
                245                 250                 255

Phe Asp Ile Thr Gln Ile Gly Asp Asn Ser Leu Asn Ile Lys Phe Ser
            260                 265                 270

Lys Asn Leu Asn Val Asp Val Phe Gly Arg Tyr Asp Val Ile Lys Asp
        275                 280                 285

Asn Thr Leu Leu Val Asp Ile Ile Asn Gly His Gly Ala Ser Phe Val
290                 295                 300

Leu Lys Ile Ile Asn Asp Glu Ile Tyr Ile Asp Ile Asn Val Ser Val
305                 310                 315                 320

Pro Phe Asp Lys Lys Ile Ala Thr Thr Asn Lys Val Val Gly Ile Asp
                325                 330                 335

Val Asn Ile Lys His Met Leu Leu Ala Thr Asn Ile Leu Asp Asp Gly
            340                 345                 350

Asn Val Lys Gly Tyr Val Asn Ile Tyr Lys Glu Val Ile Asn Asp Ser
            355                 360                 365

Asp Phe Lys Lys Val Cys Asn Ser Thr Val Met Lys Tyr Phe Thr Asp
370                 375                 380

Phe Ser Lys Phe Val Thr Phe Cys Pro Leu Glu Phe Asp Phe Leu Phe
385                 390                 395                 400

Ser Arg Val Cys Asn Gln Lys Gly Ile Tyr Asn Asp Asn Ser Val Met
            405                 410                 415

Glu Lys Ser Phe Ser Asp Val Leu Asn Lys Leu Lys Trp Asn Phe Ile
            420                 425                 430

Glu Thr Gly Asp Asn Thr Lys Arg Ile Tyr Ile Glu Asn Val Met Lys
            435                 440                 445

Leu Arg Thr Gln Met Lys Ala Tyr Ala Ile Val Lys Asn Ala Tyr Tyr
450                 455                 460

Lys Gln Gln Ser Glu Tyr Asp Phe Gly Lys Ser Glu Glu Phe Ile Gln
465                 470                 475                 480

Glu His Pro Phe Ser Asn Thr Asp Lys Gly Ile Glu Ile Leu His Lys
            485                 490                 495

Leu Asp Asn Ile Ser Lys Lys Ile Leu Gly Cys Arg Asn Asn Ile Ile
            500                 505                 510

Gln Tyr Ser Tyr Asn Leu Phe Glu Ile Asn Gly Tyr Asp Met Ile Ser
            515                 520                 525

Leu Glu Lys Leu Thr Ser Ser Gln Phe Lys Lys Ser Phe Pro Thr
530                 535                 540

Val Asn Ser Leu Leu Lys Tyr His Lys Ile Leu Gly Cys Thr Gln Glu
545                 550                 555                 560

Glu Met Glu Lys Lys Asp Ile Tyr Ser Val Ile Lys Lys Gly Tyr Tyr
            565                 570                 575

Asp Ile Ile Phe Asp Asn Asp Val Val Thr Asp Ala Lys Leu Ser Thr
            580                 585                 590

Lys Gly Glu Leu Ser Lys Phe Lys Asp Asp Phe Phe Asn Leu Met Ile
            595                 600                 605

Lys Ser Ile His Phe Ala Asp Ile Lys Asp Tyr Phe Ile Thr Leu Ser
610                 615                 620

Asn Asn Gly Thr Ala Gly Val Ser Leu Val Pro Ser Phe Phe Thr Ser
625                 630                 635                 640

Gln Met Asp Ser Ile Asp His Lys Ile Tyr Phe Val Gln Asp Asn Lys
            645                 650                 655

Ser Gly Lys Leu Lys Leu Ala Asn Lys His Lys Val Arg Ser Ser Gln
            660                 665                 670

Glu Lys His Ile Asn Gly Leu Asn Ala Asp Tyr Asn Ala Ala Arg Asn
            675                 680                 685

Ile Ala Tyr Ile Met Glu Asn Thr Glu Cys Arg Asn Met Phe Met Lys
690                 695                 700

Gln Ser Arg Thr Asp Lys Ser Leu Tyr Asn Lys Pro Ser Tyr Glu Thr
705                 710                 715                 720

Phe Ile Lys Thr Gln Gly Ser Ala Val Ala Lys Leu Lys Lys Glu Gly
            725                 730                 735

Phe Met Lys Ile Leu Asp Glu Ala Ser Val
            740                 745

<210> SEQ ID NO 6
<211> LENGTH: 733
<212> TYPE: PRT

<213> ORGANISM: Unknown
<220> FEATURE:
<223> OTHER INFORMATION: Description of Unknown: bovine gut metagenome sequence

<400> SEQUENCE: 6

```
Met Ala His Lys Lys Asn Ile Gly Ala Glu Ile Val Lys Thr Tyr Ser
1               5                   10                  15

Phe Lys Val Lys Asn Thr Asn Gly Ile Thr Met Glu Lys Leu Met Asn
            20                  25                  30

Ala Ile Asp Glu Tyr Gln Ser Tyr Tyr Asn Leu Cys Ser Asp Trp Ile
        35                  40                  45

Cys Lys Asn Leu Thr Thr Met Thr Ile Gly Asp Leu Asp Arg Tyr Ile
    50                  55                  60

Pro Glu Lys Ala Lys Asp Asn Ile Tyr Ala Thr Val Leu Leu Asp Glu
65                  70                  75                  80

Val Trp Lys Asn Gln Pro Leu Tyr Lys Ile Phe Gly Lys Lys Tyr Ser
                85                  90                  95

Ser Asn Asn Arg Asn Asn Ala Leu Tyr Cys Ala Leu Ser Ser Val Ile
            100                 105                 110

Asp Met Thr Lys Glu Asn Val Leu Gly Phe Ser Lys His Tyr Ile
        115                 120                 125

Arg Asn Gly Tyr Ile Leu Asn Val Ile Ser Asn Tyr Ala Ser Lys Leu
    130                 135                 140

Ser Lys Leu Asn Thr Gly Val Lys Ser Arg Ala Ile Lys Glu Thr Ser
145                 150                 155                 160

Asp Glu Ala Thr Ile Ile Glu Gln Val Ile Tyr Glu Met Glu His Asn
                165                 170                 175

Lys Trp Glu Ser Ile Glu Asp Trp Lys Asn Gln Ile Glu Tyr Leu Asn
            180                 185                 190

Ser Lys Thr Asp Tyr Asn Pro Thr Tyr Met Glu Arg Met Lys Thr Leu
        195                 200                 205

Ser Ala Tyr Tyr Ser Thr His Lys Ser Glu Val Asp Ala Lys Met Gln
    210                 215                 220

Glu Met Ala Val Glu Asn Leu Val Lys Phe Gly Gly Cys Arg Arg Asn
225                 230                 235                 240

Asn Ser Lys Lys Ser Met Phe Ile Met Gly Ser Asn Thr Thr Asn Tyr
                245                 250                 255

Thr Ile Ser Tyr Ile Gly Asp Asn Cys Phe Asn Ile Asn Phe Ala Asn
            260                 265                 270

Ile Leu Asn Phe Asp Val Tyr Gly Arg Arg Asp Val Val Lys Asn Gly
        275                 280                 285

Glu Val Leu Val Asp Ile Met Ala Asn His Gly Asp Ser Ile Val Leu
    290                 295                 300

Lys Ile Val Asn Gly Glu Leu Tyr Ala Asp Val Pro Cys Ser Val Thr
305                 310                 315                 320

Leu Asn Lys Val Glu Ser Asn Phe Asp Lys Val Val Gly Ile Asp Val
                325                 330                 335

Asn Met Lys His Met Leu Leu Ser Thr Ser Val Thr Asp Asn Gly Ser
            340                 345                 350

Ser Asp Phe Val Asn Ile Tyr Lys Glu Met Ser Asn Asn Ala Glu Phe
        355                 360                 365

Met Ala Leu Cys Pro Glu Lys Asp Arg Lys Tyr Tyr Lys Asp Ile Ser
    370                 375                 380
```

Gln Tyr Val Thr Phe Ala Pro Leu Glu Leu Asp Leu Leu Phe Ser Arg
385                 390                 395                 400

Ile Ser Lys Gln Gly Glu Val Lys Met Glu Lys Ala Tyr Ser Glu Ile
            405                 410                 415

Leu Glu Ser Leu Lys Trp Lys Phe Phe Ala Asn Gly Asp Asn Lys Asn
            420                 425                 430

Arg Ile Tyr Val Glu Ser Ile Gln Lys Ile Arg Gln Gln Ile Lys Ala
            435                 440                 445

Leu Cys Val Ile Lys Asn Ala Tyr Tyr Glu Gln Gln Ser Ala Tyr Asp
450                 455                 460

Ile Asp Lys Thr Gln Glu Tyr Ile Glu Thr His Pro Phe Ser Leu Thr
465                 470                 475                 480

Glu Lys Gly Met Ser Ile Lys Ser Lys Met Asp Lys Ile Cys Gln Thr
            485                 490                 495

Ile Ile Gly Cys Arg Asn Asn Ile Ile Asp Leu Ala Tyr Ser Phe Phe
            500                 505                 510

Glu Arg Asn Gly Tyr Ser Ile Ile Gly Leu Glu Lys Leu Thr Ser Ser
            515                 520                 525

Gln Phe Lys Asn Thr Lys Ser Met Pro Thr Cys Lys Ser Leu Leu Asn
530                 535                 540

Leu His Lys Val Leu Gly His Thr Leu Ser Glu Leu Glu Thr Leu Pro
545                 550                 555                 560

Ile Asn Asp Ile Val Lys Tyr Tyr Thr Phe Thr Thr Asp Asn Glu Gly
            565                 570                 575

Arg Ile Thr Asp Ala Ser Leu Ser Glu Lys Gly Lys Ile Arg Lys Met
            580                 585                 590

Lys Asp Arg Phe Leu Asn Gln Ala Ile Lys Ala Ile His Phe Ala Asp
            595                 600                 605

Val Lys Asp Tyr Phe Ala Thr Leu Ser Asn Asn Gly Gln Thr Gly Ile
610                 615                 620

Phe Phe Val Pro Ser Gln Phe Ser Gln Met Asp Ser Asn Thr His
625                 630                 635                 640

Asn Leu Tyr Phe Glu Val Asp Lys Asn Gly Gly Leu Lys Met Ala Ser
            645                 650                 655

Lys Asp Lys Thr Arg Pro Lys Gln Glu Tyr His Arg Asn Gly Leu Pro
            660                 665                 670

Ala Asp Tyr Asn Ala Ala Arg Asn Ile Ala Tyr Ile Gly Leu Asp Glu
            675                 680                 685

Thr Met Arg Asn Thr Phe Leu Lys Lys Val Asn Ser Asn Lys Ser Leu
690                 695                 700

Tyr Asn Gln Pro Ile Tyr Asp Thr Gly Ile Lys Lys Thr Ala Gly Val
705                 710                 715                 720

Phe Ser Arg Met Lys Lys Leu Lys Arg Tyr Glu Ile Ile
            725                 730

<210> SEQ ID NO 7
<211> LENGTH: 744
<212> TYPE: PRT
<213> ORGANISM: Unknown
<220> FEATURE:
<223> OTHER INFORMATION: Description of Unknown:
      bovine gut metagenome sequence

<400> SEQUENCE: 7

Met Ile Lys Ser Ile Lys Leu Lys Val Lys Gly Asp Cys Pro Ile Thr
1               5                   10                  15

```
Lys Asp Val Ile Asn Glu Tyr Lys Glu Tyr Tyr Asn Arg Cys Ser Asp
             20                  25                  30

Trp Ile Lys Asn Asn Leu Thr Ser Ile Thr Ile Gly Glu Ile Gly Lys
             35                  40                  45

Phe Leu Gln Asp Val Thr Gly Lys Thr Thr Gly Tyr Ile Glu Val Ala
 50                  55                  60

Leu Ser Asp Lys Trp Lys Asp Lys Pro Met Tyr Tyr Leu Phe Thr Asp
 65                  70                  75                  80

Gln Tyr Asp Thr Asn His Ala Asn Asn Leu Leu Tyr Ser Phe Ile Gln
                 85                  90                  95

Glu Asn Asn Leu Asp Gly Tyr Asp Gly Asn Ser Leu Asn Ile Ser Gly
            100                 105                 110

Thr Tyr Tyr Arg Lys Gln Gly Tyr Phe Lys Leu Val Ser Ser Asn Tyr
            115                 120                 125

Arg Thr Lys Ile Arg Thr Leu Asn Cys Lys Ile Lys Arg Lys Lys Val
130                 135                 140

Asp Val Asp Ser Thr Ser Glu Asp Ile Glu Ser Gln Val Met Tyr Glu
145                 150                 155                 160

Ile Ile Asn Arg Ser Leu Asn Lys Lys Ser Asp Trp Asp Ser Phe Ile
                165                 170                 175

Ser Tyr Ile Glu Asn Val Glu Asn Pro Asn Ile Asp Ser Ile Asn Arg
            180                 185                 190

Tyr Thr Leu Leu Arg Asp Tyr Phe Cys Asp Asn Glu Asp Val Ile Lys
            195                 200                 205

Asn Lys Ile Glu Leu Leu Ser Ile Glu Gln Leu Lys Asp Phe Gly Gly
210                 215                 220

Cys Ile Met Lys Gln His Ile Asn Thr Met Ser Leu Asn Ile Gln His
225                 230                 235                 240

Phe Lys Ile Glu Glu Lys Glu Asn Ser Leu Gly Phe Ile Leu Tyr Leu
                245                 250                 255

Pro Leu Asn Lys Lys Gln Tyr Gln Ile Glu Leu Trp Gly His Arg Gln
            260                 265                 270

Ile Lys Lys Gly Ser Lys Glu Ser Cys Glu Thr Leu Val Asp Phe Ile
            275                 280                 285

Asn Thr Tyr Gly Glu Asn Ile Val Phe Thr Ile Asn Asn Asp Glu Leu
290                 295                 300

Tyr Val Val Phe Ser Tyr Glu Ser Glu Phe Gly Lys Glu Thr Asn
305                 310                 315                 320

Phe Glu Lys Ser Val Gly Leu Asp Ile Asn Phe Lys His Ala Leu Phe
                325                 330                 335

Val Thr Ser Glu Leu Asp Asn Asp Gln Phe Asp Gly Tyr Ile Asn Leu
            340                 345                 350

Tyr Lys Tyr Ile Leu Ser His Ser Glu Phe Thr Asn Leu Leu Thr Glu
            355                 360                 365

Asp Glu Arg Lys Asp Tyr Glu Glu Leu Ser Lys Val Val Thr Phe Cys
            370                 375                 380

Pro Phe Glu Asn Gln Leu Leu Phe Ala Arg Tyr Asp Lys Met Ser Lys
385                 390                 395                 400

Phe Cys Lys Lys Glu Gln Val Leu Ser Lys Leu Leu Tyr Ser Leu Gln
                405                 410                 415

Lys Lys Leu Lys Asn Glu Asn Arg Thr Lys Glu Tyr Ile Tyr Val Ser
            420                 425                 430
```

```
Cys Val Asn Lys Leu Arg Ala Lys Tyr Ile Ser Tyr Phe Ile Leu Arg
        435                 440                 445

Glu Lys Tyr Asp Glu Lys Asn Lys Glu Tyr Asp Ile Glu Met Gly Phe
    450                 455                 460

Val Asp Asp Ser Thr Glu Ser Lys Glu Ser Met Asp Lys Arg Arg Phe
465                 470                 475                 480

Glu Asn Pro Phe Arg Asn Thr Leu Val Ala Asn Glu Leu Leu Ala Lys
                485                 490                 495

Met Ser Lys Val Gln Gln Asp Ile Asn Gly Cys Met Ser Asn Ile Ile
                500                 505                 510

Asn Tyr Val Tyr Lys Val Phe Glu Gln Asn Gly Tyr Asn Ile Ile Ala
            515                 520                 525

Leu Glu Asn Leu Glu Asn Ser Asn Phe Glu Lys Arg Gln Val Leu Pro
530                 535                 540

Thr Ile Lys Ser Leu Leu Lys Tyr His Lys Leu Glu Asn Gln Asn Ile
545                 550                 555                 560

Asn Asp Ile Lys Ala Ser Asp Lys Ile Lys Glu Tyr Ile Glu Asn Gly
                565                 570                 575

Tyr Tyr Ser Phe Thr Thr Asn Glu Asn Asn Glu Ile Val Asp Ala Lys
            580                 585                 590

Tyr Thr Ala Lys Gly Asp Ile Lys Val Lys Asn Ala Lys Phe Phe Asn
        595                 600                 605

Leu Met Met Lys Ile Leu His Phe Ala Ser Ile Lys Asp Glu Phe Val
    610                 615                 620

Leu Leu Ser Asn Asn Gly Lys Ser Gln Ile Ala Leu Val Pro Pro Glu
625                 630                 635                 640

Tyr Thr Ser Gln Met Asp Ser Ile Asp His Cys Ile Tyr Met Thr Glu
                645                 650                 655

Asn Asp Lys Gly Lys Ile Val Lys Val Asp Lys Arg Lys Val Arg Thr
            660                 665                 670

Lys Gln Glu Arg His Ile Asn Gly Leu Asn Ala Asp Phe Asn Ala Ala
        675                 680                 685

Asn Asn Ile Lys Tyr Ile Val Ser Asn Glu Lys Trp Arg Asn Val Phe
    690                 695                 700

Cys Thr Pro Lys Lys Ala Lys Tyr Asn Thr Pro Ala Leu Asp Ala Thr
705                 710                 715                 720

Lys Lys Gly Gln Phe Arg Ile Leu Asp Asp Met Lys Lys Leu Asn Ala
                725                 730                 735

Thr Lys Leu Leu Glu Ile Glu Lys
            740

<210> SEQ ID NO 8
<211> LENGTH: 754
<212> TYPE: PRT
<213> ORGANISM: Unknown
<220> FEATURE:
<223> OTHER INFORMATION: Description of Unknown:
      bovine gut metagenome sequence

<400> SEQUENCE: 8

Met Tyr Gln Leu Asn Gln Tyr Ile Met Ala Ser His Lys Lys Thr Glu
1               5                   10                  15

Ser Asn Gln Ile Ile Lys Thr Phe Ser Phe Lys Ile Lys Asn Ala Asn
            20                  25                  30

Gly Leu Ser Leu Asp Val Leu Asn Asp Ala Ile Thr Glu Tyr Gln Asn
        35                  40                  45
```

```
Tyr Tyr Asn Ile Cys Ser Asp Trp Ile Lys Asp His Leu Thr Met Lys
         50                  55                  60

Ile Ser Glu Leu Tyr Lys Tyr Ile Pro Asp Glu Lys Lys Asn Ser Gly
 65                  70                  75                  80

Tyr Ala Leu Thr Leu Ile Ser Asp Glu Trp Lys Asp Lys Pro Met Tyr
                     85                  90                  95

Met Met Phe Lys Lys Gly Tyr Pro Ala Asn Asn Arg Asp Asn Ala Ile
                100                 105                 110

Tyr Glu Thr Leu Asn Thr Cys Asn Thr Glu His Tyr Thr Gly Asn Ile
            115                 120                 125

Leu Asn Phe Ser Asp Thr Tyr Tyr Arg Arg Phe Gly Tyr Val Ala Ser
        130                 135                 140

Ala Ile Ser Asn Tyr Val Thr Lys Ile Ser Lys Met Ser Thr Gly Ser
145                 150                 155                 160

Arg Tyr Lys Asn Ile Ser Asn Asp Ser Asp Val Asp Thr Ile Met Glu
                165                 170                 175

Gln Val Ile Tyr Glu Met Glu His Asn Gly Trp Thr Ser Val Lys Asp
                180                 185                 190

Trp Glu Asn Gln Met Glu Tyr Leu Glu Ser Lys Thr Asp Ser Asn Pro
            195                 200                 205

Asn Phe Val Tyr Arg Met Thr Thr Leu Tyr Glu Phe Tyr Lys Ser His
        210                 215                 220

Ile Asp Glu Val Asn Ser Lys Met Glu Thr Met Ser Ile Asp Ser Leu
225                 230                 235                 240

Ile Lys Phe Gly Gly Cys Arg Arg Lys Asp Ser Lys Lys Ser Met Tyr
                245                 250                 255

Ile Met Gly Gly Ser Asn Thr Pro Phe Asp Ile Thr Gln Ile Gly Gly
            260                 265                 270

Asn Ser Leu Asn Ile Lys Phe Ser Lys Asn Leu Asn Val Asp Val Phe
        275                 280                 285

Gly Arg Tyr Asp Val Ile Lys Asp Asn Thr Leu Leu Val Asp Ile Ile
290                 295                 300

Asn Gly His Gly Ala Ser Phe Val Leu Lys Ile Ile Asn Asp Glu Ile
305                 310                 315                 320

Tyr Ile Asp Ile Asn Val Ser Val Pro Phe Asp Lys Lys Ile Ala Thr
                325                 330                 335

Thr Asn Lys Val Val Gly Ile Asp Val Asn Ile Lys His Met Leu Leu
            340                 345                 350

Ala Thr Asn Ile Leu Asp Asp Gly Asn Val Lys Gly Tyr Val Asn Ile
        355                 360                 365

Tyr Lys Glu Val Ile Asn Asp Ser Asp Phe Lys Lys Val Cys Asn Ser
370                 375                 380

Thr Val Met Lys Tyr Phe Thr Asp Phe Ser Lys Phe Val Thr Phe Cys
385                 390                 395                 400

Pro Leu Glu Phe Asp Phe Leu Phe Ser Arg Val Cys Asn Gln Lys Gly
                405                 410                 415

Ile Tyr Asn Asp Asn Ser Ala Met Glu Lys Ser Phe Ser Asp Val Leu
            420                 425                 430

Asn Lys Leu Lys Trp Asn Phe Ile Glu Thr Gly Asp Asn Thr Lys Arg
        435                 440                 445

Ile Tyr Ile Glu Asn Val Met Lys Leu Arg Ser Gln Met Lys Ala Tyr
450                 455                 460
```

```
Ala Ile Val Lys Asn Ala Tyr Tyr Lys Gln Gln Ser Glu Tyr Asp Phe
465                 470                 475                 480

Gly Lys Ser Glu Glu Phe Ile Gln Glu His Pro Phe Ser Asn Thr Asp
                485                 490                 495

Lys Gly Ile Glu Ile Leu His Lys Leu Asp Asn Ile Ser Lys Lys Ile
            500                 505                 510

Leu Gly Cys Arg Asn Asn Ile Ile Gln Tyr Ser Tyr Asn Leu Phe Glu
            515                 520                 525

Ile Asn Gly Tyr Asp Met Ile Ser Leu Glu Lys Leu Thr Ser Ser Gln
530                 535                 540

Phe Lys Lys Lys Pro Phe Pro Thr Val Asn Ser Leu Leu Lys Tyr His
545                 550                 555                 560

Lys Ile Leu Gly Cys Thr Gln Glu Glu Met Glu Lys Lys Asp Ile Tyr
                565                 570                 575

Ser Val Ile Lys Lys Gly Tyr Tyr Asp Ile Ile Phe Asp Asn Gly Val
            580                 585                 590

Val Ile Asp Ala Lys Leu Ser Ala Lys Gly Glu Leu Ser Lys Phe Lys
            595                 600                 605

Asp Asp Phe Phe Asn Leu Met Ile Lys Ser Ile His Phe Ala Asp Ile
610                 615                 620

Lys Asp Tyr Phe Ile Thr Leu Ser Asn Asn Gly Thr Ala Gly Val Ser
625                 630                 635                 640

Leu Val Pro Ser Tyr Phe Thr Ser Gln Met Asp Ser Ile Asp His Lys
                645                 650                 655

Ile Tyr Phe Val Gln Asp Asn Lys Ser Gly Lys Leu Lys Leu Ala Asn
            660                 665                 670

Lys His Lys Val Arg Ser Ser Gln Glu Lys His Ile Asn Gly Leu Asn
            675                 680                 685

Ala Asp Tyr Asn Ala Ala Arg Asn Ile Ala Tyr Ile Met Glu Asn Thr
690                 695                 700

Glu Cys Arg Asn Met Phe Met Lys Gln Ser Arg Thr Asp Lys Ser Leu
705                 710                 715                 720

Tyr Asn Lys Pro Ser Tyr Glu Thr Phe Ile Lys Thr Gln Gly Ser Ala
                725                 730                 735

Val Ser Lys Leu Lys Lys Asp Gly Phe Val Lys Ile Leu Asp Glu Ala
            740                 745                 750

Ser Val

<210> SEQ ID NO 9
<211> LENGTH: 746
<212> TYPE: PRT
<213> ORGANISM: Unknown
<220> FEATURE:
<223> OTHER INFORMATION: Description of Unknown:
      bovine gut metagenome sequence

<400> SEQUENCE: 9

Met Ala Ser His Lys Lys Thr Glu Ser Asn Gln Ile Ile Lys Thr Phe
1               5                   10                  15

Ser Phe Lys Ile Lys Asn Ala Asn Gly Leu Ser Leu Asp Val Leu Asn
            20                  25                  30

Asp Ala Ile Thr Glu Tyr Gln Asn Tyr Asn Ile Cys Ser Asp Trp
        35                  40                  45

Ile Lys Asp His Leu Thr Met Lys Ile Ser Glu Leu Tyr Lys Tyr Ile
50                  55                  60
```

-continued

```
Pro Asp Glu Lys Lys Asn Ser Gly Tyr Ala Leu Thr Leu Ile Ser Asp
 65                  70                  75                  80

Glu Trp Lys Asp Lys Pro Met Tyr Met Met Phe Lys Lys Gly Tyr Pro
                 85                  90                  95

Ala Asn Asn Arg Asp Asn Ala Ile Tyr Glu Thr Leu Asn Thr Cys Asn
                100                 105                 110

Thr Glu His Tyr Thr Gly Asn Ile Leu Asn Phe Ser Asp Thr Tyr Tyr
            115                 120                 125

Arg Arg Phe Gly Tyr Val Ala Ser Ala Ile Ser Asn Tyr Val Thr Lys
        130                 135                 140

Ile Ser Lys Met Ser Thr Gly Ser Arg Tyr Lys Asn Ile Ser Asn Asp
145                 150                 155                 160

Ser Asp Val Asp Thr Ile Met Glu Gln Val Ile Tyr Glu Met Glu His
                165                 170                 175

Asn Gly Trp Thr Ser Val Lys Asp Trp Glu Asn Gln Met Glu Tyr Leu
            180                 185                 190

Glu Ser Lys Thr Asp Ser Asn Pro Asn Phe Val Tyr Arg Met Thr Thr
        195                 200                 205

Leu Tyr Glu Phe Tyr Lys Ser His Ile Asp Glu Val Asn Ser Lys Met
210                 215                 220

Glu Thr Met Ser Ile Asp Ser Leu Ile Lys Phe Gly Gly Cys Arg Arg
225                 230                 235                 240

Lys Asp Ser Lys Lys Ser Met Tyr Ile Met Gly Gly Ser Asn Thr Pro
                245                 250                 255

Phe Asp Ile Thr Gln Ile Gly Gly Asn Ser Leu Asn Ile Lys Phe Ser
            260                 265                 270

Lys Asn Leu Asn Val Asp Val Phe Gly Arg Tyr Asp Val Ile Lys Asp
        275                 280                 285

Asn Thr Leu Leu Val Asp Ile Ile Asn Gly His Gly Ala Ser Phe Val
290                 295                 300

Leu Lys Ile Ile Asn Asp Glu Ile Tyr Ile Asp Ile Asn Val Ser Val
305                 310                 315                 320

Pro Phe Asp Lys Lys Ile Ala Thr Thr Asn Lys Val Val Gly Ile Asp
                325                 330                 335

Val Asn Ile Lys His Met Leu Leu Ala Thr Asn Ile Leu Asp Asp Gly
            340                 345                 350

Asn Val Lys Gly Tyr Val Asn Ile Tyr Lys Glu Val Ile Asn Asp Ser
        355                 360                 365

Asp Phe Lys Lys Val Cys Asn Ser Thr Val Met Lys Tyr Phe Thr Asp
370                 375                 380

Phe Ser Lys Phe Val Thr Phe Cys Pro Leu Glu Phe Asp Phe Leu Phe
385                 390                 395                 400

Ser Arg Val Cys Asn Gln Lys Gly Ile Tyr Asn Asp Asn Ser Ala Met
                405                 410                 415

Glu Lys Ser Phe Ser Asp Val Leu Asn Lys Leu Lys Trp Asn Phe Ile
            420                 425                 430

Glu Thr Gly Asp Asn Thr Lys Arg Ile Tyr Ile Glu Asn Val Met Lys
        435                 440                 445

Leu Arg Ser Gln Met Lys Ala Tyr Ala Ile Val Lys Asn Ala Tyr Tyr
450                 455                 460

Lys Gln Gln Ser Glu Tyr Asp Phe Gly Lys Ser Glu Glu Phe Ile Gln
465                 470                 475                 480

Glu His Pro Phe Ser Asn Thr Asp Lys Gly Ile Glu Ile Leu His Lys
```

```
            485                 490                 495
Leu Asp Asn Ile Ser Lys Lys Ile Leu Gly Cys Arg Asn Asn Ile Ile
            500                 505                 510

Gln Tyr Ser Tyr Asn Leu Phe Glu Ile Asn Gly Tyr Asp Met Ile Ser
            515                 520                 525

Leu Glu Lys Leu Thr Ser Ser Gln Phe Lys Lys Pro Phe Pro Thr
            530                 535             540

Val Asn Ser Leu Leu Lys Tyr His Lys Ile Leu Gly Cys Thr Gln Glu
545                 550                 555                 560

Glu Met Glu Lys Lys Asp Ile Tyr Ser Val Ile Lys Lys Gly Tyr Tyr
            565                 570                 575

Asp Ile Ile Phe Asp Asn Gly Val Val Ile Asp Ala Lys Leu Ser Ala
            580                 585                 590

Lys Gly Glu Leu Ser Lys Phe Lys Asp Asp Phe Phe Asn Leu Met Ile
            595                 600                 605

Lys Ser Ile His Phe Ala Asp Ile Lys Asp Tyr Phe Ile Thr Leu Ser
            610                 615                 620

Asn Asn Gly Thr Ala Gly Val Ser Leu Val Pro Ser Tyr Phe Thr Ser
625                 630                 635                 640

Gln Met Asp Ser Ile Asp His Lys Ile Tyr Phe Val Gln Asp Asn Lys
            645                 650                 655

Ser Gly Lys Leu Lys Leu Ala Asn Lys His Lys Val Arg Ser Ser Gln
            660                 665                 670

Glu Lys His Ile Asn Gly Leu Asn Ala Asp Tyr Asn Ala Ala Arg Asn
            675                 680                 685

Ile Ala Tyr Ile Met Glu Asn Thr Glu Cys Arg Asn Met Phe Met Lys
            690                 695                 700

Gln Ser Arg Thr Asp Lys Ser Leu Tyr Asn Lys Pro Ser Tyr Glu Thr
705                 710                 715                 720

Phe Ile Lys Thr Gln Gly Ser Ala Val Ser Lys Leu Lys Lys Asp Gly
            725                 730                 735

Phe Val Lys Ile Leu Asp Glu Ala Ser Val
            740                 745

<210> SEQ ID NO 10
<211> LENGTH: 745
<212> TYPE: PRT
<213> ORGANISM: Unknown
<220> FEATURE:
<223> OTHER INFORMATION: Description of Unknown:
      bovine gut metagenome sequence

<400> SEQUENCE: 10

Met Ile Lys Ser Ile Gln Leu Lys Val Lys Gly Glu Cys Pro Ile Thr
1               5                   10                  15

Lys Asp Val Ile Asn Glu Tyr Lys Glu Tyr Tyr Asn Asn Cys Ser Asp
            20                  25                  30

Trp Ile Lys Asn Asn Leu Thr Ser Ile Thr Ile Gly Glu Met Ala Lys
        35                  40                  45

Phe Leu Gln Ser Leu Ser Asp Lys Glu Val Ala Tyr Ile Ser Met Gly
    50                  55                  60

Leu Ser Asp Glu Trp Lys Asp Lys Pro Leu Tyr His Leu Phe Thr Lys
65                  70                  75                  80

Lys Tyr His Thr Lys Asn Ala Asp Asn Leu Leu Tyr Tyr Tyr Ile Lys
                85                  90                  95
```

```
Glu Lys Asn Leu Asp Gly Tyr Lys Gly Asn Thr Leu Asn Ile Ser Asn
            100                 105                 110

Thr Ser Phe Arg Gln Phe Gly Tyr Phe Lys Leu Val Val Ser Asn Tyr
            115                 120                 125

Arg Thr Lys Ile Arg Thr Leu Asn Cys Lys Ile Lys Arg Lys Lys Ile
            130                 135                 140

Asp Ala Asp Ser Thr Ser Glu Asp Ile Glu Met Gln Val Met Tyr Glu
145                 150                 155                 160

Ile Ile Lys Tyr Ser Leu Asn Lys Lys Ser Asp Trp Asp Asn Phe Ile
            165                 170                 175

Ser Tyr Ile Glu Asn Val Glu Asn Pro Asn Ile Asp Asn Ile Asn Arg
            180                 185                 190

Tyr Lys Leu Leu Arg Glu Cys Phe Cys Glu Asn Glu Asn Met Ile Lys
            195                 200                 205

Asn Lys Leu Glu Leu Leu Ser Val Glu Gln Leu Lys Lys Phe Gly Gly
            210                 215                 220

Cys Ile Met Lys Pro His Ile Asn Ser Met Thr Ile Asn Ile Gln Asp
225                 230                 235                 240

Phe Lys Ile Glu Glu Lys Glu Asn Ser Leu Gly Phe Ile Leu His Leu
            245                 250                 255

Pro Leu Asn Lys Lys Gln Tyr Gln Ile Glu Leu Leu Gly Asn Arg Gln
            260                 265                 270

Ile Lys Lys Gly Thr Lys Glu Ile His Glu Thr Leu Val Asp Ile Thr
            275                 280                 285

Asn Thr His Gly Glu Asn Ile Val Phe Thr Ile Lys Asn Asp Asn Leu
            290                 295                 300

Tyr Ile Val Phe Ser Tyr Glu Ser Glu Phe Glu Lys Glu Glu Val Asn
305                 310                 315                 320

Phe Ala Lys Thr Val Gly Leu Asp Val Asn Phe Lys His Ala Phe Phe
            325                 330                 335

Val Thr Ser Glu Lys Asp Asn Cys His Leu Asp Gly Tyr Ile Asn Leu
            340                 345                 350

Tyr Lys Tyr Leu Leu Glu His Asp Glu Phe Thr Asn Leu Leu Thr Glu
            355                 360                 365

Asp Glu Arg Lys Asp Tyr Glu Glu Leu Ser Lys Val Val Thr Phe Cys
370                 375                 380

Pro Phe Glu Asn Gln Leu Leu Phe Ala Arg Tyr Asn Lys Met Ser Lys
385                 390                 395                 400

Phe Cys Lys Lys Glu Gln Val Leu Ser Lys Leu Leu Tyr Ala Leu Gln
            405                 410                 415

Lys Lys Leu Lys Asp Glu Asn Arg Thr Lys Glu Tyr Ile Tyr Val Ser
            420                 425                 430

Cys Val Asn Lys Leu Arg Ala Lys Tyr Val Ser Tyr Phe Ile Leu Lys
            435                 440                 445

Glu Lys Tyr Tyr Glu Lys Gln Lys Glu Tyr Asp Ile Glu Met Gly Phe
            450                 455                 460

Val Asp Asp Ser Thr Glu Ser Lys Glu Ser Met Asp Lys Arg Arg Thr
465                 470                 475                 480

Glu Tyr Pro Phe Arg Asn Thr Pro Val Ala Asn Glu Leu Leu Ser Lys
            485                 490                 495

Leu Asn Asn Val Gln Gln Asp Ile Asn Gly Cys Leu Lys Asn Ile Ile
            500                 505                 510

Asn Tyr Ile Tyr Lys Ile Phe Glu Gln Asn Gly Tyr Lys Val Val Ala
```

```
                515                 520                 525
Leu Glu Asn Leu Glu Asn Ser Asn Phe Glu Lys Lys Gln Val Leu Pro
    530                 535                 540
Thr Ile Lys Ser Leu Leu Lys Tyr His Lys Leu Glu Asn Gln Asn Val
545                 550                 555                 560
Asn Asp Ile Lys Ala Ser Asp Lys Val Lys Glu Tyr Ile Glu Asn Gly
                565                 570                 575
Tyr Tyr Glu Leu Met Thr Asn Glu Asn Asn Glu Ile Val Asp Ala Lys
            580                 585                 590
Tyr Thr Glu Lys Gly Ala Met Lys Val Lys Asn Ala Asn Phe Phe Asn
                595                 600                 605
Leu Met Met Lys Ser Leu His Phe Ala Ser Val Lys Asp Glu Phe Val
            610                 615                 620
Leu Leu Ser Asn Asn Gly Lys Thr Gln Ile Ala Leu Val Pro Ser Glu
625                 630                 635                 640
Phe Thr Ser Gln Met Asp Ser Thr Asp His Cys Leu Tyr Met Lys Lys
                645                 650                 655
Asn Asp Lys Gly Lys Leu Val Lys Ala Asp Lys Lys Glu Val Arg Thr
            660                 665                 670
Lys Gln Glu Arg His Ile Asn Gly Leu Asn Ala Asp Phe Asn Ala Ala
                675                 680                 685
Asn Asn Ile Lys Tyr Ile Val Glu Asn Glu Val Trp Arg Gly Ile Phe
            690                 695                 700
Cys Thr Arg Pro Lys Lys Thr Glu Tyr Asn Val Pro Ser Leu Asp Thr
705                 710                 715                 720
Thr Lys Lys Gly Pro Ser Ala Ile Leu Asn Met Leu Lys Lys Ile Glu
                725                 730                 735
Ala Ile Lys Val Leu Glu Thr Glu Lys
            740                 745

<210> SEQ ID NO 11
<211> LENGTH: 744
<212> TYPE: PRT
<213> ORGANISM: Unknown
<220> FEATURE:
<223> OTHER INFORMATION: Description of Unknown:
      bovine gut metagenome sequence

<400> SEQUENCE: 11

Met Ile Lys Ser Ile Val Phe Lys Val Lys Gly Asp Cys Pro Ile Thr
1               5                   10                  15
Lys Asp Val Ile Lys Glu Tyr Lys Glu Tyr Tyr Asn Arg Cys Ser Glu
                20                  25                  30
Trp Ile Lys Asn Asn Leu Thr Ser Ile Thr Ile Gly Glu Ile Gly Lys
            35                  40                  45
Phe Leu Gln Asp Thr Met Gly Lys Thr His Gly Tyr Ile Lys Val Ala
        50                  55                  60
Leu Ser Asp Glu Trp Lys Asp Lys Pro Met Tyr Tyr Leu Phe Thr Glu
65                  70                  75                  80
Lys Tyr Asp Thr Lys His Ala Asn Asn Leu Leu Tyr Tyr Phe Ile Gln
                85                  90                  95
Glu Asn Asn Leu Asp Arg Tyr Glu Gly Asn Ser Leu Asn Ile Pro Ser
                100                 105                 110
Tyr Tyr Tyr Lys Arg Glu Gly Tyr Phe Lys Leu Val Thr Ser Asn Tyr
            115                 120                 125
```

```
Arg Thr Lys Ile Arg Thr Leu Asn Cys Lys Ile Lys Arg Lys Lys Ile
    130                 135                 140

Asp Val Asp Ser Thr Cys Val Asp Ile Glu Asn Gln Val Ile Tyr Glu
145                 150                 155                 160

Ile Ile Lys Lys Gly Leu Asn Lys Lys Ser Asp Trp Asp Asn Tyr Ile
                165                 170                 175

Ser Tyr Ile Glu Asn Ile Glu Met Pro Asn Ile Asp Ser Ile Asn Arg
                180                 185                 190

Tyr Lys Leu Leu Arg Asp Tyr Phe Cys Glu Asn Glu Asn Val Ile Lys
                195                 200                 205

Asn Lys Ile Glu Leu Leu Ser Ile Glu Gln Leu Lys Asn Phe Gly Gly
    210                 215                 220

Cys Ile Met Lys Gln His Ile Asn Thr Met Ile Leu Asn Ile Lys Arg
225                 230                 235                 240

Leu Lys Ile Glu Glu Lys Glu Asn Ser Leu Gly Phe Ile Leu His Leu
                245                 250                 255

Pro Leu Asn Lys Lys Gln Tyr Gln Ile Glu Leu Trp Gly Asn Arg Gln
                260                 265                 270

Ile Lys Lys Gly Thr Lys Glu Ser Asn Glu Thr Leu Val Asp Phe Ile
                275                 280                 285

Asn Thr Tyr Gly Glu Asp Val Val Phe Thr Ile Lys Lys Asn Glu Leu
    290                 295                 300

Tyr Ala Lys Phe Ser Tyr Glu Cys Glu Phe Glu Lys Glu Glu Thr Asn
305                 310                 315                 320

Phe Glu Lys Ser Val Gly Leu Asp Ile Asn Phe Lys His Ala Leu Phe
                325                 330                 335

Val Thr Ser Glu Leu Asp Asp Gln Phe Tyr Gly Tyr Ile Asn Leu
                340                 345                 350

Tyr Lys Tyr Ile Leu Ser His Ser Glu Phe Thr Asn Leu Leu Thr Glu
                355                 360                 365

Asp Glu Lys Lys Asp Tyr Glu Asp Leu Ser Asn Ala Ile Thr Phe Cys
    370                 375                 380

Pro Phe Glu Asn Gln Leu Leu Phe Thr Arg Tyr Asp Lys Lys Ser Lys
385                 390                 395                 400

Leu Tyr Lys Lys Glu Gln Val Leu Ser Lys Ile Leu Tyr Ser Leu Gln
                405                 410                 415

Lys Lys Leu Lys Asp Glu Asn Arg Lys Gln Glu Tyr Ile Tyr Val Ser
                420                 425                 430

Cys Val Asn Lys Leu Arg Ala Lys Tyr Val Ser Tyr Phe Ile Leu Lys
    435                 440                 445

Glu Lys Tyr Asn Glu Lys Gln Lys Glu Tyr Asp Ile Glu Met Gly Phe
450                 455                 460

Val Asp Asp Ser Thr Glu Ser Lys Glu Ser Met Asp Lys Arg Arg Tyr
465                 470                 475                 480

Glu Tyr Pro Phe Arg Asn Thr Pro Val Ala Asn Glu Leu Leu Glu Lys
                485                 490                 495

Met Asn Asn Val Gln Gln Asp Ile Ser Gly Cys Leu Lys Asn Ile Ile
                500                 505                 510

Asn Tyr Ala Tyr Lys Val Phe Glu Gln Asn Gly Tyr Asn Ile Val Ala
                515                 520                 525

Leu Glu Asn Leu Glu Asn Ser Asn Phe Glu Lys Arg Asn Val Leu Pro
    530                 535                 540

Thr Ile Lys Ser Leu Leu Lys Tyr His Lys Leu Glu Asn Gln Asn Ile
```

```
                545                 550                 555                 560
        Thr Asp Ile Lys Ala Ser Asp Lys Ile Lys Glu Tyr Ile Glu Asn Gly
                        565                 570                 575

Tyr Tyr Glu Leu Ile Thr Asn Glu Asn Asn Glu Ile Ile Asp Ala Lys
                        580                 585                 590

Tyr Thr Glu Asn Gly Asp Ile Lys Val Lys Asn Ala Arg Phe Phe Asn
                        595                 600                 605

Leu Met Met Lys Ser Leu His Phe Ala Ser Ile Lys Asp Glu Phe Val
                        610                 615                 620

Leu Leu Ser Asn Asn Gly Lys Ser Gln Ile Ala Leu Val Pro Ser Glu
        625                 630                 635                 640

Tyr Thr Ser Gln Met Asp Ser Thr Asp His Cys Ile Tyr Met Thr Glu
                        645                 650                 655

Asn Asp Lys Gly Lys Leu Val Lys Val Asp Lys Arg Lys Val Arg Thr
                        660                 665                 670

Lys Gln Glu Arg His Ile Asn Gly Leu Asn Ala Asp Phe Asn Ala Ala
                        675                 680                 685

Asn Asn Ile Lys Tyr Ile Val Glu Asn Glu Lys Trp Arg Lys Val Phe
                        690                 695                 700

Cys Ala Pro Gln Lys Ala Lys Tyr Asn Thr Pro Thr Leu Asp Ala Thr
        705                 710                 715                 720

Lys Lys Gly Gln Phe Arg Ile Leu Glu Asp Leu Lys Lys Leu Lys Ala
                        725                 730                 735

Thr Lys Leu Leu Glu Ile Gly Lys
                        740

<210> SEQ ID NO 12
<211> LENGTH: 745
<212> TYPE: PRT
<213> ORGANISM: Unknown
<220> FEATURE:
<223> OTHER INFORMATION: Description of Unknown:
      bovine gut metagenome sequence

<400> SEQUENCE: 12

Met Ile Lys Ser Ile Gln Leu Lys Val Lys Gly Glu Cys Pro Ile Thr
        1               5                   10                  15

Lys Asp Val Ile Asn Glu Tyr Lys Glu Tyr Tyr Asn Asn Cys Ser Asp
                        20                  25                  30

Trp Ile Lys Asn Asn Leu Thr Ser Ile Thr Ile Gly Glu Met Ala Lys
                        35                  40                  45

Phe Leu Gln Ser Leu Ser Asp Lys Glu Val Ala Tyr Ile Ser Met Gly
                        50                  55                  60

Leu Ser Asp Glu Trp Lys Asp Lys Pro Leu Tyr His Leu Phe Thr Lys
        65                  70                  75                  80

Lys Tyr His Thr Lys Asn Ala Asp Asn Leu Leu Tyr Tyr Ile Lys
                        85                  90                  95

Glu Lys Asn Leu Asp Gly Tyr Lys Gly Asn Thr Leu Asn Ile Ser Asn
                        100                 105                 110

Thr Ser Phe Arg Gln Phe Gly Tyr Phe Lys Leu Val Val Ser Asn Tyr
                        115                 120                 125

Arg Thr Lys Ile Arg Thr Leu Asn Cys Lys Ile Lys Arg Lys Lys Ile
                        130                 135                 140

Asp Ala Asp Ser Thr Ser Glu Asp Ile Glu Met Gln Val Met Tyr Glu
        145                 150                 155                 160
```

-continued

Ile Ile Lys Tyr Ser Leu Asn Lys Lys Ser Asp Trp Asp Asn Phe Ile
        165                 170                 175

Ser Tyr Ile Glu Asn Val Glu Asn Pro Asn Ile Asp Asn Ile Asn Arg
        180                 185                 190

Tyr Lys Leu Leu Arg Glu Cys Phe Cys Glu Asn Glu Asn Met Ile Lys
        195                 200                 205

Asn Lys Leu Glu Leu Leu Ser Val Glu Gln Leu Lys Lys Phe Gly Gly
        210                 215                 220

Cys Ile Met Lys Pro His Ile Asn Ser Met Thr Ile Asn Ile Gln Asp
225                 230                 235                 240

Phe Lys Ile Glu Glu Lys Glu Asn Ser Leu Gly Phe Ile Leu His Leu
                245                 250                 255

Pro Leu Asn Lys Lys Gln Tyr Gln Ile Glu Leu Leu Gly Asn Arg Gln
                260                 265                 270

Ile Lys Lys Gly Thr Lys Glu Ser His Glu Thr Leu Val Asp Ile Thr
            275                 280                 285

Asn Thr His Gly Glu Asn Ile Val Phe Thr Ile Lys Asn Asp Asn Leu
        290                 295                 300

Tyr Ile Val Phe Ser Tyr Glu Ser Glu Phe Glu Lys Glu Val Asn
305                 310                 315                 320

Phe Ala Lys Thr Val Gly Leu Asp Val Asn Phe Lys His Ala Phe Phe
                325                 330                 335

Val Thr Ser Glu Lys Asp Asn Cys His Leu Asp Gly Tyr Ile Asn Leu
                340                 345                 350

Tyr Lys Tyr Leu Leu Glu His Asp Glu Phe Thr Asn Leu Leu Thr Glu
            355                 360                 365

Asp Glu Arg Lys Asp Tyr Glu Glu Leu Ser Lys Val Val Thr Phe Cys
        370                 375                 380

Pro Phe Glu Asn Gln Leu Leu Phe Ala Arg Tyr Asn Lys Met Ser Lys
385                 390                 395                 400

Phe Cys Lys Lys Glu Gln Val Leu Ser Lys Leu Leu Tyr Ala Leu Gln
                405                 410                 415

Lys Lys Leu Lys Asp Glu Asn Arg Thr Lys Glu Tyr Ile Tyr Val Ser
            420                 425                 430

Cys Val Asn Lys Leu Arg Ala Lys Tyr Val Ser Tyr Phe Ile Leu Lys
        435                 440                 445

Glu Lys Tyr Tyr Glu Lys Gln Lys Glu Tyr Asp Ile Glu Met Gly Phe
    450                 455                 460

Val Asp Asp Ser Thr Glu Ser Lys Glu Ser Met Asp Lys Arg Arg Thr
465                 470                 475                 480

Glu Tyr Pro Phe Arg Asn Thr Pro Val Ala Asn Glu Leu Leu Ser Lys
                485                 490                 495

Leu Asn Asn Val Gln Gln Asp Ile Asn Gly Cys Leu Lys Asn Ile Ile
            500                 505                 510

Asn Tyr Ile Tyr Lys Ile Phe Glu Gln Asn Gly Tyr Lys Val Val Ala
        515                 520                 525

Leu Glu Asn Leu Glu Asn Ser Asn Phe Glu Lys Lys Gln Val Leu Pro
        530                 535                 540

Thr Ile Lys Ser Leu Leu Lys Tyr His Lys Leu Glu Asn Gln Asn Val
545                 550                 555                 560

Asn Asp Ile Lys Ala Ser Asp Lys Val Lys Glu Tyr Ile Glu Asn Gly
                565                 570                 575

Tyr Tyr Glu Leu Met Thr Asn Glu Asn Asn Glu Ile Val Asp Ala Lys

```
                        580                 585                 590
Tyr Thr Glu Lys Gly Ala Met Lys Val Lys Asn Ala Asn Phe Phe Asn
                    595                 600                 605

Leu Met Met Lys Ser Leu His Phe Ala Ser Val Lys Asp Glu Phe Val
                610                 615                 620

Leu Leu Ser Asn Asn Gly Lys Thr Gln Ile Ala Leu Val Pro Ser Glu
625                 630                 635                 640

Phe Thr Ser Gln Met Asp Ser Thr Asp His Cys Leu Tyr Met Lys Lys
                    645                 650                 655

Asn Asp Lys Gly Lys Leu Val Lys Ala Asp Lys Lys Glu Val Arg Thr
                660                 665                 670

Lys Gln Glu Arg His Ile Asn Gly Leu Asn Ala Asp Phe Asn Ala Ala
                675                 680                 685

Asn Asn Ile Lys Tyr Ile Val Glu Asn Glu Val Trp Arg Gly Ile Phe
                690                 695                 700

Cys Thr Arg Pro Lys Lys Thr Glu Tyr Asn Val Pro Ser Leu Asp Thr
705                 710                 715                 720

Thr Lys Lys Gly Pro Ser Ala Ile Leu Asn Met Leu Lys Lys Ile Glu
                    725                 730                 735

Ala Val Lys Ile Leu Glu Thr Glu Lys
                740                 745

<210> SEQ ID NO 13
<211> LENGTH: 712
<212> TYPE: PRT
<213> ORGANISM: Unknown
<220> FEATURE:
<223> OTHER INFORMATION: Description of Unknown:
      bovine gut metagenome sequence

<400> SEQUENCE: 13

Met Lys Asn Asn Leu Thr Thr Val Thr Ile Gly Glu Met Ala Lys Phe
1               5                   10                  15

Leu Gln Glu Thr Thr Gly Lys Asn Val Thr Tyr Ile Thr Met Gly Leu
                20                  25                  30

Ser Glu Glu Trp Lys Asp Lys Pro Leu Tyr His Leu Phe Tyr Gly Lys
            35                  40                  45

Tyr His Thr Lys Asn Ala Asp Asn Leu Leu Tyr Tyr Phe Ile Lys Ala
        50                  55                  60

Lys Lys Leu Asp Glu Tyr Asp Gly Asn Met Leu Asn Leu Gly Asp Thr
65                  70                  75                  80

Tyr Tyr Arg Gln Phe Gly Tyr Phe Lys Leu Val Val Ser Asn Tyr Arg
                85                  90                  95

Thr Lys Ile Arg Thr Leu Asn Leu Asn Val Lys Arg Lys Arg Val Asp
                100                 105                 110

Val Asp Ser Thr Ser Glu Asp Ile Glu Ser Gln Val Met Tyr Glu Ile
            115                 120                 125

Val Lys Arg Asn Leu Asn Thr Ile Ser Asp Trp Glu Asn Tyr Ile Ser
        130                 135                 140

Tyr Ile Glu Asp Val Glu Thr Pro Asn Ile Asp Asn Ile Asn Arg Tyr
145                 150                 155                 160

Lys Phe Leu Gln Asn Tyr Phe Cys Glu Asn Glu Asp Ile Lys Asn
                165                 170                 175

Lys Ile Glu Phe Leu Ser Ile Glu Gln Leu Lys Asp Phe Gly Gly Cys
                180                 185                 190
```

```
Ile Met Lys Pro His Ile Asn Ser Met Thr Ile Asn Ile Gln Asp Phe
            195                 200                 205

Lys Ile Glu Glu Ile Glu Asn Ser Leu Gly Phe Val Leu Gln Leu Pro
    210                 215                 220

Leu Asn Lys Lys Tyr His Gln Ile Glu Leu Tyr Gly Asn Arg Gln Val
225                 230                 235                 240

Lys Lys Gly Thr Lys Glu Asn Tyr Lys Thr Leu Val Asp Ile Ile Asn
                245                 250                 255

Thr His Gly Glu Asn Ile Val Phe Thr Ile Glu Asn Asn Glu Leu Tyr
            260                 265                 270

Val Val Phe Ser Tyr Glu Tyr Glu Leu Lys Lys Lys Asp Ile Asn Phe
        275                 280                 285

Glu Lys Met Ala Gly Ile Asp Val Asn Phe Lys His Ala Leu Phe Val
    290                 295                 300

Thr Ser Glu Thr Asp Asn Asn Gln Leu Asn His Tyr Ile Asn Leu Tyr
305                 310                 315                 320

Lys His Ile Leu Glu His Asn Glu Phe Thr Thr Leu Leu Thr Asp Ser
                325                 330                 335

Glu Arg Lys Asp Tyr Glu Glu Ile Ala Lys Thr Val Thr Phe Cys Pro
            340                 345                 350

Phe Glu Tyr Gln Leu Leu Phe Thr Arg Phe Asp Lys Asn Ser Asn Ala
        355                 360                 365

Asn Val Lys Glu Gln Ala Leu Ser Lys Ile Leu Tyr Asp Leu Gln Lys
    370                 375                 380

Lys Leu Lys Ser Gln Asn Lys Ile Lys Glu Tyr Ile Tyr Val Ser Cys
385                 390                 395                 400

Val Asn Lys Leu Arg Ala Lys Tyr Val Ser Tyr Phe Ile Leu Lys Glu
                405                 410                 415

Lys Tyr Tyr Glu Lys Gln Lys Glu Tyr Asp Ile Gln Met Gly Phe Val
            420                 425                 430

Asp Asp Ser Thr Glu Ser Lys Ser Ser Met Val Lys Arg Arg Val Glu
        435                 440                 445

Tyr Pro Phe Arg Asn Thr Pro Val Ala Asn Ala Leu Leu Ala Ile Val
    450                 455                 460

Asn Asn Val Gln Gln Asp Ile Asn Gly Cys Leu Lys Asn Ile Ile Asn
465                 470                 475                 480

Tyr Ala Tyr Lys Val Phe Glu Leu Asn Asp Tyr Asn Val Val Ala Leu
                485                 490                 495

Glu Asn Leu Glu Asn Ala Asn Phe Glu Lys Lys Gln Val Ile Pro Thr
            500                 505                 510

Ile Lys Ser Leu Leu Lys Tyr His Lys Leu Glu Met Gln Asn Ile Asn
        515                 520                 525

Asp Ile Lys Ala Asn Asp Thr Ile Lys Lys Tyr Ile Glu Asn Glu Tyr
    530                 535                 540

Tyr Gln Leu Ile Thr Asn Glu Asn Asn Glu Ile Val Asn Ala Ile Tyr
545                 550                 555                 560

Thr Pro Lys Gly Ile Thr Lys Leu Lys Tyr Ala Asn Phe Phe Asn Leu
                565                 570                 575

Leu Met Lys Ser Leu His Phe Ala Ser Ile Lys Asp Glu Phe Ile Leu
            580                 585                 590

Leu Ser Asn Asn Gly Asn Thr Asn Ile Ala Leu Val Pro His Glu Tyr
        595                 600                 605

Thr Ser Gln Met Asp Ser Ile Asp His Cys Ile Tyr Met Val Gln Asn
```

```
                    610               615               620
Asp Lys Gly Asn Leu Val Lys Ala His Lys Thr Lys Val Arg Thr Lys
625                 630               635               640

Gln Glu Lys His Ile Asn Gly Leu Asn Ala Asp Phe Asn Ala Ala Asn
                645               650               655

Asn Ile Lys Tyr Ile Val Glu Asn Glu Lys Trp Arg Asn Ile Phe Cys
            660               665               670

Lys Ile Pro Lys Lys Ile Glu Tyr Asn Thr Pro Val Leu Asp Val Thr
        675               680               685

Lys Lys Gly Gln Ser Asn Ile Ile Lys Thr Leu Lys Asn Leu Asn Ala
    690               695               700

Thr Lys Ile Leu Glu Ile Lys Lys
705                 710
```

<210> SEQ ID NO 14
<211> LENGTH: 741
<212> TYPE: PRT
<213> ORGANISM: Unknown
<220> FEATURE:
<223> OTHER INFORMATION: Description of Unknown:
      terrestrial metagenome sequence

<400> SEQUENCE: 14

```
Met Lys Lys Ser Ile Lys Phe Lys Val Lys Gly Asn Cys Pro Ile Thr
1               5                   10                  15

Lys Asp Val Ile Asn Glu Tyr Lys Glu Tyr Tyr Asn Lys Cys Ser Asp
            20                  25                  30

Trp Ile Lys Asn Asn Leu Thr Ser Ile Thr Ile Gly Glu Met Ala Lys
        35                  40                  45

Phe Leu Gln Glu Thr Leu Gly Lys Asp Val Ala Tyr Ile Ser Met Gly
50                  55                  60

Leu Ser Asp Glu Trp Lys Asp Lys Pro Leu Tyr His Leu Phe Thr Lys
65                  70                  75                  80

Lys Tyr His Thr Asn Asn Ala Asp Asn Leu Leu Tyr Tyr Tyr Ile Lys
                85                  90                  95

Glu Lys Asn Leu Asp Gly Tyr Lys Gly Asn Thr Leu Asn Ile Gly Asn
            100                 105                 110

Thr Phe Phe Arg Gln Phe Gly Tyr Phe Lys Leu Val Val Ser Asn Tyr
        115                 120                 125

Arg Thr Lys Ile Arg Thr Leu Asn Cys Glu Ile Lys Arg Lys Lys Ile
130                 135                 140

Asp Ala Asp Ser Thr Ser Glu Asp Ile Glu Met Gln Thr Met Tyr Glu
145                 150                 155                 160

Ile Ile Lys His Asn Leu Asn Lys Lys Thr Asp Trp Asp Glu Phe Ile
                165                 170                 175

Ser Tyr Ile Glu Asn Val Glu Asn Pro Asn Ile Asp Asn Ile Asn Arg
            180                 185                 190

Tyr Lys Leu Leu Arg Lys Cys Phe Cys Glu Asn Glu Asn Met Ile Lys
        195                 200                 205

Asn Lys Leu Glu Leu Leu Ser Ile Glu Gln Leu Lys Asn Phe Gly Gly
210                 215                 220

Cys Ile Met Lys Gln His Ile Asn Ser Met Thr Leu Ile Ile Gln His
225                 230                 235                 240

Phe Lys Ile Glu Glu Lys Glu Asn Ser Leu Gly Phe Ile Leu Asn Leu
                245                 250                 255
```

```
Pro Leu Asn Lys Lys Gln Tyr Gln Ile Glu Leu Trp Gly Asn Arg Gln
            260                 265                 270

Val Asn Lys Gly Thr Lys Glu Arg Asp Ala Phe Leu Asn Thr Tyr Gly
        275                 280                 285

Glu Asn Ile Val Phe Ile Ile Asn Asn Asp Glu Leu Tyr Val Val Phe
    290                 295                 300

Ser Tyr Glu Tyr Glu Leu Glu Lys Glu Glu Ala Asn Phe Val Lys Thr
305                 310                 315                 320

Val Gly Leu Asp Val Asn Phe Lys His Ala Phe Phe Val Thr Ser Glu
                325                 330                 335

Lys Asp Asn Cys His Leu Asp Gly Tyr Ile Asn Leu Tyr Lys Tyr Leu
            340                 345                 350

Leu Glu His Asp Glu Phe Thr Asn Leu Leu Thr Asn Asp Glu Lys Lys
        355                 360                 365

Asp Tyr Glu Glu Leu Ser Lys Val Val Thr Phe Cys Pro Phe Glu Asn
    370                 375                 380

Gln Leu Leu Phe Ala Arg Tyr Asn Lys Met Ser Lys Phe Cys Lys Lys
385                 390                 395                 400

Glu Gln Val Leu Ser Lys Leu Leu Tyr Ala Leu Gln Lys Gln Leu Lys
                405                 410                 415

Asp Glu Asn Arg Thr Lys Glu Tyr Ile Tyr Val Ser Cys Val Asn Lys
            420                 425                 430

Leu Arg Ala Lys Tyr Val Ser Tyr Phe Ile Leu Lys Glu Lys Tyr Tyr
        435                 440                 445

Glu Lys Gln Lys Glu Tyr Asp Ile Glu Met Gly Phe Val Asp Asp Ser
    450                 455                 460

Thr Glu Ser Lys Glu Ser Met Asp Lys Arg Arg Thr Glu Phe Pro Phe
465                 470                 475                 480

Arg Asn Thr Pro Val Ala Asn Glu Leu Leu Ser Lys Leu Asn Asn Val
                485                 490                 495

Gln Gln Asp Ile Asn Gly Cys Leu Lys Asn Ile Ile Asn Tyr Ile Tyr
            500                 505                 510

Lys Ile Phe Glu Gln Asn Gly Tyr Lys Ile Val Ala Leu Glu Asn Leu
        515                 520                 525

Glu Asn Ser Asn Phe Glu Lys Lys Gln Val Leu Pro Thr Ile Lys Ser
    530                 535                 540

Leu Leu Lys Tyr His Lys Leu Glu Asn Gln Asn Val Asn Asp Ile Lys
545                 550                 555                 560

Ala Ser Asp Lys Val Lys Glu Tyr Ile Glu Asn Gly Tyr Tyr Glu Leu
                565                 570                 575

Ile Thr Asn Glu Asn Asn Glu Ile Val Asp Ala Lys Tyr Thr Glu Lys
            580                 585                 590

Gly Ala Met Lys Val Lys Asn Ala Asn Phe Phe Asn Leu Met Met Lys
        595                 600                 605

Ser Leu His Phe Ala Ser Val Lys Asp Glu Phe Val Leu Leu Ser Asn
    610                 615                 620

Asn Gly Lys Thr Gln Ile Ala Leu Val Pro Ser Glu Phe Thr Ser Gln
625                 630                 635                 640

Met Asp Ser Thr Asp His Cys Leu Tyr Met Lys Lys Asn Asp Lys Gly
                645                 650                 655

Lys Leu Val Lys Ala Asp Lys Glu Val Arg Thr Lys Gln Glu Lys
            660                 665                 670

His Ile Asn Gly Leu Asn Ala Asp Phe Asn Ala Ala Asn Asn Ile Lys
```

```
              675                 680                 685
Tyr Ile Val Glu Asn Glu Val Trp Arg Glu Ile Phe Cys Thr Arg Pro
    690                 695                 700

Lys Lys Ala Glu Tyr Asn Val Pro Ser Leu Asp Thr Thr Lys Lys Gly
705                 710                 715                 720

Pro Ser Ala Ile Leu His Met Leu Lys Lys Ile Glu Ala Ile Lys Ile
                725                 730                 735

Leu Glu Thr Glu Lys
            740

<210> SEQ ID NO 15
<211> LENGTH: 752
<212> TYPE: PRT
<213> ORGANISM: Unknown
<220> FEATURE:
<223> OTHER INFORMATION: Description of Unknown:
      feces metagenome sequence

<400> SEQUENCE: 15

Met Ala Lys Ser Ile Met Lys Ser Ile Lys Phe Lys Val Lys Gly
1               5                   10                  15

Asn Ser Pro Ile Asn Glu Asp Ile Ile Asn Glu Tyr Lys Gly Tyr Tyr
                20                  25                  30

Asn Thr Cys Ser Asn Trp Ile Asn Asn Leu Thr Ser Ile Thr Ile
            35                  40                  45

Gly Glu Met Gly Lys Phe Leu Lys Asp Val Met Arg Lys Thr Thr Gly
    50                  55                  60

Tyr Ile Asp Val Ala Leu Ser Asp Glu Trp Lys Asp Lys Pro Met Tyr
65                  70                  75                  80

Tyr Leu Phe Thr Lys Lys Tyr Asn Pro Lys His Ala Asn Asn Leu Leu
                85                  90                  95

Tyr Tyr Phe Ile Lys Glu Lys Lys Leu Asp Lys Phe Asn Gly Asn Ile
            100                 105                 110

Leu Asn Val Pro Glu Tyr Tyr Arg Lys Glu Gly Tyr Phe Lys Leu
    115                 120                 125

Val Ala Gly Asn Tyr Arg Thr Lys Ile Asn Thr Leu Asn Phe Lys Ile
    130                 135                 140

Lys Ser Lys Lys Val Asp Ala Asn Ser Leu Ser Glu Asp Ile Glu Met
145                 150                 155                 160

Gln Thr Ile Tyr Glu Ile Val Lys Arg Gly Leu Asn Lys Lys Ser Asp
                165                 170                 175

Trp Asp Ser Tyr Ile Ser Tyr Ile Glu Cys Val Gln Asn Pro Asn Ile
            180                 185                 190

Asp Asn Ile Asn Arg Tyr Lys Leu Leu Arg Asp Tyr Phe Cys Glu Asn
        195                 200                 205

Glu Asp Val Ile Lys Asn Lys Ile Glu Ile Leu Ser Ile Glu Gln Ile
    210                 215                 220

Lys Glu Phe Gly Gly Cys Ile Met Lys Pro His Ile Asn Ser Met Thr
225                 230                 235                 240

Phe Gly Ile Gln Lys Phe Lys Ile Glu Glu Ile Glu Asn Ser Leu Gly
                245                 250                 255

Phe Thr Phe Asn Leu Pro Leu Asn Lys Asn Asn Tyr Lys Ile Glu Leu
            260                 265                 270

Trp Gly His Arg Gln Leu Lys Lys Gly Asn Lys Glu Ser Asn Val Asn
        275                 280                 285
```

```
Val Ser Leu Asp Asp Phe Ile Asn Thr Tyr Gly Gln Asn Val Val Phe
    290                 295                 300

Thr Ile Lys Arg Lys Lys Leu Tyr Ile Val Phe Ser Tyr Asp Tyr Glu
305                 310                 315                 320

Phe Glu Arg Gly Glu Cys Asn Phe Glu Lys Ser Val Gly Leu Asp Val
                325                 330                 335

Asn Phe Lys His Ser Leu Phe Val Thr Ser Glu Ile Asp Asn Asn Gln
            340                 345                 350

Phe Asp Gly Tyr Ile Asn Leu Tyr Lys Tyr Ile Leu Ser Asn Asn Glu
        355                 360                 365

Phe Thr Ser Leu Leu Thr Asp Ser Glu Arg Lys Asp Tyr Glu Asp Leu
370                 375                 380

Ala Asn Ile Val Thr Phe Cys Pro Phe Glu Tyr Gln Leu Leu Phe Ser
385                 390                 395                 400

Arg Tyr Asp Lys Leu Ser Lys Ile Ser Glu Lys Glu Lys Val Leu Ser
                405                 410                 415

Lys Ile Leu Tyr Ser Leu Gln Lys Lys Leu Lys Asn Glu Lys Arg Thr
            420                 425                 430

Lys Glu Tyr Ile Tyr Val Ser Cys Val Asn Lys Leu Arg Ala Lys Tyr
        435                 440                 445

Val Ser Tyr Phe Lys Leu Lys Gln Lys Tyr Asn Glu Lys Gln Lys Glu
450                 455                 460

Tyr Asp Ile Glu Met Gly Phe Val Asp Asp Ser Thr Glu Ser Lys Glu
465                 470                 475                 480

Ser Met Asp Lys Arg Arg Phe Glu Asn Pro Phe Ile Asn Thr Pro Val
                485                 490                 495

Ala Lys Glu Leu Leu Glu Lys Met Asn Asn Val Lys Gln Asp Ile Asn
            500                 505                 510

Gly Cys Lys Lys Asn Ile Val Val Tyr Ala Tyr Lys Val Leu Glu Gln
        515                 520                 525

Asn Gly Tyr Asn Ile Ile Ala Leu Glu Asn Leu Glu Asn Ser Asn Phe
530                 535                 540

Glu Lys Ile Arg Val Leu Pro Lys Ile Lys Ser Leu Leu Glu Tyr His
545                 550                 555                 560

Lys Phe Glu Asn Lys Asn Ile Asn Asp Ile Lys Asn Ser Asp Lys Tyr
                565                 570                 575

Lys Glu Phe Ile Glu Pro Gly Tyr Phe Glu Leu Ile Thr Asn Glu Asn
            580                 585                 590

Asn Glu Ile Ile Asp Ala Lys Tyr Thr Gln Lys Gly Asp Ile Lys Ile
        595                 600                 605

Lys Asn Ala Asp Phe Ile Asn Ile Met Ile Lys Ala Leu Asn Phe Ala
610                 615                 620

Ser Ile Lys Asp Glu Phe Ile Leu Leu Ser His Asn Gly Lys Ser Gln
625                 630                 635                 640

Ile Ala Leu Val Pro Ala Glu Tyr Thr Ser Gln Met Asp Ser Ile Asp
                645                 650                 655

His Cys Ile Tyr Met Thr Lys Asn Asp Lys Gly Lys Leu Val Lys Val
            660                 665                 670

Asp Lys Arg Lys Val Arg Thr Lys Gln Glu Arg His Ile Asn Gly Leu
        675                 680                 685

Asn Ala Asp Phe Asn Ala Ala Cys Asn Ile Lys Tyr Ile Val Thr Asn
690                 695                 700

Glu Asp Trp Arg Lys Val Phe Cys Ile Lys Pro Lys Lys Glu Asp Tyr
```

```
                          705                 710                 715                 720
              Asn Thr Pro Leu Leu Asp Ala Thr Lys Asn Gly Gln Phe Arg Ile Leu
                              725                 730                 735
              Asp Lys Leu Lys Lys Leu Asn Ala Thr Lys Leu Leu Glu Met Glu Lys
                              740                 745                 750

<210> SEQ ID NO 16
<211> LENGTH: 766
<212> TYPE: PRT
<213> ORGANISM: Unknown
<220> FEATURE:
<223> OTHER INFORMATION: Description of Unknown:
      feces metagenome sequence

<400> SEQUENCE: 16

Met Ala Asn Lys Lys Phe Lys Leu Thr Lys Asn Glu Val Val Lys Ser
1               5                   10                  15

Phe Val Leu Lys Val Ala Asn Gln Lys Lys Cys Ala Ile Thr Asn Glu
                20                  25                  30

Thr Leu Gln Glu Tyr Lys Asn Tyr Asn Lys Val Ser Gln Trp Ile
                35                  40                  45

Asn Asn Asn Leu Thr Lys Met Thr Ile Gly Asp Leu Ile Gln Tyr Ala
            50                  55                  60

Pro Thr Val Ser Lys Lys Gly Lys Lys Gln Pro Asp Gly Thr Met Val
65                  70                  75                  80

Tyr Asp Thr Pro Leu Tyr Val Thr Tyr Ala Met Ser Asp Glu Trp Lys
                85                  90                  95

Asn Lys Pro Leu Tyr Tyr Ile Phe Lys Lys Glu Tyr Asn Thr Asn Asn
                100                 105                 110

Ala Asn Asn Leu Leu Tyr Glu Ala Ile Arg Asn Leu Asn Val Asp Glu
            115                 120                 125

Tyr Asp Gly Asn Gln Leu Asn Phe Asn Ser Thr Tyr Tyr Arg Thr Gln
            130                 135                 140

Gly Tyr Val Asn Arg Val Phe Ser Asn Tyr Arg Thr Lys Ile Asn Thr
145                 150                 155                 160

Leu Asp Ile Lys Ile Lys Lys Ser Lys Val Asp Glu Asn Ser Asp Val
                165                 170                 175

Glu Thr Leu Glu Leu Gln Thr Met Tyr Glu Ile Asn Lys Leu Asn Leu
                180                 185                 190

Lys Thr Asn Lys Asp Trp Glu Glu Arg Leu Gln Tyr Leu Thr Met Gln
            195                 200                 205

Glu Asn Pro Asn Gln Asn Thr Ile Asp Arg Thr Lys Ile Leu Phe Asn
            210                 215                 220

Tyr Phe Ile Asn Asn Asp Thr Ile Phe Gln Lys Met Glu Glu Leu
225                 230                 235                 240

Ser Ile Lys Gln Leu Thr Glu Phe Gly Gly Cys Lys Met Lys Asp Asn
                245                 250                 255

Thr Thr Ser Met Thr Ile Asn Ile Gln Asp Phe Lys Ile Lys Arg Lys
            260                 265                 270

Glu Asn Ser Ile Gly Tyr Ile Met Thr Ile Pro Phe Asn Lys Lys Asn
            275                 280                 285

Val Asp Val Glu Leu Tyr Gly His Lys Gln Thr Ile Lys Gly His Lys
            290                 295                 300

Asn Ser Tyr Thr Glu Ile Val Asp Ile Val Asn Lys His Gly Asn Thr
305                 310                 315                 320
```

-continued

```
Ile Thr Phe Lys Ile Lys Asn Asn Gln Leu Phe Ala Ile Ile Thr Ser
                325                 330                 335
Asp Thr Glu Val Thr Lys Pro Glu Pro Gln Tyr Glu Lys Ile Val Gly
            340                 345                 350
Val Asp Val Asn Ile Lys His Thr Leu Met Val Thr Ser Glu Lys Asp
            355                 360                 365
Asn Gly Lys Leu Lys Gly Tyr Ile Asn Leu Tyr Lys Glu Val Leu Lys
        370                 375                 380
Asn Asp Glu Phe Lys Lys Leu Leu Asn Lys Thr Glu Leu Asp Asn Phe
385                 390                 395                 400
Lys Ser Leu Ser Gln Ile Val Thr Phe Cys Pro Ile Glu Tyr Asp Phe
                405                 410                 415
Leu Phe Ser Arg Ile Phe Asp Asp Glu Asn Thr Lys Lys Glu Leu Ala
            420                 425                 430
Phe Ser Asn Val Leu Tyr Asp Ile Gln Lys Gln Leu Lys Asn Thr Asn
            435                 440                 445
Asn Ile Leu Gln Tyr Asn Tyr Ile Ala Cys Val Asn Lys Leu Arg Ala
        450                 455                 460
Lys Tyr Lys Ala Tyr Phe Val Leu Lys Met Ser Tyr Met Lys Gln Gln
465                 470                 475                 480
Lys Ile Tyr Asp Thr Asn Met Gly Phe Phe Asp Ile Ser Thr Glu Ser
                485                 490                 495
Lys Glu Thr Met Asp Gln Arg Arg Ser Leu Tyr Pro Phe Ile Asn Thr
            500                 505                 510
Glu Ile Ala Gln Asn Ile Ile Thr Lys Met Asn Asn Val Gln Gln Asp
            515                 520                 525
Ile Asn Gly Cys Leu Lys Asn Ile Phe Lys Tyr Thr Tyr Thr Val Phe
        530                 535                 540
Glu Asn Asn Asn Tyr Asp Thr Ile Val Leu Glu Asn Leu Glu Asn Ala
545                 550                 555                 560
Asn Phe Glu Lys His Asn Pro Leu Pro Asn Ile Thr Ser Leu Leu Lys
                565                 570                 575
Tyr His Lys Val Gln Gly Leu Thr Ile Gln Glu Ala Glu Gln His Glu
            580                 585                 590
Lys Val Gly Asn Leu Ile Gln Asn Asp Asn Tyr Ile Phe Gln Leu Asn
        595                 600                 605
Glu Asp Asn Lys Ile Ile Asn Ala Asp Tyr Ser Gln Lys Ala Tyr Tyr
610                 615                 620
Lys Val Cys Lys Ala Leu Phe Phe Asn Gln Ala Ile Lys Thr Leu His
625                 630                 635                 640
Phe Ala Ser Val Lys Asp Glu Met Ile Lys Leu Ser Asn Asn Asn Lys
                645                 650                 655
Val Cys Val Ala Ile Ile Pro Pro Glu Tyr Thr Ser Gln Ile Asp Ser
                660                 665                 670
Asn Thr His Lys Leu Tyr Phe Ile Asn Lys Asp Gly Lys Leu Leu Lys
            675                 680                 685
Ala Asp Lys Lys Thr Val Arg Lys Thr Gln Glu Lys His Ile Asn Gly
        690                 695                 700
Leu Asn Ala Asp Phe Asn Ala Ala Ser Asn Ile Lys Tyr Ile Val Gln
705                 710                 715                 720
Asn Glu Thr Trp Arg Asn Leu Phe Thr Asn Lys Thr Asn Asn Thr Tyr
                725                 730                 735
Gly Leu Pro Ile Leu Thr Pro Ser Lys Lys Gly Gln Ser Asn Ile Ile
```

```
                        740                 745                 750
Thr Gln Leu Met Lys Ile Asn Ala Thr Gln Glu Leu Val Val
            755                 760                 765

<210> SEQ ID NO 17
<211> LENGTH: 784
<212> TYPE: PRT
<213> ORGANISM: Unknown
<220> FEATURE:
<223> OTHER INFORMATION: Description of Unknown:
      sheep gut metagenome sequence

<400> SEQUENCE: 17

Met Tyr Asn Ser Lys Lys Gly Glu Gly Asp Ile Gln Lys Ser Phe
1               5                   10                  15

Lys Phe Lys Val Lys Thr Asp Lys Glu Thr Val Glu Leu Phe Arg Lys
                20                  25                  30

Ala Ala Val Glu Tyr Ser Glu Tyr Tyr Lys Arg Leu Thr Thr Phe Leu
            35                  40                  45

Cys Glu Arg Leu Thr Asp Met Thr Trp Gly Glu Val Ala Ser Phe Ile
        50                  55                  60

Pro Glu Lys Tyr Arg Lys Asn Glu Tyr Tyr Lys Tyr Leu Ile Lys Glu
65                  70                  75                  80

Glu Asn Lys Asp Leu Pro Leu Tyr Lys Met Phe Thr Lys Ala Ala Ser
                85                  90                  95

Ser Met Phe Ile Asp His Ser Ile Glu Arg Tyr Val Glu Ala Leu Asn
            100                 105                 110

Pro Glu Gly Asn Thr Gly Asn Ile Leu Gly Phe Cys Lys Ser Ser Tyr
        115                 120                 125

Val Arg Gly Gly Tyr Leu Lys Asn Val Val Ser Asn Ile Arg Thr Lys
130                 135                 140

Phe Ala Thr Leu Lys Thr Gly Ile Lys Tyr Lys Lys Phe Asn Pro Ala
145                 150                 155                 160

Glu Asp Asp Glu Glu Thr Ile Leu Gly Gln Thr Val Phe Glu Met Glu
                165                 170                 175

Lys Arg Gly Leu Glu Phe Lys Cys Asp Phe Glu Lys Thr Ile Lys Tyr
            180                 185                 190

Leu Asn Glu Lys Gly Lys Thr Gln Glu Ala Glu Arg Leu Gln Cys Leu
        195                 200                 205

Met Glu Tyr Phe Ser Thr Asn Thr Asp Lys Ile Asn Glu Tyr Arg Glu
210                 215                 220

Ser Leu Val Leu Asp Asp Ile Arg Lys Phe Gly Gly Cys Asn Arg Ser
225                 230                 235                 240

Lys Ser Asn Ser Phe Ser Val Thr Leu Glu Lys Ala Asp Ile Lys Glu
                245                 250                 255

Asp Gly Leu Thr Gly Tyr Thr Met Lys Val Ser Lys Lys Leu Lys Glu
            260                 265                 270

Ile His Leu Leu Gly His Arg Val Val Glu Val Asn Gly Arg
        275                 280                 285

Arg Val Asn Leu Val Asp Ile Cys Gly Asp Lys Ser Gly Asp Ser Lys
290                 295                 300

Val Phe Val Val Asp Gly Asp Asn Leu Tyr Val Cys Ile Ser Ala Pro
305                 310                 315                 320

Val Lys Phe Ser Lys Asn Gly Met Glu Ala Lys Lys Tyr Ile Gly Val
                325                 330                 335
```

-continued

Asp Met Asn Met Lys His Ser Ile Ile Ser Val Ser Asp Asn Ala Ser
                340                 345                 350

Asp Met Lys Gly Phe Leu Asn Ile Tyr Lys Glu Leu Leu Lys Asp Glu
            355                 360                 365

Gly Phe Arg Lys Thr Leu Asn Ala Thr Glu Leu Glu Lys Tyr Glu Lys
        370                 375                 380

Leu Ala Glu Gly Val Asn Ile Gly Ile Ile Glu Tyr Asp Gly Leu Tyr
385                 390                 395                 400

Glu Arg Ile Val Lys Gln Lys Lys Glu Asn Ser Val Asp Gly Leu Lys
                405                 410                 415

Val Gln Ala Glu Lys Lys Leu Ile Glu Arg Glu Ala Ala Ile Glu Arg
            420                 425                 430

Val Leu Asp Lys Leu Arg Lys Gly Thr Ser Asp Thr Asp Thr Glu Asn
        435                 440                 445

Tyr Ile Asn Tyr Asn Lys Ile Leu Arg Ala Lys Ile Lys Ser Ala Tyr
    450                 455                 460

Ile Leu Lys Asp Lys Tyr Tyr Glu Met Leu Gly Lys Tyr Asp Ser Glu
465                 470                 475                 480

Arg Ala Gly Ser Gly Asp Leu Ser Glu Glu Asn Lys Ile Lys Tyr Lys
                485                 490                 495

Asp Glu Phe Asn Glu Thr Glu Lys Gly Lys Glu Ile Leu Gly Lys Leu
            500                 505                 510

Asn Asn Val Tyr Lys Asp Ile Ile Gly Cys Arg Asp Asn Ile Val Thr
        515                 520                 525

Tyr Ala Val Asn Leu Phe Ile Arg Asn Gly Tyr Asp Thr Val Ala Leu
    530                 535                 540

Glu Tyr Leu Glu Ser Ser Gln Met Lys Ala Arg Arg Ile Pro Ser Thr
545                 550                 555                 560

Gly Gly Leu Leu Lys Gly His Lys Leu Glu Gly Lys Pro Glu Gly Glu
                565                 570                 575

Val Thr Ala Tyr Leu Lys Ala Asn Lys Ile Pro Lys Ser Tyr Tyr Ser
            580                 585                 590

Phe Glu Tyr Asp Gly Asn Gly Met Leu Thr Asp Val Lys Tyr Ser Asp
        595                 600                 605

Met Gly Glu Lys Ala Arg Gly Arg Asn Arg Phe Lys Asn Leu Val Pro
    610                 615                 620

Lys Phe Leu Arg Trp Ala Ser Ile Lys Asp Lys Phe Val Gln Leu Ser
625                 630                 635                 640

Asn Tyr Lys Asp Ile Gln Met Val Tyr Val Pro Ser Pro Tyr Thr Ser
                645                 650                 655

Gln Thr Asp Ser Arg Thr His Ser Leu Tyr Tyr Ile Glu Thr Val Lys
            660                 665                 670

Val Asp Glu Lys Thr Gly Lys Glu Lys Lys Glu His Ile Val Ala Pro
        675                 680                 685

Lys Glu Ser Val Arg Thr Glu Gln Glu Ser Phe Val Asn Gly Met Asn
    690                 695                 700

Ala Asp Thr Asn Ser Ala Asn Asn Ile Lys Tyr Ile Phe Glu Asn Glu
705                 710                 715                 720

Thr Leu Arg Asp Lys Phe Leu Lys Arg Thr Lys Asp Gly Thr Glu Met
                725                 730                 735

Tyr Asn Arg Pro Ala Phe Asp Leu Lys Glu Cys Tyr Lys Lys Asn Ser
            740                 745                 750

Asn Val Ser Val Phe Asn Thr Leu Lys Lys Thr Leu Gly Ala Ile Tyr

```
                    755                 760                 765
Gly Lys Leu Asp Glu Asn Gly Asn Phe Ile Glu Asn Glu Cys Asn Lys
    770                 775                 780

<210> SEQ ID NO 18
<211> LENGTH: 782
<212> TYPE: PRT
<213> ORGANISM: Unknown
<220> FEATURE:
<223> OTHER INFORMATION: Description of Unknown:
      gut metagenome sequence

<400> SEQUENCE: 18

Met Ala Gly His Ser Lys Ile Lys Glu Asn His Ile Met Lys Ala Phe
1               5                   10                  15

Leu Met Lys Val Lys Glu Thr Arg Lys Lys Gln Trp Gln Ser Asn Phe
            20                  25                  30

Ile Arg Ser Glu Ile Ala Lys Phe Thr Asn Tyr Tyr Asn Gly Leu Ser
        35                  40                  45

Lys Phe Ile Ala Asp Arg Leu Leu Asp Asp Met Val Thr Thr Leu Ala
    50                  55                  60

Pro Leu Ile Glu Glu Lys Lys Arg Asn Ser Glu Tyr Tyr Lys Tyr Leu
65                  70                  75                  80

Thr Asn Gly Asp Trp Asp Gly Lys Pro Leu Tyr Phe Ile Phe Lys Glu
                85                  90                  95

Gly Phe Asn Ser Thr Asn Ala Asp Asn Ile Leu Ala Asn Ser Leu Val
            100                 105                 110

Arg Val Tyr Cys Glu Gln Asn Tyr Thr Gly Asn Gly Phe Gly Leu Ser
        115                 120                 125

Tyr Ser Tyr Tyr Val Val Ile Gly Phe Ala Lys Glu Val Ile Ala Asn
    130                 135                 140

Tyr Arg Ser Ser Phe Gln Lys Pro Lys Val Lys Ile Lys Lys Lys Lys
145                 150                 155                 160

Leu Ser Glu Asn Pro Thr Glu Asp Glu Leu Ile Glu Gln Cys Ile Tyr
                165                 170                 175

Thr Ile Tyr Tyr Glu Phe Asn Glu Lys Lys Asp Ile Gln Lys Trp Lys
            180                 185                 190

Asp Glu Ile Lys Phe Leu Lys Glu Arg Gly Glu Ser Lys Glu Thr Arg
        195                 200                 205

Leu Lys Arg Ile Gln Thr Leu Phe Glu Phe Tyr Lys Asp Lys Ser His
    210                 215                 220

Lys Glu Leu Val Asp Glu Arg Val Ala Asn Leu Val Val Asp Asn Ile
225                 230                 235                 240

Lys Glu Phe Gly Gly Cys Lys Arg Asp Ile Asp Cys Pro Ser Met Gly
                245                 250                 255

Ile Gln Ile Gln His Asn Phe Asp Ile Ser Ile Asn Glu Lys Arg Asn
            260                 265                 270

Gly Tyr Thr Ile Cys Phe Gly Pro Asn Lys Asn Leu Thr Lys Leu
        275                 280                 285

Glu Val Phe Gly Asn Arg Met Val Leu Leu Asn Gly Glu Glu Ile Val
    290                 295                 300

Asp Leu Pro Asn Thr His Gly Glu Lys Leu Thr Leu Ile Asp Arg Gly
305                 310                 315                 320

Asn Ala Ile Tyr Ala Ala Ile Thr Ala Gln Val Pro Phe Glu Lys His
                325                 330                 335
```

```
Met Pro Asp Gly Asn Lys Thr Val Gly Ile Asp Leu Asn Leu Lys His
                340                 345                 350

Ser Val Phe Ala Thr Ser Ile Val Asp Asn Gly Lys Leu Ala Gly Tyr
            355                 360                 365

Ile Ser Ile Tyr Lys Glu Leu Leu Lys Asp Asp Glu Phe Val Lys Tyr
        370                 375                 380

Cys Pro Lys Asp Leu Leu Arg Phe Met Lys Asp Ala Ser Lys Tyr Val
385                 390                 395                 400

Phe Phe Ala Pro Ile Glu Ile Glu Leu Leu Arg Ser Arg Val Ile Tyr
                405                 410                 415

Asn Lys Gly Tyr Ala Cys Val Glu Asn Tyr Glu Asn Val Tyr Lys Ala
            420                 425                 430

Glu Val Ala Phe Val Asn Val Ile Lys Arg Leu Gln Ser Gln Cys Glu
        435                 440                 445

Ala Asn Gly Asp Ala Gln Gly Ala Leu Tyr Met Ser Tyr Leu Ser Lys
    450                 455                 460

Met Arg Ala Gln Leu Lys Asn Tyr Ile Asn Leu Lys Leu Ala Tyr Tyr
465                 470                 475                 480

Asp His Gln Ser Ala Tyr Asp Leu Lys Met Gly Phe Thr Asp Ile Ser
                485                 490                 495

Thr Glu Ser Lys Glu Thr Met Asp Glu Arg Arg Lys Leu Phe Pro Phe
            500                 505                 510

Asn Lys Glu Lys Glu Ala Gln Glu Ile Leu Ala Lys Met Lys Asn Ile
        515                 520                 525

Ser Asn Val Ile Ile Ala Cys Arg Asn Asn Ile Ala Val Tyr Met Tyr
    530                 535                 540

Lys Met Phe Glu Arg Asn Gly Tyr Asp Phe Ile Gly Leu Glu Lys Leu
545                 550                 555                 560

Glu Ser Ser Gln Met Lys Lys Arg Gln Ser Arg Ser Phe Pro Thr Val
                565                 570                 575

Lys Ser Leu Leu Asn Tyr His Lys Leu Ala Gly Met Thr Met Asp Glu
            580                 585                 590

Ile Lys Lys Gln Glu Val Ser Ser Asn Ile Lys Lys Gly Phe Tyr Asp
        595                 600                 605

Leu Glu Phe Asp Ala Asp Gly Lys Leu Tyr Gly Ala Lys Tyr Ser Asn
    610                 615                 620

Lys Gly Asn Val His Phe Ile Glu Asp Glu Phe Tyr Ile Ser Gly Leu
625                 630                 635                 640

Lys Ala Ile His Phe Ala Asp Met Lys Asp Tyr Phe Val Arg Leu Ser
                645                 650                 655

Asn Asn Gly Lys Val Ser Val Ala Leu Val Pro Pro Ser Phe Thr Ser
            660                 665                 670

Gln Met Asp Ser Val Glu His Lys Phe Phe Met Lys Lys Asn Ala Asn
        675                 680                 685

Gly Lys Leu Ile Val Ala Asp Lys Lys Asp Val Arg Ser Cys Gln Glu
    690                 695                 700

Lys His Lys Ile Asn Gly Leu Asn Ala Asp Tyr Asn Ala Ala Cys Asn
705                 710                 715                 720

Ile Gly Phe Ile Val Glu Asp Asp Tyr Met Arg Glu Ser Leu Leu Gly
                725                 730                 735

Ser Pro Thr Gly Gly Thr Tyr Asp Thr Ala Tyr Phe Asp Thr Lys Ile
            740                 745                 750

Gln Gly Ser Lys Gly Val Tyr Asp Lys Ile Lys Glu Asn Gly Glu Thr
```

```
                755                 760                 765
Tyr Ile Ala Val Leu Ser Asp Asp Val Ile Thr Ala Glu Val
    770                 775                 780

<210> SEQ ID NO 19
<211> LENGTH: 735
<212> TYPE: PRT
<213> ORGANISM: Unknown
<220> FEATURE:
<223> OTHER INFORMATION: Description of Unknown:
      human gut metagenome sequence

<400> SEQUENCE: 19

Met Ala His Lys Lys Asn Val Gly Ala Glu Ile Val Lys Thr Tyr Ser
1               5                   10                  15

Phe Lys Val Lys Asn Thr Asn Gly Ile Thr Met Glu Lys Leu Met Asn
            20                  25                  30

Ala Ile Asp Glu Phe Gln Ser Tyr Tyr Asn Leu Cys Ser Asp Trp Ile
        35                  40                  45

Cys Lys Asn Leu Thr Thr Met Thr Ile Gly Asp Leu Asp Gln Tyr Ile
    50                  55                  60

Pro Glu Lys Ala Lys Gly Asn Thr Tyr Ala Thr Val Leu Leu Asp Glu
65                  70                  75                  80

Ala Trp Lys Asn Gln Pro Leu Tyr Lys Ile Phe Gly Lys Lys Tyr Ser
                85                  90                  95

Ser Asn Asn Arg Asn Asn Ala Leu Tyr Cys Ala Leu Ser Ser Val Ile
            100                 105                 110

Asp Met Thr Lys Glu Asn Val Leu Gly Phe Ser Lys Thr His Tyr Ile
        115                 120                 125

Arg Asn Asp Tyr Ile Leu Asn Val Ile Ser Asn Tyr Ala Ser Lys Leu
    130                 135                 140

Ser Lys Leu Asn Thr Gly Val Lys Ser Arg Ala Ile Lys Glu Thr Ser
145                 150                 155                 160

Asp Glu Ala Thr Ile Ile Glu Gln Val Ile Tyr Glu Met Glu His Asn
                165                 170                 175

Lys Trp Glu Ser Ile Glu Asp Trp Lys Asn Gln Ile Glu Tyr Leu Asn
            180                 185                 190

Ser Lys Thr Asp Tyr Asn Pro Thr Tyr Met Glu Arg Met Lys Thr Leu
        195                 200                 205

Ser Ala Tyr Tyr Ser Thr His Lys Ser Glu Val Asp Ala Lys Met Gln
    210                 215                 220

Glu Met Ala Val Glu Asn Leu Val Lys Phe Gly Gly Cys Arg Arg Asn
225                 230                 235                 240

Asn Ser Lys Lys Ser Met Phe Ile Met Gly Ser Asn Thr Thr Asn Tyr
                245                 250                 255

Thr Ile Ser Tyr Ile Gly Gly Asn Ser Phe Asn Ile Asn Phe Ala Asn
            260                 265                 270

Ile Leu Asn Phe Asp Val Tyr Gly Arg Arg Asp Val Val Lys Asn Gly
        275                 280                 285

Glu Val Leu Val Asp Ile Met Ala Asn His Gly Asp Ser Ile Val Leu
    290                 295                 300

Lys Ile Val Asn Gly Glu Leu Tyr Ala Asp Val Pro Cys Ser Val Thr
305                 310                 315                 320

Leu Asn Lys Val Glu Ser Asn Phe Asp Lys Val Val Gly Ile Asp Val
                325                 330                 335
```

Asn Met Lys His Met Leu Leu Ser Thr Ser Ile Thr Asp Asn Gly Ser
                340                 345                 350

Ser Asp Phe Leu Asn Ile Tyr Lys Glu Met Ser Asn Asn Ala Glu Phe
            355                 360                 365

Met Ala Leu Cys Pro Glu Glu Asp Arg Lys Tyr Tyr Lys Asp Ile Ser
    370                 375                 380

Lys Tyr Val Thr Phe Ala Pro Leu Glu Leu Asp Leu Leu Phe Ser Arg
385                 390                 395                 400

Ile Ser Lys Gln Gly Lys Val Lys Met Glu Lys Val Tyr Ser Glu Ile
                405                 410                 415

Leu Glu Ala Leu Lys Trp Lys Phe Phe Ala Asn Gly Asp Asn Lys Asn
            420                 425                 430

Arg Ile Tyr Val Glu Ser Ile Gln Lys Ile Arg Gln Gln Ile Lys Ala
        435                 440                 445

Leu Cys Val Ile Lys Asn Ala Tyr Tyr Glu Gln Gln Ser Ala Tyr Asp
    450                 455                 460

Ile Asp Lys Thr Gln Glu Tyr Ile Glu Thr His Pro Phe Ser Leu Thr
465                 470                 475                 480

Glu Lys Gly Met Ser Ile Lys Ser Lys Met Asp Lys Ile Cys Gln Thr
                485                 490                 495

Ile Ile Gly Cys Arg Asn Asn Ile Ile Asp Tyr Ala Tyr Ser Phe Phe
            500                 505                 510

Glu Arg Asn Gly Tyr Ser Ile Ile Gly Leu Glu Lys Leu Thr Ser Ser
        515                 520                 525

Gln Phe Glu Lys Thr Lys Ser Met Pro Thr Cys Lys Ser Leu Leu Asn
    530                 535                 540

Phe His Lys Val Leu Gly His Thr Leu Ser Glu Leu Glu Thr Leu Pro
545                 550                 555                 560

Ile Asn Asp Val Val Lys Lys Gly Tyr Tyr Thr Phe Thr Thr Asp Asn
                565                 570                 575

Glu Gly Lys Ile Thr Asp Ala Ser Leu Ser Glu Lys Gly Lys Val Arg
            580                 585                 590

Lys Met Lys Asp Asp Phe Phe Asn Gln Ala Ile Lys Ala Ile His Phe
        595                 600                 605

Ala Asp Val Lys Asp Tyr Phe Ala Thr Leu Ser Asn Asn Gly Gln Thr
    610                 615                 620

Gly Ile Phe Phe Val Pro Ser Gln Phe Thr Ser Gln Met Asp Ser Asn
625                 630                 635                 640

Thr His Asn Leu Tyr Phe Glu Asn Ala Lys Asn Gly Gly Leu Lys Leu
                645                 650                 655

Ala Pro Lys Tyr Lys Val Arg Gln Thr Gln Glu Tyr His Leu Asn Gly
            660                 665                 670

Leu Pro Ala Asp Tyr Asn Ala Ala Arg Asn Ile Ala Tyr Ile Gly Leu
        675                 680                 685

Asp Glu Thr Met Arg Asn Thr Phe Leu Lys Lys Ala Asn Ser Asn Lys
    690                 695                 700

Ser Leu Tyr Asn Gln Pro Ile Tyr Asp Thr Gly Ile Lys Lys Thr Ala
705                 710                 715                 720

Gly Val Phe Ser Arg Met Lys Lys Leu Lys Arg Tyr Glu Ile Ile
                725                 730                 735

<210> SEQ ID NO 20
<211> LENGTH: 774
<212> TYPE: PRT

```
<213> ORGANISM: Unknown
<220> FEATURE:
<223> OTHER INFORMATION: Description of Unknown:
      mammals-digestive system-asian elephant fecal-elephas maximus
      sequence

<400> SEQUENCE: 20
```

Met Leu Asn Ile Lys Asn Asn Gly Glu Ser Val Asp Met Asn Thr Ile
1               5                   10                  15

Glu Leu Ala Met Lys Glu Tyr Asn Arg Tyr Tyr Asn Ile Cys Ser Asp
            20                  25                  30

Trp Ile Cys Asn Asn Leu Met Thr Pro Ile Gly Ser Leu Tyr Gln Tyr
        35                  40                  45

Ile Asp Asp Lys Cys Lys Asn Asn Ala Tyr Ala Gln Asn Leu Ile Ala
    50                  55                  60

Glu Glu Trp Lys Asp Lys Pro Leu Tyr Tyr Met Phe Tyr Lys Gly Tyr
65                  70                  75                  80

Asn Ala Asn Asn Cys Ala Asn Ala Ile Cys Cys Ala Ile Arg Ser Gln
                85                  90                  95

Val Pro Glu Val Asn Lys Ala Glu Asn Ile Leu Asn Leu Ser Tyr Thr
            100                 105                 110

Tyr Tyr Phe Arg Asn Gly Val Ile Lys Ser Val Ile Ser Asn Tyr Ala
        115                 120                 125

Ser Lys Met Arg Ile Leu Ser Asp Lys Gln Ile Lys Tyr Cys Ile Val
    130                 135                 140

Ser Glu Asn Thr Pro Asp Lys Ile Leu Ile Glu Gln Cys Ile Leu Glu
145                 150                 155                 160

Leu Lys Arg Arg His Glu Asp Leu Lys Asp Trp Glu Glu Asn Leu Lys
                165                 170                 175

Tyr Leu Ile Leu Lys Gly Asn Glu Ser Ala Ile Thr Arg Phe Thr Ile
            180                 185                 190

Leu Lys Asp Phe Tyr Ser Lys Asn Ile Glu Arg Val Lys Glu Glu Arg
        195                 200                 205

Glu Ile Met Ala Ile Ala Glu Leu Lys Asp Phe Gly Gly Cys Arg Arg
    210                 215                 220

Lys Asp Asp Lys Leu Ser Met Cys Ile Gln Ser Ala Gly Asn Ser Lys
225                 230                 235                 240

Asp Ile Lys Val Ser Arg Val Leu Thr Thr His Asn Tyr Thr Glu Leu
                245                 250                 255

Val Asp Asp Tyr Thr Glu Asn Phe Asn Ile Lys Phe Ser Ala Leu Asp
            260                 265                 270

Phe Asn Val Met Gly Arg Arg Asp Val Val Lys Thr Lys Leu Asn Lys
        275                 280                 285

Thr Glu Asp Asp Ser Asn Thr Trp Gly Gly Thr Glu Leu Leu Val Asp
    290                 295                 300

Ile Ile Asn Asn His Gly Cys Ser Leu Thr Phe Lys Leu Val Asp Asp
305                 310                 315                 320

Lys Leu Tyr Val Asp Ile Pro Ile Asp Thr Glu His Ile Asn Lys Thr
                325                 330                 335

Thr Asp Phe Lys Lys Ser Val Gly Ile Asp Val Asn Leu Lys His Ser
            340                 345                 350

Leu Leu Asn Thr Asp Ile Leu Asp Asn Gly Gly Ile Asn Gly Tyr Ile
        355                 360                 365

Asn Ile Tyr Lys Lys Leu Leu Ala Asp Asp Ala Phe Met Ser Ala Cys
    370                 375                 380

```
Thr Lys Ala Asp Leu Val Asn Tyr Ile Asp Ile Ala Lys Thr Val Thr
385                 390                 395                 400

Phe Cys Pro Ile Glu Ala Asp Phe Ile Ile Ser Asn Val Val Glu Lys
            405                 410                 415

Tyr Leu His Met Lys Asp Asn Thr Asn Lys Met Glu Ile Ala Phe Ser
        420                 425                 430

Ser Val Leu Met Asn Ile Arg Lys Glu Leu Glu Ile Lys Leu Leu His
            435                 440                 445

Ser Ser Lys Glu Glu Ser Pro Leu Ile Arg Lys Gln Ile Ile Tyr Ile
        450                 455                 460

Asn Cys Ile Ile Cys Leu Arg Asn Glu Leu Lys Gln Tyr Ala Ile Ala
465                 470                 475                 480

Lys His Arg Tyr Tyr Lys Lys Gln Gln Glu Tyr Asp Thr Leu Cys Asp
                485                 490                 495

Thr Leu His Gly Val Asp Tyr Lys Gln Ile His Pro Tyr Ala Gln Ser
            500                 505                 510

Lys Glu Gly Ala Glu Gln Met Lys Lys Met Lys Thr Ile Glu Asn Asn
        515                 520                 525

Leu Ile Ala Asn Arg Asn Asn Ile Ile Glu Tyr Ala Tyr Thr Val Phe
        530                 535                 540

Glu Leu Asn Asn Phe Asp Leu Ile Ala Leu Glu Asn Ile Thr Lys Asp
545                 550                 555                 560

Ile Met Glu Asp Lys Lys Lys Arg Lys Ser Phe Pro Ser Ile Asn Ser
                565                 570                 575

Leu Leu Lys Tyr His Lys Val Ile Asn Cys Thr Glu Asp Asn Ile Asn
            580                 585                 590

Asp Asn Glu Thr Tyr Gln Lys Phe Ala Lys Tyr Asn Val Ser Tyr
        595                 600                 605

Glu Asn Gly Lys Val Thr Gly Ala Thr Leu Ser Gln Glu Gly Asn Lys
        610                 615                 620

Val Lys Leu Lys Asp Asp Phe Tyr Asp Lys Leu Leu Lys Val Leu His
625                 630                 635                 640

Phe Thr Ser Ile Lys Asp Tyr Phe Thr Thr Leu Ser Asn Lys Arg Lys
                645                 650                 655

Ile Ala Val Ala His Val Pro Ala Tyr Tyr Thr Ser Gln Ile Asp Ser
                660                 665                 670

Ile Asp Asn Lys Ile Cys Met Ile Lys Ser Thr Asp Lys Asn Gly Lys
        675                 680                 685

Ser Thr Tyr Lys Ile Ala Asp Lys Thr Ile Val Arg Pro Thr Gln Glu
        690                 695                 700

Lys His Ile Asn Gly Leu Asn Ala Asp Tyr Asn Ala Ala Arg Asn Ile
705                 710                 715                 720

Asn Phe Ile Val Ala Asp Glu Lys Trp Arg Lys Lys Phe Val Arg Pro
                725                 730                 735

Thr Asn Thr Asn Lys Pro Leu Tyr Asn Ser Pro Val Phe Ser Pro Ala
                740                 745                 750

Val Lys Ser Glu Gly Gly Thr Ile Lys Asn Leu Gln Ile Leu Ser Ala
            755                 760                 765

Thr Lys Thr Ile Ile Leu
        770

<210> SEQ ID NO 21
<211> LENGTH: 755
```

<212> TYPE: PRT
<213> ORGANISM: Unknown
<220> FEATURE:
<223> OTHER INFORMATION: Description of Unknown:
      mammals-digestive system-cattle and sheep rumen sequence

<400> SEQUENCE: 21

```
Met Ala His Val Arg Thr Lys Asn Glu Gly Asn Met Ala Lys Thr Tyr
1               5                   10                  15

Ser Phe Lys Val Arg Glu Thr Asn Leu Lys Lys Asp Val Met Ile Glu
            20                  25                  30

Tyr Asn Glu Tyr Tyr Asn Arg Leu Ser Asp Trp Ile Cys Gly Asn Leu
        35                  40                  45

Thr Lys Met Thr Ile Gly Glu Leu Ala Glu Leu Val Pro Glu Lys Lys
    50                  55                  60

Arg Asn Thr Ser Tyr Tyr Leu Ala Ala Thr Asp Glu Lys Trp Ile Asn
65                  70                  75                  80

Glu Pro Met Tyr Lys Leu Phe Thr Asp Glu Tyr Thr Lys Lys Ser Ser
                85                  90                  95

Phe Thr Asp Pro Leu Val Ala Asn Ser Asn Asn Cys Asp Asn Leu Ile
            100                 105                 110

Leu Thr Ala Thr Asp Val Leu Asn Pro Glu Gly Tyr Glu Gly Asn Leu
        115                 120                 125

Leu Ser Leu Cys Lys Ser Thr Tyr Arg Thr Phe Gly Tyr Ala Lys Gln
    130                 135                 140

Ile Ile Ser Asn Met Lys Thr Lys Ile Gly Ala Leu Lys Pro Asn Val
145                 150                 155                 160

Lys Arg Arg Val Leu Gly Glu Asn Pro Thr Tyr Asp Glu Lys Met Ile
                165                 170                 175

Gln Val Leu Tyr Glu Met Tyr Asn Asn Gly Ile Ala Asp Val Thr Gly
            180                 185                 190

Phe Asn Asp Arg Ile Lys Tyr Leu Lys Lys Gln Glu Thr Pro Asn Glu
        195                 200                 205

Lys Leu Ile Ser Arg Met Lys Met Leu Arg Asp Phe Phe Lys Glu Asn
    210                 215                 220

Arg Asn Asp Ile Met Asp Lys Cys Arg Ile Met Ala Val Glu Gln Leu
225                 230                 235                 240

Val Ser Phe Gly Gly Cys Lys Arg Asn Ile Asn Gly Ala Ser Met Thr
                245                 250                 255

Leu Arg Asn Gln Cys Ile Ser Val Lys Arg Lys Asp Gly Cys Gln Gly
            260                 265                 270

Tyr Val Val Ala Ile Pro Val Gly Thr Lys Asn Ser Ile Val Phe Asp
        275                 280                 285

Leu Tyr Gly Arg Arg Asp Val Ile Lys Asp Gly Val Glu Leu Val Asp
    290                 295                 300

Val Cys Gly Lys His Thr Asp Thr Ile Thr Ile Lys Ser Val Asn Gly
305                 310                 315                 320

Glu Leu Phe Leu Asp Met Pro Val Ala Ile Asn Phe Glu Lys Lys Ser
                325                 330                 335

Gly Lys Cys Thr Lys Thr Val Gly Ile Asp Val Asn Thr Lys His Met
            340                 345                 350

Leu Ile Gln Thr Ser Val Lys Asp Asn Gly Lys Phe Asp Tyr Tyr Val
        355                 360                 365

Asn Leu Tyr Lys Ile Phe Ala Glu Asp Glu Glu Leu Asn Lys Ile Leu
    370                 375                 380
```

```
Gly Asp Asp Glu Val Met Val Asn Ile Lys Lys Asn Ala Glu Asn Leu
385                 390                 395                 400

Ser Phe Leu Pro Leu Glu Met Asp Leu Leu Tyr Ser Arg Ile Leu Asp
            405                 410                 415

Gly Pro Gln Lys Tyr Lys Leu Ala Glu Asp Arg Ile Thr Glu Leu Leu
            420                 425                 430

Lys Gln Trp Gly Ile Asn Phe Asp Ala Gly Cys Met Ser Gln Glu Arg
            435                 440                 445

Ile Tyr Val Gln Cys Val Arg Lys Leu Arg Gly Asn Leu Lys Arg Leu
450                 455                 460

Leu Tyr Leu Gln Asn Lys Tyr Tyr Glu Ala Gln Gln Glu Tyr Asp Lys
465                 470                 475                 480

Lys Met Gly Phe Asp Asp Lys Ser Thr Asp Ser Lys Glu Thr Met Asp
            485                 490                 495

Lys Arg Arg Trp Glu Ser Pro Phe Arg Asn Thr Glu Glu Gly Thr Lys
            500                 505                 510

Leu Tyr Asp Glu Ile Asn Thr Tyr Gln Asn Arg Ile Ile Gly Ile Arg
            515                 520                 525

Asn Ser Ile Ile Asp Tyr Ala Tyr Leu Val Leu Glu Tyr Asn Gly Tyr
530                 535                 540

Asp Asn Leu Ser Leu Glu Tyr Leu Thr Ser Ser Gln Phe Lys Val Asn
545                 550                 555                 560

Lys Thr Phe Pro Thr Thr Asn Ser Leu Leu Lys Tyr His Lys Leu Gln
            565                 570                 575

Gly Lys Thr Lys Thr Glu Ala Glu Lys Cys Asp Ala Tyr Ile Ser His
            580                 585                 590

Lys Ser Lys Tyr Lys Leu Ser Leu Lys Asp Gly Val Ile Asp Ser Ile
            595                 600                 605

Asp Tyr Ser Ala Glu Gly Leu Lys Gln Ile Lys Lys Asp Arg Ser Arg
            610                 615                 620

Asn Ile Ile Lys Ala Ile His Phe Ala Asp Val Lys Asp Arg Phe
625                 630                 635                 640

Val Leu Ser Ser Asn Asn Gly Asn Ala Ser Val Thr Phe Val Pro Ser
            645                 650                 655

Tyr His Thr Ser Gln Ile Asp Ser Thr Asp His Lys Met Phe Val Thr
            660                 665                 670

Asn Lys Gly Lys Ile Val Asp Lys Arg Lys Val Arg Gln Ile Gln Glu
            675                 680                 685

Thr His Val Asn Gly Leu Asn Ser Asp Phe Asn Ala Ala Arg Asn Ile
            690                 695                 700

Gln Tyr Ile Ser Glu Asn Glu Glu Trp Arg Asn Ala Leu Cys Lys Pro
705                 710                 715                 720

Thr Glu Asn Met Tyr Asn Glu Pro Ile Tyr Val Pro Leu Val Lys Ser
            725                 730                 735

Gln Asn Gly Met Phe Lys Ala Ile Lys Lys Leu Gly Ala Thr Lys Ile
            740                 745                 750

Trp Gln Glu
    755

<210> SEQ ID NO 22
<211> LENGTH: 789
<212> TYPE: PRT
<213> ORGANISM: Unknown
<220> FEATURE:
```

<223> OTHER INFORMATION: Description of Unknown:
      mammals-digestive system-cattle and sheep rumen sequence

<400> SEQUENCE: 22

Met Ala His Arg Asn Lys Asn Leu Ala Glu Asn Cys Ile Asn Lys Thr
1               5                   10                  15

Phe Ser Phe Lys Val Lys Ala Glu Lys Glu Ile Asn Ser Lys Trp
            20                  25                  30

Ile Pro Ala Ile Lys Glu Tyr Thr Ala Tyr Tyr Asn Arg Ile Ser Asp
            35                  40                  45

Trp Ile Cys Asp Arg Leu Thr Asn Thr Thr Val Gly Glu Leu Ile Gly
50                      55                  60

Ile Ile Gly Tyr Lys Thr Asp Lys Lys Gly Asn Ala Leu Ala Tyr Ile
65                  70                  75                  80

Lys Asp Gly Ser Ser Glu Lys Tyr Arg Asn Leu Pro Leu Tyr Cys Met
                85                  90                  95

Phe Lys Lys Asn Phe Pro Ala Thr Thr Ala Asp Asn Ile Met Tyr Gln
            100                 105                 110

Val Ile Glu Lys Leu Gly Val Asp Lys Tyr Asn Gly Asn Ser Leu Gly
            115                 120                 125

Leu Ser Gly Thr Tyr Tyr Arg Arg Ile Gly Tyr Ile Ala Asn Val Ile
130                 135                 140

Gly Asn Tyr Arg Thr Lys Val Arg Gly Met Lys Ala Ser Val Lys Tyr
145                 150                 155                 160

Arg Asn Phe Asp Pro Asn Asp Val Thr Glu Asp Val Leu Glu Asn Gln
            165                 170                 175

Thr Ile Phe Glu Ile Asn Lys Asn Gly Phe Glu Cys Lys Gly Asp Phe
            180                 185                 190

Glu Lys His Ile Glu Tyr Leu Lys Asn Arg Glu Leu Thr Asp Arg Leu
            195                 200                 205

Asn Lys Leu Ile Leu Arg Met Glu Cys Leu Tyr Asn Tyr Tyr Val Glu
210                 215                 220

His Glu Asp Ala Val Lys Ala Lys Met Glu Asn Tyr Ala Ile Glu Ser
225                 230                 235                 240

Phe Lys Thr Phe Gly Gly Cys His Arg Asn Ser Asn Arg Ser Met Ser
            245                 250                 255

Ile Gln Phe Thr Asn Asn Ser Pro Leu Glu Ile Lys Lys Val Gly Lys
            260                 265                 270

Thr Ser Phe Asp Leu Tyr Met Pro Ile Asn Gly Glu Val Ala Cys Leu
            275                 280                 285

Gln Leu Met Gly Asn Lys Gln Ala Val Cys Val Gly Glu Asn Gly Glu
            290                 295                 300

Arg Cys Asp Leu Val Asp Ile Val Asn Ser His Ser Lys Thr Ile Thr
305                 310                 315                 320

Ile Lys Ile Ile Asn Gly Glu Met Tyr Val Asp Ile Pro Cys Val Val
                325                 330                 335

Asn Phe Glu Lys Lys Asp Glu Asp Thr Ile Lys Ser Val Gly Val Asp
            340                 345                 350

Val Asn Ile Lys His Glu Ile Leu Ala Thr Ser Val Ile Asp Asn Gly
            355                 360                 365

Gln Leu Asn Gly Tyr Phe Asn Ile Tyr Lys Glu Leu Ile Asn Asn Lys
            370                 375                 380

Glu Phe Val Asp Thr Phe Asn Gly Asp Ile Lys Ala Phe Glu Ala Phe
385                 390                 395                 400

```
Lys Asp Asn Ala Ala Tyr Val Thr Phe Gly Leu Leu Glu Pro Asp Leu
            405                 410                 415

Leu Phe Thr Arg Phe Tyr Glu Arg Ser Gly Phe Glu Lys Asp Asp Arg
        420                 425                 430

His Ile Lys Leu Arg Glu Arg Ile Leu Thr Gly Ile Leu Lys
        435                 440                 445

Arg Ile Gly Gln Glu His Ser Asp Val Asp Val Arg Asn Tyr Val Arg
    450                 455                 460

Phe Val Asn Met Leu Arg Ser Lys Tyr Glu Ser Tyr Phe Val Leu Lys
465                 470                 475                 480

Asn Lys Tyr Tyr Glu Lys Met Gln Glu Phe Asp Ser Thr Gln Asn Tyr
                485                 490                 495

Val Asp Val Ser Thr Ala Ser Lys Glu Thr Met Asp Lys Arg Arg Phe
            500                 505                 510

Asp Asn Pro Phe Arg Asn Thr Glu Val Ala Asn Glu Leu Leu Gly Lys
        515                 520                 525

Ile Asp Asn Val Leu Gly Asp Ile Lys Gly Cys Met Ala Asn Ile Ile
    530                 535                 540

Thr Tyr Ala Phe Lys Val Leu Gln Lys Asn Gly Tyr Asn Thr Ile Gly
545                 550                 555                 560

Leu Glu Tyr Leu Asp Ser Ser Gln Phe Glu Asn Met Arg Thr Leu Thr
                565                 570                 575

Pro Thr Ser Ile Leu Lys Tyr His Lys Met Glu Gly Lys Ser Val Asp
            580                 585                 590

Ala Val Glu Ser Trp Ile Lys Glu Asn Lys Ile Pro Ser Asn Arg Tyr
        595                 600                 605

Asp Phe Ile Tyr Glu Asp Asn His Leu Thr Asp Val Leu Leu Asn Ser
    610                 615                 620

Asn Gly Ile Ala Tyr Gln Lys Lys Asn Leu Phe Met Asn Leu Val Ile
625                 630                 635                 640

Lys Ala Ile Ser Phe Ala Asp Ile Lys Asn Lys Phe Val Gln Leu Ser
                645                 650                 655

Asn Asn Thr Asn Val Ser Ile Leu Phe Ala Pro Ala Ala Phe Thr Ser
            660                 665                 670

Gln Met Asp Ser Asn Arg His Val Ile Tyr Thr Val Lys Asn Asn Lys
        675                 680                 685

Gly Lys Leu Ala Leu Val Asp Lys Lys Arg Val Arg Pro Asn Gln Glu
    690                 695                 700

Lys His Ile Asn Gly Leu His Ser Gly Tyr Asn Ala Ala Cys Asn Val
705                 710                 715                 720

Lys Phe Ile Cys Asp Asn Glu Phe Phe Arg Asn Thr Met Thr Ile Ser
                725                 730                 735

Asn Lys Gly Lys Asn Leu Tyr Ser Gln Pro Thr Tyr Asp Ile Lys Glu
            740                 745                 750

Ala Tyr Lys Lys Asn Ala Gly Cys Lys Val Ile Asn Asp Phe Ile Lys
        755                 760                 765

Asn Gly Asn Ala Val Ile Cys Cys Ile Glu Asn Asn Lys Leu Ile Glu
    770                 775                 780

Thr Asn Gly Arg Gln
785

<210> SEQ ID NO 23
<211> LENGTH: 766
```

```
<212> TYPE: PRT
<213> ORGANISM: Unknown
<220> FEATURE:
<223> OTHER INFORMATION: Description of Unknown:
      mammals-digestive system-fecal sequence

<400> SEQUENCE: 23
```

Met Ala Asn Lys Lys Phe Lys Leu Thr Lys Asn Glu Val Val Lys Ser
1               5                   10                  15

Phe Val Leu Lys Val Ala Asn Gln Lys Lys Cys Ala Ile Thr Asn Glu
            20                  25                  30

Thr Leu Gln Glu Tyr Lys Asn Tyr Asn Lys Val Ser Gln Trp Ile
        35                  40                  45

Asn Asn Asn Leu Thr Lys Met Thr Ile Gly Asp Leu Ile Gln Tyr Ala
    50                  55                  60

Pro Thr Val Ser Lys Lys Gly Lys Lys Gln Pro Asp Gly Thr Met Val
65                  70                  75                  80

Tyr Asp Thr Pro Leu Tyr Val Thr Tyr Ala Met Ser Asp Glu Trp Lys
                85                  90                  95

Asn Lys Pro Leu Tyr Tyr Ile Phe Lys Lys Glu Tyr Asn Thr Asn Asn
            100                 105                 110

Ala Asn Asn Leu Leu Tyr Glu Ala Ile Arg Asn Leu Asn Val Asp Glu
        115                 120                 125

Tyr Asp Gly Asn Gln Leu Asn Phe Asn Ser Thr Tyr Tyr Arg Thr Gln
    130                 135                 140

Gly Tyr Val Asn Arg Val Phe Ser Asn Tyr Arg Thr Lys Ile Asn Thr
145                 150                 155                 160

Leu Asp Ile Lys Ile Lys Lys Ser Lys Val Asp Glu Asn Ser Asp Val
                165                 170                 175

Glu Thr Leu Glu Pro Gln Thr Met Tyr Glu Ile Asn Lys Leu Asn Leu
            180                 185                 190

Lys Thr Asn Lys Asp Trp Glu Glu Arg Leu Gln Tyr Leu Thr Met Gln
        195                 200                 205

Glu Asn Pro Asn Gln Asn Thr Ile Asp Arg Thr Lys Ile Leu Phe Asn
    210                 215                 220

Tyr Phe Ile Asn Asn Asn Asp Thr Ile Phe Gln Lys Met Glu Glu Leu
225                 230                 235                 240

Ser Ile Lys Gln Leu Thr Glu Phe Gly Gly Cys Lys Met Lys Asp Asn
                245                 250                 255

Thr Thr Ser Met Thr Ile Asn Ile Gln Asp Phe Lys Ile Lys Arg Lys
            260                 265                 270

Glu Asn Ser Ile Gly Tyr Ile Met Thr Ile Pro Phe Asn Lys Lys Asn
        275                 280                 285

Val Asp Val Glu Leu Tyr Gly His Lys Gln Thr Ile Lys Gly His Lys
    290                 295                 300

Asn Ser Tyr Thr Glu Ile Val Asp Ile Val Asn Lys His Gly Asn Thr
305                 310                 315                 320

Ile Thr Phe Lys Ile Lys Asn Asn Gln Leu Phe Ala Ile Ile Thr Ser
                325                 330                 335

Asp Thr Glu Val Thr Lys Pro Glu Pro Gln Tyr Glu Lys Ile Val Gly
            340                 345                 350

Val Asp Val Asn Ile Lys His Thr Leu Met Val Thr Ser Glu Lys Asp
        355                 360                 365

Asn Gly Lys Leu Lys Gly Tyr Ile Asn Leu Tyr Lys Glu Val Leu Lys
    370                 375                 380

```
Asn Asp Glu Phe Lys Lys Leu Leu Asn Lys Thr Glu Leu Asp Asn Phe
385                 390                 395                 400

Lys Ser Leu Ser Gln Ile Val Thr Phe Cys Pro Ile Glu Tyr Asp Phe
            405                 410                 415

Leu Phe Ser Arg Ile Phe Asp Asp Glu Asn Thr Lys Lys Glu Leu Ala
            420                 425                 430

Phe Ser Asn Val Leu Tyr Asp Ile Gln Lys Gln Leu Lys Asn Thr Asn
        435                 440                 445

Asn Ile Leu Gln Tyr Asn Tyr Ile Ala Cys Val Asn Lys Leu Arg Ala
    450                 455                 460

Lys Tyr Lys Ala Tyr Phe Val Leu Lys Met Ser Tyr Met Lys Gln Gln
465                 470                 475                 480

Lys Ile Tyr Asp Thr Asn Met Gly Phe Phe Asp Ile Ser Thr Glu Ser
                485                 490                 495

Lys Glu Thr Met Asp Gln Arg Arg Ser Leu Tyr Pro Phe Ile Asn Thr
            500                 505                 510

Glu Ile Ala Gln Asn Ile Ile Thr Lys Met Asn Asn Val Gln Gln Asp
        515                 520                 525

Ile Asn Gly Cys Leu Lys Asn Ile Phe Lys Tyr Thr Tyr Thr Val Phe
    530                 535                 540

Glu Asn Asn Asn Tyr Asp Thr Ile Val Leu Glu Asn Leu Glu Asn Ala
545                 550                 555                 560

Asn Phe Glu Lys His Asn Pro Leu Pro Asn Ile Thr Ser Leu Leu Lys
                565                 570                 575

Tyr His Lys Val Gln Gly Leu Thr Ile Gln Glu Ala Glu Gln His Glu
            580                 585                 590

Lys Val Gly Asn Leu Ile Gln Asn Asp Asn Tyr Ile Phe Gln Leu Asn
        595                 600                 605

Glu Asp Asn Lys Ile Ile Asn Ala Asp Tyr Ser Gln Lys Ala Tyr Tyr
    610                 615                 620

Lys Val Cys Lys Ala Leu Phe Phe Asn Gln Ala Ile Lys Thr Leu His
625                 630                 635                 640

Phe Ala Ser Val Lys Asp Glu Met Ile Lys Leu Ser Asn Asn Asn Lys
                645                 650                 655

Val Cys Val Ala Ile Ile Pro Pro Glu Tyr Thr Ser Gln Ile Asp Ser
            660                 665                 670

Asn Thr His Lys Leu Tyr Phe Ile Asn Lys Asp Gly Lys Leu Leu Lys
        675                 680                 685

Ala Asp Lys Lys Thr Val Arg Lys Thr Gln Glu Lys His Ile Asn Gly
    690                 695                 700

Leu Asn Ala Asp Phe Asn Ala Ala Ser Asn Ile Lys Tyr Ile Val Gln
705                 710                 715                 720

Asn Glu Thr Trp Arg Asn Leu Phe Thr Asn Lys Thr Asn Asn Thr Tyr
                725                 730                 735

Gly Leu Pro Ile Leu Thr Pro Ser Lys Lys Gly Gln Ser Asn Ile Ile
            740                 745                 750

Thr Gln Leu Met Lys Ile Asn Ala Thr Gln Glu Leu Val Val
        755                 760                 765

<210> SEQ ID NO 24
<211> LENGTH: 752
<212> TYPE: PRT
<213> ORGANISM: Unknown
<220> FEATURE:
```

<223> OTHER INFORMATION: Description of Unknown:
mammals-digestive system-fecal sequence

<400> SEQUENCE: 24

| | | | | | | | | | | | | | | | |
|---|---|---|---|---|---|---|---|---|---|---|---|---|---|---|---|
| Met | Ala | Lys | Ser | Ile | Met | Lys | Ser | Ile | Lys | Phe | Lys | Val | Lys | Gly | |
| 1 | | | | 5 | | | | | 10 | | | | | 15 | |
| Asn | Ser | Pro | Ile | Asn | Glu | Asp | Ile | Ile | Asn | Glu | Tyr | Lys | Gly | Tyr | Tyr |
| | | | 20 | | | | | 25 | | | | | 30 | | |
| Asn | Thr | Cys | Ser | Asn | Trp | Ile | Asn | Asn | Asn | Leu | Thr | Ser | Ile | Thr | Ile |
| | | 35 | | | | | 40 | | | | | 45 | | | |
| Gly | Glu | Met | Gly | Lys | Phe | Leu | Lys | Asp | Val | Met | Arg | Lys | Thr | Thr | Gly |
| 50 | | | | | 55 | | | | | 60 | | | | | |
| Tyr | Ile | Asp | Val | Ala | Leu | Ser | Asp | Glu | Trp | Lys | Asp | Lys | Pro | Met | Tyr |
| 65 | | | | | 70 | | | | | 75 | | | | | 80 |
| Tyr | Leu | Phe | Thr | Lys | Lys | Tyr | Asn | Pro | Lys | His | Ala | Asn | Asn | Leu | Leu |
| | | | | 85 | | | | | 90 | | | | | 95 | |
| Tyr | Tyr | Phe | Ile | Lys | Glu | Lys | Lys | Leu | Asp | Lys | Phe | Asn | Gly | Asn | Ile |
| | | | 100 | | | | | 105 | | | | | 110 | | |
| Leu | Asn | Val | Pro | Glu | Tyr | Tyr | Arg | Lys | Glu | Gly | Tyr | Phe | Lys | Leu | |
| | | 115 | | | | | 120 | | | | | 125 | | | |
| Val | Ala | Gly | Asn | Tyr | Arg | Thr | Lys | Ile | Asn | Thr | Leu | Asn | Phe | Lys | Ile |
| | 130 | | | | | 135 | | | | | 140 | | | | |
| Lys | Ser | Lys | Lys | Val | Asp | Ala | Asn | Ser | Leu | Ser | Glu | Asp | Ile | Glu | Met |
| 145 | | | | | 150 | | | | | 155 | | | | | 160 |
| Gln | Thr | Ile | Tyr | Glu | Ile | Val | Lys | Arg | Gly | Leu | Asn | Lys | Lys | Ser | Asp |
| | | | | 165 | | | | | 170 | | | | | 175 | |
| Trp | Asp | Ser | Tyr | Ile | Ser | Tyr | Ile | Glu | Cys | Val | Gln | Asn | Pro | Asn | Ile |
| | | | 180 | | | | | 185 | | | | | 190 | | |
| Asp | Asn | Ile | Asn | Arg | Tyr | Lys | Leu | Leu | Arg | Asp | Tyr | Phe | Cys | Glu | Asn |
| | | | 195 | | | | | 200 | | | | | 205 | | |
| Glu | Asp | Val | Ile | Lys | Asn | Lys | Ile | Glu | Ile | Leu | Ser | Ile | Glu | Gln | Ile |
| | 210 | | | | | 215 | | | | | 220 | | | | |
| Lys | Glu | Phe | Gly | Gly | Cys | Ile | Met | Lys | Pro | His | Ile | Asn | Ser | Met | Thr |
| 225 | | | | | 230 | | | | | 235 | | | | | 240 |
| Phe | Gly | Ile | Gln | Lys | Phe | Lys | Ile | Glu | Glu | Ile | Asn | Ser | Leu | Gly | |
| | | | | 245 | | | | | 250 | | | | | 255 | |
| Phe | Thr | Phe | Asn | Leu | Pro | Leu | Asn | Lys | Asn | Asn | Tyr | Lys | Ile | Glu | Leu |
| | | | 260 | | | | | 265 | | | | | 270 | | |
| Trp | Gly | His | Arg | Gln | Leu | Lys | Lys | Gly | Asn | Lys | Glu | Ser | Asn | Val | Asn |
| | | 275 | | | | | 280 | | | | | 285 | | | |
| Val | Ser | Leu | Asp | Asp | Phe | Ile | Asn | Thr | Tyr | Gly | Gln | Asn | Val | Val | Phe |
| | 290 | | | | | 295 | | | | | 300 | | | | |
| Thr | Ile | Lys | Arg | Lys | Lys | Leu | Tyr | Ile | Val | Phe | Ser | Tyr | Asp | Tyr | Glu |
| 305 | | | | | 310 | | | | | 315 | | | | | 320 |
| Phe | Glu | Arg | Gly | Glu | Cys | Asn | Phe | Glu | Lys | Ser | Val | Gly | Leu | Asp | Val |
| | | | 325 | | | | | 330 | | | | | 335 | | |
| Asn | Phe | Lys | His | Ser | Leu | Phe | Val | Thr | Ser | Glu | Ile | Asp | Asn | Asn | Gln |
| | | | 340 | | | | | 345 | | | | | 350 | | |
| Phe | Asp | Gly | Tyr | Ile | Asn | Leu | Tyr | Lys | Tyr | Ile | Leu | Ser | Asn | Asn | Glu |
| | | | 355 | | | | | 360 | | | | | 365 | | |
| Phe | Thr | Ser | Leu | Leu | Thr | Asp | Ser | Glu | Arg | Lys | Asp | Tyr | Glu | Asp | Leu |
| | 370 | | | | | 375 | | | | | 380 | | | | |
| Ala | Asn | Ile | Val | Thr | Phe | Cys | Pro | Phe | Glu | Tyr | Gln | Leu | Leu | Phe | Ser |
| 385 | | | | | 390 | | | | | 395 | | | | | 400 |

Arg Tyr Asp Lys Leu Ser Lys Ile Ser Glu Lys Val Leu Ser
                405                 410                 415

Lys Ile Leu Tyr Ser Leu Gln Lys Leu Lys Asn Glu Lys Arg Thr
                420                 425                 430

Lys Glu Tyr Ile Tyr Val Ser Cys Val Asn Lys Leu Arg Ala Lys Tyr
                435                 440                 445

Val Ser Tyr Phe Lys Leu Lys Gln Lys Tyr Asn Glu Lys Gln Lys Glu
450                 455                 460

Tyr Asp Ile Glu Met Gly Phe Val Asp Ser Thr Glu Ser Lys Glu
465                 470                 475                 480

Ser Met Asp Lys Arg Arg Phe Glu Asn Pro Phe Ile Asn Thr Pro Val
                485                 490                 495

Ala Lys Glu Leu Leu Glu Lys Met Asn Asn Val Lys Gln Asp Ile Asn
                500                 505                 510

Gly Cys Lys Lys Asn Ile Val Val Tyr Ala Tyr Lys Val Leu Glu Gln
                515                 520                 525

Asn Gly Tyr Asn Ile Ile Ala Leu Glu Asn Leu Glu Asn Ser Asn Phe
                530                 535                 540

Glu Lys Ile Arg Val Leu Pro Lys Ile Lys Ser Leu Leu Glu Tyr His
545                 550                 555                 560

Lys Phe Glu Asn Lys Asn Ile Asn Asp Ile Lys Asn Ser Asp Lys Tyr
                565                 570                 575

Lys Glu Phe Ile Glu Pro Gly Tyr Phe Glu Leu Ile Thr Asn Glu Asn
                580                 585                 590

Asn Glu Ile Ile Asp Ala Lys Tyr Thr Gln Lys Gly Asp Ile Lys Ile
                595                 600                 605

Lys Asn Ala Asp Phe Ile Asn Ile Met Ile Lys Ala Leu Asn Phe Ala
                610                 615                 620

Ser Ile Lys Asp Glu Phe Ile Leu Leu Ser His Asn Gly Lys Ser Gln
625                 630                 635                 640

Ile Ala Leu Val Pro Ala Glu Tyr Thr Ser Gln Met Asp Ser Ile Asp
                645                 650                 655

His Cys Ile Tyr Met Thr Lys Asn Asp Lys Gly Lys Leu Val Lys Val
                660                 665                 670

Asp Lys Arg Lys Val Arg Thr Lys Gln Glu Arg His Ile Asn Gly Leu
                675                 680                 685

Asn Ala Asp Phe Asn Ala Ala Cys Asn Ile Lys Tyr Ile Val Thr Asn
                690                 695                 700

Glu Asp Trp Arg Lys Val Phe Cys Ile Lys Pro Lys Glu Asp Tyr
705                 710                 715                 720

Asn Thr Pro Leu Leu Asp Ala Thr Lys Asn Gly Gln Phe Arg Ile Leu
                725                 730                 735

Asp Lys Leu Lys Lys Leu Asn Ala Thr Lys Leu Leu Glu Met Glu Lys
                740                 745                 750

<210> SEQ ID NO 25
<211> LENGTH: 814
<212> TYPE: PRT
<213> ORGANISM: Unknown
<220> FEATURE:
<223> OTHER INFORMATION: Description of Unknown:
      mammals-digestive system-rumen-bos taurus sequence

<400> SEQUENCE: 25

Met Val Lys Val Phe Ile Asn Val Phe Leu Ser Glu Lys Asn Gln Ile

-continued

```
1               5                   10                  15
Thr Thr Asn Ile Phe Asp Thr Glu Lys Ile Ser Asn Ser Tyr Ile Asn
            20                  25                  30
His Ile Asn His Gln Phe Met Ala Thr His Lys Lys Thr Asp Asn Gln
            35                  40                  45
Thr Ile Val Lys Ala Tyr Val Met Lys Ala Lys Met Ser Lys His Asp
            50                  55                  60
Ile Glu Arg Val Trp Lys Pro Thr Ile Asp Glu Tyr Ile Asn Tyr Tyr
65                  70                  75                  80
Asn Lys Leu Ser Asp Trp Ile Cys Lys Asn Leu Thr Ser Val Thr Ile
                85                  90                  95
Gly Asp Leu Leu Lys Tyr Val Gly Glu Lys Gln Ile Asn Lys Gly Val
                100                 105                 110
Gly Tyr Tyr Thr Tyr Phe Ile Asp Glu Gln Lys Thr Asp Leu Pro Leu
                115                 120                 125
Tyr Thr Leu Phe Thr Asp Cys Pro Lys Thr His Ala Asp Asn Leu Leu
                130                 135                 140
Phe Glu Ala Val Arg Lys Ile Asn Pro Glu Asn Tyr Asn Gly Asn Leu
145                 150                 155                 160
Leu Ser Leu Phe Glu Thr Gly Tyr Arg Arg Asn Gly Tyr Phe Asp Asn
                165                 170                 175
Val Ile Ser Asn Tyr Arg Thr Lys Met Thr Thr Leu Lys Ile Asn Pro
                180                 185                 190
Lys Tyr Lys Arg Phe Ser Ser Glu Asn Met Pro Thr Asp Glu Val Leu
                195                 200                 205
Leu Glu Gln Thr Val Tyr Glu Val Thr Lys Asn Asp Phe Lys Asn Asp
                210                 215                 220
Asp Asp Trp Lys Lys Ser Ile Asp Tyr Met Lys Gln Lys Ser Glu Pro
225                 230                 235                 240
Asn Thr Ala Leu Ile Phe Arg Met Glu Thr Leu Phe Asp Tyr Trp Lys
                245                 250                 255
Asp His Lys Gln Asp Val Glu Gln Tyr Ile Asn Gln Lys Arg Val Glu
                260                 265                 270
Cys Leu Lys Asp Phe Gly Gly Cys Lys Arg Arg Ala Asp Gly Leu Ser
                275                 280                 285
Met Val Ile Leu Leu Asn Lys Lys Leu Thr Lys Ile Glu Ala Asp Gly
                290                 295                 300
Leu Thr Ser Tyr Lys Leu Thr Thr Asn Leu Phe Gly Gly Lys Tyr Met
305                 310                 315                 320
Ile Asn Ile Phe Gly His Arg Ala Leu Val Ser Val Cys Asn Gly Glu
                325                 330                 335
Arg Ala Glu Asn Glu Asn Ile Asp Ile Cys Asn Lys His Gly Glu Arg
                340                 345                 350
Phe Thr Phe Lys Ile Glu Asn Gly Asn Leu Phe Val Ala Leu Thr Ala
                355                 360                 365
Asp Tyr Asn Tyr Glu Lys Gln Pro Asn Leu Pro Lys Asn Ile Val Gly
                370                 375                 380
Val Asp Ile Asn Ile Lys His Ser Met Leu Asn Ser Ser Ile Glu Asp
385                 390                 395                 400
Lys Gly Lys Val Lys Gly Tyr Val Asn Leu Tyr Lys Glu Phe Leu Ser
                405                 410                 415
Asp Lys Asn Phe Arg Lys Thr Ile Thr Ser Asp Glu Glu Leu Asn Gln
                420                 425                 430
```

Tyr Ile Glu Leu Ser Lys Tyr Ala Thr Phe Gly Ile Thr Glu Leu Asp
            435                 440                 445

Ser Leu Phe Ala Arg Ala Thr Asp Thr Glu Lys Ser Ile Leu Cys Lys
    450                 455                 460

Arg Glu Leu Ala Met Gln Asp Val Phe Glu Lys Leu Glu Lys Arg Tyr
465                 470                 475                 480

Lys Asp Asp His Lys Ile Lys Phe Tyr Leu Gly Ser Thr Gln Lys Leu
                485                 490                 495

Arg Ala Gln Tyr Ile Ser Tyr Phe Lys Ile Lys Glu Ala Tyr Asn Arg
            500                 505                 510

Lys Gln Gln Glu Tyr Asp Leu Ala His Gly Lys Thr Asp Asn Pro Asp
            515                 520                 525

Glu Val Tyr Lys Ser Asp Phe Ile Asn Glu Pro Ser Ala Lys Glu Met
            530                 535                 540

Leu Val Lys Leu Asn Arg Ile Glu Arg Lys Ile Ile Gly Cys Arg Asn
545                 550                 555                 560

Asn Ile Val Thr Tyr Ala Phe Asn Val Ile Lys Asn Gly Tyr Asp
                565                 570                 575

Thr Ile Gly Val Glu Tyr Leu Thr Ser Ser Gln Phe Lys Lys Arg
            580                 585                 590

Arg Leu Pro Ser Ile Lys Ser Leu Leu Asn Tyr Arg Lys Leu Leu Gly
            595                 600                 605

Lys Pro Lys Asp Glu Trp Asn Leu Lys Glu Trp Asn Asp Val Tyr Met
610                 615                 620

Cys Tyr Arg Pro Glu Leu Asp Asp Ala Gly Asn Ile Met Asn Phe Thr
625                 630                 635                 640

Ile Thr Asn Glu Gly Ile Lys Arg Asn Lys Glu Ser Thr Phe Tyr Asn
                645                 650                 655

Ser Phe Ile Lys Ala Ile His Phe Ala Asp Val Lys Asp Lys Phe Ala
            660                 665                 670

Gln Leu Thr Asn Asn Asn Thr Met Asn Thr Val Phe Ile Pro Ser Ser
            675                 680                 685

Phe Thr Ser Gln Ile Asp Ser Lys Thr Arg Lys Leu Tyr Leu Leu Glu
            690                 695                 700

Tyr Thr Glu Lys Cys Asp Asn Gly Lys Thr Lys Lys Val Val Lys Phe
705                 710                 715                 720

Ile Asn Lys Arg Val Leu Arg Lys Ile Gln Glu Gln His Leu Asn Gly
                725                 730                 735

Met Asn Ala Asp Asn Asn Ala Ala Arg Asn Ile Arg Asp Ile Thr Lys
            740                 745                 750

Asn Leu Arg Asp Val Phe Thr Lys Lys Gln Thr Asp Lys Asn Cys Tyr
            755                 760                 765

Asn Ser Ala Glu Phe Met Ile Gln Thr Lys Phe Lys Lys Arg Leu Pro
            770                 775                 780

Gln Ala Thr Val Phe Gly Glu Leu Asn Arg Asn Gly Tyr Val Lys Val
785                 790                 795                 800

Leu Thr Gln Glu Glu Tyr Asp Glu Leu Thr Lys Ser Ala Lys
                805                 810

<210> SEQ ID NO 26
<211> LENGTH: 776
<212> TYPE: PRT
<213> ORGANISM: Unknown
<220> FEATURE:

<223> OTHER INFORMATION: Description of Unknown:
    mammals-digestive system-rumen-bos taurus sequence

<400> SEQUENCE: 26

```
Met Ala Thr His Lys Lys Thr Asp Asn Gln Thr Ile Val Lys Ala Tyr
1               5                   10                  15

Val Met Lys Ala Lys Met Ser Lys His Asp Ile Glu Arg Val Trp Lys
            20                  25                  30

Pro Thr Ile Asp Glu Tyr Ile Asn Tyr Tyr Asn Lys Leu Ser Asp Trp
        35                  40                  45

Ile Cys Lys Asn Leu Thr Ser Val Thr Ile Gly Asp Leu Leu Lys Tyr
    50                  55                  60

Val Gly Glu Lys Gln Ile Asn Lys Gly Val Gly Tyr Tyr Thr Tyr Phe
65                  70                  75                  80

Ile Asp Glu Gln Lys Thr Asp Leu Pro Leu Tyr Thr Leu Phe Thr Asp
                85                  90                  95

Cys Pro Lys Thr His Ala Asp Asn Leu Leu Phe Glu Ala Val Arg Lys
            100                 105                 110

Ile Asn Pro Glu Asn Tyr Asn Gly Asn Leu Leu Ser Leu Phe Glu Thr
        115                 120                 125

Gly Tyr Arg Arg Asn Gly Tyr Phe Asp Asn Val Ile Ser Asn Tyr Arg
    130                 135                 140

Thr Lys Met Thr Thr Leu Lys Ile Asn Pro Lys Tyr Lys Arg Phe Ser
145                 150                 155                 160

Ser Glu Asn Met Pro Thr Asp Glu Val Leu Leu Glu Gln Thr Val Tyr
                165                 170                 175

Glu Val Thr Lys Asn Asp Phe Lys Asn Asp Asp Trp Lys Lys Ser
            180                 185                 190

Ile Asp Tyr Met Lys Gln Lys Ser Glu Pro Asn Thr Ala Leu Ile Phe
        195                 200                 205

Arg Met Glu Thr Leu Phe Asp Tyr Trp Lys Asp His Lys Gln Asp Val
    210                 215                 220

Glu Gln Tyr Ile Asn Gln Lys Arg Val Glu Cys Leu Lys Asp Phe Gly
225                 230                 235                 240

Gly Cys Lys Arg Arg Ala Asp Gly Leu Ser Met Val Ile Leu Leu Asn
                245                 250                 255

Lys Lys Leu Thr Lys Ile Glu Ala Asp Gly Leu Thr Ser Tyr Lys Leu
            260                 265                 270

Thr Thr Asn Leu Phe Gly Gly Lys Tyr Met Ile Asn Ile Phe Gly His
        275                 280                 285

Arg Ala Leu Val Ser Val Cys Asn Gly Glu Arg Ala Glu Asn Glu Asn
    290                 295                 300

Ile Asp Ile Cys Asn Lys His Gly Glu Arg Phe Thr Phe Lys Ile Glu
305                 310                 315                 320

Asn Gly Asn Leu Phe Val Ala Leu Thr Ala Asp Tyr Asn Tyr Glu Lys
                325                 330                 335

Gln Pro Asn Leu Pro Lys Asn Ile Val Gly Val Asp Ile Asn Ile Lys
            340                 345                 350

His Ser Met Leu Asn Ser Ser Ile Glu Asp Lys Gly Lys Val Lys Gly
        355                 360                 365

Tyr Val Asn Leu Tyr Lys Glu Phe Leu Ser Asp Lys Asn Phe Arg Lys
    370                 375                 380

Thr Ile Thr Ser Asp Glu Glu Leu Asn Gln Tyr Ile Glu Leu Ser Lys
385                 390                 395                 400
```

Tyr Ala Thr Phe Gly Ile Thr Glu Leu Asp Ser Leu Phe Ala Arg Ala
            405                 410                 415

Thr Asp Thr Glu Lys Ser Ile Leu Cys Lys Arg Glu Leu Ala Met Gln
        420                 425                 430

Asp Val Phe Glu Lys Leu Glu Lys Arg Tyr Lys Asp Asp His Lys Ile
    435                 440                 445

Lys Phe Tyr Leu Gly Ser Thr Gln Lys Leu Arg Ala Gln Tyr Ile Ser
450                 455                 460

Tyr Phe Lys Ile Lys Glu Ala Tyr Asn Arg Lys Gln Gln Glu Tyr Asp
465                 470                 475                 480

Leu Ala His Gly Lys Thr Asp Asn Pro Asp Glu Val Tyr Lys Ser Asp
            485                 490                 495

Phe Ile Asn Glu Pro Ser Ala Lys Glu Met Leu Val Lys Leu Asn Arg
        500                 505                 510

Ile Glu Arg Lys Ile Ile Gly Cys Arg Asn Asn Ile Val Thr Tyr Ala
    515                 520                 525

Phe Asn Val Ile Lys Asn Asn Gly Tyr Asp Thr Ile Gly Val Glu Tyr
530                 535                 540

Leu Thr Ser Ser Gln Phe Glu Lys Lys Arg Arg Leu Pro Ser Ile Lys
545                 550                 555                 560

Ser Leu Leu Asn Tyr Arg Lys Leu Leu Gly Lys Pro Lys Asp Glu Trp
            565                 570                 575

Asn Leu Lys Glu Trp Asn Asp Val Tyr Met Cys Tyr Arg Pro Glu Leu
        580                 585                 590

Asp Asp Ala Gly Asn Ile Met Asn Phe Thr Ile Thr Asn Glu Gly Ile
    595                 600                 605

Lys Arg Asn Lys Glu Ser Thr Phe Tyr Asn Ser Phe Ile Lys Ala Ile
610                 615                 620

His Phe Ala Asp Val Lys Asp Lys Phe Ala Gln Leu Thr Asn Asn Asn
625                 630                 635                 640

Thr Met Asn Thr Val Phe Ile Pro Ser Ser Phe Thr Ser Gln Ile Asp
            645                 650                 655

Ser Lys Thr Arg Lys Leu Tyr Leu Leu Glu Tyr Thr Glu Lys Cys Asp
        660                 665                 670

Asn Gly Lys Thr Lys Lys Val Val Lys Phe Ile Asn Lys Arg Val Leu
    675                 680                 685

Arg Lys Ile Gln Glu Gln His Leu Asn Gly Met Asn Ala Asp Asn Asn
690                 695                 700

Ala Ala Arg Asn Ile Arg Asp Ile Thr Lys Asn Leu Arg Asp Val Phe
705                 710                 715                 720

Thr Lys Lys Gln Thr Asp Lys Asn Cys Tyr Asn Ser Ala Glu Phe Met
            725                 730                 735

Ile Gln Thr Lys Phe Lys Lys Arg Leu Pro Gln Ala Thr Val Phe Gly
        740                 745                 750

Glu Leu Asn Arg Asn Gly Tyr Val Lys Val Leu Thr Gln Glu Glu Tyr
    755                 760                 765

Asp Glu Leu Thr Lys Ser Ala Lys
    770                 775

<210> SEQ ID NO 27
<211> LENGTH: 778
<212> TYPE: PRT
<213> ORGANISM: Unknown
<220> FEATURE:

<223> OTHER INFORMATION: Description of Unknown:
    mammals-digestive system-rumen-bos taurus sequence

<400> SEQUENCE: 27

```
Met Ala His Lys Gly Glu Lys Glu Gly Tyr Gln Ile Lys Thr Leu Lys
1               5                   10                  15

Phe Lys Val Arg Ser His Asp Ile Gly Lys Ser Leu Tyr Asp Ile Val
            20                  25                  30

Asn Glu Tyr Thr Asn Tyr Tyr Asn Lys Val Ser Lys Trp Ile Cys Asp
            35                  40                  45

Asn Leu Asp Thr Pro Ile Gly Glu Leu Ser Lys Asn Ile Ser Glu Lys
            50                  55                  60

Arg His Asn Ser Lys Tyr Tyr Arg Ala Thr Asn Asp Pro Asn Trp Lys
65                  70                  75                  80

Asn Glu Pro Met Trp Lys Ile Phe Thr Lys Phe Ser Asn Gly Glu
                85                  90                  95

Thr Phe Ser Glu Gln Gly Lys Asn Asp Lys Leu Ala Asn Leu Ser Asn
                100                 105                 110

Cys Asp Asn Ile Leu Ser Tyr Ser Ile Ile Asp Tyr Asn Ile Asp Gly
            115                 120                 125

Tyr Thr Gly Asn Ile Leu Gly Leu Thr Asp Thr Ser Tyr Arg Leu Asn
        130                 135                 140

Gly Tyr Ile Ser Asn Cys Ile Ser Asn Tyr Lys Thr Lys Ile Arg Thr
145                 150                 155                 160

Ala Lys Pro Lys Val Arg Ser Thr Ala Ile Thr Glu His Ser Thr Val
                165                 170                 175

Glu Glu Lys Thr Asn Asn Thr Ile Tyr Glu Met Val Arg Lys Gly Phe
                180                 185                 190

Met Ser Pro Asn Asp Phe Lys Asn Gln Ile Lys Tyr Leu Thr Glu Lys
            195                 200                 205

Glu Asn Pro Asn Asp Lys Leu Ile Asp Arg Leu Ser Ile Leu His Ser
        210                 215                 220

Phe Tyr Thr Glu Asn Glu Glu Asp Val Asn Asn Ala Phe Ser Arg Met
225                 230                 235                 240

Ser Val Glu Met Leu Lys Asn Asn Asn Gly Cys Thr Arg Asn Gly Asp
                245                 250                 255

Lys Lys Thr Leu Asn Ile Ser Ser Ile Asp Tyr Lys Val Thr Arg Lys
            260                 265                 270

Glu Gly Cys Asp Gly Tyr Ile Leu Ser Phe Gly Ser Arg Asn Gln Lys
            275                 280                 285

Tyr Asn Ile Asp Leu Trp Gly Arg Arg Asp Thr Ile Ser Asn Gly Lys
        290                 295                 300

Glu Leu Ile Asp Leu Ser Glu His Gly Glu Pro Leu Thr Ile Thr Ser
305                 310                 315                 320

Glu Asn Gly Asp Tyr Tyr Val Cys Met Thr Val Asp Val Pro Phe Glu
                325                 330                 335

Lys Lys Ser Thr Gly Ser Thr Glu Lys Val Ala Ser Val Asp Val Asn
            340                 345                 350

Thr Lys His Thr Met Leu Ser Thr Asp Val Ile Asp Asp Gly Thr Leu
            355                 360                 365

Lys Gly Tyr Leu Asn Ile Tyr Lys Lys Leu Leu Leu Asp Thr Glu Leu
        370                 375                 380

Thr Ser Leu Leu His Lys Gln Asp Phe Asp Asp Met Lys Glu Leu Ser
385                 390                 395                 400
```

His Asn Val Cys Phe Gly Pro Ile Glu Tyr Asn Phe Leu Leu Ser Arg
            405                 410                 415

Ile Leu Asp Leu Asp Ala Tyr Glu Lys Lys Val Glu Asp Arg Ile Thr
            420                 425                 430

His Ser Met Lys Glu Met Leu Lys Thr Glu Thr Asp Glu Arg Asn Lys
            435                 440                 445

Met Tyr Leu Gly Ser Val Ile Lys Met Arg Ala Leu Leu Lys Val Tyr
            450                 455                 460

Ile Ser Thr Lys Asn Arg Tyr His Lys Glu Gln Gln Ser Tyr Asp Glu
465                 470                 475                 480

Ser Met Gly Phe Thr Asp Thr Ser Thr Ala Ser Lys Asp Thr Met Asp
            485                 490                 495

Lys Arg Arg Phe Glu Asn Pro Phe Ser Glu Thr Glu Thr Gly Lys Lys
            500                 505                 510

Leu Asn Asn Asp Leu Ser Ala Leu Ser Lys Lys Ile Ile Gly Cys Arg
            515                 520                 525

Asp Asn Ile Val Arg Tyr Ala Tyr Thr Thr Leu Gln Asp Asn Gly Tyr
            530                 535                 540

Thr Met Ile Gly Val Glu Asp Leu Asn Ser Ser Thr Phe Ala Asn Thr
545                 550                 555                 560

Arg Asn Pro Phe Pro Thr Ile Lys Ser Leu Leu Asn Tyr His His Leu
            565                 570                 575

Ser Gly Lys Thr Pro Glu Glu Ala Arg Asn Ile Asp Thr Tyr Ser Lys
            580                 585                 590

Phe Ser Asp His Tyr Thr Leu Thr Thr Asp Glu Glu Gly Lys Ile Thr
            595                 600                 605

Asp Ala Lys Tyr Thr Lys Lys Ala Glu Thr Lys Ile Lys Lys Lys Arg
            610                 615                 620

Ala Arg Asp Thr Ile Ile Lys Ala Ile His Phe Ala Glu Val Lys Asp
625                 630                 635                 640

Val Met Cys Val Met Ser Asn Asn Gly Thr Ala Ser Val Ala Phe Glu
            645                 650                 655

Pro Ser Tyr Phe Ser Ser Gln Met Asp Ser Ala Thr His Lys Val Tyr
            660                 665                 670

Thr Thr Arg Asn Lys Lys Gly Lys Asp Val Ile Ala Ser Lys Glu Thr
            675                 680                 685

Val Arg Pro Arg Gln Glu Lys His Ile Asn Gly Met Asn Cys Asp Ile
            690                 695                 700

Asn Ser Pro Lys Asn Leu Ser Tyr Leu Ile Thr Asn Glu Glu Phe Arg
705                 710                 715                 720

Glu Met Phe Leu Thr Pro Thr Lys Asn Gly Tyr Asn Glu Pro Phe Tyr
            725                 730                 735

Lys Ser Arg Val Lys Ser Ala Ala Ser Met Met Ser Gly Leu Lys Lys
            740                 745                 750

Leu Gly Ala Thr Met Pro Leu Thr Asp Glu Asn Ala Ile Phe Ser Thr
            755                 760                 765

Pro Lys Pro Lys Lys Asn Ile Gly Lys Gln
            770                 775

<210> SEQ ID NO 28
<211> LENGTH: 772
<212> TYPE: PRT
<213> ORGANISM: Unknown
<220> FEATURE:

<223> OTHER INFORMATION: Description of Unknown:
      mammals-digestive system-rumen-bos taurus sequence

<400> SEQUENCE: 28

```
Met Gly Asn Lys Val Gln Ser Asn Glu Thr Ile Val Lys Thr Tyr Thr
1               5                   10                  15

Phe Lys Val Arg Glu Phe Ile Ser Gly Ala Thr His Glu Ile Met Lys
                20                  25                  30

Ser Ala Ile Lys Gln Tyr Ile Glu Asp Ser Asn Asn Leu Ser Asp Trp
            35                  40                  45

Ile Asn Asn Gln Leu Thr Asn Lys Thr Ile Cys Glu Val Gly Ala Leu
50                  55                  60

Ile Pro Ile Glu Lys Arg Glu Thr Ser Tyr Tyr Lys Ser Thr Val Asp
65                  70                  75                  80

Glu Leu Trp Ala Asn Lys Pro Cys Phe Lys Met Phe Thr Asn Asp Phe
                85                  90                  95

Thr Lys Glu Glu Asn Phe Ala Thr Arg Asn Ile Gly Asn Gly Lys Asn
                100                 105                 110

Cys Lys Asn Ile Ile Thr Ser Ala Tyr Lys Ser Thr Val Asn Pro Ser
            115                 120                 125

Phe Arg Asn Val Leu Asp Leu Thr Glu Lys Val Tyr Phe Ser Asp Gly
            130                 135                 140

Tyr Gly Ala Asn Val Cys Ser Asn Tyr Lys Thr Lys Leu Arg Thr Leu
145                 150                 155                 160

Lys Pro Ala Lys Ile Lys Leu Val Ser Ser Leu Ser Asp Cys Asp Asp
                165                 170                 175

Asn Thr Leu Thr Glu Gln Val Ile Arg Glu Lys Gln Lys Tyr Gly Tyr
            180                 185                 190

Ser Thr Pro Lys Asp Phe Glu Lys Arg Ile Glu Tyr Leu Asn Glu Lys
            195                 200                 205

Glu Lys Ser Glu Gln Asn Ser Lys Ile Ile Glu Arg Leu Gln Lys Leu
            210                 215                 220

Tyr Glu Phe Tyr Asp Asn Asn Thr Lys Leu Val Glu Glu Lys Glu Leu
225                 230                 235                 240

Glu Leu Ser Val Lys Ser Leu Val Glu Phe Gly Gly Cys Arg Arg Gly
                245                 250                 255

Glu Lys Thr Met Thr Leu Asn Leu Pro Asp Ile Gly Tyr Glu Ile Gln
                260                 265                 270

Arg Lys Asp Asp Lys Tyr Gly Tyr Ile Phe Thr Leu Lys Cys Ser Lys
            275                 280                 285

Lys Arg Lys Ile Ile Ile Asp Val Trp Gly Ser Lys Ala Thr Ile Asp
290                 295                 300

Ser Asn Gly Asn Asp Lys Val Asp Ile Ile Asn Thr His Gly Lys Ser
305                 310                 315                 320

Ile Asn Phe Lys Ile Ile Asn Asn Glu Met Tyr Ile Asp Ile Thr Val
                325                 330                 335

Asp Val Pro Phe Ala Lys Arg Lys Leu Gly Ile Lys Lys Val Val Gly
                340                 345                 350

Ile Asp Val Asn Thr Lys His Met Leu Met Ala Thr Asn Ile Lys Val
            355                 360                 365

Thr Asp Ser Ile Lys Gly Tyr Val Asn Leu Tyr Lys Glu Phe Leu Asn
370                 375                 380

Ser Lys Glu Ile Met Asp Val Ala Ser Pro Glu Thr Lys Lys Asn Phe
385                 390                 395                 400
```

Glu Asp Met Ser Met Phe Val Asn Phe Cys Pro Ile Glu Tyr Asn Thr
            405                 410                 415

Met Phe Ala Leu Ile Phe Lys Leu Asn Asn Gly Asp Ile Arg Thr Glu
        420                 425                 430

Gln Ala Ile Arg Arg Thr Leu His Gln Leu Ser Lys Lys Phe Ser Asp
            435                 440                 445

Gly Asn His Glu Thr Glu Arg Ile Tyr Val Gln Asn Val Phe Ser Ile
        450                 455                 460

Arg Glu Gln Leu Lys His Phe Ile Leu Leu Ser Asn Arg Tyr Tyr Ser
465                 470                 475                 480

Glu Gln Ser Asp Tyr Asp Thr Lys Met Gly Phe Ile Asp Glu Asn Thr
            485                 490                 495

Thr Ser Asn Ala Thr Met Asp Lys Arg Arg Phe Asp Lys Ser Leu Met
        500                 505                 510

Phe Arg Tyr Thr Gln Arg Gly Arg Gln Leu Tyr Glu Glu Arg Ile Glu
            515                 520                 525

Cys Gly Arg Lys Ile Thr Glu Ile Arg Asp Asn Ile Ile Thr Tyr Ala
        530                 535                 540

Arg Asn Val Phe Val Leu Asn Gly Tyr Asp Thr Ile Ala Leu Glu Tyr
545                 550                 555                 560

Leu Thr Asn Ala Thr Ile Gln Lys Pro Thr Arg Pro Thr Ser Pro Lys
            565                 570                 575

Ser Leu Leu Asp Tyr Phe Lys Leu Lys Gly Lys Pro Val Val Glu Ala
        580                 585                 590

Glu Lys Asn Glu Arg Ile Thr Lys Asn Arg Lys Tyr Tyr Asn Leu Ile
            595                 600                 605

Pro Asp Glu Asn Asp Asn Val Ile Asn Ile Glu Tyr Thr Glu Glu Gly
        610                 615                 620

Lys Val Ala Ile Lys Lys Ser Ile Ala Arg Asp His Ile Met Lys Ala
625                 630                 635                 640

Val His Phe Ala Glu Val Lys Asp Lys Phe Ile Gln Leu Ser Asn Asn
            645                 650                 655

Gly Lys Thr Gln Val Ala Leu Val Pro Ser Asn Tyr Thr Ser Gln Met
        660                 665                 670

Asn Ser Glu Thr His Thr Val Tyr Leu Met Lys Asn Pro Lys Thr Lys
            675                 680                 685

Lys Leu Val Ile Met Asp Lys Asp Lys Val Arg Pro Ile Gln Glu Lys
        690                 695                 700

Tyr Lys Leu Asn Gly Leu Asn Ala Asp Phe Asn Ser Ala Arg Asn Ile
705                 710                 715                 720

Ala Tyr Ile Val Glu Asn Glu Ile Leu Arg Asn Ser Phe Leu Lys Glu
            725                 730                 735

Glu Thr Lys Lys Tyr Thr Tyr Asn Thr Pro Leu Phe Thr Pro Arg Leu
        740                 745                 750

Lys Ser Ser Glu Lys Ile Ile Thr Glu Leu Lys Lys Leu Gly Met Thr
            755                 760                 765

Thr Val Ile Glu
    770

<210> SEQ ID NO 29
<211> LENGTH: 781
<212> TYPE: PRT
<213> ORGANISM: Unknown
<220> FEATURE:

<223> OTHER INFORMATION: Description of Unknown:
    mammals-digestive system-rumen-bos taurus sequence

<400> SEQUENCE: 29

```
Met Ala Asn Lys Ser Thr Lys Gly Asn Leu Pro Lys Thr Ile Ile Met
1               5                   10                  15

Lys Ala Asn Leu Ser Pro Asp Gly Phe Thr Gln Trp Glu Arg Val Val
            20                  25                  30

Lys Glu Tyr Gln Ala Tyr Lys Asp Thr Leu Ser Lys Trp Val Ala Gln
        35                  40                  45

Asn Leu Thr Ala Met Lys Ile Gly Asp Leu Leu Pro Tyr Leu Asp Lys
    50                  55                  60

Tyr Ser Lys Lys Thr Asn Lys Glu Thr Gly Glu Arg Pro Val Asn Val
65                  70                  75                  80

Tyr Tyr Gln Leu Cys Glu Gln His Lys Asp Pro Leu Tyr Lys Leu
                85                  90                  95

Phe Thr Tyr Asp Ser Asn Ser Arg Asn Asn Ala Met Tyr Glu Ile Ile
                100                 105                 110

Arg Lys Thr Asn Cys Asp Gly Tyr Lys Gly Asn Ile Leu Gly Ile Ser
            115                 120                 125

Glu Thr His Tyr Arg Arg Asn Gly Phe Val Lys Asn Ile Leu Ala Asn
        130                 135                 140

Tyr Thr Lys Ile Ser Thr Leu Glu Leu Ser Glu Arg Lys Arg Lys
145                 150                 155                 160

Ile Asp Ser Asp Ser Pro Glu Asp Leu Ile Arg Ser Gln Val Val Tyr
                165                 170                 175

Glu Met Gln Lys Asn Asn Ile Lys Asp Ala Lys Gly Phe Lys Ser Ile
            180                 185                 190

Ile Glu Tyr Leu Lys Ser Lys Lys Glu Val Asn Ile Gln Tyr Leu Glu
        195                 200                 205

Arg Leu Gln Ile Leu Tyr Glu Tyr Phe Lys Asn His Glu Asn Glu Ile
    210                 215                 220

Lys Glu Tyr Ile Thr Leu Ala Ala Val Glu Gln Leu Lys Ser Phe Gly
225                 230                 235                 240

Gly Val Arg Val Asn Asn Glu Lys Ser Ser Met Asn Leu Glu Ile Gln
                245                 250                 255

Gly Phe Ser Ile Thr Arg Val Asp Gly Ala Cys Thr Tyr Ile Leu His
            260                 265                 270

Leu Pro Ile Asn Gly Lys Ile His Gly Ile Lys Leu Trp Gly Asn Arg
        275                 280                 285

Gln Val Val Asn Lys Asp Gly Thr Pro Val Asp Ile Leu Asp Leu
    290                 295                 300

Thr Asn Gln His Gly Ser Thr Ile Asn Ile Thr Ile Lys Asn Gly Glu
305                 310                 315                 320

Ile Tyr Phe Ala Phe Thr Val Thr Ser Asp Phe Val Lys Pro Glu His
                325                 330                 335

Gln Ile Lys Asn Val Val Gly Val Asp Val Asn Thr Lys His Met Leu
            340                 345                 350

Met Gln Ser Asn Ile Thr Asp Asn Gly Asn Val Lys Gly Tyr Phe Asn
        355                 360                 365

Ile Tyr Lys Val Leu Val Glu Asp Arg Arg Phe Thr Ser Leu Leu Ser
    370                 375                 380

Glu Glu Gln Leu Lys Tyr Phe Cys Glu Leu Ala Asn Ile Val Ser Phe
385                 390                 395                 400
```

Cys Pro Ile Glu Thr Glu Phe Leu Phe Ala Arg Tyr Ala Glu Tyr Lys
            405                 410                 415

Lys Met Ser Asn Asn Ala Glu Met Arg Gln Ile Glu Lys Val Phe Ser
        420                 425                 430

Asp Ile Leu Asp Glu Gln Tyr Lys Lys Tyr Lys Asp Ile Asp Thr Ser
            435                 440                 445

Ile Ala Asn Tyr Ile Ser Tyr Val Arg Lys Leu Arg Ser Gln Cys Cys
450                 455                 460

Ala Tyr Phe Lys Leu Lys Met Lys Tyr Lys Glu Leu Gln Arg Gln Phe
465                 470                 475                 480

Asp Lys Glu Gln Asp Tyr Lys Asp Leu Ser Thr Glu Ser Lys Glu Thr
            485                 490                 495

Met Asp Lys Arg Arg Trp Glu Asn Pro Phe Arg Asn Thr Pro Glu Ala
                500                 505                 510

Ser Lys Leu Ile Lys Lys Met Asp Asn Val Ser Arg Gln Leu Ile Gly
            515                 520                 525

Cys Arg Asp Asn Ile Ile Thr Tyr Ala Tyr Arg Val Phe Glu Lys Asn
530                 535                 540

Gly Tyr Asp Thr Ile Ser Leu Glu Asn Leu Glu Ser Ser Gln Phe Glu
545                 550                 555                 560

Asn Asn Asp His Val Ile Ala Pro Lys Ser Leu Leu Glu Tyr His His
                565                 570                 575

Leu Lys Gly Lys Thr Met Asn Tyr Leu Leu Ser Asp Glu Cys Lys Val
            580                 585                 590

Arg Ile Thr Thr Lys Asp Gly Lys Val Lys Glu Trp Tyr His Val Glu
595                 600                 605

Leu Asn Asp Lys Asp Glu Ile Asp Asn Ile Phe Leu Thr Pro Glu Gly
            610                 615                 620

Glu Thr Glu Lys Glu Lys Asn Leu Phe Asn Asn Met Val Ile Lys Ile
625                 630                 635                 640

Val His Phe Ala Asp Ile Lys Asp Lys Phe Ile Gln Leu Gly Asn Tyr
                645                 650                 655

Asn Lys Leu Gln Thr Val Leu Val Pro Ser Tyr Phe Thr Ser Gln Met
            660                 665                 670

Asp Ser Lys Thr His Ser Val Tyr Val Val Glu Thr Ala Asn Thr Lys
            675                 680                 685

Thr Ser Lys Lys Glu Leu Lys Leu Val Ser Lys Arg Val Arg Arg
690                 695                 700

Gln Gln Glu Trp His Ile Asn Gly Leu Asn Ala Asp Tyr Asn Ala Ala
705                 710                 715                 720

Cys Asn Ile Ala His Ile Ala Lys Asn Ile Glu Leu Arg Gln Ile Met
                725                 730                 735

Cys Lys Thr Pro Gln Thr Lys Asn Gly Tyr Ser Ser Pro Val Leu Thr
            740                 745                 750

Ser Lys Val Lys Ser Gln Val Glu Met Val Arg Glu Leu Lys Lys Met
            755                 760                 765

Gly Lys Thr Ile Leu Tyr Ser Asn Asp Ser Leu Pro Phe
770                 775                 780

<210> SEQ ID NO 30
<211> LENGTH: 798
<212> TYPE: PRT
<213> ORGANISM: Unknown
<220> FEATURE:

<223> OTHER INFORMATION: Description of Unknown:
      mammals-digestive system-rumen-bos taurus sequence

<400> SEQUENCE: 30

```
Met Ala His Arg Lys Lys Asp Asp Glu Ala Thr Leu Ser Tyr Lys
1               5                   10                  15

Phe Lys Val Lys Val Ile Glu Gly Asp Leu Thr Ala Asp Ile Thr
            20                  25                  30

Lys Cys Ile Ala Glu Asn Ala Glu Gln Gly Asn His Phe Ser Glu Phe
        35                  40                  45

Ile His Lys Asn Leu Thr Ser Lys Thr Ile Gly Glu Phe Ala Ser Gln
    50                  55                  60

Leu Pro Val Glu Lys Arg Gln Phe Gly Tyr Tyr Gln Tyr Ala Ile Gly
65              70                  75                  80

Gly Thr Met Pro Ala Lys Lys Asn Ala Ser Asp Glu Asp Lys Pro Lys
                85                  90                  95

Gly Glu Leu Ile Asp Trp Ser Lys Lys Pro Phe Tyr Val Leu Phe Ser
            100                 105                 110

Lys Gly Tyr Ser Ala Thr His Ala Val Asn Leu Ile Phe Asn Val Tyr
        115                 120                 125

Leu Asn Ser Glu Glu Gly Lys Ala Phe Ser Ala Lys Asn Ser Met Asn
    130                 135                 140

Leu Ser Lys Ser Gln Phe Ala Tyr Ser Gly Phe Val Gln Ile Val Cys
145                 150                 155                 160

Ala Asn Tyr Ala Ser Met Leu Ala Asn Ala Arg Pro Asp Lys Ile Lys
                165                 170                 175

Phe Glu Glu Ile Thr Glu Ala Thr Asp Asp Gly Thr Lys Lys Met Gln
            180                 185                 190

Val Val Arg Glu Met Ala Glu Arg Tyr Leu Met Lys Pro Lys Asn Phe
        195                 200                 205

Ala Ser Arg Ile Glu Tyr Leu Glu Ala Asn Asn Thr Lys Gly Lys Phe
    210                 215                 220

Asp Lys Thr Ile Gln Arg Leu Arg Leu Leu Gln Pro Phe Phe Glu Lys
225                 230                 235                 240

Asn Glu Glu Gly Ile Thr Glu Leu Tyr Tyr Asp Leu Ser Val Lys Ala
                245                 250                 255

Leu Glu His Ser Gly Gln Cys Thr Tyr Lys Gly Gly Arg Thr Ile Ser
            260                 265                 270

Ile Leu Glu Ile Gly Asp Ile Arg Ile Ser Arg Lys Glu Asn Ala Lys
        275                 280                 285

Gly Tyr Leu Leu Thr Ile Pro Ile Asn Arg Lys Ser Val Val Phe Asp
    290                 295                 300

Leu Tyr Gly Arg Lys Asp Thr Ile Gly Gly Asp Gly Arg Asp Leu Ile
305                 310                 315                 320

Asp Ile Met Asn Thr His Gly Ser Ser Leu Gln Phe Thr Ala Asp Gly
                325                 330                 335

Asn Asp Ile Tyr Leu Thr Ile Thr Ala Thr Lys Asn Phe Ile Lys Glu
            340                 345                 350

Lys Pro Thr Phe Asn Glu Asp Thr Val Leu Gly Gly Asp Val Asn Ile
        355                 360                 365

Lys His Ser Tyr Thr Val Phe Ser Thr Ser Pro Lys Asp Ile Pro Asp
    370                 375                 380

Phe Val Asn Phe Tyr Glu Tyr Phe Ala Lys Asp Gly Glu Ile Met Lys
385                 390                 395                 400
```

```
Leu Ala Pro Lys Pro Met Trp Asp Tyr Ile Val Ala Ala Thr Lys
            405                 410                 415

Phe Leu Thr Ile Leu Pro Ile Glu Thr Pro Ala Ile Ser Ala Thr Val
            420                 425                 430

Tyr Gly Lys Arg Thr Glu Glu Gly Ile Ser Arg Ala Thr Phe Arg Glu
            435                 440                 445

Thr Gln Lys Leu Ile Ala Leu Glu Lys Ala Ile Glu Arg Val Met Lys
        450                 455                 460

Gln Val Phe Asp Lys Tyr Asn Asp Gly Lys His Pro Leu Glu Ala Ile
465                 470                 475                 480

Tyr Ile Gly Asn Ala Ile Lys Tyr Arg Arg Leu Ile Lys Gly Tyr Leu
                485                 490                 495

Ala Gln Lys Lys Lys Tyr Tyr Ser Ala His Ser Glu Tyr Asp Lys Ala
                500                 505                 510

Met Gly Tyr Thr Asp Asp Thr Asp Arg Lys Glu Asn Met Asp Glu
        515                 520                 525

Arg Arg Phe Asp Asp Ser Lys Lys Phe Arg Tyr Thr Pro Glu Ala Gln
    530                 535                 540

Ala Leu Leu Asp Thr Met His Thr Ile Glu Lys Lys Ile Val Gly Cys
545                 550                 555                 560

Val Ser Asn Ala Ile Ser Tyr Ala Tyr His Lys Phe Asp Glu Asn Gly
                565                 570                 575

Phe Asn Val Ile Ala Leu Glu Asn Leu Thr Ser Ala Thr Phe Ala Lys
                580                 585                 590

Lys Tyr Lys Ser Asp Lys Pro Glu Ser Ile Lys Lys Leu Leu Asn Phe
            595                 600                 605

Asp Lys Leu Leu Gly Lys Thr Leu Asp Glu Ala Lys Ala Ser Lys Ser
        610                 615                 620

Ile Ser Lys His Pro Asn Trp Tyr Glu Leu Val Ala Asp Glu Asn Gly
625                 630                 635                 640

Cys Val Ser Asp Ile Arg Ile Thr Asp Glu Gly Gln Ser Ala Thr Tyr
                645                 650                 655

Arg Ser Leu Val Thr Glu Thr Ile Met Lys Val Ser His Phe Ala Glu
            660                 665                 670

Thr Lys Asp Arg Phe Ile Gly Leu Ala Asn Ser Gly Arg Leu Gln Val
        675                 680                 685

Gly Leu Val Pro Ser Gln Tyr Thr Ser Tyr Ile Asp Ser Thr Thr His
    690                 695                 700

Thr Leu Tyr Ala Val Ile Glu Asp Gly Lys Thr Val Leu Ala Pro Lys
705                 710                 715                 720

Glu Val Val Arg Ala Ser Gln Glu Arg His Ile Asn Gly Leu Asn Ala
                725                 730                 735

Asp Tyr Asn Ser Ala Leu Asn Leu Lys Tyr Met Ile Thr Asp Glu Asn
            740                 745                 750

Phe Arg Lys Thr Phe Thr Ser Glu Thr Ser Ala Asp Lys Phe Gly Trp
        755                 760                 765

Gly Lys Pro Met Phe Ser Pro Thr Thr Arg Ser Gln Asp Glu Val Phe
    770                 775                 780

Ser Ala Ile Lys Lys Ile Gly Ala Ile Thr Val Leu Glu Asp
785                 790                 795

<210> SEQ ID NO 31
<211> LENGTH: 786
```

```
<212> TYPE: PRT
<213> ORGANISM: Unknown
<220> FEATURE:
<223> OTHER INFORMATION: Description of Unknown:
      mammals-digestive system-rumen-bos taurus sequence

<400> SEQUENCE: 31

Met Ala Gln His Lys Ser Asn Asn Glu Glu Ser Ala Ile Asn Lys Thr
1               5                   10                  15

Phe Ile Phe Lys Ala Lys Cys Glu Lys Asn Asp Val Ile Ser Leu Trp
                20                  25                  30

Glu Pro Ala Ala Lys Glu Tyr Gly Asp Tyr Tyr Asn Lys Val Ser Lys
                35                  40                  45

Trp Ile Ala Asp Asn Leu Ile Thr Met Lys Ile Gly Asp Leu Ala Gln
        50                  55                  60

Tyr Ile Thr Asn Gln Asn Ser Lys Tyr Tyr Thr Ala Val Thr Asn Lys
65                  70                  75                  80

Lys Lys Lys Asp Leu Pro Leu Tyr Arg Ile Phe Gln Lys Gly Phe Ser
                85                  90                  95

Ser Gln Cys Ala Asp Asn Ala Leu Tyr Cys Ala Ile Lys Ser Ile Asn
                100                 105                 110

Pro Glu Asn Tyr Lys Gly Asn Ser Leu Gly Ile Gly Glu Ser Asp Tyr
                115                 120                 125

Arg Arg Phe Gly Tyr Ile Gln Ser Val Val Ser Asn Phe Arg Thr Lys
130                 135                 140

Met Ser Ser Leu Lys Val Ser Val Lys Tyr Lys Lys Phe Asp Val Ser
145                 150                 155                 160

Asn Val Asp Asp Glu Thr Leu Lys Ile Gln Thr Ile Tyr Asp Val Asp
                165                 170                 175

Lys Tyr Gly Ile Glu Thr Ala Lys Glu Phe Lys Glu Leu Ile Glu Thr
                180                 185                 190

Leu Lys Thr Arg Val Glu Thr Pro Gln Leu Asn Asp Thr Ile Ala Arg
                195                 200                 205

Leu Lys Cys Leu Cys Asp Tyr Tyr Ser Lys Asn Glu Lys Ala Ile Asn
        210                 215                 220

Asn Glu Ile Glu Thr Met Ala Ile Ala Asp Leu Gln Lys Phe Gly Gly
225                 230                 235                 240

Cys Gln Arg Lys Ser Leu Asn Ala Phe Thr Ile His Lys Gln Asp Ser
                245                 250                 255

Leu Met Glu Lys Val Gly Asn Thr Ser Phe Arg Leu Gln Leu Ser Phe
                260                 265                 270

Arg Lys Lys Thr Tyr Val Ile Asn Leu Leu Gly Asn Arg Gln Val Val
                275                 280                 285

Asn Phe Val Asn Gly Lys Arg Val Asp Leu Ile Asp Ile Ala Glu Asn
290                 295                 300

His Gly Asp Leu Ile Thr Phe Asn Ile Lys Asn Gly Glu Leu Phe Leu
305                 310                 315                 320

His Ile Thr Ser Pro Ile Val Phe Asp Lys Asp Val Arg Asp Ile Arg
                325                 330                 335

Asn Val Val Gly Ile Asp Val Asn Ile Lys His Ser Met Leu Ala Thr
                340                 345                 350

Ser Ile Lys Asp Asp Gly Asn Val Lys Gly Tyr Ile Asn Leu Tyr Lys
                355                 360                 365

Glu Leu Leu Asn Asp Asp Val Phe Val Ser Thr Cys Asn Glu Ser Glu
                370                 375                 380
```

Leu Ala Leu Tyr Arg Gln Met Ser Glu Asn Val Asn Phe Gly Ile Leu
385                 390                 395                 400

Glu Thr Asp Ser Leu Phe Glu Arg Ile Val Asn Gln Ser Lys Gly Gly
            405                 410                 415

Cys Leu Lys Asn Lys Leu Ile Arg Arg Glu Leu Ala Met Gln Lys Val
        420                 425                 430

Phe Glu Arg Ile Thr Lys Thr Asn Lys Asp Gln Asn Ile Val Asp Tyr
    435                 440                 445

Val Asn Tyr Val Lys Met Met Arg Ala Lys Cys Lys Ala Ser Tyr Ile
450                 455                 460

Leu Lys Glu Lys Tyr Asp Glu Lys Gln Lys Glu Tyr Tyr Val Lys Met
465                 470                 475                 480

Gly Phe Thr Asp Glu Ser Thr Glu Ser Lys Glu Thr Met Asp Lys Arg
            485                 490                 495

Arg Glu Glu Phe Pro Phe Val Asn Thr Asp Thr Ala Lys Glu Leu Leu
            500                 505                 510

Val Lys Gln Asn Asn Ile Arg Gln Asp Ile Ile Gly Cys Arg Asp Asn
        515                 520                 525

Ile Val Thr Tyr Ala Phe Asn Val Phe Lys Asn Glu Tyr Asp Thr
        530                 535                 540

Leu Ser Val Glu Tyr Leu Asp Ser Ser Gln Phe Asp Lys Arg Arg Ile
545                 550                 555                 560

Pro Thr Pro Lys Ser Leu Leu Lys Tyr His Lys Phe Glu Gly Lys Thr
            565                 570                 575

Lys Asp Glu Val Glu Asn Met Met Lys Ser Glu Lys Leu Ser Asn Ala
            580                 585                 590

Tyr Tyr Thr Phe Lys Tyr Glu Asn Asp Val Val Ser Asp Ile Asp Tyr
        595                 600                 605

Ser Asp Glu Gly Asn Leu Arg Arg Ser Lys Leu Asn Phe Gly Asn Trp
        610                 615                 620

Ile Ile Lys Ala Ile His Phe Ala Asp Ile Lys Asp Lys Phe Val Gln
625                 630                 635                 640

Leu Ser Asn Asn Asn Lys Met Asn Ile Val Phe Cys Pro Ser Ala Phe
            645                 650                 655

Ser Ser Gln Met Asp Ser Ile Thr His Thr Leu Tyr Tyr Val Glu Lys
            660                 665                 670

Ile Thr Lys Asn Lys Lys Gly Lys Glu Lys Lys Lys Tyr Val Leu Ala
        675                 680                 685

Asn Lys Lys Met Val Arg Thr Gln Gln Glu Thr His Ile Asn Gly Leu
        690                 695                 700

Asn Ala Asp Tyr Asn Ser Ala Cys Asn Leu Lys Tyr Ile Ala Leu Asn
705                 710                 715                 720

Tyr Glu Leu Arg Asp Lys Met Thr Asp Arg Phe Lys Ala Ser Lys Lys
            725                 730                 735

Ile Lys Thr Met Tyr Asn Ile Pro Ala Tyr Asn Ile Lys Ser Asn Phe
            740                 745                 750

Lys Lys Asn Leu Ser Ala Lys Thr Ile Gln Thr Phe Arg Glu Leu Gly
        755                 760                 765

His Tyr Arg Asp Gly Lys Ile Asn Glu Asp Gly Met Phe Val Glu Ile
        770                 775                 780

Leu Glu
785

```
<210> SEQ ID NO 32
<211> LENGTH: 781
<212> TYPE: PRT
<213> ORGANISM: Unknown
<220> FEATURE:
<223> OTHER INFORMATION: Description of Unknown:
      mammals-digestive system-rumen-bos taurus sequence

<400> SEQUENCE: 32
```

| | | | | | | | | | | | | | | |
|---|---|---|---|---|---|---|---|---|---|---|---|---|---|---|
| Met | Ala | His | Lys | Asn | Ser | Asp | Gly | Glu | Asn | Thr | Ile | Asn | Lys | Thr | Phe |
| 1 | | | | 5 | | | | | 10 | | | | | 15 | |
| Ile | Phe | Lys | Val | Lys | Cys | Glu | Lys | Asn | Asp | Ile | Ile | Ser | Phe | Trp | Lys |
| | | | 20 | | | | | 25 | | | | | 30 | | |
| Pro | Ala | Ala | Glu | Glu | Tyr | Cys | Asn | Tyr | Tyr | Asn | Lys | Leu | Ser | Glu | Trp |
| | | | 35 | | | | 40 | | | | | 45 | | | |
| Ile | Gly | Lys | Asn | Leu | Ile | Ser | Met | Lys | Ile | Gly | Asp | Leu | Ala | Lys | Tyr |
| | 50 | | | | | 55 | | | | | 60 | | | | |
| Ile | Asp | Asn | Pro | Lys | Ser | Lys | Tyr | Tyr | Leu | Ser | Val | Thr | Asp | Glu | Asn |
| 65 | | | | | 70 | | | | | 75 | | | | | 80 |
| Lys | Lys | Asp | Leu | Pro | Leu | Tyr | Lys | Ile | Phe | Gln | Lys | Gly | Phe | Ser | Ser |
| | | | | 85 | | | | | 90 | | | | | 95 | |
| Ile | Asp | Ala | Asp | Asn | Ala | Leu | Tyr | Cys | Ala | Ile | Asp | Lys | Leu | Asn | Pro |
| | | | 100 | | | | | 105 | | | | | 110 | | |
| Glu | Gly | Tyr | Asn | Gly | Asn | Ile | Leu | Gly | Val | Gly | Lys | Ser | Asp | Tyr | Arg |
| | | | 115 | | | | | 120 | | | | | 125 | | |
| Arg | Asn | Gly | Tyr | Val | Ser | Ser | Val | Ile | Gly | Asn | Phe | Arg | Thr | Lys | Met |
| | 130 | | | | | 135 | | | | | 140 | | | | |
| Val | Ser | Leu | Lys | Ala | Asn | Val | Arg | Trp | Lys | Lys | Ile | Asp | Ile | Gly | Asn |
| 145 | | | | | 150 | | | | | 155 | | | | | 160 |
| Val | Asp | Glu | Glu | Thr | Leu | Arg | Arg | Gln | Thr | Ile | Cys | Asp | Val | Glu | Lys |
| | | | | 165 | | | | | 170 | | | | | 175 | |
| Tyr | Arg | Ile | Glu | Ser | Glu | Lys | Asp | Phe | Arg | Asp | Leu | Ile | Asp | Ile | Leu |
| | | | 180 | | | | | 185 | | | | | 190 | | |
| Lys | Ala | Arg | Glu | Glu | Thr | Pro | Arg | Leu | Lys | Glu | Lys | Ile | Ser | Arg | Leu |
| | | | 195 | | | | | 200 | | | | | 205 | | |
| Glu | Leu | Leu | Tyr | Asp | Tyr | Tyr | Ser | Lys | Asn | Thr | Lys | Thr | Ile | Lys | Ser |
| | 210 | | | | | 215 | | | | | 220 | | | | |
| Glu | Met | Glu | Asn | Met | Ala | Ile | Ser | Asp | Leu | Gln | Lys | Phe | Gly | Gly | Cys |
| 225 | | | | | 230 | | | | | 235 | | | | | 240 |
| Val | Arg | Lys | Ser | Leu | Asn | Thr | Ile | Thr | Ile | His | Lys | Gln | Asp | Ser | Lys |
| | | | | 245 | | | | | 250 | | | | | 255 | |
| Ile | Glu | Lys | Glu | Gly | Asn | Thr | Ser | Phe | Arg | Leu | His | Met | Val | Phe | Asn |
| | | | 260 | | | | | 265 | | | | | 270 | | |
| Lys | Lys | Pro | Tyr | Thr | Ile | Thr | Leu | Leu | Gly | Asn | Arg | Gln | Val | Val | Lys |
| | | | 275 | | | | | 280 | | | | | 285 | | |
| Tyr | Ile | Asp | Gly | Lys | Arg | Val | Asp | Ile | Val | Asn | Ile | Val | Glu | Lys | His |
| | 290 | | | | | 295 | | | | | 300 | | | | |
| Gly | Asp | Trp | Ile | Thr | Phe | Asn | Ile | Lys | Asn | Gly | Glu | Leu | Phe | Val | His |
| 305 | | | | | 310 | | | | | 315 | | | | | 320 |
| Leu | Thr | Lys | Cys | Val | Glu | Phe | Ser | Lys | Gly | Gln | Lys | Glu | Ile | Lys | Lys |
| | | | | 325 | | | | | 330 | | | | | 335 | |
| Ala | Ala | Gly | Val | Asp | Val | Asn | Ile | Lys | His | Ala | Met | Leu | Ala | Ala | Ser |
| | | | 340 | | | | | 345 | | | | | 350 | | |
| Ile | Val | Asp | Asp | Gly | Gln | Leu | Lys | Gly | Tyr | Val | Asn | Leu | Tyr | Arg | Glu |
| | | | 355 | | | | | 360 | | | | | 365 | | |

```
Leu Ile Glu Asp Asp Phe Val Ser Thr Phe Gly Asp Ser Asp Ser
    370                 375                 380

Gly Lys Thr Glu Leu Gly Met Tyr Gln Lys Met Ala Lys Thr Val Phe
385                 390                 395                 400

Phe Gly Val Leu Glu Val Glu Ser Leu Phe Glu Arg Val Val Asn Gln
                405                 410                 415

Gln Ser Gly Trp Lys Leu Asp Asn Gln Leu Ile Arg Arg Glu Arg Ala
                420                 425                 430

Met Glu Lys Val Phe Asp Arg Ile Val Lys Thr Thr Ser Asn Lys His
            435                 440                 445

Ile Ile Asp Tyr Val Asn Tyr Val Lys Met Leu Arg Ala Lys Tyr Lys
    450                 455                 460

Ala Tyr Phe Ile Leu Asp Glu Lys Tyr His Glu Lys Gln Arg Glu Tyr
465                 470                 475                 480

Asp Leu Ser Met Gly Phe Thr Asp Glu Ser Asp Glu Arg Arg Glu Leu
                485                 490                 495

Tyr Pro Phe Ile Asn Thr Glu Thr Ala Lys Glu Ile Leu Gly Lys Lys
                500                 505                 510

Arg Asn Val Glu Gln Asp Leu Ile Gly Cys Arg Asp Asn Ile Val Thr
            515                 520                 525

Tyr Ala Phe Asn Val Leu Arg Asn Asn Gly Tyr Asp Thr Ile Ser Val
            530                 535                 540

Glu Tyr Leu Asp Ser Ser Gln Phe Asp Lys Arg Arg Met Pro Thr Pro
545                 550                 555                 560

Lys Ser Leu Leu Glu Tyr His Lys Phe Lys Gly Lys Thr Gln Asp Glu
                565                 570                 575

Val Glu Arg Leu Met Ser Glu Lys Lys Phe Ala Lys Thr Asn Tyr Asp
            580                 585                 590

Ile His Tyr Asp Gly Glu Asn Lys Val Asp Gly Ile Val Tyr Ser Lys
            595                 600                 605

Glu Gly Glu Leu Arg Gln Lys Lys Leu Asn Phe Met Asn Leu Val Ile
610                 615                 620

Lys Ala Ile His Phe Ala Asp Ile Lys Asp Lys Phe Ala Gln Leu Cys
625                 630                 635                 640

Asn Asn Asn Asp Val Asn Val Val Phe Gly Pro Ser Ala Phe Thr Ser
                645                 650                 655

Gln Met Asp Ser Glu Thr His Ser Leu Tyr Tyr Val Glu Lys Glu Thr
                660                 665                 670

Asn Gly Lys Asn Gly Lys Thr Gly Lys Lys Phe Val Leu Ala Asp Lys
            675                 680                 685

Lys Ser Val Arg Arg Gln Glu Thr His Ile Asn Gly Leu Asn Ala
690                 695                 700

Asp Phe Asn Ala Ala Arg Asn Leu Glu Tyr Ile Ala Ser Asn Pro Glu
705                 710                 715                 720

Leu Leu Glu Arg Met Thr Lys Arg Thr Lys Ser Gly Lys Asp Met Tyr
                725                 730                 735

Asn Thr Pro Ser Trp Asn Ile Arg Gln Glu Phe Lys Lys Asn Leu Ser
            740                 745                 750

Val Arg Thr Ile Asn Thr Phe Arg Glu Leu Gly Asn Val Lys Tyr Gly
            755                 760                 765

Lys Ile Asn Asn Glu Gly Leu Phe Val Glu Asp Val
770                 775                 780
```

<210> SEQ ID NO 33
<211> LENGTH: 798
<212> TYPE: PRT
<213> ORGANISM: Unknown
<220> FEATURE:
<223> OTHER INFORMATION: Description of Unknown:
    mammals-digestive system-rumen-bos taurus sequence

<400> SEQUENCE: 33

Met Ala His Arg Lys Lys Asp Asp Glu Ala Thr Leu Ser Tyr Lys
1               5                   10                  15

Phe Lys Val Lys Val Ile Glu Gly Asp Leu Thr Ala Asp Ile Thr
                20                  25                  30

Lys Cys Ile Ala Glu Asn Ala Glu Gln Gly Asn His Phe Ser Glu Phe
            35                  40                  45

Ile His Lys Asn Leu Thr Ser Lys Thr Ile Gly Glu Phe Ala Ser Gln
    50                  55                  60

Leu Pro Ala Glu Lys Arg Gln Phe Gly Tyr Tyr Gln Tyr Ala Ile Gly
65                  70                  75                  80

Gly Thr Met Pro Ala Lys Lys Asn Ala Ser Asp Glu Lys Pro Lys
                85                  90                  95

Gly Glu Leu Ile Asp Trp Ser Lys Lys Pro Phe Tyr Val Leu Phe Ser
                100                 105                 110

Lys Gly Tyr Ser Ala Thr His Ala Val Asn Leu Ile Phe Asn Val Tyr
            115                 120                 125

Leu Asn Ser Glu Glu Gly Lys Ala Phe Ser Ala Lys Asn Ser Met Asn
    130                 135                 140

Leu Ser Lys Ser Gln Phe Ala Tyr Ser Gly Phe Val Gln Ile Val Cys
145                 150                 155                 160

Ala Asn Tyr Ala Ser Met Leu Ala Asn Ala Arg Pro Asp Lys Ile Lys
                165                 170                 175

Phe Glu Glu Ile Thr Glu Ala Thr Asp Asp Gly Thr Lys Lys Met Gln
                180                 185                 190

Val Val Arg Glu Met Ala Glu Arg Tyr Leu Met Lys Pro Lys Asn Phe
            195                 200                 205

Ala Ser Arg Ile Glu Tyr Leu Glu Ala Asn Asn Thr Lys Gly Lys Phe
    210                 215                 220

Asp Lys Thr Ile Gln Arg Leu Arg Leu Leu Gln Pro Phe Phe Glu Lys
225                 230                 235                 240

Asn Glu Glu Ser Ile Thr Glu Leu Tyr Tyr Asp Leu Ser Val Lys Ala
                245                 250                 255

Leu Glu His Ser Gly Gln Cys Thr Tyr Lys Gly Gly Arg Thr Ile Ser
            260                 265                 270

Ile Leu Glu Ile Gly Asp Ile Arg Ile Ser Arg Lys Glu Asn Ala Lys
    275                 280                 285

Gly Tyr Leu Leu Thr Ile Pro Ile Asn Arg Lys Ser Val Val Phe Asp
        290                 295                 300

Leu Tyr Gly Arg Lys Asp Thr Ile Gly Gly Asp Gly Arg Asp Leu Ile
305                 310                 315                 320

Asp Ile Met Asn Thr His Gly Ser Ser Leu Gln Phe Thr Ala Asp Glu
                325                 330                 335

Asn Asp Ile Tyr Leu Thr Ile Thr Ala Thr Lys Asn Phe Ile Lys Glu
            340                 345                 350

Lys Pro Thr Phe Asn Glu Asp Thr Val Leu Gly Gly Asp Val Asn Ile
        355                 360                 365

-continued

Lys His Ser Tyr Thr Val Phe Ser Ala Ser Pro Lys Asp Ile Pro Asp
        370                     375                 380

Phe Val Asn Phe Tyr Glu Tyr Phe Ala Lys Asp Gly Glu Ile Met Lys
385                     390                 395                 400

Leu Ala Pro Lys Pro Met Trp Asp Tyr Ile Val Ala Ala Thr Lys
                405                 410                 415

Phe Leu Thr Ile Leu Pro Ile Glu Thr Pro Ala Ile Ser Ala Thr Val
                420                 425                 430

Tyr Gly Lys Arg Thr Glu Gly Ile Ser Arg Ala Thr Phe Arg Glu
            435                 440                 445

Thr Gln Lys Leu Ile Ala Leu Glu Lys Ala Ile Glu Arg Val Met Lys
        450                     455                 460

Gln Val Phe Asp Lys Tyr Asn Asp Gly Lys His Pro Leu Glu Ala Ile
465                 470                 475                 480

Tyr Ile Gly Asn Ala Ile Lys Tyr Arg Arg Leu Ile Lys Gly Tyr Leu
                485                 490                 495

Ala Gln Lys Lys Lys Tyr Tyr Ser Ala His Ser Glu Tyr Asp Lys Ala
            500                 505                 510

Met Gly Tyr Thr Asp Asp Thr Asp Arg Lys Glu Asn Met Asp Glu
        515                 520                     525

Arg Arg Phe Asp Asp Ser Lys Lys Phe Arg Tyr Thr Pro Glu Ala Gln
530                 535                 540

Ala Leu Leu Asp Thr Met His Thr Ile Glu Lys Lys Ile Val Gly Cys
545                 550                 555                 560

Val Ser Asn Ala Ile Ser Tyr Ala Tyr His Lys Phe Asp Glu Asn Gly
                565                 570                 575

Phe Asn Val Ile Ala Leu Glu Asn Leu Thr Ser Ala Thr Phe Ala Lys
                580                 585                 590

Lys Tyr Lys Ser Asp Lys Pro Glu Ser Ile Lys Lys Leu Leu Asn Phe
            595                 600                 605

Asp Lys Leu Leu Gly Lys Thr Leu Asp Glu Ala Lys Ala Ser Lys Ser
            610                 615                 620

Ile Ser Lys His Pro Asn Trp Tyr Glu Leu Val Ala Asp Glu Asn Gly
625                 630                 635                 640

Cys Val Ser Asp Ile Arg Ile Thr Asp Glu Gly Gln Ser Ala Thr Tyr
                645                 650                 655

Arg Ser Leu Val Thr Glu Thr Ile Met Lys Val Ser His Phe Ala Glu
                660                 665                 670

Thr Lys Asp Arg Phe Ile Gly Leu Ala Asn Ser Gly Arg Leu Gln Val
            675                 680                 685

Gly Leu Val Pro Ser Gln Tyr Thr Ser Tyr Ile Asp Ser Thr Thr His
        690                     695                 700

Thr Leu Tyr Ala Val Ile Glu Asp Gly Lys Thr Val Leu Ala Pro Lys
705                     710                 715                 720

Glu Val Val Arg Ala Ser Gln Glu Arg His Ile Asn Gly Leu Asn Ala
                725                 730                 735

Asp Tyr Asn Ser Ala Leu Asn Leu Lys Tyr Met Ile Thr Asp Glu Asn
                740                 745                 750

Phe Arg Lys Thr Phe Thr Ser Glu Thr Ser Ala Asp Lys Phe Gly Trp
            755                 760                 765

Gly Lys Pro Met Phe Ser Pro Thr Thr Arg Ser Gln Asp Glu Val Phe
770                 775                 780

```
Ser Ala Ile Lys Lys Ile Gly Ala Ile Thr Val Leu Glu Asp
785                 790                 795
```

```
<210> SEQ ID NO 34
<211> LENGTH: 724
<212> TYPE: PRT
<213> ORGANISM: Unknown
<220> FEATURE:
<223> OTHER INFORMATION: Description of Unknown:
      mammals-digestive system-rumen-bos taurus sequence

<400> SEQUENCE: 34

Met Val Thr Thr Leu Ala Pro Leu Ile Glu Glu Lys Lys Arg Asp Ser
1               5                   10                  15

Glu Tyr Tyr Lys Tyr Leu Thr Asn Gly Asp Trp Asp Gly Lys Pro Leu
                20                  25                  30

Tyr Phe Ile Phe Lys Glu Gly Phe Asn Ser Thr Asn Ala Asp Asn Ile
            35                  40                  45

Leu Ala Asn Ser Leu Val Arg Val Tyr Cys Glu Gln Asn Tyr Thr Gly
50                  55                  60

Asn Gly Phe Gly Leu Ser Tyr Ser Tyr Tyr Val Val Ile Gly Phe Ala
65                  70                  75                  80

Lys Glu Val Ile Ala Asn Tyr Arg Ser Ser Phe Gln Lys Pro Lys Val
                85                  90                  95

Lys Ile Lys Lys Lys Lys Leu Ser Glu Asn Pro Thr Glu Asp Glu Leu
            100                 105                 110

Ile Glu Gln Cys Ile Tyr Thr Ile Tyr Glu Phe Asn Glu Lys Lys
            115                 120                 125

Asp Ile Lys Lys Trp Lys Asp Glu Ile Lys Phe Leu Lys Glu Arg Gly
130                 135                 140

Glu Ser Lys Glu Thr Arg Leu Lys Arg Ile Gln Thr Leu Phe Glu Phe
145                 150                 155                 160

Tyr Lys Asp Lys Asn His Lys Glu Leu Val Asp Glu Arg Val Ala Asn
                165                 170                 175

Leu Val Val Asp Asn Ile Lys Glu Phe Gly Gly Cys Lys Arg Asp Ile
            180                 185                 190

Gly Cys Pro Ser Met Gly Ile Gln Ile Gln His Asn Phe Asp Ile Ser
        195                 200                 205

Ile Asn Glu Lys Arg Asn Gly Tyr Thr Ile Cys Phe Gly Pro Asn Lys
210                 215                 220

Lys Asn Leu Thr Lys Leu Glu Val Phe Gly Asn Arg Met Val Leu Leu
225                 230                 235                 240

Asn Gly Glu Glu Ile Val Asp Leu Pro Asn Thr His Gly Glu Lys Leu
                245                 250                 255

Thr Leu Ile Asp Arg Gly Asn Ala Ile Tyr Ala Ala Leu Thr Ala Gln
            260                 265                 270

Val Pro Phe Glu Lys His Met Pro Asp Gly Asn Lys Thr Val Gly Ile
        275                 280                 285

Asp Leu Asn Leu Lys His Ser Val Phe Ala Thr Ser Ile Val Asp Asn
    290                 295                 300

Gly Lys Leu Ala Gly Tyr Ile Ser Ile Tyr Lys Glu Leu Leu Lys Asp
305                 310                 315                 320

Asp Glu Phe Val Lys Tyr Cys Pro Lys Asp Leu Leu Arg Phe Met Lys
                325                 330                 335

Asp Ala Ser Lys Tyr Val Phe Phe Ala Pro Ile Glu Ile Glu Leu Leu
            340                 345                 350
```

```
Arg Ser Arg Val Ile Tyr Asn Lys Gly Tyr Ala Cys Val Glu Asn Tyr
        355                 360                 365

Glu Asn Val Tyr Lys Ala Glu Val Ala Phe Val Asn Val Ile Lys Arg
    370                 375                 380

Leu Gln Ser Gln Cys Glu Ala Asn Gly Asp Ala Gln Gly Ala Leu Tyr
385                 390                 395                 400

Met Ser Tyr Leu Ser Lys Met Arg Ala Gln Leu Lys Asn Tyr Ile Asn
                405                 410                 415

Leu Lys Leu Ala Tyr Tyr Asp His Gln Ser Ala Tyr Asp Leu Lys Met
                420                 425                 430

Gly Phe Asn Asp Ile Ser Ala Glu Ser Lys Glu Thr Ile Asp Glu Arg
                435                 440                 445

Arg Lys Leu Phe Pro Phe Ser Lys Glu Lys Glu Ala Gln Glu Ile Leu
        450                 455                 460

Ala Lys Met Lys Asn Ile Ser Asn Val Ile Ile Ala Cys Arg Asn Asn
465                 470                 475                 480

Ile Ala Val Tyr Met Tyr Lys Met Phe Glu Arg Asn Gly Tyr Asp Phe
                485                 490                 495

Ile Gly Leu Glu Lys Leu Glu Ser Ser Gln Met Lys Lys Arg Gln Ser
            500                 505                 510

Arg Ser Phe Pro Thr Val Lys Ser Leu Leu Asn Tyr His Lys Leu Ala
        515                 520                 525

Gly Met Thr Met Asp Glu Ile Lys Lys Gln Glu Val Ser Ser Asn Ile
    530                 535                 540

Lys Lys Gly Phe Tyr Asp Leu Glu Phe Asp Ala Asp Gly Lys Leu Tyr
545                 550                 555                 560

Gly Ala Lys Tyr Ser Asn Lys Gly Asn Val His Phe Ile Glu Asp Glu
                565                 570                 575

Phe Tyr Ile Ser Gly Leu Lys Ala Ile His Phe Ala Asp Met Lys Asp
                580                 585                 590

Tyr Phe Val Arg Leu Ser Asn Asn Gly Lys Val Ser Val Ala Leu Val
        595                 600                 605

Pro Pro Ser Phe Thr Ser Gln Met Asp Ser Val Glu His Lys Phe Phe
        610                 615                 620

Met Lys Lys Asn Ala Asn Gly Lys Leu Ile Val Ala Asp Lys Lys Asp
625                 630                 635                 640

Val Arg Ser Cys Gln Glu Lys His Lys Ile Asn Gly Leu Asn Ala Asp
                645                 650                 655

Tyr Asn Ala Ala Cys Asn Ile Gly Phe Ile Val Glu Asp Asp Tyr Met
                660                 665                 670

Arg Glu Ser Leu Leu Gly Ser Pro Thr Gly Thr Tyr Asp Thr Ala
        675                 680                 685

Tyr Phe Asp Thr Lys Ile Gln Gly Ser Lys Gly Val Tyr Asp Lys Ile
        690                 695                 700

Lys Glu Asn Gly Glu Thr Tyr Ile Ala Val Leu Ser Asp Asp Val Ile
705                 710                 715                 720

Thr Ala Glu Glu

<210> SEQ ID NO 35
<211> LENGTH: 772
<212> TYPE: PRT
<213> ORGANISM: Unknown
<220> FEATURE:
<223> OTHER INFORMATION: Description of Unknown:
``` mammals-digestive system-rumen-bos taurus sequence

<400> SEQUENCE: 35

```
Met Gly Asn Lys Val Gln Ser Asn Glu Thr Ile Val Lys Thr Tyr Thr
1               5                   10                  15

Phe Lys Val Arg Glu Phe Ile Ser Gly Ala Thr His Glu Ile Met Lys
                20                  25                  30

Ser Ala Ile Lys Gln Tyr Ile Glu Asp Ser Asn Asn Leu Ser Asp Trp
            35                  40                  45

Ile Asn Asn Gln Leu Thr Asn Lys Thr Ile Cys Glu Val Gly Ala Leu
50                  55                  60

Ile Pro Ile Glu Lys Arg Glu Thr Ser Tyr Tyr Lys Ser Thr Val Asp
65                  70                  75                  80

Glu Leu Trp Ala Asn Lys Pro Cys Phe Lys Met Phe Thr Asn Asp Phe
                85                  90                  95

Thr Lys Glu Glu Asn Phe Ala Thr Arg Asn Ile Gly Asn Gly Lys Asn
                100                 105                 110

Cys Lys Asn Ile Ile Thr Ser Ala Tyr Lys Ser Thr Val Asn Pro Ser
            115                 120                 125

Phe Arg Asn Val Leu Asp Leu Thr Glu Lys Val Tyr Phe Ser Asp Gly
130                 135                 140

Tyr Gly Ala Asn Val Cys Ser Asn Tyr Lys Thr Lys Leu Arg Thr Leu
145                 150                 155                 160

Lys Pro Ala Lys Ile Lys Leu Val Ser Ser Leu Ser Asp Cys Asp Asp
                165                 170                 175

Asn Thr Leu Thr Glu Gln Val Ile Arg Glu Lys Gln Lys Tyr Gly Tyr
                180                 185                 190

Ser Thr Pro Lys Asp Phe Glu Lys Arg Ile Glu Tyr Leu Asn Glu Lys
            195                 200                 205

Glu Lys Ser Glu Gln Asn Ser Lys Ile Ile Glu Arg Leu Gln Lys Leu
210                 215                 220

Tyr Glu Phe Tyr Asp Asn Asn Thr Lys Leu Val Glu Glu Lys Glu Leu
225                 230                 235                 240

Glu Leu Ser Val Lys Ser Leu Val Glu Phe Gly Gly Cys Arg Arg Gly
                245                 250                 255

Glu Lys Thr Met Thr Leu Asn Leu Pro Asp Ile Gly Tyr Glu Ile Gln
                260                 265                 270

Arg Lys Asp Asp Lys Tyr Gly Tyr Ile Phe Thr Leu Lys Cys Ser Lys
            275                 280                 285

Lys Arg Lys Ile Ile Ile Asp Val Trp Gly Ser Lys Ala Thr Ile Asp
290                 295                 300

Ser Asn Gly Asn Asp Lys Val Asp Ile Ile Asn Thr His Gly Lys Ser
305                 310                 315                 320

Ile Asn Phe Lys Ile Ile Asn Asn Glu Met Tyr Ile Asp Ile Thr Val
                325                 330                 335

Asp Val Pro Phe Ala Lys Arg Lys Leu Gly Ile Lys Lys Val Val Gly
                340                 345                 350

Ile Asp Val Asn Thr Lys His Met Leu Met Ala Thr Asn Ile Lys Val
            355                 360                 365

Thr Asp Ser Ile Lys Gly Tyr Val Asn Leu Tyr Lys Glu Phe Leu Asn
370                 375                 380

Ser Lys Glu Ile Met Asp Val Ala Ser Pro Glu Thr Lys Lys Asn Phe
385                 390                 395                 400
```

```
Glu Asp Met Ser Met Phe Val Asn Phe Cys Pro Ile Glu Tyr Asn Thr
                405                 410                 415

Met Phe Ala Leu Ile Phe Lys Leu Asn Asn Gly Asp Ile Arg Thr Glu
            420                 425                 430

Gln Ala Ile Arg Arg Thr Leu His Gln Leu Ser Lys Lys Phe Ser Asp
        435                 440                 445

Gly Asn His Glu Thr Glu Arg Ile Tyr Val Gln Asn Val Phe Ser Ile
    450                 455                 460

Arg Glu Gln Leu Lys His Phe Ile Leu Leu Ser Asn Arg Tyr Tyr Ser
465                 470                 475                 480

Glu Gln Ser Asp Tyr Asp Thr Lys Met Gly Phe Ile Asp Glu Asn Thr
                485                 490                 495

Thr Ser Asn Ala Thr Met Asp Lys Arg Arg Phe Asp Lys Ser Leu Met
            500                 505                 510

Phe Arg Tyr Thr Gln Arg Gly Arg Gln Leu Tyr Glu Glu Arg Ile Glu
        515                 520                 525

Cys Gly Arg Lys Ile Thr Glu Ile Arg Asp Asn Ile Ile Thr Tyr Ala
    530                 535                 540

Arg Asn Val Phe Val Leu Asn Gly Tyr Asp Thr Ile Ala Leu Glu Tyr
545                 550                 555                 560

Leu Thr Asn Ala Thr Ile Gln Lys Pro Thr Arg Pro Thr Ser Pro Lys
                565                 570                 575

Ser Leu Leu Asp Tyr Phe Lys Leu Lys Gly Lys Pro Val Val Glu Ala
            580                 585                 590

Glu Lys Asn Glu Arg Ile Thr Lys Asn Arg Lys Tyr Tyr Asn Leu Ile
        595                 600                 605

Pro Asp Glu Asn Asp Asn Val Ile Asn Ile Glu Tyr Thr Glu Glu Gly
    610                 615                 620

Lys Val Ala Ile Lys Lys Ser Ile Ala Arg Asp His Ile Met Lys Ala
625                 630                 635                 640

Val His Phe Ala Glu Val Lys Asp Lys Phe Ile Gln Leu Ser Asn Asn
                645                 650                 655

Gly Lys Thr Gln Val Ala Leu Val Pro Ser Asn Tyr Thr Ser Gln Met
            660                 665                 670

Asn Ser Glu Thr His Thr Val Tyr Leu Met Lys Asn Pro Lys Thr Lys
        675                 680                 685

Lys Leu Val Ile Met Asp Lys Asp Lys Val Arg Pro Ile Gln Glu Lys
    690                 695                 700

Tyr Lys Leu Asn Gly Leu Asn Ala Asp Phe Asn Ser Ala Arg Asn Ile
705                 710                 715                 720

Ala Tyr Ile Val Glu Asn Glu Ile Leu Arg Asn Ser Phe Leu Lys Glu
                725                 730                 735

Glu Thr Lys Lys Tyr Thr Tyr Asn Thr Pro Leu Phe Thr Pro Arg Leu
            740                 745                 750

Lys Ser Ser Glu Lys Ile Ile Thr Glu Leu Lys Lys Leu Gly Met Thr
        755                 760                 765

Thr Val Ile Glu
    770

<210> SEQ ID NO 36
<211> LENGTH: 781
<212> TYPE: PRT
<213> ORGANISM: Unknown
<220> FEATURE:
<223> OTHER INFORMATION: Description of Unknown:
```

-continued mammals-digestive system-rumen-bos taurus sequence

<400> SEQUENCE: 36

Met Ala Asn Lys Ser Thr Lys Gly Asn Leu Pro Lys Thr Ile Ile Met
1               5                   10                  15

Lys Ala Asn Leu Ser Pro Asp Gly Phe Thr Gln Trp Glu Arg Val Val
            20                  25                  30

Lys Glu Tyr Gln Ala Tyr Lys Asp Thr Leu Ser Lys Trp Val Ala Gln
        35                  40                  45

Asn Leu Thr Ala Met Lys Ile Gly Asp Leu Leu Pro Tyr Leu Asp Lys
    50                  55                  60

Tyr Ser Lys Lys Thr Asn Lys Glu Thr Gly Glu Arg Pro Val Asn Val
65                  70                  75                  80

Tyr Tyr Gln Leu Cys Glu Gln His Lys Asp Glu Pro Leu Tyr Lys Leu
                85                  90                  95

Phe Thr Tyr Asp Ser Asn Ser Arg Asn Asn Ala Met Tyr Glu Ile Ile
            100                 105                 110

Arg Lys Thr Asn Cys Asp Gly Tyr Lys Gly Asn Ile Leu Gly Ile Ser
        115                 120                 125

Glu Thr His Tyr Arg Arg Asn Gly Phe Val Lys Asn Ile Leu Ala Asn
    130                 135                 140

Tyr Thr Thr Lys Ile Ser Thr Leu Glu Leu Ser Glu Arg Lys Arg Lys
145                 150                 155                 160

Ile Asp Ser Asp Ser Pro Glu Asp Leu Ile Arg Ser Gln Val Val Tyr
                165                 170                 175

Glu Met Gln Lys Asn Asn Ile Lys Asp Ala Lys Gly Phe Lys Ser Ile
            180                 185                 190

Ile Glu Tyr Leu Lys Ser Lys Lys Glu Val Asn Ile Gln Tyr Leu Glu
        195                 200                 205

Arg Leu Gln Ile Leu Tyr Glu Tyr Phe Lys Asn His Glu Asn Glu Ile
    210                 215                 220

Lys Glu Tyr Ile Thr Leu Ala Ala Val Glu Gln Leu Lys Ser Phe Gly
225                 230                 235                 240

Gly Val Arg Val Asn Asn Glu Lys Ser Ser Met Asn Leu Glu Ile Gln
                245                 250                 255

Gly Phe Ser Ile Thr Arg Val Asp Gly Ala Cys Thr Tyr Ile Leu His
            260                 265                 270

Leu Pro Ile Asn Gly Lys Ile His Gly Ile Lys Leu Trp Gly Asn Arg
        275                 280                 285

Gln Val Val Asn Lys Asp Gly Thr Pro Val Asp Ile Leu Asp Leu
    290                 295                 300

Thr Asn Gln His Gly Ser Thr Ile Asn Ile Thr Ile Lys Asn Gly Glu
305                 310                 315                 320

Ile Tyr Phe Ala Phe Thr Val Thr Ser Asp Phe Val Lys Pro Glu His
                325                 330                 335

Gln Ile Lys Asn Val Val Gly Val Asp Val Asn Thr Lys His Met Leu
            340                 345                 350

Met Gln Ser Asn Ile Thr Asp Asn Gly Asn Val Lys Gly Tyr Phe Asn
        355                 360                 365

Ile Tyr Lys Val Leu Val Glu Asp Arg Arg Phe Thr Ser Leu Leu Ser
    370                 375                 380

Glu Glu Gln Leu Lys Tyr Phe Cys Glu Leu Ala Asn Ile Val Ser Phe
385                 390                 395                 400

Cys Pro Ile Glu Thr Glu Phe Leu Phe Ala Arg Tyr Ala Glu Tyr Lys
                405                 410                 415

Lys Met Ser Asn Asn Ala Glu Met Arg Gln Ile Glu Lys Val Phe Ser
            420                 425                 430

Asp Ile Leu Asp Glu Gln Tyr Lys Lys Tyr Lys Asp Ile Asp Thr Ser
            435                 440                 445

Ile Ala Asn Tyr Ile Ser Tyr Val Arg Lys Leu Arg Ser Gln Cys Cys
450                 455                 460

Ala Tyr Phe Lys Leu Lys Met Lys Tyr Lys Glu Leu Gln Arg Gln Phe
465                 470                 475                 480

Asp Lys Glu Gln Asp Tyr Lys Asp Leu Ser Thr Glu Ser Lys Glu Thr
            485                 490                 495

Met Asp Lys Arg Arg Trp Glu Asn Pro Phe Arg Asn Thr Pro Glu Ala
            500                 505                 510

Ser Lys Leu Ile Lys Lys Met Asp Asn Val Ser Arg Gln Leu Ile Gly
            515                 520                 525

Cys Arg Asp Asn Ile Ile Thr Tyr Ala Tyr Arg Val Phe Glu Lys Asn
            530                 535                 540

Gly Tyr Asp Thr Ile Ser Leu Glu Asn Leu Glu Ser Ser Gln Phe Glu
545                 550                 555                 560

Asn Asn Asp His Val Ile Ala Pro Lys Ser Leu Leu Glu Tyr His His
            565                 570                 575

Leu Lys Gly Lys Thr Met Asn Tyr Leu Leu Ser Asp Glu Cys Lys Val
            580                 585                 590

Arg Ile Thr Thr Lys Asp Gly Lys Val Lys Glu Trp Tyr His Val Glu
            595                 600                 605

Leu Asn Asp Lys Asp Glu Ile Asp Asn Ile Phe Leu Thr Pro Glu Gly
            610                 615                 620

Glu Thr Glu Lys Glu Lys Asn Leu Phe Asn Asn Met Val Ile Lys Ile
625                 630                 635                 640

Val His Phe Ala Asp Ile Lys Asp Lys Phe Ile Gln Leu Gly Asn Tyr
            645                 650                 655

Asn Lys Leu Gln Thr Val Leu Val Pro Ser Tyr Phe Thr Ser Gln Met
            660                 665                 670

Asp Ser Lys Thr His Ser Val Tyr Val Val Glu Thr Ala Asn Thr Lys
            675                 680                 685

Thr Ser Lys Lys Glu Leu Lys Leu Val Ser Lys Arg Val Arg Arg
690                 695                 700

Gln Gln Glu Trp His Ile Asn Gly Leu Asn Ala Asp Tyr Asn Ala Ala
705                 710                 715                 720

Cys Asn Ile Ala His Ile Ala Lys Asn Ile Glu Leu Arg Gln Ile Met
            725                 730                 735

Cys Lys Thr Pro Gln Thr Lys Asn Gly Tyr Ser Ser Pro Val Leu Thr
            740                 745                 750

Ser Lys Val Lys Ser Gln Val Glu Met Val Arg Glu Leu Lys Lys Met
            755                 760                 765

Gly Lys Thr Ile Leu Tyr Ser Asn Asp Ser Leu Pro Phe
770                 775                 780

<210> SEQ ID NO 37
<211> LENGTH: 798
<212> TYPE: PRT
<213> ORGANISM: Unknown
<220> FEATURE:
<223> OTHER INFORMATION: Description of Unknown:

mammals-digestive system-rumen-bos taurus sequence

<400> SEQUENCE: 37

```
Met Ala His Arg Lys Lys Asp Asp Glu Ala Thr Leu Ser Tyr Lys
1               5                   10                  15

Phe Lys Val Lys Val Ile Glu Gly Asp Leu Thr Ala Asp Asp Ile Thr
            20                  25                  30

Lys Cys Ile Ala Glu Asn Ala Glu Gln Gly Asn His Phe Ser Glu Phe
        35                  40                  45

Ile His Lys Asn Leu Thr Ser Lys Thr Ile Gly Glu Phe Ala Ser Gln
    50                  55                  60

Leu Pro Val Glu Lys Arg Gln Phe Gly Tyr Tyr Gln Tyr Ala Ile Gly
65                  70                  75                  80

Gly Thr Met Pro Ala Lys Lys Asn Ala Ser Asp Glu Asp Lys Pro Lys
                85                  90                  95

Gly Glu Leu Ile Asp Trp Ser Lys Lys Pro Phe Tyr Val Leu Phe Ser
            100                 105                 110

Lys Gly Tyr Ser Ala Thr His Ala Val Asn Leu Ile Phe Asn Val Tyr
        115                 120                 125

Leu Asn Ser Glu Glu Gly Lys Ala Phe Ser Ala Lys Asn Ser Met Asn
    130                 135                 140

Leu Ser Lys Ser Gln Phe Ala Tyr Ser Gly Phe Val Gln Ile Val Cys
145                 150                 155                 160

Ala Asn Tyr Ala Ser Met Leu Ala Asn Ala Arg Pro Asp Lys Ile Lys
                165                 170                 175

Phe Glu Glu Ile Thr Glu Ala Thr Asp Asp Gly Thr Lys Lys Met Gln
            180                 185                 190

Val Val Arg Glu Met Ala Glu Arg Tyr Leu Met Lys Pro Lys Asn Phe
        195                 200                 205

Ala Ser Arg Ile Glu Tyr Leu Glu Ala Asn Asn Thr Lys Gly Lys Phe
    210                 215                 220

Asp Lys Thr Ile Gln Arg Leu Arg Leu Leu Gln Pro Phe Phe Glu Lys
225                 230                 235                 240

Asn Glu Glu Gly Ile Thr Glu Leu Tyr Tyr Asp Leu Ser Val Lys Ala
                245                 250                 255

Leu Glu His Ser Gly Gln Cys Thr Tyr Lys Gly Gly Arg Thr Ile Ser
            260                 265                 270

Ile Leu Glu Ile Gly Asp Ile Arg Ile Ser Arg Lys Glu Asn Ala Lys
        275                 280                 285

Gly Tyr Leu Leu Thr Ile Pro Ile Asn Arg Lys Ser Val Val Phe Asp
    290                 295                 300

Leu Tyr Gly Arg Lys Asp Thr Ile Gly Gly Asp Gly Arg Asp Leu Ile
305                 310                 315                 320

Asp Ile Met Asn Thr His Gly Ser Ser Leu Gln Phe Thr Ala Asp Gly
                325                 330                 335

Asn Asp Ile Tyr Leu Thr Ile Thr Ala Thr Lys Asn Phe Ile Lys Glu
            340                 345                 350

Lys Pro Thr Phe Asn Glu Asp Thr Val Leu Gly Gly Asp Val Asn Ile
        355                 360                 365

Lys His Ser Tyr Thr Val Phe Ser Thr Ser Pro Lys Asp Ile Pro Asp
    370                 375                 380

Phe Val Asn Phe Tyr Glu Tyr Phe Ala Lys Asp Gly Glu Ile Met Lys
385                 390                 395                 400
```

Leu Ala Pro Lys Pro Met Trp Asp Tyr Ile Val Ala Ala Thr Lys
                405                 410                 415

Phe Leu Thr Ile Leu Pro Ile Glu Thr Pro Ala Ile Ser Ala Thr Val
            420                 425                 430

Tyr Gly Lys Arg Thr Glu Glu Gly Ile Ser Arg Ala Thr Phe Arg Glu
            435                 440                 445

Thr Gln Lys Leu Ile Ala Leu Glu Lys Ala Ile Glu Arg Val Met Lys
        450                 455                 460

Gln Val Phe Asp Lys Tyr Asn Asp Gly Lys His Pro Leu Glu Ala Ile
465                 470                 475                 480

Tyr Ile Gly Asn Ala Ile Lys Tyr Arg Arg Leu Ile Lys Gly Tyr Leu
                485                 490                 495

Ala Gln Lys Lys Lys Tyr Tyr Ser Ala His Ser Glu Tyr Asp Lys Ala
            500                 505                 510

Met Gly Tyr Thr Asp Asp Thr Asp Arg Lys Glu Asn Met Asp Glu
            515                 520                 525

Arg Arg Phe Asp Ser Lys Lys Phe Arg Tyr Thr Pro Glu Ala Gln
        530                 535                 540

Ala Leu Leu Asp Thr Met His Thr Ile Glu Lys Lys Ile Val Gly Cys
545                 550                 555                 560

Val Ser Asn Ala Ile Ser Tyr Ala Tyr His Lys Phe Asp Glu Asn Gly
                565                 570                 575

Phe Asn Val Ile Ala Leu Glu Asn Leu Thr Ser Ala Thr Phe Ala Lys
            580                 585                 590

Lys Tyr Lys Ser Asp Lys Pro Glu Ser Ile Lys Lys Leu Leu Asn Phe
        595                 600                 605

Asp Lys Leu Leu Gly Lys Thr Leu Asp Glu Ala Lys Ala Ser Lys Ser
    610                 615                 620

Ile Ser Lys His Pro Asn Trp Tyr Glu Leu Val Ala Asp Glu Asn Gly
625                 630                 635                 640

Cys Val Ser Asp Ile Arg Ile Thr Asp Glu Gly Gln Ser Ala Thr Tyr
                645                 650                 655

Arg Ser Leu Val Thr Glu Thr Ile Met Lys Val Ser His Phe Ala Glu
            660                 665                 670

Thr Lys Asp Arg Phe Ile Gly Leu Ala Asn Ser Gly Arg Leu Gln Val
        675                 680                 685

Gly Leu Val Pro Ser Gln Tyr Thr Ser Tyr Ile Asp Ser Thr Thr His
    690                 695                 700

Thr Leu Tyr Ala Val Ile Glu Asp Gly Lys Thr Val Leu Ala Pro Lys
705                 710                 715                 720

Glu Val Val Arg Ala Ser Gln Glu Arg His Ile Asn Gly Leu Asn Ala
                725                 730                 735

Asp Tyr Asn Ser Ala Leu Asn Leu Lys Tyr Met Ile Thr Asp Glu Asn
            740                 745                 750

Phe Arg Lys Thr Phe Thr Ser Glu Thr Ser Ala Asp Lys Phe Gly Trp
        755                 760                 765

Gly Lys Pro Met Phe Ser Pro Thr Thr Arg Ser Gln Asp Glu Val Phe
    770                 775                 780

Ser Ala Ile Lys Lys Ile Gly Ala Ile Thr Val Leu Glu Asp
785                 790                 795

<210> SEQ ID NO 38
<211> LENGTH: 781
<212> TYPE: PRT

<213> ORGANISM: Unknown
<220> FEATURE:
<223> OTHER INFORMATION: Description of Unknown:
      mammals-digestive system-rumen-bos taurus sequence

<400> SEQUENCE: 38

```
Met Ala His Lys Asn Ser Asp Gly Glu Asn Thr Ile Asn Lys Thr Phe
1               5                   10                  15

Ile Phe Lys Val Lys Cys Glu Lys Asn Asp Ile Ile Ser Phe Trp Lys
            20                  25                  30

Pro Ala Ala Glu Glu Tyr Cys Asn Tyr Tyr Asn Lys Leu Ser Glu Trp
        35                  40                  45

Ile Gly Lys Asn Leu Ile Ser Met Lys Ile Gly Asp Leu Ala Lys Tyr
    50                  55                  60

Ile Asp Asn Pro Lys Ser Lys Tyr Tyr Leu Ser Val Thr Asp Glu Asn
65                  70                  75                  80

Lys Lys Asp Leu Pro Leu Tyr Lys Ile Phe Gln Lys Gly Phe Ser Ser
                85                  90                  95

Ile Asp Ala Asp Asn Ala Leu Tyr Cys Ala Ile Asp Lys Leu Asn Pro
            100                 105                 110

Glu Gly Tyr Asn Gly Asn Ile Leu Gly Val Gly Lys Ser Asp Tyr Arg
        115                 120                 125

Arg Asn Gly Tyr Val Ser Ser Val Ile Gly Asn Phe Arg Thr Lys Met
    130                 135                 140

Val Ser Leu Lys Ala Asn Val Arg Trp Lys Lys Ile Asp Ile Gly Asn
145                 150                 155                 160

Val Asp Glu Glu Thr Leu Arg Arg Gln Thr Ile Cys Asp Val Glu Lys
                165                 170                 175

Tyr Arg Ile Glu Ser Glu Lys Asp Phe Arg Asp Leu Ile Asp Ile Leu
            180                 185                 190

Lys Ala Arg Glu Glu Thr Pro Arg Leu Lys Glu Lys Ile Ser Arg Leu
        195                 200                 205

Glu Leu Leu Tyr Asp Tyr Tyr Ser Lys Asn Thr Lys Thr Ile Lys Ser
    210                 215                 220

Glu Met Glu Asn Met Ala Ile Ser Asp Leu Gln Lys Phe Gly Gly Cys
225                 230                 235                 240

Val Arg Lys Ser Leu Asn Thr Ile Thr Ile His Lys Gln Asp Ser Lys
                245                 250                 255

Ile Glu Lys Glu Gly Asn Thr Ser Phe Arg Leu His Met Val Phe Asn
            260                 265                 270

Lys Lys Pro Tyr Thr Ile Thr Leu Leu Gly Asn Arg Gln Val Val Lys
        275                 280                 285

Tyr Ile Asp Gly Lys Arg Val Asp Ile Val Asn Ile Val Glu Lys His
    290                 295                 300

Gly Asp Trp Ile Thr Phe Asn Ile Lys Asn Gly Glu Leu Phe Val His
305                 310                 315                 320

Leu Thr Lys Cys Val Glu Phe Ser Lys Gly Gln Lys Glu Ile Lys Lys
                325                 330                 335

Ala Ala Gly Val Asp Val Asn Ile Lys His Ala Met Leu Ala Ala Ser
            340                 345                 350

Ile Val Asp Asp Gly Gln Leu Lys Gly Tyr Val Asn Leu Tyr Arg Glu
        355                 360                 365

Leu Ile Glu Asp Asp Asp Phe Val Ser Thr Phe Gly Asp Ser Asp Ser
    370                 375                 380
```

Gly Lys Thr Glu Leu Gly Met Tyr Gln Lys Met Ala Lys Thr Val Phe
385                 390                 395                 400

Phe Gly Val Leu Glu Val Glu Ser Leu Phe Glu Arg Val Asn Gln
            405                 410                 415

Gln Ser Gly Trp Lys Leu Asp Asn Gln Leu Ile Arg Arg Glu Arg Ala
            420                 425                 430

Met Glu Lys Val Phe Asp Arg Ile Val Lys Thr Thr Ser Asn Lys His
            435                 440                 445

Ile Ile Asp Tyr Val Asn Tyr Val Lys Met Leu Arg Ala Lys Tyr Lys
        450                 455                 460

Ala Tyr Phe Ile Leu Asp Glu Lys Tyr His Glu Lys Gln Arg Glu Tyr
465                 470                 475                 480

Asp Leu Ser Met Gly Phe Thr Asp Glu Ser Asp Glu Arg Arg Glu Leu
            485                 490                 495

Tyr Pro Phe Ile Asn Thr Glu Thr Ala Lys Glu Ile Leu Gly Lys Lys
            500                 505                 510

Arg Asn Val Glu Gln Asp Leu Ile Gly Cys Arg Asp Asn Ile Val Thr
            515                 520                 525

Tyr Ala Phe Asn Val Leu Arg Asn Asn Gly Tyr Asp Thr Ile Ser Val
            530                 535                 540

Glu Tyr Leu Asp Ser Ser Gln Phe Asp Lys Arg Arg Met Pro Thr Pro
545                 550                 555                 560

Lys Ser Leu Leu Glu Tyr His Lys Phe Lys Gly Lys Thr Gln Asp Glu
            565                 570                 575

Val Glu Arg Leu Met Ser Glu Lys Lys Phe Ala Lys Thr Asn Tyr Asp
            580                 585                 590

Ile His Tyr Asp Gly Glu Asn Lys Val Asp Gly Ile Val Tyr Ser Lys
        595                 600                 605

Glu Gly Glu Leu Arg Gln Lys Lys Leu Asn Phe Met Asn Leu Val Ile
        610                 615                 620

Lys Ala Ile His Phe Ala Asp Ile Lys Asp Lys Phe Ala Gln Leu Cys
625                 630                 635                 640

Asn Asn Asn Asp Val Asn Val Val Phe Gly Pro Ser Ala Phe Thr Ser
            645                 650                 655

Gln Met Asp Ser Glu Thr His Ser Leu Tyr Tyr Val Glu Lys Glu Thr
            660                 665                 670

Asn Gly Lys Asn Gly Lys Thr Gly Lys Lys Phe Val Leu Ala Asp Lys
            675                 680                 685

Lys Ser Val Arg Arg Arg Gln Glu Thr His Ile Asn Gly Leu Asn Ala
            690                 695                 700

Asp Phe Asn Ala Ala Arg Asn Leu Glu Tyr Ile Ala Ser Asn Pro Glu
705                 710                 715                 720

Leu Leu Glu Arg Met Thr Lys Arg Thr Lys Ser Gly Lys Asp Met Tyr
            725                 730                 735

Asn Thr Pro Ser Trp Asn Ile Arg Gln Glu Phe Lys Lys Asn Leu Ser
            740                 745                 750

Val Arg Thr Ile Asn Thr Phe Arg Glu Leu Gly Asn Val Lys Tyr Gly
            755                 760                 765

Lys Ile Asn Asn Glu Gly Leu Phe Val Glu Asp Val
        770                 775                 780

<210> SEQ ID NO 39
<211> LENGTH: 786
<212> TYPE: PRT

```
<213> ORGANISM: Unknown
<220> FEATURE:
<223> OTHER INFORMATION: Description of Unknown:
      mammals-digestive system-rumen-bos taurus sequence

<400> SEQUENCE: 39
```

| | | | | | | | | | | | | | | |
|---|---|---|---|---|---|---|---|---|---|---|---|---|---|---|
| Met | Ala | Gln | His | Lys | Ser | Asn | Asn | Glu | Glu | Ser | Ala | Ile | Asn | Lys | Thr |
| 1 | | | | 5 | | | | | 10 | | | | | 15 | |

Phe Ile Phe Lys Ala Lys Cys Glu Lys Asn Asp Val Ile Ser Leu Trp
              20                  25                  30

Glu Pro Ala Ala Lys Glu Tyr Gly Asp Tyr Tyr Asn Lys Val Ser Lys
              35                  40                  45

Trp Ile Ala Asp Asn Leu Ile Thr Met Lys Ile Gly Asp Leu Ala Gln
 50                  55                  60

Tyr Ile Thr Asn Gln Asn Ser Lys Tyr Tyr Thr Ala Val Thr Asn Lys
 65                  70                  75                  80

Lys Lys Lys Asp Leu Pro Leu Tyr Arg Ile Phe Gln Lys Gly Phe Ser
              85                  90                  95

Ser Gln Cys Ala Asp Asn Ala Leu Tyr Cys Ala Ile Lys Ser Ile Asn
              100                 105                 110

Pro Glu Asn Tyr Lys Gly Asn Ser Leu Gly Ile Gly Glu Ser Asp Tyr
              115                 120                 125

Arg Arg Phe Gly Tyr Ile Gln Ser Val Val Ser Asn Phe Arg Thr Lys
 130                 135                 140

Met Ser Ser Leu Lys Val Ser Val Lys Tyr Lys Lys Phe Asp Val Ser
145                 150                 155                 160

Asn Val Asp Asp Glu Thr Leu Lys Ile Gln Thr Ile Tyr Asp Val Asp
              165                 170                 175

Lys Tyr Gly Ile Glu Thr Ala Lys Glu Phe Lys Glu Leu Ile Glu Thr
              180                 185                 190

Leu Lys Thr Arg Val Glu Thr Pro Gln Leu Asn Asp Thr Ile Ala Arg
              195                 200                 205

Leu Lys Cys Leu Cys Asp Tyr Tyr Ser Lys Asn Glu Lys Ala Ile Asn
 210                 215                 220

Asn Glu Ile Glu Thr Met Ala Ile Ala Asp Leu Gln Lys Phe Gly Gly
225                 230                 235                 240

Cys Gln Arg Lys Ser Leu Asn Ala Phe Thr Ile His Lys Gln Asp Ser
              245                 250                 255

Leu Met Glu Lys Val Gly Asn Thr Ser Phe Arg Leu Gln Leu Ser Phe
              260                 265                 270

Arg Lys Lys Thr Tyr Val Ile Asn Leu Leu Gly Asn Arg Gln Val Val
              275                 280                 285

Asn Phe Val Asn Gly Lys Arg Val Asp Leu Ile Asp Ile Ala Glu Asn
 290                 295                 300

His Gly Asp Leu Ile Thr Phe Asn Ile Lys Asn Gly Glu Leu Phe Leu
305                 310                 315                 320

His Ile Thr Ser Pro Ile Val Phe Asp Lys Asp Val Arg Asp Ile Arg
              325                 330                 335

Asn Val Val Gly Ile Asp Val Asn Ile Lys His Ser Met Leu Ala Thr
              340                 345                 350

Ser Ile Lys Asp Asp Gly Asn Val Lys Gly Tyr Ile Asn Leu Tyr Lys
              355                 360                 365

Glu Leu Leu Asn Asp Asp Val Phe Val Ser Thr Cys Asn Glu Ser Glu
              370                 375                 380

```
Leu Ala Leu Tyr Arg Gln Met Ser Glu Asn Val Asn Phe Gly Ile Leu
385                 390                 395                 400

Glu Thr Asp Ser Leu Phe Glu Arg Ile Val Asn Gln Ser Lys Gly Gly
            405                 410                 415

Cys Leu Lys Asn Lys Leu Ile Arg Arg Glu Leu Ala Met Gln Lys Val
        420                 425                 430

Phe Glu Arg Ile Thr Lys Thr Asn Lys Asp Gln Asn Ile Val Asp Tyr
    435                 440                 445

Val Asn Tyr Val Lys Met Met Arg Ala Lys Cys Lys Ala Ser Tyr Ile
450                 455                 460

Leu Lys Glu Lys Tyr Asp Glu Lys Gln Lys Glu Tyr Tyr Val Lys Met
465                 470                 475                 480

Gly Phe Thr Asp Glu Ser Thr Glu Ser Lys Glu Thr Met Asp Lys Arg
            485                 490                 495

Arg Glu Glu Phe Pro Phe Val Asn Thr Asp Thr Ala Lys Glu Leu Leu
                500                 505                 510

Val Lys Gln Asn Asn Ile Arg Gln Asp Ile Ile Gly Cys Arg Asp Asn
        515                 520                 525

Ile Val Thr Tyr Ala Phe Asn Val Phe Lys Asn Asn Glu Tyr Asp Thr
    530                 535                 540

Leu Ser Val Glu Tyr Leu Asp Ser Ser Gln Phe Asp Lys Arg Arg Ile
545                 550                 555                 560

Pro Thr Pro Lys Ser Leu Leu Lys Tyr His Lys Phe Glu Gly Lys Thr
            565                 570                 575

Lys Asp Glu Val Glu Asn Met Met Lys Ser Glu Lys Leu Ser Asn Ala
            580                 585                 590

Tyr Tyr Thr Phe Lys Tyr Glu Asn Asp Val Val Ser Asp Ile Asp Tyr
        595                 600                 605

Ser Asp Glu Gly Asn Leu Arg Arg Ser Lys Leu Asn Phe Gly Asn Trp
    610                 615                 620

Ile Ile Lys Ala Ile His Phe Ala Asp Ile Lys Asp Lys Phe Val Gln
625                 630                 635                 640

Leu Ser Asn Asn Asn Lys Met Asn Ile Val Phe Cys Pro Ser Ala Phe
            645                 650                 655

Ser Ser Gln Met Asp Ser Ile Thr His Thr Leu Tyr Tyr Val Glu Lys
        660                 665                 670

Ile Thr Lys Asn Lys Lys Gly Lys Glu Lys Lys Lys Tyr Val Leu Ala
    675                 680                 685

Asn Lys Lys Met Val Arg Thr Gln Gln Glu Thr His Ile Asn Gly Leu
690                 695                 700

Asn Ala Asp Tyr Asn Ser Ala Cys Asn Leu Lys Tyr Ile Ala Leu Asn
            705                 710                 715                 720

Tyr Glu Leu Arg Asp Lys Met Thr Asp Arg Phe Lys Ala Ser Lys Lys
                725                 730                 735

Ile Lys Thr Met Tyr Asn Ile Pro Ala Tyr Asn Ile Lys Ser Asn Phe
        740                 745                 750

Lys Lys Asn Leu Ser Ala Lys Thr Ile Gln Thr Phe Arg Glu Leu Gly
    755                 760                 765

His Tyr Arg Asp Gly Lys Ile Asn Glu Asp Gly Met Phe Val Glu Ile
    770                 775                 780

Leu Glu
785
```

<210> SEQ ID NO 40
<211> LENGTH: 798
<212> TYPE: PRT
<213> ORGANISM: Unknown
<220> FEATURE:
<223> OTHER INFORMATION: Description of Unknown:
      mammals-digestive system-rumen-bos taurus sequence

<400> SEQUENCE: 40

```
Met Ala His Arg Lys Lys Asp Asp Glu Ala Thr Leu Ser Tyr Lys
1               5                   10                  15

Phe Lys Val Lys Val Ile Glu Gly Asp Leu Thr Ala Asp Ile Thr
                20                  25                  30

Lys Cys Ile Ala Glu Asn Ala Glu Gln Gly Asn His Phe Ser Glu Phe
            35                  40                  45

Ile His Lys Asn Leu Thr Ser Lys Thr Ile Gly Glu Phe Ala Ser Gln
        50                  55                  60

Leu Pro Ala Glu Lys Arg Gln Phe Gly Tyr Tyr Gln Tyr Ala Ile Gly
65                  70                  75                  80

Gly Thr Met Pro Ala Lys Lys Asn Ala Ser Asp Glu Asp Lys Pro Lys
                85                  90                  95

Gly Glu Leu Ile Asp Trp Ser Lys Pro Phe Tyr Val Leu Phe Ser
                100                 105                 110

Lys Gly Tyr Ser Ala Thr His Ala Val Asn Leu Ile Phe Asn Val Tyr
            115                 120                 125

Leu Asn Ser Glu Glu Gly Lys Ala Phe Ser Ala Lys Asn Ser Met Asn
        130                 135                 140

Leu Ser Lys Ser Gln Phe Ala Tyr Ser Gly Phe Val Gln Ile Val Cys
145                 150                 155                 160

Ala Asn Tyr Ala Ser Met Leu Ala Asn Ala Arg Pro Asp Lys Ile Lys
                165                 170                 175

Phe Glu Glu Ile Thr Glu Ala Thr Asp Asp Gly Thr Lys Lys Met Gln
            180                 185                 190

Val Val Arg Glu Met Ala Glu Arg Tyr Leu Met Lys Pro Lys Asn Phe
        195                 200                 205

Ala Ser Arg Ile Glu Tyr Leu Glu Ala Asn Asn Thr Lys Gly Lys Phe
210                 215                 220

Asp Lys Thr Ile Gln Arg Leu Arg Leu Leu Gln Pro Phe Phe Glu Lys
225                 230                 235                 240

Asn Glu Glu Ser Ile Thr Glu Leu Tyr Tyr Asp Leu Ser Val Lys Ala
                245                 250                 255

Leu Glu His Ser Gly Gln Cys Thr Tyr Lys Gly Gly Arg Thr Ile Ser
            260                 265                 270

Ile Leu Glu Ile Gly Asp Ile Arg Ile Ser Arg Lys Glu Asn Ala Lys
        275                 280                 285

Gly Tyr Leu Leu Thr Ile Pro Ile Asn Arg Lys Ser Val Val Phe Asp
290                 295                 300

Leu Tyr Gly Arg Lys Asp Thr Ile Gly Gly Asp Gly Arg Asp Leu Ile
305                 310                 315                 320

Asp Ile Met Asn Thr His Gly Ser Ser Leu Gln Phe Thr Ala Asp Glu
                325                 330                 335

Asn Asp Ile Tyr Leu Thr Ile Thr Ala Thr Lys Asn Phe Ile Lys Glu
            340                 345                 350

Lys Pro Thr Phe Asn Glu Asp Thr Val Leu Gly Gly Asp Val Asn Ile
        355                 360                 365
```

```
Lys His Ser Tyr Thr Val Phe Ser Ala Ser Pro Lys Asp Ile Pro Asp
    370                 375                 380

Phe Val Asn Phe Tyr Glu Tyr Phe Ala Lys Asp Gly Glu Ile Met Lys
385                 390                 395                 400

Leu Ala Pro Lys Pro Met Trp Asp Tyr Ile Val Ala Ala Thr Lys
                405                 410                 415

Phe Leu Thr Ile Leu Pro Ile Glu Thr Pro Ala Ile Ser Ala Thr Val
                420                 425                 430

Tyr Gly Lys Arg Thr Glu Gly Ile Ser Arg Ala Thr Phe Arg Glu
                435                 440                 445

Thr Gln Lys Leu Ile Ala Leu Glu Lys Ala Ile Glu Arg Val Met Lys
    450                 455                 460

Gln Val Phe Asp Lys Tyr Asn Asp Gly Lys His Pro Leu Glu Ala Ile
465                 470                 475                 480

Tyr Ile Gly Asn Ala Ile Lys Tyr Arg Arg Leu Ile Lys Gly Tyr Leu
                485                 490                 495

Ala Gln Lys Lys Lys Tyr Ser Ala His Ser Glu Tyr Asp Lys Ala
                500                 505                 510

Met Gly Tyr Thr Asp Asp Thr Asp Arg Lys Glu Asn Met Asp Glu
    515                 520                 525

Arg Arg Phe Asp Asp Ser Lys Lys Phe Arg Tyr Thr Pro Glu Ala Gln
530                 535                 540

Ala Leu Leu Asp Thr Met His Thr Ile Glu Lys Lys Ile Val Gly Cys
545                 550                 555                 560

Val Ser Asn Ala Ile Ser Tyr Ala Tyr His Lys Phe Asp Glu Asn Gly
                565                 570                 575

Phe Asn Val Ile Ala Leu Glu Asn Leu Thr Ser Ala Thr Phe Ala Lys
                580                 585                 590

Lys Tyr Lys Ser Asp Lys Pro Glu Ser Ile Lys Lys Leu Leu Asn Phe
    595                 600                 605

Asp Lys Leu Leu Gly Lys Thr Leu Asp Glu Ala Lys Ala Ser Lys Ser
                610                 615                 620

Ile Ser Lys His Pro Asn Trp Tyr Glu Leu Val Ala Asp Glu Asn Gly
625                 630                 635                 640

Cys Val Ser Asp Ile Arg Ile Thr Asp Glu Gly Gln Ser Ala Thr Tyr
                645                 650                 655

Arg Ser Leu Val Thr Glu Thr Ile Met Lys Val Ser His Phe Ala Glu
                660                 665                 670

Thr Lys Asp Arg Phe Ile Gly Leu Ala Asn Ser Gly Arg Leu Gln Val
                675                 680                 685

Gly Leu Val Pro Ser Gln Tyr Thr Ser Tyr Ile Asp Ser Thr Thr His
    690                 695                 700

Thr Leu Tyr Ala Val Ile Glu Asp Gly Lys Thr Val Leu Ala Pro Lys
705                 710                 715                 720

Glu Val Val Arg Ala Ser Gln Glu Arg His Ile Asn Gly Leu Asn Ala
                725                 730                 735

Asp Tyr Asn Ser Ala Leu Asn Leu Lys Tyr Met Ile Thr Asp Glu Asn
                740                 745                 750

Phe Arg Lys Thr Phe Thr Ser Glu Thr Ser Ala Asp Lys Phe Gly Trp
                755                 760                 765

Gly Lys Pro Met Phe Ser Pro Thr Thr Arg Ser Gln Asp Glu Val Phe
    770                 775                 780

Ser Ala Ile Lys Lys Ile Gly Ala Ile Thr Val Leu Glu Asp
```

<210> SEQ ID NO 41
<211> LENGTH: 771
<212> TYPE: PRT
<213> ORGANISM: Unknown
<220> FEATURE:
<223> OTHER INFORMATION: Description of Unknown:
mammals-digestive system-rumen-ovis aries sequence

<400> SEQUENCE: 41

Met Ala Asn Lys Arg Thr Asp Thr Thr Ile Asn Leu Asn Lys Thr Val
1               5                   10                  15

Ile Met Leu Thr Asn Met Leu Pro Glu Val Arg Ala Met Phe Gln Ala
            20                  25                  30

Gly Ile Arg Gln Ala Gln Ala Tyr Ala Asp Leu Val Asn Lys Trp Ile
        35                  40                  45

Cys Ser Asn Leu Thr Asn Lys Ile Gly Glu Val Leu Leu Pro Tyr Ile
    50                  55                  60

Asp Asn Lys Asn Cys Val Tyr Tyr Glu Leu Cys Tyr Lys Tyr Lys Glu
65                  70                  75                  80

Ala Pro Leu Tyr Thr Ile Phe Met Lys Gly Lys Phe Asp Leu Asn Ser
                85                  90                  95

Arg Asn Asn Ala Leu Tyr Cys Ala Val Val Ala Gln Asn Ile Asp Asn
            100                 105                 110

Tyr Ser Gly Asn Ile Phe Gly Phe Ser Gln Ser Asp Tyr Arg Arg Asn
        115                 120                 125

Gly Tyr Cys Lys Val Val Phe Ser Asn Tyr Ala Thr Lys Met Ser Ser
130                 135                 140

Leu Lys Pro Ser Ile Lys Lys Val Thr Ile Asn Glu Glu Ser Thr Glu
145                 150                 155                 160

Glu Thr Ile Gln Ser Gln Val Ile Tyr Glu Met Phe Thr Asn Gly Arg
                165                 170                 175

Gln Trp Gly Lys Pro Glu Tyr Phe Ala Glu His Leu Lys Tyr Leu Glu
            180                 185                 190

Met Lys Asp Asn Val Ser Asp Lys Leu Met Phe Arg Met Lys Thr Leu
        195                 200                 205

Cys Glu Tyr Tyr Gln Thr His Thr Asp Leu Ile Asp Thr Met Ala Met
    210                 215                 220

Asn Ala Gly Val Glu Ala Leu Lys Gln Phe Glu Gly Leu Lys Leu Asn
225                 230                 235                 240

Arg Asp Lys Phe Ser Met Thr Ile Thr Thr Asn Ser Thr Ser Pro Tyr
                245                 250                 255

Thr Leu Thr Arg Val Ala Gly Thr Cys Ala Tyr Asn Leu His Ile Pro
            260                 265                 270

Cys Arg Lys Arg Ser Tyr Asp Ile Arg Leu Trp Gly Asn Arg Gln Thr
        275                 280                 285

Val Arg Trp Val Asn Gly Glu Leu Val Asp Ile Ala Asp Ile Ile Asn
    290                 295                 300

Gln His Gly Gln Thr Ile Ile Phe Thr Ile Lys Asn Gly Asn Val Tyr
305                 310                 315                 320

Val His Ile Pro Tyr Gly Leu Asn Phe Glu Lys Thr Glu His Glu Ile
                325                 330                 335

Lys Asn Val Val Gly Val Asp Val Asn Thr Lys His Met Leu Met Gln
            340                 345                 350

```
Thr Ser Ile Lys Asp Asn Gly Trp Val Lys Gly Tyr Val Asn Ile Tyr
        355                 360                 365

Lys Ala Leu Val Glu Asp Glu Phe Val Lys Tyr Ile Ser Lys Ser
370                 375                 380

Asp Leu Lys Leu Tyr Lys Asp Leu Ser Lys Tyr Val Ser Phe Cys Pro
385                 390                 395                 400

Leu Glu Leu Asn Leu Leu Tyr Thr Arg Tyr Leu Ser Lys Lys Gly Leu
            405                 410                 415

Pro Phe Asn Glu Ala Asp Asn Asn Glu Lys Cys Val Glu Lys Val
            420                 425                 430

Leu Asn Asn Leu Val Lys Gln Tyr Glu Gly Asp Asp Val His Val Val
            435                 440                 445

Asn Tyr Ile His Asn Val Lys Lys Leu Arg Ala Leu Cys Lys Ala Ser
        450                 455                 460

Phe Val Leu Tyr Lys Lys Tyr Ala Glu Leu Gln Lys Ala Phe Asp Asp
465                 470                 475                 480

Ala Gln Gly Tyr Asn Asp Gln Ser Thr Glu Thr Lys Glu Thr Met Asp
            485                 490                 495

Lys Arg Arg Trp Glu Asn Pro Phe Ile Gln Thr Arg Glu Ala Gln Glu
            500                 505                 510

Leu Ile Ala Lys Met Asp Asn Ala Val Ala Gly Ile Ile Gly Cys Arg
            515                 520                 525

Asp Asn Ile Ile Thr Tyr Ala Tyr Lys Val Phe Gly Asp Asn Asn Tyr
            530                 535                 540

Asp Thr Val Gly Leu Glu Asn Leu Thr Thr Ser Gln Phe Asp Asn Tyr
545                 550                 555                 560

Ser Thr Val Lys Ser Pro Lys Ser Leu Leu Ser Tyr Tyr Gly Leu Leu
            565                 570                 575

Gly Gln Gln Val Asp Ser Asp Lys Tyr Asn Ala Val Met Thr Glu Ser
            580                 585                 590

Asn Lys Asp Trp Tyr Asp Phe Lys Thr Asp Gly Asp Gly Asn Ile Thr
            595                 600                 605

Asp Ile Thr Leu Thr Ala Ala Gly Glu Ala Gln Lys Ala Lys Ser Leu
610                 615                 620

Phe Asn Asn Lys Val Leu Lys Asn Ile His Phe Ala Asp Val Lys Asp
625                 630                 635                 640

Lys Phe Ile Gln Leu Gly Asn Asn Gly Ser Ile Gln Thr Val Leu Val
            645                 650                 655

Pro Pro Ser Tyr Thr Ser Gln Met Asp Ser Lys Thr His Thr Ile Tyr
            660                 665                 670

Val Lys Glu Thr Val Asp Pro Lys Asn Lys Asn Lys Lys Leu Lys
            675                 680                 685

Leu Val Asp Lys Lys Leu Val Arg His Gly Gln Glu Tyr His Lys Asn
            690                 695                 700

Gly Leu Asn Ala Asp Ile Asn Ala Ala Leu Asn Ile Ala Tyr Ile Val
705                 710                 715                 720

Glu Asn Gln Glu Met Arg Glu Val Met Cys Leu His Pro Ser Lys Lys
                725                 730                 735

Asp Gly Val Tyr Asp Gln Pro Phe Leu Lys Ala Thr Thr Lys Tyr Pro
            740                 745                 750

Ala Thr Val Ala Gly Ile Leu Leu Lys Met Gly Lys Thr Thr Asn Trp
            755                 760                 765

Gly Glu Lys
```

<210> SEQ ID NO 42
<211> LENGTH: 764
<212> TYPE: PRT
<213> ORGANISM: Unknown
<220> FEATURE:
<223> OTHER INFORMATION: Description of Unknown:
mammals-digestive system-rumen-ovis aries sequence

<400> SEQUENCE: 42

```
Met Asn Lys Ser Tyr Val Phe Lys Ser Asn Val Ala Ile Asp Asp Ile
1               5                   10                  15

Met Ser Leu Phe Glu Pro Ala Ile Glu Glu Tyr Ile Asn Tyr Tyr Asn
            20                  25                  30

Arg Thr Ser Asp Phe Ile Cys Asp Asn Leu Thr Ser Met Lys Ile Gly
        35                  40                  45

Asp Leu Ala Asn Tyr Ile Lys Asn Lys Glu Asn Val Tyr Cys Lys Phe
    50                  55                  60

Val Leu Asn Asp Asp Ile Lys Asp Leu Pro Leu Tyr Lys Ile Phe Ser
65                  70                  75                  80

Leu Asn Leu Asn Ser Ser Gln Lys Lys Asn Ala Asp Asn Ala Leu Tyr
                85                  90                  95

Glu Ala Ile Lys Val Leu Asn Ala Asp Gly Tyr Lys Gly Lys Asn Ile
            100                 105                 110

Leu Gly Leu Gly Asp Thr Tyr Phe Arg Arg Asn Gly Tyr Val Lys Asn
        115                 120                 125

Val Ile Ser Asn Tyr Arg Thr Lys Phe Val Thr Leu Lys Pro Asn Val
130                 135                 140

Lys Tyr Ser Lys Ile Asp Ile Asn Ser Val Thr Glu Gln Leu Ile Lys
145                 150                 155                 160

Thr Gln Thr Ile Phe Glu Val Val Asn Lys Lys Ile Glu Ser Glu Thr
                165                 170                 175

Asp Phe Glu Asn Leu Ile Thr Tyr Phe Lys Asn Arg Glu Thr Pro Asn
            180                 185                 190

Asp Glu Lys Ile Lys Arg Leu Glu Leu Phe Asp Tyr Tyr Thr Lys
        195                 200                 205

His Lys Asn Glu Ile Asn Glu Glu Ile Glu Lys His Ala Val Glu Ser
    210                 215                 220

Leu Lys Ser Phe Asn Gly Cys Arg Arg Asn Gly Asn Arg Lys Thr Met
225                 230                 235                 240

Thr Val Gln Met Gln Lys Met Leu Leu Lys His Gly Leu Thr Ser
                245                 250                 255

Tyr Ile Leu His Leu Val Leu Asp Lys Lys Pro Tyr Asp Ile Asn Leu
            260                 265                 270

Met Gly Asn Arg Gln Thr Val Lys Val Asp Asn Asn Gly Asn Arg Val
        275                 280                 285

Asp Leu Val Asp Ile Ser Ser Lys His Gly Tyr Asp Leu Thr Phe Glu
    290                 295                 300

Val Lys Gly Lys Thr Leu Phe Phe Thr Phe Ser Ser Glu Lys Asp Phe
305                 310                 315                 320

Ser Lys Lys Glu Gln Glu Ile Lys Asn Ile Leu Gly Ile Asp Ile Asn
                325                 330                 335

Thr Lys His Ser Met Leu Ala Thr Ser Ile Thr Asp Asn Gly Lys Val
            340                 345                 350
```

```
Lys Gly Tyr Ile Asn Ile Tyr Val Glu Leu Leu Lys Asn Lys Asp Phe
            355                 360                 365

Val Ser Thr Leu Asn Lys Glu Glu Leu Ala Tyr Tyr Thr Glu Met Ala
    370                 375                 380

Lys Phe Val Ser Phe Gly Leu Leu Glu Ile Pro Ser Leu Phe Glu Arg
385                 390                 395                 400

Val Ser Asn Gln Tyr Asp Lys Lys Asn Val Ser Ile Thr Asp Glu
                405                 410                 415

Thr Leu Leu Lys Arg Glu Ile Ala Ile Ser Gln Thr Leu Asp Asn Leu
            420                 425                 430

Ala Lys Lys Tyr Arg Asp Lys Asn Cys Lys Ile Ala Ser Tyr Ile Asp
        435                 440                 445

Tyr Thr Lys Met Leu Arg Ser Lys Tyr Lys Ser Tyr Phe Ile Leu Lys
    450                 455                 460

Gln Lys Tyr Tyr Glu Lys Asn His Glu Tyr Asp Asp Lys Met Gly Phe
465                 470                 475                 480

Ser Asp Ile Ser Thr Asn Ser Lys Glu Thr Met Asp Pro Arg Arg Phe
                485                 490                 495

Glu Asn Pro Phe Ile Asn Thr Asp Ile Ala Lys Gly Leu Ile Val Lys
            500                 505                 510

Leu Glu Asn Val Lys Cys Asp Ile Val Gly Cys Arg Asp Asn Ile Ile
        515                 520                 525

Lys Tyr Ala Tyr Asp Val Ile Val Leu Asn Gly Phe Asp Thr Ile Gly
    530                 535                 540

Leu Glu Tyr Leu Asp Ser Ser Asn Phe Glu Arg Asp Arg Leu Pro Phe
545                 550                 555                 560

Pro Thr Ala Lys Ser Leu Met Thr Tyr Tyr Gly Phe Glu Gly Lys Lys
                565                 570                 575

Tyr Ser Glu Ile Asp Lys Ser Val Phe Asn Thr Lys Tyr Tyr Asn Phe
            580                 585                 590

Ile Phe Asn Glu Asn Glu Thr Ile Lys Asp Ile Ser Tyr Ser Val Tyr
        595                 600                 605

Gly Leu Lys Glu Ile Gln Lys Lys Arg Phe Lys Asn Leu Val Ile Lys
    610                 615                 620

Ala Ile Gly Phe Ala Asp Ile Lys Asp Lys Phe Val Gln Leu Ser Asn
625                 630                 635                 640

Asn Thr Asn Met Asn Val Ile Phe Val Pro Ala Ala Phe Thr Ser Gln
                645                 650                 655

Met Asp Ser Asn Thr His Lys Ile Tyr Val Lys Glu Ile Met Asp Lys
            660                 665                 670

Asn Asn Lys Lys Gln Leu Gln Leu Ile Asp Lys Arg Lys Val Arg Thr
        675                 680                 685

Lys Gln Glu Phe His Ile Asn Gly Leu Asn Ala Asp Phe Asn Ala Ala
    690                 695                 700

Asn Asn Ile Lys Tyr Ile Ala Glu Asn Asn Asp Leu Leu Leu Thr Met
705                 710                 715                 720

Cys Thr Lys Thr Lys Glu Asn Asn Arg Tyr Gly Asn Pro Leu Tyr Asn
                725                 730                 735

Ile Lys Asp Thr Phe Lys Lys Ile Pro Ser Ser Ile Leu Asn Ile
            740                 745                 750

Phe Lys Lys Lys Asp Met Tyr Gln Ile Ile Cys Asp
        755                 760
```

-continued

```
<210> SEQ ID NO 43
<211> LENGTH: 768
<212> TYPE: PRT
<213> ORGANISM: Unknown
<220> FEATURE:
<223> OTHER INFORMATION: Description of Unknown:
      mammals-digestive system-rumen-ovis aries sequence

<400> SEQUENCE: 43

Met Phe Arg Ile Phe Ala Ala Leu Lys Leu Thr Asn Met Gly His Val
1               5                   10                  15

Arg Leu Gln Lys Arg Glu Gly Glu Val Tyr Lys Thr Tyr Lys Leu Lys
            20                  25                  30

Val Lys Ser Phe Ser Gly Asn Val Asp Ile Lys Ala Gly Ile Val Glu
        35                  40                  45

Tyr Asp Gln Lys Phe Asn Asn Val Ser Gln Trp Ile Ala Asp His Leu
    50                  55                  60

Thr Ser Met Thr Ile Gly Glu Ala Ala Ser Arg Ile Ser Pro His Lys
65                  70                  75                  80

Met Asp Ser Gln Tyr Ala Met Thr Ser Leu Ser Asp Glu Trp Lys Asp
                85                  90                  95

Gln Pro Leu Tyr Lys Ile Phe Thr Arg Gly Phe Gly Gly Met Asn Ala
            100                 105                 110

Asp Asn Leu Ile Ile Glu Cys Thr Lys Thr Glu Glu Asn Cys Lys Tyr
        115                 120                 125

Asp Lys Glu Lys Ser Leu Gly Phe Ser Glu Ser Val Phe Arg Thr Phe
    130                 135                 140

Gly Phe Ala Ala Asn Ala Ser Ser Asp Met Lys Ser Arg Met Thr Gln
145                 150                 155                 160

Ala Lys Val Lys Ile Gly Arg Lys Asn Ile Asp Glu Asp Ser Ala Asp
                165                 170                 175

Asp Glu Lys Cys Leu Gln Ala Ile Tyr Glu Ile Gln Lys Asn Glu Leu
            180                 185                 190

Leu Thr Asp Asp Asn Trp Lys Asp Arg Ile Gly Tyr Leu Glu Met Lys
        195                 200                 205

Gly Asp Gln Glu Arg Glu Leu Glu Arg Thr Thr Ile Leu Tyr Asp Tyr
    210                 215                 220

Tyr Arg Ala Asn Arg Thr Thr Val Leu Asp Lys Leu Asp Asn Leu Lys
225                 230                 235                 240

Val Glu Thr Leu Ser Lys Phe Arg Gly Ser Lys Arg Lys Ser Asp Arg
                245                 250                 255

Lys Ile Leu Thr Leu Asn Gly Ile Ser Tyr Asp Ile Lys Arg Lys Glu
            260                 265                 270

Gly Cys Gln Gly Phe Glu Leu Lys Phe Ser Val Asp Lys Asn His Met
        275                 280                 285

Glu Phe Asp Leu Leu Gly His Arg Ala Leu Ile Lys Asn Gly Glu Met
    290                 295                 300

Leu Val Asp Ile Glu Asn Cys His Gly Ser Gln Leu Ser Leu Glu Ile
305                 310                 315                 320

Asp Gly Asp Asp Met Tyr Ala Ile Ile Ser Met Arg Thr Phe Cys Glu
                325                 330                 335

Lys Asn Glu Ser Lys Leu Glu Lys Ile Ile Gly Ala Asp Val Asn Ile
            340                 345                 350

Lys His Met Phe Leu Met Thr Ser Glu Lys Asp Asp Gly Asn Thr Lys
        355                 360                 365
```

-continued

Cys Tyr Val Asn Leu Tyr Arg Glu Leu Leu Ser Asp Ser Asp Phe Thr
    370                 375                 380

Asp Val Leu Asn Lys Glu Glu Tyr Glu Ile Phe Ser Glu Leu Ser Lys
385                 390                 395                 400

Tyr Val Met Phe Gly Leu Ile Glu Thr Pro Tyr Leu Gly Ser Arg Val
            405                 410                 415

Ile Gly Thr Thr Gln His Glu Lys Ile Val Glu Asp Lys Ile Thr Ser
        420                 425                 430

Gly Met Lys Lys Ile Ala Ile Arg Leu Phe Gln Glu Gly Lys Val Arg
    435                 440                 445

Glu Arg Ile Tyr Val Gln Asn Val Leu Lys Ile Arg Ala Leu Leu Lys
450                 455                 460

Ala Leu Phe Ser Thr Lys Leu Ala Tyr Ser Asn Glu Gln Lys Ile Tyr
465                 470                 475                 480

Asp Asn Leu Met Arg Phe Gly Glu Lys Asp Asp Arg Arg Lys Asp Glu
            485                 490                 495

Gly Phe His Thr Thr Cys Arg Gly Thr Ser Leu Arg Ser Glu Met Asp
        500                 505                 510

Met Leu Ser Lys Lys Ile Leu Ala Cys Arg Asp Asn Ile Val Glu Tyr
    515                 520                 525

Gly Tyr Tyr Val Ile Gly Leu Asn Gly Phe Asp Gly Ile Ser Leu Glu
530                 535                 540

Asn Leu Glu Ser Ser Thr Phe Met Asp Val Lys Ile Ser Tyr Pro Ser
545                 550                 555                 560

Cys Asn Ser Met Leu Asp His Phe Lys Leu Lys Gly Lys Thr Ile Glu
            565                 570                 575

Glu Ala Glu Asn His Glu Thr Val Gly Lys Phe Ile Lys Lys Gly Tyr
        580                 585                 590

Tyr Val Met Thr Leu Val Asn Gly Lys Ile Asn Asp Ile Asn Tyr Ser
    595                 600                 605

Glu Lys Ala Val Met Leu His Lys Lys Asn Leu Leu Tyr Asp Thr Val
610                 615                 620

Ile Lys Ser Thr His Phe Ala Asp Val Lys Asp Lys Phe Val Glu Leu
625                 630                 635                 640

Ser Asn Asn Gly Lys Val Ser Val Val Ile Val Pro Pro Tyr Phe Ser
            645                 650                 655

Ser Gln Met Asp Ser Val Thr His Lys Val Phe Thr Glu Glu Ile Val
        660                 665                 670

Val Gln Lys Lys Ser Ser Asn Gly Lys Val Arg Lys Thr Lys Lys Thr
    675                 680                 685

Val Leu Val Asp Lys Arg Lys Val Arg Lys Thr Gln Glu Ser His Ile
690                 695                 700

Asn Gly Leu Asn Ala Asp Tyr Asn Ala Ala Leu Asn Leu Lys Tyr Ile
705                 710                 715                 720

Ala Glu Thr Ile Asp Trp Arg Ser Thr Leu Cys Phe Lys Thr Trp Asn
            725                 730                 735

Thr Tyr Gly Ser Pro Gln Trp Asp Ser Lys Ile Lys Asn Gln Lys Thr
        740                 745                 750

Met Ile Asp Arg Leu Asp Ser Leu Gly Ala Ile Glu Leu Lys Asn Trp
    755                 760                 765

<210> SEQ ID NO 44
<211> LENGTH: 789
<212> TYPE: PRT

```
<213> ORGANISM: Unknown
<220> FEATURE:
<223> OTHER INFORMATION: Description of Unknown:
      mammals-digestive system-rumen-ovis aries sequence

<400> SEQUENCE: 44
```

| | | | | | | | | | | | | | | |
|---|---|---|---|---|---|---|---|---|---|---|---|---|---|---|
| Met | Ser | His | Glu | Phe | Asn | Lys | Asn | Lys | Gly | Glu | Asn | Glu | Ile | Ser | Lys |
| 1 | | | | 5 | | | | | 10 | | | | | 15 | |

| Thr | Phe | Ile | Phe | Lys | Thr | Lys | Cys | Gly | Lys | Asn | Asp | Ile | Thr | Ser | Leu |
| | | | 20 | | | | | 25 | | | | | 30 | | |

| Trp | Val | Pro | Ala | Met | Glu | Glu | Tyr | Cys | Thr | Tyr | Tyr | Asn | Arg | Val | Ser |
| | | | 35 | | | | | 40 | | | | | 45 | | |

| Lys | Trp | Ile | Cys | Asp | Asn | Leu | Thr | Glu | Met | Arg | Ile | Gly | Asp | Leu | Ala |
| | 50 | | | | | 55 | | | | | 60 | | | | |

| Gln | Tyr | Ile | Asp | Asn | His | Gly | Ser | Ala | Tyr | Tyr | Ser | Ala | Val | Thr | Asp |
| 65 | | | | | 70 | | | | | 75 | | | | | 80 |

| Ile | Thr | Lys | Lys | Asp | Leu | Pro | Leu | Tyr | Lys | Ile | Phe | Lys | Lys | Gly | Phe |
| | | | | 85 | | | | | 90 | | | | | 95 | |

| Ser | Gly | Leu | Cys | Ala | Asp | Asn | Ala | Leu | Tyr | Cys | Ala | Ile | Ala | Lys | Leu |
| | | | 100 | | | | | 105 | | | | | 110 | | |

| Asn | Pro | Glu | Gly | Tyr | Asp | Gly | Asn | Met | Phe | Gly | Leu | Ser | Glu | Thr | Tyr |
| | | | 115 | | | | | 120 | | | | | 125 | | |

| Tyr | Arg | Arg | Gln | Gly | Tyr | Ile | Ala | Asn | Val | Phe | Gly | Asn | Tyr | Arg | Thr |
| | 130 | | | | | 135 | | | | | 140 | | | | |

| Lys | Met | Asn | Ala | Gly | Leu | Lys | Val | Gly | Cys | Ala | Lys | Trp | Lys | Lys | Phe |
| 145 | | | | | 150 | | | | | 155 | | | | | 160 |

| Asp | Thr | Asn | Asp | Val | Asp | Asp | Glu | Ile | Leu | Met | Glu | Gln | Val | Ile | Val |
| | | | | 165 | | | | | 170 | | | | | 175 | |

| Asp | Val | Val | Lys | Tyr | Asp | Ile | Asp | Ser | Lys | Asn | Glu | Phe | Lys | Glu | Tyr |
| | | | 180 | | | | | 185 | | | | | 190 | | |

| Ile | Glu | Val | Leu | Lys | Cys | Arg | Glu | Gly | Asn | Pro | Lys | Leu | Leu | Glu | Thr |
| | | | 195 | | | | | 200 | | | | | 205 | | |

| Ile | Glu | Arg | Leu | Glu | Cys | Leu | Tyr | Gly | Tyr | Tyr | Ser | Gln | His | Glu | Glu |
| | 210 | | | | | 215 | | | | | 220 | | | | |

| Asp | Ile | Lys | Lys | Lys | Ile | Glu | Glu | Leu | Val | Val | Glu | Glu | Leu | Lys | Thr |
| 225 | | | | | 230 | | | | | 235 | | | | | 240 |

| Phe | Gly | Gly | Cys | Val | Arg | Lys | Ser | Met | Thr | Ser | Cys | Thr | Ile | Thr | Val |
| | | | | 245 | | | | | 250 | | | | | 255 | |

| Gln | Asp | Phe | Val | Met | Glu | Arg | Ile | Gly | Asn | Thr | Gly | Tyr | Arg | Ile | Asn |
| | | | 260 | | | | | 265 | | | | | 270 | | |

| Leu | Thr | Phe | Asn | Lys | Lys | Pro | Tyr | Val | Leu | Gly | Leu | Leu | Gly | Asn | Arg |
| | | | 275 | | | | | 280 | | | | | 285 | | |

| Gln | Val | Val | Arg | Tyr | Val | Asp | Gly | Asp | Arg | Val | Glu | Leu | Val | Asp | Ile |
| | 290 | | | | | 295 | | | | | 300 | | | | |

| Val | Asn | His | Gly | Asn | Gln | Ile | Thr | Phe | Asn | Leu | Lys | Asn | Gly | Glu |
| 305 | | | | | 310 | | | | | 315 | | | | | 320 |

| Leu | Phe | Val | His | Leu | Thr | Ser | Gly | Val | Asp | Phe | Ser | Lys | Glu | Glu | Ser |
| | | | | 325 | | | | | 330 | | | | | 335 | |

| Ser | Met | Glu | Asn | Ile | Val | Gly | Val | Asp | Val | Asn | Ile | Lys | His | Ser | Met |
| | | | 340 | | | | | 345 | | | | | 350 | | |

| Leu | Ala | Ser | Ser | Ile | Val | Asp | Asp | Gly | Asn | Val | Asn | Gly | Tyr | Ile | Asn |
| | | | 355 | | | | | 360 | | | | | 365 | | |

| Ile | Tyr | Lys | Glu | Leu | Val | Asn | Asp | Asp | Glu | Phe | Val | Ser | Thr | Phe | Gly |
| | 370 | | | | | 375 | | | | | 380 | | | | |

```
Asp Ser Glu Ser Gly Leu Asn Glu Leu Glu Leu Tyr Arg Gln Met Ala
385                 390                 395                 400

Glu Ser Val Asn Phe Gly Leu Met Glu Thr Asp Ser Leu Phe Glu Arg
            405                 410                 415

Tyr Val Glu Gln Trp Lys Gly Ser Asp Ser Asp Ser Arg Leu Ala Arg
        420                 425                 430

Arg Glu Arg Val Val Gly Lys Val Phe Asp Arg Ile Val Lys Thr Asn
        435                 440                 445

Gly Asp Val His Val Val Asn Tyr Ile His Ala Val Lys Met Leu Arg
    450                 455                 460

Ala Lys Cys Lys Ala Tyr Phe Val Leu Lys Gln Lys Tyr Tyr Glu Lys
465             470                 475                 480

Gln Lys Glu Tyr Asp Asp Ala His Gly Tyr Thr Asp Glu Ser Thr Ala
            485                 490                 495

Ser Lys Glu Thr Met Asp Lys Arg Arg Phe Glu Asn Pro Phe Val Glu
            500                 505                 510

Thr Asp Val Ala Lys Glu Leu Leu Gly Lys Leu Ala Cys Val Glu Gln
        515                 520                 525

Asp Ile Ile Gly Cys Arg Asp Asn Ile Val Thr Tyr Ala Phe Asn Val
        530                 535                 540

Phe Arg Arg Asn Gly Tyr Asp Thr Ile Ser Leu Glu Tyr Leu Asp Ser
545                 550                 555                 560

Ser Gln Phe Lys Lys Ile Gly Met Gly Ala Pro Thr Pro Lys Ser Leu
            565                 570                 575

Leu Lys Tyr His Lys Leu Glu Gly Lys Thr Val Glu Glu Val Glu Ser
        580                 585                 590

Ile Ile Ser Glu Lys Gly Leu Lys Lys Asn Leu Tyr Val Phe Lys Phe
        595                 600                 605

Gly Asp Asn Gly Leu Leu Ser Asp Ile Glu Tyr Ser Asp Glu Gly Leu
        610                 615                 620

Ile Arg Lys Lys Lys Ala Asp Phe Gly Asn Ile Ile Thr Lys Ala Ile
625                 630                 635                 640

His Phe Ala Asp Ile Lys Asp Lys Phe Val Gln Leu Thr Asn Asn Ser
            645                 650                 655

Asp Met Gly Val Val Phe Cys Pro Ser Ala Phe Thr Ser Gln Met Asp
            660                 665                 670

Ser Lys Thr His Arg Leu Tyr Phe Val Glu Gly Leu Asp Gly Asn Gly
        675                 680                 685

Lys Asn Lys Tyr Val Leu Ala Asn Lys Trp Ser Val Arg Arg Gln Gln
        690                 695                 700

Glu Arg His Ile Asn Gly Leu Asn Ala Asp Phe Asn Ser Ala Cys Asn
705                 710                 715                 720

Cys Gln His Ile Ala Tyr Asp Pro Ile Leu Arg Asp Ala Met Thr Ile
            725                 730                 735

Lys Val Glu Ala Gly Lys Gly Met Tyr Asn Lys Pro Ser Tyr Asp Ile
            740                 745                 750

Arg Lys Lys Phe Lys Lys Asn Leu Ser Ala Ala Thr Leu Lys Thr Phe
        755                 760                 765

Ile Lys Leu Gly Asn Thr Val Lys Gly Met Ile Val Asn Gly Gln Phe
        770                 775                 780

Val Glu Met Glu Ser
785
```

```
<210> SEQ ID NO 45
<211> LENGTH: 784
<212> TYPE: PRT
<213> ORGANISM: Unknown
<220> FEATURE:
<223> OTHER INFORMATION: Description of Unknown:
      mammals-digestive system-rumen-ovis aries sequence

<400> SEQUENCE: 45

Met Tyr Asn Ser Lys Lys Gly Glu Gly Asp Ile Gln Lys Ser Phe
1               5                   10                  15

Lys Phe Lys Val Lys Thr Asp Lys Glu Thr Val Glu Leu Phe Arg Lys
                20                  25                  30

Ala Ala Val Glu Tyr Ser Glu Tyr Tyr Lys Arg Leu Thr Thr Phe Leu
                35                  40                  45

Cys Glu Arg Leu Thr Asp Met Thr Trp Gly Glu Val Ala Ser Phe Ile
                50                  55                  60

Pro Glu Lys Tyr Arg Lys Asn Glu Tyr Tyr Lys Tyr Leu Ile Lys Glu
65                  70                  75                  80

Glu Asn Lys Asp Leu Pro Leu Tyr Lys Met Phe Thr Lys Ala Ala Ser
                85                  90                  95

Ser Met Phe Ile Asp His Ser Ile Glu Arg Tyr Val Glu Ala Leu Asn
                100                 105                 110

Pro Glu Gly Asn Thr Gly Asn Ile Leu Gly Phe Cys Lys Ser Ser Tyr
                115                 120                 125

Val Arg Gly Gly Tyr Leu Lys Asn Val Val Ser Asn Ile Arg Thr Lys
                130                 135                 140

Phe Ala Thr Leu Lys Thr Gly Ile Lys Tyr Lys Lys Phe Asn Pro Ala
145                 150                 155                 160

Glu Asp Asp Glu Glu Thr Ile Leu Gly Gln Thr Val Phe Glu Met Glu
                165                 170                 175

Lys Arg Gly Leu Glu Phe Lys Cys Asp Phe Glu Lys Thr Ile Lys Tyr
                180                 185                 190

Leu Asn Glu Lys Gly Lys Thr Gln Glu Ala Glu Arg Leu Gln Cys Leu
                195                 200                 205

Met Glu Tyr Phe Ser Thr Asn Thr Asp Lys Ile Asn Glu Tyr Arg Glu
                210                 215                 220

Ser Leu Val Leu Asp Asp Ile Arg Lys Phe Gly Gly Cys Asn Arg Ser
225                 230                 235                 240

Lys Ser Asn Ser Phe Ser Val Thr Leu Glu Lys Ala Asp Ile Lys Glu
                245                 250                 255

Asp Gly Leu Thr Gly Tyr Thr Met Lys Val Ser Lys Lys Leu Lys Glu
                260                 265                 270

Ile His Leu Leu Gly His Arg Arg Val Val Glu Val Val Asn Gly Arg
                275                 280                 285

Arg Val Asn Leu Val Asp Ile Cys Gly Asp Lys Ser Gly Asp Ser Lys
                290                 295                 300

Val Phe Val Val Asp Gly Asp Asn Leu Tyr Val Cys Ile Ser Ala Pro
305                 310                 315                 320

Val Lys Phe Ser Lys Asn Gly Met Glu Ala Lys Lys Tyr Ile Gly Val
                325                 330                 335

Asp Met Asn Met Lys His Ser Ile Ile Ser Val Ser Asp Asn Ala Ser
                340                 345                 350

Asp Met Lys Gly Phe Leu Asn Ile Tyr Lys Glu Leu Leu Lys Asp Glu
                355                 360                 365
```

-continued

```
Gly Phe Arg Lys Thr Leu Asn Ala Thr Glu Leu Glu Lys Tyr Glu Lys
    370                 375                 380

Leu Ala Glu Gly Val Asn Ile Gly Ile Ile Glu Tyr Asp Gly Leu Tyr
385                 390                 395                 400

Glu Arg Ile Val Lys Gln Lys Lys Glu Asn Ser Val Asp Gly Leu Lys
                405                 410                 415

Val Gln Ala Glu Lys Lys Leu Ile Glu Arg Glu Ala Ala Ile Glu Arg
                420                 425                 430

Val Leu Asp Lys Leu Arg Lys Gly Thr Ser Asp Thr Asp Thr Glu Asn
            435                 440                 445

Tyr Ile Asn Tyr Asn Lys Ile Leu Arg Ala Lys Ile Lys Ser Ala Tyr
    450                 455                 460

Ile Leu Lys Asp Lys Tyr Tyr Glu Met Leu Gly Lys Tyr Asp Ser Glu
465                 470                 475                 480

Arg Ala Gly Ser Gly Asp Leu Ser Glu Glu Asn Lys Ile Lys Tyr Lys
                485                 490                 495

Asp Glu Phe Asn Glu Thr Glu Lys Gly Lys Glu Ile Leu Gly Lys Leu
                500                 505                 510

Asn Asn Val Tyr Lys Asp Ile Ile Gly Cys Arg Asp Asn Ile Val Thr
            515                 520                 525

Tyr Ala Val Asn Leu Phe Ile Arg Asn Gly Tyr Asp Thr Val Ala Leu
    530                 535                 540

Glu Tyr Leu Glu Ser Ser Gln Met Lys Ala Arg Arg Ile Pro Ser Thr
545                 550                 555                 560

Gly Gly Leu Leu Lys Gly His Lys Leu Glu Gly Lys Pro Glu Gly Glu
                565                 570                 575

Val Thr Ala Tyr Leu Lys Ala Asn Lys Ile Pro Lys Ser Tyr Tyr Ser
                580                 585                 590

Phe Glu Tyr Asp Gly Asn Gly Met Leu Thr Asp Val Lys Tyr Ser Asp
            595                 600                 605

Met Gly Glu Lys Ala Arg Gly Arg Asn Arg Phe Lys Asn Leu Val Pro
    610                 615                 620

Lys Phe Leu Arg Trp Ala Ser Ile Lys Asp Lys Phe Val Gln Leu Ser
625                 630                 635                 640

Asn Tyr Lys Asp Ile Gln Met Val Tyr Val Pro Ser Pro Tyr Thr Ser
                645                 650                 655

Gln Thr Asp Ser Arg Thr His Ser Leu Tyr Tyr Ile Glu Thr Val Lys
            660                 665                 670

Val Asp Glu Lys Thr Gly Lys Glu Lys Glu His Ile Val Ala Pro
    675                 680                 685

Lys Glu Ser Val Arg Thr Glu Gln Glu Ser Phe Val Asn Gly Met Asn
690                 695                 700

Ala Asp Thr Asn Ser Ala Asn Asn Ile Lys Tyr Ile Phe Glu Asn Glu
705                 710                 715                 720

Thr Leu Arg Asp Lys Phe Leu Lys Arg Thr Lys Asp Gly Thr Glu Met
                725                 730                 735

Tyr Asn Arg Pro Ala Phe Asp Leu Lys Glu Cys Tyr Lys Lys Asn Ser
            740                 745                 750

Asn Val Ser Val Phe Asn Thr Leu Lys Lys Thr Leu Gly Ala Ile Tyr
    755                 760                 765

Gly Lys Leu Asp Glu Asn Gly Asn Phe Ile Glu Asn Glu Cys Asn Lys
770                 775                 780
```

```
<210> SEQ ID NO 46
<211> LENGTH: 764
<212> TYPE: PRT
<213> ORGANISM: Unknown
<220> FEATURE:
<223> OTHER INFORMATION: Description of Unknown:
      mammals-digestive system-rumen-ovis aries sequence

<400> SEQUENCE: 46
```

| | | | | | | | | | | | | | | | |
|---|---|---|---|---|---|---|---|---|---|---|---|---|---|---|---|
| Met | Asn | Lys | Ser | Tyr | Val | Phe | Lys | Ser | Asn | Val | Ala | Ile | Asp | Asp | Ile |
| 1 | | | | 5 | | | | | 10 | | | | | 15 | |
| Met | Ser | Leu | Phe | Glu | Pro | Ala | Ile | Glu | Glu | Tyr | Ile | Asn | Tyr | Tyr | Asn |
| | | | | 20 | | | | | 25 | | | | | 30 | |
| Arg | Thr | Ser | Asp | Phe | Ile | Cys | Asp | Asn | Leu | Thr | Ser | Met | Lys | Ile | Gly |
| | | 35 | | | | | 40 | | | | | 45 | | | |
| Asp | Leu | Ala | Asn | Tyr | Ile | Lys | Asn | Lys | Glu | Asn | Val | Tyr | Cys | Lys | Phe |
| | 50 | | | | | 55 | | | | | 60 | | | | |
| Val | Leu | Asn | Asp | Asp | Ile | Lys | Asp | Leu | Pro | Leu | Tyr | Lys | Ile | Phe | Ser |
| 65 | | | | | 70 | | | | | 75 | | | | | 80 |
| Leu | Asn | Leu | Asn | Ser | Ser | Gln | Lys | Lys | Asn | Ala | Asp | Asn | Ala | Leu | Tyr |
| | | | | 85 | | | | | 90 | | | | | 95 | |
| Glu | Ala | Ile | Lys | Val | Leu | Asn | Ala | Asp | Gly | Tyr | Lys | Gly | Lys | Asn | Ile |
| | | | | 100 | | | | | 105 | | | | | 110 | |
| Leu | Gly | Leu | Gly | Asp | Thr | Tyr | Phe | Arg | Arg | Asn | Gly | Tyr | Val | Lys | Asn |
| | | | 115 | | | | | 120 | | | | | 125 | | |
| Val | Ile | Ser | Asn | Tyr | Arg | Thr | Lys | Phe | Val | Thr | Leu | Lys | Pro | Asn | Val |
| | 130 | | | | | 135 | | | | | 140 | | | | |
| Lys | Tyr | Ser | Lys | Ile | Asp | Ile | Asn | Ser | Val | Thr | Glu | Gln | Leu | Ile | Lys |
| 145 | | | | | 150 | | | | | 155 | | | | | 160 |
| Thr | Gln | Thr | Ile | Phe | Glu | Val | Val | Asn | Lys | Lys | Ile | Glu | Ser | Glu | Thr |
| | | | | 165 | | | | | 170 | | | | | 175 | |
| Asp | Phe | Glu | Asn | Leu | Ile | Thr | Tyr | Phe | Lys | Asn | Arg | Glu | Thr | Pro | Asn |
| | | | | 180 | | | | | 185 | | | | | 190 | |
| Asp | Glu | Lys | Ile | Lys | Arg | Leu | Glu | Leu | Leu | Phe | Asp | Tyr | Tyr | Thr | Lys |
| | | | 195 | | | | | 200 | | | | | 205 | | |
| His | Lys | Asn | Glu | Ile | Asn | Glu | Glu | Ile | Glu | Lys | His | Ala | Val | Glu | Ser |
| | 210 | | | | | 215 | | | | | 220 | | | | |
| Leu | Lys | Ser | Phe | Asn | Gly | Cys | Arg | Arg | Asn | Gly | Asn | Arg | Lys | Thr | Met |
| 225 | | | | | 230 | | | | | 235 | | | | | 240 |
| Thr | Val | Gln | Met | Gln | Lys | Met | Leu | Leu | Lys | Lys | His | Gly | Leu | Thr | Ser |
| | | | | 245 | | | | | 250 | | | | | 255 | |
| Tyr | Ile | Leu | His | Leu | Val | Leu | Asp | Lys | Lys | Pro | Tyr | Asp | Ile | Asn | Leu |
| | | | | 260 | | | | | 265 | | | | | 270 | |
| Met | Gly | Asn | Arg | Gln | Thr | Val | Lys | Val | Asp | Asn | Asn | Gly | Asn | Arg | Val |
| | | | 275 | | | | | 280 | | | | | 285 | | |
| Asp | Leu | Val | Asp | Ile | Ser | Ser | Lys | His | Gly | Tyr | Asp | Leu | Thr | Phe | Glu |
| | 290 | | | | | 295 | | | | | 300 | | | | |
| Val | Lys | Gly | Lys | Thr | Leu | Phe | Phe | Thr | Phe | Ser | Ser | Glu | Lys | Asp | Phe |
| 305 | | | | | 310 | | | | | 315 | | | | | 320 |
| Ser | Lys | Lys | Glu | Gln | Glu | Ile | Lys | Asn | Ile | Leu | Gly | Ile | Asp | Ile | Asn |
| | | | | 325 | | | | | 330 | | | | | 335 | |
| Thr | Lys | His | Ser | Met | Leu | Ala | Thr | Ser | Ile | Thr | Asp | Asn | Gly | Lys | Val |
| | | | | 340 | | | | | 345 | | | | | 350 | |
| Lys | Gly | Tyr | Ile | Asn | Ile | Tyr | Val | Glu | Leu | Leu | Lys | Asn | Lys | Asp | Phe |
| | | | 355 | | | | | 360 | | | | | 365 | | |

Val Ser Thr Leu Asn Lys Glu Glu Leu Ala Tyr Tyr Thr Glu Met Ala
    370                 375                 380

Lys Phe Val Ser Phe Gly Leu Leu Glu Ile Pro Ser Leu Phe Glu Arg
385                 390                 395                 400

Val Ser Asn Gln Tyr Asp Lys Lys Asn Val Ser Ile Thr Asp Glu
                405                 410                 415

Thr Leu Leu Lys Arg Glu Ile Ala Ile Ser Gln Thr Leu Asp Asn Leu
        420                 425                 430

Ala Lys Lys Tyr Arg Asp Lys Asn Cys Lys Ile Ala Ser Tyr Ile Asp
    435                 440                 445

Tyr Thr Lys Met Leu Arg Ser Lys Tyr Lys Ser Tyr Phe Ile Leu Lys
450                 455                 460

Gln Lys Tyr Tyr Glu Lys Asn His Glu Tyr Asp Asp Lys Met Gly Phe
465                 470                 475                 480

Ser Asp Ile Ser Thr Asn Ser Lys Glu Thr Met Asp Pro Arg Arg Phe
                485                 490                 495

Glu Asn Pro Phe Ile Asn Thr Asp Ile Ala Lys Gly Leu Ile Val Lys
            500                 505                 510

Leu Glu Asn Val Lys Cys Asp Ile Val Gly Cys Arg Asp Asn Ile Ile
        515                 520                 525

Lys Tyr Ala Tyr Asp Val Ile Val Leu Asn Gly Phe Asp Thr Ile Gly
    530                 535                 540

Leu Glu Tyr Leu Asp Ser Ser Asn Phe Glu Arg Asp Arg Leu Pro Phe
545                 550                 555                 560

Pro Thr Ala Lys Ser Leu Met Thr Tyr Tyr Gly Phe Glu Gly Lys Lys
                565                 570                 575

Tyr Ser Glu Ile Asp Lys Ser Val Phe Asn Thr Lys Tyr Tyr Asn Phe
            580                 585                 590

Ile Phe Asn Glu Asn Glu Thr Ile Lys Asp Ile Ser Tyr Ser Val Tyr
        595                 600                 605

Gly Leu Lys Glu Ile Gln Lys Lys Arg Phe Lys Asn Leu Val Ile Lys
    610                 615                 620

Ala Ile Gly Phe Ala Asp Ile Lys Asp Lys Phe Val Gln Leu Ser Asn
625                 630                 635                 640

Asn Thr Asn Met Asn Val Ile Phe Val Pro Ala Ala Phe Thr Ser Gln
                645                 650                 655

Met Asp Ser Asn Thr His Lys Ile Tyr Val Lys Glu Ile Met Asp Lys
            660                 665                 670

Asn Asn Lys Lys Gln Leu Gln Leu Ile Asp Lys Arg Lys Val Arg Thr
        675                 680                 685

Lys Gln Glu Phe His Ile Asn Gly Leu Asn Ala Asp Phe Asn Ala Ala
    690                 695                 700

Asn Asn Ile Lys Tyr Ile Ala Glu Asn Asn Asp Leu Leu Leu Thr Met
705                 710                 715                 720

Cys Thr Lys Thr Lys Glu Asn Asn Arg Tyr Gly Asn Pro Leu Tyr Asn
                725                 730                 735

Ile Lys Asp Thr Phe Lys Lys Ile Pro Ser Ser Ile Leu Asn Ile
            740                 745                 750

Phe Lys Lys Lys Asp Met Tyr Gln Ile Ile Cys Asp
                755                 760

<210> SEQ ID NO 47
<211> LENGTH: 758
<212> TYPE: PRT

<213> ORGANISM: Unknown
<220> FEATURE:
<223> OTHER INFORMATION: Description of Unknown:
      mammals-digestive system-rumen-ovis aries sequence

<400> SEQUENCE: 47

```
Met Ala His Lys Thr Lys Glu Ser Glu Lys Leu Val Lys Ser Phe Lys
1               5                   10                  15

Leu Lys Val Asp Ile Ser Asn Cys Glu Ile Glu Lys Lys Trp Ile Pro
                20                  25                  30

Ser Phe Glu Glu Tyr Thr Asn Tyr Asn Gly Val Ser Asn Trp Ile
            35                  40                  45

Cys Glu Asn Leu Ile Ser Met Lys Ile Gly Asp Leu Gly Gln Tyr Ile
    50                  55                  60

Lys Asn Thr Glu Ser Val Tyr Tyr Lys Phe Ile Thr Asp Glu Ser Ile
65                  70                  75                  80

Ser Asn Leu Pro Leu Tyr Lys Ile Phe Thr Leu Lys Gln Thr Gln Asn
                85                  90                  95

Val Asp Asn Ala Leu Phe Cys Ala Ile Lys Glu Ile Asn Pro Glu Lys
                100                 105                 110

Tyr Asn Gly Asn Ser Ile Gly Leu Gly Glu Thr Asp Tyr Arg Arg Phe
            115                 120                 125

Gly Tyr Val Gln Cys Val Ile Ser Asn Tyr Arg Thr Lys Ile Gly Thr
130                 135                 140

Met Lys Ala Ser Ile Lys Tyr Lys Thr Leu Pro Glu Asn Gln Ser Tyr
145                 150                 155                 160

Asp Val Ile Phe Glu Gln Thr Met Tyr Glu Met Ile Asp Lys Ser Leu
                165                 170                 175

Glu Lys Lys Glu Asp Trp Glu Asn Ile Ile Ser Asn Tyr Lys Ala Lys
            180                 185                 190

Gln Thr Glu Asn Thr Ser Lys Ile Asn Arg Met Glu Thr Leu Tyr Ser
        195                 200                 205

Phe Phe Ile Glu His Ser Glu Glu Ile Ile Glu Lys Ser Asn Leu Val
210                 215                 220

Ala Ile Glu Gln Leu Ala Leu Phe Asn Gly Cys Lys Arg Lys Ser Leu
225                 230                 235                 240

Ser Thr Met Thr Ile His Ser Gln His Ser Lys Leu Gln Lys Asn Gly
                245                 250                 255

Leu Thr Ser Phe Val Phe Cys Ile Asn Gln Lys Ile Gly Ser Ile Asn
            260                 265                 270

Leu Phe Gly Asn Arg Gln Leu Val Ser Val Asp Glu Asn Gly Asn Arg
        275                 280                 285

Asn Asp Ile Ile Asp Ile Cys Asn Asn Tyr Gly Asp Phe Ile Thr Phe
290                 295                 300

Gln Ile Lys Asn Gly Lys Met Phe Ile Ile Leu Thr Ala Lys Val Asp
305                 310                 315                 320

Phe Asp Lys Glu Asn Ile Glu Ile Lys Asn Val Val Gly Ala Asp Val
                325                 330                 335

Asn Ile Lys His Asn Met Ile Ala Ser Ser Ile Ile Asp Asn Gly Asn
            340                 345                 350

Val Phe Gly Tyr Ile Asn Ile Tyr Lys Glu Leu Leu Asn Asp Glu Asp
        355                 360                 365

Phe Cys Ser Ser Cys Thr Asn Glu Glu Leu Asp Ile Tyr Lys Glu Ile
370                 375                 380
```

Ser Lys Ser Val Asn Phe Gly Leu Leu Glu Cys Glu Ser Leu Phe Ser
385                 390                 395                 400

Arg Val Ser Ala Gln Ile Tyr Lys Glu Asn Glu Ser Ile Ser Lys Leu
            405                 410                 415

Asp Asp Arg Phe Leu Arg Arg Glu Lys Ser Ile Glu Asn Val Leu Asn
        420                 425                 430

Arg Leu Ser Lys Gln Tyr Arg Tyr Lys Asp Cys Lys Ile Ala Thr Tyr
    435                 440                 445

Ile Asp Tyr Thr Lys Ile Met Arg Asp Ser Tyr Lys Ser Tyr Phe Ile
450                 455                 460

Ile Lys Glu Lys Tyr Tyr Glu Lys Gln Lys Glu Tyr Asp Ile Ser Met
465                 470                 475                 480

Gly Tyr Val Asp Glu Ser Thr Asn Ser Lys Lys Thr Met Asp Lys Arg
            485                 490                 495

Arg Phe Glu Asn Pro Phe Ile Glu Thr Glu Thr Ala Lys Asn Ile Leu
        500                 505                 510

Ser Lys Leu Asn Arg Ile Glu Ser Arg Leu Ile Gly Cys Arg Asn Asn
    515                 520                 525

Ile Thr Asn Tyr Ala Phe Asp Val Phe Lys Asn Asn Gly Phe Asp Thr
530                 535                 540

Ile Ala Leu Glu Tyr Leu Asp Ser Ser Gln Phe Asp Lys Thr Lys Val
545                 550                 555                 560

Leu Thr Pro Ile Ser Met Leu Lys Tyr His Lys Phe Glu Gly Lys Ser
            565                 570                 575

Ile Glu Glu Val Lys Thr Leu Asn Val Lys Phe Ser Met Asp Asn Tyr
        580                 585                 590

Glu Phe Glu Phe Asp Asn Asn Gly Lys Ile Thr Asn Ile Ser Phe Ser
    595                 600                 605

Gln Leu Gly Lys Arg Glu Val Met Lys Thr Asn Phe Phe Asn Leu Ile
610                 615                 620

Ile Lys Ala Ile His Phe Ala Glu Ile Lys Asp Lys Phe Ile Gln Leu
625                 630                 635                 640

Ser Asn Asn Lys Pro Ile Asn Ile Val Leu Val Pro Ser Ala Phe Ser
            645                 650                 655

Ser Gln Met Asp Ser Lys Asp His Lys Leu Tyr Val Asp Glu Asn Gly
        660                 665                 670

Lys Leu Ile Asn Lys Arg Lys Val Arg Lys Gln Gln Glu Arg His Ile
    675                 680                 685

Asn Gly Leu Asn Ala Asp Phe Asn Ala Ala Cys Asn Leu Ser Tyr Leu
690                 695                 700

Ala Lys Asn Asn Glu Leu Leu Glu Lys Val Cys Leu Lys Arg Lys Lys
705                 710                 715                 720

Phe Gly Lys Ala Ser Tyr Ser Val Pro Tyr Trp Asn Val Lys Asp Ala
            725                 730                 735

Phe Lys Lys Asn Val Ser Ser Asn Met Ile Ala Thr Ile Lys Lys Met
        740                 745                 750

Asn Met Val Lys Val Phe
        755

<210> SEQ ID NO 48
<211> LENGTH: 785
<212> TYPE: PRT
<213> ORGANISM: Unknown
<220> FEATURE:
<223> OTHER INFORMATION: Description of Unknown:

mammals-digestive system-rumen-ovis aries sequence

<400> SEQUENCE: 48

Met Ala His Lys Thr Asn Asn Gly Glu Asn Thr Ile Asn Lys Thr Phe
1               5                   10                  15

Ile Phe Lys Ala Lys Cys Glu Lys Asn Asp Ile Ile Ser Leu Trp Lys
            20                  25                  30

Pro Ala Ala Glu Glu Tyr Cys Asn Tyr Tyr Asn Lys Leu Ser Lys Trp
        35                  40                  45

Ile Gly Asp Ser Leu Thr Thr Met Lys Ile Gly Asp Leu Ala Gln Tyr
    50                  55                  60

Ile Thr Asn Gln Asn Ser Ala Tyr Tyr Leu Ala Val Thr Asn Asp Ser
65                  70                  75                  80

Lys Lys Asp Leu Pro Leu Tyr Lys Ile Phe Gln Lys Gly Phe Ser Ser
                85                  90                  95

Gln Cys Ala Asp Asn Ala Leu Tyr Ser Ala Ile Lys Ala Ile Asn Pro
            100                 105                 110

Glu Asn Tyr Asn Gly Asn Ser Leu Glu Ile Gly Glu Thr Asp Tyr Arg
        115                 120                 125

Arg Phe Gly Tyr Val Gln Ser Val Ile Gly Asn Phe Arg Thr Lys Met
    130                 135                 140

Ser Ser Leu Lys Val Ser Val Lys Tyr Lys Phe Asp Val Asn Asp
145                 150                 155                 160

Val Asp Glu Glu Thr Leu Lys Thr Gln Thr Ile Tyr Asp Val Asp Lys
                165                 170                 175

Tyr Gly Ile Glu Ser Ile Lys Asp Phe Asn Glu Phe Ile Glu Val Leu
            180                 185                 190

Lys Leu Arg Glu Glu Thr Pro Gln Leu Asn Lys Ile Thr Arg Leu
        195                 200                 205

Glu Cys Leu Cys Gly Tyr Tyr Ser Lys Asn Glu Glu Asn Ile Lys Asn
    210                 215                 220

Glu Ile Glu Thr Met Ala Ile Ser Asp Leu Gln Lys Phe Gly Gly Cys
225                 230                 235                 240

Gln Arg Lys Ser Leu Asn Thr Leu Thr Ile His Lys Gln Asn Ser Leu
                245                 250                 255

Met Glu Lys Val Gly Asn Thr Ser Phe Thr Leu Gln Leu Ser Phe Asn
            260                 265                 270

Lys Lys Pro Tyr Thr Ile Asn Leu Leu Gly Asn Arg Gln Val Val Lys
        275                 280                 285

Phe Val Asp Gly Lys Arg Val Asp Leu Ile Asp Ile Thr Glu Lys His
    290                 295                 300

Gly Asp Trp Val Thr Phe Asn Ile Lys Asn Asp Glu Leu Phe Val His
305                 310                 315                 320

Leu Thr Ser Pro Ile Asp Phe Glu Lys Glu Val Cys Glu Ile Lys Asn
                325                 330                 335

Ala Val Gly Val Asp Val Asn Ile Lys His Asn Met Leu Ala Thr Ser
            340                 345                 350

Ile Lys Asp Asp Gly Asn Val Lys Gly Tyr Ile Asn Leu Tyr Lys Glu
        355                 360                 365

Leu Val Asn Asp Cys Asp Phe Ile Ser Thr Cys Asn Glu Asp Glu Phe
    370                 375                 380

Asp Leu Tyr Arg Gln Met Ser Glu Ser Val Asn Phe Gly Ile Leu Glu
385                 390                 395                 400

-continued

```
Thr Asp Ser Leu Phe Glu Arg Val Val Asn Gln Ser Lys Gly Gly Cys
                405                 410                 415
Leu Asn Asn Lys Phe Ile Arg Arg Glu Leu Ala Met Gln Lys Val Phe
            420                 425                 430
Asp Asn Ile Thr Lys Thr Asn Lys Asp Gln Asn Ile Val Asp Tyr Val
        435                 440                 445
Asn Tyr Val Lys Met Leu Arg Ala Lys Tyr Lys Ala Tyr Phe Ile Leu
450                 455                 460
Lys Glu Lys Tyr Tyr Glu Lys Gln Lys Glu Tyr Asp Ile Lys Met Gly
465                 470                 475                 480
Phe Thr Asp Val Ser Thr Glu Ser Lys Glu Thr Met Asp Lys Arg Arg
                485                 490                 495
Met Glu Phe Pro Phe Val Asn Thr Asp Thr Ala Lys Glu Leu Leu Ala
            500                 505                 510
Lys Leu Asn Asn Ile Glu Gln Asp Leu Ile Gly Cys Arg Asp Asn Ile
        515                 520                 525
Val Thr Tyr Ala Phe Asn Ile Phe Lys Asn Asn Gly Tyr Asp Thr Leu
530                 535                 540
Ala Val Glu Tyr Leu Asp Ser Ala Gln Phe Asp Lys Arg Arg Met Pro
545                 550                 555                 560
Thr Pro Thr Ser Leu Leu Lys Tyr His Lys Phe Glu Gly Lys Thr Lys
                565                 570                 575
Asp Glu Val Glu Asp Met Met Lys Ser Lys Lys Phe Ser Asn Ala Tyr
            580                 585                 590
Tyr Thr Phe Lys Phe Glu Asn Asp Val Val Ser Asn Ile Glu Tyr Ser
        595                 600                 605
Asn Asp Gly Ile Trp Lys Gln Lys Gln Leu Asn Phe Gly Asn Leu Ile
610                 615                 620
Ile Lys Ala Ile His Phe Ala Asp Ile Lys Asp Lys Phe Val Gln Leu
625                 630                 635                 640
Cys Asn Asn Asn Lys Met Asn Ile Val Phe Cys Pro Ser Ala Phe Thr
                645                 650                 655
Ser Gln Met Asp Ser Ile Thr His Thr Leu Tyr Tyr Val Glu Lys Ile
            660                 665                 670
Thr Lys Lys Lys Asn Gly Lys Glu Glu Lys Lys Tyr Val Leu Ala Asn
        675                 680                 685
Lys Lys Met Val Arg Thr Gln Gln Glu Thr His Ile Asn Gly Leu Asn
690                 695                 700
Ala Asp Tyr Asn Ser Ala Cys Asn Leu Lys Tyr Ile Ala Leu Asn Asp
705                 710                 715                 720
Glu Leu Arg Asn Glu Met Thr Asp Thr Phe Lys Val Thr Asn Arg Gln
                725                 730                 735
Lys Thr Met Tyr Gly Ile Pro Ala Tyr Asn Ile Lys Arg Gly Phe Lys
            740                 745                 750
Lys Asn Leu Ser Ala Lys Thr Ile Asn Thr Phe Arg Lys Leu Gly His
        755                 760                 765
Tyr Arg Asp Gly Lys Ile Asn Glu Asp Gly Met Phe Val Glu Thr Leu
770                 775                 780
Ala
785

<210> SEQ ID NO 49
<211> LENGTH: 805
<212> TYPE: PRT
```

<213> ORGANISM: Unknown
<220> FEATURE:
<223> OTHER INFORMATION: Description of Unknown:
      mammals-digestive system-rumen-ovis aries sequence

<400> SEQUENCE: 49

Met Ala His Lys Thr Asn Asn Gly Glu Asn Thr Ile Asn Lys Thr Phe
1               5                   10                  15

Ile Phe Lys Ala Lys Cys Asp Asn Asp Ile Ile Ser Leu Trp Lys
            20                  25                  30

Pro Ala Met Glu Glu Tyr Cys Thr Tyr Tyr Asn Lys Leu Ser Gln Trp
                35                  40                  45

Ile Cys Asn Asn Leu Thr Ser Met Lys Val Lys Asp Leu Phe Ala Tyr
    50                  55                  60

Leu Asp Asp Lys Gln Lys Thr Lys Pro Cys Val Asp Lys Lys Thr Gly
65                  70                  75                  80

Glu Thr Lys Ile Gly Val Gly Tyr Tyr Arg Tyr Phe Ile Glu Asn Asn
                    85                  90                  95

Lys Glu Asp Met Pro Leu Tyr Trp Leu Phe Thr Lys Asn Cys Ser Ser
                100                 105                 110

Ser His Ala Asp Asn Leu Leu Phe Glu Phe Val Arg Lys Val Asn His
            115                 120                 125

Glu Glu Tyr Asn Gly Asn Ser Leu Gly Met Gly Glu Thr Asp Tyr Arg
130                 135                 140

Arg Phe Gly Tyr Phe Gln Asn Val Ile Ser Asn Phe Arg Thr Lys Met
145                 150                 155                 160

Ser Ser Leu Lys Ala Thr Thr Lys Trp Lys Lys Phe Asp Val Asn Asp
                165                 170                 175

Val Asp Glu Asp Thr Leu Lys Asn Gln Thr Ile Tyr Ser Val Asp Lys
            180                 185                 190

Tyr Gly Ile Glu Ser Val Asn Asp Phe Asn Glu Arg Ile Asp Ile Leu
        195                 200                 205

Lys Ile Arg Glu Glu Thr Glu Gln Thr Lys Asp Lys Ile Ala Arg Leu
210                 215                 220

Glu Cys Leu Cys Lys Tyr Tyr Lys Glu His Glu Glu Asp Ile Lys Asn
225                 230                 235                 240

Glu Ile Ala Thr Met Ala Ile Ala Asp Leu Gln Lys Phe Gly Gly Cys
                245                 250                 255

Gln Arg Lys Ser Met Asn Thr Leu Thr Ile His Lys Gln Asp Ser Pro
            260                 265                 270

Met Glu Lys Val Gly Asn Thr Ser Phe Asn Leu Arg Leu Thr Phe Asn
        275                 280                 285

Lys Lys Pro Tyr Thr Leu Asn Leu Leu Gly Asn Arg Gln Val Val Lys
290                 295                 300

Phe Val Gly Gly Lys Arg Ile Asp Leu Ile Asn Ile Thr Glu Asn His
305                 310                 315                 320

Gly Asp Trp Ile Thr Phe Asn Ile Lys Asn Asn Glu Leu Phe Val His
                325                 330                 335

Met Thr Ser Pro Val Asp Phe Glu Lys Glu Val Cys Glu Ile Lys Asn
            340                 345                 350

Ala Val Gly Val Asp Val Asn Ile Lys His Met Met Leu Ala Thr Ser
        355                 360                 365

Ile Val Asp Asp Gly Asn Val Lys Gly Tyr Ile Asn Leu Tyr Arg Glu
370                 375                 380

```
Leu Val Asn Asn Asn Asp Phe Ile Ala Thr Phe Gly Asn Ser Lys Asn
385                 390                 395                 400

Gly His Gln Gly Leu Glu Ile Tyr Glu Gln Met Ala Glu Asn Val Asn
            405                 410                 415

Phe Gly Ile Leu Glu Thr Glu Ser Leu Phe Glu Arg Val Val Asn Gln
            420                 425                 430

Ser Asn Gly Gly Glu Leu Asn Asn Gln Leu Ile Arg Arg Glu Ile Ala
            435                 440                 445

Met Gln Lys Val Phe Asp Asn Ile Thr Lys Thr Asn Asn Asp Lys Asn
    450                 455                 460

Ile Val Asn Tyr Val Asn Tyr Val Lys Met Leu Arg Ala Lys Tyr Lys
465                 470                 475                 480

Ala Tyr Phe Ile Leu Lys Glu Lys Tyr Glu Lys Gln Lys Glu Tyr
            485                 490                 495

Asp Asp Met Met Gly Phe Asn Asp Glu Ser Thr Glu Asn Lys Glu Met
            500                 505                 510

Met Asp Lys Arg Arg Phe Glu Phe Ser Phe Ile Asn Thr Asp Thr Ala
    515                 520                 525

Gln Glu Leu Leu Ile Lys Leu Asn Lys Val Glu Gln Asp Leu Ile Gly
    530                 535                 540

Cys Arg Asp Asn Ile Val Thr Tyr Ala Phe Asn Val Phe Lys Thr Asn
545                 550                 555                 560

Gly Tyr Asp Thr Leu Ala Val Glu Tyr Leu Asp Ser Ala Gln Phe Asp
            565                 570                 575

Lys Ala Lys Met Pro Thr Pro Lys Ser Leu Leu Lys Tyr His Lys Phe
            580                 585                 590

Glu Gly Lys Thr Ile Asp Glu Val Lys Glu Met Met Asn Asn Lys Asn
            595                 600                 605

Phe Thr Asn Ala Tyr Tyr Asn Phe Lys Phe Glu Asn Glu Ile Val Lys
    610                 615                 620

Asp Ile Glu Tyr Ser Thr Asp Gly Ile Trp Arg Gln Lys Lys Leu Asn
625                 630                 635                 640

Phe Met Asn Leu Ile Ile Lys Ala Ile His Phe Ala Asp Ile Lys Asp
            645                 650                 655

Lys Phe Val Gln Leu Cys Asn Asn Ser Met Asn Val Val Phe Cys
            660                 665                 670

Pro Ser Ala Phe Thr Ser Gln Met Asp Ser Ile Thr His Ser Leu Tyr
            675                 680                 685

Tyr Ile Glu Lys Thr Ser Lys Thr Lys Asn Gly Lys Glu Lys Lys Gln
    690                 695                 700

Tyr Val Leu Ala Asn Lys Lys Met Val Arg Thr Gln Gln Glu Lys His
705                 710                 715                 720

Ile Asn Gly Leu Asn Ala Asp Phe Asn Ser Ala Cys Asn Leu Lys Tyr
            725                 730                 735

Ile Ala Leu Asp Glu Glu Leu Arg Asn Ala Met Thr Asp Glu Phe Asn
            740                 745                 750

Pro Lys Lys Gln Lys Thr Met Tyr Gly Val Pro Ala Tyr Asn Ile Lys
            755                 760                 765

Asn Gly Phe Lys Lys Asn Leu Ser Thr Lys Thr Ile Asn Thr Phe Arg
            770                 775                 780

Thr Leu Gly His Tyr Arg Asp Gly Lys Ile Asn Glu Asp Gly Val Phe
785                 790                 795                 800

Val Glu Asn Leu Ala
```

<210> SEQ ID NO 50
<211> LENGTH: 784
<212> TYPE: PRT
<213> ORGANISM: Unknown
<220> FEATURE:
<223> OTHER INFORMATION: Description of Unknown:
      mammals-digestive system-rumen-ovis aries sequence

<400> SEQUENCE: 50

| Met | Tyr | Asn | Ser | Lys | Lys | Gly | Glu | Gly | Asp | Ile | Gln | Lys | Ser | Phe |
|---|---|---|---|---|---|---|---|---|---|---|---|---|---|---|
| 1 | | | | 5 | | | | | 10 | | | | | 15 |

| Lys | Phe | Lys | Val | Lys | Thr | Asp | Lys | Glu | Thr | Val | Glu | Leu | Phe | Arg | Lys |
|---|---|---|---|---|---|---|---|---|---|---|---|---|---|---|---|
| | | | 20 | | | | | 25 | | | | | 30 | | |

Ala Ala Val Glu Tyr Ser Glu Tyr Tyr Lys Arg Leu Thr Thr Phe Leu
             35                  40                  45

Cys Glu Arg Leu Thr Asp Met Thr Trp Gly Glu Val Ala Ser Phe Ile
 50                  55                  60

Pro Glu Lys Tyr Arg Lys Asn Glu Tyr Tyr Lys Tyr Leu Ile Lys Glu
 65                  70                  75                  80

Glu Asn Lys Asp Leu Pro Leu Tyr Lys Met Phe Thr Lys Ala Ala Ser
                 85                  90                  95

Ser Met Phe Ile Asp His Ser Ile Glu Arg Tyr Val Glu Ala Leu Asn
             100                 105                 110

Pro Glu Gly Asn Thr Gly Asn Ile Leu Gly Phe Cys Lys Ser Ser Tyr
             115                 120                 125

Val Arg Gly Gly Tyr Leu Lys Asn Val Val Ser Asn Ile Arg Thr Lys
             130                 135                 140

Phe Ala Thr Leu Lys Thr Gly Ile Lys Tyr Lys Lys Phe Asn Pro Ala
145                 150                 155                 160

Glu Asp Asp Glu Glu Thr Ile Leu Gly Gln Thr Val Phe Glu Met Glu
                165                 170                 175

Lys Arg Gly Leu Glu Phe Lys Cys Asp Phe Glu Lys Thr Ile Lys Tyr
             180                 185                 190

Leu Asn Glu Lys Gly Lys Thr Gln Glu Ala Glu Arg Leu Gln Cys Leu
            195                 200                 205

Met Glu Tyr Phe Ser Thr Asn Thr Asp Lys Ile Asn Glu Tyr Arg Glu
210                 215                 220

Ser Leu Val Leu Asp Asp Ile Arg Lys Phe Gly Gly Cys Asn Arg Ser
225                 230                 235                 240

Lys Ser Asn Ser Phe Ser Val Thr Leu Glu Lys Ala Asp Ile Lys Glu
                245                 250                 255

Asp Gly Leu Thr Gly Tyr Thr Met Lys Val Ser Lys Lys Leu Lys Glu
            260                 265                 270

Ile His Leu Leu Gly His Arg Arg Val Val Glu Val Asn Gly Arg
            275                 280                 285

Arg Val Asn Leu Val Asp Ile Cys Gly Asp Lys Ser Gly Asp Ser Lys
            290                 295                 300

Val Phe Val Val Asp Gly Asp Asn Leu Tyr Val Cys Ile Ser Ala Pro
305                 310                 315                 320

Val Lys Phe Ser Lys Asn Gly Met Glu Ala Lys Lys Tyr Ile Gly Val
                325                 330                 335

Asp Met Asn Met Lys His Ser Ile Ile Ser Val Ser Asn Ala Ser
            340                 345                 350

Asp Met Lys Gly Phe Leu Asn Ile Tyr Lys Glu Leu Leu Lys Asp Glu
                355                 360                 365

Gly Phe Arg Lys Thr Leu Asn Ala Thr Glu Leu Glu Lys Tyr Glu Lys
    370                 375                 380

Leu Ala Glu Gly Val Asn Ile Gly Ile Ile Glu Tyr Asp Gly Leu Tyr
385                 390                 395                 400

Glu Arg Ile Val Lys Gln Lys Lys Glu Asn Ser Val Asp Gly Leu Lys
                405                 410                 415

Val Gln Ala Glu Lys Lys Leu Ile Glu Arg Ala Ala Ile Glu Arg
        420                 425                 430

Val Leu Asp Lys Leu Arg Lys Gly Thr Ser Asp Thr Asp Thr Glu Asn
    435                 440                 445

Tyr Ile Asn Tyr Asn Lys Ile Leu Arg Ala Lys Ile Lys Ser Ala Tyr
    450                 455                 460

Ile Leu Lys Asp Lys Tyr Tyr Glu Met Leu Gly Lys Tyr Asp Ser Glu
465                 470                 475                 480

Arg Ala Gly Ser Gly Asp Leu Ser Glu Glu Asn Lys Ile Lys Tyr Lys
                485                 490                 495

Asp Glu Phe Asn Glu Thr Glu Lys Gly Lys Glu Ile Leu Gly Lys Leu
            500                 505                 510

Asn Asn Val Tyr Lys Asp Ile Ile Gly Cys Arg Asp Asn Ile Val Thr
            515                 520                 525

Tyr Ala Val Asn Leu Phe Ile Arg Asn Gly Tyr Asp Thr Val Ala Leu
    530                 535                 540

Glu Tyr Leu Glu Ser Ser Gln Met Lys Ala Arg Arg Ile Pro Ser Thr
545                 550                 555                 560

Gly Gly Leu Leu Lys Gly His Lys Leu Glu Gly Lys Pro Glu Gly Glu
                565                 570                 575

Val Thr Ala Tyr Leu Lys Ala Asn Lys Ile Pro Lys Ser Tyr Tyr Ser
            580                 585                 590

Phe Glu Tyr Asp Gly Asn Gly Met Leu Thr Asp Val Lys Tyr Ser Asp
    595                 600                 605

Met Gly Glu Lys Ala Arg Gly Arg Asn Arg Phe Lys Asn Leu Val Pro
610                 615                 620

Lys Phe Leu Arg Trp Ala Ser Ile Lys Asp Lys Phe Val Gln Leu Ser
625                 630                 635                 640

Asn Tyr Lys Asp Ile Gln Met Val Tyr Val Pro Ser Pro Tyr Thr Ser
            645                 650                 655

Gln Thr Asp Ser Arg Thr His Ser Leu Tyr Tyr Ile Glu Thr Val Lys
            660                 665                 670

Val Asp Glu Lys Thr Gly Lys Glu Lys Glu His Ile Val Ala Pro
    675                 680                 685

Lys Glu Ser Val Arg Thr Glu Gln Glu Ser Phe Val Asn Gly Met Asn
690                 695                 700

Ala Asp Thr Asn Ser Ala Asn Asn Ile Lys Tyr Ile Phe Glu Asn Glu
705                 710                 715                 720

Thr Leu Arg Asp Lys Phe Leu Lys Arg Thr Lys Asp Gly Thr Glu Met
            725                 730                 735

Tyr Asn Arg Pro Ala Phe Asp Leu Lys Glu Cys Tyr Lys Lys Asn Ser
            740                 745                 750

Asn Val Ser Val Phe Asn Thr Leu Lys Lys Thr Leu Gly Ala Ile Tyr
        755                 760                 765

Gly Lys Leu Asp Glu Asn Gly Asn Phe Ile Glu Asn Glu Cys Asn Lys

<210> SEQ ID NO 51
<211> LENGTH: 764
<212> TYPE: PRT
<213> ORGANISM: Unknown
<220> FEATURE:
<223> OTHER INFORMATION: Description of Unknown:
mammals-digestive system-rumen-ovis aries sequence

<400> SEQUENCE: 51

Met Asn Lys Ser Tyr Val Phe Lys Ser Asn Val Ala Ile Asp Asp Ile
1               5                   10                  15

Met Ser Leu Phe Glu Pro Ala Ile Glu Glu Tyr Ile Asn Tyr Tyr Asn
            20                  25                  30

Arg Thr Ser Asp Phe Ile Cys Asp Asn Leu Thr Ser Met Lys Ile Gly
        35                  40                  45

Asp Leu Ala Asn Tyr Ile Lys Asn Lys Glu Asn Val Tyr Cys Lys Phe
    50                  55                  60

Val Leu Asn Asp Asp Ile Lys Asp Leu Pro Leu Tyr Lys Ile Phe Ser
65                  70                  75                  80

Leu Asn Leu Asn Ser Ser Gln Lys Lys Asn Ala Asp Asn Ala Leu Tyr
                85                  90                  95

Glu Ala Ile Lys Val Leu Asn Ala Asp Gly Tyr Lys Gly Lys Asn Ile
            100                 105                 110

Leu Gly Leu Gly Asp Thr Tyr Phe Arg Arg Asn Gly Tyr Val Lys Asn
        115                 120                 125

Val Ile Ser Asn Tyr Arg Thr Lys Phe Val Thr Leu Lys Pro Asn Val
130                 135                 140

Lys Tyr Ser Lys Ile Asp Ile Asn Ser Val Thr Glu Gln Leu Ile Lys
145                 150                 155                 160

Thr Gln Thr Ile Phe Glu Val Val Asn Lys Lys Ile Glu Ser Glu Thr
                165                 170                 175

Asp Phe Glu Asn Leu Ile Thr Tyr Phe Lys Asn Arg Glu Thr Pro Asn
            180                 185                 190

Asp Glu Lys Ile Lys Arg Leu Glu Leu Phe Asp Tyr Tyr Thr Lys
        195                 200                 205

His Lys Asn Glu Ile Asn Glu Glu Ile Glu Lys His Ala Val Glu Ser
    210                 215                 220

Leu Lys Ser Phe Asn Gly Cys Arg Arg Asn Gly Asn Arg Lys Thr Met
225                 230                 235                 240

Thr Val Gln Met Gln Lys Met Leu Leu Lys Lys His Gly Leu Thr Ser
                245                 250                 255

Tyr Ile Leu His Leu Val Leu Asp Lys Lys Pro Tyr Asp Ile Asn Leu
            260                 265                 270

Met Gly Asn Arg Gln Thr Val Lys Val Asp Asn Asn Gly Asn Arg Val
        275                 280                 285

Asp Leu Val Asp Ile Ser Ser Lys His Gly Tyr Asp Leu Thr Phe Glu
    290                 295                 300

Val Lys Gly Lys Thr Leu Phe Phe Thr Phe Ser Ser Glu Lys Asp Phe
305                 310                 315                 320

Ser Lys Lys Glu Gln Glu Ile Lys Asn Ile Leu Gly Ile Asp Ile Asn
                325                 330                 335

Thr Lys His Ser Met Leu Ala Thr Ser Ile Thr Asp Asn Gly Lys Val
            340                 345                 350

-continued

```
Lys Gly Tyr Ile Asn Ile Tyr Val Glu Leu Leu Lys Asn Lys Asp Phe
            355                 360                 365
Val Ser Thr Leu Asn Lys Glu Glu Leu Ala Tyr Tyr Thr Glu Met Ala
    370                 375                 380
Lys Phe Val Ser Phe Gly Leu Leu Glu Ile Pro Ser Leu Phe Glu Arg
385                 390                 395                 400
Val Ser Asn Gln Tyr Asp Lys Lys Asn Asn Val Ser Ile Thr Asp Glu
                405                 410                 415
Thr Leu Leu Lys Arg Glu Ile Ala Ile Ser Gln Thr Leu Asp Asn Leu
                420                 425                 430
Ala Lys Lys Tyr Arg Asp Lys Asn Cys Lys Ile Ala Ser Tyr Ile Asp
            435                 440                 445
Tyr Thr Lys Met Leu Arg Ser Lys Tyr Lys Ser Tyr Phe Ile Leu Lys
    450                 455                 460
Gln Lys Tyr Tyr Glu Lys Asn His Glu Tyr Asp Asp Lys Met Gly Phe
465                 470                 475                 480
Ser Asp Ile Ser Thr Asn Ser Lys Glu Thr Met Asp Pro Arg Arg Phe
                485                 490                 495
Glu Asn Pro Phe Ile Asn Thr Asp Ile Ala Lys Gly Leu Ile Val Lys
            500                 505                 510
Leu Glu Asn Val Lys Cys Asp Ile Val Gly Cys Arg Asp Asn Ile Ile
            515                 520                 525
Lys Tyr Ala Tyr Asp Val Ile Val Leu Asn Gly Phe Asp Thr Ile Gly
            530                 535                 540
Leu Glu Tyr Leu Asp Ser Ser Asn Phe Glu Arg Asp Arg Leu Pro Phe
545                 550                 555                 560
Pro Thr Ala Lys Ser Leu Met Thr Tyr Tyr Gly Phe Glu Gly Lys Lys
                565                 570                 575
Tyr Ser Glu Ile Asp Lys Ser Val Phe Asn Thr Lys Tyr Tyr Asn Phe
            580                 585                 590
Ile Phe Asn Glu Asn Glu Thr Ile Lys Asp Ile Ser Tyr Ser Val Tyr
            595                 600                 605
Gly Leu Lys Glu Ile Gln Lys Lys Arg Phe Lys Asn Leu Val Ile Lys
610                 615                 620
Ala Ile Gly Phe Ala Asp Ile Lys Asp Lys Phe Val Gln Leu Ser Asn
625                 630                 635                 640
Asn Thr Asn Met Asn Val Ile Phe Val Pro Ala Ala Phe Thr Ser Gln
                645                 650                 655
Met Asp Ser Asn Thr His Lys Ile Tyr Val Lys Glu Ile Met Asp Lys
                660                 665                 670
Asn Asn Lys Lys Gln Leu Gln Leu Ile Asp Lys Arg Lys Val Arg Thr
            675                 680                 685
Lys Gln Glu Phe His Ile Asn Gly Leu Asn Ala Asp Phe Asn Ala Ala
    690                 695                 700
Asn Asn Ile Lys Tyr Ile Ala Glu Asn Asn Asp Leu Leu Leu Thr Met
705                 710                 715                 720
Cys Thr Lys Thr Lys Glu Asn Asn Arg Tyr Gly Asn Pro Leu Tyr Asn
                725                 730                 735
Ile Lys Asp Thr Phe Lys Lys Ile Pro Ser Ser Ile Leu Asn Ile
            740                 745                 750
Phe Lys Lys Lys Asp Met Tyr Gln Ile Ile Cys Asp
    755                 760
```

<210> SEQ ID NO 52
<211> LENGTH: 768
<212> TYPE: PRT
<213> ORGANISM: Unknown
<220> FEATURE:
<223> OTHER INFORMATION: Description of Unknown:
      mammals-digestive system-rumen-ovis aries sequence

<400> SEQUENCE: 52

```
Met Phe Arg Ile Phe Ala Ala Leu Lys Leu Thr Asn Met Gly His Val
1               5                   10                  15

Arg Leu Gln Lys Arg Glu Gly Glu Val Tyr Lys Thr Tyr Lys Leu Lys
            20                  25                  30

Val Lys Ser Phe Ser Gly Asn Val Asp Ile Lys Ala Gly Ile Val Glu
        35                  40                  45

Tyr Asp Gln Lys Phe Asn Asn Val Ser Gln Trp Ile Ala Asp His Leu
    50                  55                  60

Thr Ser Met Thr Ile Gly Glu Ala Ala Ser Arg Ile Ser Pro His Lys
65                  70                  75                  80

Met Asp Ser Gln Tyr Ala Met Thr Ser Leu Ser Asp Glu Trp Lys Asp
                85                  90                  95

Gln Pro Leu Tyr Lys Ile Phe Thr Arg Gly Phe Gly Gly Met Asn Ala
            100                 105                 110

Asp Asn Leu Ile Ile Glu Cys Thr Lys Thr Glu Glu Asn Cys Lys Tyr
        115                 120                 125

Asp Lys Glu Lys Ser Leu Gly Phe Ser Glu Ser Val Phe Arg Thr Phe
    130                 135                 140

Gly Phe Ala Ala Asn Ala Ser Ser Asp Met Lys Ser Arg Met Thr Gln
145                 150                 155                 160

Ala Lys Val Lys Ile Gly Arg Lys Asn Ile Asp Glu Asp Ser Ala Asp
                165                 170                 175

Asp Glu Lys Cys Leu Gln Ala Ile Tyr Glu Ile Gln Lys Asn Glu Leu
            180                 185                 190

Leu Thr Asp Asp Asn Trp Lys Asp Arg Ile Gly Tyr Leu Glu Met Lys
        195                 200                 205

Gly Asp Gln Glu Arg Glu Leu Glu Arg Thr Thr Ile Leu Tyr Asp Tyr
    210                 215                 220

Tyr Arg Ala Asn Arg Thr Thr Val Leu Asp Lys Leu Asp Asn Leu Lys
225                 230                 235                 240

Val Glu Thr Leu Ser Lys Phe Arg Gly Ser Lys Arg Lys Ser Asp Arg
                245                 250                 255

Lys Ile Leu Thr Leu Asn Gly Ile Ser Tyr Asp Ile Lys Arg Lys Glu
            260                 265                 270

Gly Cys Gln Gly Phe Glu Leu Lys Phe Ser Val Asp Lys Asn His Met
        275                 280                 285

Glu Phe Asp Leu Leu Gly His Arg Ala Leu Ile Lys Asn Gly Glu Met
    290                 295                 300

Leu Val Asp Ile Glu Asn Cys His Gly Ser Gln Leu Ser Leu Glu Ile
305                 310                 315                 320

Asp Gly Asp Asp Met Tyr Ala Ile Ile Ser Met Arg Thr Phe Cys Glu
                325                 330                 335

Lys Asn Glu Ser Lys Leu Glu Lys Ile Ile Gly Ala Asp Val Asn Ile
            340                 345                 350

Lys His Met Phe Leu Met Thr Ser Glu Lys Asp Asp Gly Asn Thr Lys
        355                 360                 365
```

Cys Tyr Val Asn Leu Tyr Arg Glu Leu Leu Ser Asp Ser Asp Phe Thr
370                 375                 380

Asp Val Leu Asn Lys Glu Glu Tyr Glu Ile Phe Ser Glu Leu Ser Lys
385                 390                 395                 400

Tyr Val Met Phe Gly Leu Ile Glu Thr Pro Tyr Leu Gly Ser Arg Val
            405                 410                 415

Ile Gly Thr Thr Gln His Glu Lys Ile Val Glu Asp Lys Ile Thr Ser
            420                 425                 430

Gly Met Lys Lys Ile Ala Ile Arg Leu Phe Gln Glu Gly Lys Val Arg
            435                 440                 445

Glu Arg Ile Tyr Val Gln Asn Val Leu Lys Ile Arg Ala Leu Leu Lys
450                 455                 460

Ala Leu Phe Ser Thr Lys Leu Ala Tyr Ser Asn Glu Gln Lys Ile Tyr
465                 470                 475                 480

Asp Asn Leu Met Arg Phe Gly Lys Asp Asp Arg Arg Lys Asp Glu
                485                 490                 495

Gly Phe His Thr Thr Cys Arg Gly Thr Ser Leu Arg Ser Glu Met Asp
                500                 505                 510

Met Leu Ser Lys Lys Ile Leu Ala Cys Arg Asp Asn Ile Val Glu Tyr
            515                 520                 525

Gly Tyr Tyr Val Ile Gly Leu Asn Gly Phe Asp Gly Ile Ser Leu Glu
            530                 535                 540

Asn Leu Glu Ser Ser Thr Phe Met Asp Val Lys Ile Ser Tyr Pro Ser
545                 550                 555                 560

Cys Asn Ser Met Leu Asp His Phe Lys Leu Lys Gly Lys Thr Ile Glu
                565                 570                 575

Glu Ala Glu Asn His Glu Thr Val Gly Lys Phe Ile Lys Lys Gly Tyr
                580                 585                 590

Tyr Val Met Thr Leu Val Asn Gly Lys Ile Asn Asp Ile Asn Tyr Ser
            595                 600                 605

Glu Lys Ala Val Met Leu His Lys Lys Asn Leu Leu Tyr Asp Thr Val
610                 615                 620

Ile Lys Ser Thr His Phe Ala Asp Val Lys Asp Lys Phe Val Glu Leu
625                 630                 635                 640

Ser Asn Asn Gly Lys Val Ser Val Val Ile Pro Pro Tyr Phe Ser
                645                 650                 655

Ser Gln Met Asp Ser Val Thr His Lys Val Phe Thr Glu Glu Ile Val
            660                 665                 670

Val Gln Lys Lys Ser Ser Asn Gly Lys Val Arg Lys Thr Lys Thr
            675                 680                 685

Val Leu Val Asp Lys Arg Lys Val Arg Lys Thr Gln Glu Ser His Ile
690                 695                 700

Asn Gly Leu Asn Ala Asp Tyr Asn Ala Ala Leu Asn Leu Lys Tyr Ile
705                 710                 715                 720

Ala Glu Thr Ile Asp Trp Arg Ser Thr Leu Cys Phe Lys Thr Trp Asn
            725                 730                 735

Thr Tyr Gly Ser Pro Gln Trp Asp Ser Lys Ile Lys Asn Gln Lys Thr
            740                 745                 750

Met Ile Asp Arg Leu Asp Ser Leu Gly Ala Ile Glu Leu Lys Asn Trp
            755                 760                 765

<210> SEQ ID NO 53
<211> LENGTH: 764
<212> TYPE: PRT

<213> ORGANISM: Unknown
<220> FEATURE:
<223> OTHER INFORMATION: Description of Unknown:
      mammals-digestive system-rumen-ovis aries sequence

<400> SEQUENCE: 53

Met Asn Lys Ser Tyr Val Phe Lys Ser Asn Val Ala Ile Asp Asp Ile
1               5                   10                  15

Met Ser Leu Phe Glu Pro Ala Ile Glu Glu Tyr Ile Asn Tyr Asn
            20                  25                  30

Arg Thr Ser Asp Phe Ile Cys Asp Asn Leu Thr Ser Met Lys Ile Gly
                35                  40                  45

Asp Leu Ala Asn Tyr Ile Lys Asn Lys Glu Asn Val Tyr Cys Lys Phe
        50                  55                  60

Val Leu Asn Asp Asp Ile Lys Asp Leu Pro Leu Tyr Lys Ile Phe Ser
65                  70                  75                  80

Leu Asn Leu Asn Ser Ser Gln Lys Lys Asn Ala Asp Asn Ala Leu Tyr
                85                  90                  95

Glu Ala Ile Lys Val Leu Asn Ala Asp Gly Tyr Lys Gly Lys Asn Ile
                100                 105                 110

Leu Gly Leu Gly Asp Thr Tyr Phe Arg Arg Asn Gly Tyr Val Lys Asn
            115                 120                 125

Val Ile Ser Asn Tyr Arg Thr Lys Phe Val Thr Leu Lys Pro Asn Val
        130                 135                 140

Lys Tyr Ser Lys Ile Asp Ile Asn Ser Val Thr Glu Gln Leu Ile Lys
145                 150                 155                 160

Thr Gln Thr Ile Phe Glu Val Val Asn Lys Ile Glu Ser Glu Thr
                165                 170                 175

Asp Phe Glu Asn Leu Ile Thr Tyr Phe Lys Asn Arg Gly Thr Pro Asn
            180                 185                 190

Asp Glu Lys Ile Lys Arg Leu Glu Leu Leu Phe Asp Tyr Tyr Thr Lys
                195                 200                 205

His Lys Asn Glu Ile Asn Glu Glu Ile Glu Lys His Ala Val Glu Ser
            210                 215                 220

Leu Lys Ser Phe Asn Gly Cys Arg Arg Asn Gly Asn Arg Lys Thr Met
225                 230                 235                 240

Thr Val Gln Met Gln Lys Met Leu Leu Lys Lys His Gly Leu Thr Ser
                245                 250                 255

Tyr Ile Leu His Leu Val Leu Asp Lys Lys Pro Tyr Asp Ile Asn Leu
            260                 265                 270

Met Gly Asn Arg Gln Thr Val Lys Val Asp Asn Asn Gly Asn Arg Val
                275                 280                 285

Asp Leu Val Asp Ile Ser Ser Lys His Gly Tyr Asp Leu Thr Phe Glu
        290                 295                 300

Val Lys Gly Lys Thr Leu Phe Phe Thr Phe Ser Ser Glu Lys Asp Phe
305                 310                 315                 320

Ser Lys Lys Glu Gln Glu Ile Lys Asn Ile Leu Gly Ile Asp Ile Asn
                325                 330                 335

Thr Lys His Ser Met Leu Ala Thr Ser Ile Thr Asp Asn Gly Lys Val
            340                 345                 350

Lys Gly Tyr Ile Asn Ile Tyr Val Glu Leu Leu Lys Asn Lys Asp Phe
            355                 360                 365

Val Ser Thr Leu Asn Lys Glu Glu Leu Ala Tyr Tyr Thr Glu Met Ala
        370                 375                 380

```
Lys Phe Val Ser Phe Gly Leu Leu Glu Ile Pro Ser Leu Phe Glu Arg
385                 390                 395                 400

Val Ser Asn Gln Tyr Asp Lys Lys Asn Val Ser Ile Thr Asp Glu
            405                 410                 415

Thr Leu Leu Lys Arg Glu Ile Ala Ile Ser Gln Thr Leu Asp Asn Leu
            420                 425                 430

Ala Lys Lys Tyr Arg Asp Lys Asn Cys Lys Ile Ala Ser Tyr Ile Asp
            435                 440                 445

Tyr Thr Lys Met Leu Arg Ser Lys Tyr Lys Ser Tyr Phe Ile Leu Lys
            450                 455                 460

Gln Lys Tyr Tyr Glu Lys Asn His Glu Tyr Asp Asp Lys Met Gly Phe
465                 470                 475                 480

Ser Asp Ile Ser Thr Asn Ser Lys Glu Thr Met Asp Pro Arg Arg Phe
            485                 490                 495

Glu Asn Pro Phe Ile Asn Thr Asp Ile Ala Lys Gly Leu Ile Val Lys
            500                 505                 510

Leu Glu Asn Val Lys Cys Asp Ile Val Gly Cys Arg Asp Asn Ile Ile
515                 520                 525

Lys Tyr Ala Tyr Asp Val Ile Val Leu Asn Gly Phe Asp Thr Ile Gly
            530                 535                 540

Leu Glu Tyr Leu Asp Ser Ser Asn Phe Glu Arg Asp Arg Leu Pro Phe
545                 550                 555                 560

Pro Thr Ala Lys Ser Leu Met Thr Tyr Tyr Gly Phe Glu Gly Lys Lys
            565                 570                 575

Tyr Ser Glu Ile Asp Lys Ser Val Phe Asn Thr Lys Tyr Tyr Asn Phe
            580                 585                 590

Ile Phe Asn Glu Asn Glu Thr Ile Lys Asp Ile Ser Tyr Ser Val Tyr
            595                 600                 605

Gly Leu Lys Glu Ile Gln Lys Lys Arg Phe Lys Asn Leu Val Ile Lys
            610                 615                 620

Ala Ile Gly Phe Ala Asp Ile Lys Asp Lys Phe Val Gln Leu Ser Asn
625                 630                 635                 640

Asn Thr Asn Met Asn Val Ile Phe Val Pro Ala Ala Phe Thr Ser Gln
            645                 650                 655

Met Asp Ser Asn Thr His Lys Ile Tyr Val Lys Glu Ile Met Asp Lys
            660                 665                 670

Asn Asn Lys Lys Gln Leu Gln Leu Ile Asp Lys Arg Lys Val Arg Thr
            675                 680                 685

Lys Gln Glu Phe His Ile Asn Gly Leu Asn Ala Asp Phe Asn Ala Ala
690                 695                 700

Asn Asn Ile Lys Tyr Ile Ala Glu Asn Asn Asp Leu Leu Leu Thr Met
705                 710                 715                 720

Cys Thr Lys Thr Lys Glu Asn Asn Arg Tyr Gly Asn Pro Leu Tyr Asn
            725                 730                 735

Ile Lys Asp Thr Phe Lys Lys Ile Pro Ser Ser Ile Leu Asn Ile
            740                 745                 750

Phe Lys Lys Lys Asp Met Tyr Gln Ile Ile Cys Asp
    755                 760

<210> SEQ ID NO 54
<211> LENGTH: 805
<212> TYPE: PRT
<213> ORGANISM: Unknown
<220> FEATURE:
<223> OTHER INFORMATION: Description of Unknown:
```

-continued mammals-digestive system-rumen-ovis aries sequence

<400> SEQUENCE: 54

Met Ala His Lys Thr Asn Asn Gly Glu Asn Thr Ile Asn Lys Thr Phe
1               5                   10                  15

Ile Phe Lys Ala Lys Cys Asp Asn Asp Ile Ile Ser Leu Trp Lys
            20                  25                  30

Pro Ala Met Glu Glu Tyr Cys Thr Tyr Tyr Asn Lys Leu Ser Gln Trp
            35                  40                  45

Ile Cys Asn Asn Leu Thr Ser Met Lys Val Lys Asp Leu Phe Ala Tyr
        50                  55                  60

Leu Asp Asp Lys Gln Lys Thr Lys Pro Cys Val Asp Lys Lys Thr Gly
65                  70                  75                  80

Glu Thr Lys Ile Gly Val Gly Tyr Tyr Arg Tyr Phe Ile Glu Asn Asn
                    85                  90                  95

Lys Glu Asp Met Pro Leu Tyr Trp Leu Phe Thr Lys Asn Cys Ser Ser
            100                 105                 110

Ser His Ala Asp Asn Leu Leu Phe Glu Phe Val Arg Lys Val Asn His
            115                 120                 125

Glu Glu Tyr Asn Gly Asn Ser Leu Gly Met Gly Glu Thr Asp Tyr Arg
130                 135                 140

Arg Phe Gly Tyr Phe Gln Asn Val Ile Ser Asn Phe Arg Thr Lys Met
145                 150                 155                 160

Ser Ser Leu Lys Ala Thr Thr Lys Trp Lys Lys Phe Asp Val Asn Asp
                165                 170                 175

Val Asp Glu Asp Thr Leu Lys Asn Gln Thr Ile Tyr Val Asp Lys
            180                 185                 190

Tyr Gly Ile Glu Ser Val Asn Asp Phe Asn Glu Arg Ile Asp Ile Leu
            195                 200                 205

Lys Ile Arg Glu Glu Thr Glu Gln Thr Lys Asp Lys Ile Ala Arg Leu
            210                 215                 220

Glu Cys Leu Cys Lys Tyr Tyr Lys Glu His Glu Glu Asp Ile Lys Asn
225                 230                 235                 240

Glu Ile Ala Thr Met Ala Ile Ala Asp Leu Gln Lys Phe Gly Gly Cys
                245                 250                 255

Gln Arg Lys Ser Met Asn Thr Leu Thr Ile His Lys Gln Asp Ser Pro
            260                 265                 270

Met Glu Lys Val Gly Asn Thr Ser Phe Asn Leu Arg Leu Thr Phe Asn
            275                 280                 285

Lys Lys Pro Tyr Thr Leu Asn Leu Leu Gly Asn Arg Gln Val Val Lys
            290                 295                 300

Phe Val Gly Gly Lys Arg Ile Asp Leu Ile Asn Ile Thr Glu Asn His
305                 310                 315                 320

Gly Asp Trp Ile Thr Phe Asn Ile Lys Asn Asn Glu Leu Phe Val His
                325                 330                 335

Met Thr Ser Pro Val Asp Phe Glu Lys Glu Val Cys Glu Ile Lys Asn
            340                 345                 350

Ala Val Gly Val Asp Val Asn Ile Lys His Met Met Leu Ala Thr Ser
            355                 360                 365

Ile Val Asp Asp Gly Asn Val Lys Gly Tyr Ile Asn Leu Tyr Arg Glu
            370                 375                 380

Leu Val Asn Asn Asn Asp Phe Ile Ala Thr Phe Gly Asn Ser Lys Asn
385                 390                 395                 400

```
Gly His Gln Gly Leu Glu Ile Tyr Glu Gln Met Ala Glu Asn Val Asn
                405                 410                 415

Phe Gly Ile Leu Glu Thr Glu Ser Leu Phe Glu Arg Val Val Asn Gln
            420                 425                 430

Ser Asn Gly Gly Glu Leu Asn Asn Gln Leu Ile Arg Arg Glu Ile Ala
        435                 440                 445

Met Gln Lys Val Phe Asp Asn Ile Thr Lys Thr Asn Asn Asp Lys Asn
    450                 455                 460

Ile Val Asn Tyr Val Asn Tyr Val Lys Met Leu Arg Ala Lys Tyr Lys
465                 470                 475                 480

Ala Tyr Phe Ile Leu Lys Glu Lys Tyr Glu Lys Gln Lys Glu Tyr
                485                 490                 495

Asp Asp Met Met Gly Phe Asn Asp Glu Ser Thr Glu Asn Lys Glu Met
            500                 505                 510

Met Asp Lys Arg Arg Phe Glu Phe Ser Phe Ile Asn Thr Asp Thr Ala
        515                 520                 525

Gln Glu Leu Leu Ile Lys Leu Asn Lys Val Gln Asp Leu Ile Gly
    530                 535                 540

Cys Arg Asp Asn Ile Val Thr Tyr Ala Phe Asn Val Phe Lys Thr Asn
545                 550                 555                 560

Gly Tyr Asp Thr Leu Ala Val Glu Tyr Leu Asp Ser Ala Gln Phe Asp
            565                 570                 575

Lys Ala Lys Met Pro Thr Pro Lys Ser Leu Leu Lys Tyr His Lys Phe
        580                 585                 590

Glu Gly Lys Thr Ile Asp Glu Val Lys Glu Met Met Asn Asn Lys Asn
    595                 600                 605

Phe Thr Asn Ala Tyr Tyr Asn Phe Lys Phe Glu Asn Glu Ile Val Lys
610                 615                 620

Asp Ile Glu Tyr Ser Thr Asp Gly Ile Trp Arg Gln Lys Lys Leu Asn
625                 630                 635                 640

Phe Met Asn Leu Ile Ile Lys Ala Ile His Phe Ala Asp Ile Lys Asp
            645                 650                 655

Lys Phe Val Gln Leu Cys Asn Asn Asn Ser Met Asn Val Val Phe Cys
        660                 665                 670

Pro Ser Ala Phe Thr Ser Gln Met Asp Ser Ile Thr His Ser Leu Tyr
    675                 680                 685

Tyr Ile Glu Lys Thr Ser Lys Thr Lys Asn Gly Lys Glu Lys Lys Gln
690                 695                 700

Tyr Val Leu Ala Asn Lys Lys Met Val Arg Thr Gln Gln Glu Lys His
705                 710                 715                 720

Ile Asn Gly Leu Asn Ala Asp Phe Asn Ser Ala Cys Asn Leu Lys Tyr
            725                 730                 735

Ile Ala Leu Asp Glu Glu Leu Arg Asn Ala Met Thr Asp Glu Phe Asn
        740                 745                 750

Pro Lys Lys Gln Lys Thr Met Tyr Gly Val Pro Ala Tyr Asn Ile Lys
    755                 760                 765

Asn Gly Phe Lys Lys Asn Leu Ser Thr Lys Thr Ile Asn Thr Phe Arg
770                 775                 780

Thr Leu Gly His Tyr Arg Asp Gly Lys Ile Asn Glu Asp Gly Val Phe
785                 790                 795                 800

Val Glu Asn Leu Ala
            805
```

<210> SEQ ID NO 55
<211> LENGTH: 785
<212> TYPE: PRT
<213> ORGANISM: Unknown
<220> FEATURE:
<223> OTHER INFORMATION: Description of Unknown:
      mammals-digestive system-rumen-ovis aries sequence

<400> SEQUENCE: 55

```
Met Ala His Lys Thr Asn Asn Gly Glu Asn Thr Ile Asn Lys Thr Phe
1               5                   10                  15

Ile Phe Lys Ala Lys Cys Glu Lys Asn Asp Ile Ile Ser Leu Trp Lys
            20                  25                  30

Pro Ala Glu Glu Tyr Cys Asn Tyr Tyr Asn Lys Leu Ser Lys Trp
        35                  40                  45

Ile Gly Asp Ser Leu Thr Thr Met Lys Ile Gly Asp Leu Ala Gln Tyr
    50                  55                  60

Ile Thr Asn Gln Asn Ser Ala Tyr Tyr Leu Ala Val Thr Asn Asp Ser
65                  70                  75                  80

Lys Lys Asp Leu Pro Leu Tyr Lys Ile Phe Gln Lys Gly Phe Ser Ser
                85                  90                  95

Gln Cys Ala Asp Asn Ala Leu Tyr Ser Ala Ile Lys Ala Ile Asn Pro
            100                 105                 110

Glu Asn Tyr Asn Gly Asn Ser Leu Glu Ile Gly Glu Thr Asp Tyr Arg
        115                 120                 125

Arg Phe Gly Tyr Val Gln Ser Val Ile Gly Asn Phe Arg Thr Lys Met
130                 135                 140

Ser Ser Leu Lys Val Ser Val Lys Tyr Lys Phe Asp Val Asn Asp
145                 150                 155                 160

Val Asp Glu Glu Thr Leu Lys Thr Gln Thr Ile Tyr Asp Val Asp Lys
                165                 170                 175

Tyr Gly Ile Glu Ser Ile Lys Asp Phe Asn Glu Phe Ile Glu Val Leu
            180                 185                 190

Lys Leu Arg Glu Glu Thr Pro Gln Leu Asn Glu Lys Ile Thr Arg Leu
        195                 200                 205

Glu Cys Leu Cys Gly Tyr Tyr Ser Lys Asn Glu Glu Asn Ile Lys Asn
210                 215                 220

Glu Ile Glu Thr Met Ala Ile Ser Asp Leu Gln Lys Phe Gly Gly Cys
225                 230                 235                 240

Gln Arg Lys Ser Leu Asn Thr Leu Thr Ile His Lys Gln Asn Ser Leu
                245                 250                 255

Met Glu Lys Val Gly Asn Thr Ser Phe Thr Leu Gln Leu Ser Phe Asn
            260                 265                 270

Lys Lys Pro Tyr Thr Ile Asn Leu Leu Gly Asn Arg Gln Val Val Lys
        275                 280                 285

Phe Val Asp Gly Lys Arg Val Asp Leu Ile Asp Ile Thr Glu Lys His
290                 295                 300

Gly Asp Trp Val Thr Phe Asn Ile Lys Asn Asp Glu Leu Phe Val His
305                 310                 315                 320

Leu Thr Ser Pro Ile Asp Phe Glu Lys Glu Val Cys Glu Ile Lys Asn
                325                 330                 335

Ala Val Gly Val Asp Val Asn Ile Lys His Asn Met Leu Ala Thr Ser
            340                 345                 350

Ile Lys Asp Asp Gly Asn Val Lys Gly Tyr Ile Asn Leu Tyr Lys Glu
        355                 360                 365
```

-continued

Leu Val Asn Asp Cys Asp Phe Ile Ser Thr Cys Asn Glu Asp Glu Phe
370                 375                 380

Asp Leu Tyr Arg Gln Met Ser Glu Ser Val Asn Phe Gly Ile Leu Glu
385                 390                 395                 400

Thr Asp Ser Leu Phe Glu Arg Val Val Asn Gln Ser Lys Gly Gly Cys
            405                 410                 415

Leu Asn Asn Lys Phe Ile Arg Arg Glu Leu Ala Met Gln Lys Val Phe
            420                 425                 430

Asp Asn Ile Thr Lys Thr Asn Lys Asp Gln Asn Ile Val Asp Tyr Val
            435                 440                 445

Asn Tyr Val Lys Met Leu Arg Ala Lys Tyr Lys Ala Tyr Phe Ile Leu
450                 455                 460

Lys Glu Lys Tyr Tyr Glu Lys Gln Lys Glu Tyr Asp Ile Lys Met Gly
465                 470                 475                 480

Phe Thr Asp Val Ser Thr Glu Ser Lys Glu Thr Met Asp Lys Arg Arg
            485                 490                 495

Met Glu Phe Pro Phe Val Asn Thr Asp Thr Ala Lys Glu Leu Leu Ala
            500                 505                 510

Lys Leu Asn Asn Ile Glu Gln Asp Leu Ile Gly Cys Arg Asp Asn Ile
            515                 520                 525

Val Thr Tyr Ala Phe Asn Ile Phe Lys Asn Asn Gly Tyr Asp Thr Leu
530                 535                 540

Ala Val Glu Tyr Leu Asp Ser Ala Gln Phe Asp Lys Arg Arg Met Pro
545                 550                 555                 560

Thr Pro Thr Ser Leu Leu Lys Tyr His Lys Phe Glu Gly Lys Thr Lys
            565                 570                 575

Asp Glu Val Glu Asp Met Met Lys Ser Lys Lys Phe Ser Asn Ala Tyr
            580                 585                 590

Tyr Thr Phe Lys Phe Glu Asn Asp Val Val Ser Asn Ile Glu Tyr Ser
            595                 600                 605

Asn Asp Gly Ile Trp Lys Gln Lys Gln Leu Asn Phe Gly Asn Leu Ile
610                 615                 620

Ile Lys Ala Ile His Phe Ala Asp Ile Lys Asp Lys Phe Val Gln Leu
625                 630                 635                 640

Cys Asn Asn Lys Met Asn Ile Val Phe Cys Pro Ser Ala Phe Thr
            645                 650                 655

Ser Gln Met Asp Ser Ile Thr His Thr Leu Tyr Tyr Val Glu Lys Ile
            660                 665                 670

Thr Lys Lys Lys Asn Gly Lys Glu Glu Lys Lys Tyr Val Leu Ala Asn
            675                 680                 685

Lys Lys Met Val Arg Thr Gln Gln Glu Thr His Ile Asn Gly Leu Asn
            690                 695                 700

Ala Asp Tyr Asn Ser Ala Cys Asn Leu Lys Tyr Ile Ala Leu Asn Asp
705                 710                 715                 720

Glu Leu Arg Asn Glu Met Thr Asp Thr Phe Lys Val Thr Asn Arg Gln
            725                 730                 735

Lys Thr Met Tyr Gly Ile Pro Ala Tyr Asn Ile Lys Arg Gly Phe Lys
            740                 745                 750

Lys Asn Leu Ser Ala Lys Thr Ile Asn Thr Phe Arg Lys Leu Gly His
            755                 760                 765

Tyr Arg Asp Gly Lys Ile Asn Glu Asp Gly Met Phe Val Glu Thr Leu
770                 775                 780

Ala

<210> SEQ ID NO 56
<211> LENGTH: 735
<212> TYPE: PRT
<213> ORGANISM: Unknown
<220> FEATURE:
<223> OTHER INFORMATION: Description of Unknown:
      pig gut metagenome sequence

<400> SEQUENCE: 56

Met Ala His Lys Lys Asn Ile Gly Ala Glu Ile Val Lys Thr Tyr Ser
1               5                   10                  15

Phe Lys Val Lys Asn Thr Asn Gly Ile Thr Met Glu Lys Leu Met Ala
            20                  25                  30

Ala Ile Asp Glu Tyr Gln Ser Tyr Tyr Asn Leu Cys Ser Asp Trp Ile
        35                  40                  45

Cys Lys Asn Leu Thr Thr Met Thr Ile Gly Asp Leu Asp Arg Tyr Ile
    50                  55                  60

Pro Glu Lys Ser Lys Asp Asn Ile Tyr Ala Thr Val Leu Leu Asp Glu
65                  70                  75                  80

Val Trp Lys Asn Gln Pro Leu Tyr Lys Ile Phe Gly Lys Lys Tyr Ser
                85                  90                  95

Ala Asn Asn Arg Asn Asn Ala Leu Tyr Cys Ala Leu Ser Ser Val Ile
            100                 105                 110

Asp Met Asn Lys Glu Asn Val Leu Gly Phe Ser Lys Thr His Tyr Val
        115                 120                 125

Arg Asn Gly Tyr Ile Leu Asn Val Ile Ser Asn Tyr Ala Ser Lys Leu
    130                 135                 140

Ser Lys Leu Asn Thr Gly Val Lys Ser Arg Ala Ile Lys Glu Thr Ser
145                 150                 155                 160

Asp Glu Ala Thr Ile Ile Glu Gln Val Ile Tyr Glu Met Glu His Asn
                165                 170                 175

Lys Trp Glu Ser Ile Glu Asp Trp Lys Asn Gln Ile Glu Tyr Leu Asn
            180                 185                 190

Ser Lys Thr Asp Tyr Asn Pro Thr Tyr Met Glu Arg Met Lys Thr Leu
        195                 200                 205

Ser Ala Tyr Tyr Ser Glu His Lys Ser Glu Ile Asp Ala Lys Met Gln
    210                 215                 220

Glu Met Ala Val Glu Asn Leu Val Lys Phe Gly Gly Cys Arg Arg Asn
225                 230                 235                 240

Asn Ser Lys Lys Ser Met Phe Ile Met Gly Ser Asn His Thr Asn Tyr
                245                 250                 255

Thr Ile Ser Tyr Ile Gly Glu Asn Cys Phe Asn Ile Asn Phe Ala Asn
            260                 265                 270

Ile Leu Asn Phe Asp Val Tyr Gly Arg Arg Asp Val Val Lys Asn Gly
        275                 280                 285

Glu Val Leu Val Asp Ile Met Ala Asn His Gly Asp Ser Ile Val Leu
    290                 295                 300

Lys Ile Val Asn Gly Glu Leu Tyr Ala Asp Val Pro Cys Ser Val Thr
305                 310                 315                 320

Leu Asn Lys Val Glu Ser Asn Phe Asp Lys Val Val Gly Ile Asp Val
                325                 330                 335

Asn Met Lys His Met Leu Leu Ser Thr Ser Val Thr Asn Gly Ser
            340                 345                 350

```
Leu Asp Phe Leu Asn Ile Tyr Lys Glu Met Ser Asn Asn Ala Glu Phe
            355                 360                 365

Met Ala Leu Cys Pro Glu Lys Asp Arg Lys Tyr Tyr Lys Asp Ile Ser
370                 375                 380

Gln Tyr Val Thr Phe Ala Pro Leu Glu Leu Asp Leu Leu Phe Ser Arg
385                 390                 395                 400

Ile Ser Lys Gln Asp Lys Val Lys Met Glu Lys Ala Tyr Ser Glu Ile
            405                 410                 415

Leu Glu Ala Leu Lys Trp Lys Phe Phe Ala Asn Gly Asp Asn Lys Asn
            420                 425                 430

Arg Ile Tyr Val Glu Ser Ile Gln Lys Ile Arg Gln Gln Ile Lys Ala
            435                 440                 445

Leu Cys Val Ile Lys Asn Ala Tyr Tyr Glu Gln Gln Ser Ala Tyr Asp
            450                 455                 460

Ile Asp Lys Thr Gln Glu Tyr Ile Glu Thr His Pro Phe Ser Leu Thr
465                 470                 475                 480

Glu Lys Gly Met Ser Ile Lys Ser Lys Met Asp Lys Ile Cys Gln Thr
            485                 490                 495

Ile Ile Gly Cys Arg Asn Asn Ile Ile Asp Tyr Ala Tyr Ser Phe Phe
            500                 505                 510

Glu Arg Asn Gly Tyr Thr Ile Ile Gly Leu Glu Lys Leu Thr Ser Ser
            515                 520                 525

Gln Phe Glu Lys Thr Lys Ser Met Pro Thr Cys Lys Ser Leu Leu Asn
            530                 535                 540

Phe His Lys Val Leu Gly His Thr Leu Ser Glu Leu Glu Thr Leu Pro
545                 550                 555                 560

Ile Asn Asp Val Val Lys Lys Gly Tyr Tyr Ala Phe Thr Thr Asp Asn
            565                 570                 575

Glu Gly Arg Ile Thr Asp Ala Ser Leu Ser Glu Lys Gly Lys Val Arg
            580                 585                 590

Lys Met Lys Asp Asp Phe Phe Asn Gln Ala Ile Lys Ala Ile His Phe
            595                 600                 605

Ala Asp Val Lys Asp Tyr Phe Ala Thr Leu Ser Asn Asn Gly Gln Thr
610                 615                 620

Gly Ile Phe Phe Val Pro Ser Gln Phe Thr Ser Gln Met Asp Ser Asn
625                 630                 635                 640

Thr His Asn Leu Tyr Phe Glu Asn Ala Lys Asn Gly Gly Leu Lys Leu
            645                 650                 655

Ala Ser Lys Ser Lys Val Arg Lys Ser Gln Glu Tyr His Leu Asn Gly
            660                 665                 670

Leu Pro Ala Asp Tyr Asn Ala Ala Arg Asn Ile Ala Tyr Ile Gly Leu
            675                 680                 685

Asp Glu Ile Met Arg Asn Thr Phe Leu Lys Ala Asn Ser Asn Lys
690                 695                 700

Ser Leu Tyr Asn Gln Pro Ile Tyr Asp Thr Gly Ile Lys Lys Thr Ala
705                 710                 715                 720

Gly Val Phe Ser Arg Met Lys Lys Leu Lys Lys Tyr Lys Val Ile
                725                 730                 735

<210> SEQ ID NO 57
<211> LENGTH: 37
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 57
actatgttgg aatacatttt tataggtatt tacaact                                    37

<210> SEQ ID NO 58
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
attgttggaa tatcactttt gtagggtatt cacaac                                     36

<210> SEQ ID NO 59
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
aatgttgttc acccttttt                                                        19

<210> SEQ ID NO 60
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
cctgttgtga atactctttt ataggtatca aacaac                                     36

<210> SEQ ID NO 61
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
attgttgtaa ctcttatttt gtatggagta aacaac                                     36

<210> SEQ ID NO 62
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
attgttgtag acaccttttt ataaggattg aacaac                                     36

<210> SEQ ID NO 63
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
cttgttgtat atactctttt ataggtatta aacaac                              36

<210> SEQ ID NO 64
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
cttgttgtat atgtcctttt ataggtatt                                      29

<210> SEQ ID NO 65
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
cttgttgtat atgtctttt ataggtattg aacaac                               36

<210> SEQ ID NO 66
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66 tactctttt taggtaatga acaac                                           25

<210> SEQ ID NO 67
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
cttgttgtat atattctttt ataggtatta aacaac                              36

<210> SEQ ID NO 68
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
catgttgtac atactatttt ttaagtatta aacaac                              36

<210> SEQ ID NO 69
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 69
gatgttggac actatgtttt atacggtgga tacaac                           36

<210> SEQ ID NO 70
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
gatgttgtta tgctgttttt gtaagtaata aacaac                           36

<210> SEQ ID NO 71
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
attgttgtag acctcttttt ataaggattg aacaac                           36

<210> SEQ ID NO 72
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
attgttgtac gaaccatttt atatggtaat aacaac                           36

<210> SEQ ID NO 73
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
actgtaaaac ccctgcagat gaaaggaaag tacaacagt                        39

<210> SEQ ID NO 74
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
atcatgttgt acatactatt ttttaagtat taaacaacta                       40

<210> SEQ ID NO 75
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
```
attgttgaat ggctatgttt gtatgctatt tacaac                                36

<210> SEQ ID NO 76
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
attgttgggg tacttctttt atagggtact cacaac                                36

<210> SEQ ID NO 77
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
attgttgtag accttgtgtt ttaggggtct aacaacg                               37

<210> SEQ ID NO 78
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
actgtgttgg aatacaatat gagatgtatt tacaac                                36

<210> SEQ ID NO 79
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
attgttgtgg cataccgcaa ggcggatgct gacaac                                36

<210> SEQ ID NO 80
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
aattgttgag ataccgtttt ttatggtatt ggcaac                                36

<210> SEQ ID NO 81
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
attgttgtgg cataccgtat tacgggtgct gacaa                          35

<210> SEQ ID NO 82
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
attgttgtgg cataccgtat tacgggtgct gacaac                         36

<210> SEQ ID NO 83
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
attgtgttgg gatacacttt tataggtatt tacaac                         36

<210> SEQ ID NO 84
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
tattgttgaa tacctttctt ataaaggtaa ttacaac                        37

<210> SEQ ID NO 85
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
tgttgtaaat ggcttttat gggcaacgaa caactc                          36

<210> SEQ ID NO 86
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
attgttgaat gtattctttt ttaggacaga tacaac                         36

<210> SEQ ID NO 87
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
attgttgaat ggtatctttt atagactgat tacaact                        37

<210> SEQ ID NO 88
<211> LENGTH: 36
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 88
attgttggat aataggtttt ttatcttaat tacaac        36

<210> SEQ ID NO 89
<211> LENGTH: 36
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 89
actgttgaat agttgatttt atatcctatt tacaac        36

<210> SEQ ID NO 90
<211> LENGTH: 36
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 90
attgttgtag atacctttt gtaaggattg aacaac         36

<210> SEQ ID NO 91
<211> LENGTH: 644
<212> TYPE: DNA
<213> ORGANISM: Unknown
<220> FEATURE:
<223> OTHER INFORMATION: Description of Unknown:
      mammals-digestive system-rumen-bos taurus sequence

<400> SEQUENCE: 91
tatatcgtgg ccgaatatgt taacgcggac gacgtccgtc ttgtgaagtt tcaggacgag      60
gatttcgaca ggcttcttga caaggttaga gaatggaaca agaaacatct tgttgttgga    120
aatcggaact tcgaagaaaa atttgcgtaa tccaaaaatt ttccgtatat ttgcggcgtg    180
aaattaaaaa tatgtttaac taaaaacaaa gattatggca cacaagaatc ctgatgggga    240
gaacaccatc aacaaaactt ttattttcaa agtgaaatgc gagaagaatg atattatatc    300
gttctggaaa cccgcagctg aagagtattg caactattac aacaaactta gcgaatggat    360
tggcaaagat atgtataaca cgccgtcatg gaacatccgg caagagttca agaagaattt    420
aagtgttaga accataaaca cgtttcgtga gcttggcaat gtgaaatacg gcaaaatcaa    480
caatgaaggg ctttttgtcg aagacgatgt gtaaacatta agatttccat acgacaggat    540
tcaaaaaaac gttctttgaa atattggatt ggtggcaaga ggctgttttt tttaggctaa    600
aaagttgtgt aaatagcaga aacacagaac ataacataaa atct                     644

<210> SEQ ID NO 92
<211> LENGTH: 264
<212> TYPE: DNA
<213> ORGANISM: Unknown
<220> FEATURE:

<223> OTHER INFORMATION: Description of Unknown:
       mammals-digestive system-rumen-bos taurus sequence

<400> SEQUENCE: 92

| | | |
|---|---|---|
| aactgctaca attctgccga gtttatgatt cagacaaaat tcaaaaaaag acttccgcaa | 60 |
| gcaaccgttt ttggtgaatt gaacagaaac gggtatgtta aagtattgac ccaagaagaa | 120 |
| tatgacgaac tcacaaaatc agcaaaataa tttattactg attgaaaaat aaagcgttct | 180 |
| ttgacatatt gtataacaaa caagcatttt tgtaagagat aacccatttc attttattga | 240 |
| tatacaatga aatgaaaaga atat | 264 |

<210> SEQ ID NO 93
<211> LENGTH: 614
<212> TYPE: DNA
<213> ORGANISM: Unknown
<220> FEATURE:
<223> OTHER INFORMATION: Description of Unknown:
       bovine gut metagenome sequence

<400> SEQUENCE: 93

| | |
|---|---|
| gataaatttg cccgtaatgt tatcgggttc aagtcatatc acgaactgct tgataatgct | 60 |
| atcataaaag aaaaattaca acgggaattt ggttatgaag atgctccgaa aacgtggttg | 120 |
| ttcggacaac aaaaaaatga atgtttctaa tgtattaaaa caataattca attacaattt | 180 |
| taagattatg gcacaacaca aatcaaacaa cgaagaatca gcaatcaaca agactttcat | 240 |
| tttcaaggca aaatgcgata agaacgatgt catatcgtta tgggaaccag cggcaaagga | 300 |
| atactgcgac tattataaca aagtgagcaa gtggattaaa actatgtata acatacccgc | 360 |
| atataacatt aagtccaatt tcaagaaaaa tttgagcgcc aaaacaattc aaacttttag | 420 |
| agaacttgga cactaccgtg acggaaaaat aaatgaggat ggtatgtttg ttgaaaactt | 480 |
| ggataattc tgtatatacc aattagaatt gaaaaaaaaa cgctctttga catattgttt | 540 |
| tctacataaa aacaagattt tacacaacgc aatacatcat aaagtgttgc gttataacaa | 600 |
| ataacaaaaa ttct | 614 |

<210> SEQ ID NO 94
<211> LENGTH: 1041
<212> TYPE: DNA
<213> ORGANISM: Unknown
<220> FEATURE:
<223> OTHER INFORMATION: Description of Unknown:
       mammals-digestive system-cattle and sheep rumen sequence

<400> SEQUENCE: 94

| | |
|---|---|
| tttattcaat gcgaaccaga ggtcttgacg catgaatctg gctatacata tcgttatgcg | 60 |
| accgacgaag agaaaatatt gattaaaaga tgcaaatatt gaataggcaa ttttaaattg | 120 |
| tgaaaaaaaa aatgattgaa tataagttta cgtttgaact ggatggacat ctatcggcgt | 180 |
| acgattttgt tacgttgcaa gaacggtttg aaagggaatt gaatccttat tttgatgatg | 240 |
| ggagcatatc tggtactctt tcttatgcaa atgatgatta atatgcaaat aatatggcac | 300 |
| atgtaagaac aaaaaatgaa ggaaacatgg caaaaacata ttcttttaag gtcagagaaa | 360 |
| caaaccttaa aaaggatgtg atgattgaat ataacgaata ttataacagg ttatccgatt | 420 |
| ggatatgtgg caatttaacc aaaatctcgg aaaatgaaga atggaggaat gccttatgca | 480 |
| aaccaacaga aaacatgtac aacgaaccga tttacgttcc cttggttaaa tcacagaacg | 540 |
| gaatgttcaa ggcaattaaa aaatttgggcg caacgaagat atggcaagaa tagaaagacc | 600 |

```
gatttttaaa tctgaaatca cttctaacga attgtatact aaagaaatat aaagaatata     660
catcttttat gacattatga tattgttgta tgcatcattt cacatggtaa taacaacgaa     720
gagaaacacc gagcgaccca caaacctatt gtcgtacgca tcatttcaca tgataataac    780
aacgaatatt cctgcaagca tgatttaaca attttttaaga acctggtggt ttctccgttg    840
ggttcttttt agtatctttg ccttgttgaa acaaataaaa caaattgaat tatgatttat     900
aaaggcaaag aaatagacga aagttaccac atcaataaat gggaagatga agagatttac    960
tctggtccaa cccattatga atcattcgaa gccgatgaaa taaaagagtt ctacctcaag    1020
gcacttgcaa aggaaaagga a                                             1041
```

<210> SEQ ID NO 95
<211> LENGTH: 1545
<212> TYPE: DNA
<213> ORGANISM: Unknown
<220> FEATURE:
<223> OTHER INFORMATION: Description of Unknown:
      gut metagenome sequence

<400> SEQUENCE: 95

```
gtgcgcatat acactcaatt cgccgatgac cgtgtgtacg cgaaggattg tatcgacgga     60
ttctttagta taagacaaga taccgaaatg cgcctcgtgt ataaaaatga gatagcacgc    120
gggcttgagt gtatcaatat tgtaagatag tagtttttctg ttatttttaca tattgatgtg   180 ttttggcatg gttttttgtta aaatataatc tagcagtatt gagactgcgg agtaacgtgt    240
ctaactgttt cattataagc agtaaagact aatatttttta tatcttaaac ttatttttat    300
tatggctggt cacagcaaaa tcaaagaaaa tcacattatg aaggcgtttc ttatgaaagt    360
aaaagaaacg cgaaaaaaac agtggcaatc aaatttttatt agaagtgaga ttgctaagtt    420
tacaaattat tacaatgggc tgtcaaagtt ccttcttgga agcccgactg gagggacata    480
tgacactgca tattttgata caaagattca aggctccaag ggggtatatg ataagattaa    540
agaaaacgga gaaacttata ttgcagtatt aagtgatgac gttattacgg cagaggtgta    600
aaatcctctg ccaacatcgc aagtaactca ttgaaaatta gttaaatgcg aatgccaaca    660
aaagtgaacg aactgacttg taaagcagga tgttgttata tcttttttgta gataataagc    720 aacaagatac aatcaatcgc gagtttatac tgaaatgttg ttacactgtt tttgtaagtg    780
ttaaacaacc ttgcacaaat gtcatctacc agtacaatag atgttgttat actgttttgt    840
aggtattaaa caaccattgc gcagactgac agagtaacct ttcctgatat gttgttacac    900 attttttgtaa gtgttaaaca actgacgcat tgatattgcc ttgtctatta agaatgttgt    960 tatgctctttt ttattggtat aaacaaccga gcaactggta ctcaaatttt aaatactgtc   1020
gcgctatgtt atgtacatcg aacagctacc actcaatggc tttgtttgca accgtgatta    1080
attcaatcgc ggttgcattt gttttatgat gtgttttttgt atatattatg tatatatgga   1140
aaaggaaaac agggtatcgg agttatggag caagttctct gatattgact tgcgccgaag   1200
ccaaatgaca tatatgccaa taagaggtag taaaagatac ggcagaagaa taaaacgtag   1260
tgacatcgag tacgagtaca gatatctgta tagagcaaac aaacattggt aatatgaccg    1320
tagctaaatt atcaagtaat cataagccag cgtgccttgg acgaatctca gctttaaaca    1380
ccccgattag atttgagtgt cgggctggta atagtataag gcctggcaac atagagtata    1440
gctataaaag atgaaaaacg tcgtaatttc aactatgcac aacccgcata cgctggctta    1500
ttaccaaggt aagctggctc ctatgcattt cagacaagat acagg                   1545
```

<210> SEQ ID NO 96
<211> LENGTH: 1380
<212> TYPE: DNA
<213> ORGANISM: Unknown
<220> FEATURE:
<223> OTHER INFORMATION: Description of Unknown:
      mammals-digestive system-cattle and sheep rumen sequence

<400> SEQUENCE: 96

| | | | | |
|---|---|---|---|---|
| agcctgtata | cagggacaag | gttaagtaca | acaccaaggc | tgaggcaaag | aagagggctg | 60 |
| atgatatgaa | caaacagaat | agggtcatac | accagctgtc | tgtttatttg | tgtcctaaat | 120 |
| gtcataagtg | gcatataggt | aggagcagtg | tggagagtgt | gcgcagggaa | gggtacttta | 180 |
| gtcagatttg | aaattaattg | ttatatggcg | catagaaata | aaaacctagc | agaaaactgc | 240 |
| attaacaaaa | cattcagttt | taaagtcaaa | gccgaaaaag | aggagataaa | ttcaaaatgg | 300 |
| attccagcca | ttaaagaata | tactgcttat | tataacagga | taagtgactg | gataaacctg | 360 |
| tattcacagc | ctacttatga | tattaaggaa | gtttataaga | aaacgctgg | ttgcaaagtg | 420 |
| ataaacgact | tcattaaaaa | cggtaacgcc | gttatatgtt | gtatcgaaaa | taacaaacta | 480 |
| attgagacaa | atggaagaca | atagttcaaa | ttttaaatgt | aaaacagtca | ttaatgtatt | 540 |
| aatatataat | acatagcaaa | aatccagatg | ttgaatacat | ttcttttaag | tgtacttaca | 600 |
| acgcggtggc | attgctaaaa | tatagtcctg | tggatgttga | atacatttct | tttaagtgta | 660 |
| cttacaacca | acgctgtaca | cattgctaat | ggatgatgac | gatatagagg | tgttgaacta | 720 |
| ccttaatgaa | aactcacca | atgaaaacat | tgagtatata | cgcggttggt | ggatggatga | 780 |
| cgacgataaa | ctccagacac | ttgacaggtt | tttgaaaaat | ttttcaatat | agacctgtca | 840 |
| ctgttgcggc | tataagaaga | ccgatttgac | actgaaagac | cgatactggg | tttgccccga | 900 |
| atgcggtgca | aaactagacc | gcgataccaa | tgcaggaata | acattaaga | atgagacaat | 960 |
| tagactgata | aacaaagaat | aatgagaact | ataataggga | ggtgtacccc | cgaatttaag | 1020 |
| ccagtggaga | accatacaaa | cctatcatat | aggggttcaa | tgaatctgga | atttctgaca | 1080 |
| aaaacagggt | ttaacagcca | gtgtaccaat | gactaacaca | ggacatataa | agacaaatct | 1140 |
| aacaataaaa | aaaaatattg | accaattctg | cagaaaaaac | aggttggttt | cggttatgtt | 1200 |
| ggtgaataaa | gacagttaga | ttaattttat | atggaaatga | aaatagagac | aaaagacgag | 1260 |
| aacatctacg | tattcatcta | tgccaagtcc | gcctacttcg | gcaatacatt | tgaatatggc | 1320 |
| ggcacatttt | ccgtcggcaa | ggacgacaac | tggaacgatg | tgagaggcca | cgttaccgaa | 1380 |

<210> SEQ ID NO 97
<211> LENGTH: 853
<212> TYPE: DNA
<213> ORGANISM: Unknown
<220> FEATURE:
<223> OTHER INFORMATION: Description of Unknown:
      mammals-digestive system-rumen-ovis aries sequence

<400> SEQUENCE: 97

| | | | | |
|---|---|---|---|---|
| gacaacatcc | tggtcaagac | cgaggttaac | agaaggtact | gccgccttat | gaccgacgag | 60 |
| aacggagtgt | ggctcctgag | gaaaaacgac | aaacatccaa | catattttat | ctaccagaac | 120 |
| ggaacactct | atcaatatga | ggaagattga | ttagttgatg | ttttcataat | aattttatct | 180 |
| ggaatttgaa | aagattccag | atttttttt | tatttcgact | gtacaaaaaa | caggttccgt | 240 |
| tgcgttatat | aggtgtaaat | taaaaattca | gtcaaacaaa | aattggaata | aaatatggct | 300 |
| aacaagagaa | cagacacaac | aatcaacctt | aacaaaaccg | ttataatgtt | aacgaacatg | 360 |

```
ctgccagaag tacgggcaat gtttcaggcg ggaatacgcc aggctcaagt ttatgcagac    420
ttggtgaaca agtggatatg ttcacaggaa atgagagagg ttatgtgtct ccatccgtca    480
aaaaaggacg gggtgtacga ccaaccgttc ctgaaagcta caaccaaata cccagccacg    540
gtagctggta tcctgcttaa gatgggaaaa acaaccaatt ggggtgagaa ataatacccca    600 cccgccccat ttttttacac tgattagttc tttgacttat tgatttatat tggtttacac    660
aaattatcga cacaataaat aaaaaaaatt gtatattagt agtatgatga cagaagaaac    720
acggaagaca atagagagcg tcatagtggt tctcggcata gcaatcatgc tggcagccgc    780
cgtccgaata atgacgcaga acaaagcaat tgtgaaatat gatgaacagg ttgaaaccat    840
gcaaacttgc ata                                                       853
```

<210> SEQ ID NO 98
<211> LENGTH: 795
<212> TYPE: DNA
<213> ORGANISM: Unknown
<220> FEATURE:
<223> OTHER INFORMATION: Description of Unknown:
      gut metagenome sequence

<400> SEQUENCE: 98

```
atggaagttg tacgtggtgg aaatcaatgg gaggtttatg acaattacga tgagactatg     60
aaagcatcaa aaaatgtaag gtctgtattg ggacttccgg aagtaaaata tccacctgag    120
gattttagga catataattt ctaataaaaa tgaacggaaa aatttccgtt cattttttt     180 ttgtttattg gtgaaaaaat agtatctttg taaaaaataa atgttaaaat attttttatg    240
ggaaatacta caaaaaaagg aaatttgacg aagacttatt tattcaaagc caatcttttca    300 gaacaagact ttaaattatg gaggtctatt gttgaagagt atcaaagata taggaagtg     360 ttgagtaaat gggtatgtga ccatcttaga aatgcaatgt gtacgaaccc gaaaagtgag    420
actggatatt ctgtaccgtt cttgacttca agaatcaaga acagaacat tatggttgta     480 gaattgaaaa aatgggcat ggttgaagtc ttgaatgaaa atcaacaga atttaagaa        540 aaaaatattt atataatgta ctgaaaataa gtaaataata aatattgtgt aaaaaacttg    600
atattttttt tttgttatct ttataatata aaataaaatg taaatatgaa aaatctgtta    660
aaactcaaag aacaaatcaa ggattacaaa catcttcagt ttgtgttgga gaaagaagat    720
gaatctgaac tccattatag atgtatgact gaagattttt cgttcaaggt atctgaagaa    780
aaagacggaa cactt                                                     795
```

<210> SEQ ID NO 99
<211> LENGTH: 420
<212> TYPE: DNA
<213> ORGANISM: Unknown
<220> FEATURE:
<223> OTHER INFORMATION: Description of Unknown:
      bovine gut metagenome sequence

<400> SEQUENCE: 99

```
ttataaacat ctaaaaagaa agacttatga caacaaaaca agttaaatca atcgttttaa     60
aagtaaaaaa cactaatgaa tgccctatta caaagatgt aataaatgaa tataaaaaat     120
attataatat atgtagtgaa tggattaaag ataatctaac aagtattact attggaaacg    180
aaaatttacg aaaattattt tgtggtaaac ttaaagtaag tggatataat acaccaatat    240
tagacgcaac aaaaaaaggt caatttaata tattggcaga attaaaaaaa cagaataaaa    300
```

```
ttaaaatatt tgaaatagaa aaataagtct tatgattaca aaaataatag atttcaaaca    360 tttttttaa ttctatttta ttgactaatt cattgaaata taaataatta caaataaccc    420
```

<210> SEQ ID NO 100
<211> LENGTH: 1058
<212> TYPE: DNA
<213> ORGANISM: Unknown
<220> FEATURE:
<223> OTHER INFORMATION: Description of Unknown:
      mammals-digestive system-rumen-ovis aries sequence

<400> SEQUENCE: 100

```
gatagatata gtattgcagc atttctggct tgcgaatcat cagcaatgca aaaatgtgac     60
tattggaaca atgatgatgc ccaagattac ataagaaact acaaagaggc ttatagtaat    120
gcagtaagac ttgcgttttt taatgattaa gcaacacgct taacattgtc aaatgtaacg    180
acattaagtg cgtgtttcat aagggcagcg aacctttcgc cgcccttctt tttttgttgc    240
tgtaacggaa ttatgtttac ttttgtgcca tcaagtatat agttcccttg ataaattgta    300
tattaattaa aagtttggca caatatttga tgcgtacaaa ttaaaataaa aacatttga    360 attttaaaat ttaatttgta attttaaata agaaagtttt atttaactaa aataaaaaaa    420
atgaataaat cttatgtttt taagtcgaat gtggctattg atgacattat gtctttattt    480
gaaccggcaa ttgaagagta cataaactat tacaatagaa ccagcgattt catttgtgat    540
aatcttacat caatgaaaat cggagatttg ttgcttctaa caatgtgtac taagacaaaa    600
gaaaataata gatacggtaa ccccctctat aatatcaaag atactttta aaagaaaata    660 ccatcttcaa tacttaatat attcaaaaaa aaggatatgt atcaaataat atgtgattaa    720
ttatgccttt ttttaataaa aaattgttaa ataaactttt gtttattaat aaattataaa    780
tatcacagta aactattagg gatttgtaaa atttatggaa attatataca tgatggcact    840
aagatttggt tattaagaaa tttttctgta taagtataat aacctatta taattataat    900 tgaataaaat gtataatatg gaaaacacag gcttttatac agtttcaaat attgaaactt    960
ctcataagcc aaccgaaaat tctaatgacg aaattcttag gattttcaat aaaagaaggc   1020
cttattgccc ttcagacttt aagaagcaac attttatt                          1058
```

<210> SEQ ID NO 101
<211> LENGTH: 554
<212> TYPE: DNA
<213> ORGANISM: Unknown
<220> FEATURE:
<223> OTHER INFORMATION: Description of Unknown:
      mammals-digestive system-rumen-ovis aries sequence

<400> SEQUENCE: 101

```
aggctcaacc tcctcaaccc gatttatctt gagatcgcca agtacggaca cttcgggagg     60
aagagctatg tgaaggacgg catcaagtac ttcccgtggg aggatttgga tttggttgaa    120
gacatcagaa aaattttcga atggaatag agggaaccgg aatttttttcc ggttttctt    180 tgtcctttcg aaaataaata gtatctttgt aaaaaaacaa cagattatgt acaatagtaa    240
gaagaagggg gagggtgaca ttcagaagtc gttcaagttc aaggtcaaaa cggacaagga    300
gacggtcgaa ttattcagaa aggccgcagt cgaatactcg gaatactaca agaggctgac    360
aacattcctc tgtgagatgt ataacagacc agcgtttgac ttgaaggagt gctacaagaa    420
aaattccaat gtaagtgtct tcaacacatt gaagaaaact ctcggtgcaa tatatggaaa    480
gctcgatgaa aacggaaatt ttattgagaa tgaatgtaat aagtaactgg aataaaagaa    540
```

| | |
|---|---|
| attagacaga gtaa | 554 |

<210> SEQ ID NO 102
<211> LENGTH: 1039
<212> TYPE: DNA
<213> ORGANISM: Unknown
<220> FEATURE:
<223> OTHER INFORMATION: Description of Unknown:
      mammals-digestive system-rumen-bos taurus sequence

<400> SEQUENCE: 102

| | |
|---|---|
| ttgtattggt tgctgtatgg cgacggaagt gacatatatg atgacgggtg gtttgactgt | 60 |
| gttcataatt ttgcccgtaa tgttatcggg tttcagtcat atcacgaact gcttgataat | 120 |
| gctattataa aagaaaaatt acaacggtaa tttggttatg aagatgctcc gaaaacgtgg | 180 |
| ttgttcggac aacaaaaaaa tgaatgtttc taatgtatta aaacaataat tcaattacaa | 240 |
| ttttaagatt atggcacaac acaaatcaaa caacgaagaa tcagcaatca acaagacttt | 300 |
| cattttcaag gcaaaatgcg agaagaacga tgtcatatcg ttatgggaac cagcagcaaa | 360 |
| ggaatacggc gactattata acaaagtgag caagtggatt aaaactatgt ataacatacc | 420 |
| cgcatataac attaagtcca atttcaagaa aaatttgagc gccaaaacaa ttcaaacttt | 480 |
| tagagaactt ggacactacc gtgacggaaa aataaatgag gatggtatgt ttgttgaaat | 540 |
| tttggaataa ttctgtatat accaattaga attgaaaaaa aaacgctctt tgacatattg | 600 |
| ttttctacat aaaaacaaga ttttacacaa cgcaatacat cataaagtgt tgcgttataa | 660 |
| caaataacaa aaattctgga cgggaaagga agatgtcaga cgtttttatt gttggaatac | 720 |
| tcgttttttta cggtatttac aactgccccg tagcggaatc aaaataccac cgcattgttg | 780 |
| gagtacaagt tttacacggt attcacagta cgaacaccga atgaactgaa aaaaataaac | 840 |
| ccgaccttgc aaccgtagat ataaataaag caatacaaaa tttgaaacta tggcacacat | 900 |
| taaaaaaatt gacgaaatgg caagtcaaac tgtttcactc cgttctgacg cattgttcaa | 960 |
| aaaagcgttt gaggaatttg aaaaggagtt gaaagaagtt ctcaaatcgc acaacaatat | 1020 |
| catttattgt ggaggtgat | 1039 |

<210> SEQ ID NO 103
<211> LENGTH: 1252
<212> TYPE: DNA
<213> ORGANISM: Unknown
<220> FEATURE:
<223> OTHER INFORMATION: Description of Unknown:
      mammals-digestive system-rumen-bos taurus sequence

<400> SEQUENCE: 103

| | |
|---|---|
| ctcatcaaat tgtacaagtc gttgacggac actgaatttg acaagaagaa aatcatcaat | 60 |
| gatgtctacg acggcacttt tgagataatc ctcaaatacc caagaagaa gaacgggaca | 120 |
| ttcgtgttct ggaaacatta caagaagtaa cacaatgata cacagtatgt tgtaagaaat | 180 |
| aagatttagg ctttaatttt aatatatgaa aatatggcac acaaaggaga aaaggaaggc | 240 |
| taccaaatca agacactgaa gttcaaggta cgctcgcatg acatcgggaa atcactttat | 300 |
| gatattgtca acgaatacac caactactat aacaaagtaa gcaaatggat atgtgacaac | 360 |
| cttggttaca acgagccatt ctacaagtca agggtgaaaa gcgccgcctc catgatgtca | 420 |
| ggattgaaaa aactgggcgc caccatgcca ttgacggatg aaaatgccat ttttcaaca | 480 |
| ccaaaaccga agaaaaacat tggaaaacaa taatttacac aaagtctacg gcgggaatcg | 540 |

```
tgataaaaat gaacgagatt gttgggatat accttttata ggattttcac aacatctgag      600
ttgtttgatg ttaaaaactt taactaataa ggcaagaagt cccattcctt caggtggggg      660
tagttcattt gttgggatac tcgtttcaca cggtattcac aacttccaac caaccattaa      720
aaaaccttca atattgttg gagtacccgt tttatacggt gcaaagcctc cccgacgatt       780
tcaagttcct gtacgaagat gtcaattttg gatagcaact gttaccaata aacatattca      840
aaagtaatca aatatattca aaacaactc gtataaatat ataaagttcg tgatatttat       900
tataaagaag ccgaaggaga gagcggtttc cgaacaataa agatatacag aggttttatt      960
cttgacggca ctctctcctt tagccgcaag tttaattcct cttttttatt gcactatggt     1020
catcgacagc aaatatacca agacattcaa gtcaaacgga ctgacccatc agaaatatga     1080
cgagttgctc tcgtttgctt ctatgctgcg tgaccataag aacaccatct ccgaatatgt     1140
caatgccaac cttgaacact acctcgaata ctcaaaactc gacttcctta aggaaatgcg     1200
tgcgaggtac aaggatgtcg ttccgagttc gtttgacgct caactctaca cg             1252
```

<210> SEQ ID NO 104
<211> LENGTH: 1131
<212> TYPE: DNA
<213> ORGANISM: Unknown
<220> FEATURE:
<223> OTHER INFORMATION: Description of Unknown:
      pig gut metagenome sequence

<400> SEQUENCE: 104

```
agaatctgtc ctatatgtgg gaaacattgc gaatatgagg aaatggaggg cgaccacatt       60
gttccatggt caagggcgg taaaaccgat ataggcaacc tccaaatgct atgcaagaag       120
tgcaatcacg aaaagtccaa tagatattag tggcgtaatc aaaaatttgt ttgtgttgag      180
gaaaagcagt gaaaaaaaac attgttttc ctcaattttt atttgcataa ttcaaataat      240
tttttatttt ataggataat agagctaaca agcattaaca attattaaaa cgatttatat      300
tgaaaataaa ttttgtggga atatttattt ttactacctt tgcatcgtaa tacaattaaa     360 caaattttg attatggcac acaaaaagaa cataggagca gagatagtaa aaacttactc       420
ttttaaggtg aagaatacca atggtatcac aatggaaaaa ttaatggccg ccattgatga      480
gtatcagtcg tactataacc tttgcagtga ttggatatgc aagggtcttg acgaaataat      540
gaggaatact tttctgaaaa aagcaaatag caataaatca ttgtataatc agccaatcta      600
cgatacgggt atcaagaaaa ccgcaggtgt gtttcctaga atgaaaaaat taagaaata      660 taaagttatc tgaaataaaa tatgtatttt tctttgtgga aatacctatt aatagactga      720
tttctaataa gttataagaa atactgtatg tagtaaataa gatatcatat ttttgcggag      780
aggcacatgg agtatgctat agggttttg ctaccgagca gaaagcaaaa gaaaaaatgc       840
agggatgata tcatttcatt cttgcatttt gcttatacat attcaatcaa gtatcatttt      900
ctgtttttac tattatccta taaaataaaa ttttcctcaa catttccaaa tttaatttgc     960
aataattttt tttgataaaa agtgcaaata aattttatag attcaaaact tttgattaac     1020
tttgtaacaa gaaaaacatt aaggattatg ggttacacat atttagggt tactgatgaa      1080 agggcaaggg atgttatgcc aaaggcggct gaaatcataa aggatatttt c              1131
```

<210> SEQ ID NO 105
<211> LENGTH: 3677
<212> TYPE: DNA
<213> ORGANISM: Unknown
<220> FEATURE:

<223> OTHER INFORMATION: Description of Unknown:
     mammals-digestive system-rumen-bos taurus sequence

<400> SEQUENCE: 105

| | | |
|---|---|---|
| cttcacctcg tacagccgac aataagtttc gcttggactg aacttatgtg cgcctgcgca | 60 |
| ttcatagcgg gtggcgtatc aggctatctc atcaagggca agatgccaaa cgacgggaac | 120 |
| aagtaccagt cggtagaggg aaaggaatag gacaaaaaaa aacacatcac ccccagcgca | 180 |
| tcgggcgcgg aggtcgggtg tgcatataac ggtgtctgtg gcgcaactgg tagcgcagtg | 240 |
| gattgtggtt ccaaaggttg cgagttcgag cctcgccaga cacccattat cacacggaag | 300 |
| cattggatgg aagtgcaagt acctactggg aacttcctga aagcgcaagc aaagtcgagg | 360 |
| tctaacggta cttatgaccg aggtaatggc ggggcgttgg ttcgagtcca acacaatgtt | 420 |
| tccatttaca cggagagttg caggagtggt aactggtcag attgctaatc tgaagcccac | 480 |
| ctcgttgtgg caggggtccg aatcccttac tctccgccaa gcaacatacc cgcagagtag | 540 |
| tcgcgtatat tctgtcggtg tggtcagaaa gaagtgaatg tgatgcgaac gcgcgaaacc | 600 |
| atcgcattta gagtccgaat ctcctctgcg gtagccagtc cgcatagttt aatcaggtta | 660 |
| aaacattctg acgcttttttt aaatcgcggg agtagttcag tggtagaaca tcggcttccc | 720 |
| aagccgaggg tcgcgggttc gagtcccgtt tcccgctcaa cacataggct gtggacaagg | 780 |
| tgggcgaaag tattttttcc atagttttac accaacgccc gccttttcct aaacgcattg | 840 |
| gagagataga ggacttgcct tctaaacaag cagtacgggg gaacttgcat ccgacctccg | 900 |
| tttcaatgcg gtagaactcc gctcccgtga cagcgacgaa tgatgcaata gcggttcacg | 960 |
| agatacctca agaaacttca tttttcaaaa gccacaatag ttcaactggt agaacggcgg | 1020 |
| tatcgtaaac cgcaggttgc tggttcaatt cctgcttgtg gctcaacaat ttcgggggct | 1080 |
| tgcaacgctg ccactgcggg tggaagccag cgacaagaac ttgtgtgaag ccgaaacgca | 1140 |
| gtccttcggg agaggggcga aggggcaagc gagatgtgtc ccacttttttt aaagtaacag | 1200 |
| gctttaataa atatttatca ttcccgaaag gctgtgcgga acagcctctc ggcttttacg | 1260 |
| gggatttagt tcagttggta gaacatctgg ttcgcaatca gaaggtcgcg ggttcgactc | 1320 |
| ccgcaatctc cacaaatata aatatagtat tgccctgtgg tgcaatcggt aacacaccag | 1380 |
| attctgaatc tggaatttcg agttcgagcc tcggtggggc aacacaatag gcagccgtac | 1440 |
| tgccgaatac aagcctgtgg agaacccaac cgtggatgac cgttgcctat gcaacctaaa | 1500 |
| aagcggtggt tctgtgaagc aggaagcgga aatacaatat tccgcatacg gtggtggtgt | 1560 |
| aatcggtaac ataacaatat ccgaaaagtt taaaccatac acccgacgat tattttttatt | 1620 |
| cattgttagc gaccgccgtg aggcggacgc aggctggcgg tcggataatg acgcataatg | 1680 |
| gcggttgtga aagccgacgg aaagcactac atcgttaagt gccagccacc ataataggca | 1740 |
| gccgtactgc cgaatttaag cctgtggaga acccaaccgt ggatgaccgt tgcgtaagca | 1800 |
| acctaaaaag cgatggttct gcgaagcagg aaggaaatgc ccaatttatt aggttttttcc | 1860 |
| atacggtatg acagcctcta actgtagcgc attacaaaac aaacgctacc attacataaa | 1920 |
| tggtcagagg cataacgccg agcgcaggta tggtatgcgt tcaagtcgca gtcacggaag | 1980 |
| ccccagataa aaatggggagg tgcttgcggt caagcgagtg gtcagcgggc ttgcactcgg | 2040 |
| tgtggcaaca atggtcgttt ccgaacttac gaccattcaa aaagataagg tagtggcttg | 2100 |
| tgagtgaaaa gaaactctcg atacgctcct ttcgtctaac ggtcaggacg cgagattctc | 2160 |
| aatctcgtaa tgcgggttcg attcccgcag ggagtacaat ggcgaacaca cgacaatcca | 2220 |

| | |
|---|---|
| aactgaaggg gaactggaaa accctcgctc cgagataaca tcagcgcaga gaggttggtg | 2280 |
| aggcaaccgt aaaagtaatc ctgtgtgcaa gcaagaagga agttcgggtt caagtcccga | 2340 |
| tgaggattat tgttgaagag ggatatgatt caaccatagc acttatggtg ctgtgcaagg | 2400 |
| gttataggca gccgtactgc cgaatacaag cctgtggaga acccaacagt ggatgaccgt | 2460 |
| tgcctatgca acctaaaaag cggtggttct gcgaagcagg aaggaaatgc ccaatttatt | 2520 |
| aggttttttcc atacggtatc actactcgcg gtggatgtgg aaataaccgc gatttggtca | 2580 |
| gttggtgaag ttggttatca tacctgcctg tcacgcaggt gttcacgagt tcgagcctcg | 2640 |
| tactgaccgc agacaaagac aaagaacgag aggacttgta tgacttgcaa atgtcacgga | 2700 |
| ctcaaacaag aaaagtttat aggctattag aggatgactg tttctttaat ttgttttctt | 2760 |
| gtactgaagg tcatcactgc cgtgccacca agccgtgcaa gtccaaatgg tgcgttagtt | 2820 |
| cagttggtta aatgccagc ctgtcacgct ggaggtcgcg ggttcgattc ccgcacgcac | 2880 |
| cgcaataatc tggatatagg caaattacac atatcatatg tcgccccgcg taatcataga | 2940 |
| cgacactgcg gacgacagcg gcgagaatgt cgaaaggctc gacagcataa tgacattcga | 3000 |
| catcaccgac accccgatat acgaaggcgg ggaggaactt gagataaacg caaaattcaa | 3060 |
| cagatagaaa taattaaaac aaacggcaat ggcacacaga aaaagaaag atgacgaagc | 3120 |
| aacgctatcg tacaagttca aggtaaaggt catagagggc gacctgacgg cagacgacat | 3180 |
| aacgaagtgt atcgcggaaa acgcggagca gggcaaccat ttctccgagt tcatacacga | 3240 |
| tgagaatttc aggaagacct tcacatccga gatcagcgcg gacaagttcg gatggggcaa | 3300 |
| gccgatgttc agcccgacca ccagaagtca ggacgaagtg ttctccgcga taagaaaat | 3360 |
| cggggcgata accgtgctgg aagattagcg catattattc tcatatctaa aattggaagg | 3420 |
| acacctgcgg acgcgggtgt cctttttttct taaaatgcca atttataaat aatatataac | 3480 |
| ttatattttat tgtactttt ttgtttaact aaaacacata gacaaatatg gaaattcaac | 3540 |
| agattaggtt tataaaccca gttgattttg aagaaacaat cgttaatgta cccacggaga | 3600 |
| agggcgaaag attcctgaga acaaaaatct atacggacga gtattcaccc gaaacattca | 3660 |
| taaaactctg cgagaag | 3677 |

<210> SEQ ID NO 106
<211> LENGTH: 831
<212> TYPE: DNA
<213> ORGANISM: Unknown
<220> FEATURE:
<223> OTHER INFORMATION: Description of Unknown:
    mammals-digestive system-rumen-ovis aries sequence

<400> SEQUENCE: 106

| | |
|---|---|
| tggcgattat tcttacggca aaggccttat ccatgcatac ataaatcgag acatcaaaag | 60 |
| tttttgcttg ccaaacactt taatatgtga atgccatata ccaaaacata ccagatatat | 120 |
| tactgattac tcaggtacaa atatagccgc aaagaaaatc atcatcgaca aagttgtctg | 180 |
| ggagaaggta tgtataaaaa cataatggta ttaggggaga attttcttg gacggaatga | 240 |
| atataatttc ataccaacac cgtgcattga ttaaactaaa ttaaattatc aagcataaaa | 300 |
| agtttggcac ggttttgat atagtaaatt tgtatttaaa atttttaata tggcacacaa | 360 |
| aactaaagaa tcagaaaaat tagtaaagtc tttcaaatta aaagtagaca ttagcaattg | 420 |
| cgaaattgaa aagaaatgga ttccttcttt tgaagaatac acaaattatt ataatggagt | 480 |
| aagtaattgg atttgtgaac tattagaaaa agtttgcctg aaagaaaaa aatttggaaa | 540 |

```
ggcttcttat tcagtaccat attggaacgt taaagacgca tttaagaaaa acgttagctc    600
aaacatgatt gctacaatta aaaaaatgaa tatggtaaag gttttttaat gcgtgattat    660 ggcgttttt  aaacataaaa tcatttataa tatattgaaa acattttat  tatataaaat    720 atgcatctta gtgaaaccgt gttttcgtat agattgctgg attatacttt tttataggat    780
aattacagct cgaacttctt tgatggcatt aataagatat tgttggatta t             831
```

<210> SEQ ID NO 107
<211> LENGTH: 634
<212> TYPE: DNA
<213> ORGANISM: Unknown
<220> FEATURE:
<223> OTHER INFORMATION: Description of Unknown:
      mammals-digestive system-rumen-ovis aries sequence

<400> SEQUENCE: 107

```
atcatggctg aaagcgtccg cctgattgca gagcaaaccg caagcccgaa ggttgtcatc     60
aagagccgtt acgctctggt cgacgcaggt ttctatcctg agttgaacta tgtgaccttc    120
ttcgtgaaca ctccagatca actggtttaa tcactgcggg tagcaagcga ttgactacgg    180
aaggccgatt cgatagagtc ggtcttcttt ttttttttgta tattttcttt ttttggtttg   240
gaaatgttcc gtatatttgc agcactaaaa ctaaccaata tgggacatgt acgtttgcaa    300
aaaagagagg gagaggttta taagacctac aaacttaaag taaagagctt ttctggcaat    360
gtagacatta aagctggtat cgttgaatac gatatcgccg aaacaattga ttggagaagt    420
acgctttgtt tcaagacatg gaatacgtat ggttctcctc aatgggactc gaagatcaag    480
aaccagaaaa cgatgatcga tcgactggat tcgttgggtg caatagaatt gaaaaactgg    540
tgattttgat catggttttg aaacaaaata ttgattttc gttctttgac atgcttgtta     600
aaaattgagt atcagtttaa tataaagaat atat                                634
```

<210> SEQ ID NO 108
<211> LENGTH: 1154
<212> TYPE: DNA
<213> ORGANISM: Unknown
<220> FEATURE:
<223> OTHER INFORMATION: Description of Unknown:
      human gut metagenome sequence

<400> SEQUENCE: 108

```
ggaaacaatt ataacgatgc ctacaaaacg ttaattcaaa tgagagacaa aggaattta     60 acgcaggaag ttgtaaatgt atttacccta ttgaaagggc ggtatattaa agaaaaagaa   120
tacggaacac aatataatac tatcaattaa atttttggt  agtttcattt ggaattgcca   180
attatttttt tatttatag  aataatagag ccaacaagca ttagcaatta ttaaatcgat   240
ttatattgaa aataaatttt gtgggaatat ttattttac  tatctttgca tcgtaagata   300
attacaaaac attaacaaca tttattaaac aattaaacaa attttaatta tggcgcacaa   360
aaagaacgta ggagcagaga tagtaaaaac ttactctttt aaggtaaaga ataccaatgg   420
tatcacaatg gaaaaattga tgaacgccat tgacgagttt cagtcatact ataacctttg   480
tagcgattgg atatgcaagg gtcttgacga acaatgagg  aacactttc  tgaaaaaagc   540 aaatagcaat aaatcattgt ataatcagcc aatctacgat acgggtatca agaagaccgc   600
aggtgtgttt tccagaatga aaaattaaa  gagatatgaa attatctaaa ataaatatg    660 aattttctt  tgcggaaata cctttaata  gattgatttc taataagtta taagaaatac   720
aatagatact gaaggaaaat caaagtgtaa tcaaaaattt gtttgtgttg aggaagcagt   780
```

| | |
|---|---|
| gaagaaattt cattgtttcc tcaatttta tttgcataat ccaaaaagtt tttatttta | 840 |
| taggataata agactaacaa atctcaacga ctattaaaac gatttatata aaaaaagttt | 900 |
| tgcagttcca atcttttttg ctatctttgc agtgttgaaa gacaacaaag atttaagttt | 960 |
| aacaaacaaa tacttttat tacatatttt aattttttg tattatgaca atagaagaaa | 1020 |
| aagcaaggga agaatacct tatataaccc catctgatgg gtatgaatgc catgattata | 1080 |
| atgaagccgc taaagacggt tttattgagg gggcaaaatg gatgcttgaa aaagccgctg | 1140 |
| aatggtttaa gaat | 1154 |

<210> SEQ ID NO 109
<211> LENGTH: 1048
<212> TYPE: DNA
<213> ORGANISM: Unknown
<220> FEATURE:
<223> OTHER INFORMATION: Description of Unknown:
      mammals-digestive system-rumen-ovis aries sequence

<400> SEQUENCE: 109

| | |
|---|---|
| atatgggcaa agcgtgataa aattgaaaac aaatatgtca aagaaccatt aaaacgagtc | 60 |
| aatgaagata tgtggtggat gtactatgtt tatgaatgga atgtgtttta tgtgcttgaa | 120 |
| gaaaatgtcc atccatatat gaaaaataa attttaccac acatattatt attcgtgtca | 180 |
| tgccgatgag gtttggcacg attttgtt atatggagag acataatgtc agtcaataca | 240 |
| tgacaacttg tcacaataac tgacattaaa agtttggcac aatatttgct tataagaaaa | 300 |
| acgaacaagt aaaattaaaa ttttatagat tatggcacac aaaacaaaca acggagaaaa | 360 |
| caccatcaac aaaactttca tcttcaaagc aaaatgcgag aagaacgata ttatatcgtt | 420 |
| atggaaaccc gcagcagaag agtattgcaa ctattataac aaattgagca aatggattgg | 480 |
| taaaacaatg tacggcattc ctgcatataa catcaaaaga ggttttaaga agaatttaag | 540 |
| tgccaaaact ataaacacat ttagaaaact tggacactat cgtgatggaa aaataaatga | 600 |
| ggatggcatg tttgttgaaa ctttggcata gaatttgcat ataccaatta gaattgaaaa | 660 |
| aatcgctctt tgacacactg aaacatacaa aaacaccaca attttttaat ccttttctat | 720 |
| ttgtatttta ttgaaataaa atgtattata gtaatatatc tgctaaggtc atattttca | 780 |
| ttgttctcaa attgttggat aatgttttgt gtgtttcatt tttgtcattg tgtcaccta | 840 |
| actgacaagg tggcacattt tttatgtcaa tatgtcagtt gaggttttgg cataattttt | 900 |
| gtataatggt aaatggataa gaattgaaat tacaatgaca acaaaacaaa ggttaataaa | 960 |
| gagaataaac aaggcattcg gatttgaatt aacggatgca caccttgtt tccaccatca | 1020 |
| aggtagaaga tgggaagcg gtggttc | 1048 |

<210> SEQ ID NO 110
<211> LENGTH: 968
<212> TYPE: DNA
<213> ORGANISM: Unknown
<220> FEATURE:
<223> OTHER INFORMATION: Description of Unknown:
      mammals-digestive system-rumen-ovis aries sequence

<400> SEQUENCE: 110

| | |
|---|---|
| gaaggcggcg cgtttgaaat cgctaacgta attgaaaatg ccaagaagca gaatctcggg | 60 |
| gagggtggat acaaggaatt gtgcaatgat ttcctgaaac atgcgaggga acgttttc | 120 |
| agtgggaaat acgaacacca ttcttggtag tggatttgtt atttggtaa atataattaa | 180 |

| | |
|---|---|
| cgcggcattg tcgtcagtga atataatatt gcatttcgac agtattttat aagtattttg | 240 |
| acttataaac agtatttata agttattcgg cttataggtt aattagccta tagatgttgt | 300 |
| ttataggttg gatgacctat agtgccaagt tttgaagaaa tcgttatagt catcgttctg | 360 |
| ccctattaga tattccgtat ttctttaaga ctgttataat acaaatatac tacaaatcat | 420 |
| gcaattttg atttttaaca aaaattaaga aatagggtat tattgtgtat tgttttttgt | 480 |
| tatatatttg tcctgttagg ttaaatcacc gcgcctgatg acgaagtcgg tggtagaatt | 540 |
| agactaatat taaatatgtc tcatgaattt aacaagaata aaggtgagaa tgagattagc | 600 |
| aagacccttta ttttcaaaac aaaatgcggg aagaatgata ttacatcatt atgggttccc | 660 |
| gcgatggagg agtattgcac gtattacaac agggtaagca aatgggggaa aggtatgtac | 720 |
| aacaagccgt catatgacat acggaagaaa ttcaagaaga acttgagtgc ggctactttg | 780 |
| aaaactttca ttaagttggg aaacacggtg aaagggatga ttgtcaacgg acagtttgtt | 840 |
| gaaatggaat cataggttga cagaaacgga aaatcggttt gtttgttaga agaatatttg | 900 |
| ttgaaattca ttttctttt gctaacgtat atacaaataa ctgtaataga atatcttata | 960 |
| taagatat | 968 |

<210> SEQ ID NO 111
<211> LENGTH: 1542
<212> TYPE: DNA
<213> ORGANISM: Unknown
<220> FEATURE:
<223> OTHER INFORMATION: Description of Unknown:
       mammals-digestive system-fecal sequence

<400> SEQUENCE: 111

| | |
|---|---|
| acaaatgaaa ttatgggaca agtaaaactt aataaacctc ttctgtatat caaaatattg | 60 |
| actatcttta gacataacct tgtcaaataa taaatctaaa ttactctttt ccttttcttt | 120 |
| tttaaataat ttcatattaa atattcccat aatttattaa tatatttttt tttcattact | 180 |
| tatttctctg ttatataaat agttacataa aaaaattaaa actatttttt aaaaagtctt | 240 |
| gtgtatataa aaaaaatata gtacctttgc acccgaaatc aagatttaat cctgttttca | 300 |
| tattatattt atcaatttta tactaattaa taaacttatg gcaaataaaa aatttaaact | 360 |
| tacaaaaaat gaagtcgtga atcattcgt actcaaagtt gctaaccaaa aaaatgtgc | 420 |
| tatcactaac gaaacacttc aagaatataa aaactattat aataaggtaa gtcagtggat | 480 |
| taataacatc gtacaaaatg aaacgtggag aaatctattt actaacaaaa ccaataatac | 540 |
| atatggatta cctatactaa caccttcaaa aaaaggacaa tctaatatca ttacacaatt | 600 |
| aatgaaaatt aatgcaacac aagaacttgt tgtataatat aatctatttt taaatttata | 660 |
| atactaatat aattcattga taattaaata attatataaa attcctatat acaatagaaa | 720 |
| gactttccac agacatgttg tacatacatt ttttaagta ttaaacaacg catacccacc | 780 |
| aatggtacac gaaatttttc atgttgtaca tactattttt aggtattaaa caactcactg | 840 |
| ttttgacgat taatataggc atgttgtaca tactcttttt agatattaac aacctgtaaa | 900 |
| caataacaat atttcaaaca ataatccatt tttgaaataa tgaaaaattt tctggaaaaa | 960 |
| tttttttaaca agtctgtttt tgaaataatg aaaaaatttc tggaaaaatt tttttaacaa | 1020 |
| acccatttt gattggttca ttttttattg gaaaattagt gtgtggaact acccacccgt | 1080 |
| atatgagcaa gtgttatggg gtgtaacgtg gggagggtta catagggggg tctttggtag | 1140 |
| ggggtacata ggtagggtaa taatgggggtc tttggtaggg ggtacatagg tagtccccat | 1200 |

```
atattattat aaaaagtaaa ataaatgata tatgcaagag tttttgaaaa tttatttta      1260 ttttgctact tagactttac aaaaagtaga tatatagtat tttctttttca aaatattttg     1320 tagtttggaa aaaaagcagt acctttgcac acggaaacga aaaacaagtt taacctatta     1380 aattttagt ttatggcaat aaacattttg acttattctg ctatggcaga aaaatcttgg      1440
gaaaatttta tgcgtgaaaa ttgcggttac gagcgcatta gtacatttta tagtgatttc     1500
actattgcag accattgtgg tggtgtaaac gcaataaaag ac                        1542
```

<210> SEQ ID NO 112
<211> LENGTH: 920
<212> TYPE: DNA
<213> ORGANISM: Unknown
<220> FEATURE:
<223> OTHER INFORMATION: Description of Unknown:
      mammals-digestive system-fecal sequence

<400> SEQUENCE: 112

```
gatgtgaatg aagaatttct tggtggcttg cgaagcacta tgacatatct tggagcaaag      60
agattgaaag atattccgaa atgttgcgtt ttctatcgtg taaatcatca gttgaataca     120
atttatgaga atacaacgat aggaaaataa tataaatttt atattatttt gagaaaaaga     180
gtctaaattt gggctctttt ttcgtttttt atgaaaaaat atgaaaaaag tttgtaaaaa     240
atttgtaata ttgaaaaaat agtattatat ttgtatcaaa tttaaaaata aaatataaat     300
atggcaaaat caataatgaa aaaatcaatt aaattcaaag taaaaggaaa tagtccaata     360
aacgaagata ttataaatga gtataaaggt tattataata cctgtagtaa ttggattaat     420
aataatttaa caagcataac tattggtgaa atgaagact ggagaaaagt gttttgtatc      480
aaaccaaaaa aagaagatta caatacacct ttattggatg ctacgaaaaa tggtcaattt     540
agaatacttg acaagttgaa aaaattaaat gctactaaat tattagaaat ggaaaaataa     600
taaatatata caataaattt atataatttt gtctattttt aatttagtt cattagataa      660 tatgttcata aattcattga catataatta taaataaata tatatgcaat aaaattcgag     720
agacatttca tcagagatgt ctctttttta ttttttgtta tatttatatt atgaatatta     780
gattggaact cataaagaca aaggataaac agaacattgc aaagcgtata gtggaaagca     840
atcactcata tgttccaacc tggcgtagtg taggacgaag gatagattat cttatttatt     900
tggataatga tgttgtcgga                                                 920
```

<210> SEQ ID NO 113
<211> LENGTH: 1217
<212> TYPE: DNA
<213> ORGANISM: Unknown
<220> FEATURE:
<223> OTHER INFORMATION: Description of Unknown:
      mammals-digestive system-rumen-ovis aries sequence

<400> SEQUENCE: 113

```
gtgaactata tctacgaatc aatcgaagga atattgacaa aaacaatgaa tccaaccact      60
ttacaggata tcatccttaa cggaatcaca tatacaccag tggaagacaa cacaacaaca     120
tgcgacggat gtgaatttaa agacacataa ggccaatgta tgctaacaca cctattcgat     180
aacgacatgg tccaaaactg cctcaaggaa aaaacggcg ttgcagatat catatatgtc       240
aaaaaagaaa attaatcgga atcttgattt ggatttaat attatttgtt gtataattac      300
aatagaaaga aatttttgta tattttaaaa tttgtaaatt aaaatttaga aaaatggcac     360
acaaaacaaa caacggagaa aatacaatca ataaaacttt tatttcaaa gcaaagtgcg      420
```

```
ataataacga tattatatcg ttatggaaac ccgcaatgga agagtattgt acttattaca        480
ataaattaag ccaatggatt tgcaagacaa tgtatggagt accagcttac aacattaaaa        540
acggtttcaa aaaaaatctg agcacaaaga caatcaatac gtttagaacg cttggccact        600
atcgtgacgg aaaaataaac gaagacggcg tattcgttga aaacctggca taataaggag        660
taaaaaaatg ttctttgata ttctgacaca aatgaaaaaa caatcaaaaa tttatttctg        720
ttttgcttgt aatttattga ataaaaatgt attatataga aatatgtcgg tggataatag        780
tcaaatagtc tgttgactgt tgaatagtaa gttttttact ctattgacaa caggtgatgt        840
ggatggaaca tacaaagttt attgttgagt aataggtttt acactttac cacaacttta        900 gtgattttat gtataaaata attaaaatca tatataaaaa ttttccaga aagtagtact         960 tattgaatta aaattatatt gtgaaaaatg gttttgatt ttaatttat ttgttgtata        1020 attgaaatgt aatttaattt agaattgtat aaataaaaaa cgtaaaaatg agactgccaa       1080
cagaaattta tgagtcaggc acaatggtta gtaagatatc ggaaaaacca tttaaatcag       1140
gtttaagggt taatactgta aagtctgtag ttgaacatcc acataagatt gacccgaata       1200
ctaataaggg tgttcca                                                      1217

<210> SEQ ID NO 114
<211> LENGTH: 930
<212> TYPE: DNA
<213> ORGANISM: Unknown
<220> FEATURE:
<223> OTHER INFORMATION: Description of Unknown:
      mammals-digestive system-rumen-bos taurus sequence

<400> SEQUENCE: 114
gactacgact ggttctcaaa tgtgtacggc gccatcaggg aggaacgtga gaaaatgaga         60
agggaagagg aggaacgcag gaagaacgaa cccaagacgg tgaaaaccaa agaggttgac        120
ttgttcgggg atgatgacct gccgttctaa taaaaaaaaa aacaaacctc tccgaaattg        180
aacgtatcaa cttcggagag gttatatagg gtgatggaaa tgttaaataa aaagtttaaa        240
aataactatg ggaaacaaag tacaaagtaa tgaaacaata gttaagactt atacatttaa        300
agtgcgtgga ttcataagtg gtgctaccca cgaaataatg aaatcagcca taaaacaata        360
tatagaagat tctaacaatc tatcagattg gattaatgta gagaatgaaa tacttaggaa        420
ctctttcctt aaagaagaga ctaaaaaata cacttataat acaccattat tcactcccag        480
acttaagtca tcggaaaaaa taataacaga attgaaaaaa ttgggtatga ctacggttat        540
agaataacca ttacacattt ttttcataac aaacgttctt taacatattg gaaaataaga        600
aaatacgata ttcatataaa aatccgtccc acacaaaatt aatgtaatat cttagttttg        660
ttacatcaac actatataat taaaaaaata aaaaaatatt ttgtggattc aaaaaatcat        720
tatatatttg cgtccgaaaa ttaacactta tgtcaaacaa atttaaaatg taaaagaact        780
atgcaaacag aaacacagaa tttcacaggc gagttgagag caatcaacac aacaatgggt        840
tcaagcaaga gctacaagac aatctgccgt tgcgcacttg acatcctcaa gggatatatc        900
gttacgcacg acattaggga caacttctca                                        930

<210> SEQ ID NO 115
<211> LENGTH: 1087
<212> TYPE: DNA
<213> ORGANISM: Unknown
<220> FEATURE:
<223> OTHER INFORMATION: Description of Unknown:
``` mammals-digestive system-rumen-bos taurus sequence

<400> SEQUENCE: 115

| | | | | | |
|---|---|---|---|---|---|
| acagagggtg | tatggatagg | catgaaccac | caaggcaaaa | tactgatggc | ttgcagggag | 60 |
| gctttgtgta | acaactgtga | accccgatt | gattacaagg | cactgaacga | tgccgagata | 120 |
| tatttttatg | gaaagaagt | taaattttaa | aaattaaaag | atatggcgaa | caaaagcaca | 180 |
| aaaggaaacc | tgcccaagac | aatcataatg | aaggcaaacc | ttagccccga | tggtttcact | 240 |
| caatgggaaa | gggttgtaaa | agaataccaa | gcctacaaag | acacgttgag | taaatgggta | 300 |
| gcccaaaatc | tcagacaaat | aatgtgcaag | acaccgcaga | caaagaacgg | ctactcatca | 360 |
| cctgtgctca | cctcaaaggt | taaaagccaa | gtggaaatgg | taagagaatt | gaaaaaaatg | 420 |
| ggaaaaacca | ttcttattc | caatgattca | cttccttttt | gaaactaaaa | tgtcttatgt | 480 |
| gtatttgaat | tataggctaa | tataaagatt | gtactgtgtt | gagatacact | tttagaggta | 540 |
| tttacaacaa | aatgcgtgat | atggaaatga | agaaataact | gtgttgagat | acacttttag | 600 |
| aggtatttac | aacaccatat | aaacctgacc | atctcctgaa | tctcgcccga | cacggataat | 660 |
| gttagatatg | ttcacaatac | aactgcatgt | gctattcaag | aaaaaatagt | atatttacaa | 720 |
| tatgttggtg | cataatatta | gatgtgctta | cacaacgcag | acctgaaaag | ccaggataaa | 780 |
| agtatgcggg | attgtgtttt | tagaacactg | ttcaatccgc | tgtatgtcgc | ttgaagcgtc | 840 |
| agtaacctat | gtcgaaacaa | tccttttaga | ggtgtttacg | accgaccaga | aacagcaaga | 900 |
| cctgtattta | tgttggtata | cggttctttt | taggggatta | gtagttgaat | cccttttcac | 960 |
| ccttggtgtt | cacgggttgt | gagacattct | tcatacccat | gcgtgtcttc | tcagccatct | 1020 |
| taccgaaagt | tataggcaca | atatgttcaa | tgcctgcctg | ctgagcattg | tagcatatat | 1080 |
| cagacag | | | | | | 1087 |

<210> SEQ ID NO 116
<211> LENGTH: 1064
<212> TYPE: DNA
<213> ORGANISM: Unknown
<220> FEATURE:
<223> OTHER INFORMATION: Description of Unknown:
    gut metagenome sequence

<400> SEQUENCE: 116

| | | | | | |
|---|---|---|---|---|---|
| agaatgcttt | ccccaattga | atgtgaaaga | ctacagacac | tgccagataa | ctataccgaa | 60 |
| ggtgttagca | aatgcgcaag | atataaggca | atcggaaacg | gatggacagt | tgatgtaatt | 120 |
| tcacatattt | ttaagaattt | gaaaaattaa | tttggtattt | tgaaatattt | gacttatttt | 180 |
| tgcaacataa | aatttaaaac | aaatttatat | ggcacacgcg | aaaaaaaaat | tttgacaaag | 240 |
| gaaagcaaat | aacaaaaacg | ttctctttca | aggtgttaaa | tattaagaac | aatggcgaat | 300 |
| cagttgatat | gaatactata | gaattagcca | tgaaagagta | caataggtat | tataacattt | 360 |
| gtagtgattg | gatttgcaac | aatctaatga | cgccaattgg | ttccctatat | caatacatag | 420 |
| atgatgagaa | atggagaaaa | aaatttgttc | gcccaacaaa | cactaataaa | ccgttgtata | 480 |
| actctccagt | tttctcccct | gctgtaaaat | ctgaaggtgg | tactattaaa | aatctccaaa | 540 |
| ttttaagcgc | aacaaagacc | ataattcttt | gatttaatta | ttaatacata | tatcgttcgt | 600 |
| aaatttaata | caaccacaac | caaatatgat | aatttgcata | attaaaaaaa | ttcacatatc | 660 |
| tttgtagcat | aaaaacaaat | agagaaaaaa | tgacacttta | cagatttaca | cttttaggca | 720 |
| atacacaaat | ttatgtatat | gctggcacgt | ttgaagatgc | tctcaggaca | tttcgtaaat | 780 |

```
catatggaga tacgggattc aagtcaattg aagagcttcc tgaatttaga gataacatac    840
ttatacaact agattgattg aaacaaacgt caattaccca ccactgaagt agtgggtttc    900
tttgcagtga ttttatgaaa acgatagaag acagagcaga catagcaagc gatattgcta    960
aaagagaatt tgaagaagat agttattgga gtcattacgc agacgatatg gtaacatctg   1020
cttttgttga aggatgctat aaaggctata tttcaggtgc gaca                    1064
```

<210> SEQ ID NO 117
<211> LENGTH: 1617
<212> TYPE: DNA
<213> ORGANISM: Unknown
<220> FEATURE:
<223> OTHER INFORMATION: Description of Unknown:
      terrestrial metagenome sequence

<400> SEQUENCE: 117

```
aaggagatag attatgacag ggaaggtaat atcacaaata tatatcttta ctatgagtca     60
gatagtttat ggaatgaaaa atttgaattt atattaacat tagatggtta tgaattaaag    120
atacctattt ttatagtaag tgtaagatag ttttggcacg gaaattgcag taatgttttc    180
ctgtcaagaa caaataaaat aaaaaatatg aaaaaatcaa ttaaattcaa agtaaaagga    240
aattgtccaa taaccaaaga tgttataaat gaatataaag aatattataa taaatgcagt    300
gattggatta agaataattt aacaagcata actattgggg aaatggcaaa atttctcaat    360
gaagtgtgga gagaaatatt ttgtacaagg cctaaaaagg cagaatataa cgttccatcg    420
ttggatacaa caaaaaaagg accatctgca atattgcata tgttgaaaaa atcgaggca    480 attaaaatat tagaaacaga aaagtagtga ctatagatat aaacttctat gatagatatc    540
tgttttttaa ttctattatg caatataata tattgaaata taacaattta taaataaaac    600
gggtgtatac aacaagtttt tgttttttct tattcattat ctgtatattt gtattataaa    660
caaatacaaa tatgtataat gaatcaggaa tatattgcta taaaaacaaa ataaacggaa    720
aattatatat tggacaggcg ctaaatctta aaagaagata tttaaacttt ttaaatatca    780
accacagata tgcgggtcaa gtaatagaaa acgcacgtaa aaaatatggt gtagataact    840
ttgaatattc aatccttact cactgtccag tagacgaatt aaattattgg gaagcatttt    900
atgtagaaag attaaattgt gtcacacccc acggttataa tatgactaat gggggcgatt    960
cagtatatac ttctacacaa gcatttaaag atgcacaaac tgaaagttg aagcaaacta   1020 ttctatctaa gaatcctaat cttaatgtca gcaaagtaaa atatgaaggt aatagaattt   1080
cagttataat tacttgccca atacatggca catttaaaaa aacgcctgat tactttagaa   1140
atccagaaat aaatgatttg tgttgtccta aatgtgtgag ggaagatata agacaaaaga   1200
ctgaagatag tttctcttaaa caagcaacaa agaaatgggg agataagtat gattattcta   1260
aaactataat agtagataga attaccccag ttacaattac ttgccctata cacggagatt   1320
ttacagtatt accagggaac catgtgtgta agataaaaa tactggagga tgccaacaat   1380
gtagtgaaga aagacaacat attgaatcat tagaaaaagg tagcgtgaag gtcattaaga   1440
tgataaagaa aaagtttgga aacaaatatt cattagataa attcgaatat aggggagata   1500
aagaaaaagt aattccttatt tgccctattc atggagaatt ttcaatgacg ccaggtaatt   1560
taagatatag caacggttgt ccacaatgca ctttagaaaa tgcttatcgt ataaaat      1617
```

<210> SEQ ID NO 118
<211> LENGTH: 37
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 118
agttgtaaat acctataaaa atgtattcca acatagt                                   37

<210> SEQ ID NO 119
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
gttgtgaata ccctacaaaa gtgatattcc aacaat                                    36

<210> SEQ ID NO 120
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
aaaaagggtg aacaacatt                                                       19

<210> SEQ ID NO 121
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
gttgtttgat acctataaaa gagtattcac aacagg                                    36

<210> SEQ ID NO 122
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
gttgtttact ccatacaaaa taagagttac aacaat                                    36

<210> SEQ ID NO 123
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
gttgttcaat ccttataaaa aggtgtctac aacaat                                    36

<210> SEQ ID NO 124
<211> LENGTH: 36
<212> TYPE: DNA
<213> ORGANISM: Artificial Sequence
```

<220> FEATURE:
<223> OTHER INFORMATION: Description of Artificial Sequence: Synthetic
      oligonucleotide

<400> SEQUENCE: 124
gttgtttaat acctataaaa gagtatatac aacaag                    36

<210> SEQ ID NO 125
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
aatacctata aaaggacata tacaacaag                            29

<210> SEQ ID NO 126
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126
gttgttcaat acctataaaa agacatatac aacaag                    36

<210> SEQ ID NO 127
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
gttgttcatt acctaaaaaa gagta                                25

<210> SEQ ID NO 128
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
gttgtttaat acctataaaa gaatatatac aacaag                    36

<210> SEQ ID NO 129
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129
gttgtttaat acttaaaaaa tagtatgtac aacatg                    36

<210> SEQ ID NO 130
<211> LENGTH: 36
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 130
gttgtatcca ccgtataaaa catagtgtcc aacatc                                36

<210> SEQ ID NO 131
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131
gttgtttatt acttacaaaa acagcataac aacatc                                36

<210> SEQ ID NO 132
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
gttgttcaat ccttataaaa agaggtctac aacaat                                36

<210> SEQ ID NO 133
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
gttgttatta ccatataaaa tggttcgtac aacaat                                36

<210> SEQ ID NO 134
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
actgttgtac tttcctttca tctgcagggg ttttacagt                             39

<210> SEQ ID NO 135
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
tagttgttta atacttaaaa aatagtatgt acaacatgat                            40

<210> SEQ ID NO 136
<211> LENGTH: 36
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 136
gttgtaaata gcatacaaac atagccattc aacaat                                36

<210> SEQ ID NO 137
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137
gttgtgagta ccctataaaa gaagtacccc aacaat                                36

<210> SEQ ID NO 138
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138
cgttgttaga cccctaaaac acaaggtcta caacaat                               37

<210> SEQ ID NO 139
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
gttgtaaata catctcatat tgtattccaa cacagt                                36

<210> SEQ ID NO 140
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140
gttgtcagca tccgccttgc ggtatgccac aacaat                                36

<210> SEQ ID NO 141
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141
gttgccaata ccataaaaaa cggtatctca acaatt                                36

<210> SEQ ID NO 142
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 142
ttgtcagcac ccgtaatacg gtatgccaca acaat                                      35

<210> SEQ ID NO 143
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143
gttgtcagca cccgtaatac ggtatgccac aacaat                                     36

<210> SEQ ID NO 144
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 144
gttgtaaata cctataaaag tgtatcccaa cacaat                                     36

<210> SEQ ID NO 145
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 145
gttgtaatta cctttataag aaaggtattc aacaata                                    37

<210> SEQ ID NO 146
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 146
gagttgttcg ttgcccataa aaagccattt acaaca                                     36

<210> SEQ ID NO 147
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 147
gttgtatctg tcctaaaaaa gaatacattc aacaat                                     36

<210> SEQ ID NO 148
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 148
agttgtaatc agtctataaa agataccatt caacaat                                    37

<210> SEQ ID NO 149
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 149
gttgtaatta agataaaaaa cctattatcc aacaat                                     36

<210> SEQ ID NO 150
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 150
gttgtaaata ggatataaaa tcaactattc aacagt                                     36

<210> SEQ ID NO 151
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 151
gttgttcaat ccttacaaaa aggtatctac aacaat                                     36

<210> SEQ ID NO 152
<211> LENGTH: 103
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 152
attgggactt ccggaagtaa aatatccacc tgaggatttt aggacatata atttctaata          60
aaaatgaacg gaaaaatttc cgttcatttt tttttttgttt att                          103

<210> SEQ ID NO 153
<211> LENGTH: 105
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 153
tattgggact tccggaagta aaatatccac ctgaggattt taggacatat aatttctaat          60
aaaaatgaac ggaaaaattt ccgttcattt tttttttgtt tattg                         105

<210> SEQ ID NO 154
<211> LENGTH: 163
<212> TYPE: DNA
<213> ORGANISM: Artificial Sequence
<220> FEATURE:

<223> OTHER INFORMATION: Description of Artificial Sequence: Synthetic
      polynucleotide

<400> SEQUENCE: 154
gacgagaacg gagtgtggct cctgaggaaa aacgacaaac atccaacata ttttatctac    60
cagaacggaa cactctatca atatgaggaa gattgattag ttgatgtttt cataataatt   120
ttatctggaa tttgaaaaga ttccagattt ttttttttatt tcg    163

<210> SEQ ID NO 155
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155
gcaatcaaca agactttcat tttcaaggca aaatgcgata agaacgatgt catatcgtta    60
tgggaa    66

<210> SEQ ID NO 156
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 156
gatgctccga aaacgtggtt gttcggacaa caaaaaaatg aatgtttcta atgtattaa    59

<210> SEQ ID NO 157
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 157
gacggaaaaa taaatgagga tggtatgttt gttgaaaact tggaataatt ctgtatatac    60
caattagaat    70

<210> SEQ ID NO 158
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158
tgttgattgc tgattcttcg ttgtttgatt tgtgttgtgc cataatctta aaatt    55

<210> SEQ ID NO 159
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159
cgcaagatat aaggcaatcg gaaacggatg gacagttgat gtaatttcac atatttttaa    60

```
gaatttgaaa aattaatttg gta                                              83

<210> SEQ ID NO 160
<211> LENGTH: 95
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 160
ggacatttcg taaatcatat ggagatacgg agttcaagtc aattgaagag cttcctgaat       60
ttagagataa catacttata caactagatt gattg                                 95

<210> SEQ ID NO 161
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 161
atcaatacat agatgatgag aaatggagaa aaaaatttgt tcgcccaaca aacactaat       59

<210> SEQ ID NO 162
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 162
ctggtaatac tgtaaaatct ccgtgtatag ggcaagtaat tgtaactggg gtaattctat       60
ctactattat agttttagaa                                                 80

<210> SEQ ID NO 163
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 163
cagaagtcgt tcaagttcaa ggtcaaaacg gacaaggaga cggtcgaatt attcag          56

<210> SEQ ID NO 164
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 164
gggagggtga cattcagaag tcgttcaagt tcaaggtcaa aacggacaag gagacggtcg      60
aattat                                                                66

<210> SEQ ID NO 165
<211> LENGTH: 102
<212> TYPE: DNA
<213> ORGANISM: Artificial Sequence
```

```
<220> FEATURE:
<223> OTHER INFORMATION: Description of Artificial Sequence: Synthetic
      polynucleotide

<400> SEQUENCE: 165
aagtgtcttc aacacattga agaaaactct cggtgcaata tatggaaagc tcgatgaaaa    60
cggaaatttt attgagaatg aatgtaataa gtaactggaa ta                      102

<210> SEQ ID NO 166
<211> LENGTH: 98
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 166
ccgtgggagg atttggattt ggttgaagac atcagaaaaa ttttcgaaat ggaatagagg    60
gaaccggaat tttttccggt ttttctttgt cctttcga                           98

<210> SEQ ID NO 167
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 167
cagagtaacc ttcctgata tgttgttaca cattttgta agtgttaaac aactgacgca      60
ttgatattgc cttgtctatt aa                                            82

<210> SEQ ID NO 168
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 168
caatcgcgag tttatactga aatgttgtta cactgttttt gtaagtgtta aacaaccttg    60
cacaaatgtc atctaccagt ac                                            82

<210> SEQ ID NO 169
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 169
ccgagcgacc cacaaaccta ttgtcgtacg catcatttca catgataata acaacgaata    60
ttcctgcaag catgattt                                                 78

<210> SEQ ID NO 170
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 170
tatgacatta tgatattgtt gtatgcatca tttcacatgg taataacaac gaagagaaac    60
accgagcgac ccacaaa                                                   77

<210> SEQ ID NO 171
<211> LENGTH: 85
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 171
acatctttta tgacattatg atattgttgt atgcatcatt tcacatggta ataacaacga    60
agagaaacac cgagcgaccc acaaa                                          85

<210> SEQ ID NO 172
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 172
gctaaaatat agtcctgtgg atgttgaata catttctttt aagtgtactt acaaccaacg    60
ctgtacacat tgctaatgga tg                                             82

<210> SEQ ID NO 173
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 173
tgctaaaata tagtcctgtg gatgttgaat acatttcttt taagtgtact tacaaccaac    60
gctgtacaca ttgctaatgg atg                                            83

<210> SEQ ID NO 174
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 174
caacaccaag gctgaggcaa agaagagggc tgatgatatg aacaaacaga atagggtcat    60
acaccagctg tctgtttatt tgtgtcc                                        87

<210> SEQ ID NO 175
<211> LENGTH: 95
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 175
aattagactg ataaacaaag aataatgaga actataatag ggaggtgtac ccccgaattt    60
```
aagccagtgg agaaccatac aaacctatca tatag                          95

<210> SEQ ID NO 176
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 176
tgggtatgcg ttgtttaata cttaaaaaaa tgtatgtaca acatgtctgt ggaaagtctt    60
tctattgtat at                                                         72

<210> SEQ ID NO 177
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 177
cgttgtttaa tacttaaaaa aatgtatgta caacatgtct gtggaaagtc tttctattgt    60
atatagga                                                              68

<210> SEQ ID NO 178
<211> LENGTH: 118
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 178
tgggtatgcg ttgtttaata cttaaaaaaa tgtatgtaca acatgtctgt ggaaagtctt    60
tctattgtat ataggaattt tatataatta tttaattatc aatgaattat attagtat     118

<210> SEQ ID NO 179
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 179
ggtgggtatg cgttgtttaa tacttaaaaa aatgtatgta caacatgtct gtggaaag      58

<210> SEQ ID NO 180
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 180
aatgaacgag attgttggga tatacctttt ataggatttt cacaacatct gagttgtttg    60
atgttaaaaa ctt                                                        73

<210> SEQ ID NO 181
<211> LENGTH: 80
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 181
gataaaaatg aacgagattg ttgggatata cctttatag gattttcaca acatctgagt    60
tgtttgatgt taaaaacttt                                               80

<210> SEQ ID NO 182
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 182
gctaatataa agattgtact gtgttgagat acacttttag aggtatttac aacaaaatgc    60
gtgatatgga aatga                                                    75

<210> SEQ ID NO 183
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 183
ataccaacat aaatacaggt cttgctgttt ctggtcggtc gtaaacacct ctaaaggat    60 tgtttcgaca taggttactg acgcttcaag                                    90

<210> SEQ ID NO 184
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 184
aatgaagaaa taactgtgtt gagatacact tttagaggta tttacaacac catataaacc    60
tgaccatctc ct                                                       72

<210> SEQ ID NO 185
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 185
aggaagatgt cagacgtttt tattgttgga atactcgttt tttacggtat ttacaactgc    60
cccgtagcgg aatcaaaata ccac                                          84

<210> SEQ ID NO 186
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 186
atgtcagacg tttttattgt tggaatactc gttttttacg gtatttacaa ctgccccgta    60
gcggaatcaa aatacc    76

<210> SEQ ID NO 187
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 187
aaataacaaa aattctggac gggaaaggaa gatgtcagac gttttattg ttggaatact    60 cgttttttac ggtatttaca actgccccgt agcggaatc    99

<210> SEQ ID NO 188
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 188
ataacaaaaa ttctggacgg gaaaggaaga tgtcagacgt ttttattgtt ggaatactcg    60 tttttacgg tatttacaac tgccccgtag cggaat    96

<210> SEQ ID NO 189
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 189
tattgcaact attacaacaa acttagcgaa tggattggca agatatgta taacacgccg    60

<210> SEQ ID NO 190
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 190
attgcaacta ttacaacaaa cttagcgaat ggattggcaa agatatgtat aacacgccg    59

<210> SEQ ID NO 191
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 191
gtatgatgac agaagaaaca cggaagacaa tagagagcgt catagtggtt ctcggcatag    60
caatcatgct g    71

```
<210> SEQ ID NO 192
<211> LENGTH: 118
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 192
atgatgacag aagaaacacg gaagacaata gagagcgtca tagtggttct cggcatagca      60
atcatgctgg cagccgccgt ccgaataatg acgcagaaca aagcaattgt gaaatatg       118

<210> SEQ ID NO 193
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 193
agaaggtact gccgccttat gaccgacgag aacggagtgt ggctcctgag gaaaaac        57

<210> SEQ ID NO 194
<211> LENGTH: 163
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 194
gacgagaacg gagtgtggct cctgaggaaa acgacaaac atccaacata ttttatctac       60
cagaacggaa cactctatca atatgaggaa gattgattag ttgatgtttt cataataatt    120
ttatctggaa tttgaaaaga ttccagattt ttttttttatt tcg                     163

<210> SEQ ID NO 195
<211> LENGTH: 92
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 195
tttttgttat atatttgtcc tgttaggtta aatcaccgcg cctgatgacg aagtcggtgg      60
tagaattaga ctaatattaa atatgtctca tg                                   92

<210> SEQ ID NO 196
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 196
cctattagat attccgtatt tctttaagac tgttataata caaatatact acaaatcatg      60
caatttttga ttttaacaa aa                                               82

<210> SEQ ID NO 197
<211> LENGTH: 103
<212> TYPE: DNA
<213> ORGANISM: Artificial Sequence
```

```
<220> FEATURE:
<223> OTHER INFORMATION: Description of Artificial Sequence: Synthetic
      polynucleotide

<400> SEQUENCE: 197
tcgttgaata cgatatcgcc gaaacaattg attggagaag tacgctttgt ttcaagacat    60
ggaatacgta tggttctcct caatgggact cgaagatcaa gaa                     103

<210> SEQ ID NO 198
<211> LENGTH: 108
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 198
atcgttgaat acgatatcgc cgaaacaatt gattggagaa gtacgctttg tttcaagaca    60
tggaatacgt atggttctcc tcaatgggac tcgaagatca agaaccag                108

<210> SEQ ID NO 199
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 199
gagcttttct ggcaatgtag acattaaagc tggtatcgtt gaatacgata tcgccgaaac    60
aattgattgg aga                                                      73

<210> SEQ ID NO 200
<211> LENGTH: 98
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 200
tttttcattg ttctcaaatt gttggataat gttttgtgtg tttcattttt gtcattgtgt    60
caccttaact gacaaggtgg cacattttt atgtcaat                            98

<210> SEQ ID NO 201
<211> LENGTH: 98
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 201
ttttcattgt tctcaaattg ttggataatg ttttgtgtgt tcattttg tcattgtgtc      60 accttaactg acaaggtggc acatttttta tgtcaata                           98

<210> SEQ ID NO 202
<211> LENGTH: 122
<212> TYPE: DNA
<213> ORGANISM: Artificial Sequence
<220> FEATURE:
<223> OTHER INFORMATION: Description of Artificial Sequence: Synthetic
      polynucleotide
```

```
<400> SEQUENCE: 202
aatatatctg ctaaggtcat atttttcatt gttctcaaat tgttggataa tgttttgtgt    60
gtttcatttt tgtcattgtg tcaccttaac tgacaaggtg gcacattttt tatgtcaata   120
tg                                                                  122

<210> SEQ ID NO 203
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 203
acaaattttt gattatggca cacaaaaaga acataggagc agagatagta aaaacttact    60
cttttaaggt gaaga                                                    75

<210> SEQ ID NO 204
<211> LENGTH: 136
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 204
ttattttata ggataataga gctaacaagc attaacaatt attaaaacga tttatattga    60
aaataaattt tgtgggaata tttattttta ctacctttgc atcgtaatac aattaaacaa   120 attttgatt atggca                                                    136

<210> SEQ ID NO 205
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 205
cctgttgtga atactctttt ataggtatca acaacggaa gtggttggtc agcatggatt    60
a                                                                   61

<210> SEQ ID NO 206
<211> LENGTH: 25
<212> TYPE: DNA
<213> ORGANISM: Unknown
<220> FEATURE:
<223> OTHER INFORMATION: Description of Unknown:
      target sequence

<400> SEQUENCE: 206
ggaagtggtt ggtcagcatg gatta                                         25

<210> SEQ ID NO 207
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 207
```

```
cctgttgtga atactctttt ataggtatca aacaactgtg aagtgacctg ggagctaact    60
g                                                                   61
```

<210> SEQ ID NO 208
<211> LENGTH: 25
<212> TYPE: DNA
<213> ORGANISM: Unknown
<220> FEATURE:
<223> OTHER INFORMATION: Description of Unknown:
      target sequence

<400> SEQUENCE: 208

```
tgtgaagtga cctgggagct aactg                                         25
```

<210> SEQ ID NO 209
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 209

```
attgttgtag acaccttttt ataaggattg aacaacaacc ccgtctacc tgcccacagg    60 g                                                                   61
```

<210> SEQ ID NO 210
<211> LENGTH: 25
<212> TYPE: DNA
<213> ORGANISM: Unknown
<220> FEATURE:
<223> OTHER INFORMATION: Description of Unknown:
      target sequence

<400> SEQUENCE: 210

```
aaccccgtc tacctgccca caggg                                          25
```

<210> SEQ ID NO 211
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 211

```
cttgttgtat atgtccttttt ataggtatta aacaacgtag agggagaaat ggaatccata   60
t                                                                   61
```

<210> SEQ ID NO 212
<211> LENGTH: 25
<212> TYPE: DNA
<213> ORGANISM: Unknown
<220> FEATURE:
<223> OTHER INFORMATION: Description of Unknown:
      target sequence

<400> SEQUENCE: 212

```
gtagagggag aaatggaatc catat                                         25
```

<210> SEQ ID NO 213
<211> LENGTH: 36
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 213
cttgttgtat atgtcctttt ataggtatta aacaac                                    36

<210> SEQ ID NO 214
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 214
attgttgtag acaccttttt ataaggattg aacaacgcac caacgggtag atttggtggt         60
g                                                                          61

<210> SEQ ID NO 215
<211> LENGTH: 25
<212> TYPE: DNA
<213> ORGANISM: Unknown
<220> FEATURE:
<223> OTHER INFORMATION: Description of Unknown:
      target sequence

<400> SEQUENCE: 215
gcaccaacgg gtagatttgg tggtg                                                25

<210> SEQ ID NO 216
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: L, M, I, C, or F
<220> FEATURE:
<221> NAME/KEY: MOD_RES
<222> LOCATION: (3)..(3)
<223> OTHER INFORMATION: Y, W, or F
<220> FEATURE:
<221> NAME/KEY: MOD_RES
<222> LOCATION: (4)..(4)
<223> OTHER INFORMATION: K, T, C, R, W, Y, H, or V
<220> FEATURE:
<221> NAME/KEY: MOD_RES
<222> LOCATION: (5)..(5)
<223> OTHER INFORMATION: I, L, or M

<400> SEQUENCE: 216

Pro Xaa Xaa Xaa Xaa Phe
1               5

<210> SEQ ID NO 217
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: I, L, M, Y, T, or F
<220> FEATURE:
<221> NAME/KEY: MOD_RES
```

<222> LOCATION: (3)..(3)
<223> OTHER INFORMATION: R, Q, K, E, S, or T
<220> FEATURE:
<221> NAME/KEY: MOD_RES
<222> LOCATION: (4)..(4)
<223> OTHER INFORMATION: L, I, T, C, M, or K

<400> SEQUENCE: 217

Arg Xaa Xaa Xaa Leu
1               5

<210> SEQ ID NO 218
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: I, L, or F
<220> FEATURE:
<221> NAME/KEY: MOD_RES
<222> LOCATION: (4)..(4)
<223> OTHER INFORMATION: K, R, V, or E

<400> SEQUENCE: 218

Asn Xaa Tyr Xaa
1

<210> SEQ ID NO 219
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: T, I, N, A, S, F, or V
<220> FEATURE:
<221> NAME/KEY: MOD_RES
<222> LOCATION: (3)..(3)
<223> OTHER INFORMATION: I, V, L, or S
<220> FEATURE:
<221> NAME/KEY: MOD_RES
<222> LOCATION: (4)..(4)
<223> OTHER INFORMATION: H, S, G, or R
<220> FEATURE:
<221> NAME/KEY: MOD_RES
<222> LOCATION: (7)..(7)
<223> OTHER INFORMATION: D, S, or E
<220> FEATURE:
<221> NAME/KEY: MOD_RES
<222> LOCATION: (8)..(8)
<223> OTHER INFORMATION: I, V, M, T, or N

<400> SEQUENCE: 219

Lys Xaa Xaa Xaa Phe Ala Xaa Xaa Lys Asp
1               5                   10

<210> SEQ ID NO 220
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)

```
<223> OTHER INFORMATION: G, S, C, or T
<220> FEATURE:
<221> NAME/KEY: MOD_RES
<222> LOCATION: (4)..(4)
<223> OTHER INFORMATION: N, Y, K, or S

<400> SEQUENCE: 220

Leu Xaa Asn Xaa
1

<210> SEQ ID NO 221
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: S, P, or A
<220> FEATURE:
<221> NAME/KEY: MOD_RES
<222> LOCATION: (3)..(3)
<223> OTHER INFORMATION: Y, S, A, P, E, Y, Q, or N
<220> FEATURE:
<221> NAME/KEY: MOD_RES
<222> LOCATION: (4)..(4)
<223> OTHER INFORMATION: F, Y, or H
<220> FEATURE:
<221> NAME/KEY: MOD_RES
<222> LOCATION: (5)..(5)
<223> OTHER INFORMATION: T or S
<220> FEATURE:
<221> NAME/KEY: MOD_RES
<222> LOCATION: (8)..(8)
<223> OTHER INFORMATION: M, T, or I

<400> SEQUENCE: 221

Pro Xaa Xaa Xaa Xaa Ser Gln Xaa Asp Ser
1               5                   10

<210> SEQ ID NO 222
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: N, K, W, R, E, T, or Y
<220> FEATURE:
<221> NAME/KEY: MOD_RES
<222> LOCATION: (3)..(3)
<223> OTHER INFORMATION: M, R, L, S, K, V, E, T, I, or D
<220> FEATURE:
<221> NAME/KEY: MOD_RES
<222> LOCATION: (6)..(6)
<223> OTHER INFORMATION: L, R, H, P, T, K, Q, P, S, or A
<220> FEATURE:
<221> NAME/KEY: MOD_RES
<222> LOCATION: (7)..(7)
<223> OTHER INFORMATION: G, Q, N, R, K, E, I, T, S, or C
<220> FEATURE:
<221> NAME/KEY: MOD_RES
<222> LOCATION: (10)..(10)
<223> OTHER INFORMATION: R, W, Y, K, T, F, S, or Q

<400> SEQUENCE: 222

Lys Xaa Xaa Val Arg Xaa Xaa Gln Glu Xaa His
1               5                   10
```

```
<210> SEQ ID NO 223
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: I, K, V, or L
<220> FEATURE:
<221> NAME/KEY: MOD_RES
<222> LOCATION: (4)..(4)
<223> OTHER INFORMATION: L or M
<220> FEATURE:
<221> NAME/KEY: MOD_RES
<222> LOCATION: (5)..(5)
<223> OTHER INFORMATION: N, H, or P
<220> FEATURE:
<221> NAME/KEY: MOD_RES
<222> LOCATION: (6)..(6)
<223> OTHER INFORMATION: A, S, or C
<220> FEATURE:
<221> NAME/KEY: MOD_RES
<222> LOCATION: (8)..(8)
<223> OTHER INFORMATION: V, Y, I, F, T, N, or Y
<220> FEATURE:
<221> NAME/KEY: MOD_RES
<222> LOCATION: (10)..(10)
<223> OTHER INFORMATION: A or S
<220> FEATURE:
<221> NAME/KEY: MOD_RES
<222> LOCATION: (11)..(11)
<223> OTHER INFORMATION: S, A, or P
<220> FEATURE:
<221> NAME/KEY: MOD_RES
<222> LOCATION: (12)..(12)
<223> OTHER INFORMATION: M, C, L, R, N, S, K, or L

<400> SEQUENCE: 223

Xaa Asn Gly Xaa Xaa Xaa Asp Xaa Asn Xaa Xaa Xaa Asn
1               5                   10

<210> SEQ ID NO 224
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 224 vhtdkdddd                                                                 9

<210> SEQ ID NO 225
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 225 attgttgda                                                                 9

<210> SEQ ID NO 226
<211> LENGTH: 9
<212> TYPE: DNA
<213> ORGANISM: Artificial Sequence
<220> FEATURE:
<223> OTHER INFORMATION: Description of Artificial Sequence: Synthetic
```

```
        oligonucleotide
<220> FEATURE:
<221> NAME/KEY: modified_base
<222> LOCATION: (8)..(8)
<223> OTHER INFORMATION: a, c, t, g, unknown or other

<400> SEQUENCE: 226 hdhwdwwnv                                                                   9

<210> SEQ ID NO 227
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 227 ttttwtarg                                                                   9

<210> SEQ ID NO 228
<211> LENGTH: 5
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 228 vmmac                                                                       5

<210> SEQ ID NO 229
<211> LENGTH: 5
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 229 acaac                                                                       5

<210> SEQ ID NO 230
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (18)..(18)
<223> OTHER INFORMATION: a, c, t, g, unknown or other

<400> SEQUENCE: 230
atattgttgd akrwwyyntt ttwtargkww wwwacaacwr b                               41

<210> SEQ ID NO 231
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 231

Asn Leu Thr Ser Ile Thr Ile Gly
1               5
```

<210> SEQ ID NO 232
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

Asn Tyr Arg Thr Lys Ile Arg Thr Leu Asn
1               5                   10

<210> SEQ ID NO 233
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 233

Ile Ser Tyr Ile Glu Asn Val Glu Asn
1               5

<210> SEQ ID NO 234
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Glu Leu Leu Ser Val Glu Gln Leu Lys
1               5

<210> SEQ ID NO 235
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

His Ile Asn Ser Met Thr Ile Asn Ile Gln Asp Phe Lys Ile Glu
1               5                   10                  15

<210> SEQ ID NO 236
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Lys Glu Asn Ser Leu Gly Phe Ile Leu
1               5

<210> SEQ ID NO 237
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

Gly Asn Arg Gln Ile Lys Lys Gly
1               5

<210> SEQ ID NO 238
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Asp Val Asn Phe Lys His Ala
1               5

<210> SEQ ID NO 239
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Gly Tyr Ile Asn Leu Tyr Lys Tyr Leu Leu Glu His
1               5                   10

<210> SEQ ID NO 240
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

Lys Glu Gln Val Leu Ser Lys Leu Leu Tyr
1               5                   10

<210> SEQ ID NO 241
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 241

Glu Tyr Ile Tyr Val Ser Cys Val Asn Lys Leu Arg Ala Lys Tyr Val
1               5                   10                  15

Ser Tyr Phe Ile Leu Lys Glu Lys Tyr Tyr Lys Gln Lys Glu Tyr
            20                  25                  30

Asp Ile Glu Met Gly Phe
        35

<210> SEQ ID NO 242
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242

```
Asp Asp Ser Thr Glu Ser Lys Glu Ser Met Asp Lys Arg Arg
1               5                   10
```

<210> SEQ ID NO 243
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

```
Asn Val Gln Gln Asp Ile Asn Gly Cys Leu Lys Asn Ile Ile Asn Tyr
1               5                   10                  15
```

<210> SEQ ID NO 244
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

```
Ala Leu Glu Asn Leu Glu Asn Ser Asn Phe Glu Lys
1               5                   10
```

<210> SEQ ID NO 245
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

```
Gln Val Leu Pro Thr Ile Lys Ser Leu Leu
1               5                   10
```

<210> SEQ ID NO 246
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246

```
Tyr His Lys Leu Glu Asn Gln Asn
1               5
```

<210> SEQ ID NO 247
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 247

```
Ala Ser Asp Lys Val Lys Glu Tyr Ile Glu
1               5                   10
```

<210> SEQ ID NO 248
<211> LENGTH: 13
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 248

Thr Asn Glu Asn Asn Glu Ile Val Asp Ala Lys Tyr Thr
1               5                   10

<210> SEQ ID NO 249
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249

Ala Asn Phe Phe Asn Leu Met Met Lys Ser Leu His Phe Ala Ser
1               5                   10                  15

<210> SEQ ID NO 250
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 250

Leu Leu Ser Asn Asn Gly Lys Thr Gln Ile Ala Leu Val Pro Ser Glu
1               5                   10                  15

<210> SEQ ID NO 251
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 251

His Ile Asn Gly Leu Asn Ala Asp Phe Asn Ala Ala Asn Asn Ile Lys
1               5                   10                  15

Tyr Ile

<210> SEQ ID NO 252
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 252
cctgttgtga atactctttt ataggtatca acaacgaga ggtgagggac ttgggggta     60 a                                                                   61

<210> SEQ ID NO 253
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 253
gagaggtgag ggacttgggg ggtaa                                         25

<210> SEQ ID NO 254
<211> LENGTH: 61
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 254
cctgttgtga atactctttt ataggtatca aacaactgag aatggtgcgt cctaggtgtt    60
c                                                                  61

<210> SEQ ID NO 255
<211> LENGTH: 25
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 255
tgagaatggt gcgtcctagg tgttc                                        25

<210> SEQ ID NO 256
<211> LENGTH: 61
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 256
cctgttgtga atactctttt ataggtatca aacaacgcag cctgtgctga cccatgcagt    60
c                                                                  61

<210> SEQ ID NO 257
<211> LENGTH: 25
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 257
gcagcctgtg ctgacccatg cagtc                                        25

<210> SEQ ID NO 258
<211> LENGTH: 61
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 258
cctgttgtga atactctttt ataggtatca aacaacggaa gtggttggtc agcatggatt    60
a                                                                  61

<210> SEQ ID NO 259
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 259
ggaagtggtt ggtcagcatg gatta                                25

<210> SEQ ID NO 260
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 260
cctgttgtga atactctttt ataggtatca acaacagcc agtgttgcta gtcaagggca    60
g                                                                   61

<210> SEQ ID NO 261
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 261
agccagtgtt gctagtcaag ggcag                                25

<210> SEQ ID NO 262
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 262
cctgttgtga atactctttt ataggtatca acaacttga cattgtccac acctggaatc    60
g                                                                   61

<210> SEQ ID NO 263
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 263
ttgacattgt ccacacctgg aatcg                                25

<210> SEQ ID NO 264
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 264
cctgttgtga atactctttt ataggtatca acaacgaaa tctattgagg ctctggagag    60
a                                                                   61

<210> SEQ ID NO 265

```
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 265
gaaatctatt gaggctctgg agaga                                          25

<210> SEQ ID NO 266
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 266
cctgttgtga atactctttt ataggtatca aacaacggaa gctggatgag cctggtccat    60
g                                                                   61

<210> SEQ ID NO 267
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 267
ggaagctgga tgagcctggt ccatg                                          25

<210> SEQ ID NO 268
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 268
cctgttgtga atactctttt ataggtatca aacaacccca tactggggac caaggaagtg    60
t                                                                   61

<210> SEQ ID NO 269
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 269
cccatactgg ggaccaagga agtgt                                          25

<210> SEQ ID NO 270
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 270
cctgttgtga atactctttt ataggtatca aacaacatga tgctttgccg taacccttcg    60
``` t                                                                61

<210> SEQ ID NO 271
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 271
atgatgcttt gccgtaaccc ttcgt                                      25

<210> SEQ ID NO 272
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 272
cctgttgtga atactctttt ataggtatca aacaacaaga gtcattgccc cactttaccc   60
t                                                                61

<210> SEQ ID NO 273
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 273
aagagtcatt gccccacttt accct                                      25

<210> SEQ ID NO 274
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 274
cctgttgtga atactctttt ataggtatca aacaacgaga ggtgagggac ttgggggta   60 a                                                                61

<210> SEQ ID NO 275
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 275
gagaggtgag ggacttgggg ggtaa                                      25

<210> SEQ ID NO 276
<211> LENGTH: 61
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 276
cctgttgtga atactctttt ataggtatca aacaacgtga agttctaaac ttcatattac    60
c                                                                   61

<210> SEQ ID NO 277
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 277
gtgaagttct aaacttcata ttacc                                         25

<210> SEQ ID NO 278
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 278
cttgttgtat atgtcctttt ataggtatta acaacgtag agggagaaat ggaatccata    60
t                                                                   61

<210> SEQ ID NO 279
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 279
gtagagggag aaatggaatc catat                                         25

<210> SEQ ID NO 280
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 280
cttgttgtat atgtcctttt ataggtatta acaacgagt cgctttaact ggccctggct    60
t                                                                   61

<210> SEQ ID NO 281
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 281
gagtcgcttt aactggccct ggctt                                         25

<210> SEQ ID NO 282

```
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 282
cttgttgtat atgtcctttt ataggtatta aacaactcca cacctggaat cggctttcag    60
c                                                                    61

<210> SEQ ID NO 283
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 283
tccacacctg gaatcggctt tcagc                                          25

<210> SEQ ID NO 284
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 284
cttgttgtat atgtcctttt ataggtatta aacaacaacc cccgtctacc tgcccacagg    60
g                                                                    61

<210> SEQ ID NO 285
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 285 aaccccgtc tacctgccca caggg                                           25

<210> SEQ ID NO 286
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 286
cttgttgtat atgtcctttt ataggtatta aacaacgtag agggagaaat ggaatccata    60
t                                                                    61

<210> SEQ ID NO 287
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 287
```

```
gtagagggag aaatggaatc catat                                           25

<210> SEQ ID NO 288
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 288
cttgttgtat atgtcctttt ataggtatta aacaacgacc catgggagca gctggtcaga    60
g                                                                    61

<210> SEQ ID NO 289
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 289
gacccatggg agcagctggt cagag                                           25

<210> SEQ ID NO 290
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 290

Glu Cys Pro Ile Thr Lys Asp Val Ile Asn Glu Tyr Lys
1               5                   10

<210> SEQ ID NO 291
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 291
ccuguuguga auacucuuuu auagguauca aacaac                               36
```